United States Patent
Engle et al.

(10) Patent No.: US 12,378,320 B2
(45) Date of Patent: Aug. 5, 2025

(54) METHODS FOR TREATING PANCREATITIS

(71) Applicant: Cold Spring Harbor Laboratory, Cold Spring Harbor, NY (US)

(72) Inventors: Dannielle D. Engle, San Diego, CA (US); David A. Tuveson, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 982 days.

(21) Appl. No.: 17/274,783

(22) PCT Filed: Sep. 9, 2019

(86) PCT No.: PCT/US2019/050262
§ 371 (c)(1),
(2) Date: Mar. 9, 2021

(87) PCT Pub. No.: WO2020/055768
PCT Pub. Date: Mar. 19, 2020

(65) Prior Publication Data
US 2022/0049011 A1 Feb. 17, 2022

Related U.S. Application Data

(60) Provisional application No. 62/729,354, filed on Sep. 10, 2018.

(51) Int. Cl.
| | |
|---|---|
| *C07K 16/30* | (2006.01) |
| *A61P 1/18* | (2006.01) |
| *C07K 16/28* | (2006.01) |

(52) U.S. Cl.
CPC .......... *C07K 16/2896* (2013.01); *A61P 1/18* (2018.01); *C07K 2317/24* (2013.01); *C07K 2317/56* (2013.01); *C07K 2317/565* (2013.01); *C07K 2317/626* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,471,057 A | 9/1984 | Koprowski et al. | |
| 9,475,874 B2 * | 10/2016 | Sawada | A61K 51/1027 |
| 2005/0137218 A1 | 6/2005 | Tracey et al. | |
| 2010/0292095 A1 | 11/2010 | Laukkanen et al. | |
| 2015/0056134 A1 | 2/2015 | Sawada et al. | |
| 2016/0271221 A1 | 9/2016 | Yan et al. | |

FOREIGN PATENT DOCUMENTS

| | | |
|---|---|---|
| CL | 2022000091 A1 | 11/2022 |
| CN | 102137681 A | 7/2011 |
| EP | 0274264 A1 | 7/1988 |
| EP | 2970422 B1 | 4/2018 |
| WO | WO-2010/017500 A2 | 2/2010 |
| WO | WO-2015/053871 A2 | 4/2015 |
| WO | WO-2017189959 A1 * | 11/2017 ............. C07K 16/00 |
| WO | WO-2020/055768 A1 | 3/2020 |

OTHER PUBLICATIONS

Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Edwards et al.,J Mol Biol. Nov. 14, 2003;334(1): 103-18.*
Goel et al., J Immunol. Dec. 15, 2004; 173(12):7358-67.*
Llyod et al., Protein Eng Des Sel. Mar. 2009;22(3):159-68. doi: 10.1093/protein/gzn058. Epub Oct. 29, 2008.*
Kanyavuz et al., Nat Rev Immunol. Jun. 2019;19(6):355-368. doi: 10.1038/S41577-019-0126-7.*
Lescar, et al. Journal of Biological Chemistry 270.30 (1995): 18067-18076.*
Kirkegard et al., Am J Gastroenterol. Sep. 2017;112(9):1366-1372. doi: 10.1038/ajg.2017.218. Epub Aug. 1, 2017. PMID: 28762376.*
Walling et al., Prim Care. Dec. 2017;44(4):609-620. doi: 10.1016/j.pop.2017.07.004. Epub Oct. 5, 2017. PMID: 29132523.*
Aronica, A. et al., Unexpected distribution of CA19.9 and other type 1 chain Lewis antigens in normal and cancer tissues of colon and pancreas: Importance of the detection method and role of glycosyltransferase regulations // Biochimica et Biophysica Acta (BBA)—General Subjects.—2017,—vol. 1861.—No. 1.—p. 3210-3220 URL:https://www.sciencedirect.com/science/article/pii/s0304416516302860 (p. 3213, the left column, paragraph 3; p. 3219, the left column, the last paragraph—the right column paragraph 1).
Jakubke, H. D. et al., Amino acids, peptides, proteins, Mir, 456 sh. p. 9394 (1985). Non-English.
Mohamed, A. et al., Can Serum ICAM 1 distinguish pancreatic cancer from chronic pancreatis?, Asian Pacific Journal of Cancer Prevention, 17(10):4671-4675 (2016).
Mould, D. R. and Green, B., Pharmacokinetics and Pharmacodynamics of Monoclonal Antibodies. BioDrugs 24, 23-39 (2010).
Sawada, R. et al., Human monoclonal antibodies to sialyl-Lewis (CA19.9) with potent CDC, ADCC, and antitumor activity, Clin Cancer Res., 17(5):1024-32 (2011).
Scara S. et al., CA 19-9: biochemical and clinical aspects // Advances in Cancer Biomarkers: From Biochemistry to clinical for a critical revision.—2015. pp. 247-260.
Selezneva, A.I. et al., A complex approach to the study of pharmacological substances in vitro, ex vivo, in vivo, International Scientific and Research Journal 37(6):125-127 (2015). Non-English; English Abstract only.

(Continued)

*Primary Examiner* — Michael Szperka
(74) *Attorney, Agent, or Firm* — Choate, Hall & Stewart LLP; Brenda Herschbach Jarrell; Rolando Medina

(57) ABSTRACT

Provided herein is a method for preventing, treating, ameliorating, or managing pancreatitis in a subject in need thereof comprising administering to the subject a therapeutically effective amount of an antibody or functional fragment thereof that binds to CA19-9.

38 Claims, 123 Drawing Sheets

Specification includes a Sequence Listing.

(56) References Cited

OTHER PUBLICATIONS

Tyagi, R., and Gupta, N., Use of chemical modification and chemical crosslinking to stabilize proteins (enzymes), Biochemistry, 63(3):395-407 (1998).
International Search Report for PCT/US2019/050262 (Methods for Treating Pancreatitis, filed Sep. 9, 2019), received from ISA/US, 4 pages (Dec. 2, 2019).
Written Opinion for PCT/US2019/050262 (Methods for Treating Pancreatitis, filed Sep. 9, 2019), received from ISA/US, 7 pages (Dec. 2, 2019).
De Marchi, G. et al., Very high serum levels of CA 19-9 in autoimmune pancreatitis: Report of four cases and brief review of literature, Journal of Digestive Diseases, 17:697-702 (2016).
Engle, D. et al., The glycan CA19-9 promotes pancreatitis and pancreatic cancer in mice, Science, 364:1156-1162 (2019).
Habtezion, A. and Algul, H., Immune modulation in acute and chronic pancreatitis, Pancreapedia, 13 pages (2016).
Minghini, A. et al., Specificity of elevated CA 19-9 levels in chronic pancreatitis, Surgery, 124:103-105 (1998).
Teng, D. et al., Significant increased CA199 levels in acute pancreatitis patients predicts the presence of pancreatic cancer, Oncotarget, 9(16):12745-12753 (2018).
Akinosoglou, K. and Gogos, K., Immune-modulating therapy in acute pancreatitis: fact or fiction, World J Gastroenterol., 20(41):15200-15 (2014).

* cited by examiner

A

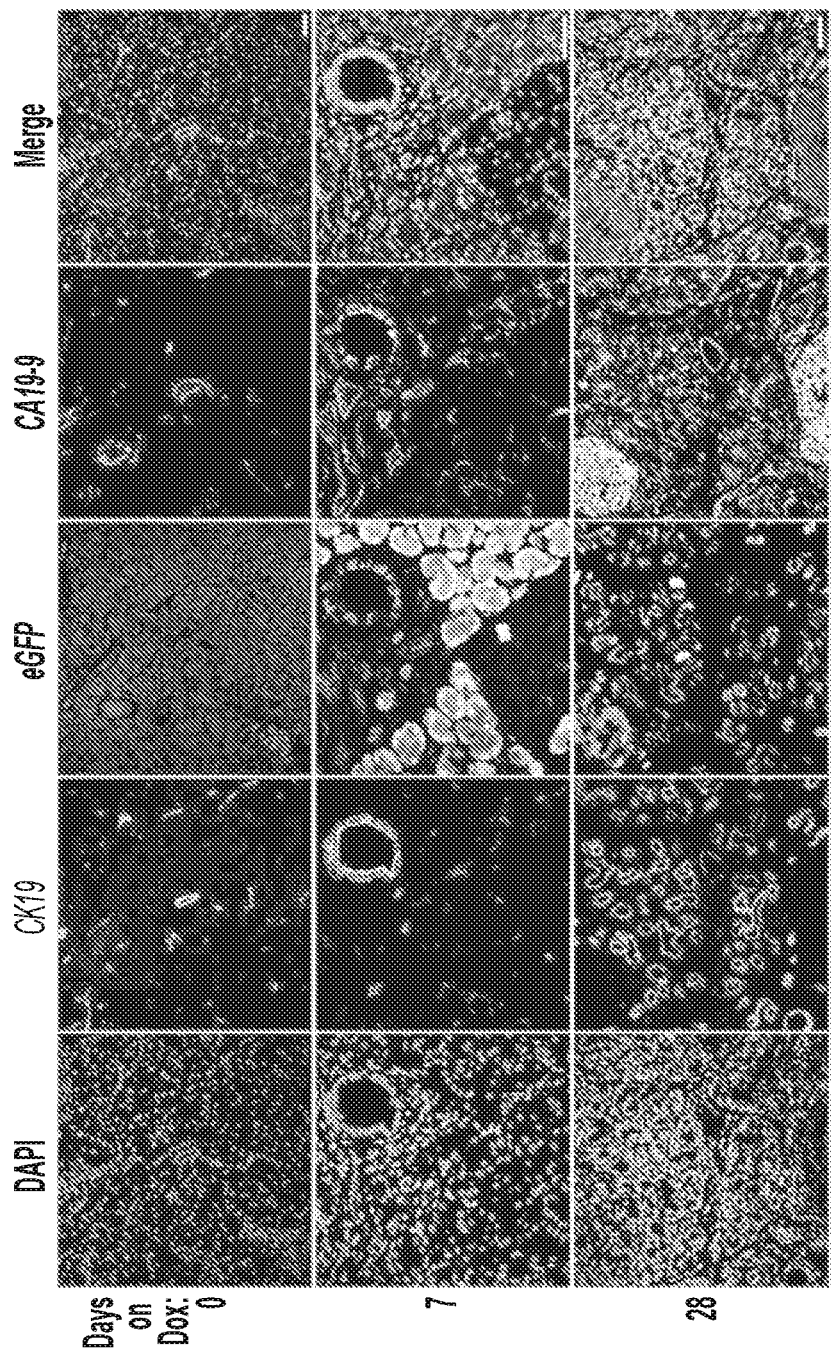

B

B

C

C

C

C

A

A

B

B

B

D

B

B

C

C

METHODS FOR TREATING PANCREATITIS

This application is the National Stage of International Application No. PCT/US2019/050262, filed Sep. 9, 2019, which claims the benefit of U.S. Provisional Application No. 62/729,354 filed Sep. 10, 2018, the content of each of which is hereby incorporated by reference herein in its entirety.

This invention was made with government support under CA045508, CA190092, CA148056, CA204725, and CA211506 awarded by the National Institutes of Health. The government has certain rights in the invention.

1. FIELD

Provided herein are methods for preventing and treating pancreatitis. Specifically, provided herein are methods for treating and/or preventing pancreatitis using molecules that bind to CA19-9.

2. SEQUENCE LISTING

This present specification makes reference to a Sequence Listing (submitted electronically as a .txt file named "2013237-0154_Sequence_Listing.txt" on Mar. 9, 2021). The .txt file was created on Sep. 10, 2018, and is 22,976 bytes in size. The entire contents of the Sequence Listing are hereby incorporated by reference.

3. BACKGROUND OF THE INVENTION

Pancreatitis results in 275,000 hospital admissions each year in the United States (Forsmark C E, et al., N Engl J Med. 2016; 375(20):1972-81). Pancreatitis includes chronic pancreatitis and acute pancreatitis and can be accompanied by severe abdominal pain. The mortality rate in patients having chronic pancreatitis is higher than that in the general population, with the 10-year survival after diagnosis estimated at between 69-80% (Seicean A. et al., J Gastrointestin Liver Dis. 2006; 15(1):21-6). As a result of complications and morbidity associated with chronic pancreatitis, patients with chronic pancreatitis have a life expectancy that is roughly 8 years shorter than that of the general population (Bang U C. et al., Gastroenterology. 2014; 146(4):989-94). In severe acute pancreatitis, the mortality rate can be as high as 16.3%, with more than 40% of the death occurring within 14 days of admission to hospital (Fu C. et al., World J Gastroenterol. 2007; 13(13): 1966-1969).

Despite the elevated mortality and significant morbidity associated with pancreatitis, there have been few advances in how this debilitating disease is treated. Before the present disclosure, acute pancreatitis is often treated with general supportive care that consists of intravenous hydration, with varying rate of fluid resuscitation as the foundation of care depending on the volume status of the patient (Chapter 37-Acute Pancreatitis, GI/Liver Secrets Plus, 4th edition, edited by McNally PR, 2010). The pain accompanying severe pancreatitis is managed simultaneously with intravenous analgesia (Chapter 37-Acute Pancreatitis, GI/Liver Secrets Plus, 4th edition, edited by McNally PR, 2010). Chronic pancreatitis is often only treated with medication to treat the pain or complications of pancreatitis, leaving the underlying chronic pancreatitis itself not directly treated (Chapter 38-Chronic Pancreatitis, GI/Liver Secrets Plus, 4th edition, edited by McNally PR, 2010).

There has been a lack of success in therapeutic agents developed so far to directly treat, prevent, manage, or ameliorate pancreatitis or target the mechanisms that underlying the development of pancreatitis. Thus there is need to identify a therapeutic agent that can treat, prevent, manage, or ameliorate pancreatitis including chronic and acute pancreatitis.

4. SUMMARY OF INVENTION

In one aspect, provided herein is a method for preventing, treating, ameliorating, or managing pancreatitis in a subject in need thereof comprising administering to the subject a therapeutically effective amount of an antibody or functional fragment thereof that binds to Sialyl-Lewis$^a$ (anti-sLe$^a$).

In another aspect, provided herein is a method for preventing, treating, ameliorating, or managing pancreatitis in a subject in need thereof comprising:
(1) administering to the subject at a first dose an antibody or functional fragment thereof that binds to Sialyl-Lewis$^a$ (anti-sLe$^a$),
(2) determining a severity of pancreatitis in said subject, and
(3) administering a second dose of the antibody or functional fragment thereof that binds to anti-sLe$^a$ at the same or lower amount than the first dose if the severity of pancreatitis in the subject is reduced in comparison to the severity of pancreatitis in the subject before administration of the anti-sLe$^a$, or administering a second dose of the anti-sLe$^a$ at a higher amount than the first dose if the severity of pancreatitis in the subject is not reduced.

In certain aspect, provided herein is a method for preventing, treating, ameliorating, or managing pancreatitis in a subject in need thereof comprising administering to the subject a therapeutically effective amount of a therapeutic agent that binds to a CA19-9.

In one aspect, provided herein is a method for preventing, treating, ameliorating, or managing pancreatitis in a subject in need thereof comprising:
(1) administering to the subject at a first dose a therapeutic agent that binds to a CA19-9,
(2) determining a severity of pancreatitis in said subject, and
(3) administering a second dose of the therapeutic agent at the same or lower amount than the first dose if the severity of pancreatitis in the subject is reduced in comparison to the severity of pancreatitis in the subject before administration of the agent, or administering a second dose of the therapeutic agent at a higher amount than the first dose if the severity of pancreatitis in the subject is not reduced.

In some embodiments of the methods provided herein, the anti-sLe$^a$ antibody or functional fragment thereof comprises a variable heavy chain (VH) domain, said VH domain comprising an amino acid sequence selected from the group consisting of residues 20-142 of SEQ ID NO: 2, residues 20-142 of SEQ ID NO: 6, residues 20-142 of SEQ ID NO: 10, and residues 20-145 of SEQ ID NO: 14.

In certain embodiments of the methods provided herein, the anti-sLe$^a$ antibody or functional fragment thereof comprises a variable light chain (VL) domain, said VL domain comprising an amino acid sequence selected from the group consisting of residues 20-130 of SEQ ID NO: 4, residues 20-129 of SEQ ID NO: 8, residues 20-130 of SEQ ID NO: 12, and residues 23-130 of SEQ ID NO: 16.

In other embodiments of the methods provided herein, the anti-sLe$^a$ antibody or functional fragment thereof comprises a variable heavy chain (VH) domain and a variable light chain (VL) domain, where said VH domain and said VL domain respectively comprise an amino acid sequence selected from the group consisting of residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; and residues 20-145 of SEQ ID NO: 14 and residues 23-130 of SEQ ID NO: 16.

In some embodiments of the methods provided herein, the anti-sLe$^a$ antibody or functional fragment thereof comprises a heavy chain variable region comprising three complementarity determining regions (CDRs) having the amino acid sequence of the three heavy chain variable region CDRs according to Kabat numbering of an antibody produced by a hybridoma deposited under American Type Culture Collection (ATCC) Accession No. HB-8059, and a light chain variable region comprising three CDRs having the amino acid sequence of the three light chain variable region CDRs according to Kabat numbering of an antibody produced by a hybridoma deposited under ATCC Accession No. HB-8059.

In certain embodiments of the methods provided herein, the anti-sLe$^a$ antibody or functional fragment thereof comprises a heavy chain variable region consisting of the amino acid sequence of the heavy chain variable region of an antibody produced by a hybridoma deposited under American Type Culture Collection (ATCC) Accession No. HB-8059, and a light chain variable region consisting of the amino acid sequence of the light chain variable region of an antibody produced by a hybridoma deposited under ATCC Accession No. HB-8059.

In other embodiments of the methods provided herein, the anti-sLe$^a$ antibody or functional fragment thereof comprises a heavy chain consisting of the amino acid sequence of the heavy chain of an antibody produced by a hybridoma deposited under ATCC. Accession No. HB-8059, and a light chain consisting of the amino acid sequence of the light chain of an antibody produced by a hybridoma deposited under ATCC. Accession No. HB-8059.

In some embodiments of the methods provided herein, the anti-sLe$^a$ antibody functional fragment is selected from the group consisting of a Fab, a Fab', a F(ab')$_2$, a scFV, a diabody, a triabody, a minibody and a single-domain antibody (sdAB). In certain embodiments, the anti-sLe$^a$ antibody or functional fragment thereof is a diabody. In further embodiments, the diabody comprises the amino acid sequence of SEQ ID NO: 18 or 20.

In certain embodiments of the methods provided herein, the anti-sLe$^a$ antibody or functional fragment thereof is a monoclonal antibody. In some embodiments of the methods provided herein, the anti-sLe$^a$ antibody or functional fragment thereof is an IgG or IgM isotype. In certain embodiments, the IgG antibody is an IgG1, IgG2, IgG3, or IgG4 subclass.

In some embodiments of the methods provided herein, the anti-sLe$^a$ antibody or functional fragment thereof is formulated as a pharmaceutical composition comprising a pharmaceutically acceptable carrier. In certain embodiments, the antibody or functional fragment thereof is administered to a subject by a parenteral route of administration. In some embodiments, the parenteral administration is selected from a group consisting of subcutaneous injection, intramuscular injection, and intravenous injection.

In some embodiments of the methods provided herein, the antibody or functional fragment thereof is administered to a subject at a dose range from about 0.1 mg/kg/dose to about 10 mg/kg/dose. In certain embodiments, the antibody or functional fragment thereof is administered to a subject weekly, bi-weekly, monthly, or bi-monthly. In some embodiments, the antibody or functional fragment thereof is administered for about one, two, three, four, five, or six months.

In certain embodiments of the methods provided herein, the therapeutic agent is an antibody or functional fragment thereof that binds to Sialyl-Lewis$^a$ (anti-sLe$^a$).

In some embodiments of the methods provided herein, the therapeutic agent is a peptide or peptidomimetic molecule. In certain embodiments, the peptide or peptidomimetic has the property of specifically binding to Sialyl-Lewis$^a$.

In certain embodiments of the methods provided herein, the pancreatitis is characterized by one or more markers. In some embodiments of the methods provided herein, the severity of the pancreatitis is determined by one or more markers. In certain embodiments of the methods provided herein, the subject has elevated levels of one or more markers for pancreatitis. In some embodiments of the methods provided herein, the administering of the therapeutic agent results in reduced levels of one or more markers for pancreatitis in the subject. In certain embodiments, the one or more markers are selected from a group consisting of a physiological marker, a histological marker, a serological marker, and a signaling marker. In some embodiments, the histological marker is selected from a group consisting of immune cell invasion, collagen deposition, fibrotic tissue, fat necrosis, interstitial edema, acinar and blood vessel destruction, interstitial hemorrhage, ductal dilation, acinar cell homogenization, and expression level of CA19-9. In certain embodiments, the one or more markers comprise expression level of CA19-9. In other embodiments, the one or more markers are determined by immunohistochemistry. In certain embodiments, the serological marker is selected from a group consisting of serum lipase level, serum amylase level, and serum C reactive protein level. In some embodiments, the one or more markers is a serum lipase level over 200 U/L. In certain embodiments, the one or more markers is a serum amylase level over 200 U/L. In some embodiments, the one or more markers is a serum amylase level three times over the upper limit of normal serum amylase level of a control subject. In certain embodiments, the one or more markers is a serum lipase level three times over the upper limit of normal serum lipase level of a control subject. In some embodiments, the physiological marker is selected from a group consisting of weight loss, malabsorption of food, pancreatic atrophy, pancreatic enlargement, pancreatic inflammation, and bile reflux.

In one aspect, provided herein is a method for preventing, treating, ameliorating, or managing pancreatitis in a subject having elevated pancreatic sLe$^a$, said method comprising administering to the subject a therapeutically effective amount of a therapeutic agent that specifically binds to sLe$^a$.

In certain embodiments of the methods provided herein, the pancreatitis is a pancreatitis selected from a group consisting of chronic pancreatitis and acute pancreatitis. In some embodiments, the chronic pancreatitis is selected from a group consisting of mild chronic pancreatitis, moderate chronic pancreatitis, and severe chronic pancreatitis. In certain embodiments, the acute pancreatitis is selected from a group consisting of mild acute pancreatitis, moderate acute pancreatitis, and severe acute pancreatitis.

In some embodiments of the methods provided herein, the subject is a mammal. In certain embodiments of the methods provided herein, the mammal is a human.

5. BRIEF DESCRIPTION OF THE DRAWINGS

FIG. 1A shows the percentage of human chronic pancreatitis patients exhibiting high levels of pancreatic tissue CA19-9 (left panel), and representative immunohistochemistry (IHC) showing CA19-9 predominantly in pancreatic ducts (right two panels, indicated by open arrows). FIG. 1B shows example CA19-9 IHC from excluded (left), CA19-9 high (middle), and CA19-9 low/negative (right) human chronic pancreatitis specimens. Scale bars=100 µm. FIG. 1C shows schematic representation of Lewis antigen production. FIG. 1D shows that ectopic FUT3 induces Lewis' (Lex) but not CA19-9/Sialyl-Lewis$^a$ (SLe$^a$) expression in mouse pancreatic ductal adenocarcinoma (PDAC) cells by flow cytometric analysis. FIG. 1E shows CA19-9 flow cytometry of mouse PDAC cells stably and constitutively expressing FUT3 with β3GALT5 compared to parental KPC cell controls. The expression of both FUT3 and β3GALT5 led to the cell surface expression of CA19-9 at levels equivalent to those observed in a human cancer cell line (Colo205). FIG. 1F shows CA19-9 immunofluorescent evaluation of the human PDAC cell line Suit2 (top panels) and mouse PDAC cells (bottom panels) stably and constitutively expressing FUT3 and β3GALT5 or PDAC cells expressing empty vector control. Scale bars=25 µm. FIG. 1G shows circulating CA19-9 levels in nude mice transplanted with the CA19-9 negative human PDAC cell line MiaPaCa2, the CA19-9 positive human PDAC cell line Suit2, the mouse PDAC cell lines transfected with empty vector control, and the mouse PDAC cells stably and constitutively expressing FUT3 and β3GALT5.

FIG. 2A shows immunoprecipitation/mass spectrometry (IP/MS) strategy for mouse PDAC cells stably and constitutively expressing FUT3 and β3GALT5 (left panel), immunoblot validation of CA19-9 IP efficiency (middle panel), and overlap of CA19-9 protein carriers between three biological replicate lines (FC1199, FC1242, and FC1245) (right panel). FIG. 2B shows IP/MS strategy for human PDAC cells (left panel), immunoblot validation of CA19-9 IP efficiency (middle panel), and overlap of CA19-9 protein carriers between three biological replicate lines (Capan2, hM1-2D, and Suit2) (right panel). FIG. 2C shows overlap between CA19-9 protein carriers identified in 3 out of 3 human PDAC cell lines (n=936) with three independent mouse PDAC cell lines expressing FUT3 and β3GALT5.

FIGS. 3A-3D show CA19-9 genetically engineered mouse model design, validation, and generation. FIG. 3A shows schematic representation of inducible CA19-9 mouse models. FIG. 3B shows immuno-slot blot confirmation of CA19-9 production in mES cell clones following Cre transfection and Dox treatment. FIG. 3C show southern blot for eGFP in positive control wildtype mES cell gDNA with targeting vector spiked in at 1-5 copies per genome and in mES cell targeted clones. The correct integration size is 5.548 kb (non-targeted=4.04 kb). FIG. 3D show eGFP qPCR copy number evaluation of the targeted mES cell clones relative to a previously validated targeted mES cell clone harboring a single and correct integration of the ColA1 targeting vector (P12).

Figure 25:
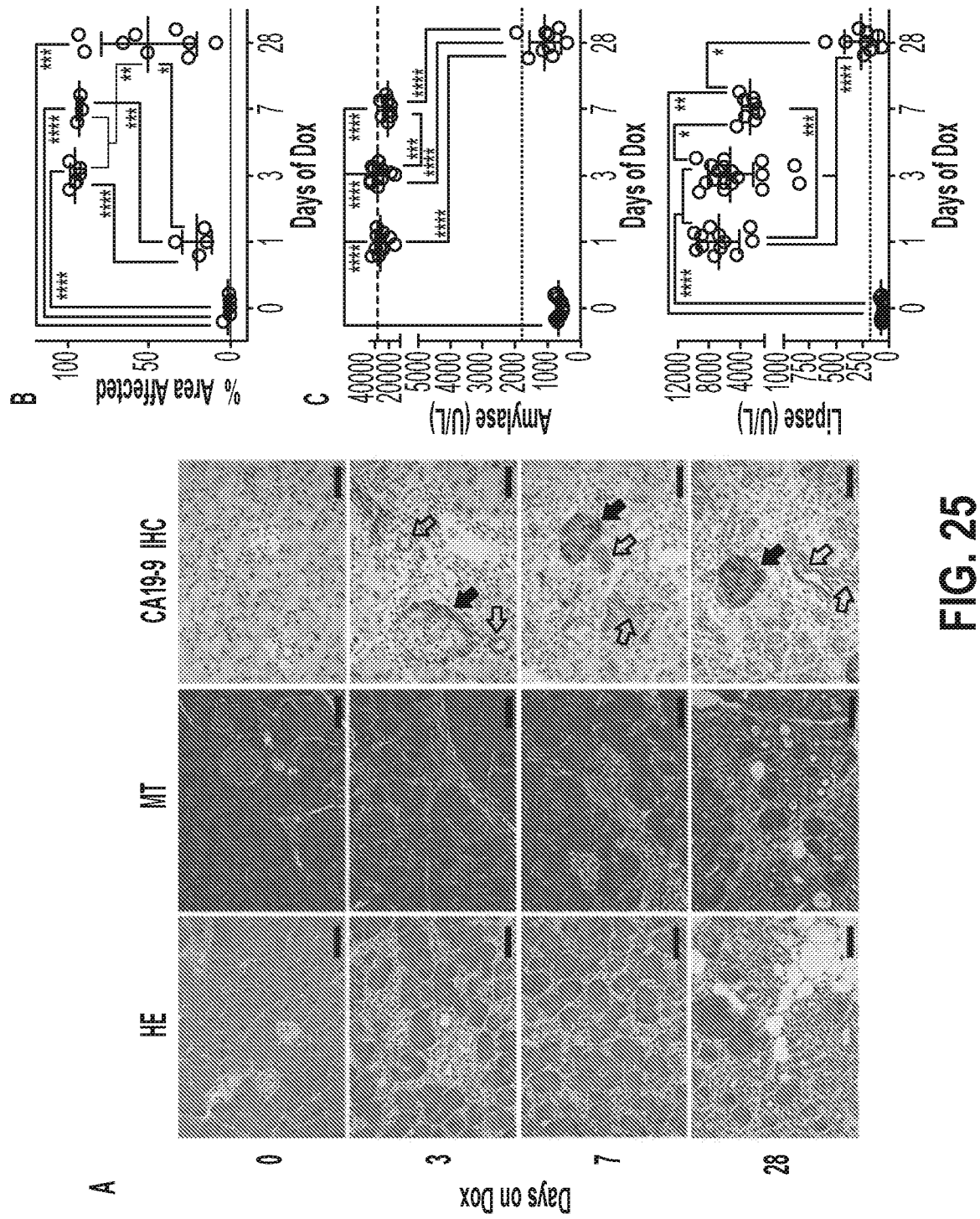

FIG. 25A shows histologic evaluation of $C^{PDX};R^{LSL};F$ pancreata by H&E staining, Masson's trichrome staining (MT, blue indicates collagen deposition) and CA19-9 expression (open arrow, CA19-9+ duct; closed arrow, CA19-9+ islet) by IHC following treatment with Dox. Scale bars=50 µm. FIG. 25B shows quantification of the percentage pancreatic area exhibiting histologic signs of pancreatitis following treatment of $C^{PDX};R^{LSL};F$ mice with Dox. n=5, 4, 5, 3, 9, respectively (F $(4,21)=22.46$, $p<0.0001$). FIG. 25C shows circulating levels of amylase (F $(5,61)=74.44$, $p<0.0001$) and lipase (F $(5,61)=27.59$, $p<0.0001$) (U/L) following treatment of $C^{PDX};R^{LSL};F$ mice with Dox. The dotted line indicates the threshold elevation required for the diagnosis of pancreatitis. The dashed line indicates the maximum level of detection. n=14, 12, 19, 8, and 9, respectively. Middle horizontal red lines represent the mean and error bars represent the standard deviation; each data point represents a measurement from an individual mouse. $*p<0.05$, $p<0.01$, $*p<0.001$, $****p<0.0001$ for multiple comparisons using Holm-Sidak's procedure following a one-way ANOVA.

Figure 26:
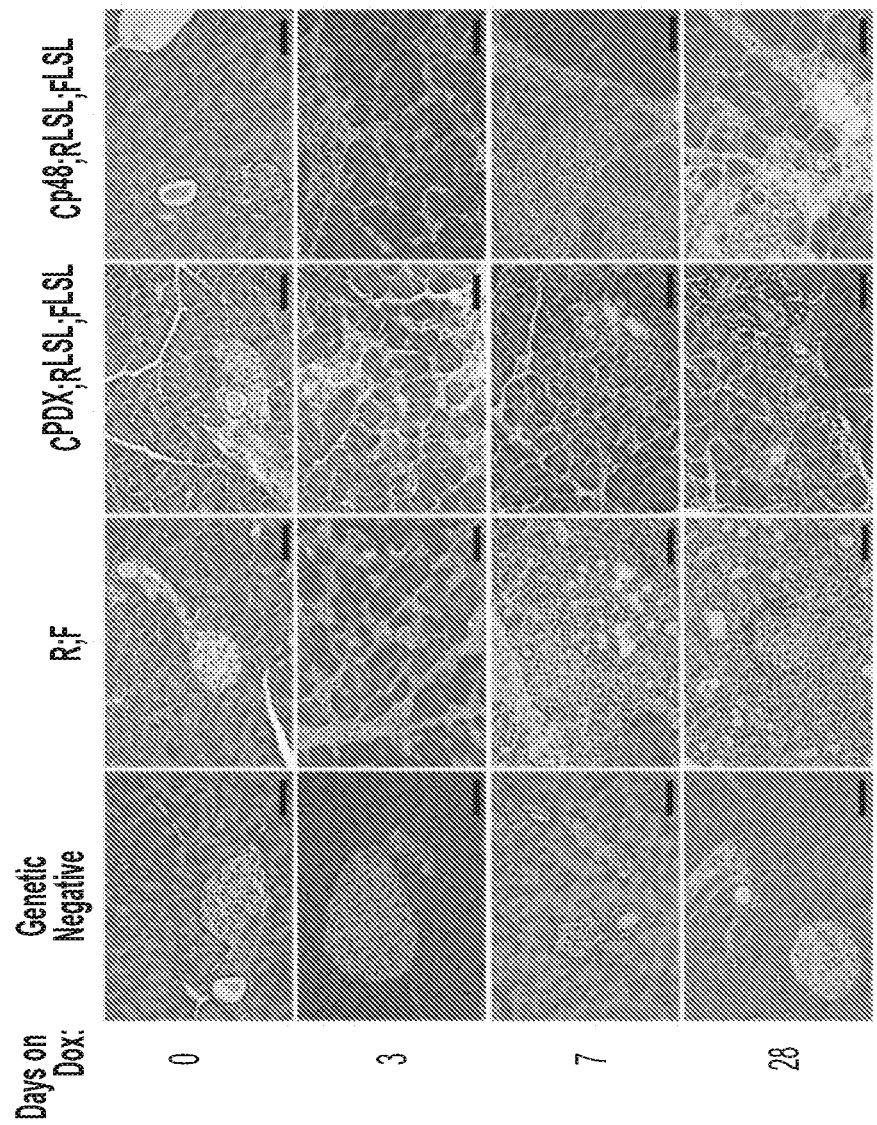

FIG. 26 shows mouse model comparison of pancreatitis severity using H&E histological evaluation of mouse pancreata from genetically negative control littermates, R;F, $C^{PDX};R^{LSL};F^{LSL}$ or $C^{p48};R^{LSL};F^{LSL}$ mice treated with Dox. Scale bars=50 µm.

Figure 27:
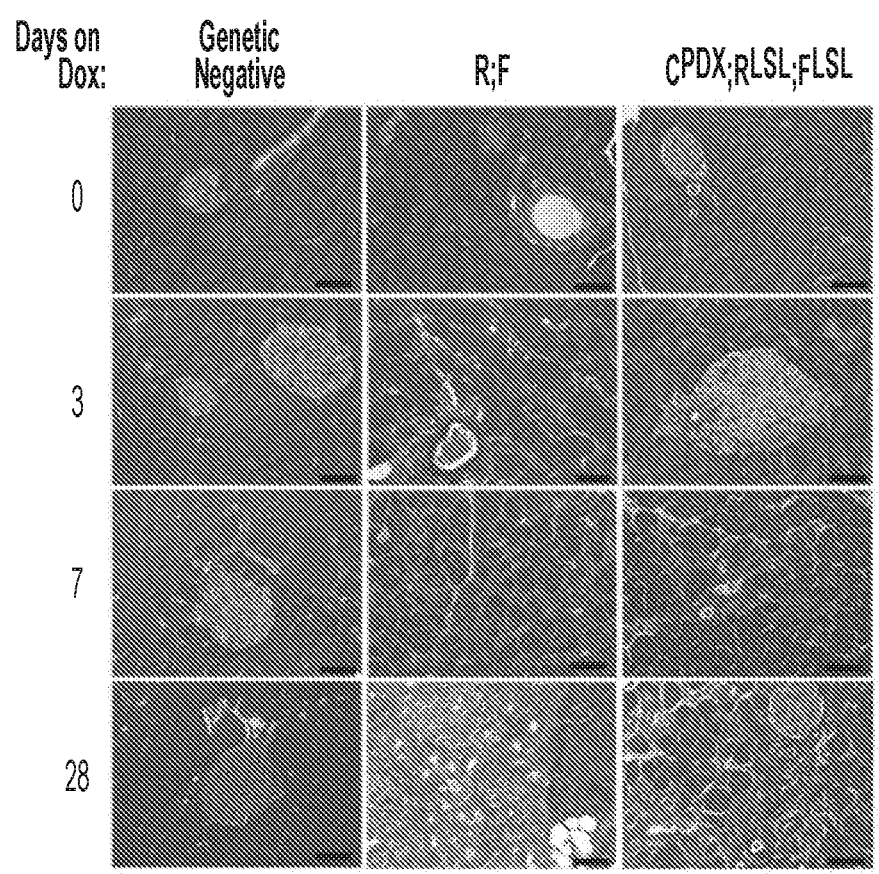

FIG. 27 shows mouse model comparison for stromal abundance using Masson's trichrome staining (blue, collagen deposition) of mouse pancreata from genetically negative control littermates, R;F or $C^{PDX};R^{LSL};F^{LSL}$ mice treated with Dox. Scale bars=50 µm.

Figure 28:
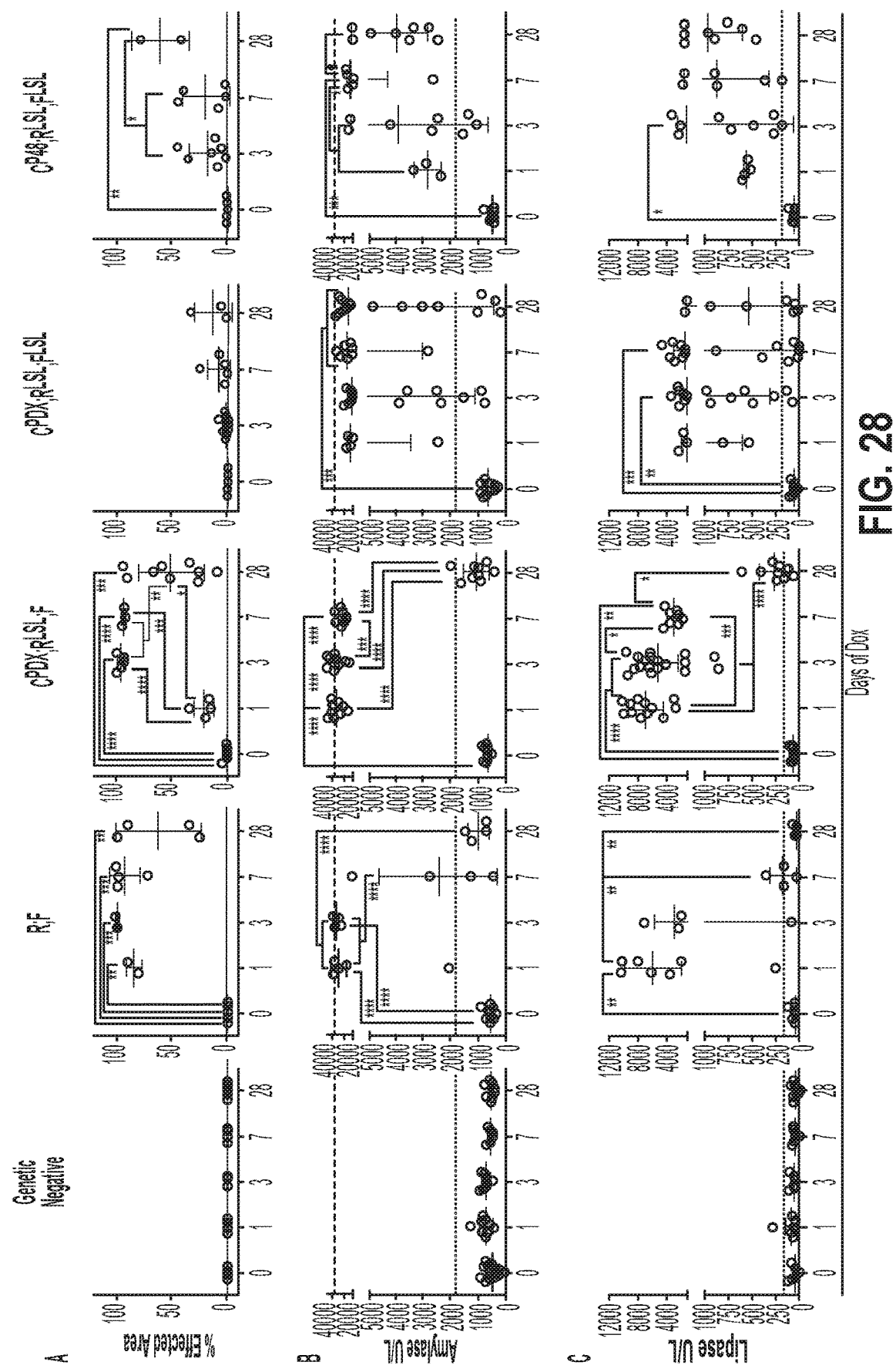

FIGS. 28A-28C show mouse model comparison of pancreatitis severity in genetically engineered mice. Genetically negative control littermates, R;F, $C^{PDX};R^{LSL};F^{LSL}$ or $C^{p48};R^{LSL};F^{LSL}$ mice treated with Dox (Days). Data for the $C;R^{LSL};F$ model from FIGS. 25B-25C is included for relative comparison. FIG. 28A shows percentage pancreatic area affected with histological signs of pancreatitis (F $(4,22)=0.5589$; $(4,12)=16.02$; $(4,21)=22.46$; $(3,19)=2.705$). FIGS. 28B-28C show circulating levels (U/L) of the pancreatic enzymes amylase (B) (F $(4, 71)=8.828$; $(4,22)=25.07$; $(5,61)= 74.44$; $(4, 58)=6.343$) and lipase (C) (F $(4,71)=2.967$; $(4,22)=7.108$; $5,61)=27.59$; $(4,58)=5.637$) following treatment with Dox (Days). The dotted line indicates the threshold elevation required for the diagnosis of pancreatitis. The dashed line indicates the maximum level of detection possible for amylase. Lines represent the mean; each data point represents a measurement from an individual mouse. $*p<0.05$, $p<0.01$, $*p<0.001$, $****p<0.0001$ using one-way ANOVA with multiple comparisons.

Figure 29A:
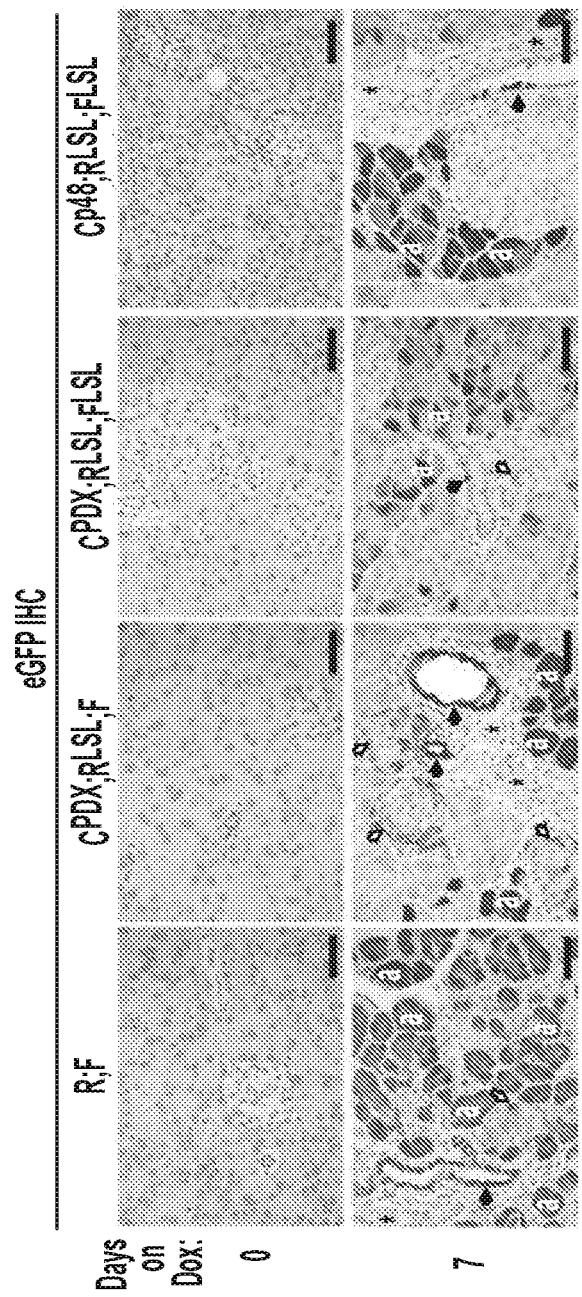
Figure 29B:
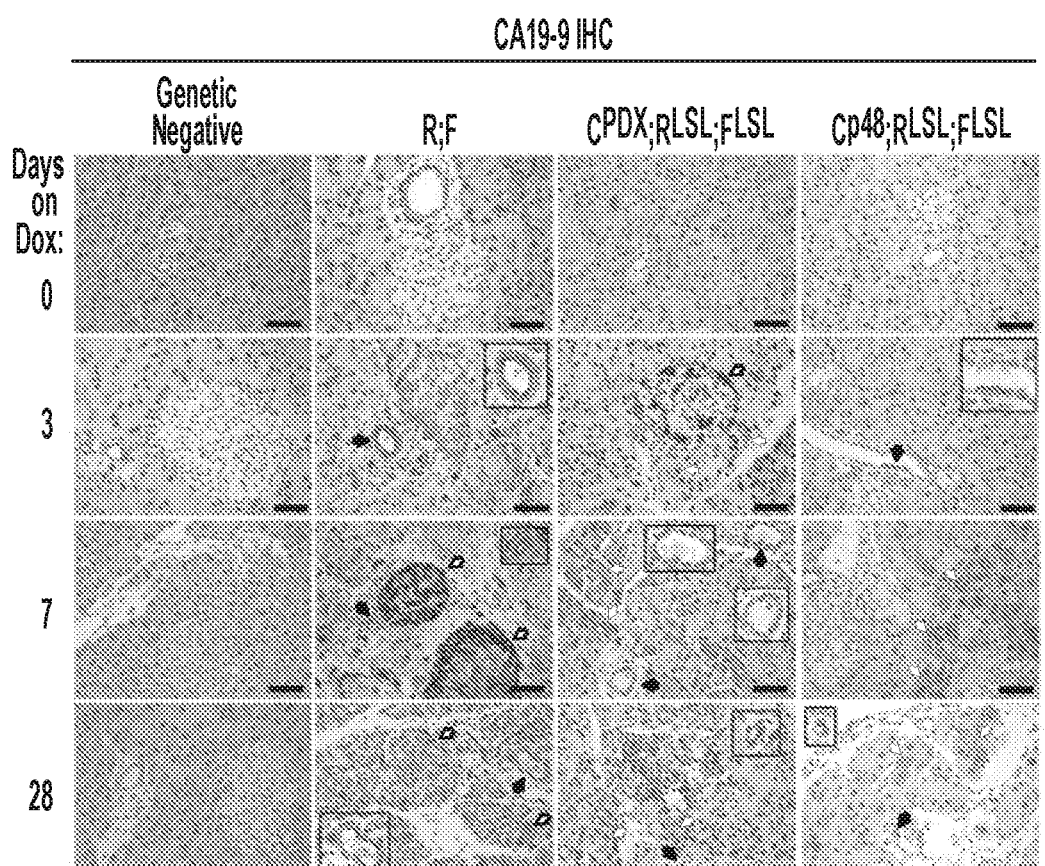

FIGS. 29A-29B show IHC for eGFP and CA19-9 in the pancreata of each CA19-9 mouse model. FIG. 29A shows eGFP IHC of mouse pancreata from R;F, $C^{PDX};R^{LSL};F$, $C^{PDX};R^{LSL};F^{LSL}$ or $C^{p48};R^{LSL};F^{LSL}$ mice treated with Dox for 0 or 7 days. Open arrows indicate positive islet cells, closed arrows indicate positive ducts, * indicates negative vessels and "a" indicates positive acinar cells. Scale bars=50 µm. FIG. 29B shows CA19-9 IHC of mouse pancreata from genetically negative control littermates, R;F, $C^{PDX};R^{LSL};F^{LSL}$ or $C^{p48};R^{LSL};F^{LSL}$ mice treated with Dox. Open arrows indicate positive islet cells, closed arrows indicate positive ducts, orange arrows indicate positive acinar cells. Inset show magnification of positive ducts indicated by closed arrows. Scale bars=50 µm.

Figure 30B:
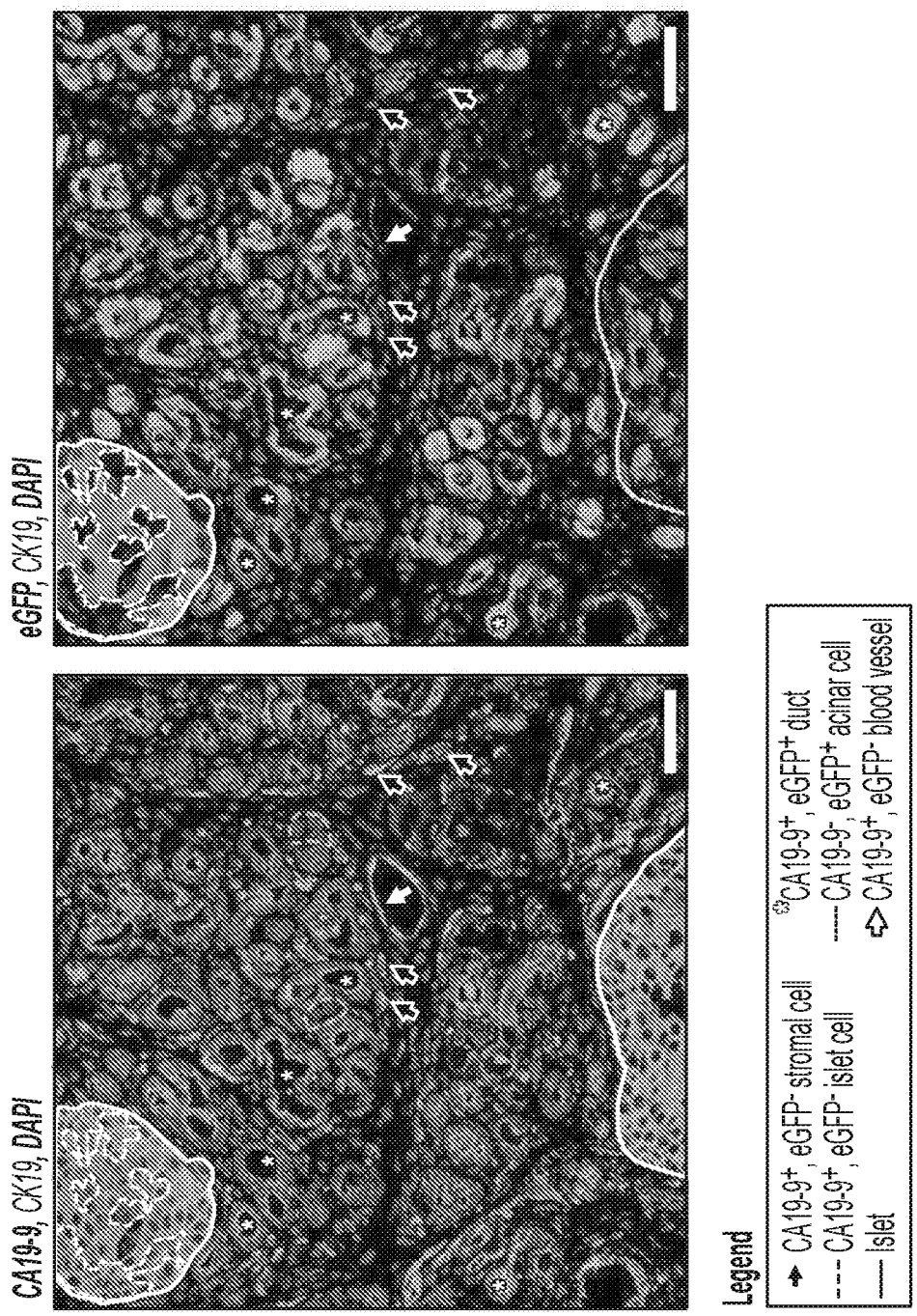

FIGS. 30A-30B show pancreatic lineage immunofluorescence (IF) of the whole body, R;F CA19-9 mouse model. FIG. 30A shows IF of the ductal marker, CK19, as well as eGFP (Dox-dependent recombination marker), DAPI, and CA19-9 in mouse pancreata from R;F mice treated with Dox for 0, 7 or 28 days. FIG. 30B shows annotated IF image from A. Scale bars=50 µm.

Figure 31:
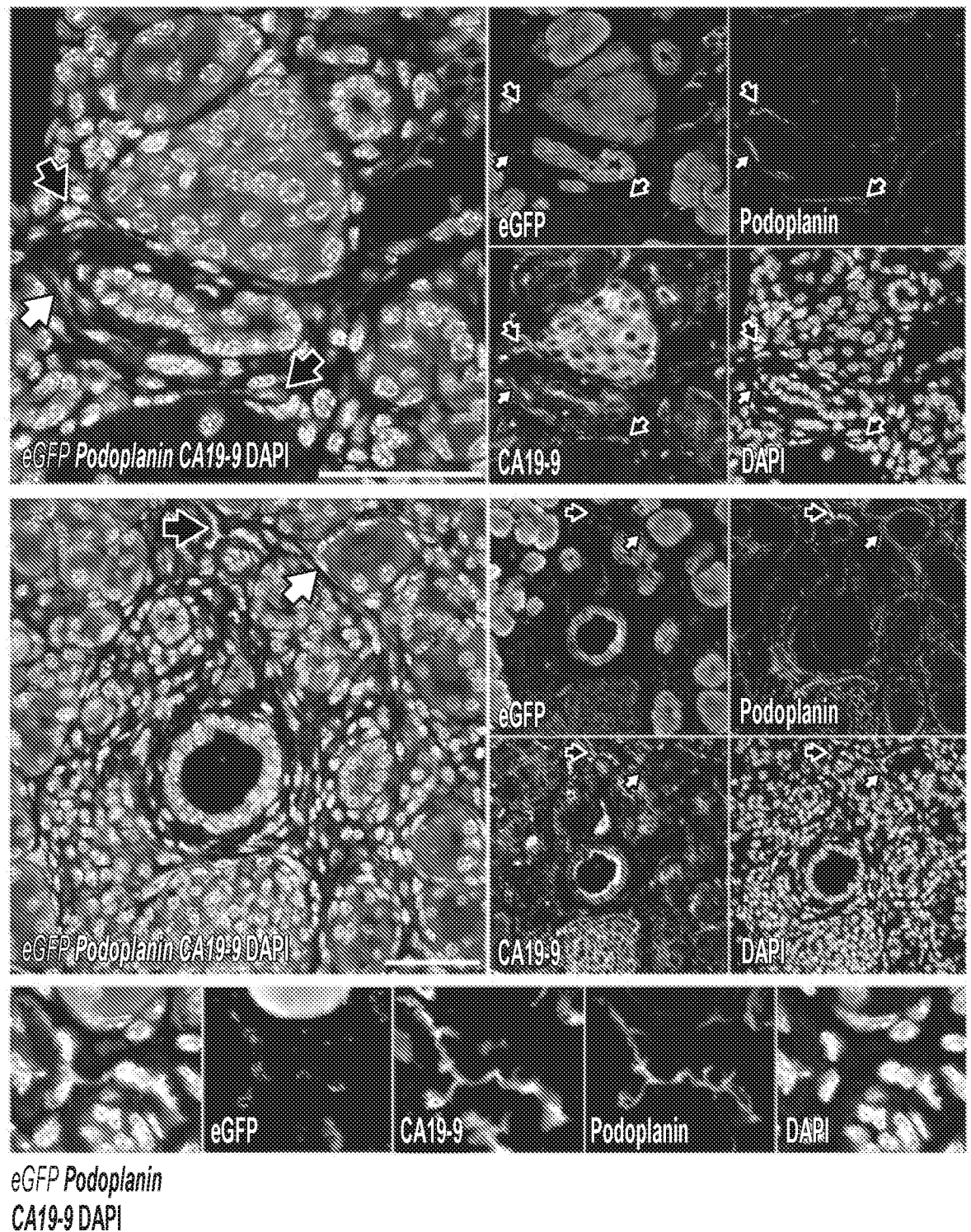

FIG. 31 shows pancreatic lineage immunofluorescence (IF) of the whole body, R;F CA19-9 mouse model. IF of the fibroblast marker, Podoplanin, as well as eGFP (Dox-dependent recombination marker), DAPI, and CA19-9 in mouse pancreata from R;F mice treated with Dox for 28 days. CA19-9+, Podoplanin+, eGFP-cells are indicated with an open pink arrow. CA19-9-, Podoplanin+, eGFP-cells are indicated by a closed red arrow. Scale bars=50 µm.

Figure 32:
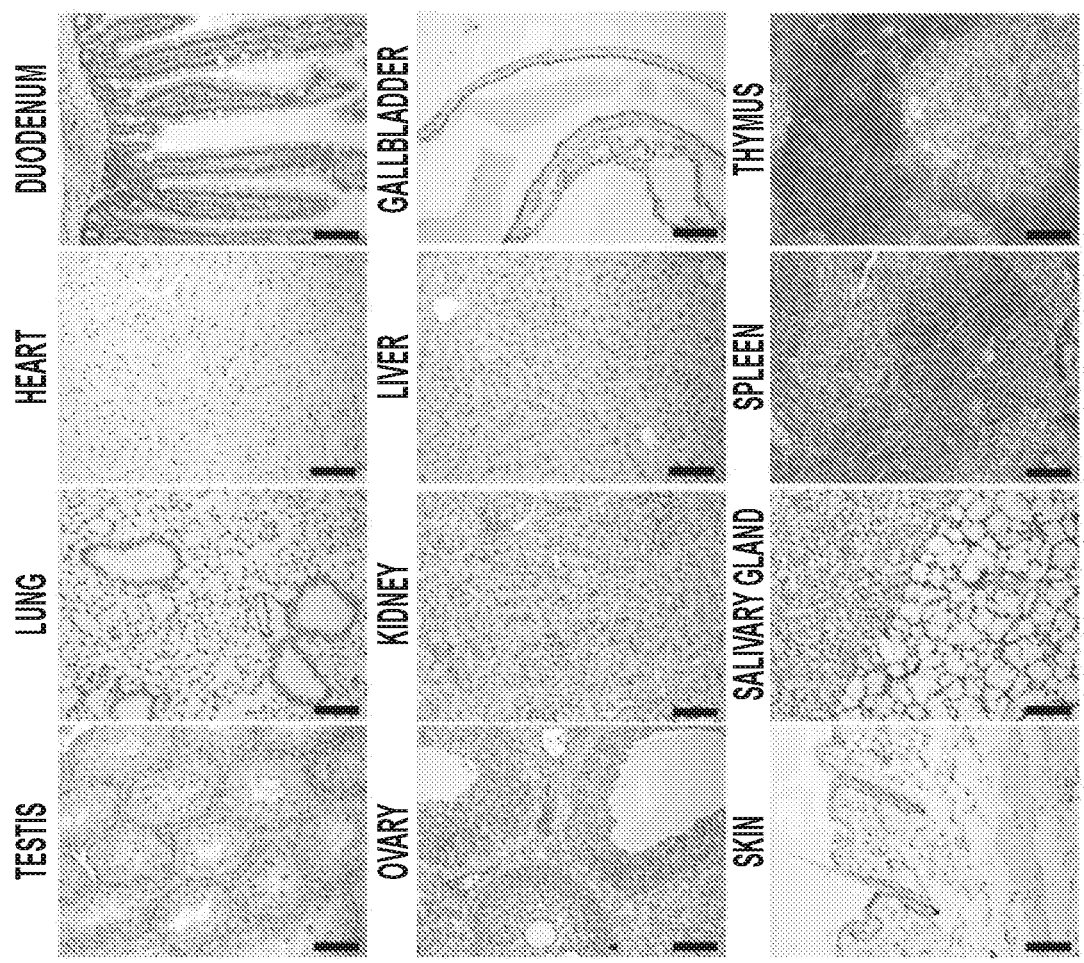

FIG. 32 shows whole body CA19-9 mouse model: eGFP expression in non-pancreatic tissues. eGFP IHC of mouse tissues from untreated R;F is shown. Scale bars=100 m.

Figure 33:
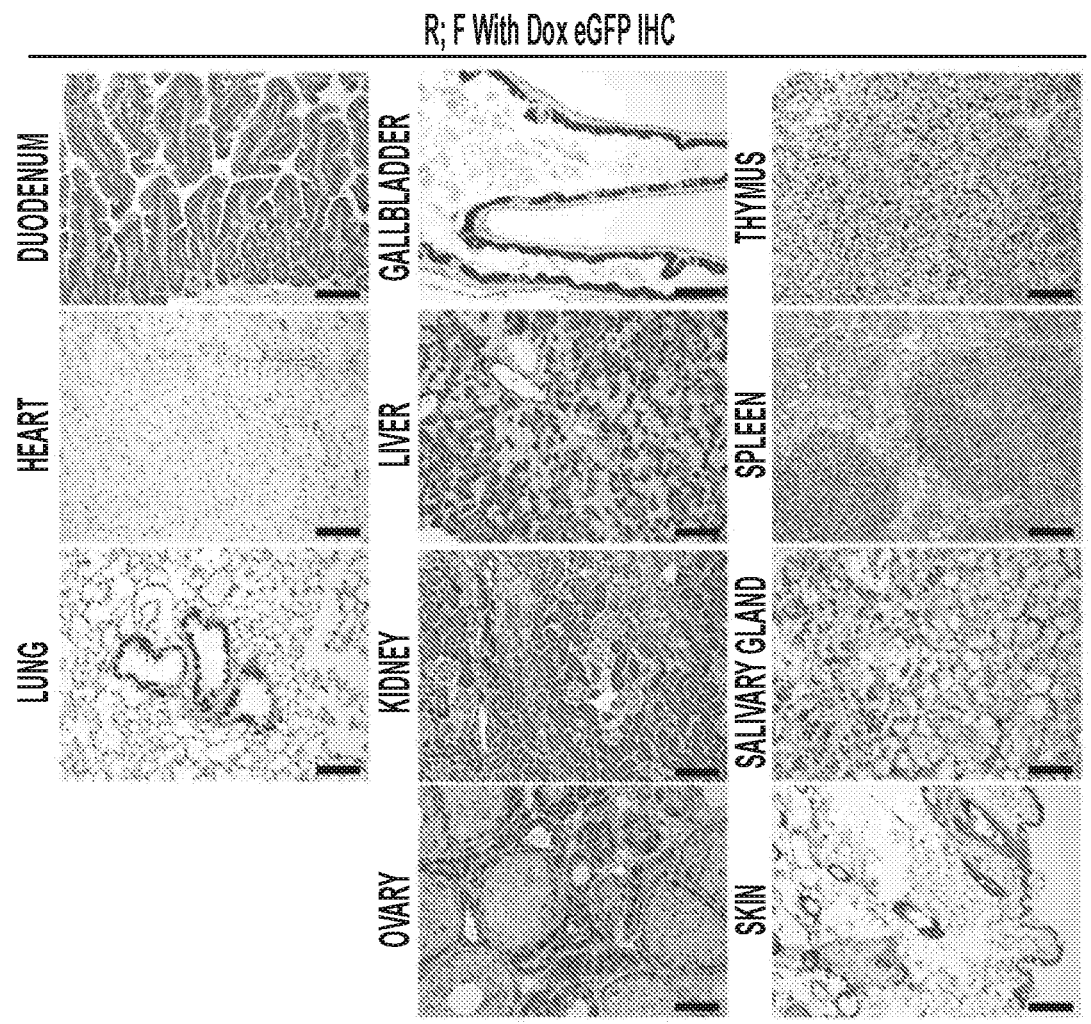

FIG. 33 shows whole body CA19-9 mouse model: eGFP expression in non-pancreatic tissues. eGFP IHC of mouse tissues from R;F mice treated with Dox is shown. Scale bars=100 µm.

Figure 34:
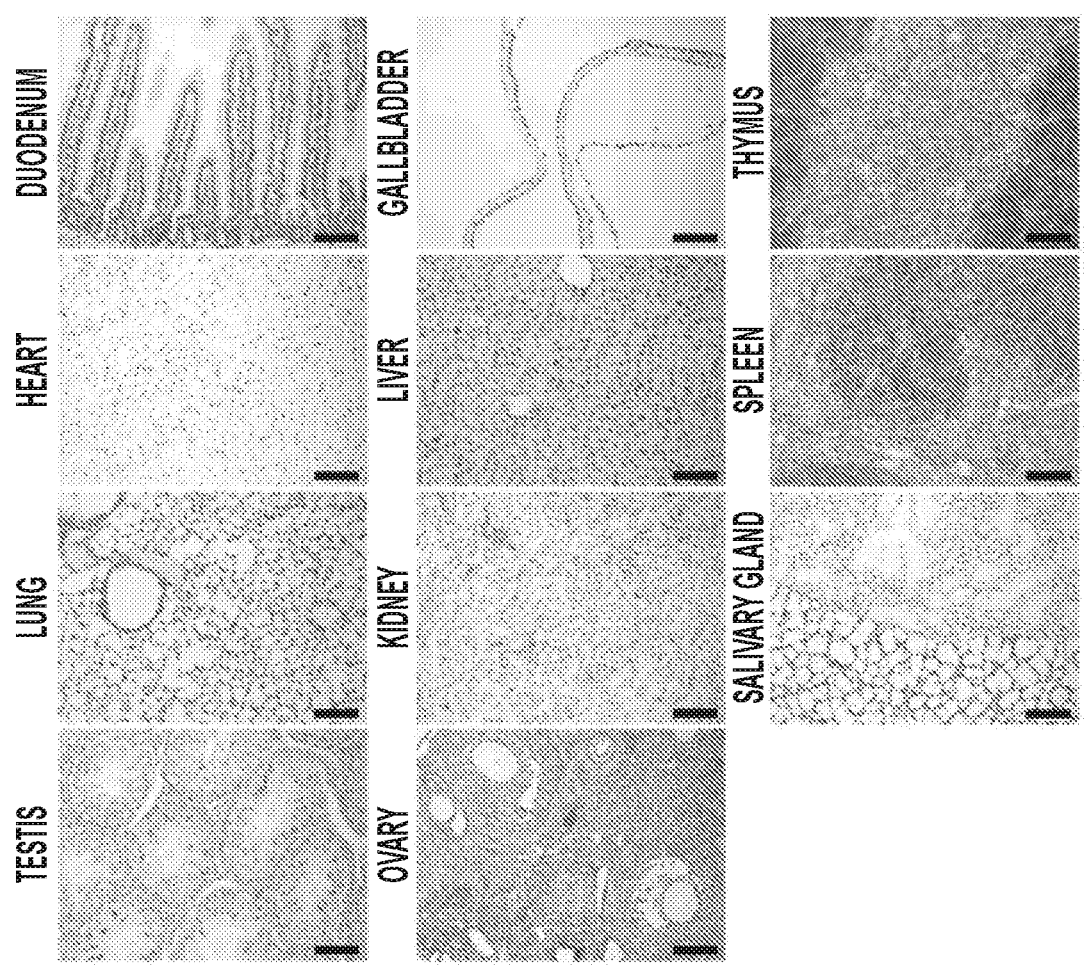

FIG. 34 shows whole pancreas CA19-9 mouse model: eGFP expression in non-pancreatic tissues. eGFP IHC of mouse tissues from untreated $C^{PDX};R^{LSL};F$ mice is shown. Scale bars=100 µm.

Figure 35:
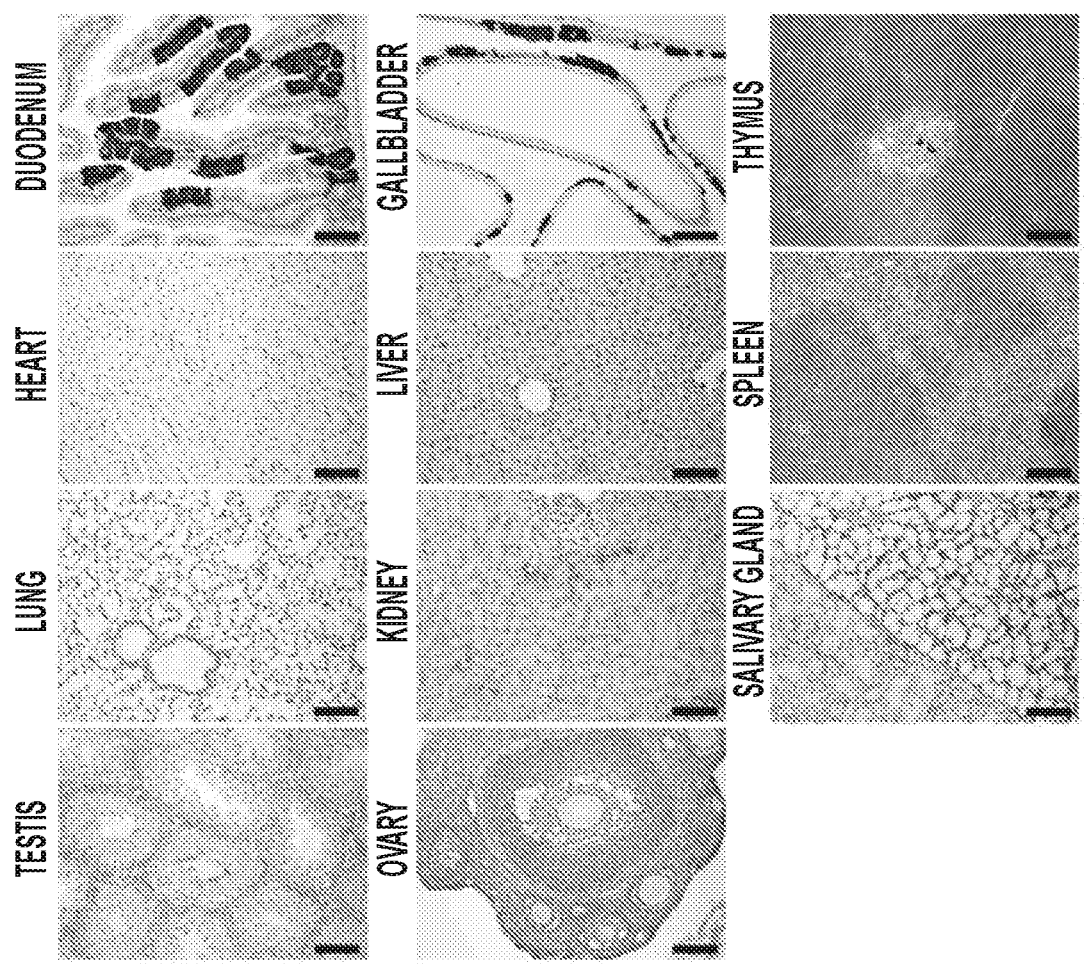

FIG. 35 shows whole pancreas CA19-9 mouse model: eGFP expression in non-pancreatic tissues. eGFP IHC of mouse tissues from $C^{PDX};R^{LSL};F$ mice treated with Dox is shown. Scale bars=100 µm.

Figure 36:
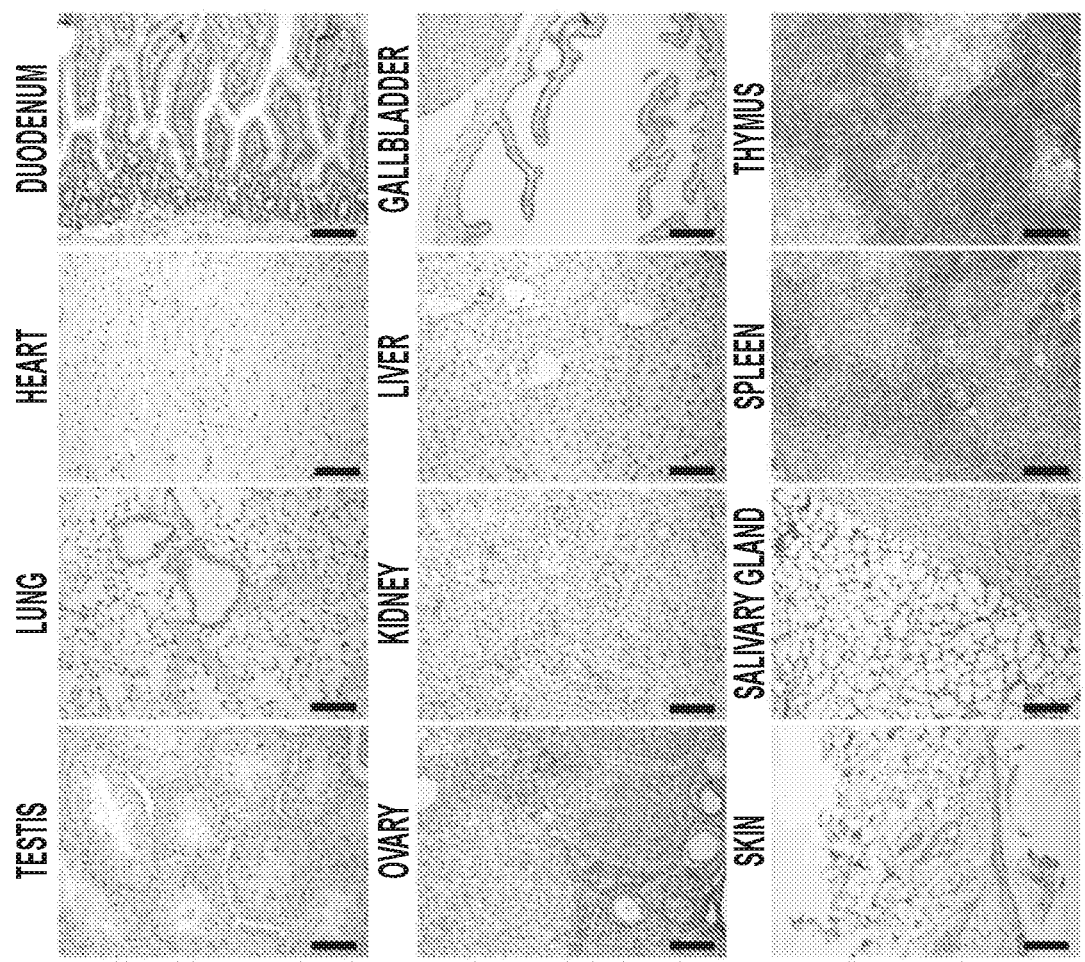

FIG. 36 shows focal pancreas, PDX1-Cre driven CA19-9 mouse model: eGFP expression in non-pancreatic tissues. eGFP IHC of mouse tissues from untreated $C^{PDX};R^{LSL};F^{LSL}$ mice is shown. Scale bars=100 µm.

Figure 37:
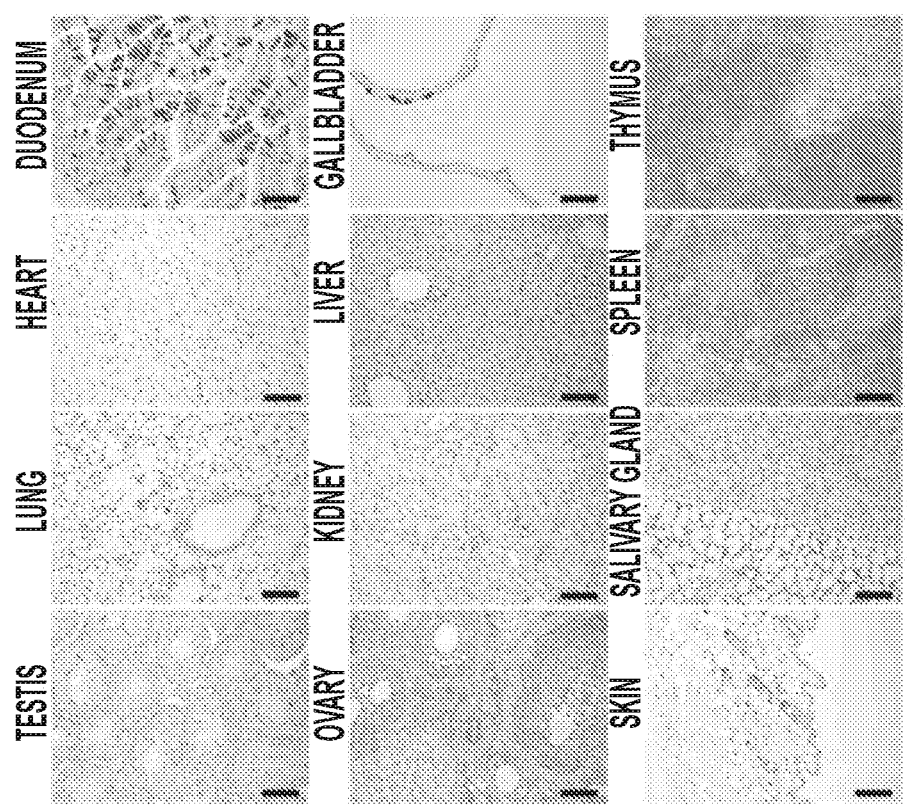

FIG. 37 shows focal pancreas, PDX1-Cre driven CA19-9 mouse model: eGFP expression in non-pancreatic tissues. eGFP IHC of mouse tissues from $C^{PDX};R^{LSL};F^{LSL}$ mice treated with Dox is shown. Scale bars=100 µm.

Figure 38:
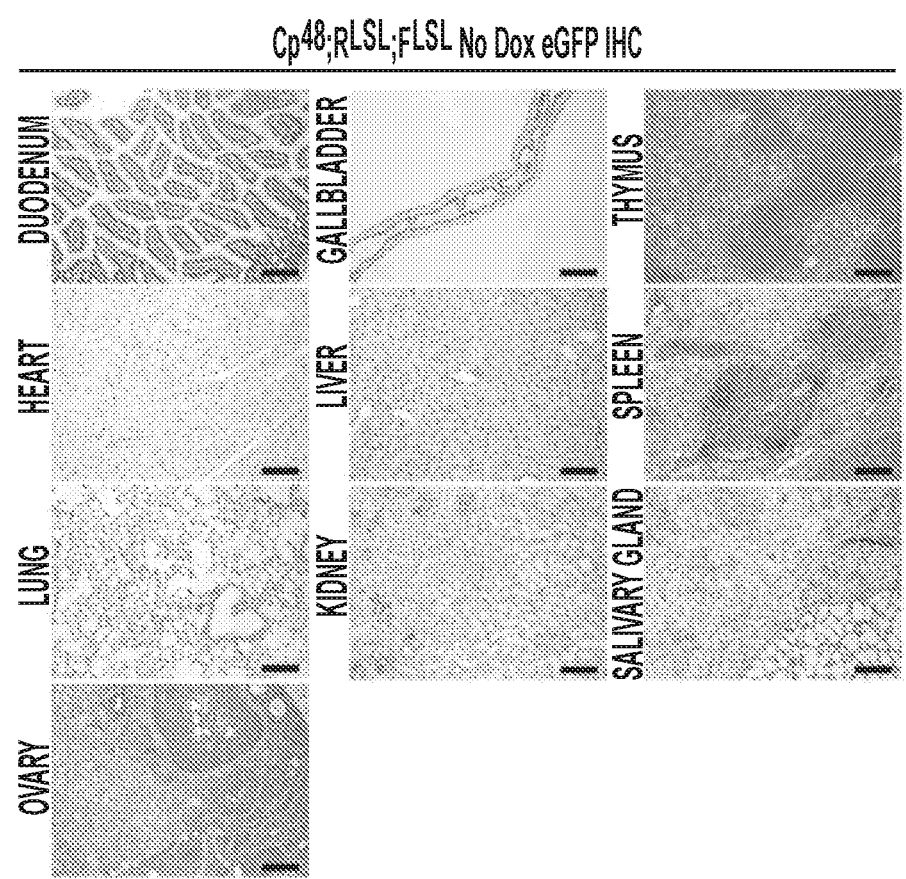

FIG. 38 shows focal pancreas, p48-Cre driven CA19-9 mouse model: eGFP expression in non-pancreatic tissues. eGFP IHC of mouse tissues from untreated $C^{p48};R^{LSL};F^{LSL}$ mice. Scale bars=100 µm.

Figure 39:
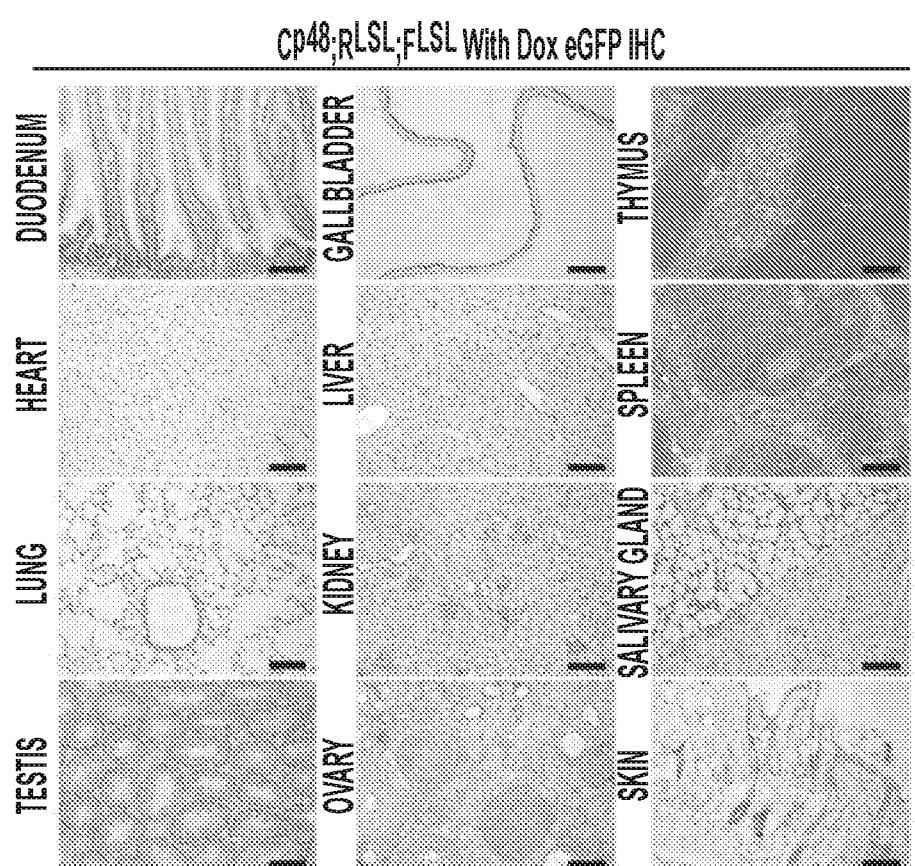

FIG. 39 shows focal pancreas, p48-Cre driven CA19-9 mouse model: eGFP expression in non-pancreatic tissues. eGFP IHC of mouse tissues from $C^{p48};R^{LSL};F^{LSL}$ mice treated with Dox is shown. Scale bars=100 µm.

Figure 40:
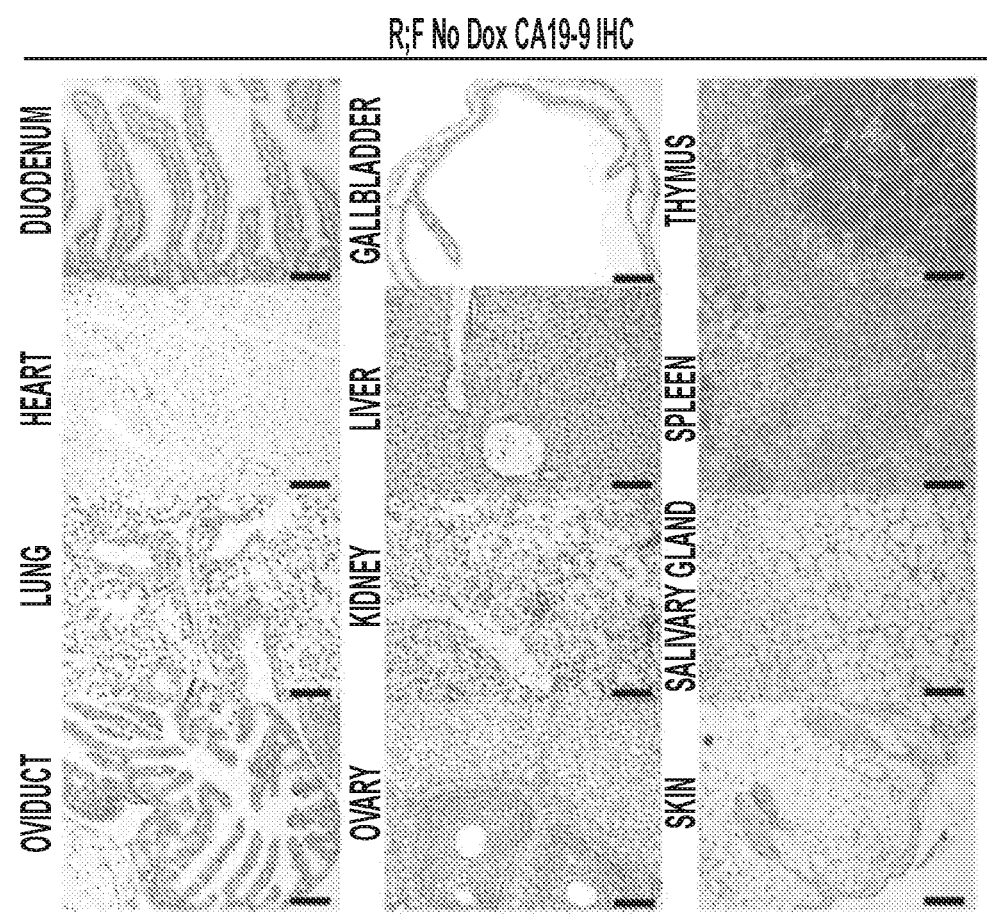

FIG. 40 shows whole body CA19-9 mouse model: CA19-9 expression in non-pancreatic tissues. CA19-9 IHC of mouse tissues from untreated R;F mice is shown. Scale bars=100 µm.

Figure 41:
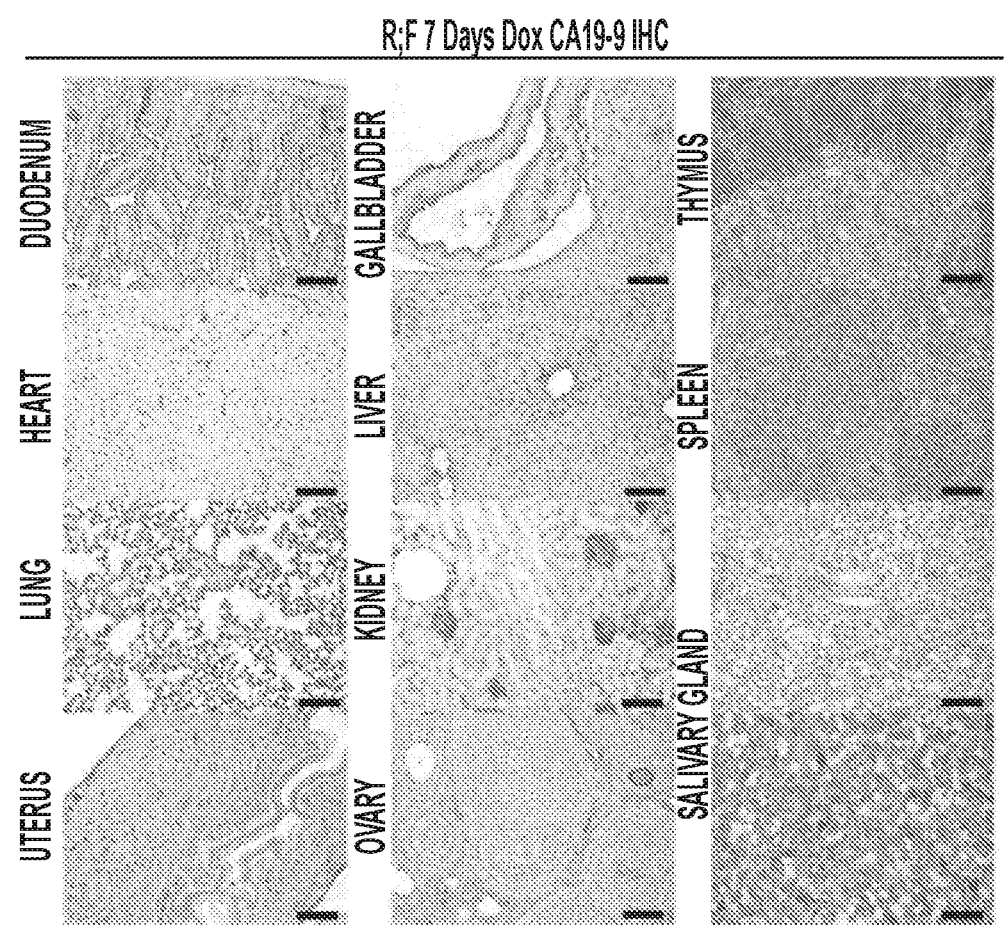

FIG. 41 shows whole body CA19-9 mouse model: CA19-9 expression in non-pancreatic tissues. CA19-9 IHC of mouse tissues from R;F mice treated with Dox for 7 days is shown. Scale bars=100 µm.

Figure 42:
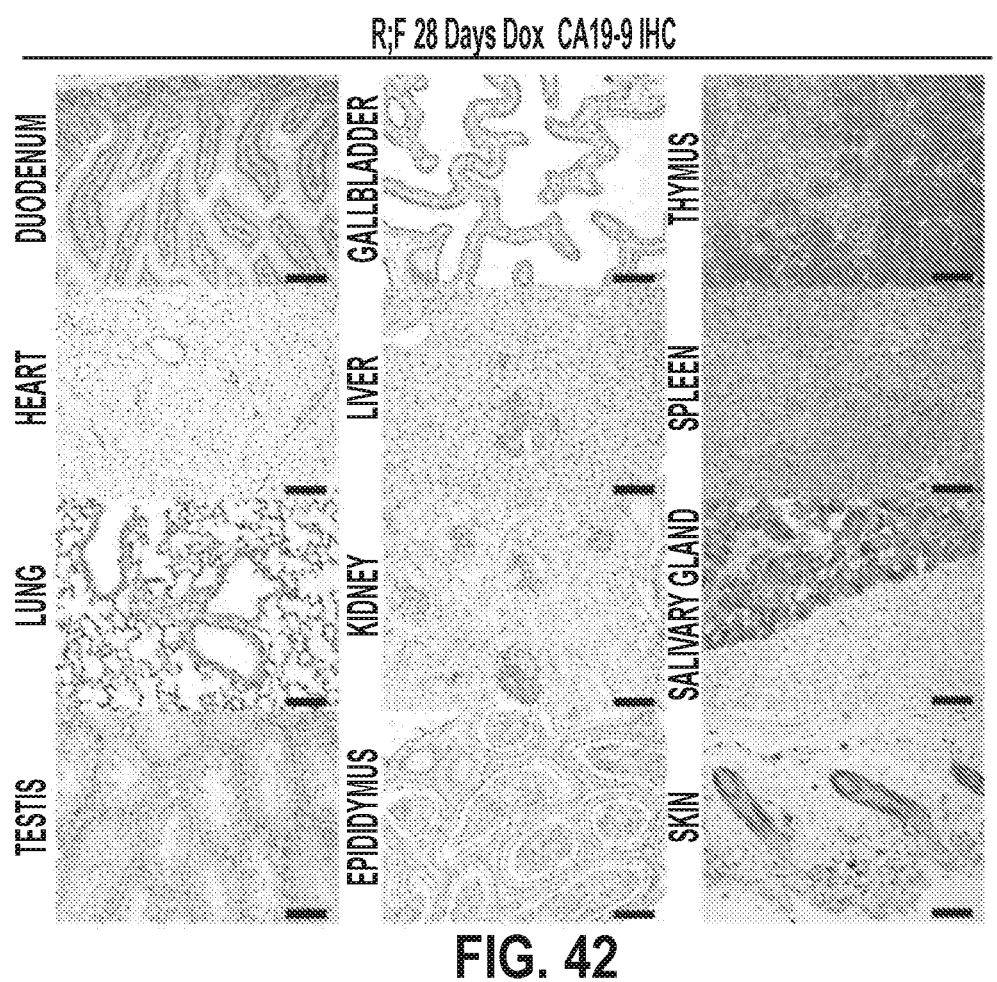

FIG. 42 shows hole body CA19-9 mouse model: CA19-9 expression in non-pancreatic tissues. CA19-9 IHC of mouse tissues from R;F mice treated with Dox for 28 days is shown. Scale bars=100 µm.

Figure 43:
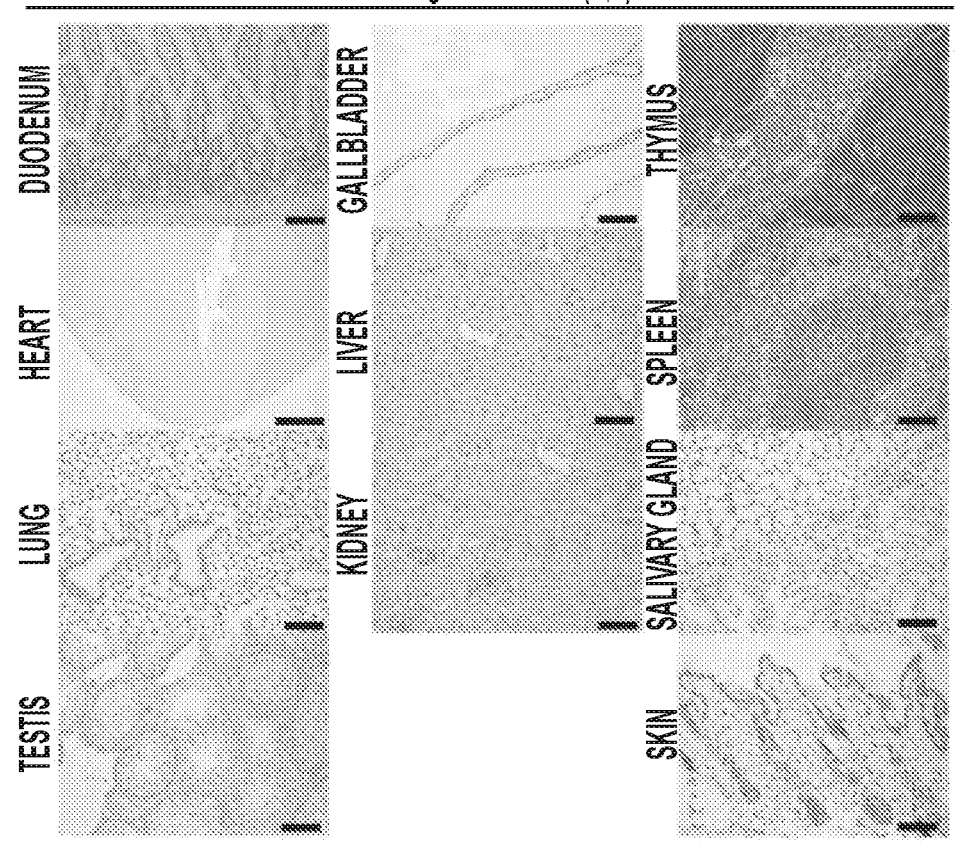

FIG. 43 shows whole body CA19-9 mouse model: CA19-9 expression in non-pancreatic tissues. CA19-9 IHC of mouse tissues from untreated R;F genetically negative control littermates is shown. Scale bars=100 µm except for the heart, where the scale bar=500 µm.

Figure 44:
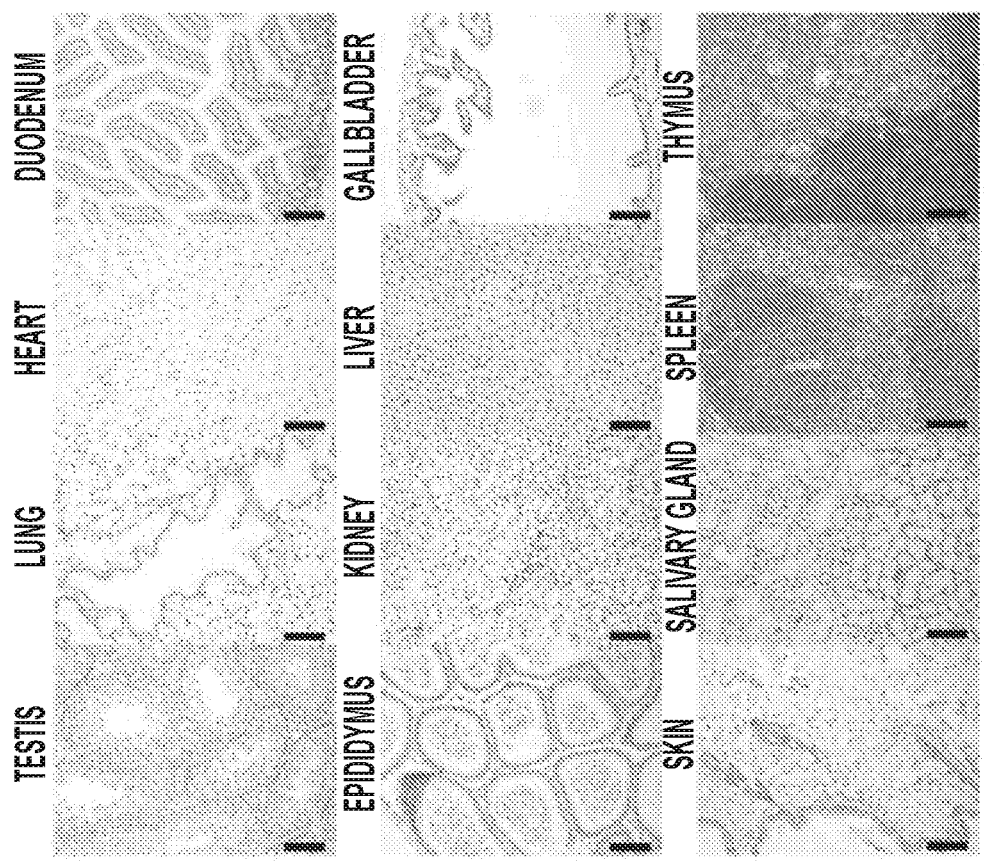

FIG. 44 shows focal pancreas CA19-9 mouse model: CA19-9 expression in non-pancreatic tissues. CA19-9 IHC of mouse tissues from untreated $C^{PDX}$;$R^{LSL}$;$F^{LSL}$ and $C^{p48}$;$R^{LSL}$;$F^{LSL}$ mice is shown. Scale bars=100 µm.

Figure 45:
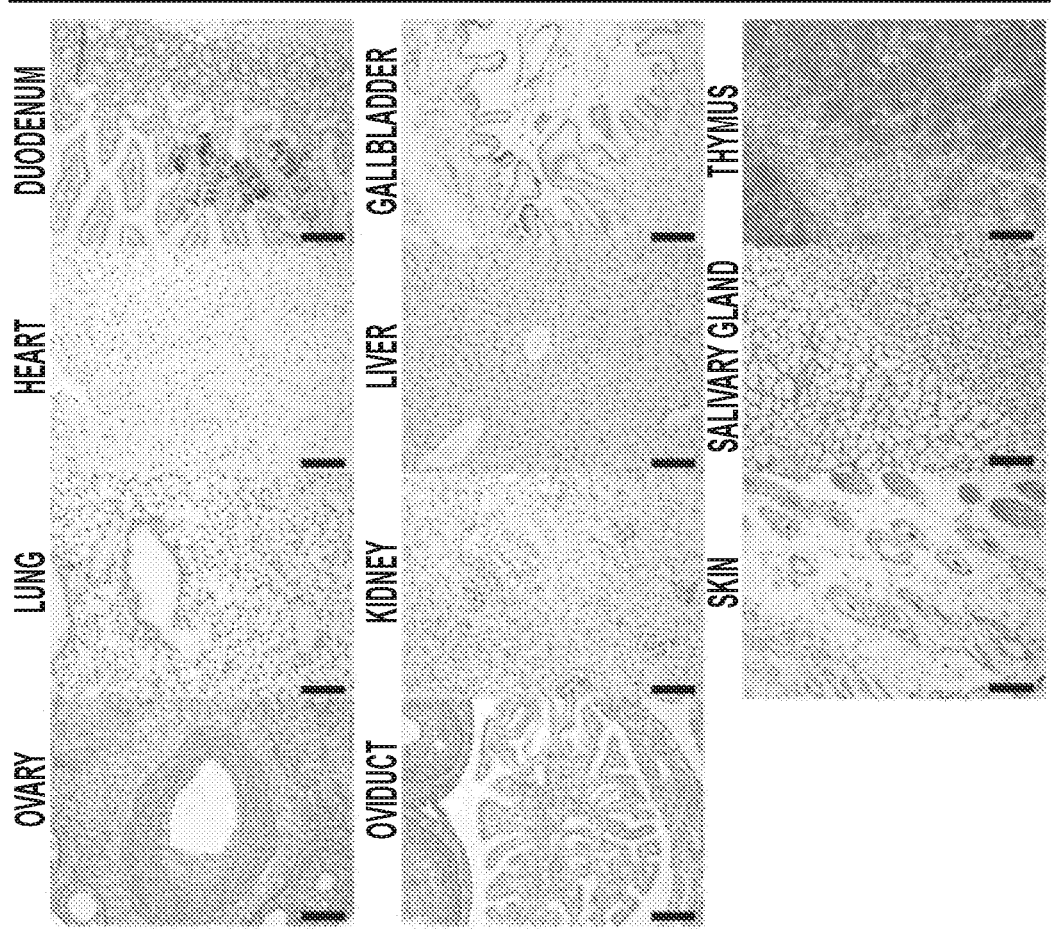
Figure 45:
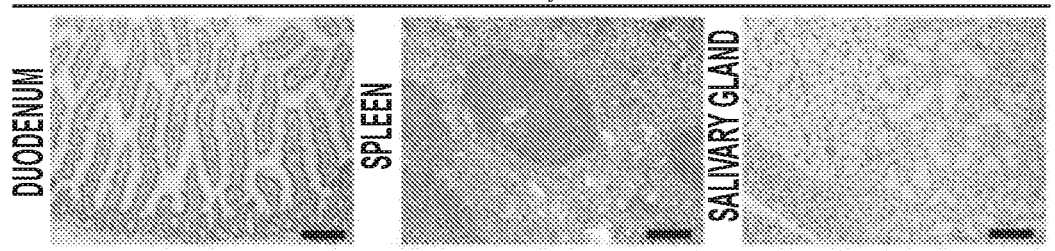

FIG. 45 shows focal pancreas CA19-9 mouse model: CA19-9 expression in non-pancreatic tissues. CA19-9 IHC of mouse tissues from $C^{PDX}$;$R^{LSL}$;$F^{LSL}$ and $C^{p48}$;$R^{LSL}$;$F^{LSL}$ mice treated with Dox for 7 days is shown. Scale bars=100 µm.

Figure 46:
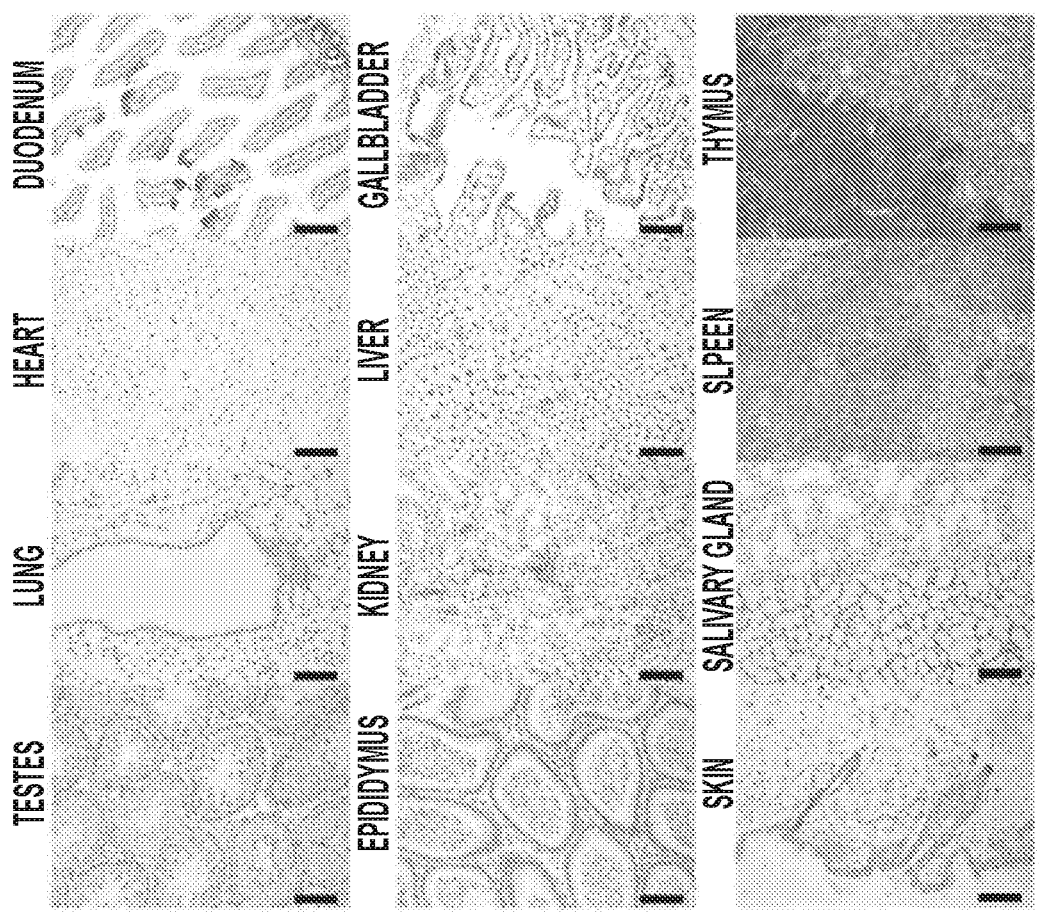
Figure 46:
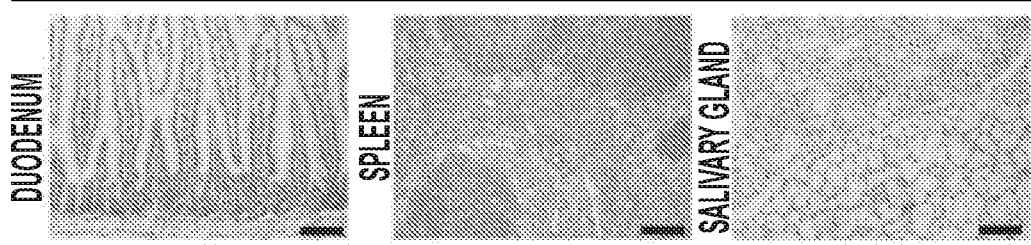

FIG. 46 shows focal pancreas CA19-9 mouse model: CA19-9 expression in non-pancreatic tissues. CA19-9 IHC of mouse tissues from $C^{PDX}$;$R^{LSL}$;$F^{LSL}$ and $C^{p48}$;$R^{LSL}$;$F^{LSL}$ mice treated with Dox for 28 days is shown. Scale bars=100 µm.

Figure 47:
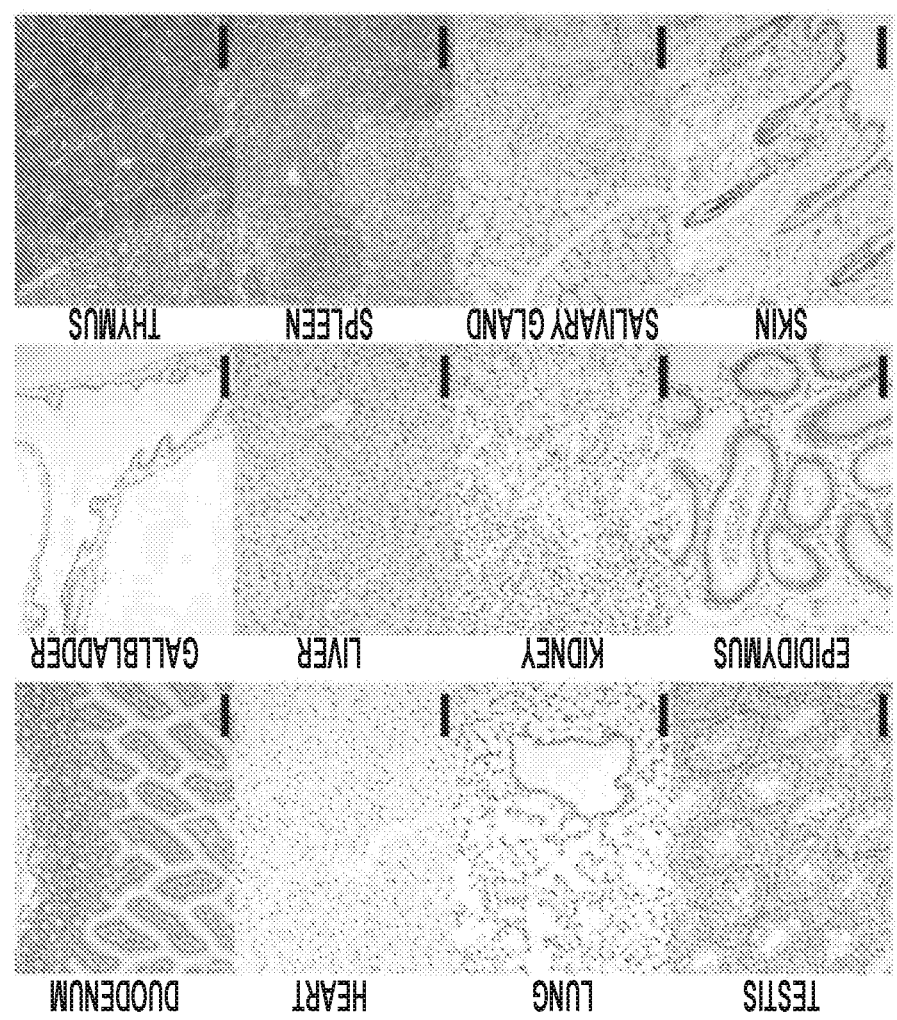

FIG. 47 shows focal pancreas CA19-9 mouse model: CA19-9 expression in non-pancreatic tissues. CA19-9 IHC of mouse tissues from untreated $C^{PDX}$;$R^{LSL}$;$F^{LSL}$ and $C^{p48}$;$R^{LSL}$;$F^{LSL}$ genetically negative control littermates. Scale bars=100 µm.

Figure 48:
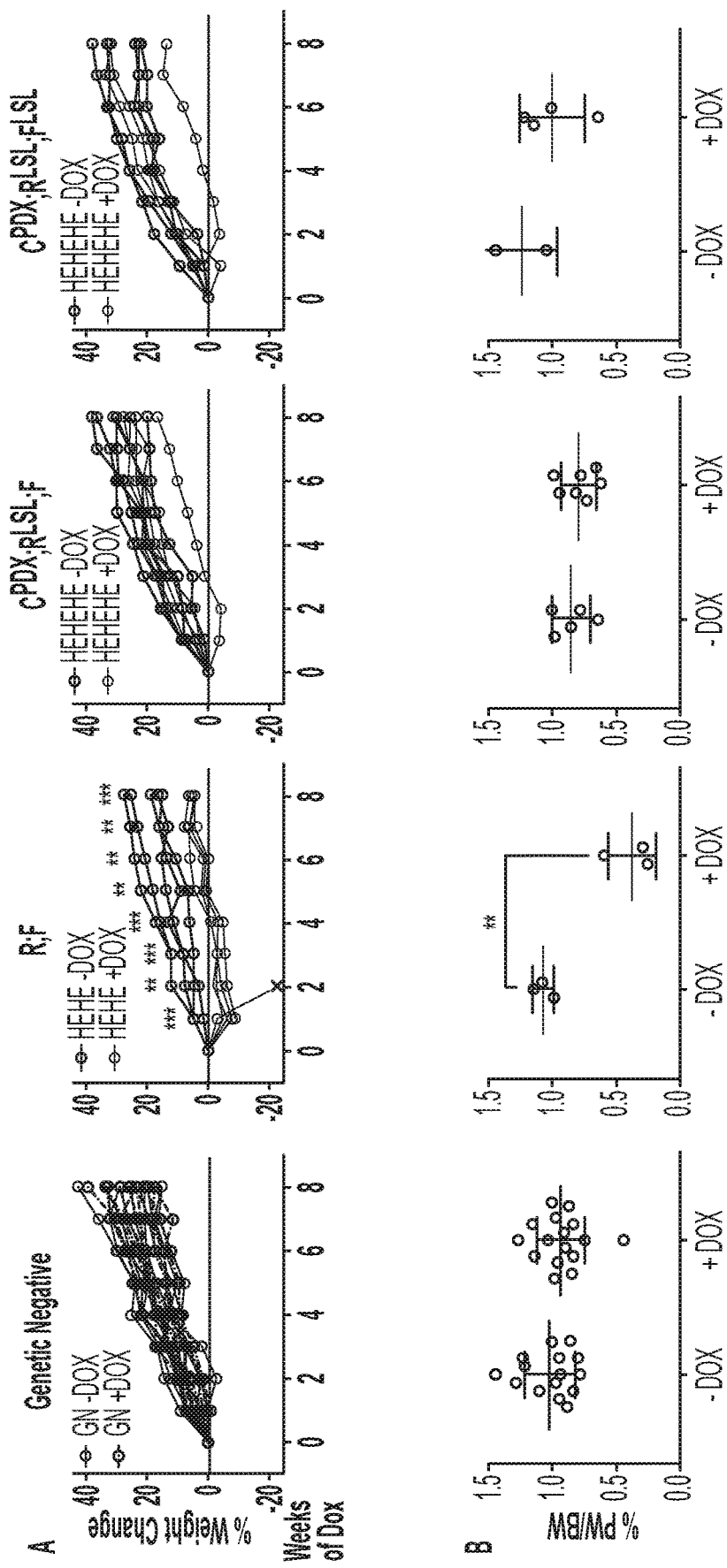

FIGS. 48A-48B show mouse model comparison of body and pancreatic weight. FIG. 48A shows percentage change in bodyweight of genetically negative control littermates, R;F, $C^{PDX}$;$R^{LSL}$;F or $C^{PDX}$;$R^{LSL}$;$F^{LSL}$ mice treated with Dox (Weeks). Each data point line represents the same individual mouse over time. p value determined by multiple t tests (Holm-Sidak) without assuming a consistent SD. FIG. 48B shows percentage pancreatic weight normalized to body weight after 12 weeks of Dox treatment of genetically negative control littermates, R;F, $C^{PDX}$;$R^{LSL}$;F or $C^{PDX}$;$R^{LSL}$;$F^{LSL}$ mice. p value determined by unpaired, parametric, two-tailed t test (t=1.225, 5.874, 0.7731, 1.059; df=29, 4, 10, 4. Lines represent the mean; each data point represents a measurement from an individual mouse. *p<0.05, p<0.01, *p<0.001, ****p<0.0001.

Figure 49:
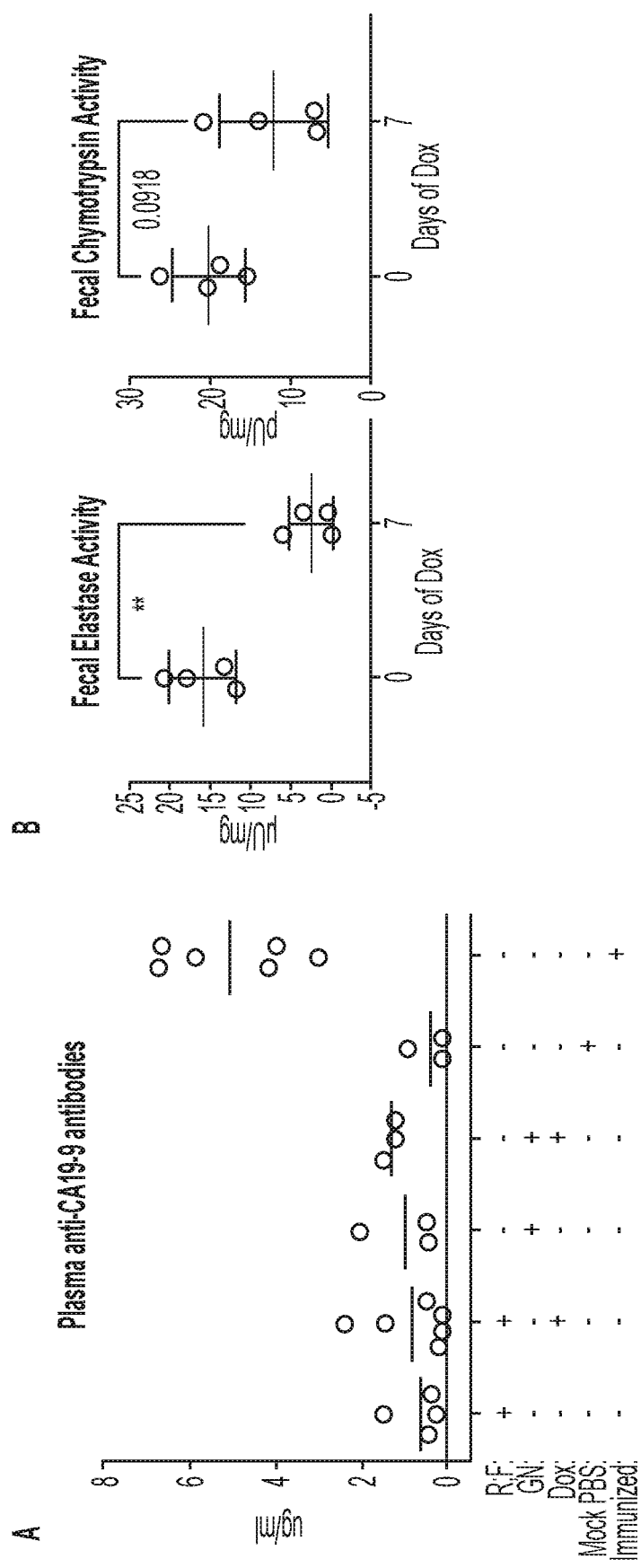
Figure 49:
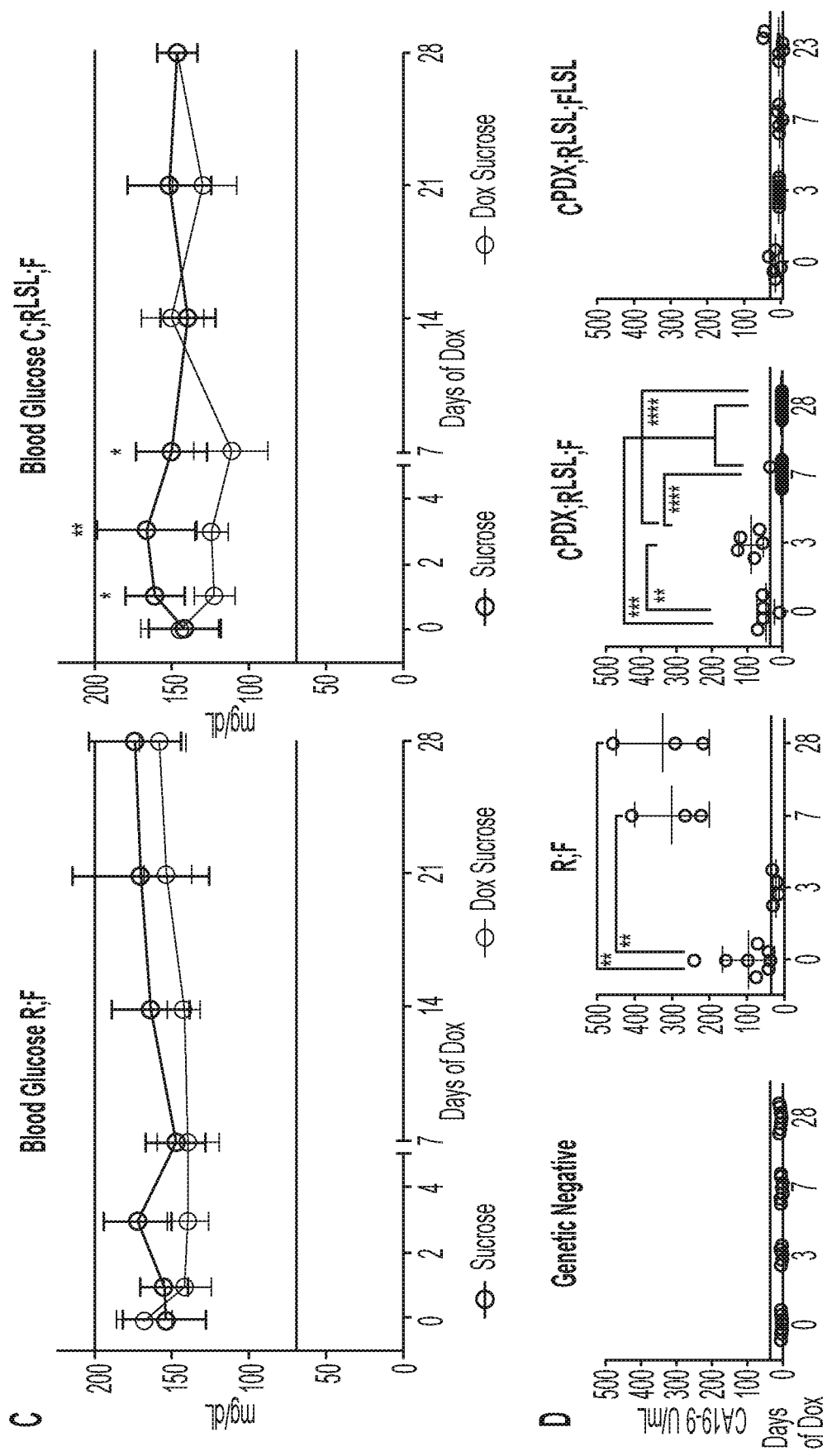

FIGS. 49A-49D show evaluation of indicators of autoimmunity, pancreatic exocrine insufficiency, glucose homeostasis, and CA19-9 secretion. FIG. 49A shows serological measurement of CA19-9-directed antibodies in the plasma of mice from the R;F whole body CA19-9 mouse model as well as from mice directly immunized with CA19-9. FIG. 49B shows fecal levels of Chymotrypsin and Elastase measured in R;F mice following 0 or 7 days of Dox treatment. FIG. 49C shows blood glucose levels were measured in random fed mice from R;F and $C^{PDX}$;$R^{LSL}$;F models following treatment with Sucrose vehicle water or Dox Sucrose water for 7 days followed by switching to Dox or normal chow. FIG. 49D shows the circulating level of CA19-9 (U/ml) following treatment of genetically negative control littermates, R;F, C;$R^{LSL}$;F or C;$R^{LSL}$;$F^{LSL}$ mice with Dox (Days). p value determined by using one-way ANOVA with multiple comparisons (F (3,30)=2.305; (3,14)=13.46; (3,24)= 35.36; (3, 35)=4.667). Lines represent the mean; each data point represents a measurement from an individual mouse. Values that exceed 37 U/ml (dotted line) are considered to be elevated. *p<0.05, p<0.01, *p<0.001, ****p<0.0001.

Figure 50:
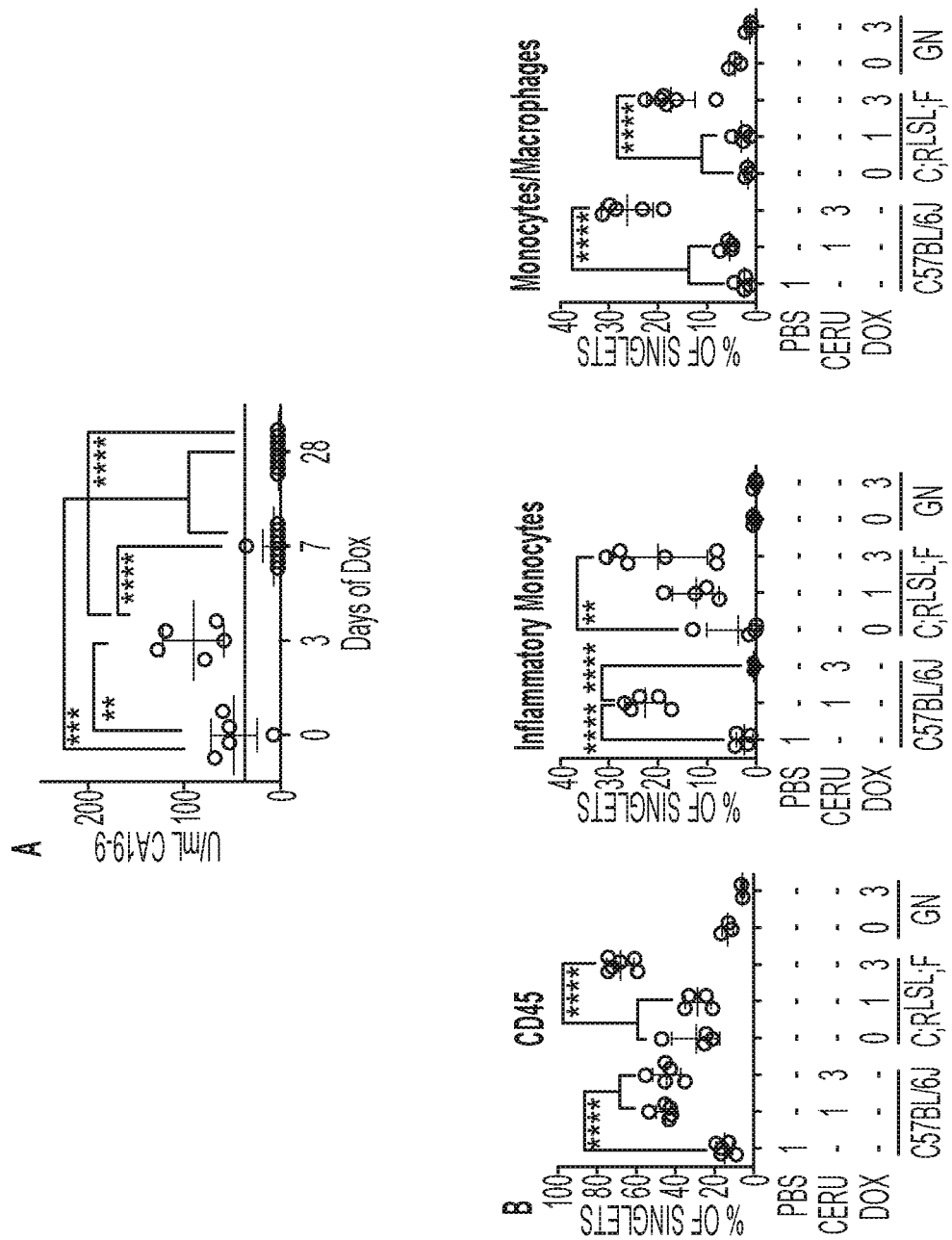

FIG. 50A shows the circulating level of CA19-9 (U/ml) following treatment of $C^{PDX}$;$R^{LSL}$;F mice with Dox. Values that exceed 37 U/ml (dotted line) are elevated (F (3,24)= 35.36, p<0.0001). n=5, 5, 8, and 10, respectively. FIG. 50B shows immune cell infiltration evaluated by flow cytometry in mice treated with Cerulein (C57Bl/6j, n=5, 5, and 5, respectively) and $C^{PDX}$;$R^{LSL}$;F mice treated with Dox (n=4, 4, and 6, respectively) compared to genetically negative controls (GN, n=3 and 3, respectively) (F (7,26/27/26)= 41.06, 14.38, 41.23, p<0.0001 for all). For FIGS. 50A-50B, middle horizontal red lines represent the mean and error bars represent the standard deviation; each data point represents a measurement from an individual mouse; *p<0.05, p<0.01, *p<0.001, ****p<0.0001 for multiple comparisons using Holm-Sidak's procedure following a one-way ANOVA.

Figure 51:
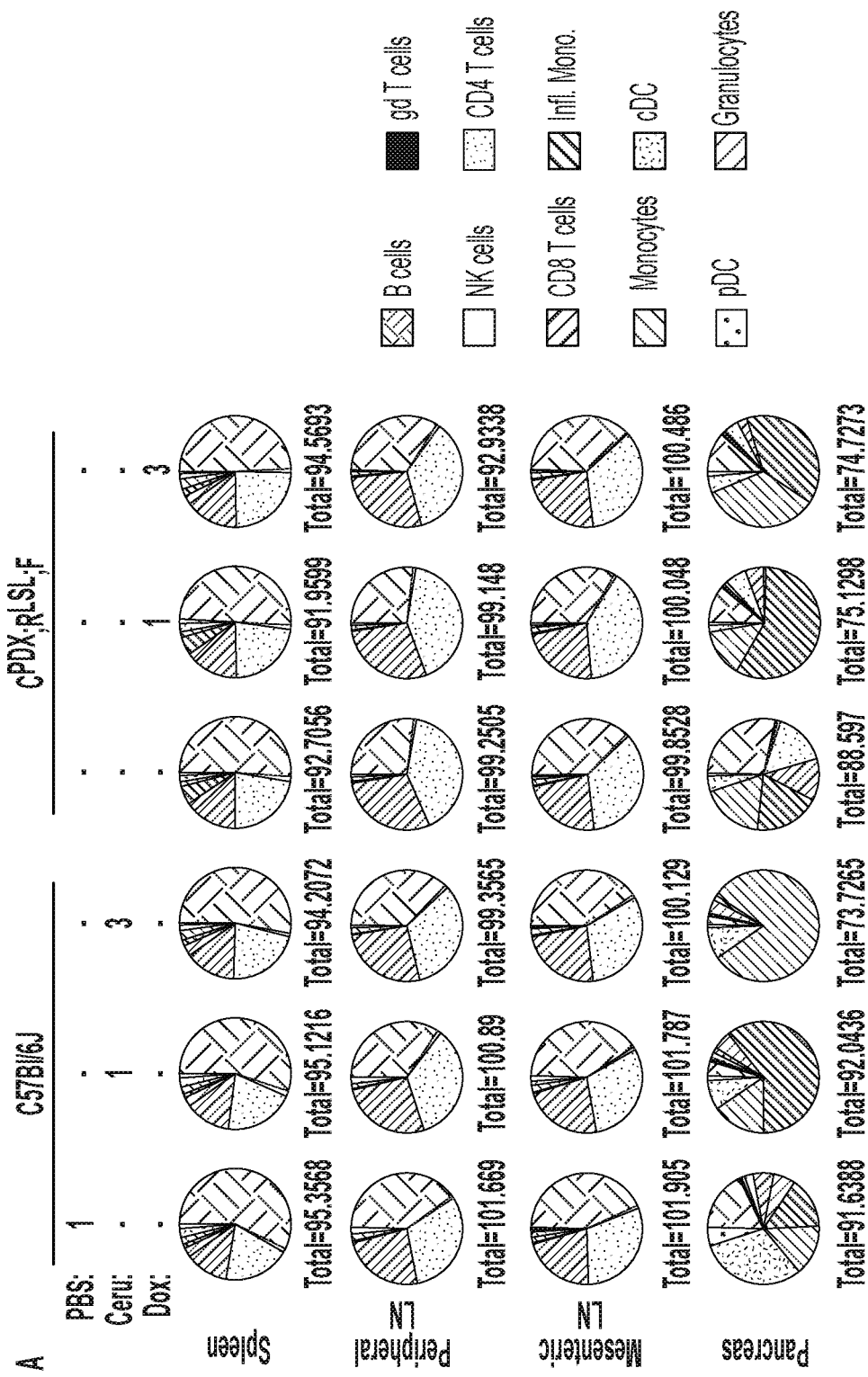
Figure 51:
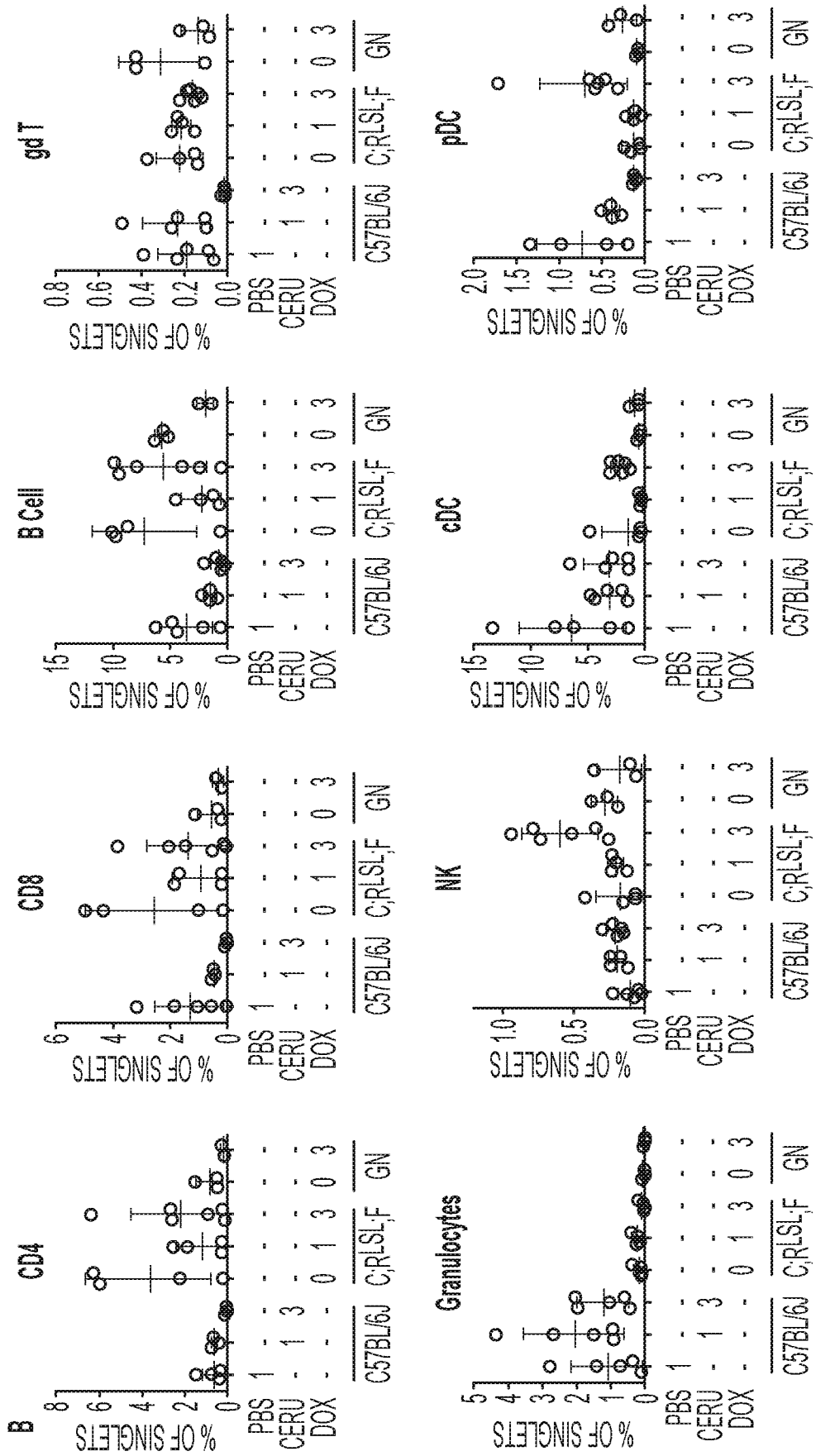

FIG. 51A shows immune cell representation during pancreatitis induction in mice. Immune cell type representation was determined by flow cytometry in spleen, peripheral lymph nodes, mesenteric lymph nodes and pancreas in mice treated with Cerulein for the induction of acute pancreatitis (C57Bl/6j) and $C^{PDX}$;$R^{LSL}$;F mice treated with Dox for 0, 1, or 3 days compared to genetically negative littermate controls (GN). Data are represented as the percentage of CD45-positive cells. FIG. 51B shows immune cell type representation as determined by flow cytometry in the pancreata of mice treated with Cerulein for the induction of acute pancreatitis (C57Bl/6j) and $C^{PDX}$;$R^{LSL}$;F mice treated with Dox for 0, 1, or 3 days compared to genetically negative littermate controls (GN). Lines represent the mean; each data point represents a measurement from an individual mouse. *p<0.05, p<0.01, *p<0.001, ****p<0.0001 using one-way ANOVA with multiple comparisons (F (8,30)=2.709; 2.034; 3.049; 3.784; 4.739; 6.46; 3.986; 4.688).

Figure 52:
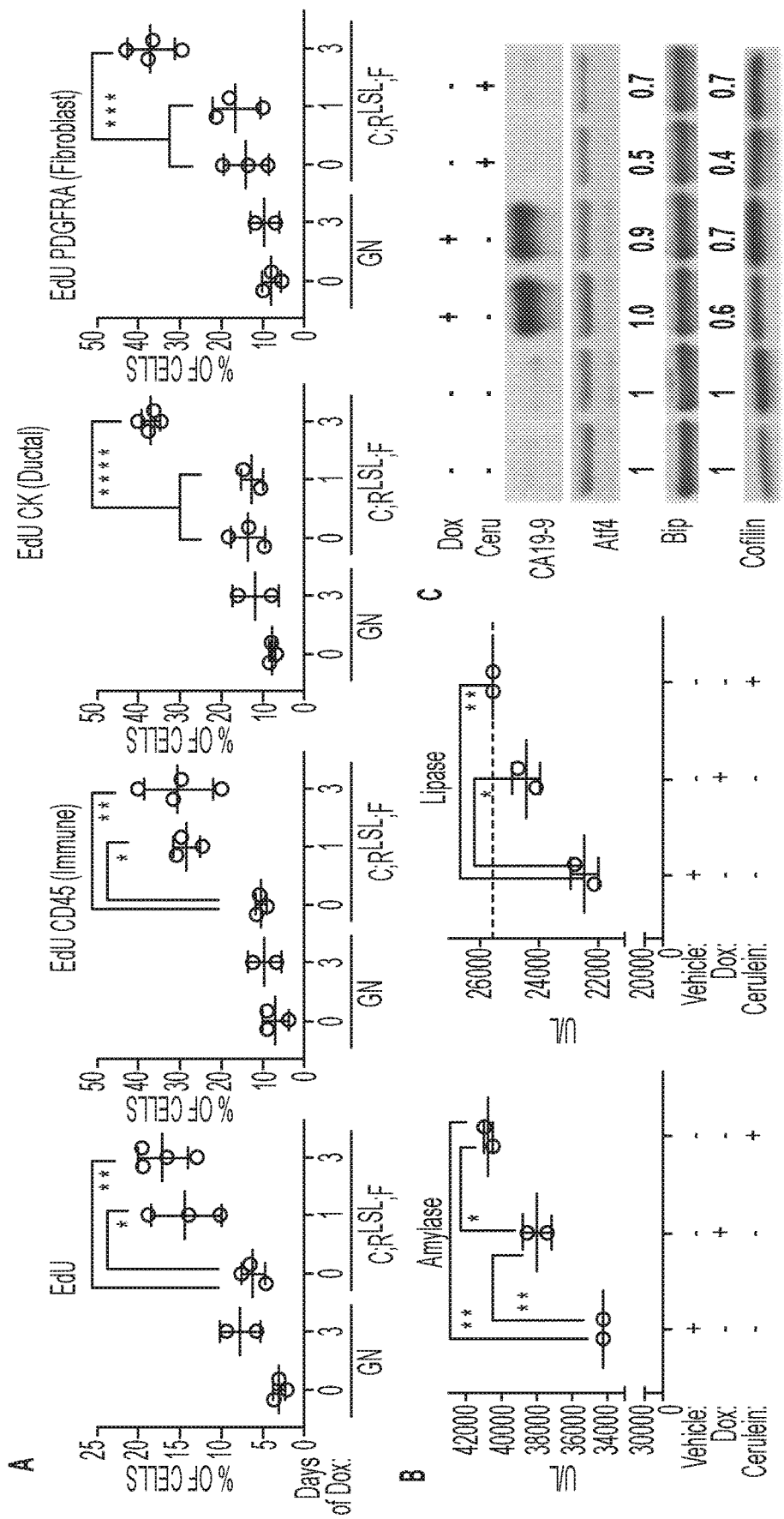

FIG. 52A shows that CA19-9 expression causes ductal proliferation. EdU incorporation was evaluated by flow cytometry in $C^{PDX}$;$R^{LSL}$;F mice (n=3, 3, and 4, respectively) and genetically negative littermate controls (GN, n=3 and 2, respectively) following treatment with Dox. The percentage of EdU positive cells in the entire pancreas (F (4,10)=14.48, p<0.0004), infiltrating immune compartment (CD45, F (4,10)=14.82, p<0.0003), or ductal epithelial lineage (CK19, F (4,9)=48.35, p<0.0001) is shown. Lines represent the mean; each data point represents a measurement from an individual mouse. FIGS. 52B-52C shows evaluation of proteotoxic stress markers in primary acinar cultures following Dox treatment. FIG. 52B shows Amylase and Lipase levels in the conditioned media from $C^{PDX}$;$R^{LSL}$;F acinar cell explants treated with vehicle (PBS), Dox or Cerulein for 12 hours. p<0.01, *p<0.001, ****p<0.0001 using one way ANOVA with multiple comparisons (F (2,3)=92.37; 37.17). FIG. 52C shows the levels of Atf4 and Bip which were quantified relative to the loading control, Cofilin, and the untreated time point by immunoblot on whole cell lysates from $C^{PDX}$;$R^{LSL}$;F acinar cell explants treated with vehicle (PBS), Dox or Cerulein for 12 hours.

Figure 53:
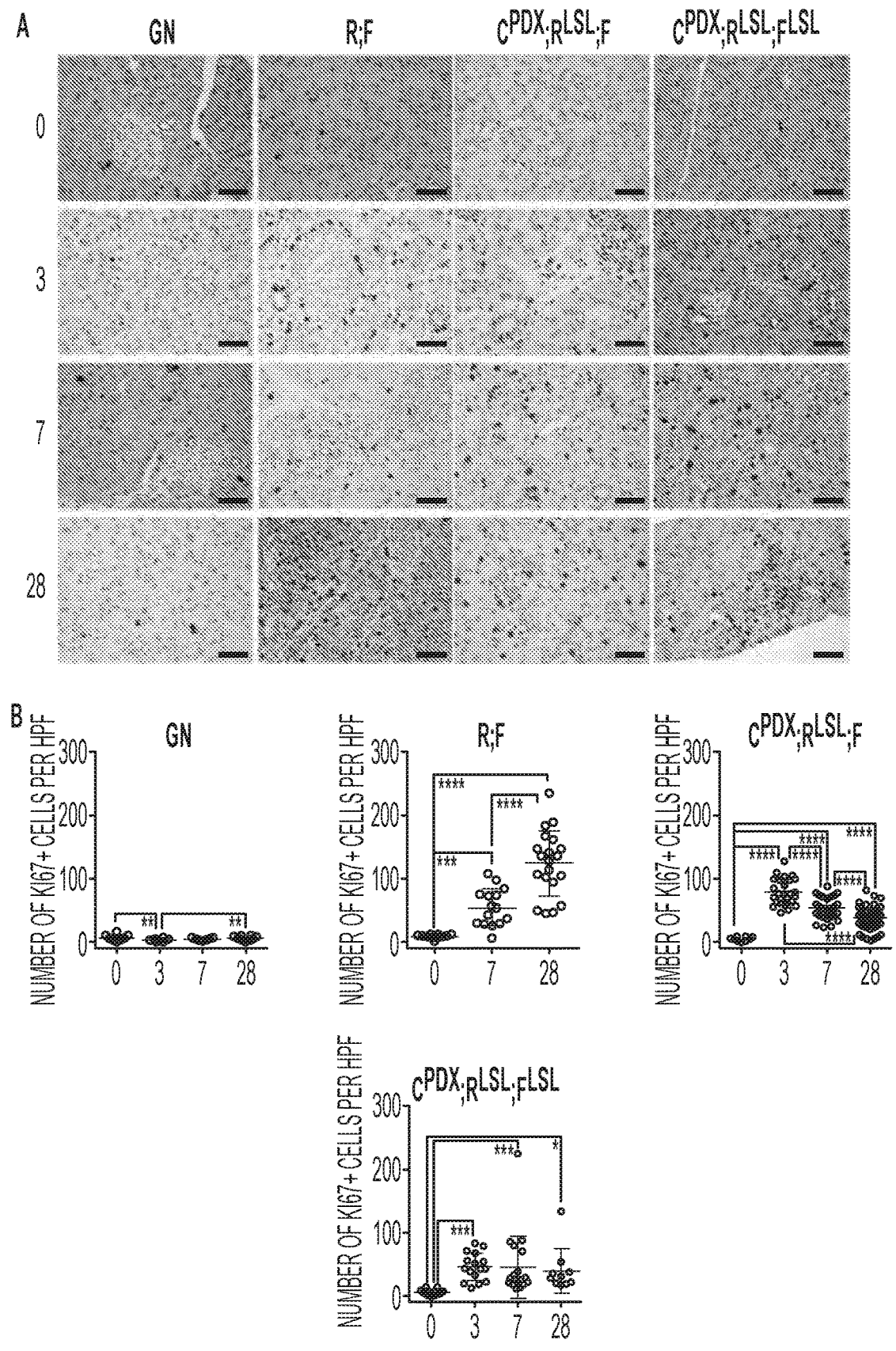

FIGS. 53A-53B show proliferation patterns during pancreatitis induction in mice. FIG. 53A shows Ki67 IHC on genetically negative control littermates, R;F, $C^{PDX}$;$R^{LSL}$;F or $C^{PDX}$;$R^{LSL}$;$F^{LSL}$ mice treated with Dox (Days). FIG. 53B shows quantification of Ki67 IHC from at least three mice counting five high power fields per animal. *p<0.05, p<0.01, *p<0.001, ****p<0.0001 using one-way ANOVA with multiple comparisons (F (3,91)=5.097; (4,75)= 57.28; (7,197)=113.1; (4,86)=12.16). Scale bars=50 µm.

Figure 54:
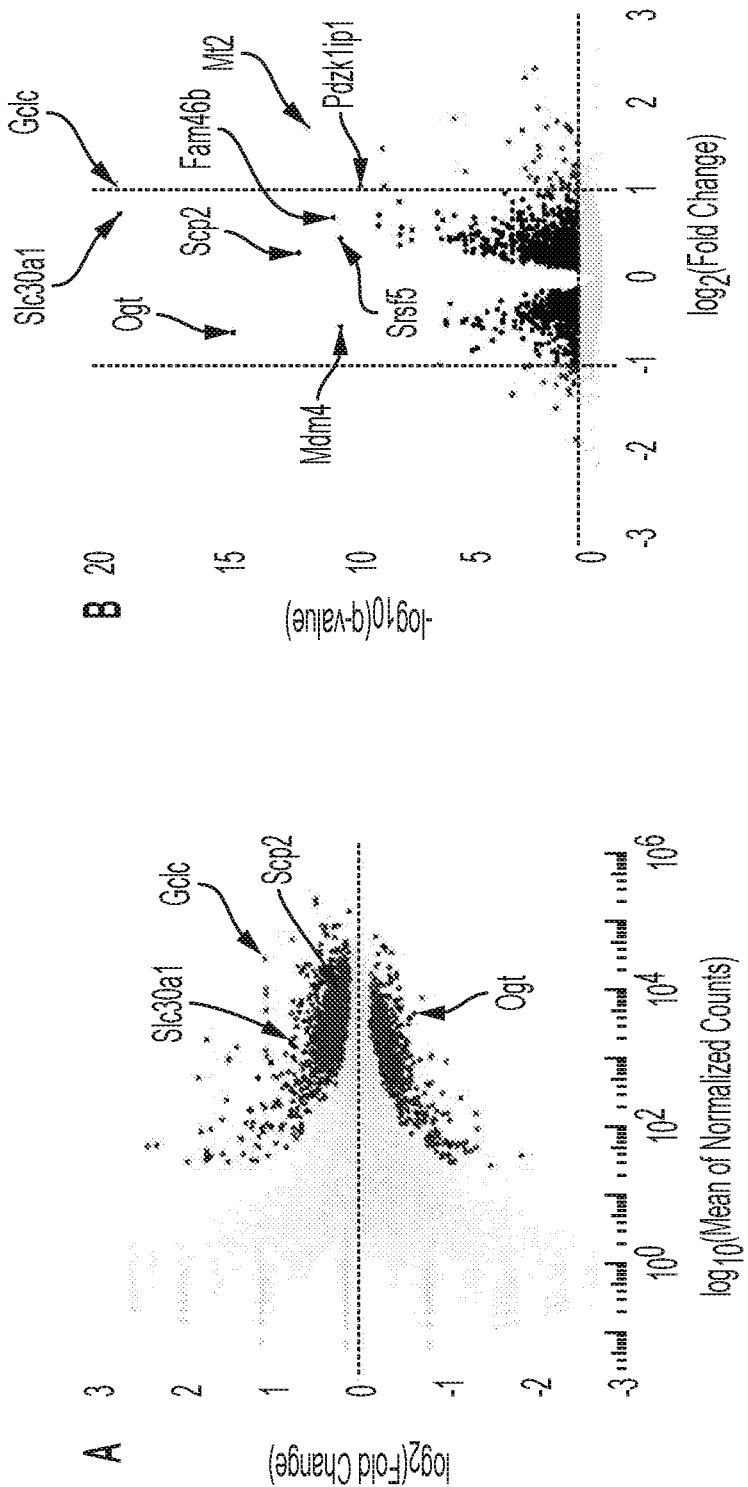
Figure 54:
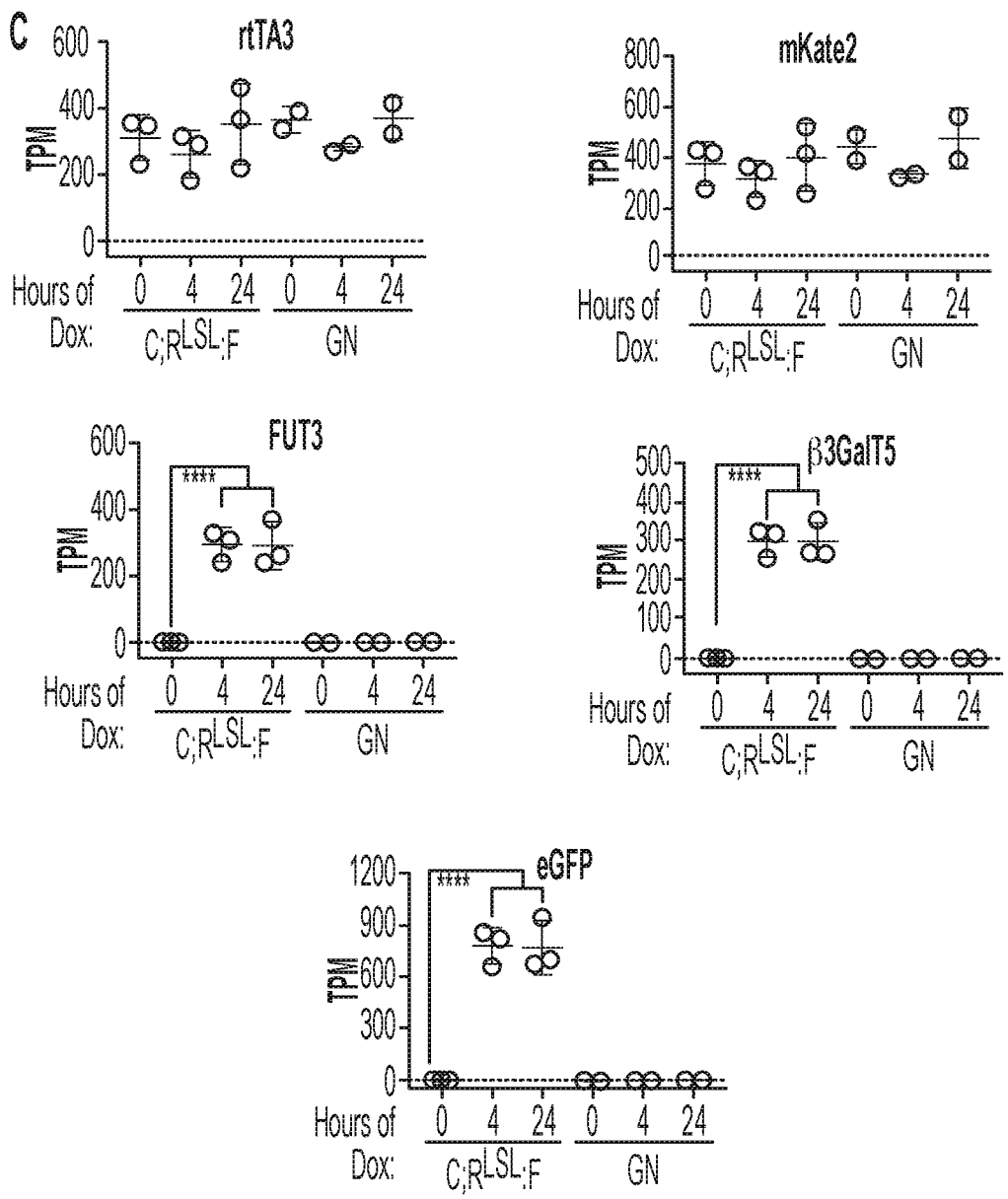
Figure 54:
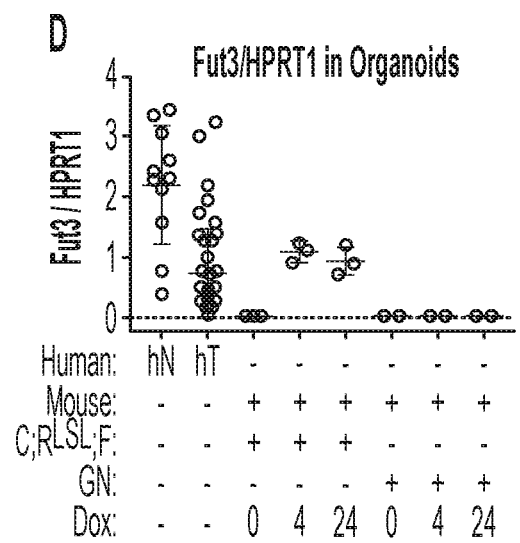
Figure 54:
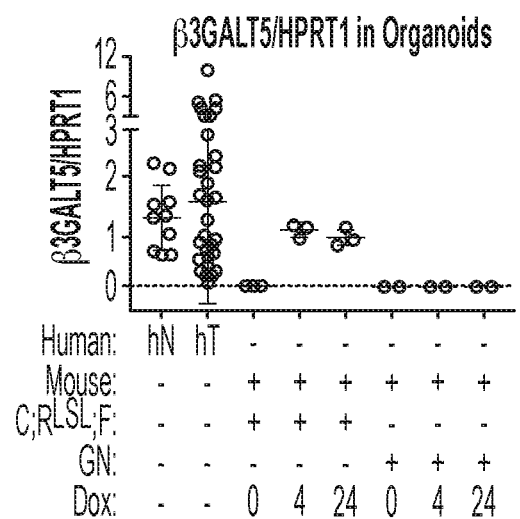
Figure 54:
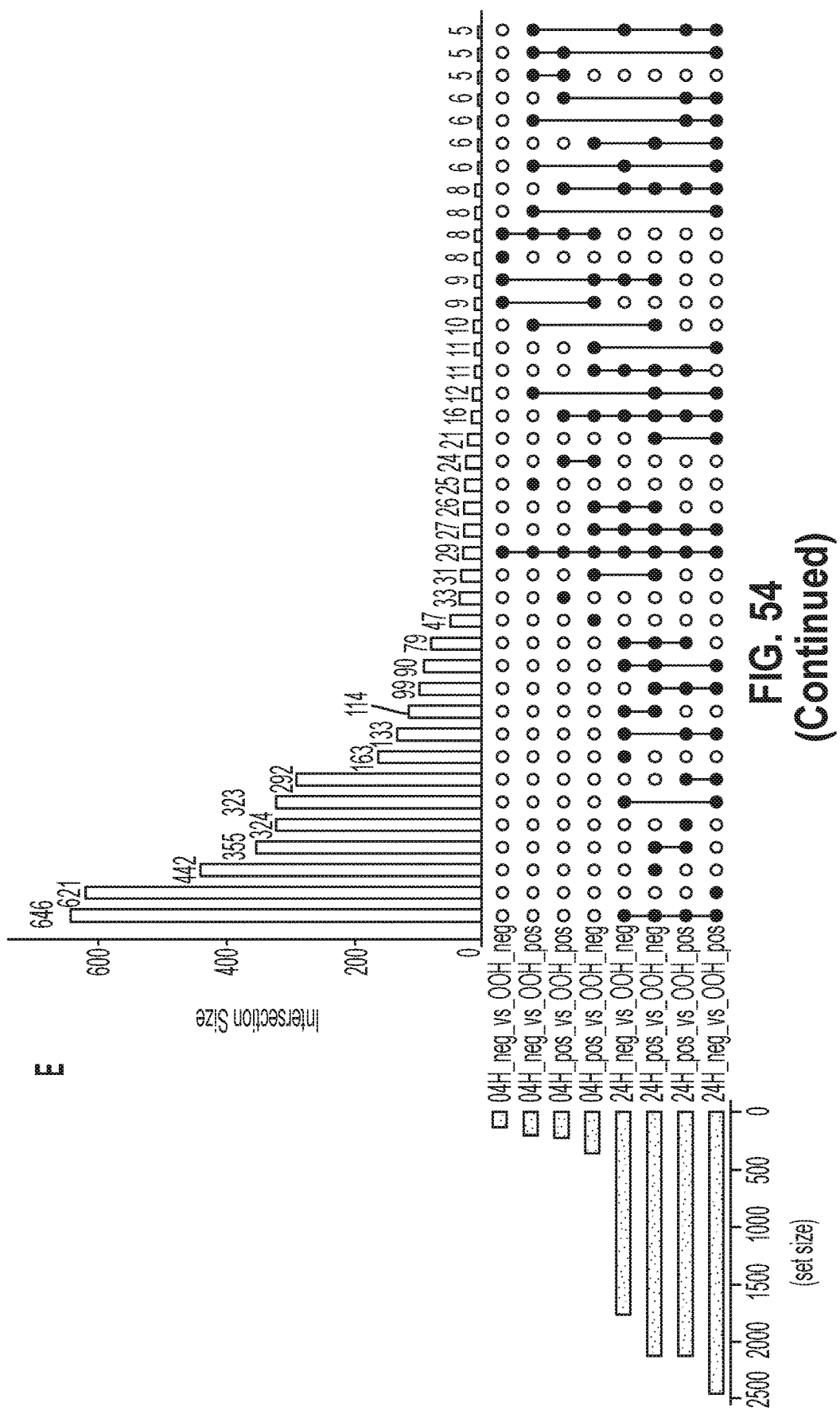
Figure 54:
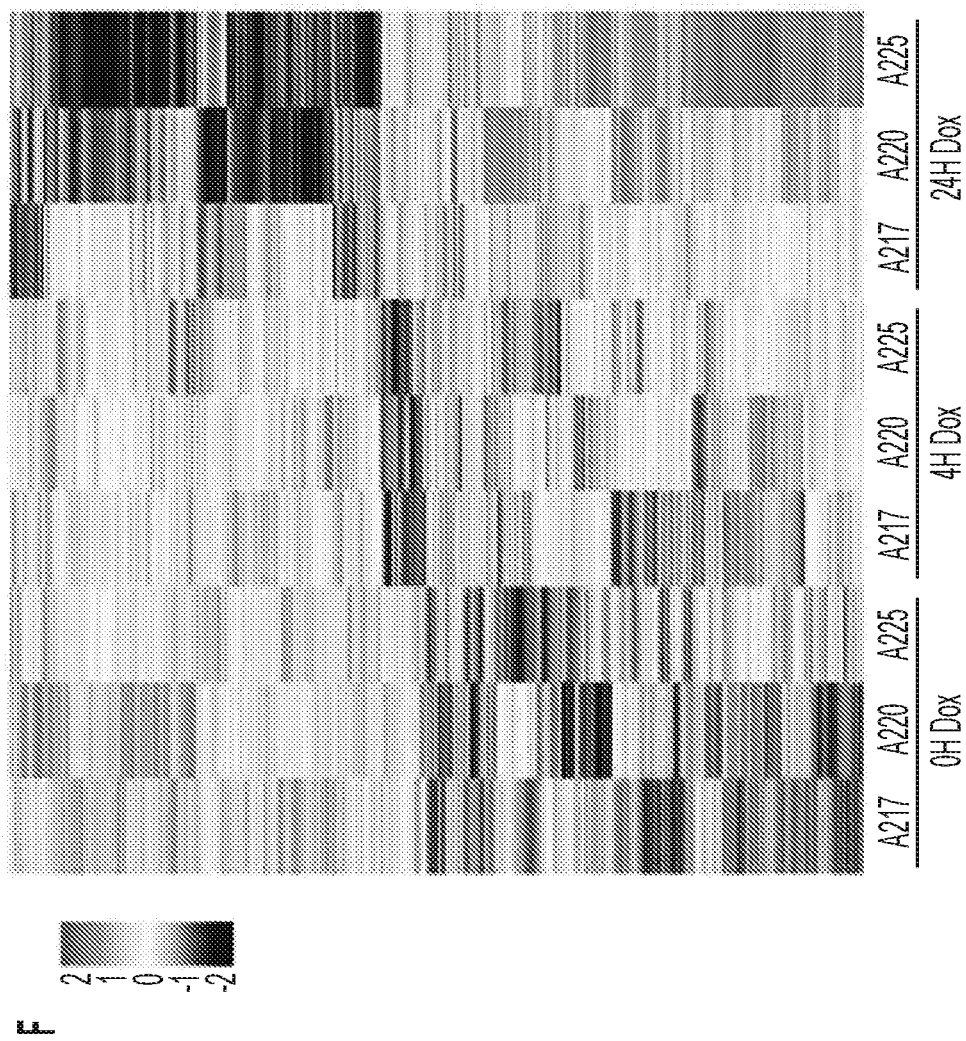

FIGS. 54A-54F show RNAseq analyses of $C^{PDX}$;$R^{LSL}$;F organoids. FIG. 54A shows MA plot (Bland-Altman, mean expression vs. fold chance). FIG. 54B shows volcano plot (fold change vs. q-value). In FIGS. 54A and 54B, significantly differentially expressed genes are annotated in blue and the most differentially expressed genes are further annotated. FIG. 54C shows transcripts per million for the transgenes introduced into the genetically engineered mouse model. FIG. 54D shows the expression levels of Fut3 and β3GalT5 which were normalized to HPRT1 and compared between organoids isolated from normal or malignant human pancreas and the $C^{PDx}$;$R^{LSL}$;F mouse normal organoids following Dox treatment. FIG. 54E shows upset plot showing the overlap between $C^{PDX}$;$R^{LSL}$;F and genetically negative control organoids. Genes that are differentially expressed in response to Dox in the absence of CA19-9 were subtracted from the differentially expressed gene list of $C^{PDX}$;$R^{LSL}$;F organoids. FIG. 54F shows heat map of genes differentially expressed in the 0 versus 24 hour treated $C^{PDX}$;$R^{LSL}$;F organoids following subtraction of Dox-induced gene expression changes.

Figure 55:
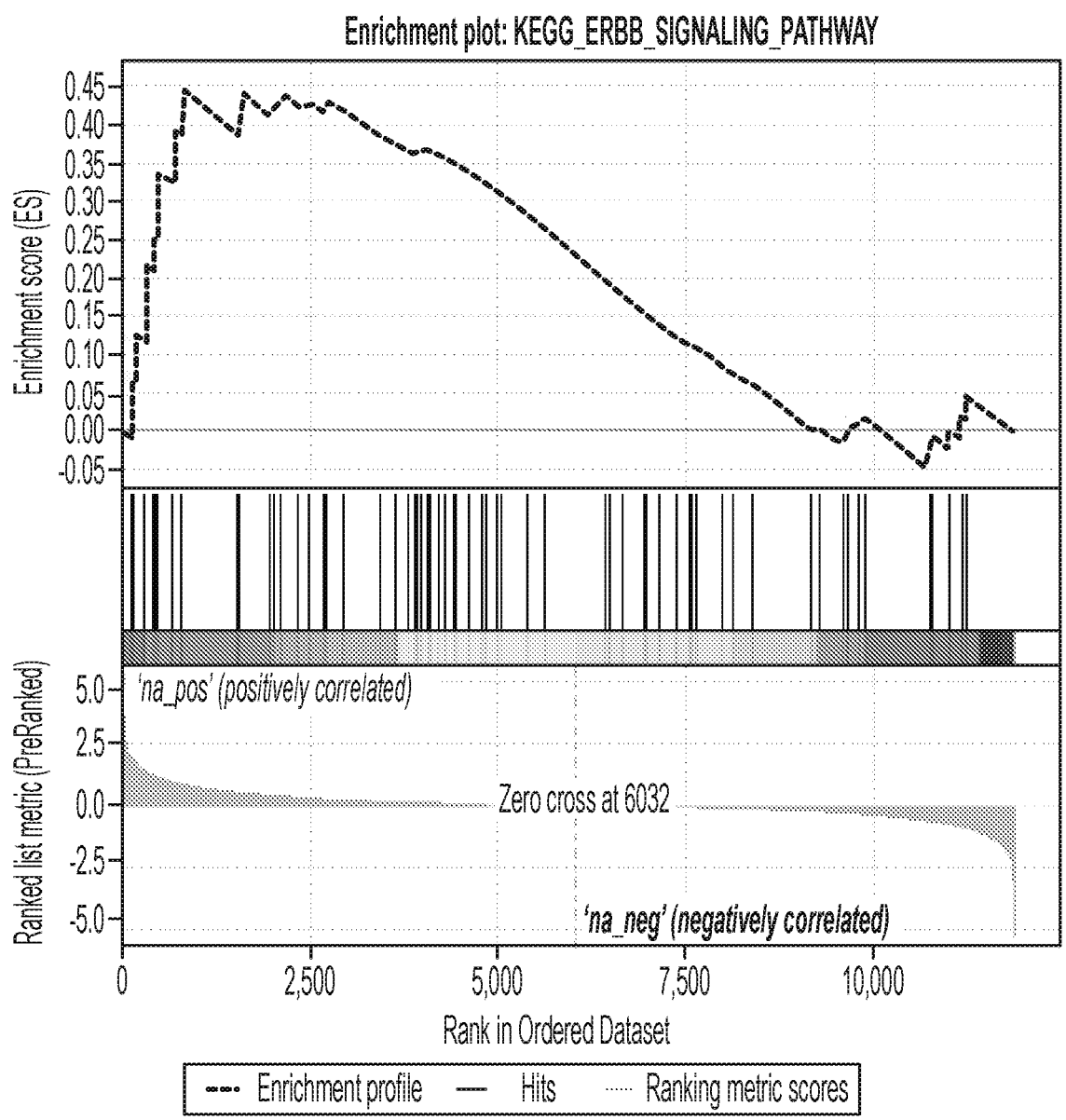
Figure 55:
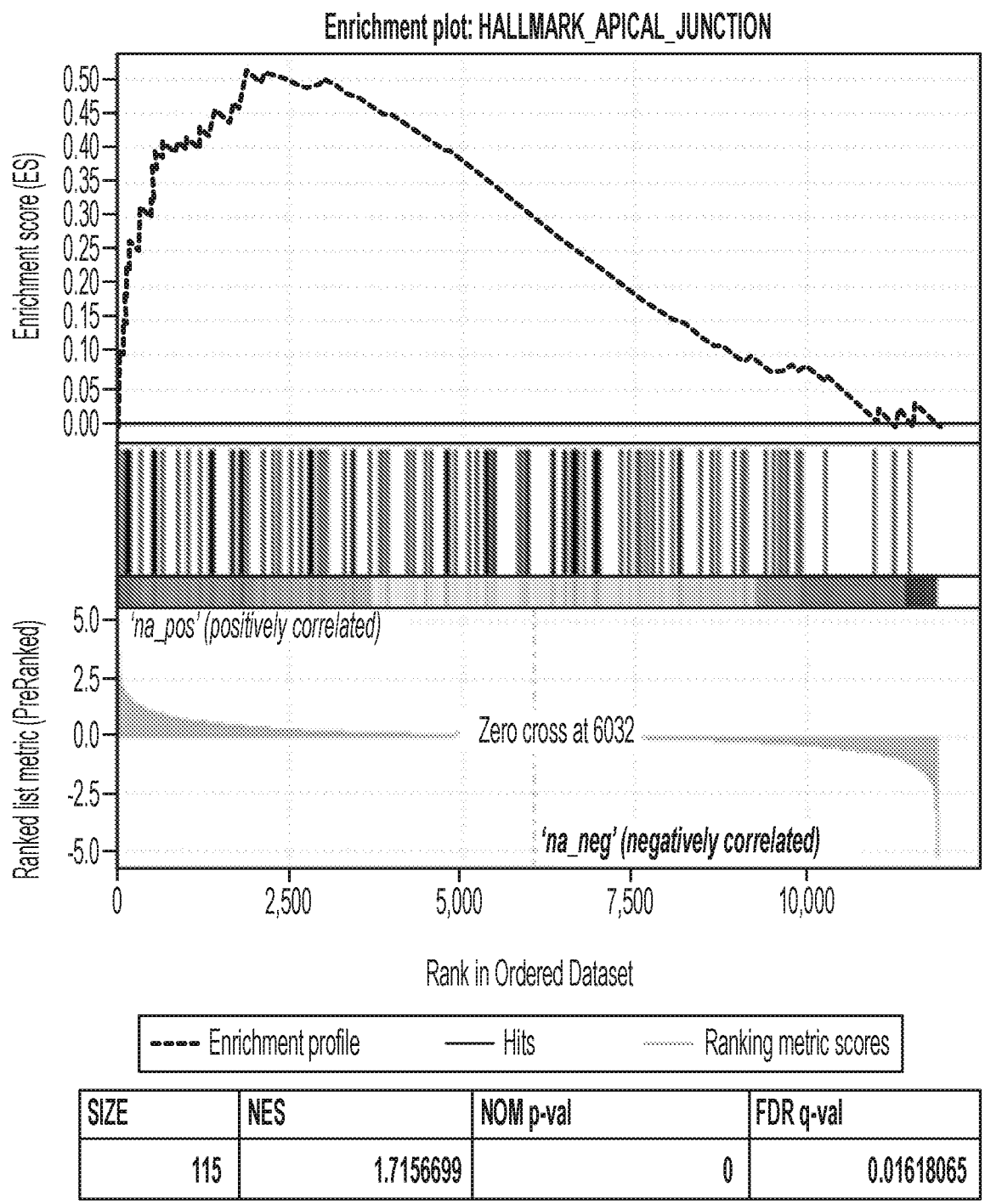
Figure 55:
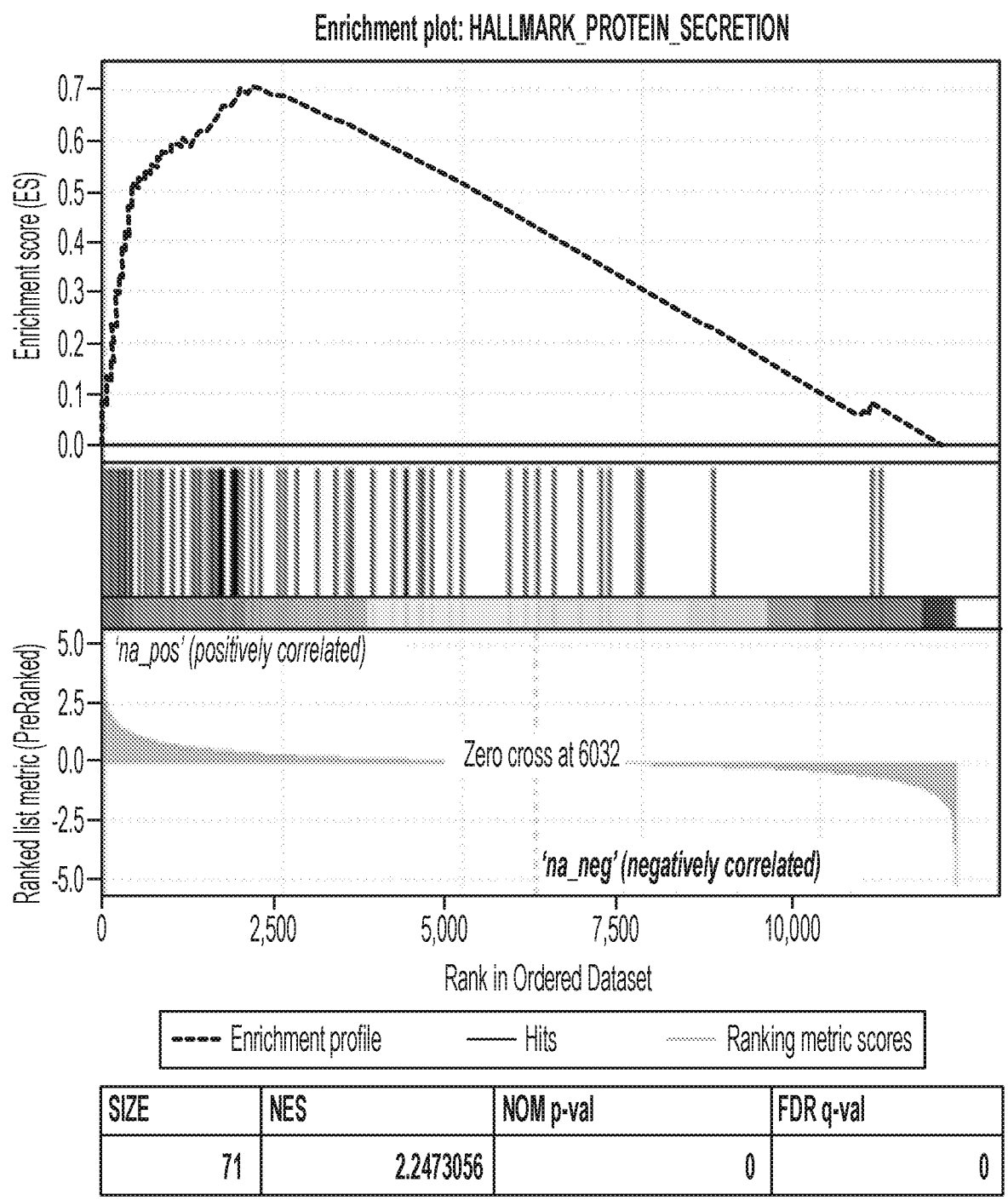
Figure 55:
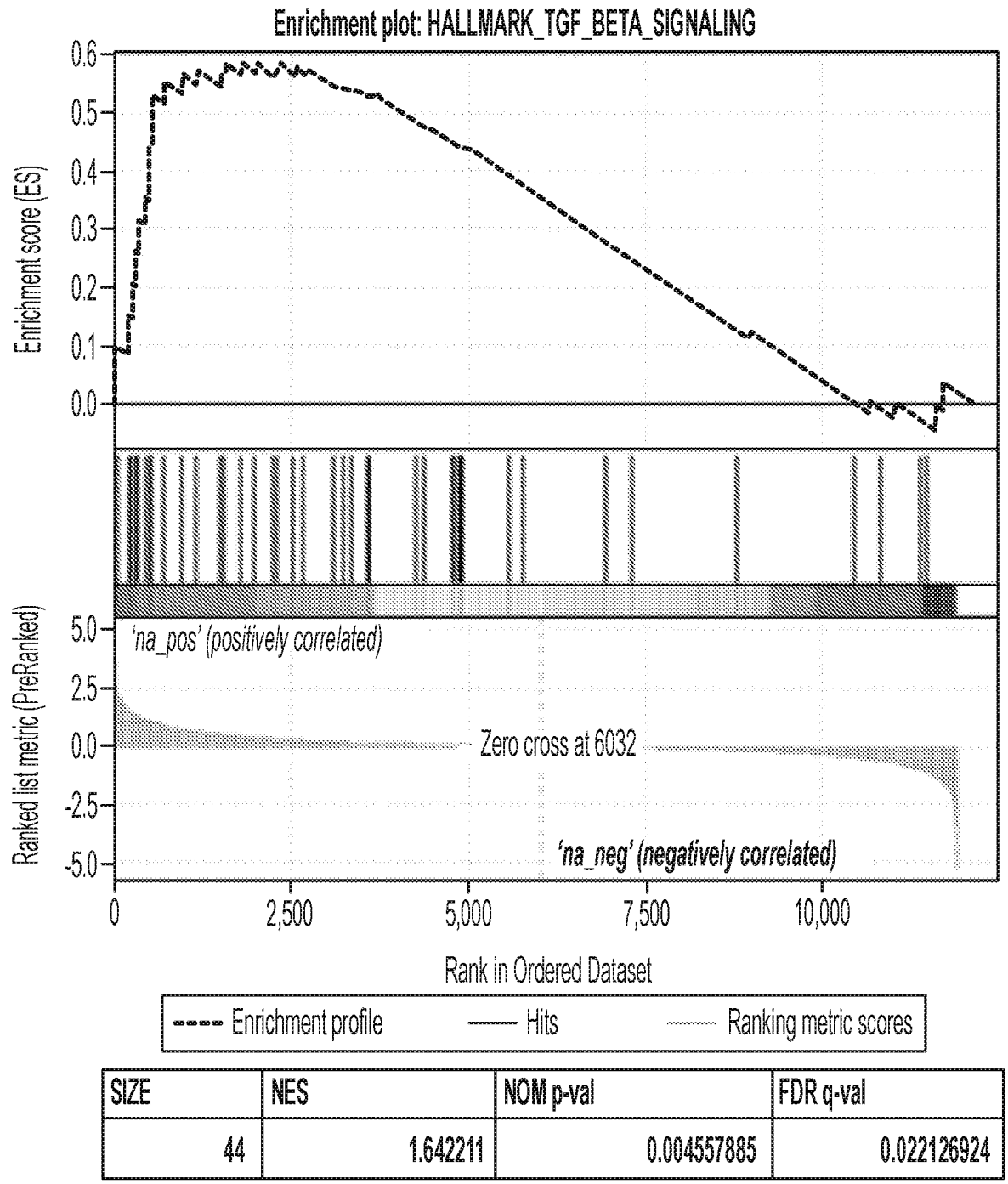
Figure 55:
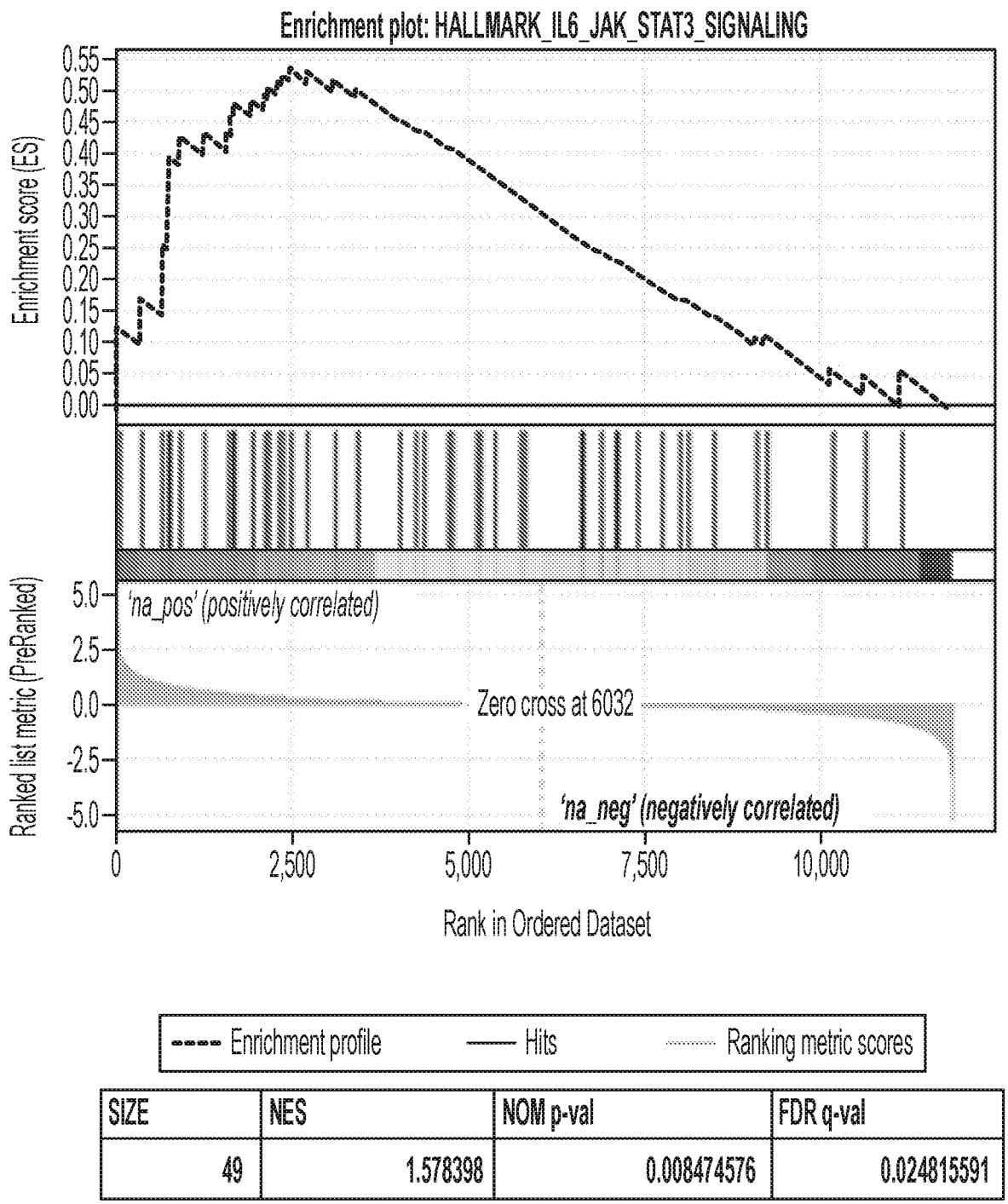
Figure 55:
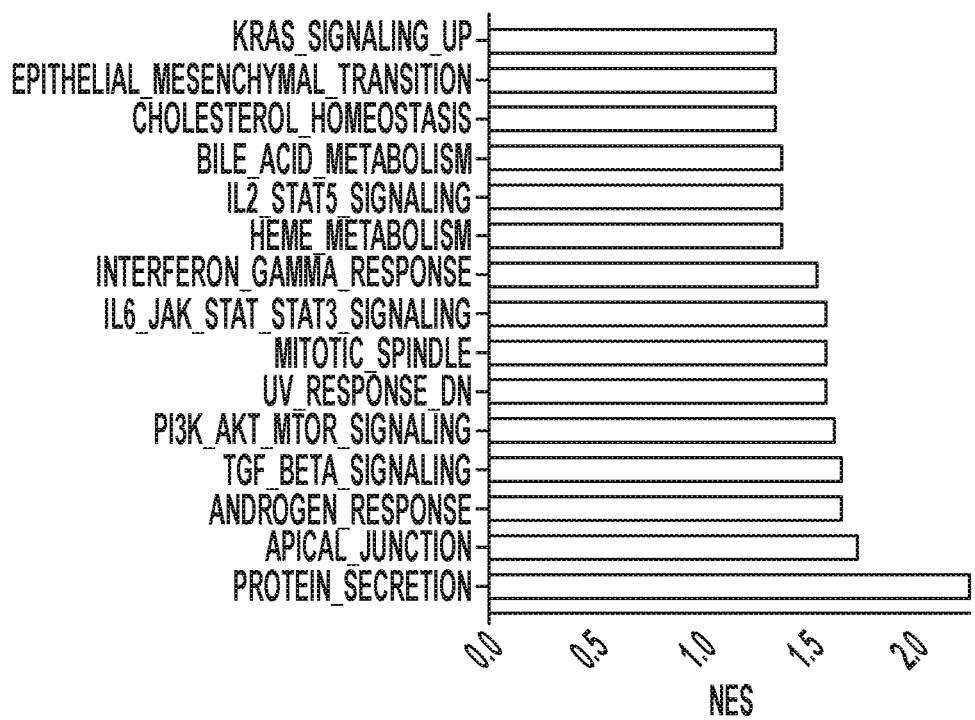
Figure 55:
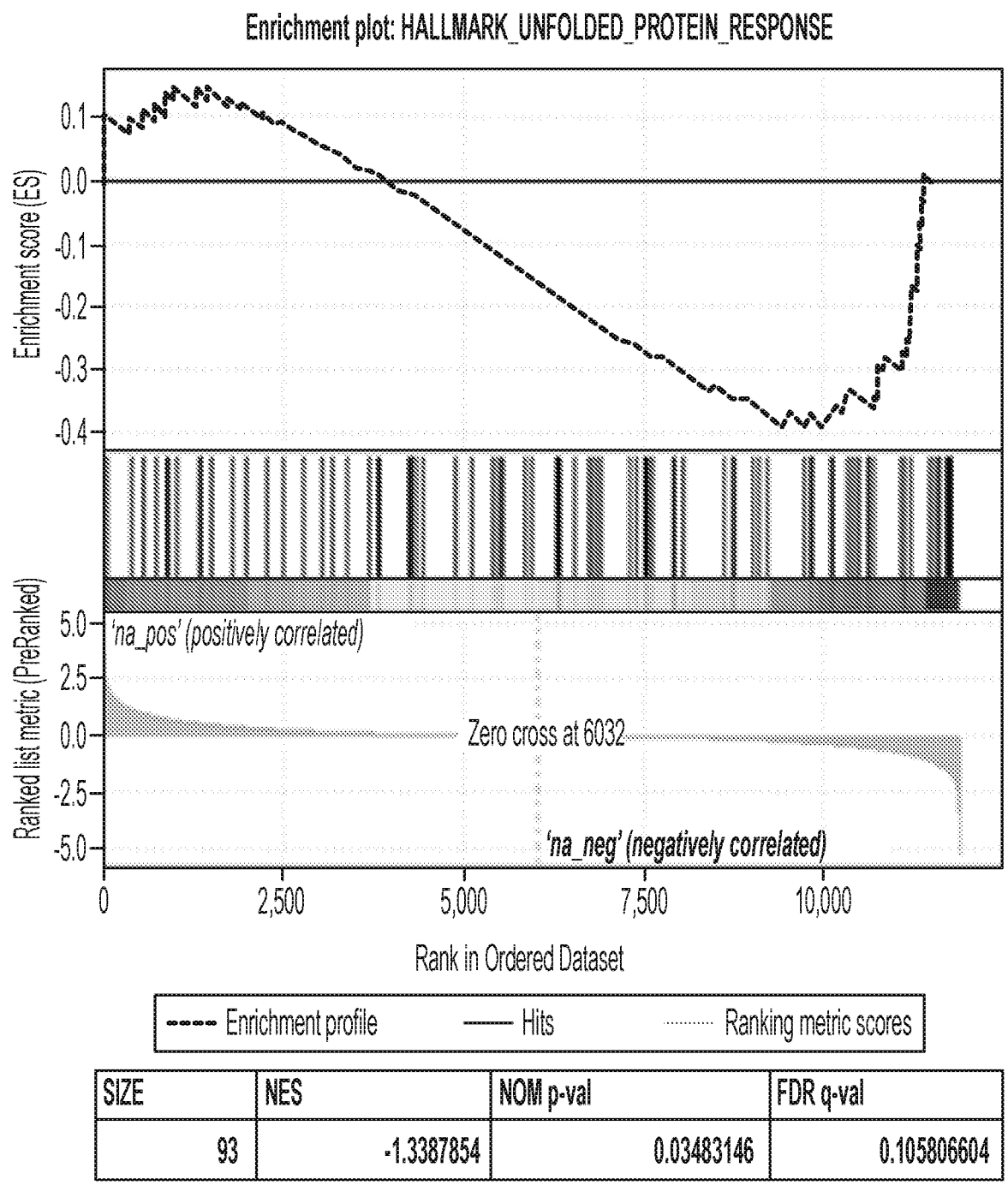
Figure 55:
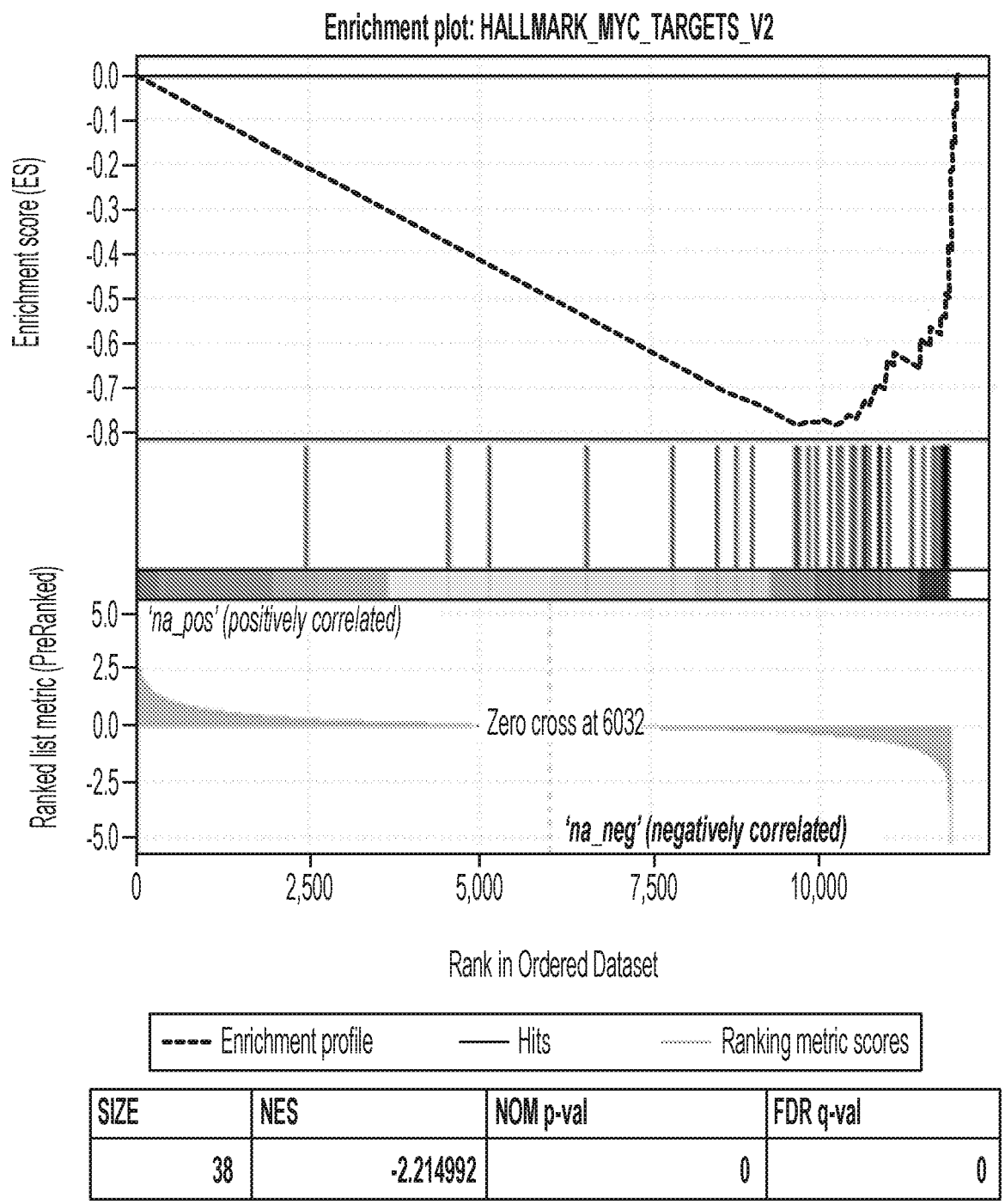
Figure 55:
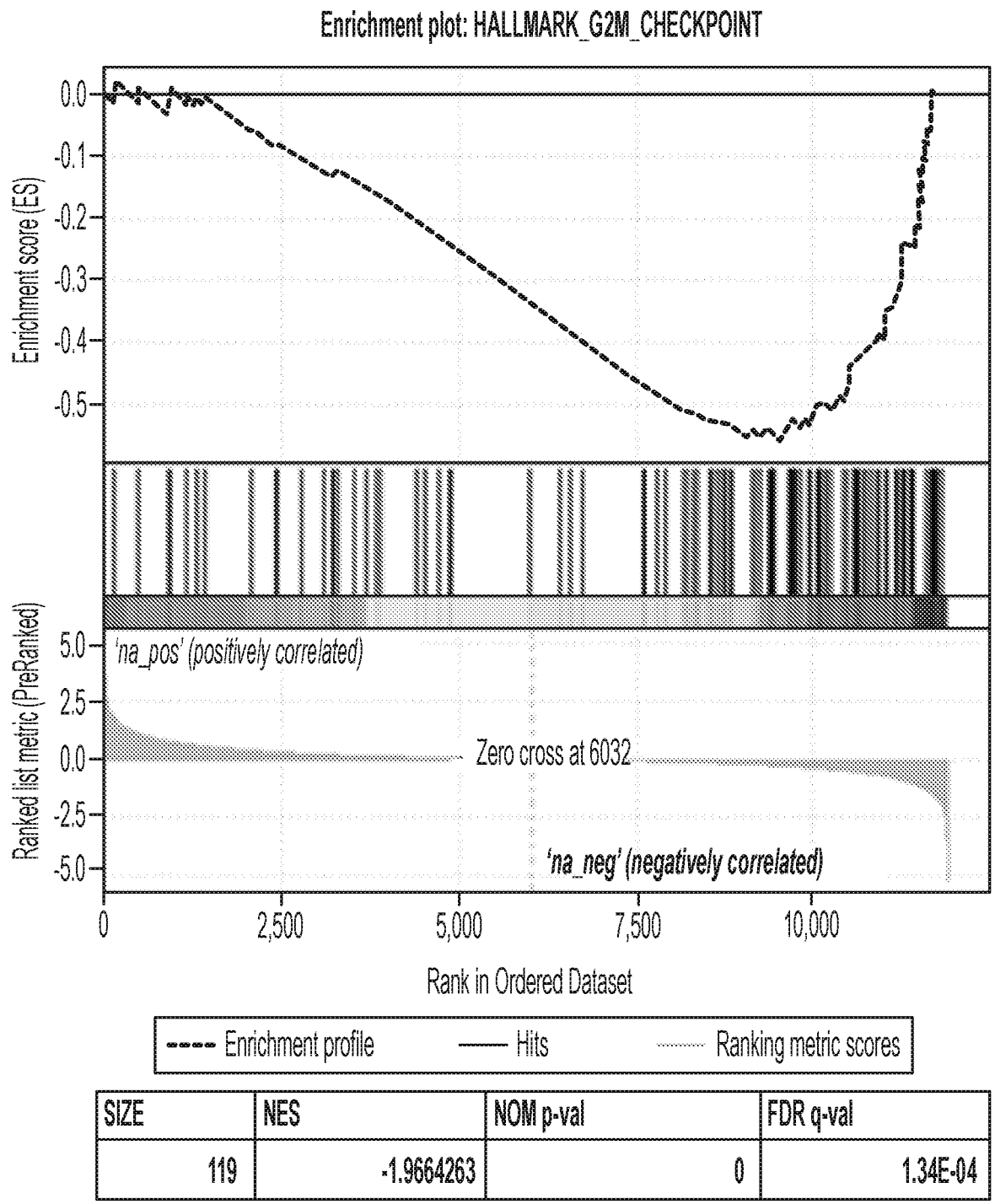
Figure 55:
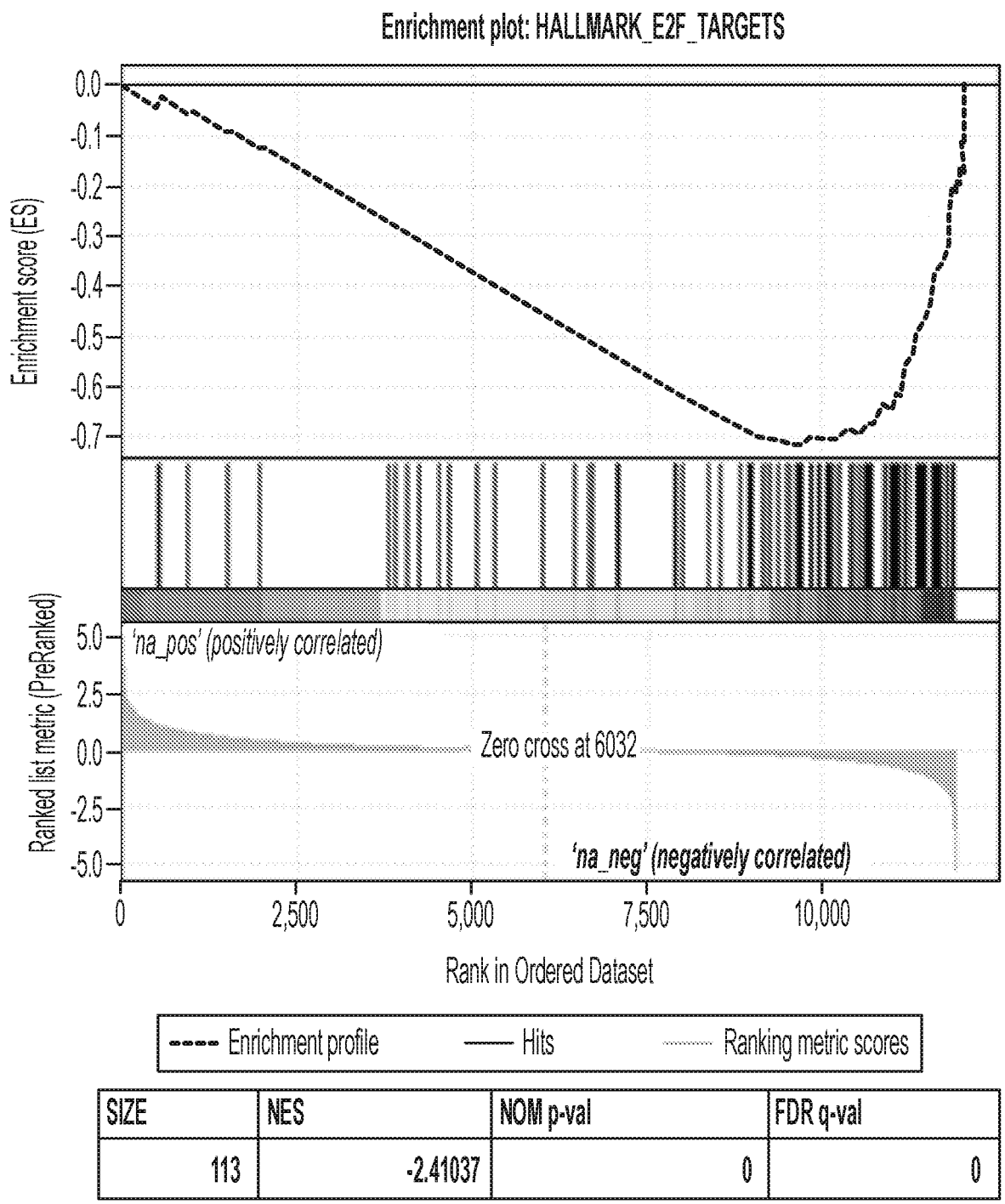
Figure 55:
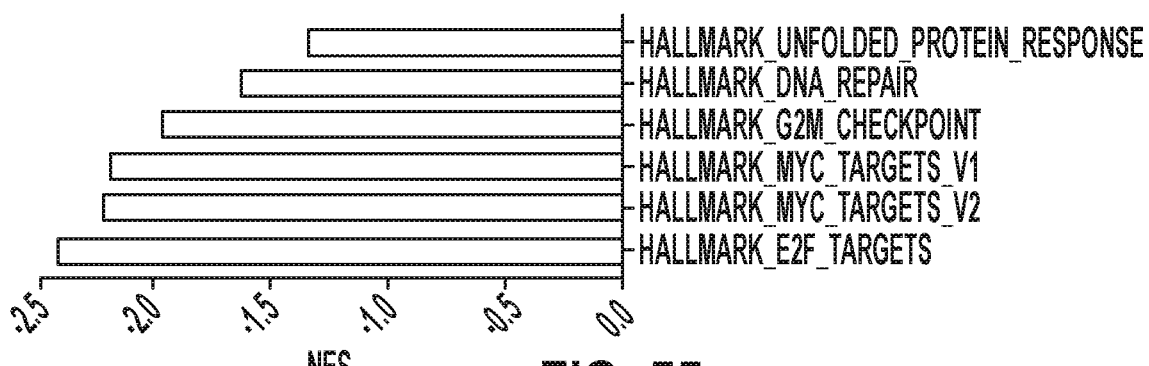

FIG. 55A shows GSEA of $C^{PDX}$;$R^{LSL}$;F organoids identified enrichment in ERBB signaling. FIGS. 55B and 55C show GSEA of differentially expressed genes from the RNAseq analyses of $C^{PDx}$;$R^{LSL}$;F organoids. Depicted are bar graphs of the normalized enrichment score (NES) for pathways with p<0.05 and FDR<0.15 and selected GSEA plots from the Hallmarks of Cancer gene sets that were enriched (FIG. 55B) or depleted (FIG. 55C) following Dox treatment of $C^{PDX}$;$R^{LSL}$;F organoids.

Figure 56:
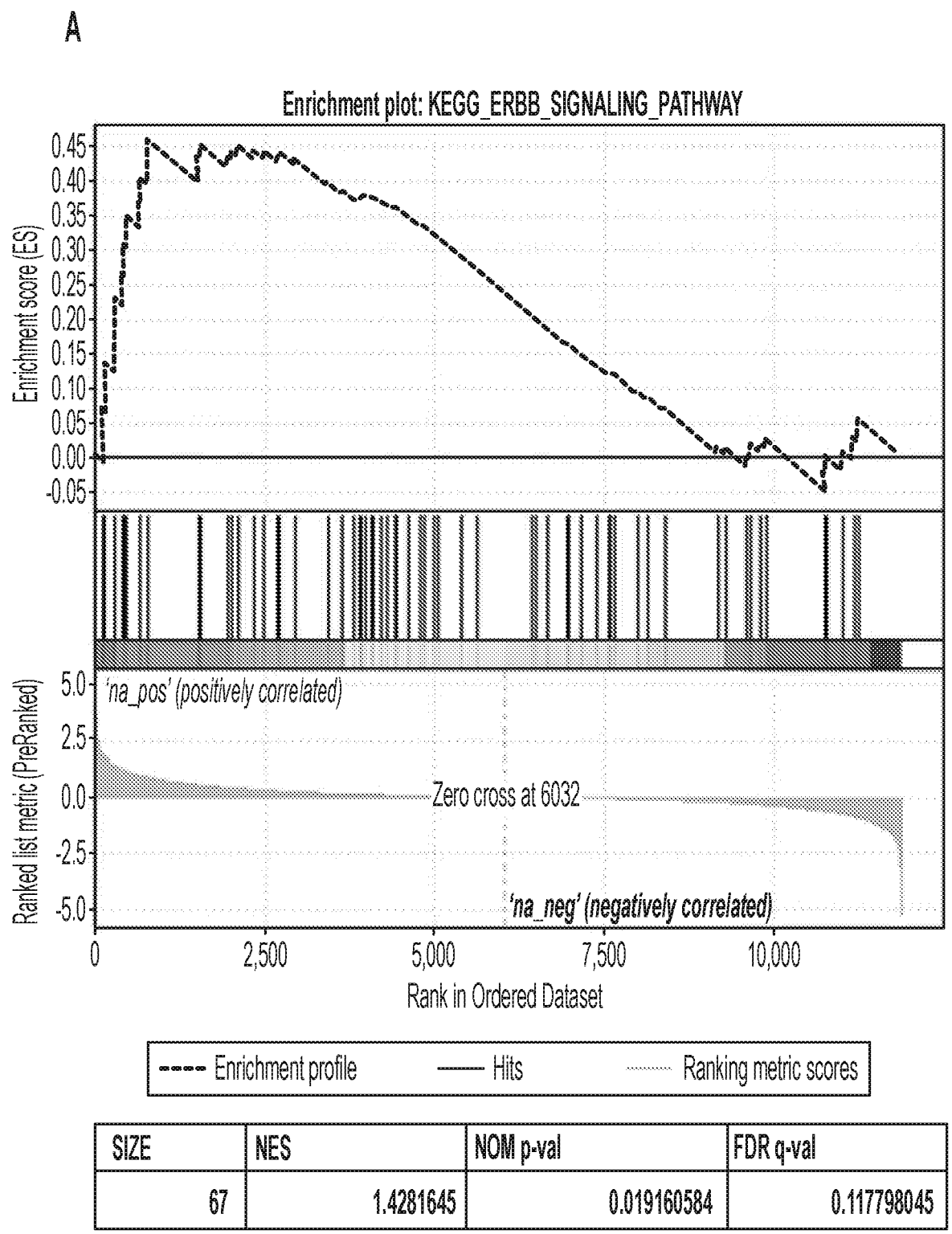
Figure 56:
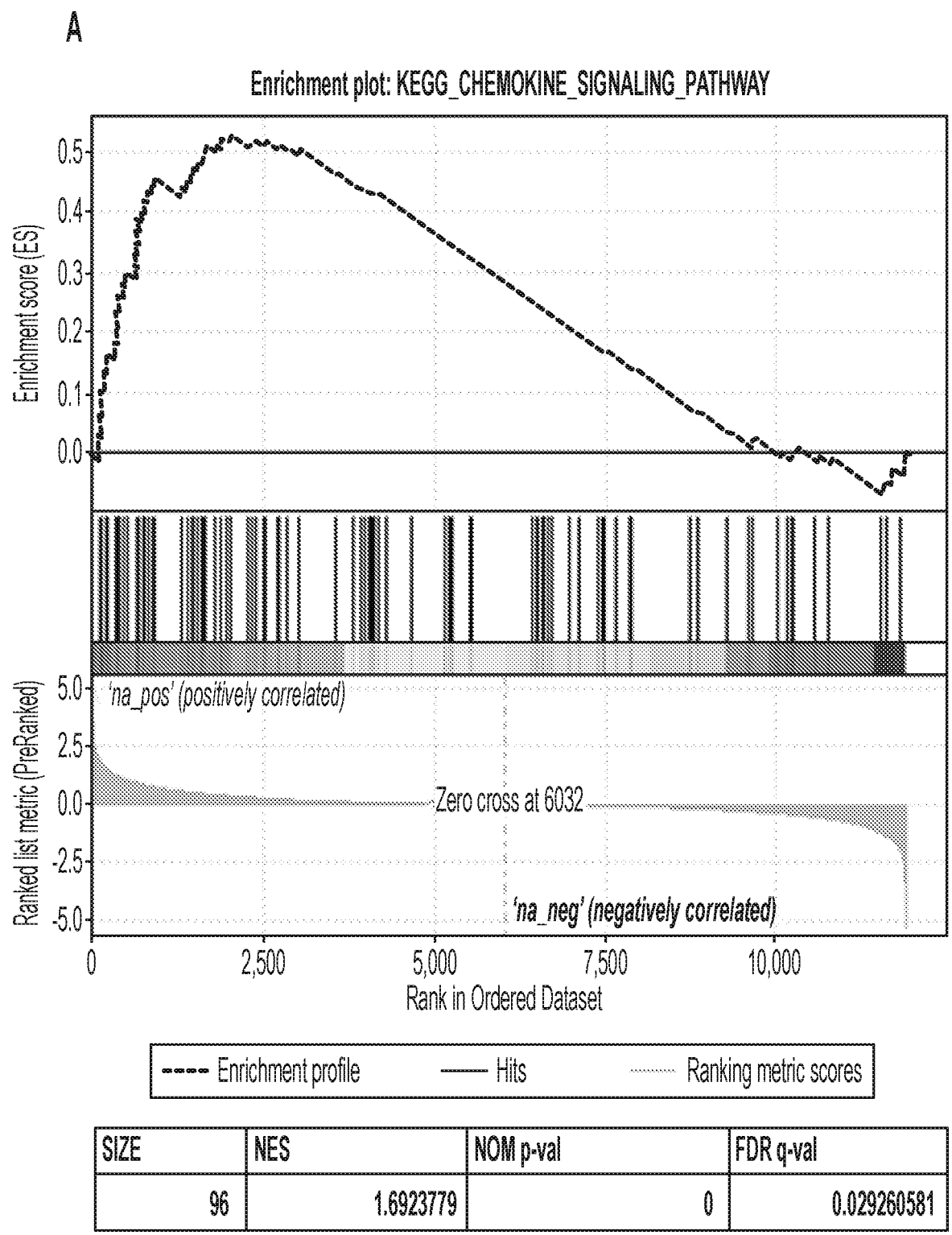
Figure 56:
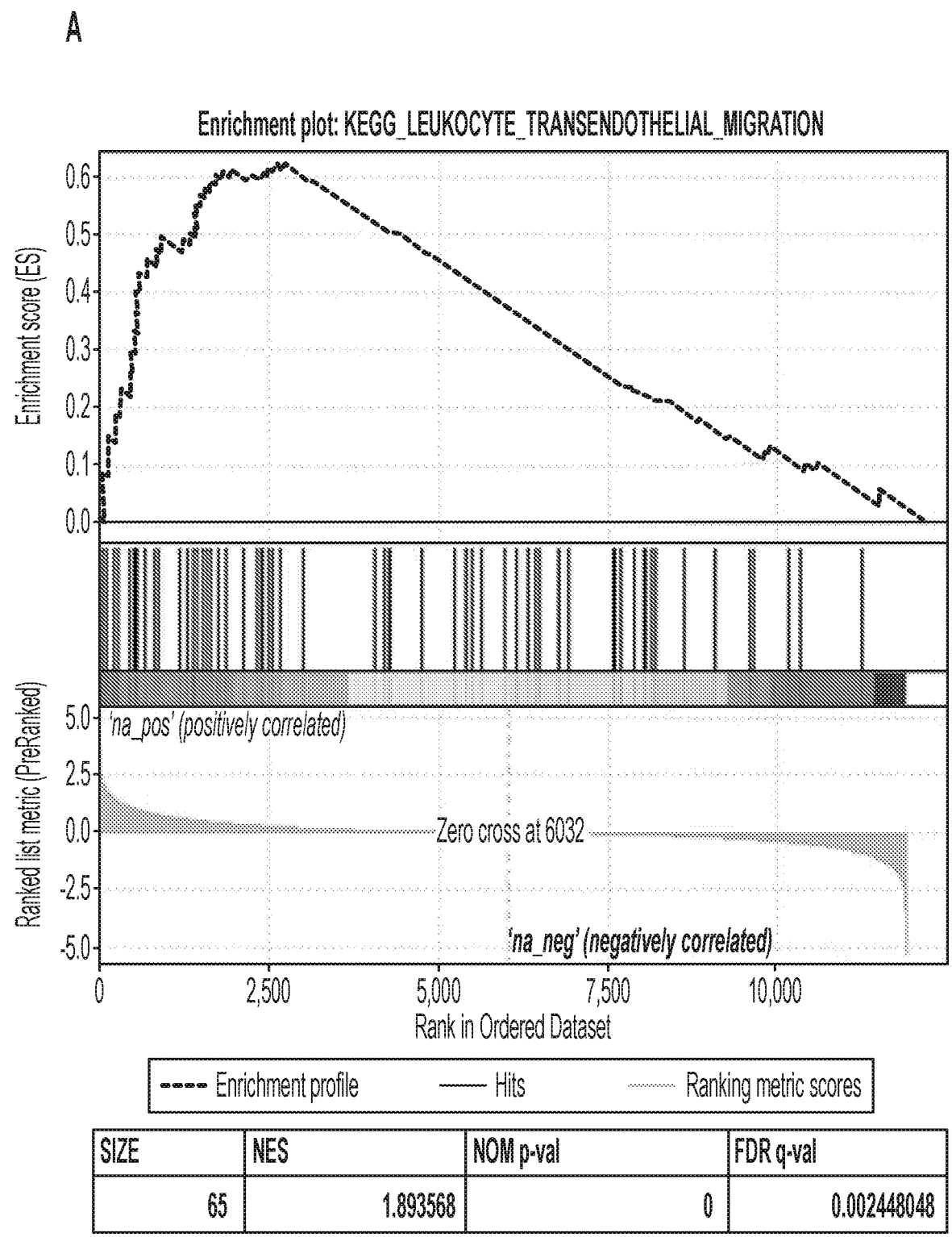
Figure 56:
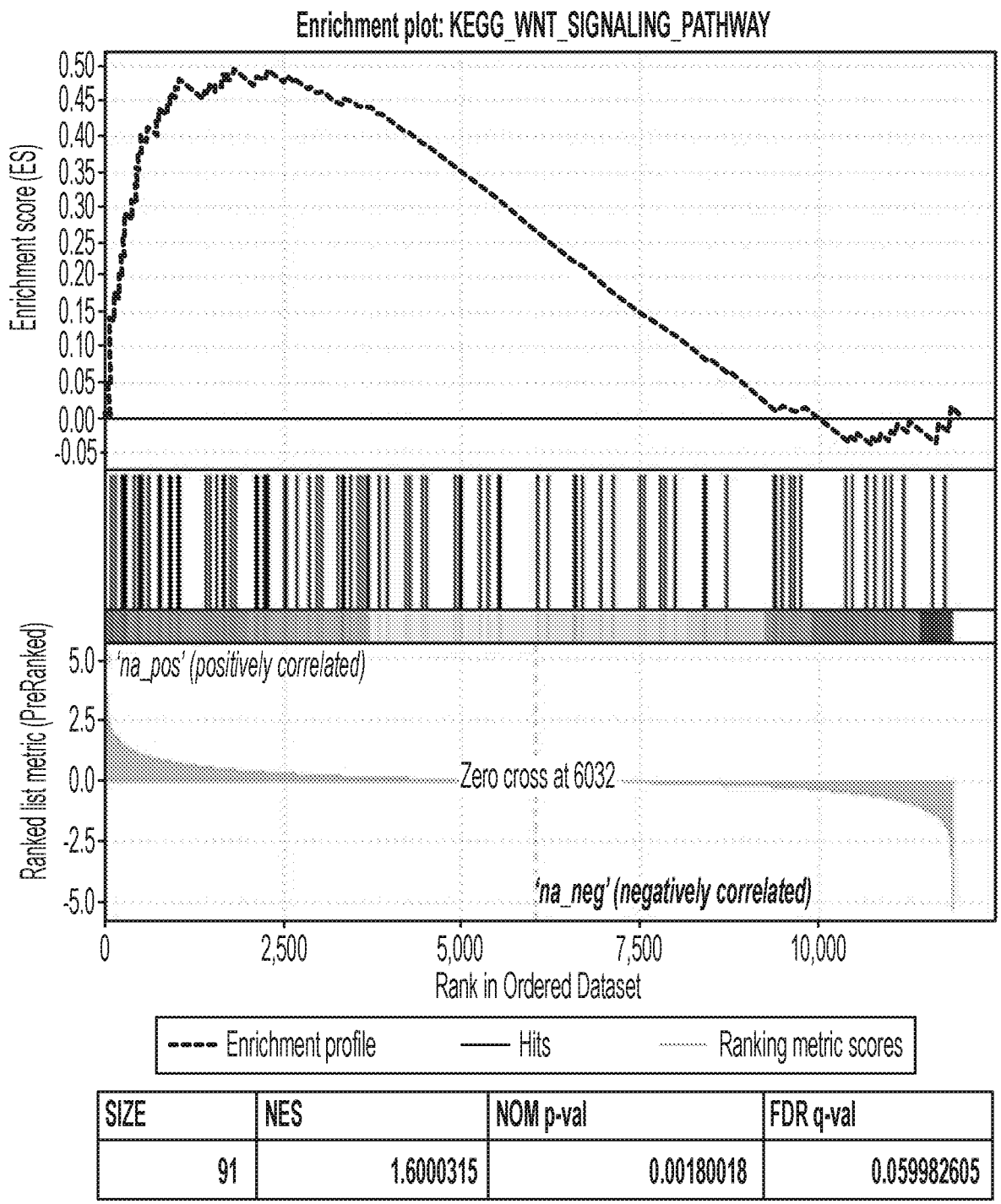
Figure 56:
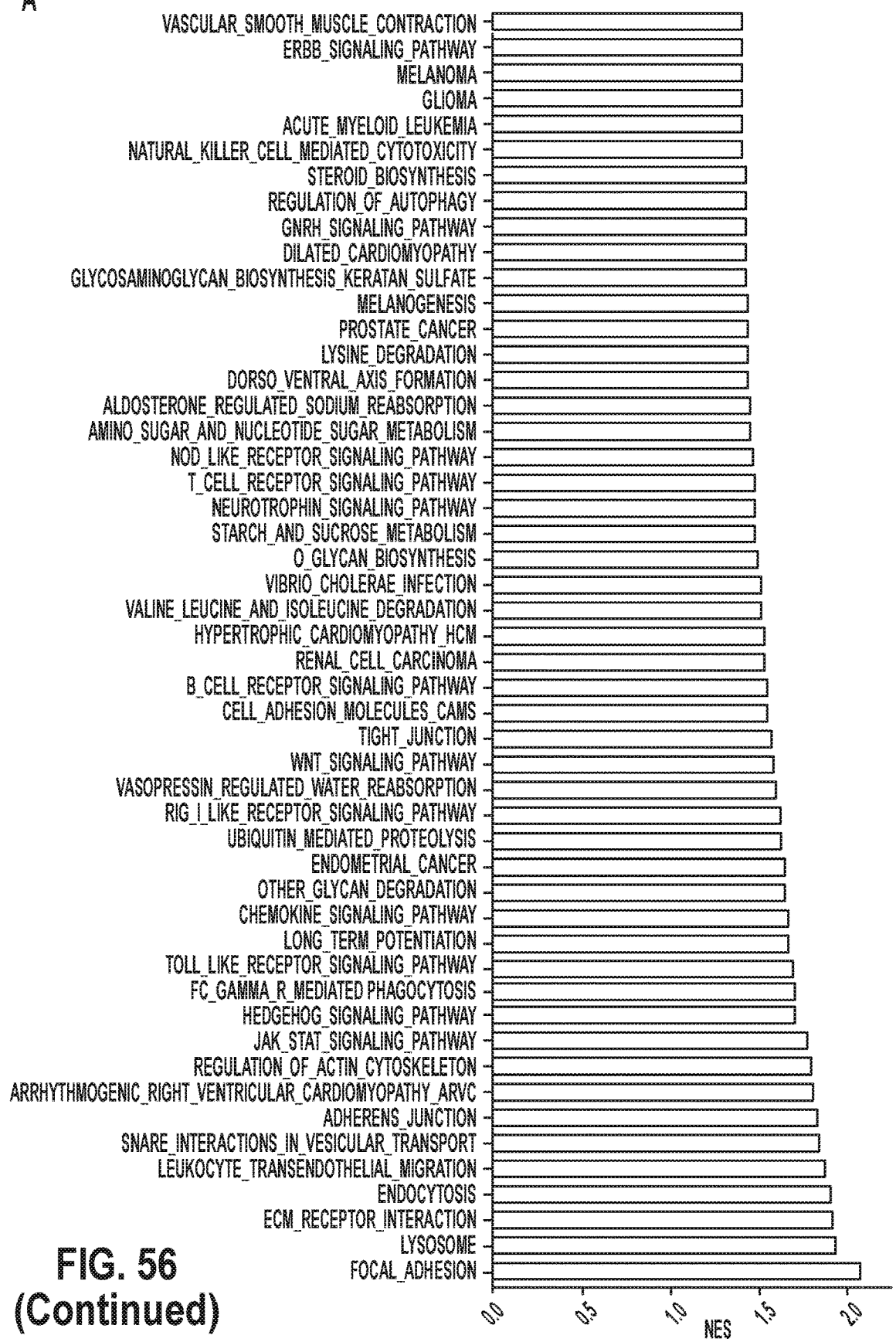
Figure 56:
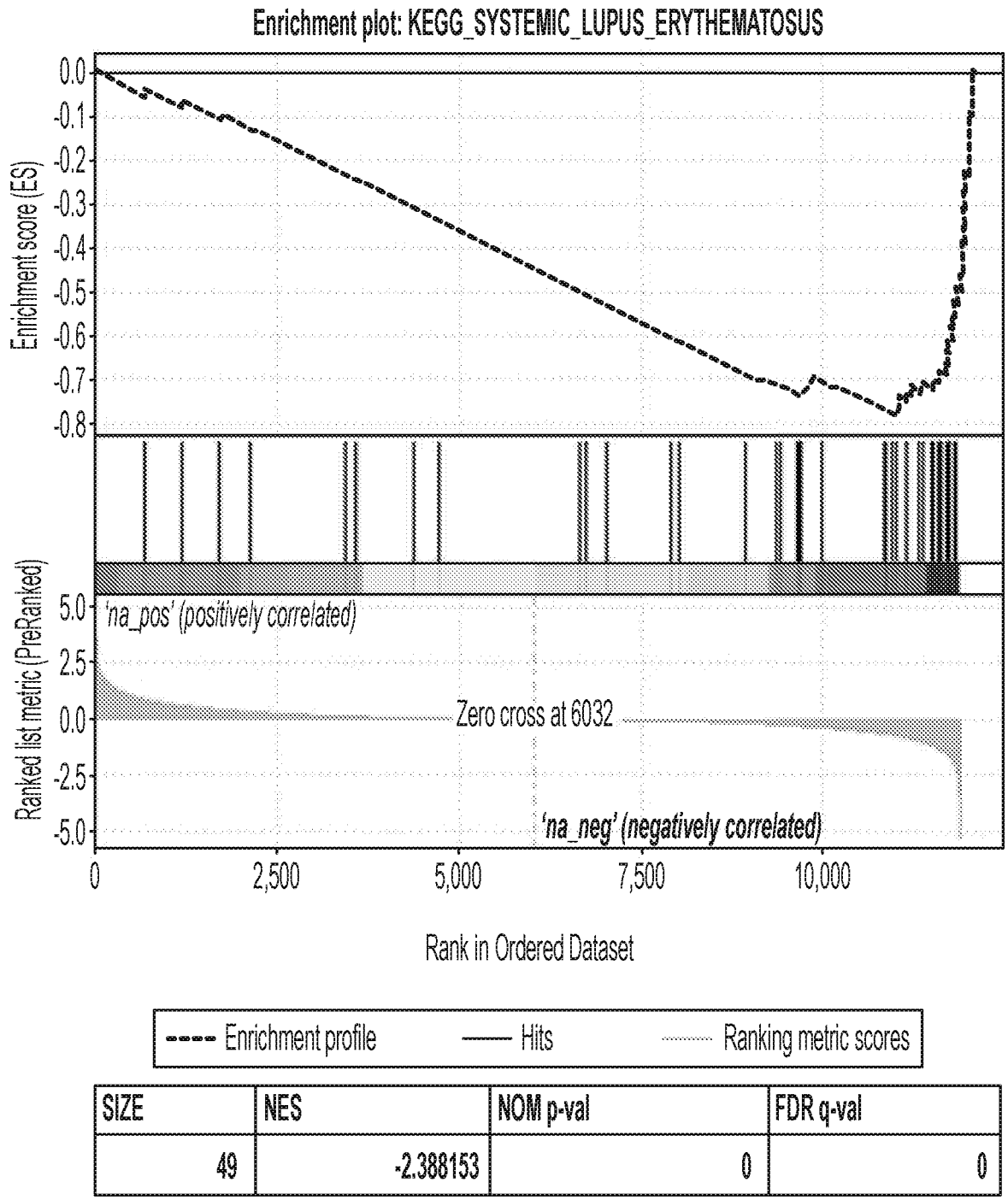
Figure 56:
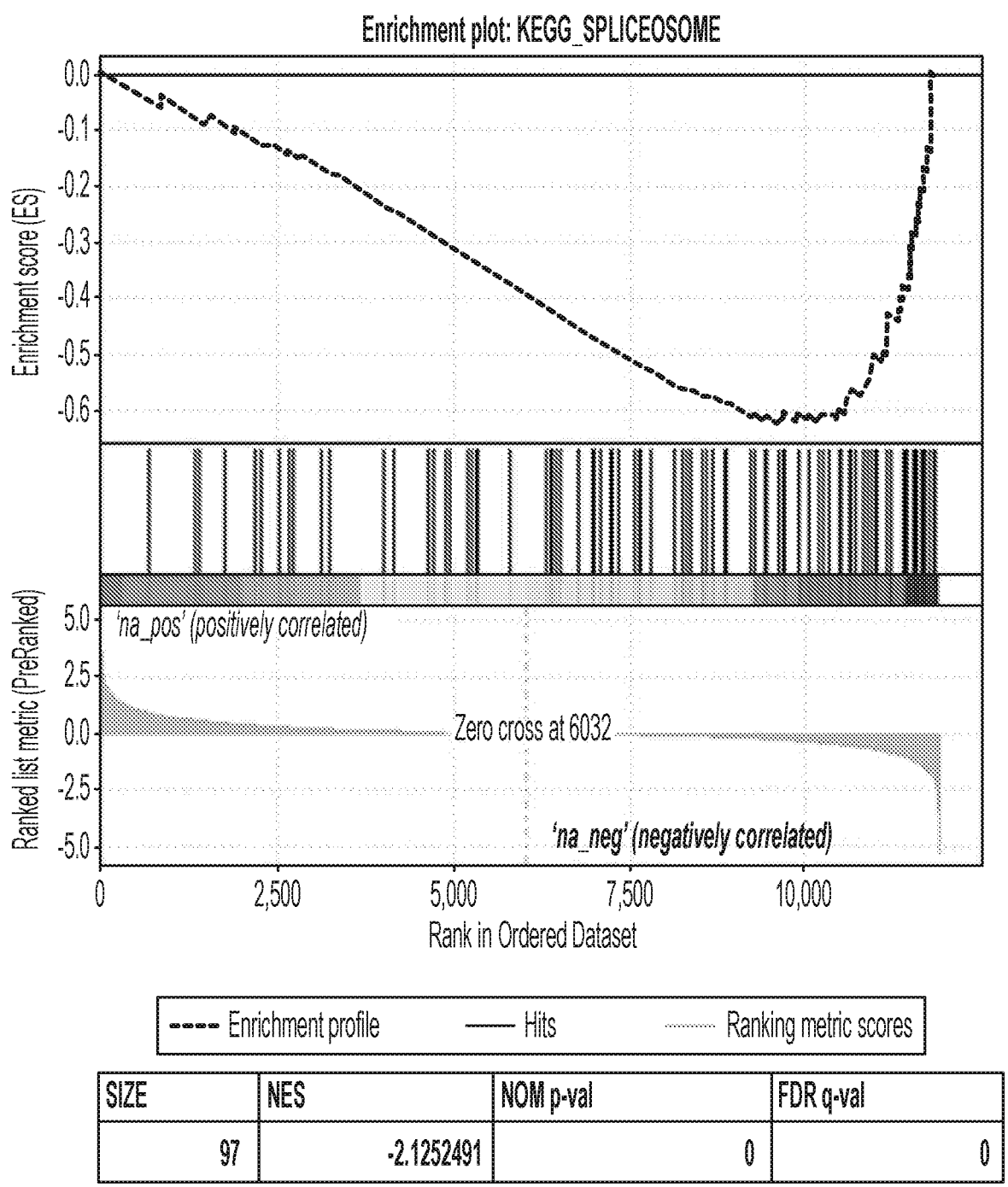
Figure 56:
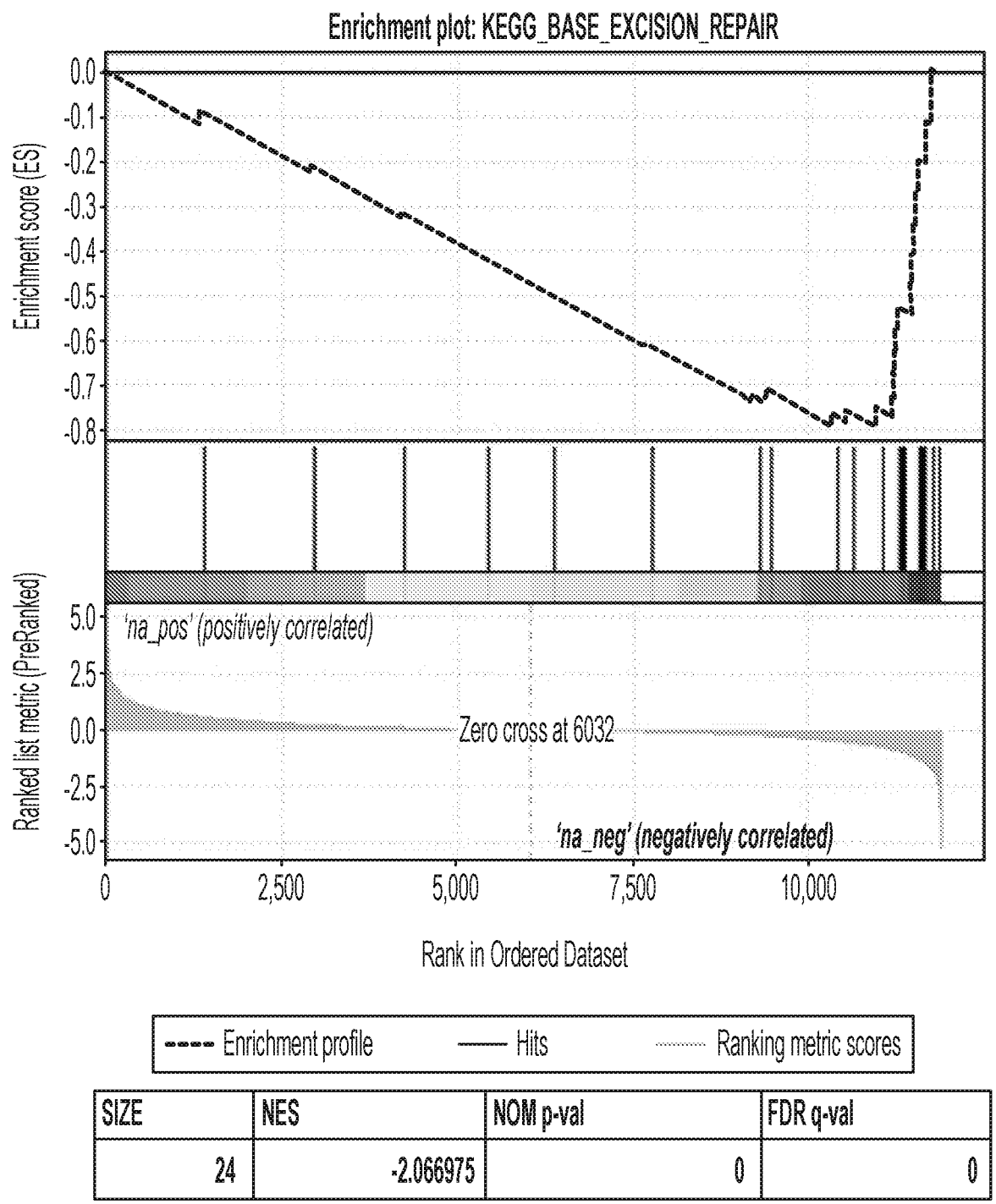
Figure 56:
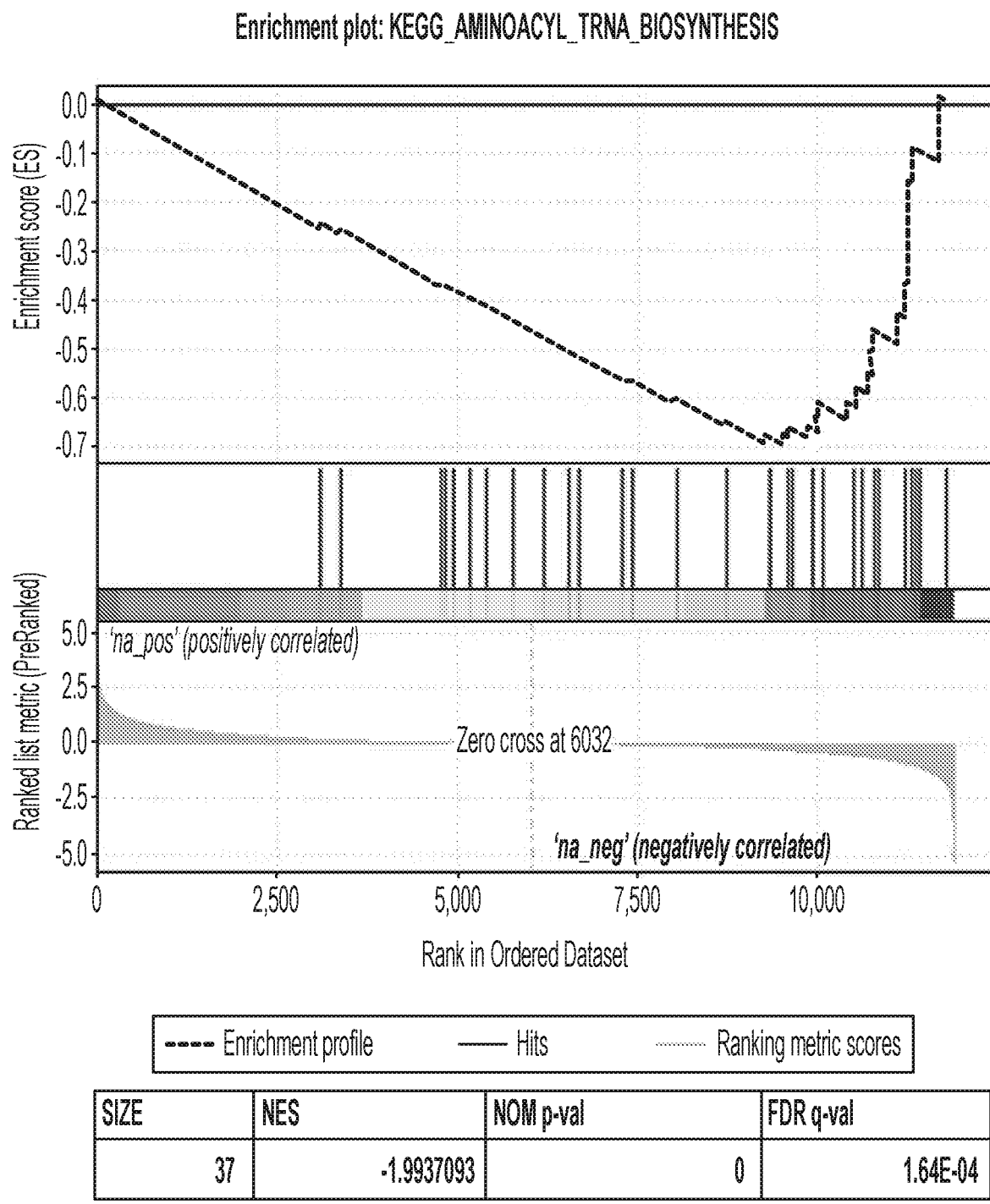
Figure 56:
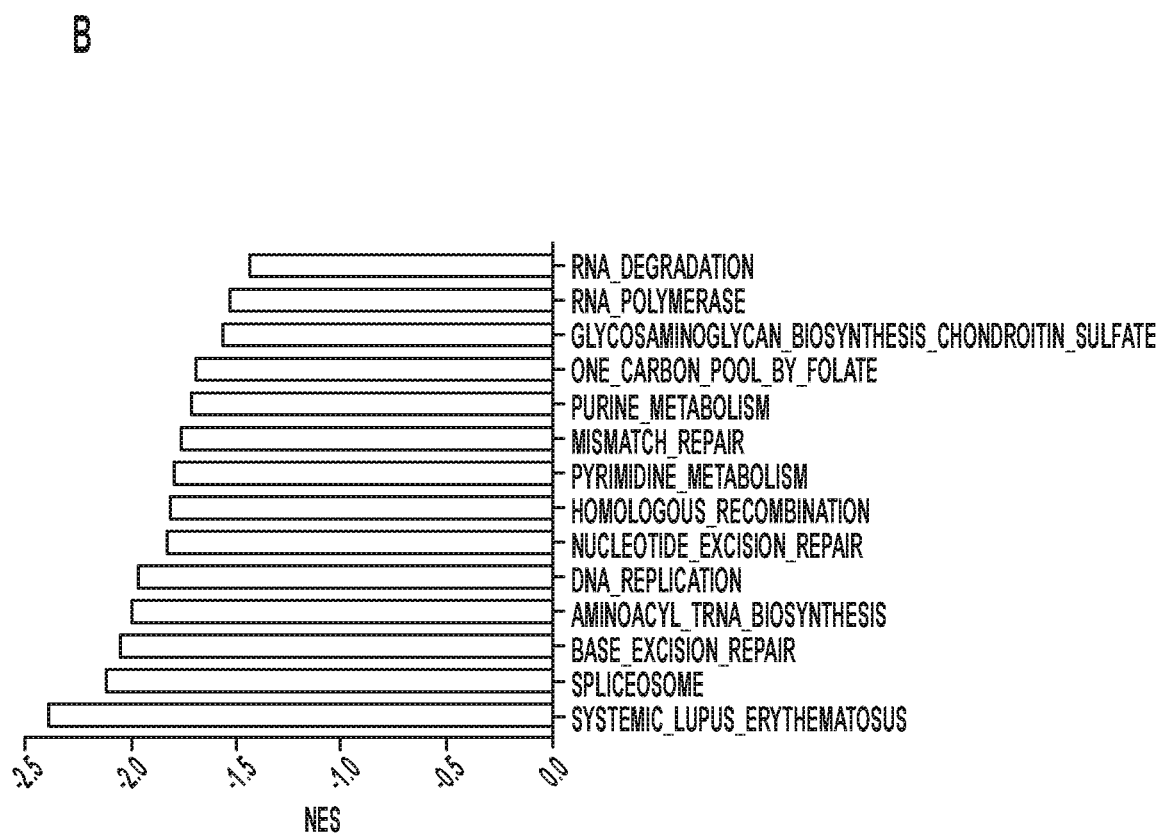

FIGS. 56A-56B show GSEA of differentially expressed genes from the RNAseq analyses of $C^{PDX}$;$R^{LSL}$;F organoids. Depicted are bar graphs of the normalized enrichment score (NES) for pathways with p<0.05 and FDR<0.15 and selected GSEA plots from the KEGG pathway gene sets that were enriched (FIG. 56A) or depleted (FIG. 56B) following Dox treatment of $C^{PDX}$;$R^{LSL}$;F organoids.

Figure 57:
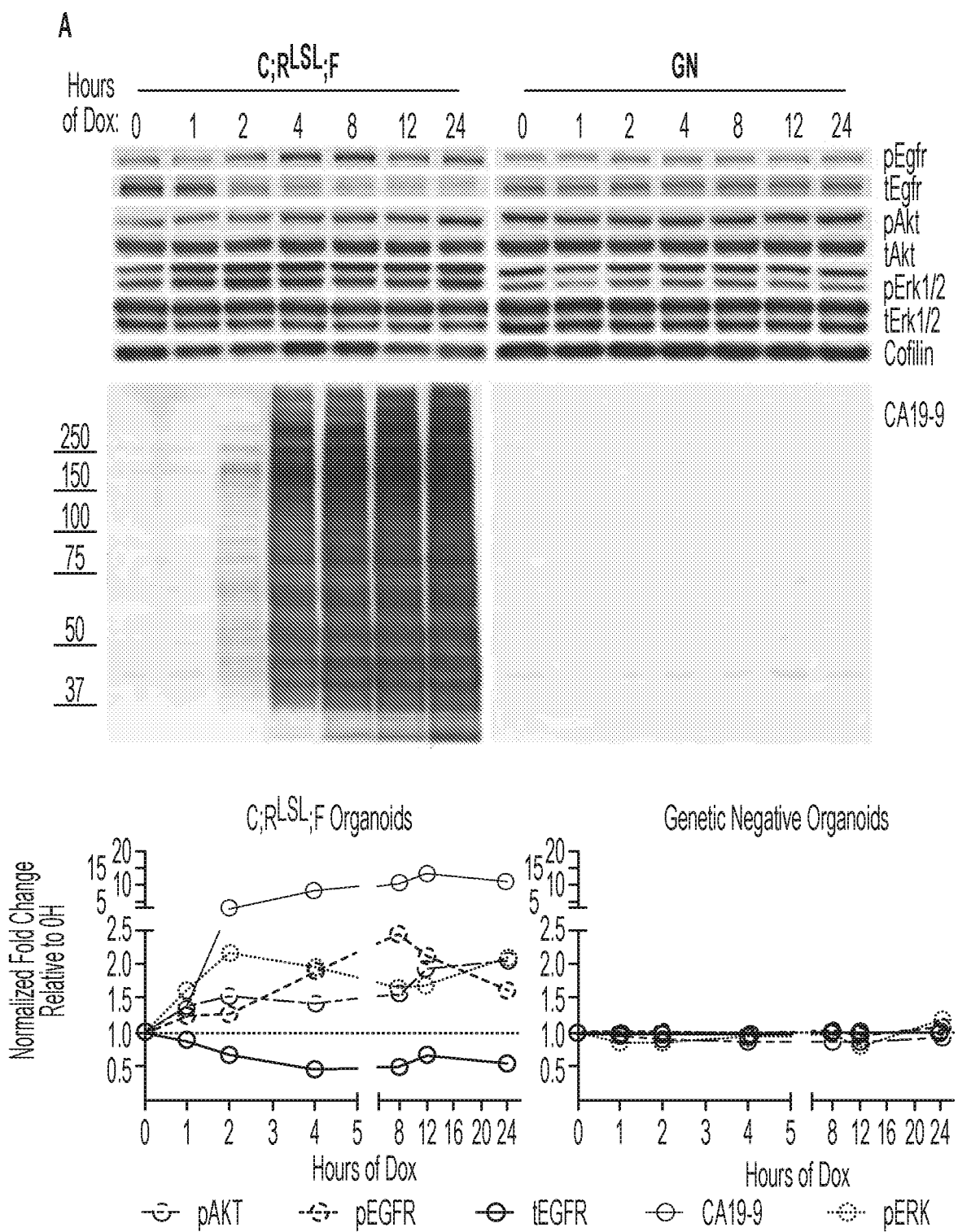
Figure 57:
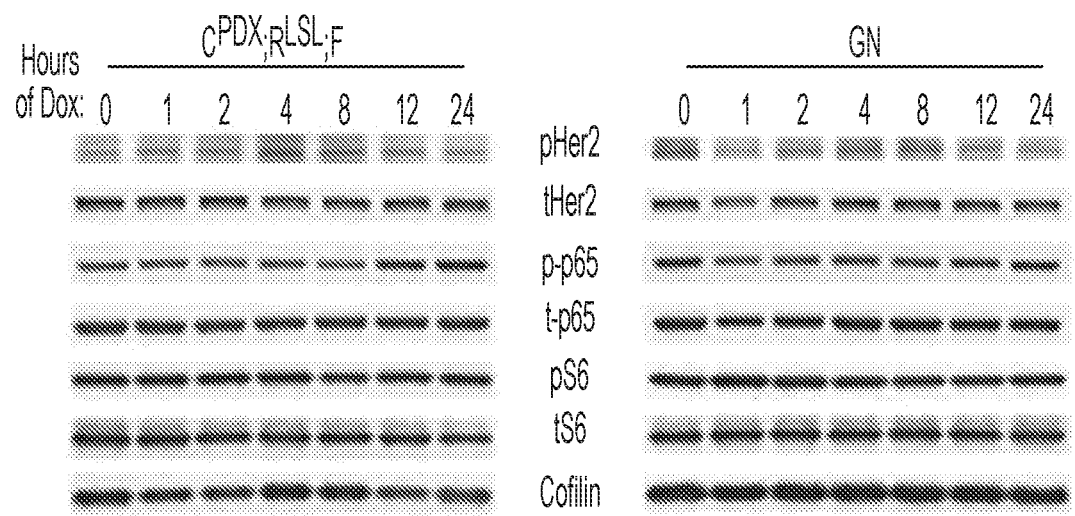
Figure 57:
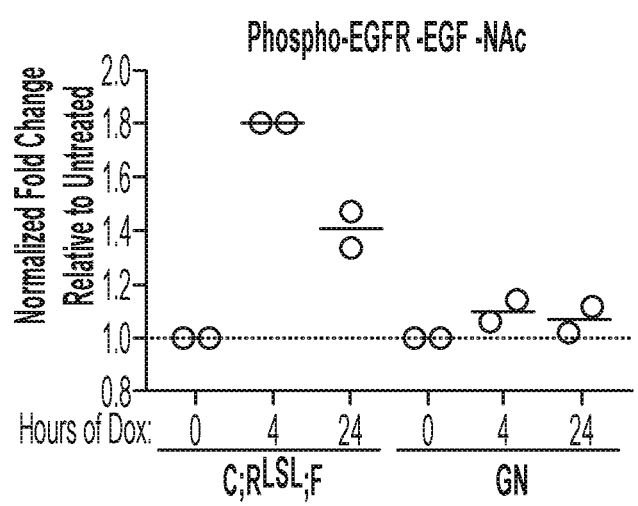
Figure 57:
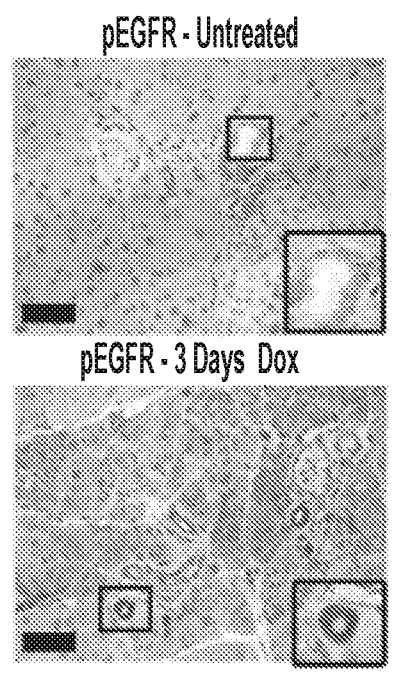
Figure 58:
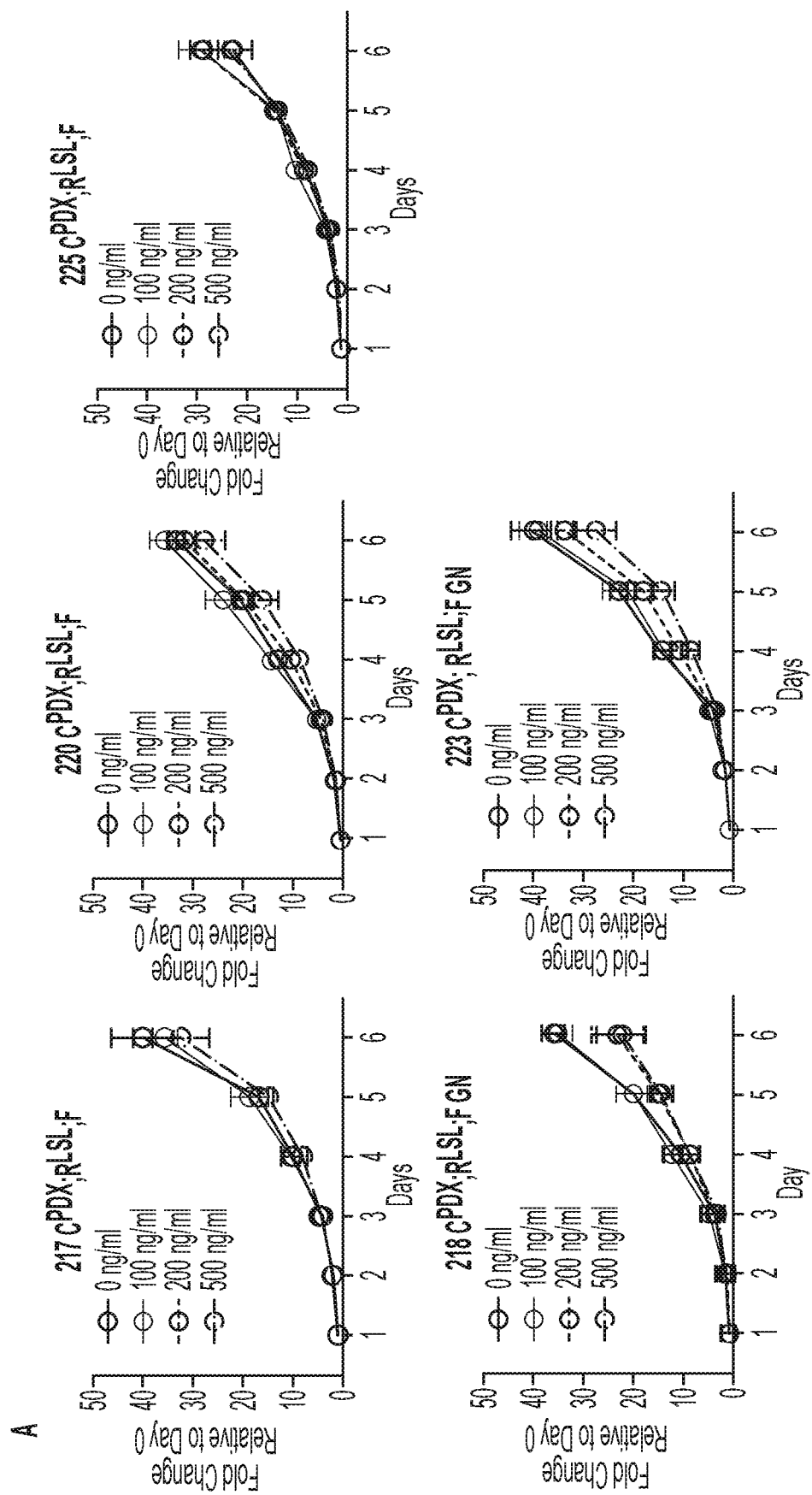
Figure 58:
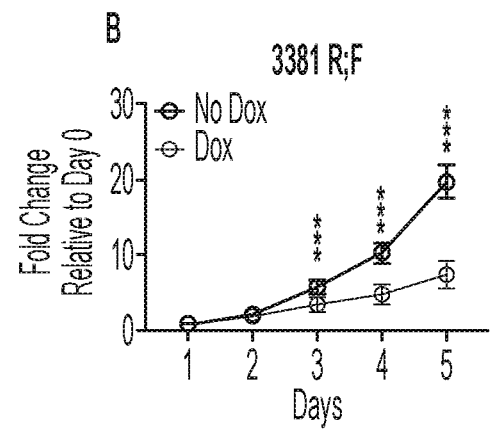
Figure 58:
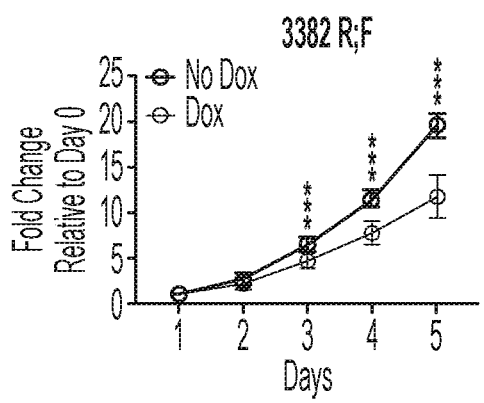
Figure 58:
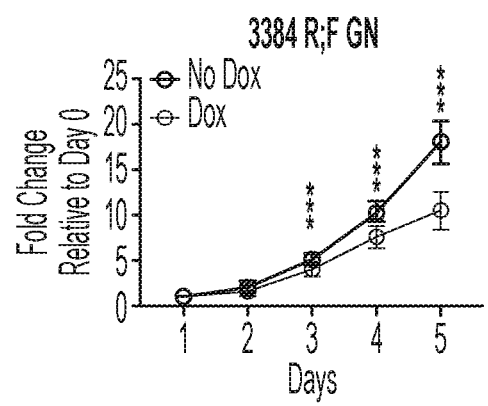
Figure 58:
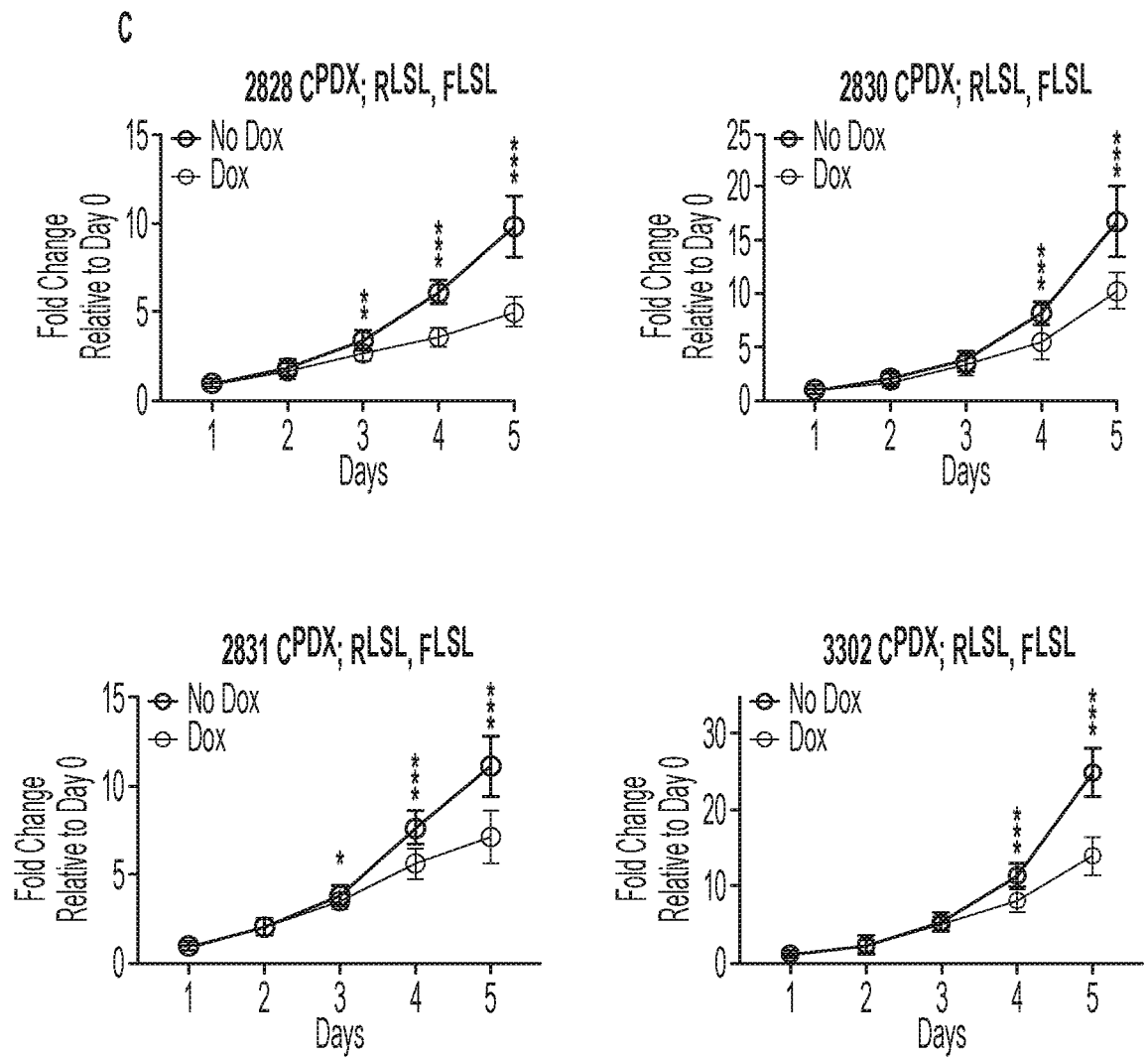
Figure 58:
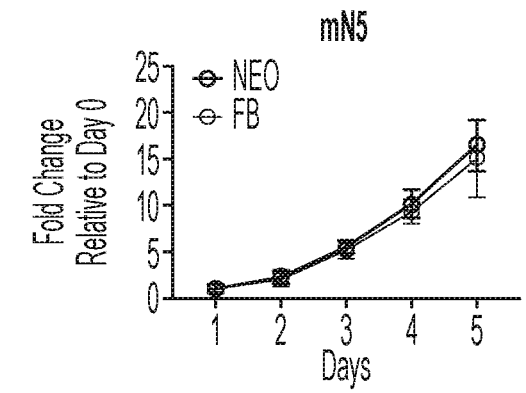
Figure 58:
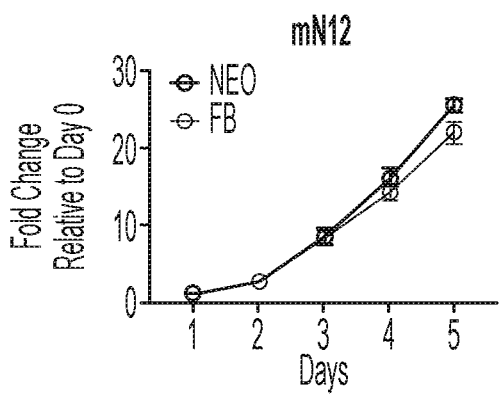
Figure 58:
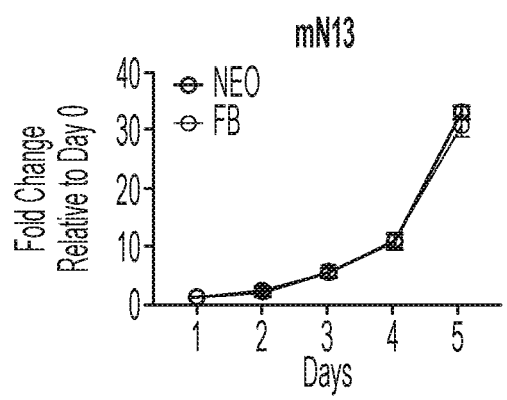

FIG. 57A shows $C^{PDX}$;$R^{LSL}$;F organoids (n=3 biological replicates) and genetically negative organoids (GN, n=2 biological replicates) as evaluated by immunoblot for the activation of signaling pathways following treatment with Dox. Blots are representative of three technical replicates, three biological replicates of $C^{PDX}$;$R^{LSL}$;F organoids and two biological replicates of GN organoids. Quantification was performed relative to the untreated time point after normalization to Cofilin. FIGS. 57B-57C show organoid pathway activation following induction of CA19-9 expression. FIG. 57B shows normal ductal organoids from $C^{PDX}$;$R^{LSL}$;F and genetically negative littermate controls (GN) as evaluated by immunoblot following treatment with Dox (Hours). FIG. 57C shows normal ductal organoids from $C^{PDX}$;$R^{LSL}$;F (n=2) and genetically negative littermate controls (GN, n=2) as evaluated by immunoblot following treatment with Dox (Hours) in organoid media lacking EGF and NAC. FIG. 57D shows representative phosphorylated-EGFR immunohistochemistry (IHC) in $C^{PDX}$;$R^{LSL}$;F mice that were treated for 0 (n=4) or 3 (n=5) days with Dox. Insets are higher magnification of pancreatic ducts. Scale bars=50 μm.

FIGS. 58A-58D show organoid proliferative status following induction of CA19-9 expression. Depicted are $C^{PDX}$;$R^{LSL}$;F (FIG. 58A), R;F (FIG. 58B), $C^{PDX}$;$R^{LSL}$;$F^{LSL}$ (FIG. 58C) and constitutive CA19-9 expressing mouse normal organoids (FIG. 58D) as evaluated daily by Cell Titer Glo to evaluate growth for several days. Genetic negative controls are included for $C^{PDX}$;$R^{LSL}$;F (218, 223) and R;F (3384) organoid lines.

Figure 59:
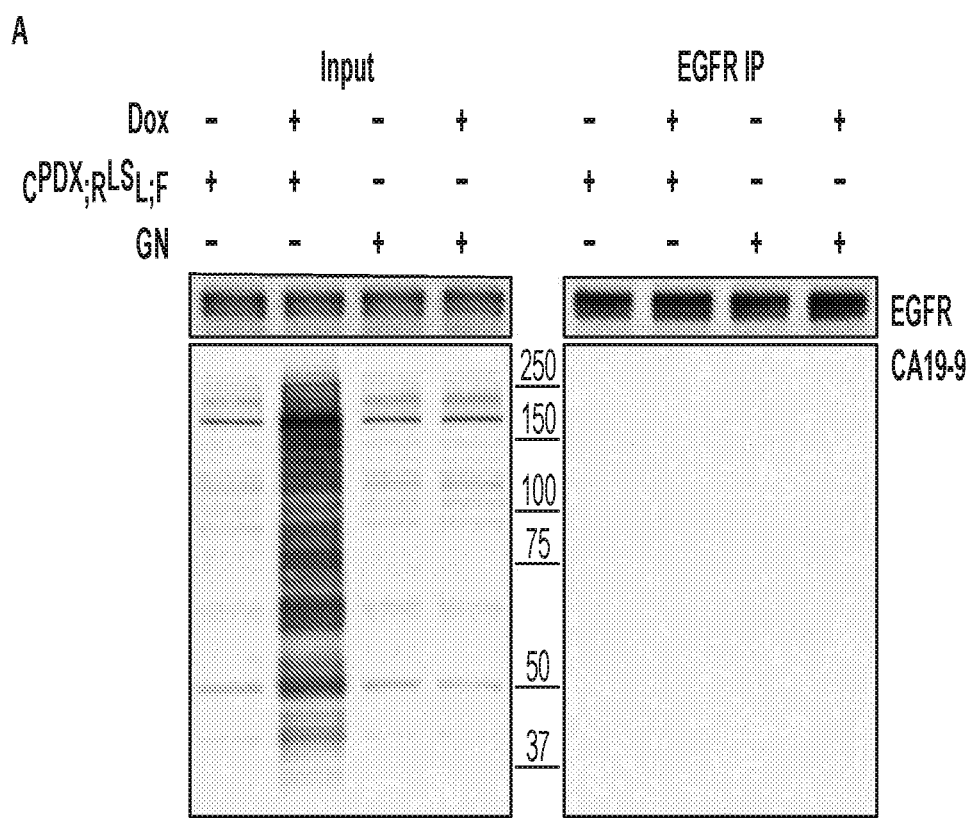
Figure 59:
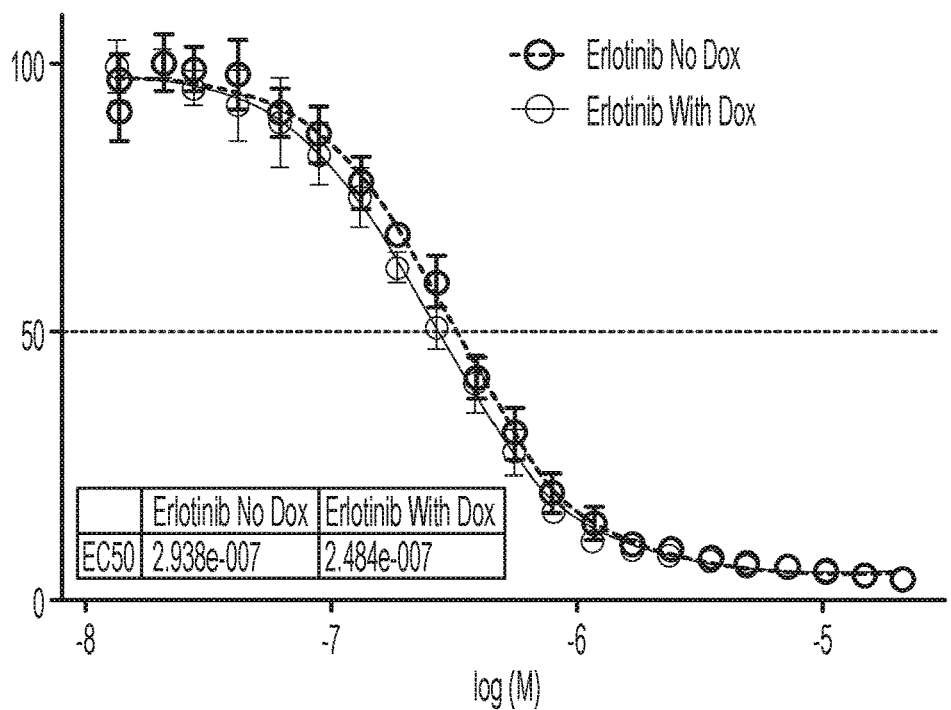
Figure 59:
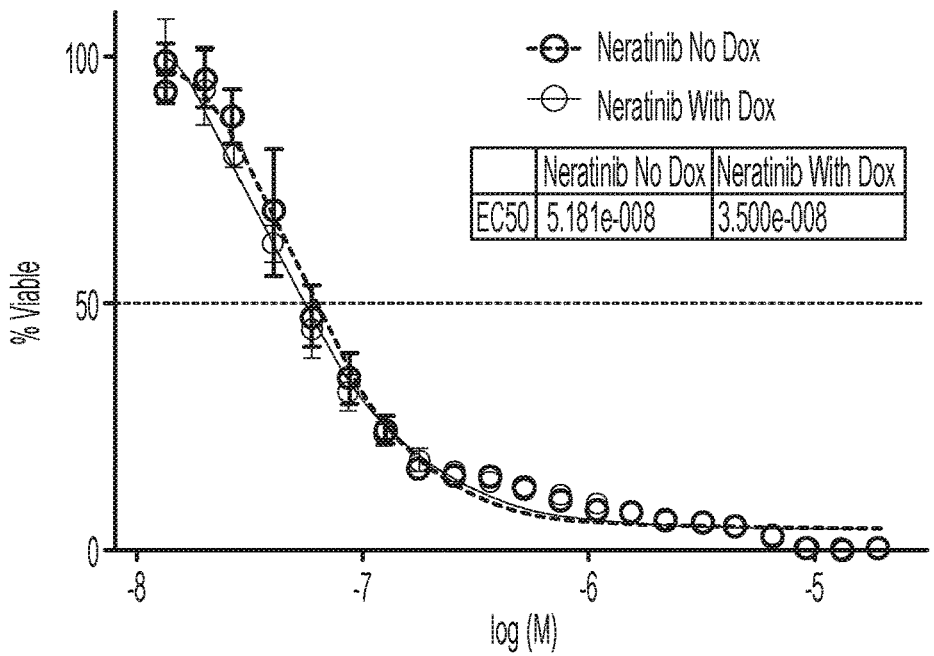
Figure 59:
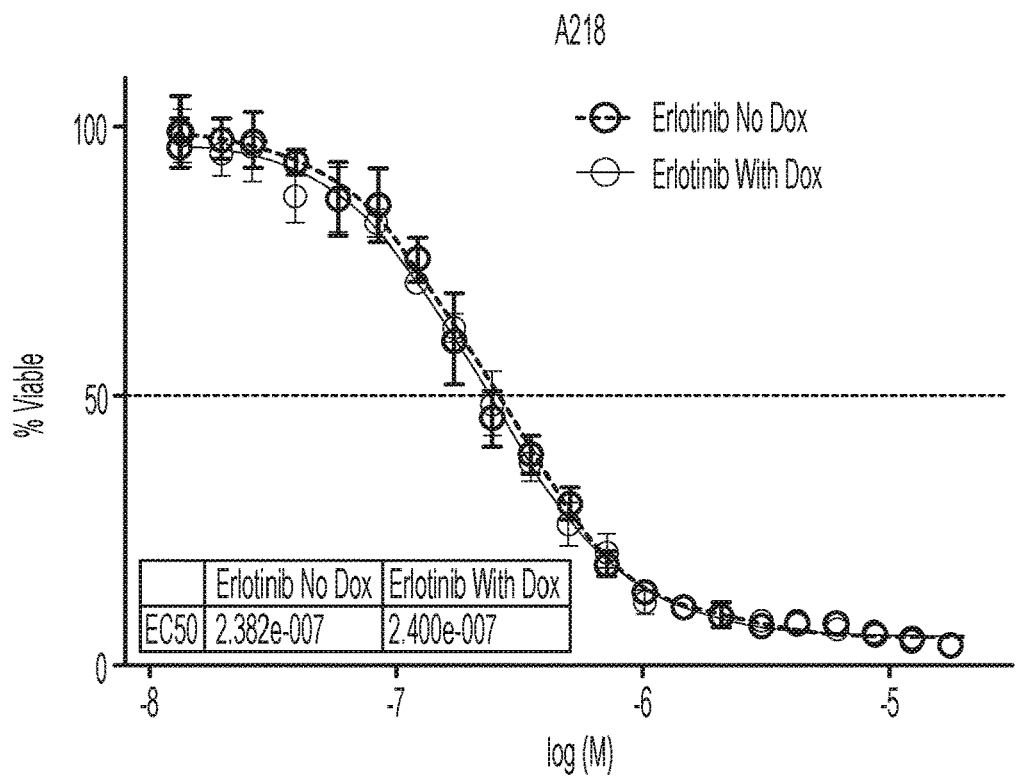
Figure 59:
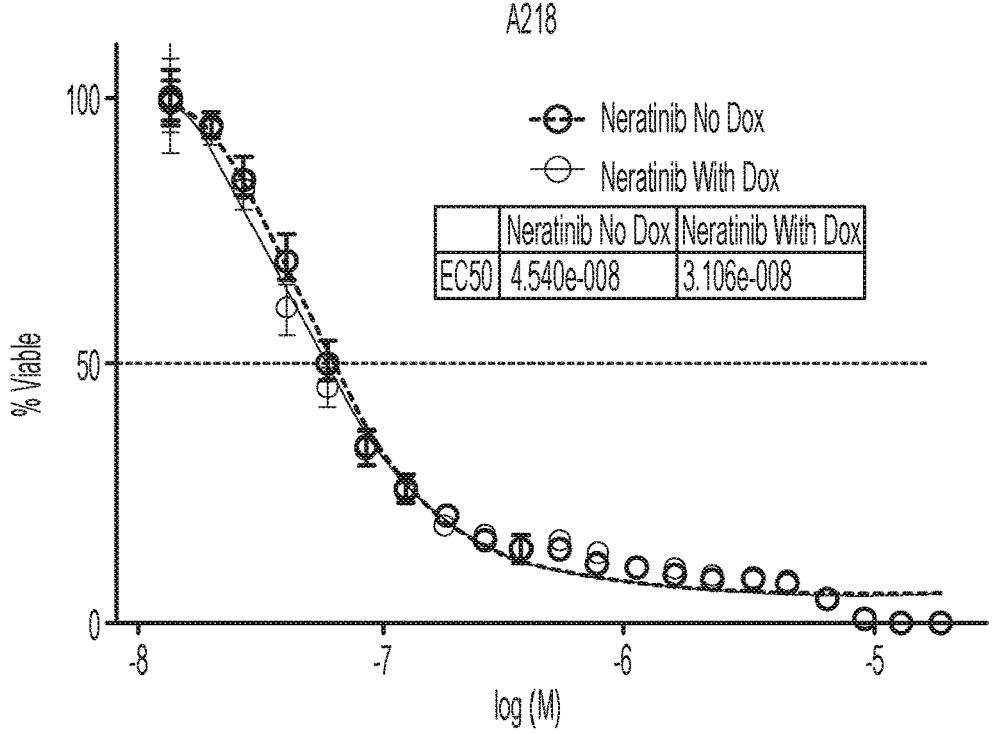
Figure 59:
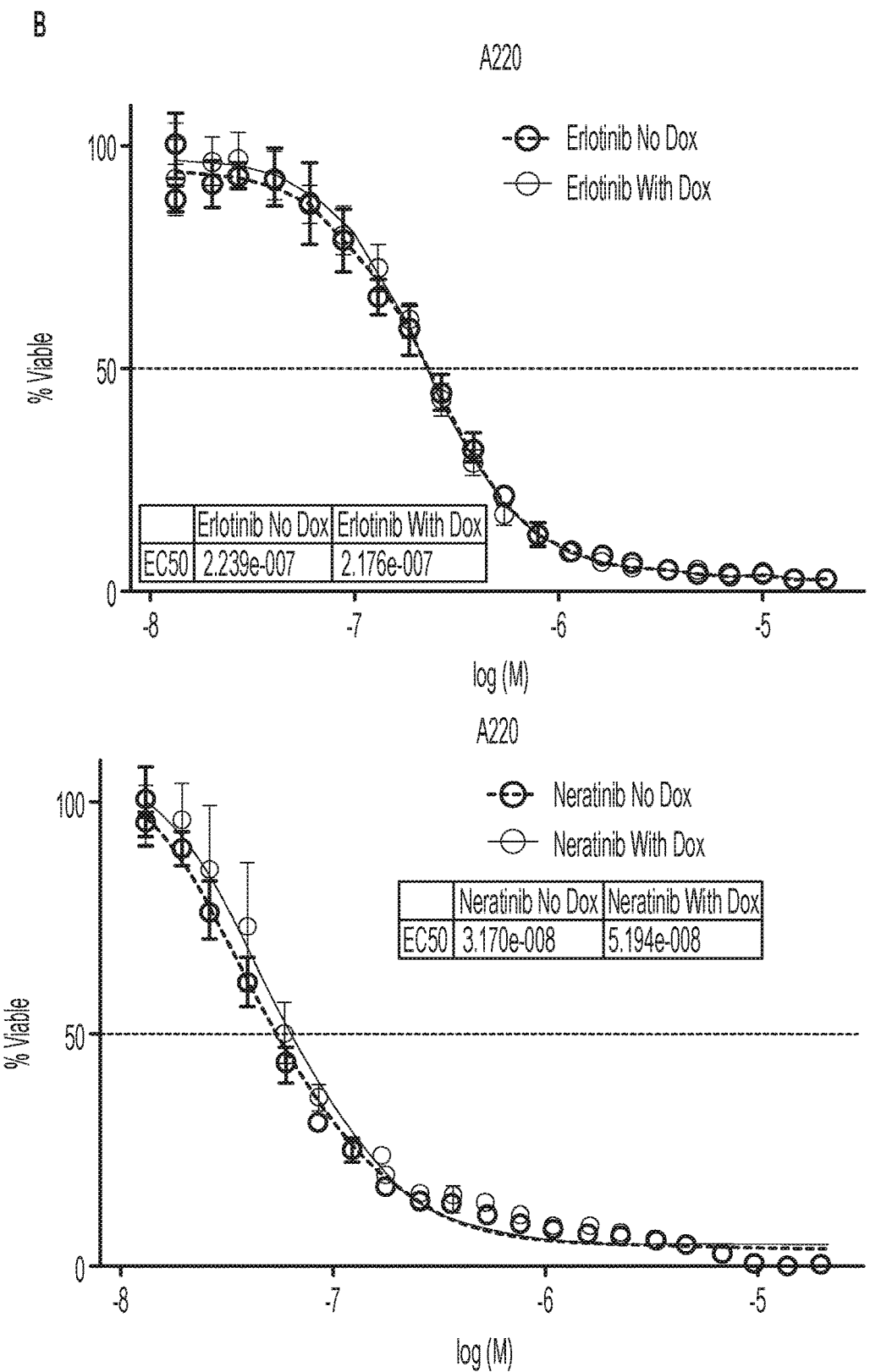
Figure 59:
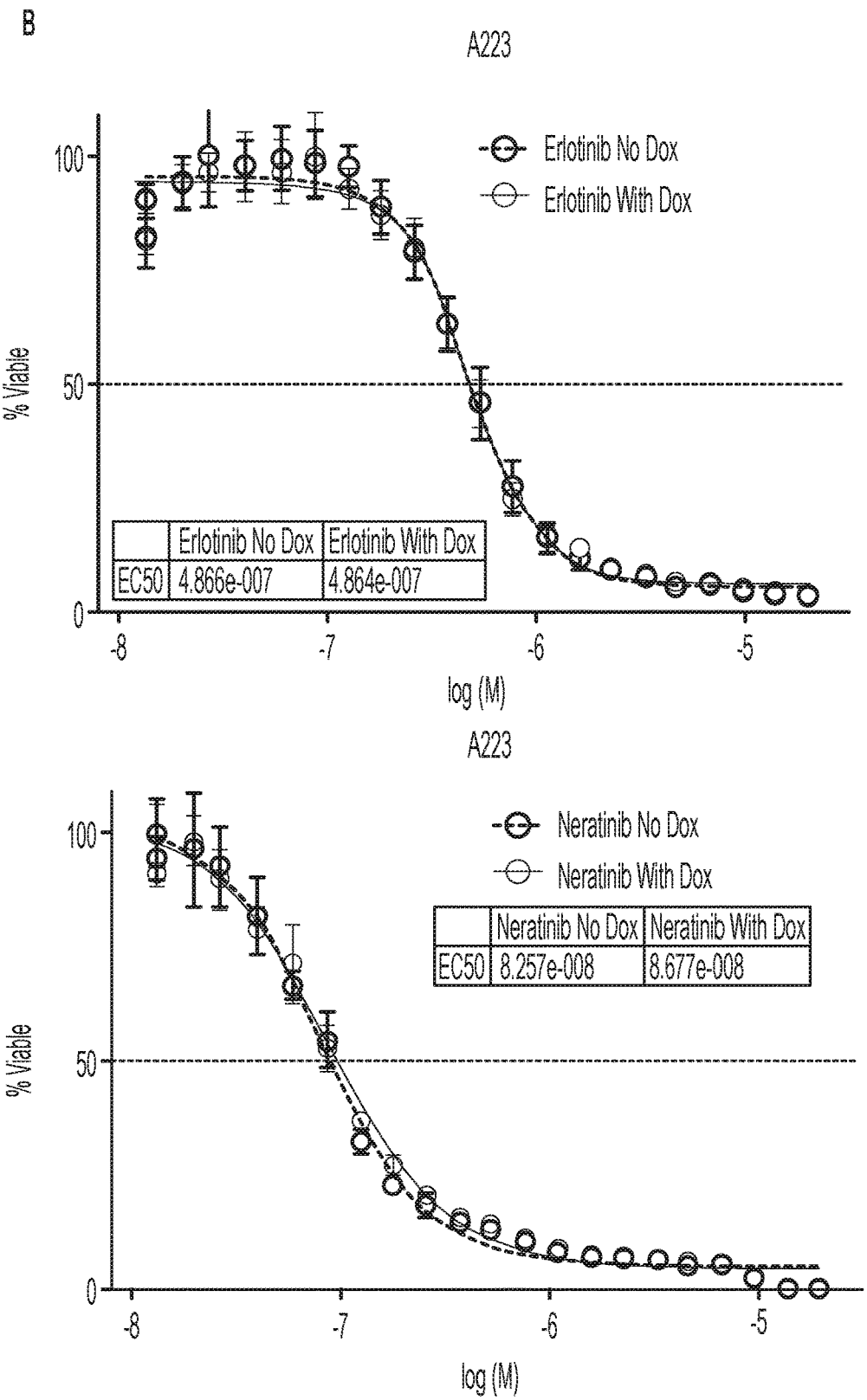
Figure 59:
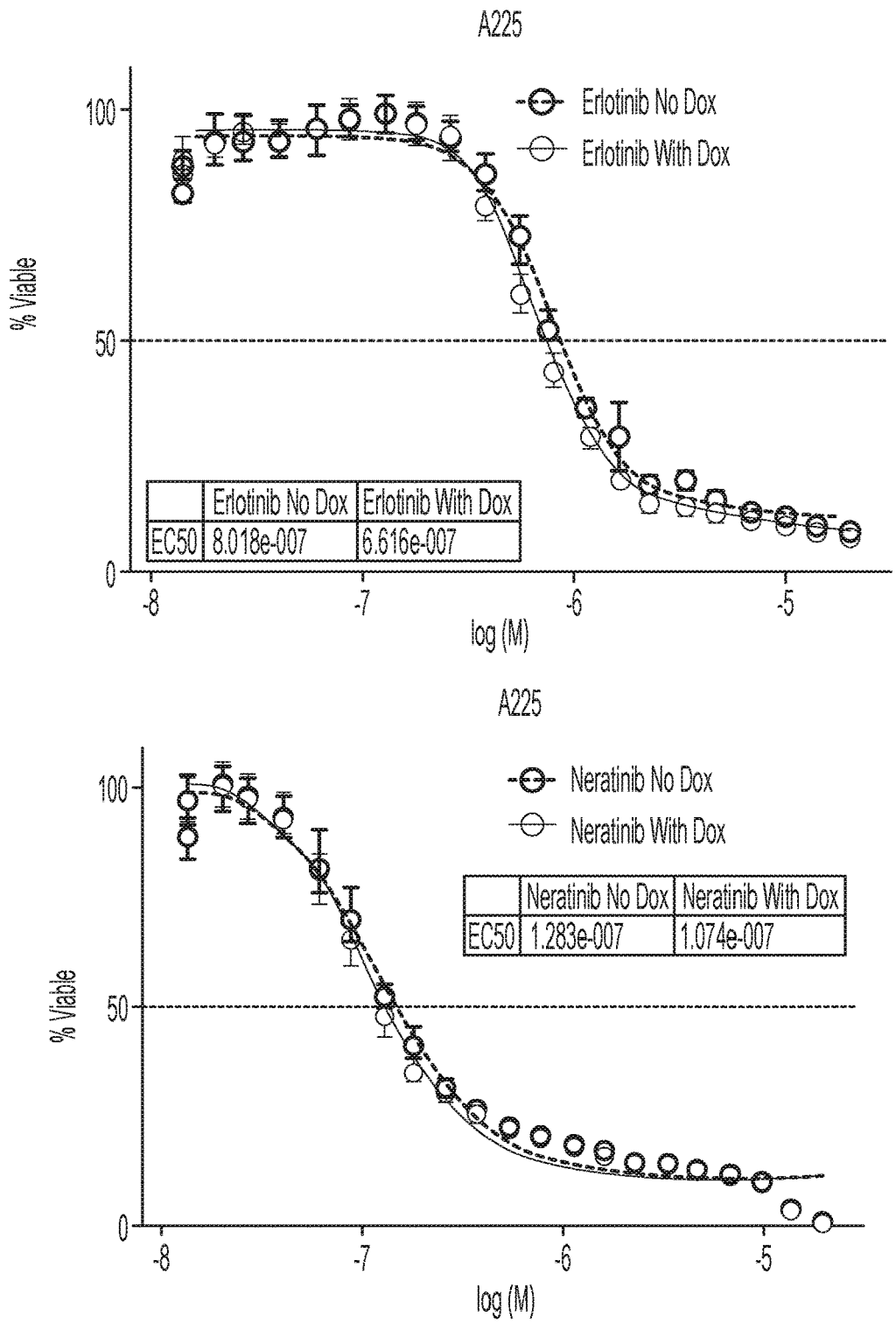
Figure 59:
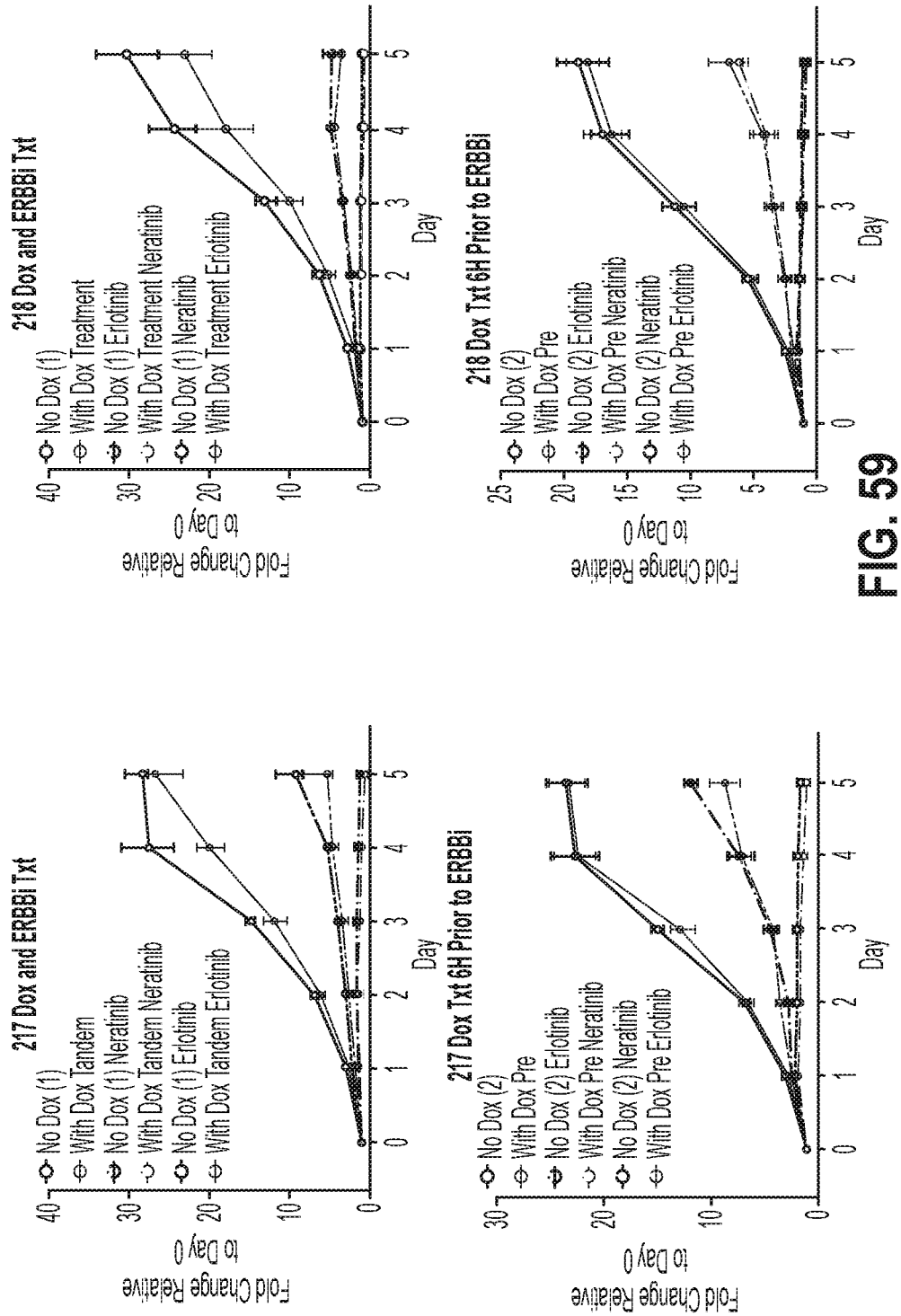
Figure 59:
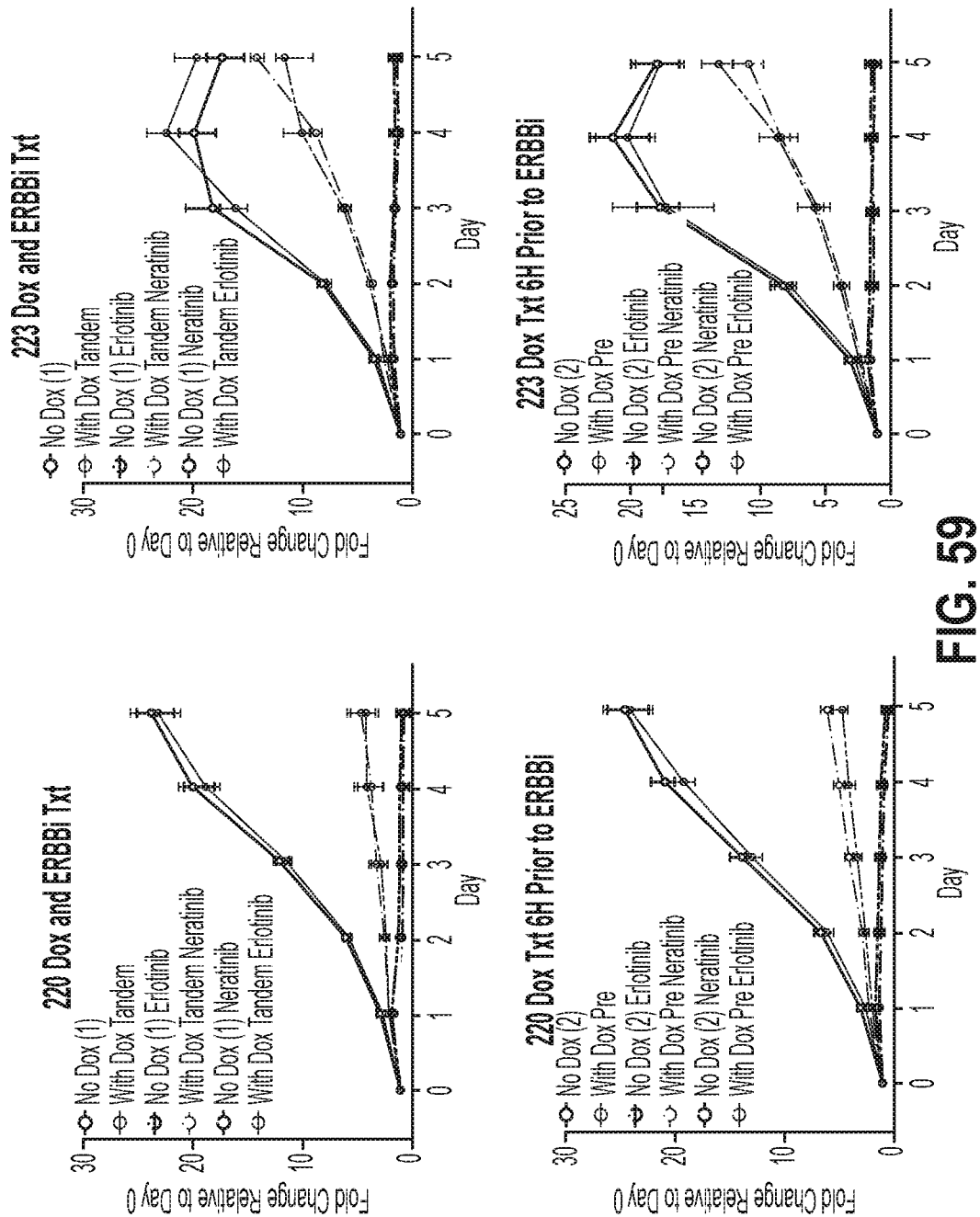
Figure 59:
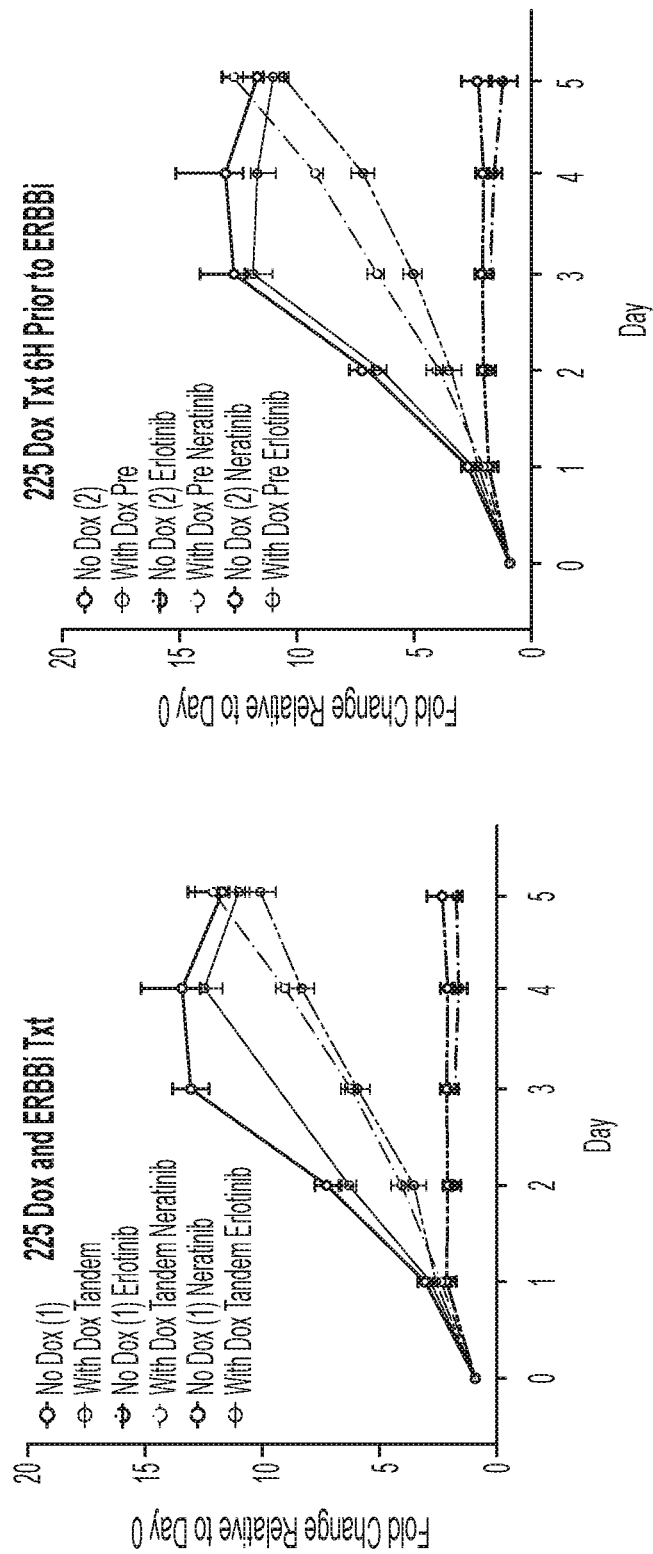

FIGS. 59A-59C show that CA19-9 is not detected on EGFR in $C^{PDX}$;$R^{LSL}$;F organoids. FIG. 59A shows EGFR IP, followed by CA19-9 immunoblotting using protein lysates from $C^{PDX}$;$R^{LSL}$;F and genetically negative (GN) normal ductal organoids following Dox treatment for 0-8 hours. FIG. 59B shows that CA19-9 expression does not affect the sensitivity of C;$R^{LSL}$;F and genetically negative (GN) normal ductal organoids to ErbB kinase inhibition using either Erlotinib or Neratinib. GN organoids: A218. A223. $C^{PDX}$; $R^{LSL}$;F organoids: A217, A220, A225.

Figure 60:
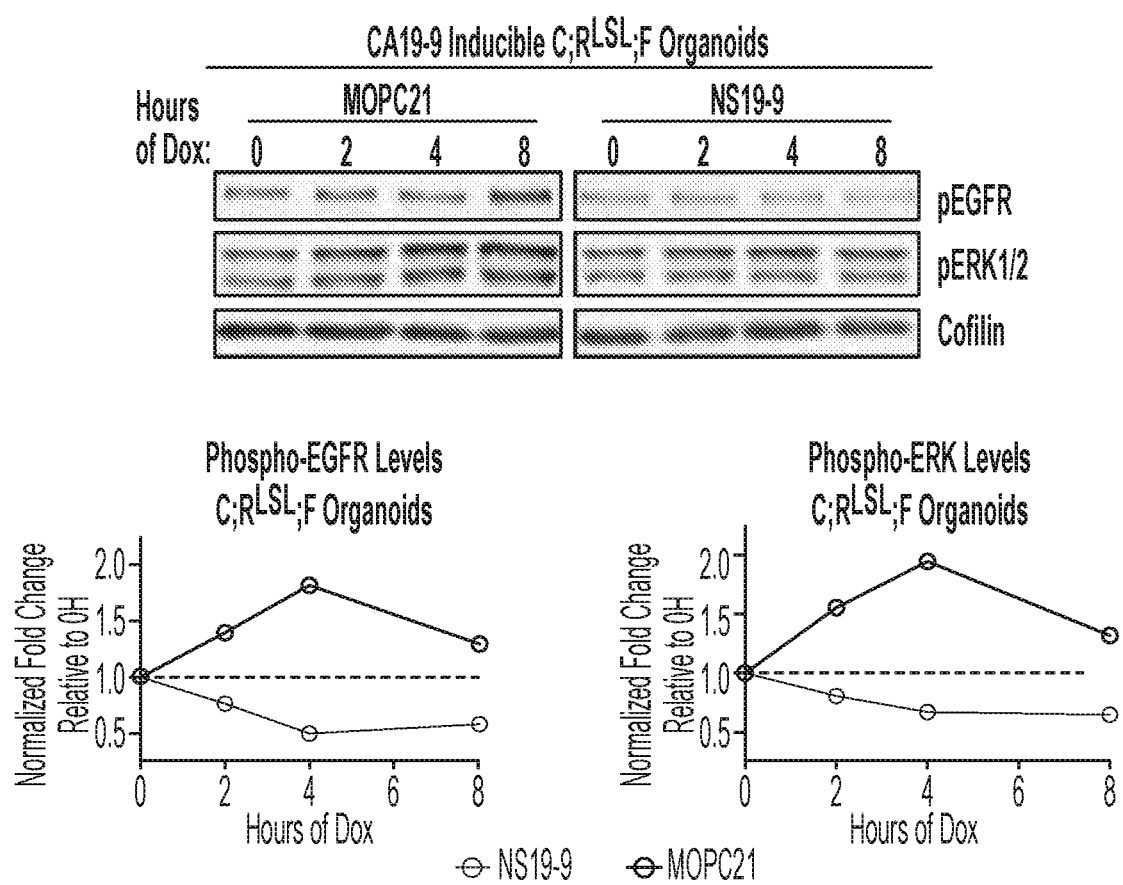

FIG. 60 shows signaling in $C^{PDX}$;$R^{LSL}$;F organoids (n=3 biological replicates) after treatment with Dox (Hours) in the presence of isotype control (MOPC21) or CA19-9 blocking mAb (NS19-9) as evaluated by immunoblot. Quantification was performed relative to the untreated timepoint after normalization to Cofilin. Blots are representative of two technical and three biological replicates.

Figure 61:
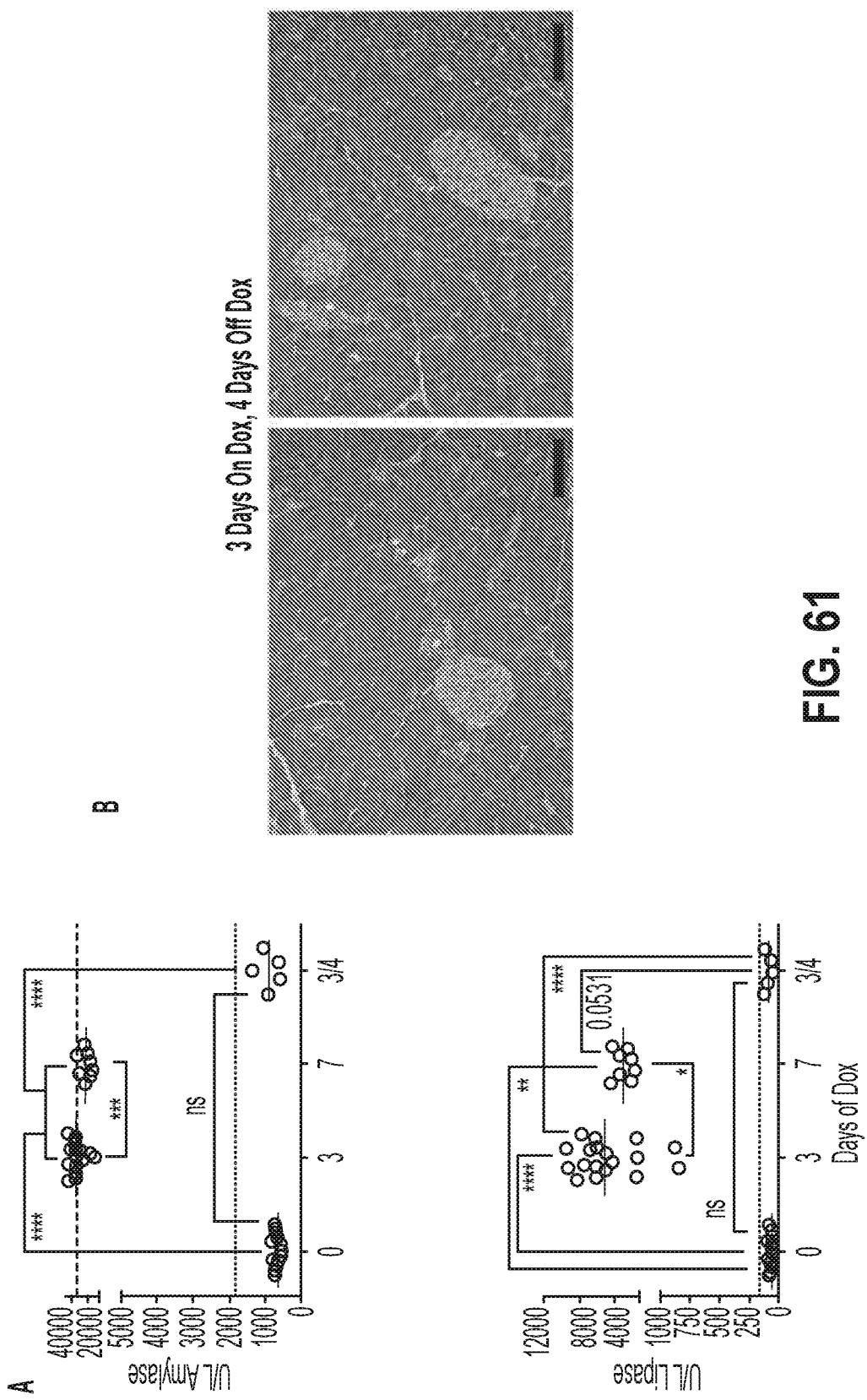

FIGS. 61A-61B show that CA19-9 mediated pancreatitis is reversible. FIG. 61A shows Serological levels of amylase and lipase of $C^{PDX}$;$R^{LSL}$;F mice pulsed with Dox for 3 days and chased for 4 days. Serological levels of amylase and lipase are shown with data from FIG. 25C shown for comparison. FIG. 61B shows H&E staining of $C^{PDX}$;$R^{LSL}$;F mice pulsed with Dox for 3 days and chased for 4 days. Scale bars=100 μm.

Figure 62:
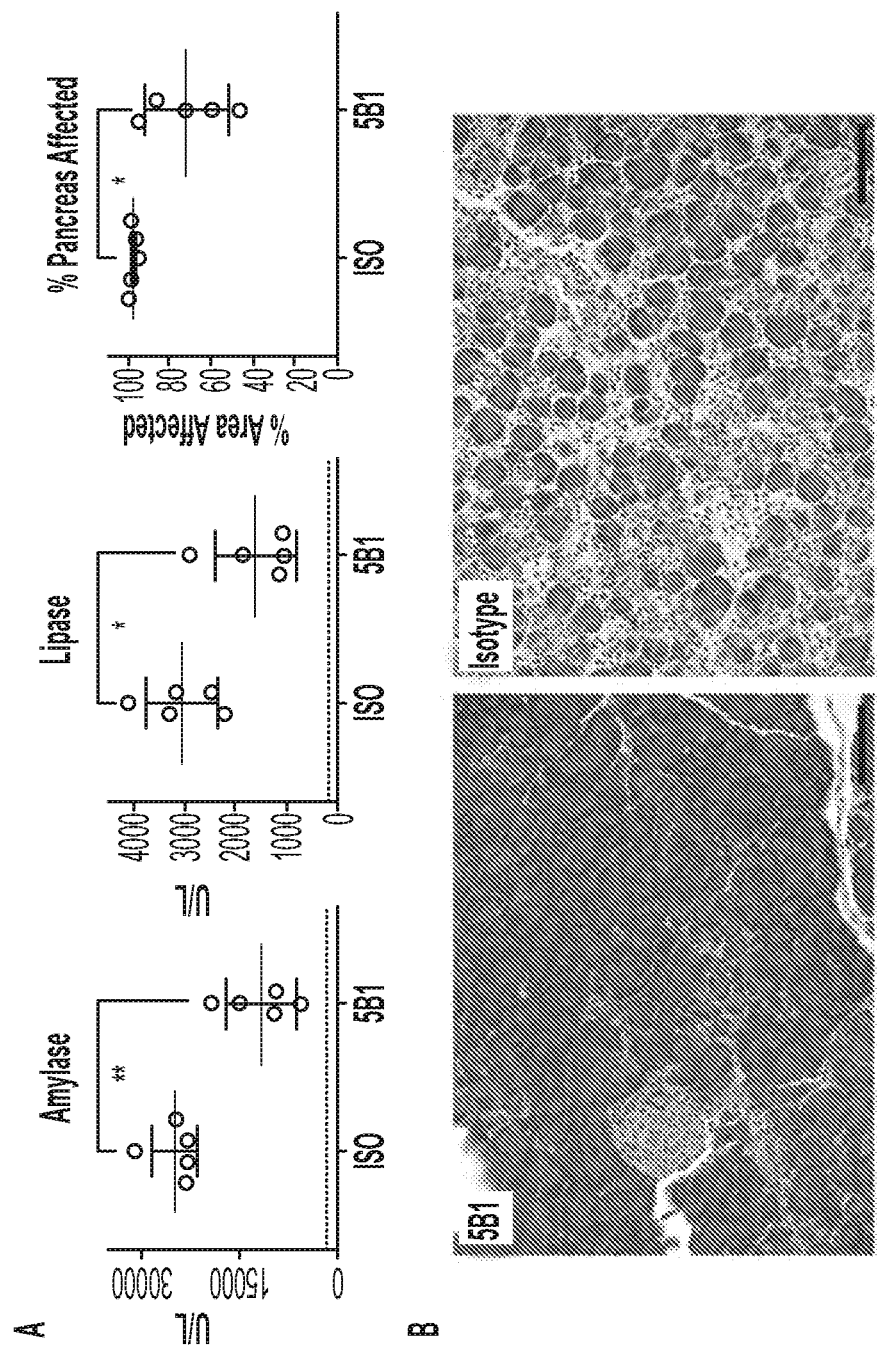
Figure 62:
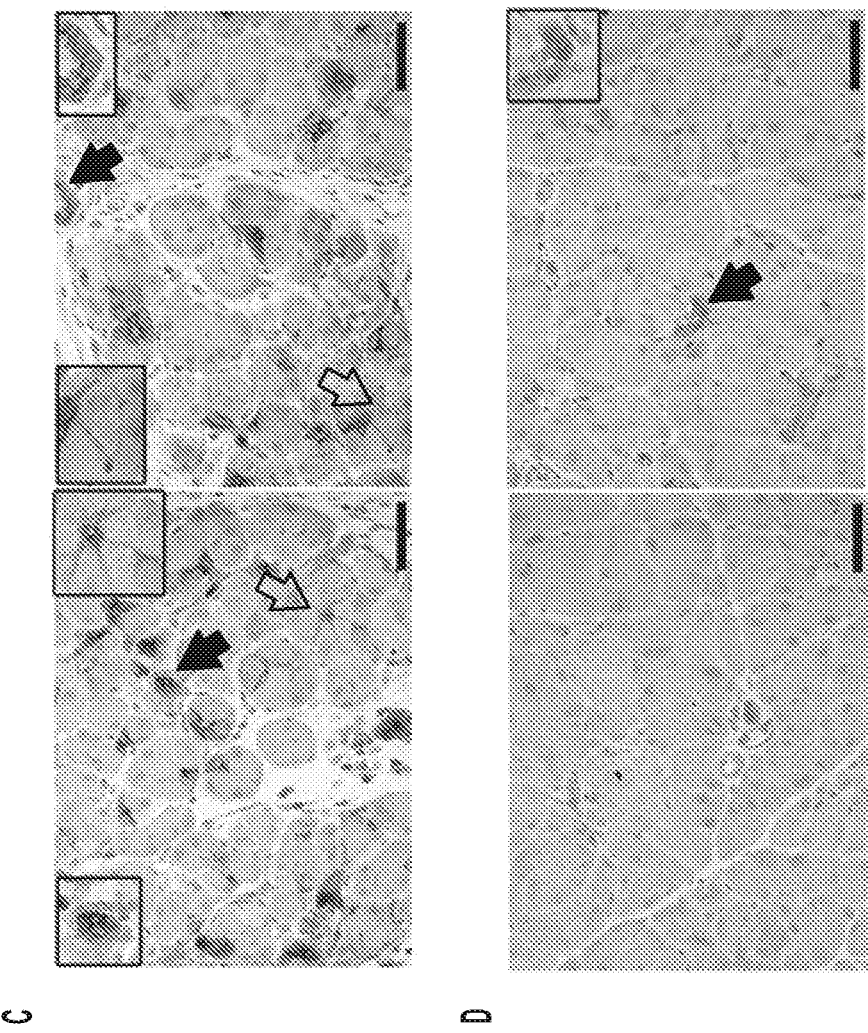

FIG. 62A shows serum amylase and lipase levels, and the percentage pancreatic tissue area exhibiting histological signs of pancreatitis in $C^{PDX}$;$R^{LSL}$;F mice following treatment human Isotype control (n=5) or 5B1 (n=5) for 8 days and Dox for the last 7 days. Middle horizontal red lines represent the mean and error bars represent the standard deviation; each data point represents a measurement from an individual mouse. p value determined using unpaired, parametric, two-tailed t test for the amylase and lipase comparisons (t=4.611, 2.981; df=8) and unpaired, parametric t test with Welch's correction for the percentage of affected pancreas (t=2.935, df=4.065); *p<0.05, p<0.01, *p<0.001, ****p<0.0001. FIG. 62B shows H&E staining of representative areas from mice treated with Isotype or 5B1 as described above. Scale bars=100 m. FIGS. 62C-62D show pEGFR IHC on representative mice treated with either Isotype (FIG. 62C) or 5B1 (FIG. 62D) as described above. Scale bars=100 μm.

Figure 63:
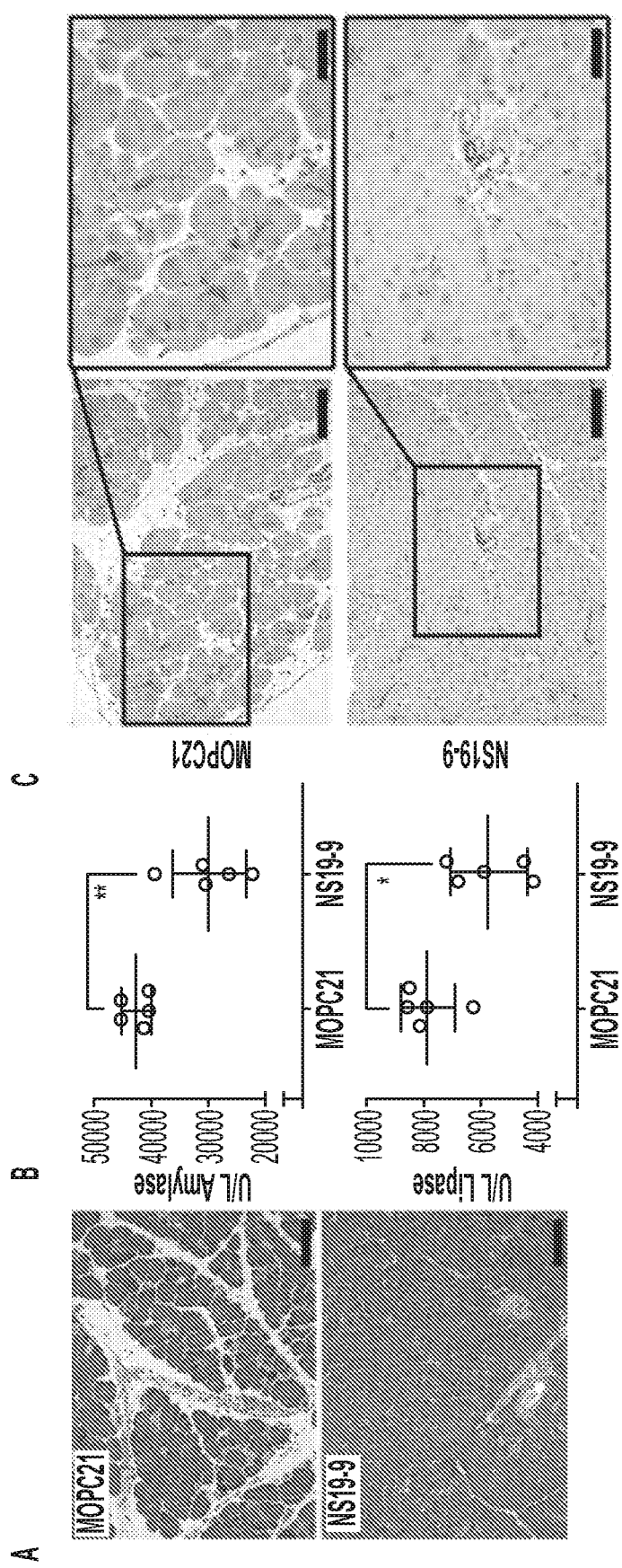

FIGS. 63A-63C show CA19-9 mediated pancreatitis can be attenuated by CA19-9 antibody in vivo. Depicted in the figures are H&E staining (FIG. 63A), serum amylase and lipase levels (FIG. 63B), and pEGFR IHC (FIG. 63C) in $C^{PDX}$;$R^{LSL}$;F mice following treatment MOPC21 or NS19-9 for 96 hours and Dox for the last 24 hours. Scale bars=100 μm, Inset scale bars=50 μm. In FIG. 63B, sample sizes were MOPC21 (n=5) or NS19-9 (n=5). Lines represent the mean; each data point represents a measurement from an individual mouse. p value determined using unpaired, parametric, two-tailed t test (t=4.108, 2.961, 3.216; df=8, 8, 7).

Figure 64:
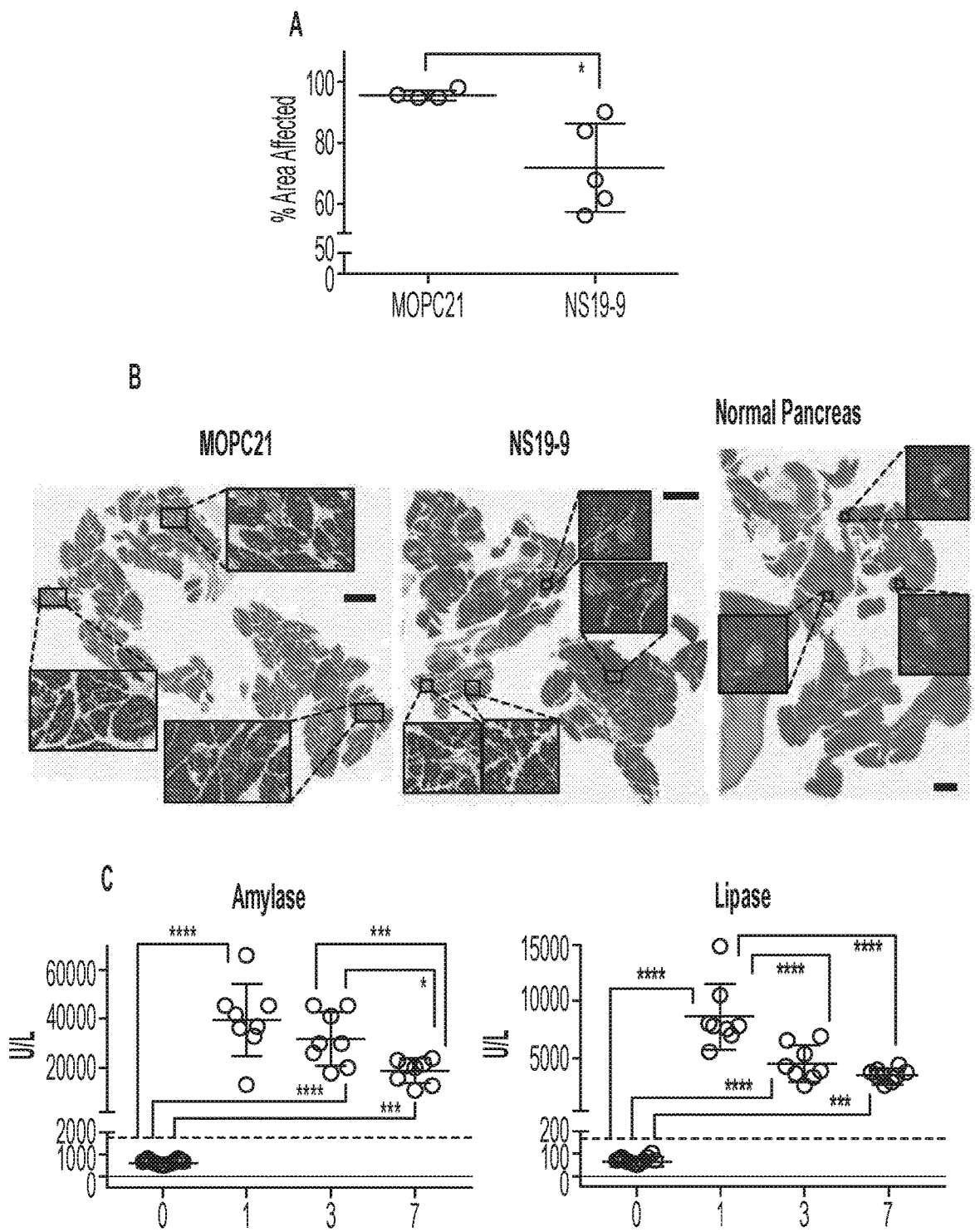

FIGS. 64A-64C show CA19-9 mediated pancreatitis can be attenuated by CA19-9 antibody in vivo. FIG. 64A shows the percentage pancreatic tissue area exhibiting histological signs of pancreatitis in $C^{PDX}$;$R^{LSL}$;F mice following treatment MOPC21 (n=5) or NS19-9 (n=5) for 96 hours and Dox for the last 24 hours. FIG. 64B shows representative whole pancreata histology (H&E) from a normal mouse or $C^{PDX}$;$R^{LSL}$;F mice treated with Dox in the presence of the isotype control, MOPC21, or the CA19-9 antibody, NS19-9. Orange insets are representative higher magnifications of pancreatitis areas. Black insets are representative higher magnifications of normal pancreatic areas containing ductal structures. Scale bars=100 μm. FIG. 64C shows amylase and lipase levels following treatment of $C^{PDx}$;$R^{LSL}$;F mice with a lower dose of Dox in their drinking water (0.5 g/L). Lines represent the mean; each data point represents a measurement from an individual mouse. p value determined using unpaired, parametric, two-tailed t test.

Figure 65:
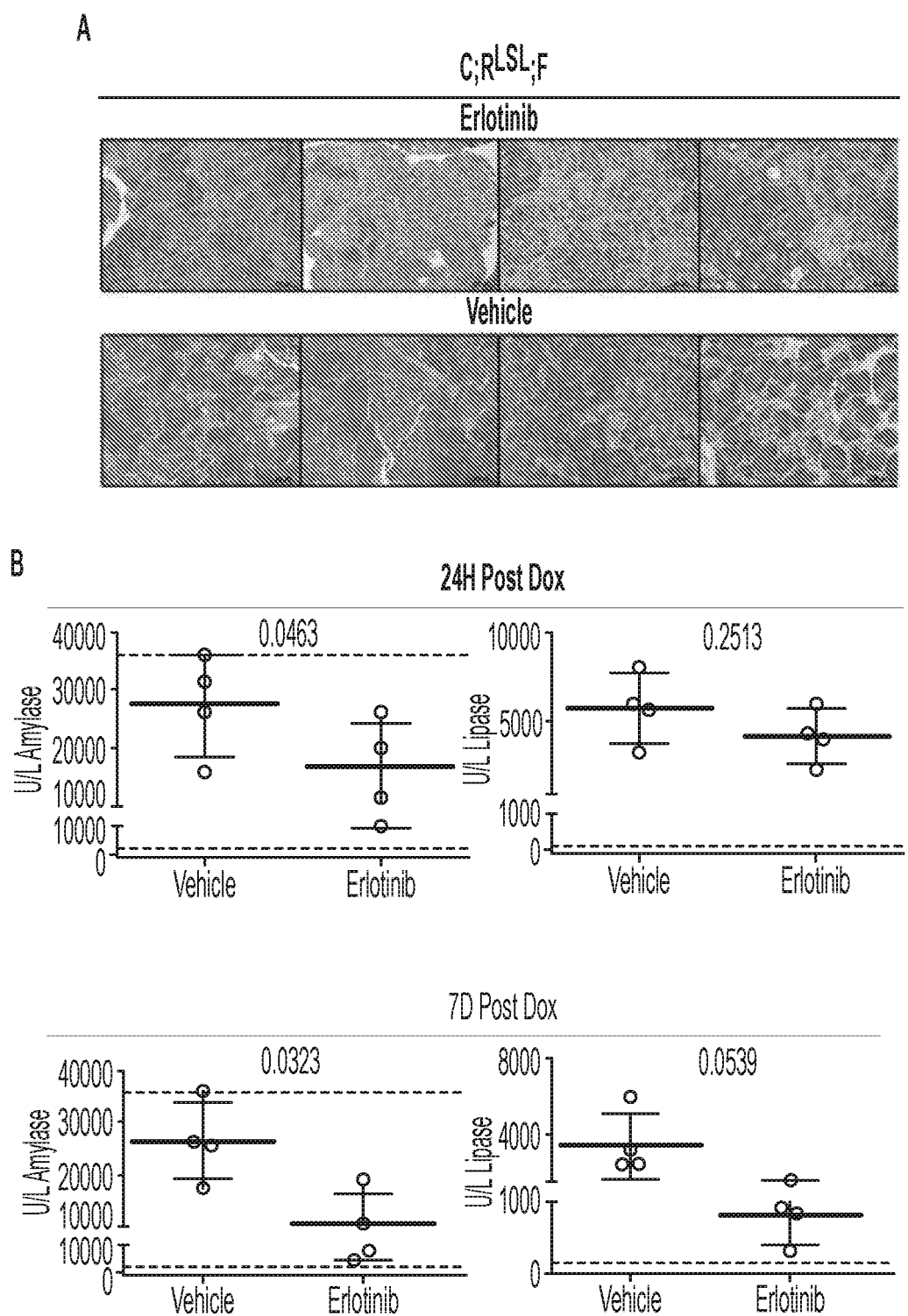
Figure 65:
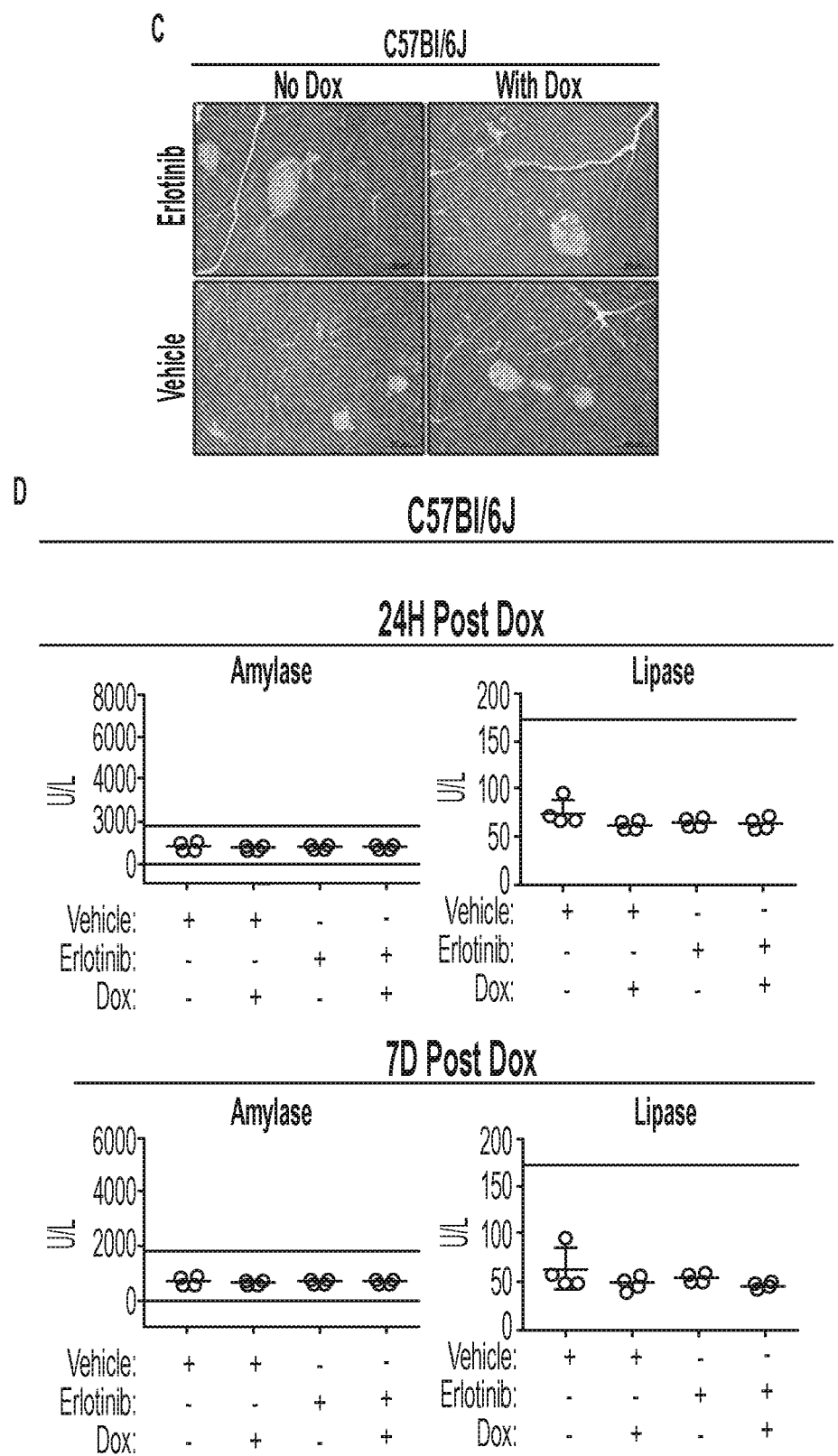

FIG. 65A shows H&E staining of $C^{PDX};R^{LSL};F$ mouse pancreata following treatment with Dox as well as either Erlotinib or Vehicle. Scale bars are 200 µm, 200 µm, 100 µm, and 50 µm from left to right. FIG. 65B shows serological levels of amylase and lipase of $C^{PDX};R^{LSL};F$ mice following treatment with Dox as well as either Erlotinib or Vehicle. FIG. 65C shows H&E staining of C57Bl/6J mouse pancreata following treatment with either Sucrose or Dox Sucrose and either Vehicle or Erlotinib. Scale bars=100 µm. FIG. 65D shows serological levels of amylase and lipase of C57Bl/6J mouse pancreata following treatment with either Sucrose or Dox Sucrose and either Vehicle or Erlotinib.

Figure 66:
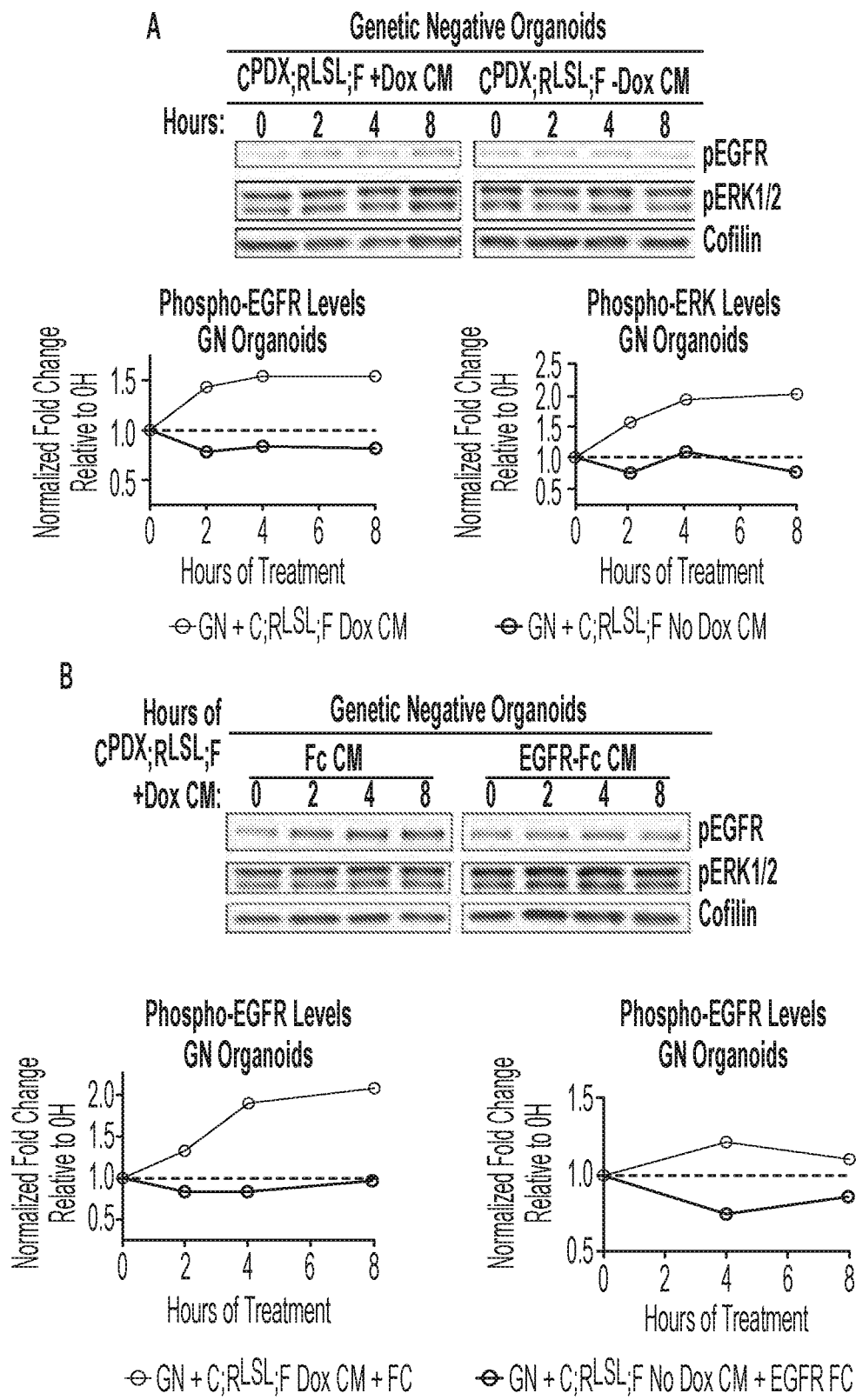

FIGS. 66A-66B show that secretion of CA19-9 ligands activates EGFR. FIG. 66A shows immunoblot evaluation of organoids from genetically negative (GN) littermates that were incubated with conditioned media from $C^{PDX};R^{LSL};F$ organoids previously treated with Dox or vehicle (24 hours). Quantification was performed relative to the untreated timepoint after normalization to Cofilin. FIG. 66B shows immunoblot evaluation of organoids from GN littermates that were incubated with conditioned media from $C^{PDX};R^{LSL};F$ organoids previously treated with Dox (24 hours) in the presence of Fc-control or EGFR conjugated Fc. Quantification was performed relative to the untreated timepoint after normalization to Cofilin.

Figure 67:
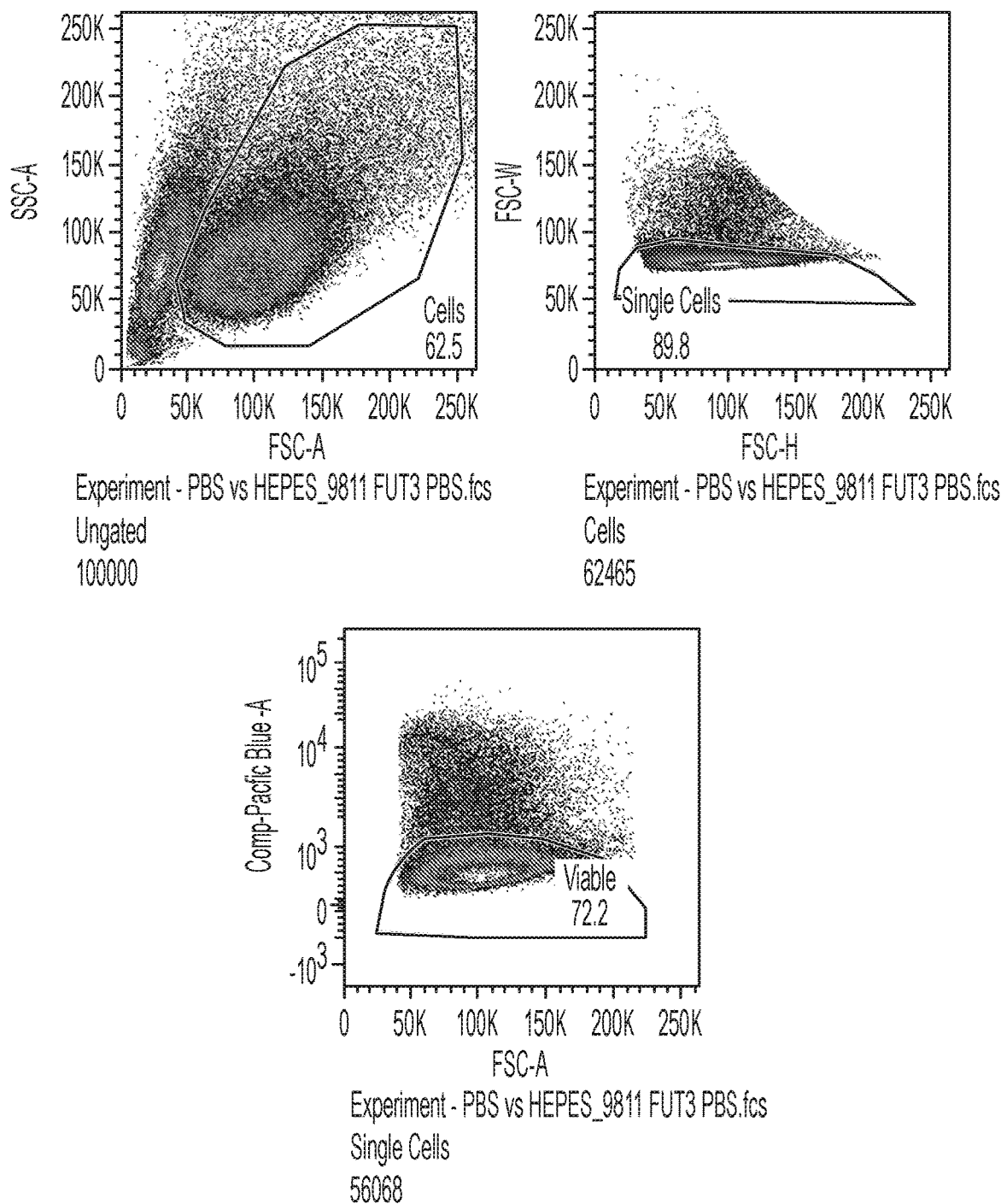
Figure 67:
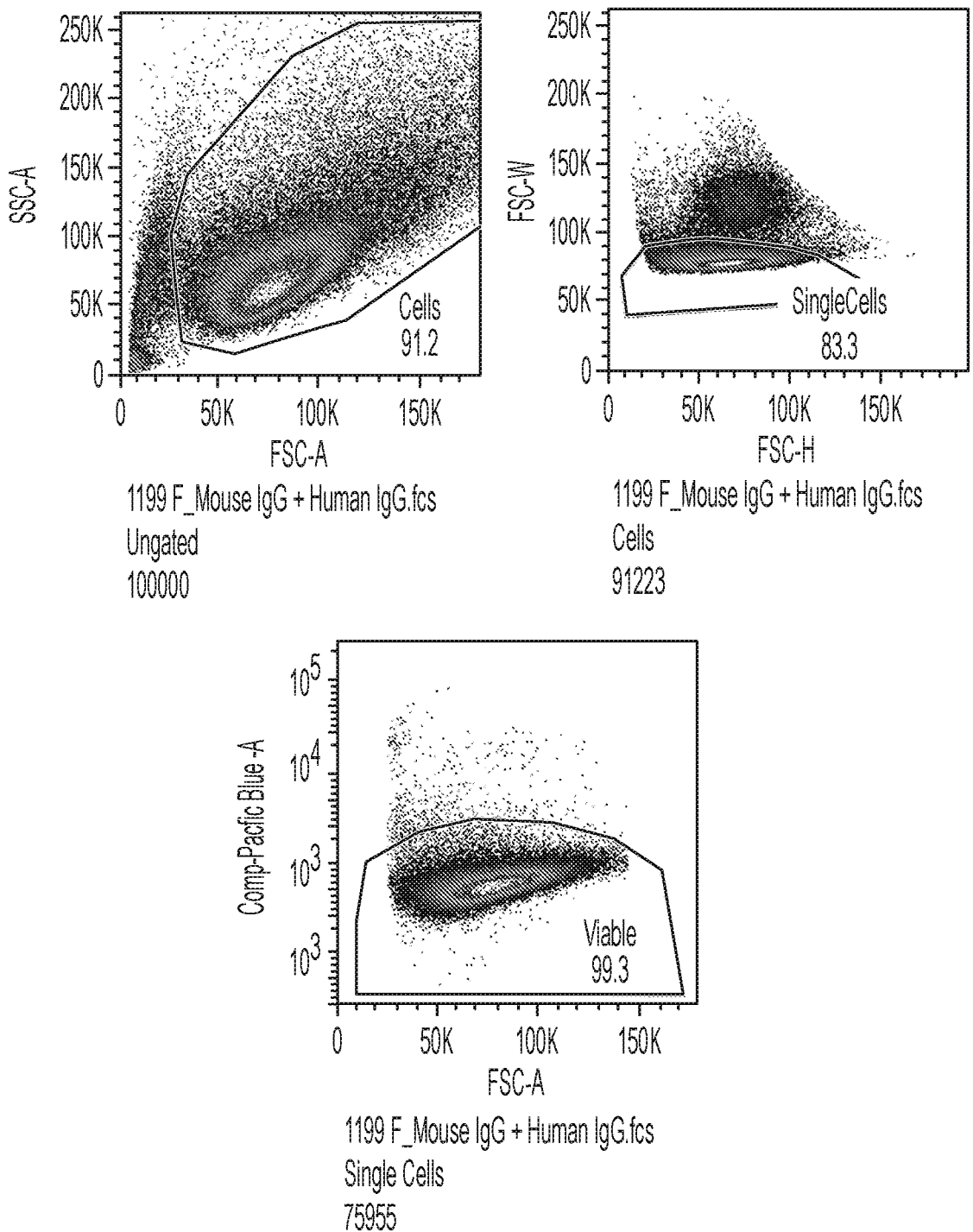
Figure 67:
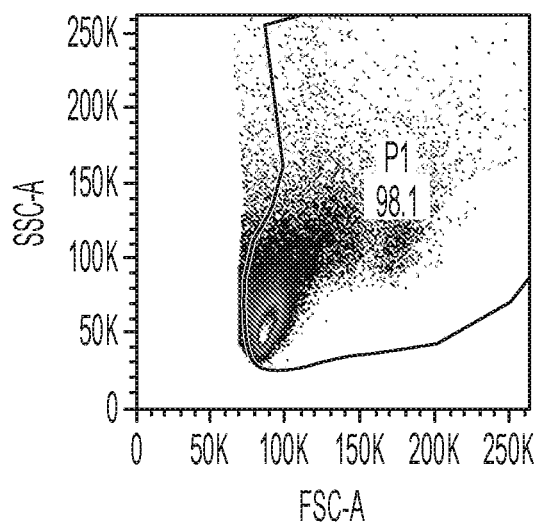
Figure 67:
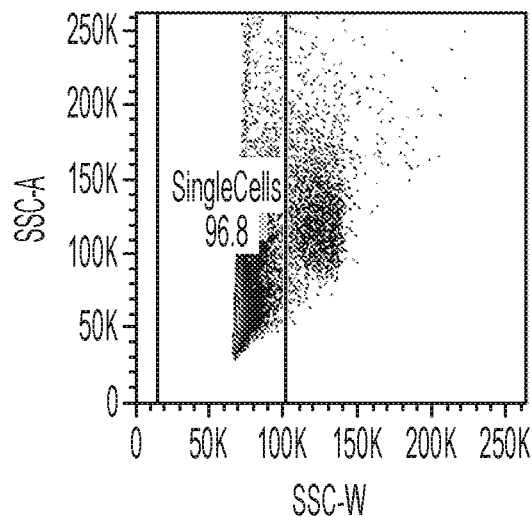
Figure 67:
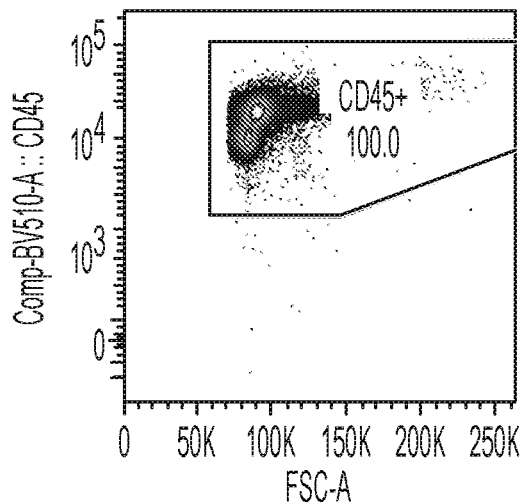
Figure 67:
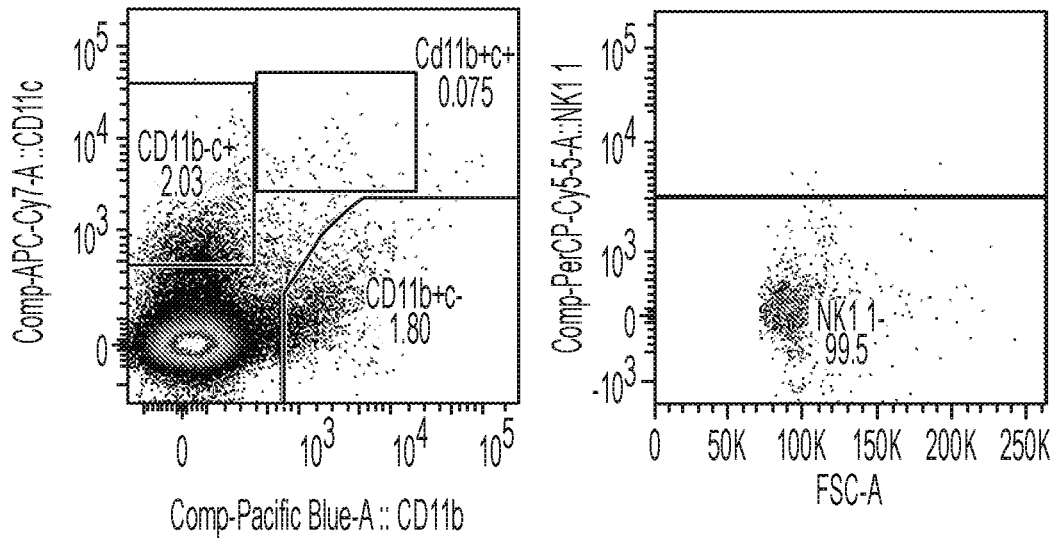
Figure 67:
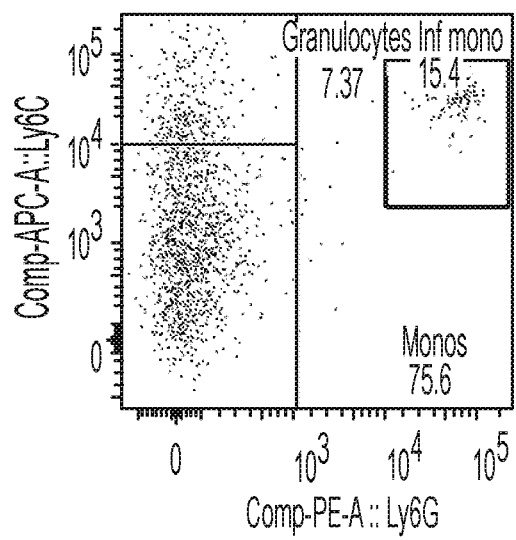
Figure 67:
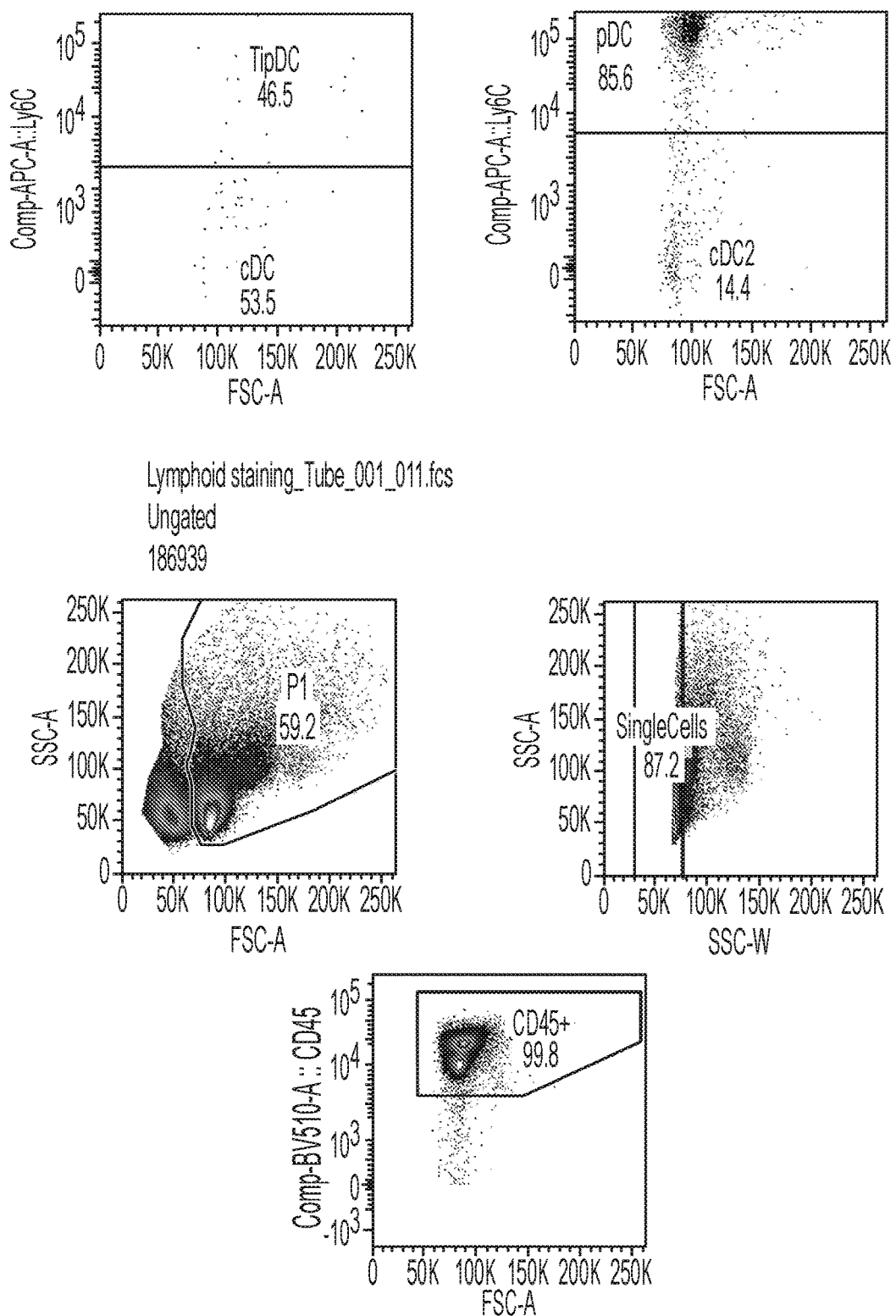
Figure 67:
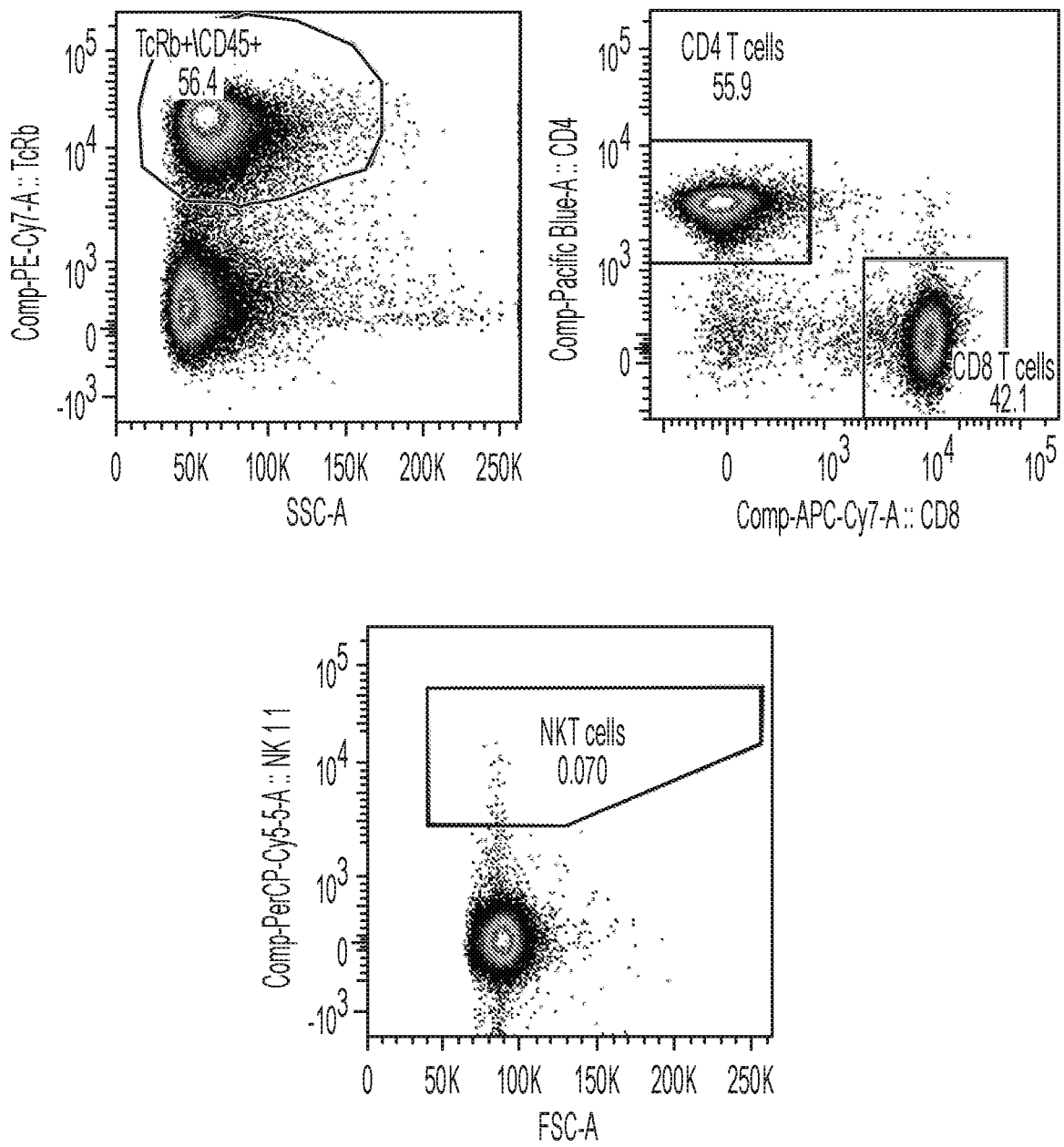
Figure 67:
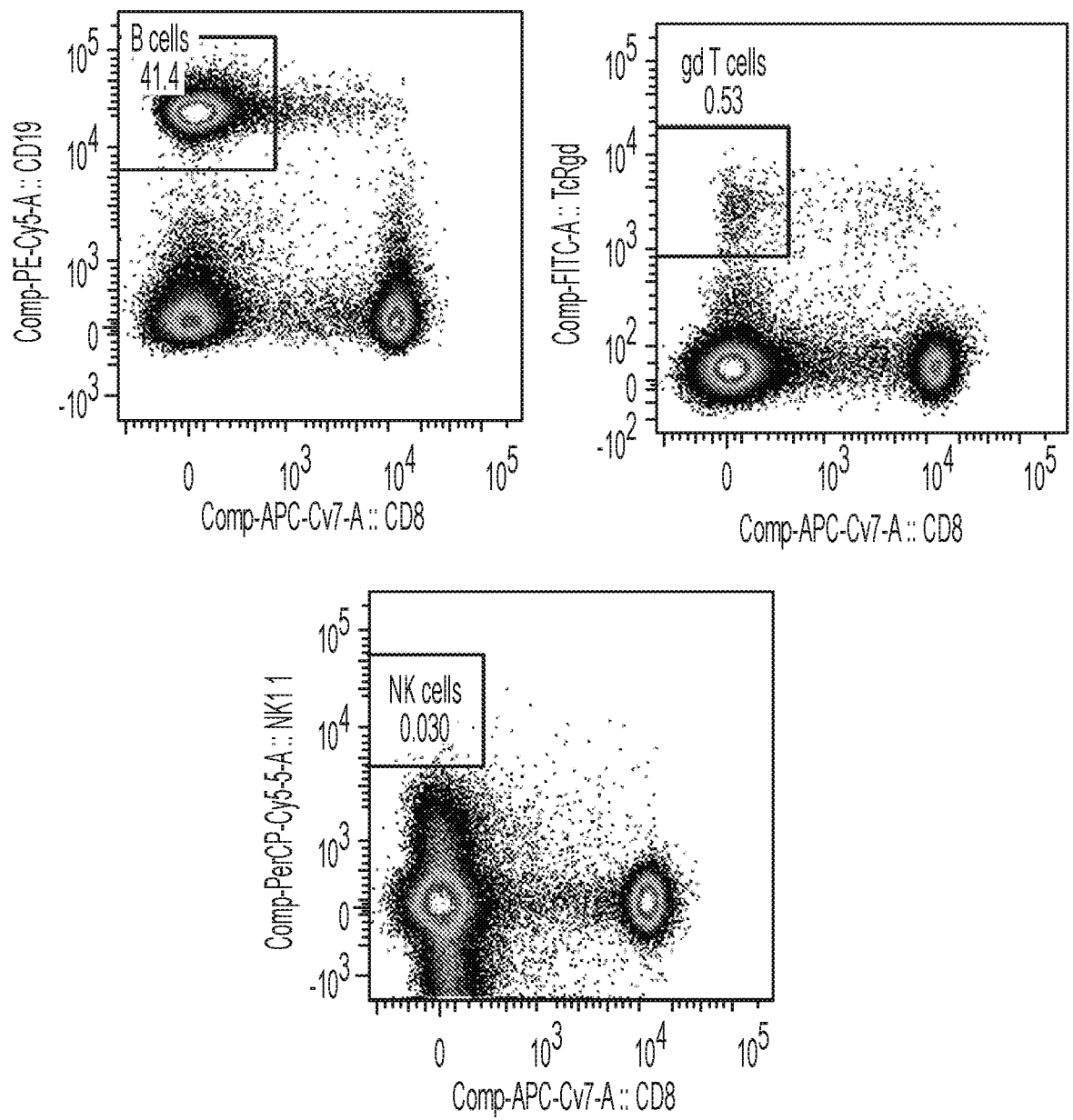
Figure 67:
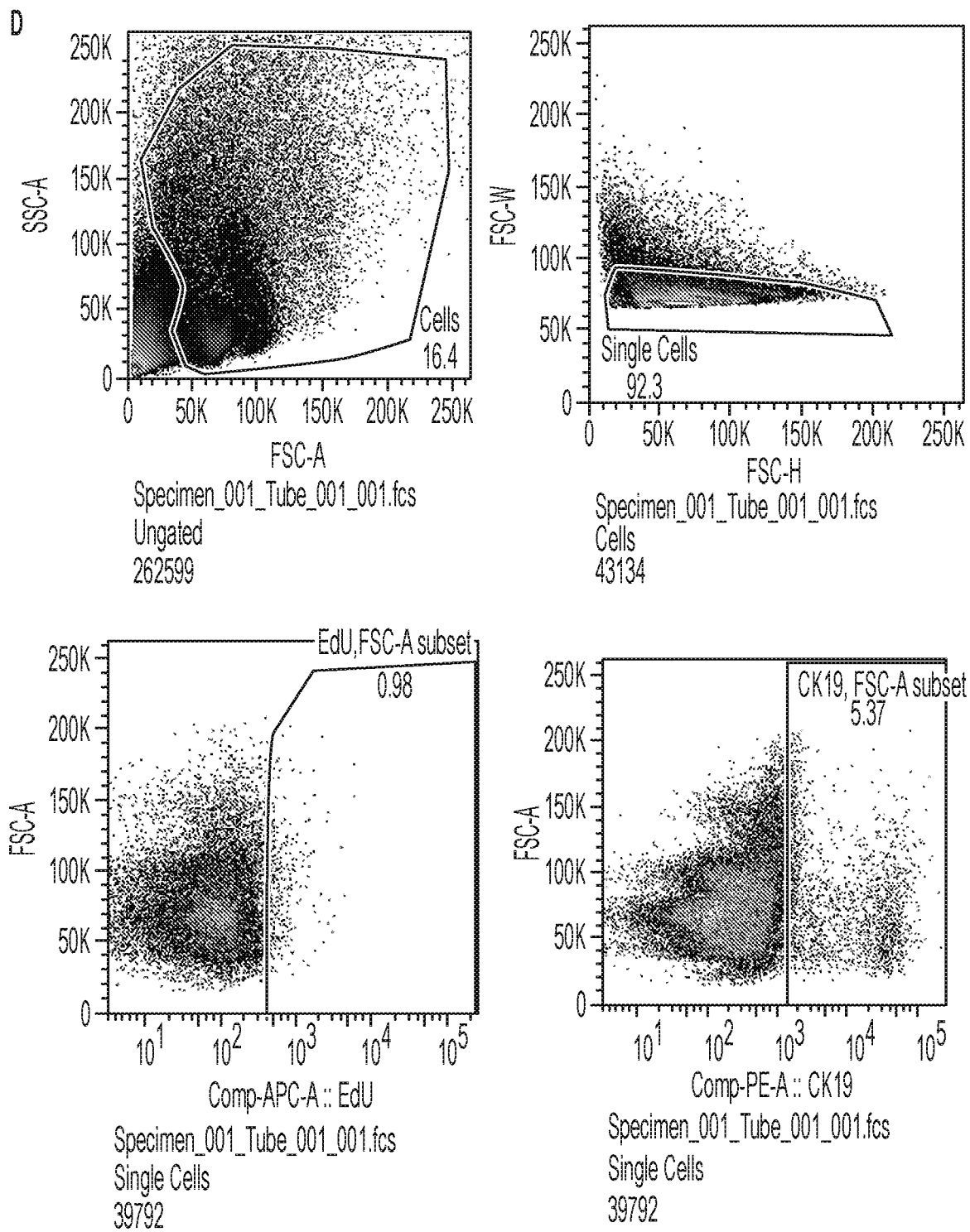
Figure 67:
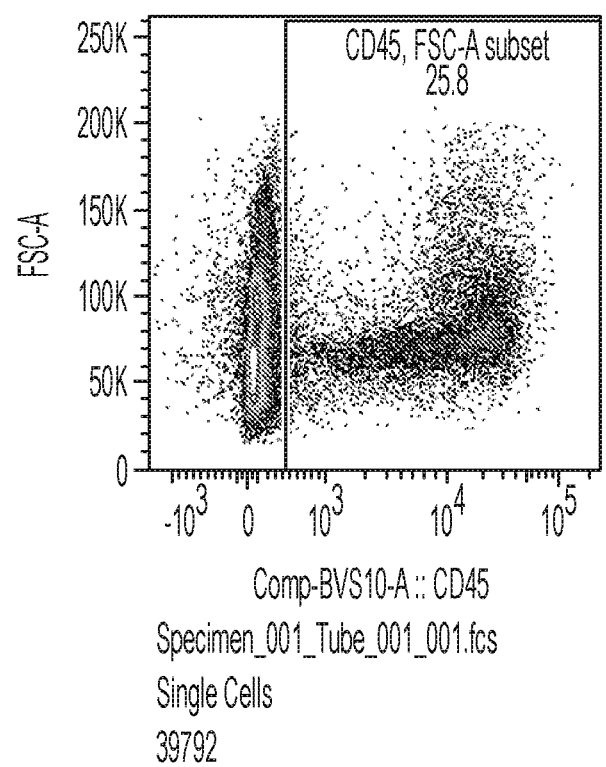

FIGS. 67A-67D show exemplary gating strategies for flow cytometric experiments. FIG. 67A shows flow cytometric back gating for FIG. 1D. FIG. 67B shows flow cytometric back gating for FIG. 1E. FIG. 67C shows flow cytometric back gating for FIG. 50B. FIG. 67D shows flow cytometric back gating for FIG. 52A.

6. DETAILED DESCRIPTION OF THE INVENTION

6.1 Definitions

As used herein, the term "Sialyl-Lewis$^a$" (sLe$^a$), also known or referred to as sialyl Le$^a$, Sialyl-Lewis A, Sialylated Lewis a, is intended to mean a compound of a tetrasaccharide with a molecular formula of $C_{31}H_{52}N_2O_{23}$ and a molar mass of 820.74 g/mol. The structure of sLe$^a$ can include Neu5Acα2-3Galβ1-3(Fucα1-4)GlcNAcβ and Neu5Gcα2-3Galβ1-3(Fucα1-4)GlcNAcµ. sLe$^a$ is also a known ligand for E-selectin, also known as endothelial leukocyte adhesion molecule (ELAM). The term Sialyl-Lewis$^a$ includes that having all possible conformation, including bioactive conformation and non-bioactive conformation.

As used herein, the terms "CA19-9," "CA 19-9," "CA-19.9," or "CA 19.9," refer to any antigen bearing an epitope of Sialyl Lewis$^a$. CA19-9 encompasses proteins, for example glycoproteins, that have been modified with one or more Sialyl Lewis$^a$ moieties. For example, CA19-9 includes Sialyl Lewis$^a$-carrying glycoproteins such as C2, CD59, F5, SPARC, MUC1, MUC5AC, MUC16, apolipoproteins, kininogen, A2M, ADAM9, AFP, B3GNT5, CD44, CSF3, CTBS, CTSL2, EFNB3, EPHA3, FGFBP1, IGFBP5, IL18RAP, INHBC, MSLN, NPY, PDGFA, PROM1, RAF1, S100A7, TFF3, TGFB2, TNFRSF10A, WISP1, and WNT9B. CA19-9 also includes lipids, for example glycolipids, that have been modified with one or more Sialyl Lewis$^a$ and thus bear an epitope of Sialyl Lewis$^a$. Exemplary glycolipids CA19-9 includes glycolipids associated with the bile globular membrane, a membrane vesicle secreted by normal bile, as described in Uozumi, N et al., J. Proteome Res. 2010, 9, 6345-6353, which is hereby incorporated in its entirety by reference. Additional examples of CA19-9 were described in Rho J et al., J Proteomics. 2014 Jan. 16; 96: 291-299, and Trinchera M et al., Biology (Basel). 2017 Feb. 23; 6(1). pii: E16, which are hereby incorporated in their entirety by reference.

The terms "preventing," "prevent," or "prevention," when used with respect to pancreatitis, and/or the damage (e.g. physical or functional), effects or symptoms of pancreatitis, are intended to mean delaying the onset, hindering the progress, hindering the appearance, protection against, inhibiting or eliminating the emergence, or reducing the incidence, of pancreatitis, or damages, effects or symptoms of pancreatitis. For example, even though some patients in a patient population who are treated with the antibody or antibody fragment provided herein develop pancreatitis, the antibody or antibody fragment still "prevents" pancreatitis, so long as that the patient population who are treated with the antibody or antibody fragment exhibits a reduction in the damage, effects, incidence, rate of occurrences, or symptoms of pancreatitis when compared to a population who are untreated.

As used herein, the terms "treat" or "treatment," when used with respect to pancreatitis, are intended to mean the elimination, reduction, management or control of pancreatitis, or a disorder, damage including for example physical or functional damage, and/or effects or symptoms resulting from pancreatitis.

As used herein, the term "ameliorate," when used with respect to pancreatitis, is intended to mean to reduce, alleviate, or ease pancreatitis, or a disorder, damage including for example physical and functional damage, and/or effects or the symptoms resulting from pancreatitis. For example, a person skilled in the art can ameliorate the symptoms of pancreatitis by making it more bearable, slow down the progression of the disease, or restore a subject towards a state free of pancreatitis.

As used herein, the terms "manage," "managing," or "management," when used with respect to pancreatitis, are intended to mean achieving one or more beneficial effects for a patient through administration of an antibody or antibody fragment as provided herein. The beneficial effects can be, for example, regression, stop of progression, or less rapid progression of the pancreatitis, alleviation, maintenance, or retardation of the worsening of the symptom or effects of the pancreatitis, and reversal, maintenance, or retardation of the spread of the damage associated with the pancreatitis. In certain embodiments, a patient is administered an antibody or antibody fragment as provided herein to limit or control the symptoms of pancreatitis so as to prevent the progression or worsening of the symptoms of pancreatitis.

As used herein, the terms "subject" and "subjects" are intended to mean an animal, for example, a mammal. The mammal encompassed by the term "subject" includes, for example, a non-primate mammal such as a cow, a pig, a horse, a cat, a dog, a rat, and a mouse, and a primate mammal such as a monkey, an ape, and a human. A "patient" refers to a human that is a suitable target for the methods provided herein As used herein, the term "pancreatitis" is intended to mean a disease in which the pancreas becomes inflamed and damaged. Pancreatitis includes acute pancreatitis and chronic pancreatitis. Acute pancreatitis refers to a sudden inflammation in the pancreas that lasts for a short time. Chronic pancreatitis refers to a long-lasting inflammation of the pancreas. Chronic pancreatitis can happen after an episode of acute pancreatitis. Chronic pancreatitis further includes mild, moderate, and severe chronic pancreatitis.

As used herein, the phrase "therapeutic agent" or is intended to mean any agent that can be used in the prevention, treatment, management or amelioration of pancreatitis associated with expression of a CA19-9 and sLe$^a$ and/or a symptom related thereto. Therapeutic agents provided herein include antibodies (as defined further below), proteins, peptides, nucleic acids, peptidomimetics, peptoids, or and the like. Proteins include natural proteins, de novo designed proteins, and proteins produced by an animal or a cell upon stimulation, engineering, or both. Examples of proteins include ligands, soluble moieties of receptors, and other biological products formed predominantly with amino acids. Nucleic acids as therapeutic agents include aptamers or those having nucleic acid sequences to achieve certain secondary structures for desired functional properties (such as binding or blocking), wherein the sequence can be designed or identified by screen a library of nucleic acid sequences. Peptides include those having certain sequences to achieve desired functional properties (such as binding or blocking), wherein the sequence can be designed or identified by screen a library of peptide sequences. For example, a therapeutic agent can be an antibody or functional fragment of the disclosure. For another example, a therapeutic agent can be a molecule other than an antibody or functional fragment of the disclosure. A therapeutic agent can also be any molecule provided by the disclosure as useful for the prevention, treatment, management or amelioration of a disease associated with expression of a CA19-9 and sLe$^a$ and/or one or more symptoms related thereto.

As used herein, the terms "pancreatitis markers" or "markers for pancreatitis" are intended to mean any determinable and/or observable indicators of pancreatitis. Pancreatitis markers can include physical changes or damages in the pancreas, functional or physiological changes in the pancreas, functional measurements of pancreas, histology changes in the pancreas, abnormalities in the pancreas in imaging test, abnormalities in expression or structure of one or more proteins including glycoproteins in the pancreas, abnormalities in expression or structure of one or more carbohydrates in the pancreas, abnormalities in DNA, RNA, microRNA sequence or structure, abnormalities in serum indicators of pancreatic inflammation, and any measurement or indicator of pancreatic inflammation and/or pancreatic function. Examples of pancreatitis markers include histological markers such as immune cell invasion, collagen deposition, presence and the level of fibrotic tissue, fat necrosis, interstitial edema, acinar and blood vessel destruction, interstitial hemorrhage, ductal dilation, acinar cell homogenization, and expression level of CA19-9. Pancreatitis markers also include physiological markers such as weight loss, malabsorption of food, pancreatic atrophy, pancreatic enlargement, pancreatic inflammation, and bile reflux. Pancreatitis markers can further include serum lipase level, serum amylase level, and serum C reactive protein (CRP) levels.

As used herein, the term "a signaling marker" when used in reference to pancreas or pancreatitis is intended to mean a molecule in a signaling cascade (for example, a chain of interconnected biochemical reactions, biophysical reactions, quantity changes (such as expression level changes), and/or locational changes of the components of the cascade) in the pancreas or pancreatic cells, wherein the activation, stimulation, blockade, inhibition or alteration of the signaling cascade underlies the disease mechanism of pancreatitis. Such signaling markers include, for example, elevated Akt phosphorylation in the pancreas, elevated EGFR phosphorylation in the pancreas, elevated Erk1/2 phosphorylation in the pancreas, and elevation of CA19-9 expression.

As used herein, the term, "amylase," refers to a group of enzymes that hydrolyze starch and glycogen. The exemplary chemical bonds hydrolyzed by amylase include glucosidic bonds present in starch. Amylase includes, for example, α-amylase (EC 3.2.1.1 according to the numerical classification scheme for enzymes known as the Enzyme Commission number; hereinafter an EC number similarly indicates enzyme classification scheme according to the Enzyme Commission number; alternative names: 1,4-α-D-glucan glucanohydrolase; glycogenase) that catalyzes the endohydrolysis of (1→4)-alpha-D-glucosidic linkages in polysaccharides containing three or more (1→4)-alpha-linked D-glucose units. Amylase also includes β-amylase (EC 3.2.1.2; alternative names: 1,4-α-D-glucan maltohydrolase; glycogenase; saccharogen amylase) that catalyzes the hydrolysis of (1→4)-alpha-D-glucosidic linkages in polysaccharides so as to remove successive maltose units from the non-reducing ends of the chains. Amylase further includes, for example, γ-amylase (EC 3.2.1.3; alternative names: Glucan 1,4-α-glucosidase; amyloglucosidase; Exo-1,4-α-glucosidase; glucoamylase; lysosomal α-glucosidase; 1,4-α-D-glucan glucohydrolase) that catalyzes the hydrolysis of terminal (1→4)-linked alpha-D-glucose residues successively from non-reducing ends of the chains with release of beta-D-glucose. "Serum amylase" or "serological amylase" refers to the aggregate or total amylase in the serum. Approximately 35%-45% of normal serum amylase is of pancreatic origin. Increased serum amylase level can be a marker for pancreatitis because when the pancreas is inflamed, increased levels of amylase will be released into the blood. The normal serum level for amylase in a healthy human subject is 0-137 U/L, which can be method and population dependent. Therefore, in some embodiments, normal serum amylase levels can vary from laboratory to laboratory and from one human population to another.

As used herein the term, "lipase," refers to a subclass of the esterases that catalyzes the hydrolysis of fats (lipids). The term lipase can include the triacylglycerol lipase (EC 3.1.1.3) that catalyzes, for example, the hydrolysis of triacylglycerols to glycerol, diacylglycerols, monoglycerols, and free fatty acids. The term lipase also includes the acylglycerol lipase (EC 3.1.1.23) that catalyzes, for example, hydrolysis of glycerol monoesters of long-chain fatty acids. "Serum lipase" or "serological lipase" refers to the aggregate or total lipase in the serum. Lipase of pancreatic origin accounts for a significant and important fraction of the serum lipase. Increased serum lipase level can be a marker for pancreatitis because when the pancreas is inflamed, increased levels of lipase will be released into blood. The normal serum level for lipase in a healthy human subject is 12-70 U/L, which is method and population dependent. Therefore, in some embodiments, normal serum lipase levels can vary from laboratory to laboratory and from one human population to another.

As used herein, the term "elevated levels" in reference to a marker is intended to mean that the level of the marker is higher than that of a normal reference range or a corresponding control subject with normal pancreatic histology, physiology and/or function. Such elevated level can be 110%, 120%, 130%, 140%, 150%, 160%, 170%, 180%, 190%, 200%, 250%, 300%, 400%, 500%, 600%, 700%, 800%, 900%, 10 fold, 20 fold, 30 fold, 40 fold, 50 fold, 100 fold, 200 fold, 300 fold, 400 fold, 500 fold, 600 fold, 700 fold, 800 fold, 1000 fold, 2000 fold, 3000 fold, 4000 fold, 5000 fold, or higher of that in a control subject with normal pancreatic histology, physiology and/or function or that of the normal reference range. Such reference ranges are described further below.

As used herein, the term "antibody" is intended to mean a polypeptide product of B cells within the immunoglobulin class of polypeptides or its equivalent synthetically or recombinantly produced that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). In the context of the present disclosure, the specific molecular antigen that can be bound by an antibody of the disclosure includes the target carbohydrate sLe$^a$. The term antibody encompasses, for example, individual anti-sLe$^a$ monoclonal antibodies and anti-CA-19-9 monoclonal antibodies (including agonist, antagonist, neutralizing antibodies, full length or intact monoclonal antibodies), anti-sLe$^a$ antibody and anti-CA-19-9 antibody compositions with polyepitopic or monoepitopic specificity, polyclonal antibodies, monovalent antibodies, multivalent antibodies, multispecific antibodies (e.g., bispecific antibodies so long as they exhibit the desired biological activity) as described below. An antibody can be human, humanized, chimeric and/or affinity matured, as well as an antibody from other species, for example, mouse and rabbit, etc. The antibodies provided herein can be of any class (for example, IgG, IgE, IgM, IgD, and IgA) or any subclass (for example, IgG1, IgG2, IgG3, IgG4, IgA1, and IgA2) of immunoglobulin molecule. The antibodies provided herein include those biologically produced, recombinantly produced, or synthetically produced.

The term "human" when used in reference to an antibody or a functional fragment thereof refers an antibody or functional fragment thereof that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. A human antibody, in the context of the present disclosure, can include an antibody that binds to sLe$^a$ and is encoded by a nucleic acid sequence that is a naturally occurring somatic variant of the human germline immunoglobulin nucleic acid sequence. Exemplary methods of producing human antibodies are provided in Example I, but any method well known to those skilled in the art can be used.

The term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane, *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, the term "functional fragment" when used in reference to an antibody is intended to refer to a portion of the antibody including heavy or light chain polypeptides that retains some or all of the binding activity as the antibody from which the fragment was derived. Such functional fragments can include, for example, an Fd, Fv, Fab, F(ab'), F(ab)$_2$, F(ab')$_2$, single chain Fv (scFv), diabody, triabody, tetrabody and minibody. Other functional fragments can include, for example, heavy or light chain polypeptides, variable region polypeptides or Complementarity-determining region (CDR) polypeptides or portions thereof so long as such functional fragments retain binding activity. Such antibody binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E.D., *Advanced Immunochemistry*, Second Ed., Wiley-Liss, Inc., New York, NY (1990).

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\epsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while $\mu$ and $\epsilon$ contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) of lambda ($\lambda$) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) 5$^{th}$ ed. A variable region can be a human variable region.

A CDR refers to one of three hypervariable regions ($H_1$, $H_2$ or $H_3$) within the non-framework region of the immunoglobulin (Ig or antibody) VH μ-sheet framework, or one of three hypervariable regions (L0, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved s-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to either the Kabat (hypervariable) or Chothia (structural) designations, are set forth in the Table 1 below.

TABLE 1

CDR Definitions

| | Kabat[1] | Chothia[2] | Loop Location |
|---|---|---|---|
| $V_H$ CDR1 | 31-35 | 26-32 | linking B and C strands |
| $V_H$ CDR2 | 50-65 | 53-55 | linking C' and C" strands |
| $V_H$ CDR3 | 95-102 | 96-101 | linking F and G strands |
| $V_L$ CDR1 | 24-34 | 26-32 | linking B and C strands |
| $V_L$ CDR2 | 50-56 | 50-52 | linking C' and C" strands |
| $V_L$ CDR3 | 89-97 | 91-96 | linking F and G strands |

[1]Residue numbering follows the nomenclature of Kabat et al., supra
[2]Residue numbering follows the nomenclature of Chothia et al., supra One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

Isolated refers to a referenced molecule as being free of at least one component as it is found in nature. The term includes an antibody or an antibody functional fragment that is removed from some or all other components as it is found in its natural environment. Components of an antibody's natural environment include, for example, erythrocytes, leukocytes, thrombocytes, plasma, proteins, nucleic acids, salts and nutrients. Components of an antibody functional fragment's natural environment include, for example, lipid membranes, cell organelles, proteins, nucleic acids, salts and nutrients. An antibody or an antibody functional fragment provided herein can also be free or all the way to substantially free from all of these components or any other component of the cells from which it is isolated or recombinantly produced.

As used herein, "isotype" refers to the antibody class that is encoded by heavy chain constant region genes. The heavy chains of a given antibody or functional fragment determine the class of that antibody or functional fragment: IgM, IgG, IgA, IgD or IgE. Each class can have either κ or λ light chains. The term "subclass" refers to the minor differences in amino acid sequences of the heavy chains that differentiate the subclasses. In humans there are two subclasses of IgA (subclasses IgA1 and IgA2) and there are four subclasses of IgG (subclasses IgG1, IgG2, IgG3 and IgG4). Such classes and subclasses are well known to those skilled in art.

The terms "binds" or "binding" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. Binding of an antibody or functional fragment thereof can be detected using, for example, an enzyme-linked immunosorbant assay, a method provided in Section 6.3.1 or any one of a number of methods that are well known to those skilled in the art.

The strength of the total non-covalent interactions between a single antigen-binding site on an antibody or functional fragment and a single epitope of a target molecule, such as sLe$^a$, is the affinity of the antibody or functional fragment for that epitope. The ratio of association ($k_1$) to dissociation ($k_{-1}$) of an antibody or functional fragment thereof to a monovalent antigen ($k_1/k_{-1}$) is the association constant K, which is a measure of affinity. The value of K varies for different complexes of antibody or functional fragment and antigen and depends on both $k_1$ and $k_{-1}$. The association constant K for an antibody or functional fragment of the disclosure can be determined using any method provided herein or any other method well known to those skilled in the art.

The affinity at one binding site does not always reflect the true strength of the interaction between an antibody or functional fragment and an antigen. When complex antigens containing multiple, repeating antigenic determinants, such as a polyvalent sLe$^a$, come in contact with antibodies containing multiple binding sites, the interaction of antibody or functional fragment with antigen at one site will increase the probability of a reaction at a second site. The strength of such multiple interactions between a multivalent antibody and antigen is called the avidity. The avidity of an antibody or functional fragment can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The specificity of an antibody or functional fragment thereof refers to the ability of an individual antibody or functional fragment thereof to react with only one antigen. An antibody or functional fragment can be considered specific when it can distinguish differences in the primary, secondary or tertiary structure of an antigen or isomeric forms of an antigen.

As used herein, the term, "therapeutically effective amount," is intended to mean the amount of a therapeutic agent, for example, an antibody or functional fragment provided herein or any other therapeutic agent provided herein, which is sufficient to achieve a beneficial or an intended therapeutic outcome, for example treating a disease, reducing and/or ameliorating the severity and/or duration of a given disease and/or a symptom related thereto. A therapeutically effective amount of a therapeutic agent can be an amount necessary for the regression, reduction or amelioration of the disease, the reduction or amelioration of the advancement or progression of a given disease, reduction or amelioration of the recurrence, development or onset of a given disease, and/or to improve or enhance the prophylactic or therapeutic effect of another therapy (e.g., a therapy other than the administration of an antibody or functional fragment provided herein). The disclosure provides a therapeutically effective amount of the antibody and antibody fragment provided herein.

As used herein, an "amount" when referring to a dose as a higher quantity, for example a dose at "a higher amount," is intended to mean that the dose at "a higher amount" contains higher quantity of the antibody or antibody fragment to achieve a beneficial or an intended effect. Such dose at "a higher amount" includes, for example, the dose where the aggregate quantity of the antibody or antibody fragment administered over a defined period of time is increased or higher as compared to a control or basal dose in the same period of time. Such dose at "a higher amount" includes a dose of more frequent administration in a defined time window. For example a dose of 4 injections per day is a dose of higher amount comparing to a dose of 3 injections per day, with everything else equal. A dose at "a higher amount" also includes increased or higher quantity of the antibody or antibody fragment per administration while keeping the frequency of administration the same, for example, 3 injections of 2 mg of antibody per day as compared to 3 injections of 1 mg of antibody per day. A dose at "a higher amount" further includes both altered administration frequency and altered quantity per administration in a given time window, so long as the product of the frequency of administration in a given window and the quantity per administration is higher than that in the control or basal dose. For example, a dose of 6 injections of 1 mg of antibody in a day is a dose of "higher amount" than a dose of 3 injections of 1.5 mg of antibody in a day. Similarly, in a continuous administration, a dose of "higher amount" include a dose where the product of the rate of administration and the duration of the administration is higher than that of a control dose. An "amount" when referring to a dose as a lower quantity, for example a dose at "a lower amount," is intended to mean the converse of a dose at "a higher amount" as provided herein.

As used herein, the term "effector" when used in reference to a CA19-9, is intended to mean a molecule in the pancreas or pancreatic cells in a signaling cascade that underlies the disease mechanism of pancreatitis, wherein the molecule will have a response, for example undergoing biochemical, biophysical, expression level, or locational changes, to the presence or stimulation of the CA19-9. Examples of a CA19-9 effector include molecules in the EGFR signaling pathway such as EGFR, Akt, and Erk, and molecules that can directly or indirectly bind to the CA19-9, and molecules that can be directly or indirectly impacted by CA19-9 with observable biological effects.

As used herein, the terms "peptidomimetic molecule" or "peptidomimetics" are intended to mean a peptide-like molecule that has the activity of the peptide upon which it is structurally based. Such peptidomimetics include chemically modified peptides, peptide-like molecules containing non-naturally occurring amino acids, and peptoids, and have an activity such as the selective binding activity of the peptide upon which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons (1995), pages 803-861). A peptidomimetic molecule includes a molecule that contains a mimic of an amino acid residue (an amino acid mimetic), including but not limited to piperazine core molecules, keto-piperazine core molecules and diazepine core molecules. Such an amino acid mimetic can include both a carboxyl group and amino group, and a group corresponding to an amino acid side chain, or in the case of a mimetic of Glycine, no side chain other than hydrogen.

6.2 Methods of Treating Pancreatitis

Provided herein is a method for preventing, treating, ameliorating, or managing pancreatitis in a subject in need thereof including administering to the subject a therapeutically effective amount of an antibody or functional fragment thereof that binds to Sialyl-Lewis$^a$ (anti-sLe$^a$). Also provided herein is a method for preventing, treating, ameliorating, or managing pancreatitis in a subject in need thereof including: (1) administering to the subject at a first dose an antibody or functional fragment thereof that binds to Sialyl-Lewis$^a$ (anti-sLe$^a$), (2) determining a severity of pancreatitis in said subject, and (3) administering a second dose of the antibody or functional fragment thereof that binds to anti-sLe$^a$ at the same or lower amount than the first dose if the severity of pancreatitis in the subject is reduced in comparison to the severity of pancreatitis in the subject before administration of the anti-sLe$^a$ antibody, or administering a second dose of the antibody or functional fragment thereof that binds to anti-sLe$^a$ at a higher amount than the first dose if the severity of pancreatitis in the subject is not reduced. Anti-sLe$^a$ antibodies that can be used in the methods are described in Section 6.2.1.1.

Also provided herein is a method for preventing, treating, ameliorating, or managing pancreatitis in a subject in need thereof including administering to the subject a therapeutically effective amount of a therapeutic agent that binds to CA19-9.

Additionally provided herein is a method for preventing, treating, ameliorating, or managing pancreatitis in a subject in need thereof including: (1) administering to the subject at a first dose a therapeutic agent that binds to CA19-9, (2) determining a severity of pancreatitis in said subject, and (3) administering a second dose of the agent at the same or lower amount than the first dose if the severity of pancreatitis in the subject is reduced in comparison to the severity of pancreatitis in the subject before administration of the agent, or administering a second dose of the agent at a higher amount than the first dose if the severity of pancreatitis in the subject is not reduced.

In all the methods provided herein and specifically those described in the preceding three paragraphs: the therapeutic agents that can be used are described in Section 6.2.1, selection of patients for treatment is described in Section 6.2.2, dosing regimens for administering the agent are described in Section 6.2.3 below, the biomarkers that can be used for identifying the therapeutic agents, selecting the patients, determining the outcome of these methods, and/or serving as criteria in any way for these methods are described in Section 6.2.2 below, the therapeutic outcomes are described in Section 6.2.2 below. Therefore, a person skilled in the art would understand that the methods provided herein include all permutations and combinations of the patients, therapeutic agents, dosing regiments, biomarkers, and therapeutic outcomes as described above and below.

As described in the below Section 6.2.2 on Patient Populations, the pancreatitis treatable, preventable, manageable, and ameliorable by the methods provided herein includes chronic pancreatitis including various stages of chronic pancreatitis and acute pancreatitis as described in details in definition and Patient Population section above and below. In some embodiments, the methods provided herein are applicable to mild chronic pancreatitis, moderate chronic pancreatitis, and/or severe chronic pancreatitis. The methods provided herein can be also used for mild acute pancreatitis, moderate acute pancreatitis, and/or severe acute pancreatitis. As a patient having acute pancreatitis can recover but develop chronic pancreatitis, a patient having chronic pancreatitis can develop acute pancreatitis, and a patient can develop from one stage of chronic or acute pancreatitis into another stage of either chronic and acute pancreatitis, the methods provided herein can be used for a patient having a medical record of any permutation or combination of the various stages of chronic or acute pancreatitis as described herein.

As described below in the Section 6.2.1 on therapeutic agent, the agent provided herein includes an anti-Sialyl-Lewis$^a$ antibody, a peptide or peptidomimetic that binds to Sialyl-Lewis$^a$ and/or modulates Sialyl-Lewis$^a$ activity, or any permutation or combination of any of the suitable therapeutic agent as provided by the disclosure.

The therapeutic agent provided herein also includes an anti-CA19-9 antibody, a peptide or peptidomimetic that binds to a CA19-9 and/or modulates CA19-9 activity, or any permutation or combination of any of the suitable therapeutic agent as provided by the disclosure.

As described in the below Section 6.2.1 on therapeutic agent, the agent provided herein in the methods of treating pancreatitis can be isolated or purified with various levels of purity and impurities; and the agent provided herein can also be in various pharmaceutical composition and be formulated for various route of administration. Therefore, the methods provided herein include the use of an agent that is isolated or purified with various levels of purity and impurities, an agent that is in various pharmaceutical compositions, and an agent that is formulated for various route of administration as provided by the disclosure.

The methods provided herein can be used for various subjects as disclosed herein, including a mammal. In one embodiment, the methods provided herein can be used for a human.

As disclosed in the below Section 6.2.2 on Patient Populations and Biomarkers, various patients can receive the methods provided herein, and various biomarkers can be used for selecting patients and assessing the outcome of the methods provided here. In some embodiments, methods provided herein can be used for selective populations of patients including patients with mild, moderate, or severe chronic pancreatitis, and patients with mild, moderate, or severe acute pancreatitis. In other embodiments, methods provided herein can be used for selective populations of patients including patients with pancreatic atrophy, elevated pancreatic inflammation, elevated immune cell invasion in pancreatitis, elevated collagen deposition in pancreatitis, elevated fibrotic tissue in pancreatitis, elevated fat necrosis in pancreatitis, elevated interstitial edema in pancreatitis, elevated acinar and blood vessel destruction in pancreatitis, elevated interstitial hemorrhage in pancreatitis, elevated ductal dilation in pancreatitis, elevated acinar cell homogenization in pancreatitis, elevated expression level of sLe$^a$ in pancreatitis, elevated expression of a CA19-9, elevated serum lipase level, elevated serum amylase level, elevated serum C reactive protein level, or any permutation or combination of the patient criteria as recited herein. The methods provided herein can also be used in all permutations and combinations with various patient populations and various biomarkers as described herein.

In other embodiments, methods provided herein can be used in various patients or with various biomarkers for therapeutic outcomes of these methods as provided in Section 6.2.2, which can include a reduction in pancreatic atrophy, a reduction in pancreatic inflammation, a reduction in immune cell invasion in pancreatitis, a reduction in collagen deposition in pancreatitis, a reduction in fibrotic tissue in pancreatitis, a reduction in fat necrosis in pancreatitis, a reduction in interstitial edema in pancreatitis, a reduction in acinar and blood vessel destruction in pancreatitis, a reduction in interstitial hemorrhage in pancreatitis, a reduction in ductal dilation in pancreatitis, a reduction in acinar cell homogenization in pancreatitis, a reduction in expression level of sLe$^a$ in pancreatitis, a reduction in expression level of a CA19-9, a reduction in serum lipase level, a reduction in serum amylase level, a reduction in serum C reactive protein level, or any permutation or combination of the outcome as recited herein. The methods provided herein can be further used in all permutations and combinations with various patient populations, various biomarkers and/or therapeutic outcome, as provided herein.

6.2.1 Therapeutic Agents for Use with the Methods of Treating Pancreatitis

Various kinds of molecules having the described properties can be used in the methods provided herein. The disclosure provides that elevated expression of a CA19-9 in the pancreas triggers signaling and/or pathological pathways, which underlies the initiation, development, and worsening of pancreatitis. Accordingly, the disclosure provides that a therapeutic agent that can inhibit, block, reverse, reduce, or attenuate the elevated expression of a CA19-9, elevated levels of Sialyl-Lewis$^a$, or the combination thereof, can be used in the methods provided herein for preventing, treating, ameliorating, or managing pancreatitis. The disclosure further provides that elevated expression or CA19-9 leads to the activation of EGFR signaling pathway. In some specific embodiments, the therapeutic agents that can be used in the methods provided herein include the agents that have the activity of reducing one or more signaling markers in the pancreas, wherein the signaling marker is selected from a group consisting of Akt phosphorylation in the pancreas, EGFR phosphorylation in the pancreas, Erk1/2 phosphorylation in the pancreas, levels of CA19-9 in the pancreas, and levels of Sialyl-Lewis$^a$ in the pancreas.

As discussed above, CA19-9 encompass proteins, such as glycoproteins, and lipids, such as glycolipids, bearing an epitope of Sialyl Lewis$^a$. The disclosure provides a list of CA19-9 identified by immunoprecipitation assays with an anti-CA19-9 antibody (such as 5B1 and NS19-9 in Examples 1, 2 and 3. The disclosure also provides CA19-9 including proteins, such as glycoproteins, and lipids, such as glycolipids, that is known to a person skilled in the art to carry Sialyl Lewis$^a$, such as those described in the definition of CA19-9 above.

As stated above, the therapeutic agents that can be used in the methods provided herein include various categories of agents, for example antibody agents such as anti-CA19-9 as described in Section 6.2.1.1 and peptide or peptidomimetics as described in Section 6.2.1.2.

The therapeutic agent may modulate the activity of CA19-9. To "modulate" an activity of a molecule refers to altering an activity of the molecule. For example, to modulate a activity of a CA19-9 includes causing an increase or a decrease in the magnitude of a certain activity of a CA19-9 compared to the magnitude of the activity of the CA19-9 in the absence of such modulation. In certain examples, to modulate a CA19-9 activity includes decreasing the magnitude of one or more activities of the CA19-9. In some examples, to modulate a CA19-9 activity includes completely preventing one or more activities of the CA19-9. In other examples, to modulate a CA19-9 activity includes increasing the magnitude of at least one activity of the CA19-9. In another example, to modulate a CA19-9 activity includes inducing an activity of the CA19-9 that does not normally occur in the absence of such modulation. A "modulator" in reference to a target molecule that is being modulated refers to a molecule that can "modulate" the an activity of the target molecule as described in this paragraph.

Activity of CA19-9 refers to an activity of CA19-9 in a cell, a tissue, an organ, an organism, or any biological system, for example in the pancreas or pancreatic cells. Effects of CA19-9 refer to the consequences of the CA19-9 activities in a cell, a tissue, an organ, an organism, or any biological system, for example in the pancreas or pancreatic cells. Such activities of CA19-9 include the immediate activities of CA19-9 such as inducing biochemical, biophysical, locational, or quantity changes on another molecule that directly binds to or otherwise interacts with the CA19-9. The corresponding effects of CA19-9 would then include the consequences such as biochemical, biophysical, locational, or quantity changes induced by CA19-9 of the other molecule that directly binds to or otherwise interacts with the CA19-9. Such activities also include activities such as inducing biochemical, biophysical, locational, or quantity changes on another molecule that does not directly bind to or otherwise interact with the CA 19-9 but respond to the presence or stimulation of the CA19-9 further downstream of a activity cascade (e.g. signaling cascade) induced by the CA19-9. The corresponding effects of CA19-9 would then include the consequences such as biochemical, biophysical, locational, or quantity changes induced by a CA19-9 of another molecule that does not directly bind to or otherwise interact with the CA19-9 but respond to the presence or stimulation of the CA19-9 further downstream of a activity cascade (e.g. signaling cascade) of CA19-9. Examples of a CA19-9 activity includes activation of the EGFR signaling pathway which leads to increased phosphorylation of molecules such as EGFR, Akt, and Erk, binding with molecules that can directly or indirectly interact with CA19-9 such as selectins including E-selectin, and changes in levels of molecules that can be directly or indirectly impacted by CA19-9 with observable biological effects.

In some embodiments, the therapeutic agent provided herein can antagonize a CA19-9 or a CA19-9 activity. Such a therapeutic CA19-9 antagonist can inhibit, decrease, or otherwise completely block one or more of the biological activities of a CA19-9. An antagonist of a CA19-9 activity includes a molecule that can block, inhibit, or decrease CA19-9-mediated or CA19-9-dependent signaling in a cell expressing a CA19-9 or in a cell expressing a CA19-9 ligand, such as a CA19-9 receptor. An antagonist of a CA19-9 activity also includes a molecule that can block, inhibit, or decrease CA19-9 signaling. In some embodiments, an antagonist of a CA19-9 activity further includes molecules that can block, inhibit, or decrease CA19-9 binding to a natural CA19-9-binding molecule. In other embodiments, an antagonist of a CA19-9 activity additionally includes molecules that can block, inhibit, or decrease CA 19-9 binding to a CA19-9 ligand such as a CA19-9 receptor. In another embodiment, an antagonist of a CA19-9 activity also includes molecules that can block, inhibit, or decrease the remodeling, processing, conformational change, or modification of a CA19-9 binding molecule or a CA19-9 effector. An "antagonist" of a target molecule is "antagonistic" to the target molecule.

In some embodiments, the therapeutic agent provided herein can be a blocking antibody, a neutralizing antibody, or an antagonist antibody to a CA19-9 or a CA19-9 activity, wherein the antibody binds to the CA19-9 and act as an antagonist to the CA19-9 or the CA19-9 activity as defined above.

6.2.1.1. Antibodies as Therapeutic Agents in the Methods

In some embodiments, the therapeutic agents that can be used in the methods provided herein are antibodies that have the activities of inhibiting, blocking, reversing, reducing, or attenuating the elevated expression of CA19-9 in the pancreas, elevated levels of Sialyl-Lewis$^a$ in the pancreas, or any combination thereof. Exemplary antibodies suitable for the methods include an anti-CA19-9 antibody and an anti-Sialyl-Lewis$^a$ antibody. In one embodiment, the exemplary antibodies suitable for the methods are blocking or neutralizing antibodies.

In some specific embodiments, the therapeutic agent that can be used in the methods provided herein is an anti-CA19-9 antibody or an anti-Sialyl-Lewis$^a$ antibody. In other specific embodiments, the therapeutic agent that can be used in the methods provided herein is a blocking anti-CA19-9 antibody or a blocking anti-Sialyl-Lewis$^a$ antibody.

As a person of ordinary skill in the art will understand, anti-Sialyl-Lewis$^a$ antibody can be a subset of anti-CA19-9 antibody and both antibodies can be used in the methods provided herein. In some embodiments, the antibody that can be used in the methods provided herein can be an antibody or a functional fragment thereof that binds to a CA19-9 and/or Sialyl-Lewis$^a$, wherein the antibody includes a VH domain that has an amino acid sequence selected from the group consisting of residues 20-142 of SEQ ID NO: 2, residues 20-142 of SEQ ID NO: 6, residues 20-142 of SEQ ID NO: 10, and residues 20-145 of SEQ ID NO: 14.

In another embodiment, the antibody that can be used in the methods provided herein can be an antibody or a functional fragment thereof that binds to a CA19-9 and/or Sialyl-Lewis$^a$, wherein the antibody includes a VL domain that has an amino acid sequence selected from the group consisting of residues 20-130 of SEQ ID NO: 4, residues 20-129 of SEQ ID NO: 8, residues 20-130 of SEQ ID NO: 12, and residues 23-130 of SEQ ID NO: 16.

In another embodiment, the anti-CA19-9 antibody in the methods provided herein can be an antibody or a functional fragment thereof, wherein the antibody heavy or light chain or functional fragment thereof has one or more of the complementarity determining regions (CDRs) depicted in FIGS. 1-8 or listed in Table 2. In another aspect, the anti-CA19-9 antibody in the methods provided herein can include the complement dependent cytotoxicity (CDC) activity and/or antibody-dependent cell-mediated cytotoxicity (ADCC) activity of any one of the clonal isolates 5B1, 9H3, 5H11 or 7E3 described in U.S. Pat. No. 9,475,874, which is incorporated in its entirety by reference. Methods for assessing the specificity, affinity and/or avidity of an antibody or functional fragment thereof are well known in the art and exemplary methods are provided herein.

include the amino acid residues 45-52, 70-72 and 109-120 of SEQ ID NO: 4, or alternatively the amino acid residues 45-52, 70-72 and 109-119 of SEQ ID NO: 8, or alternatively the amino acid residues 45-52, 70-72 and 109-120 of SEQ ID NO: 12, or alternatively the amino acid residues 49-53, 72-74 and 111-120 of SEQ ID NO: 16.

In some embodiments, the present disclosure provides a therapeutic anti-CA19-9 antibody or functional fragment thereof, wherein the antibody binds to sLe$^a$. Accordingly, in some aspects, the disclosure provides an isolated antibody or

TABLE 2

CDRs of Clonal Isolates

| Variable Domain | Nucleic Acid Residues (SEQ ID NO:) | | | Amino Acid Residues (SEQ ID NO:) | | |
|---|---|---|---|---|---|---|
| | CDR1 | CDR2 | CDR3 | CDR1 | CDR2 | CDR3 |
| 5B1 VH | 133-156 (NO: 1) | 208-231 (NO: 1) | 346-393 (NO: 1) | 55-62 (NO: 2) | 70-77 (NO: 2) | 116-131 (NO: 2) |
| 5B1 VL | 133-156 (NO: 3) | 208-216 (NO: 3) | 325-360 (NO: 3) | 45-52 (NO: 4) | 70-72 (NO: 4) | 109-120 (NO: 4) |
| 9H3 VH | 133-156 (NO: 5) | 208-231 (NO: 5) | 346-393 (NO: 5) | 45-52 (NO: 6) | 70-77 (NO: 6) | 116-131 (NO: 6) |
| 9H3 VL | 133-156 (NO: 7) | 208-216 (NO: 7) | 325-357 (NO: 7) | 45-52 (NO: 8) | 70-72 (NO: 8) | 109-119 (NO: 8) |
| 5H11 VH | 133-156 (NO: 9) | 208-231 (NO: 9) | 346-393 (NO: 9) | 45-52 (NO: 10) | 70-77 (NO: 10) | 116-131 (NO: 10) |
| 5H11 VL | 134-156 (NO: 11) | 208-216 (NO: 11) | 325-360 (NO: 11) | 45-52 (NO: 12) | 70-72 (NO: 12) | 109-120 (NO: 12) |
| 7E3 VH | 133-156 (NO: 13) | 208-231 (NO: 13) | 346-402 (NO: 13) | 45-52 (NO: 14) | 70-77 (NO: 14) | 116-134 (NO: 14) |
| 7E3 VK | 145-162 (NO: 15) | 214-222 (NO: 15) | 331-360 (NO: 15) | 49-53 (NO: 16) | 72-74 (NO: 16) | 111-120 (NO: 16) |

In some embodiments, the anti-CA19-9 antibody in the methods provided herein can include the antibody or functional fragment thereof having less than six CDRs. In some embodiments, the therapeutic anti-CA19-9 antibody or functional fragment thereof includes one, two, three, four, or five CDRs selected from the group consisting of VH CDR1, VH CDR2, VH CDR3, VL CDR1, VL CDR2, and/or VL CDR3. In specific embodiments, the therapeutic anti-CA19-9 antibody or functional fragment thereof includes one, two, three, four, or five CDRs selected from the group consisting of VH CDR1, VH CDR2, VH CDR3, VL CDR1, VL CDR2, and/or VL CDR3 of clonal isolates 5B1, 9H3, 5H11 or 7E3 described in U.S. Pat. No. 9,475,874, which is incorporated in its entirety by reference.

In some embodiments, the disclosure provides an therapeutic anti-CA19-9 antibody or functional fragment thereof, wherein the antibody or functional fragment includes a variable heavy (VH) chain domain having the CDR1, CDR2 and CDR3 amino acid sequence of the clonal isolate 5B1, 9H3, 5H11 or 7E3 as described in U.S. Pat. No. 9,475,874. Such VH domains can include the amino acid residues 55-62, 70-77 and 116-131 of SEQ ID NO: 2, or alternatively the amino acid residues 45-52, 70-77 and 116-131 of SEQ ID NO: 6, or alternatively the amino acid residues 45-52, 70-77 and 116-131 of SEQ ID NO: 10, or alternatively the amino acid residues 45-52, 70-77 and 116-134 of SEQ ID NO: 14.

In another embodiment, the disclosure provides a therapeutic anti-CA19-9 antibody or functional fragment thereof, wherein the antibody includes a variable light (VL) chain domain having the CDR1, CDR2 and CDR3 amino acid sequence of the clonal isolate 5B1, 9H3, 5H11 or 7E3 as described in U.S. Pat. No. 9,475,874. Such VL domain can functional fragment thereof that binds to sLe$^a$, wherein the antibody or functional fragment thereof includes a VH domain having an amino acid sequence selected from the group consisting of residues 20-142 of SEQ ID NO: 2, residues 20-142 of SEQ ID NO: 6, residues 20-142 of SEQ ID NO: 10, and residues 20-145 of SEQ ID NO: 14.

In some embodiments, the disclosure provides a therapeutic anti-CA19-9 antibody or functional fragment thereof that binds to sLe$^a$, wherein the antibody or functional fragment thereof includes a VL domain having an amino acid sequence selected from the group consisting of residues 20-130 of SEQ ID NO: 4, residues 20-129 of SEQ ID NO: 8, residues 20-130 of SEQ ID NO: 12, and residues 23-130 of SEQ ID NO: 16.

In some embodiments, the disclosure provides an therapeutic anti-CA19-9 antibody or functional fragment thereof that binds to sLe$^a$, wherein the antibody or functional fragment thereof includes both a VH domain and a VL domain, where the VH domain and the VL domain respectively include an amino acid sequence selected from the group consisting of residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; and residues 20-145 of SEQ ID NO: 14 and residues 23-130 of SEQ ID NO: 16.

In some embodiments, the disclosure provides a therapeutic anti-CA19-9 antibody or functional fragment thereof that binds sLe$^a$, wherein the antibody or the functional fragment has one or more of the CDRs depicted listed in Table 2. In some further embodiments, the disclosure provides a therapeutic anti-CA19-9 antibody or functional fragment thereof that includes one or more of the CDRs (in particular CDR3) and can specifically bind to sLe$^a$ as described in U.S. Pat. No. 9,475,874. In some aspects, an therapeutic anti-CA19-9 antibody or functional fragment thereof in the methods provided herein can include the CDC activity and/or ADCC activity of any one of the clonal isolates 5B1, 9H3, 5H11 or 7E3 as described in U.S. Pat. No. 9,475,874.

In some embodiments, the disclosure provides a therapeutic anti-CA19-9 antibody or functional fragment thereof in the methods, wherein the antibody includes a VH chain domain having the CDR1, CDR2 and CDR3 amino acid sequence of the clonal isolate 5B1, 9H3, 5H111 or 7E3 as described in U.S. Pat. No. 9,475,874. Such VH domains can include the amino acid residues 55-62, 70-77 and 116-131 of SEQ ID NO: 2, or alternatively the amino acid residues 45-52, 70-77 and 116-131 of SEQ ID NO: 6, or alternatively the amino acid residues 45-52, 70-77 and 116-131 of SEQ ID NO: 10, or alternatively the amino acid residues 45-52, 70-77 and 116-134 of SEQ ID NO: 14.

In some embodiments, the disclosure provides a therapeutic anti-CA19-9 antibody or functional fragment thereof in the methods, wherein the antibody includes a VL chain domain having the CDR1, CDR2 and CDR3 amino acid sequence of the clonal isolate 5B1, 9H3, 5H111 or 7E3 as described in U.S. Pat. No. 9,475,874. Such VL domain can include the amino acid residues 45-52, 70-72 and 109-120 of SEQ ID NO: 4, or alternatively the amino acid residues 45-52, 70-72 and 109-119 of SEQ ID NO: 8, or alternatively the amino acid residues 45-52, 70-72 and 109-120 of SEQ ID NO: 12, or alternatively the amino acid residues 49-53, 72-74 and 111-120 of SEQ ID NO: 16.

In some embodiments, the therapeutic anti-CA19-9 antibody or functional fragment thereof in the methods is a monoclonal antibody. In some embodiments, the therapeutic anti-CA19-9 antibody or functional fragment thereof in the methods is an IgG or IgM isotype. In a further embodiment, the therapeutic anti-CA19-9 antibody or functional fragment thereof in the methods is an antibody of the IgG1, IgG2, IgG3, or IgG4 subclass.

In some embodiments, the therapeutic anti-CA19-9 antibody or functional fragment thereof in the methods can be, but is not limited to, a Fab, a Fab', a F(ab')$_2$, a Fabc, a scFV, a diabody, a triabody, minibody or a single-domain antibody (sdAB). In some aspects, the disclosure provides for the methods a diabody that includes the amino acid sequence of SEQ ID NO: 18 or 20. Such diabodies of the disclosure can be, in some aspects, encoded by a polynucleotide having the nucleic acid sequence of SEQ ID NO: 17 or 19. With respect to antibodies and functional fragments thereof, various forms, alterations and modifications are well known in the art. The sLe$^a$ or CA19-9 specific antibody fragments of the disclosure can include any of such various antibody forms, alterations and modifications. Examples of such various forms and terms as they are known in the art are set forth below.

In some embodiments, the antibody that can be used in the methods provided herein can be an antibody or a functional fragment thereof that binds to a CA19-9 and/or Sialyl-Lewis$^a$, wherein the antibody includes a heavy chain consisting of the amino acid sequence of the heavy chain of an antibody produced by a hybridoma deposited under ATCC. Accession No. HB-8059. In another embodiment, the antibody that can be used in the methods provided herein can be an antibody or a functional fragment thereof that binds to a CA19-9 and/or Sialyl-Lewis$^a$, wherein the antibody includes a light chain consisting of the amino acid sequence of the light chain of an antibody produced by a hybridoma deposited under ATCC. Accession No. HB-8059. In a further embodiment, the antibody that can be used in the methods provided herein can be an antibody or a functional fragment thereof that binds to a CA19-9 and/or Sialyl-Lewis$^a$, wherein the antibody includes a light chain consisting of the amino acid sequence of the light chain of an antibody produced by a hybridoma deposited under ATCC. Accession No. HB-8059 and a heavy chain consisting of the amino acid sequence of the heavy chain of an antibody produced by a hybridoma deposited under ATCC. Accessiond No. HB-8059.

In another embodiment, the anti-CA19-9 antibody in the methods provided herein can be an antibody or a functional fragment thereof, wherein the antibody heavy or light chain or functional fragment thereof has-one or more of the complementarity determining regions (CDRs) of an antibody produced by a hybridoma deposited under ATCC. Accession No. HB-8059. In another aspect, the anti-CA19-9 antibody in the methods provided herein can include the complement dependent cytotoxicity (CDC) activity and/or antibody-dependent cell-mediated cytotoxicity (ADCC) activity of an antibody produced by a hybridoma deposited under ATCC. Accession No. HB-8059. Methods for assessing the specificity, affinity and/or avidity of an antibody or functional fragment thereof are well known in the art and exemplary methods are provided herein.

In some embodiments, the anti-CA19-9 antibody in the methods provided herein can include the antibody or functional fragment thereof having less than six CDRs. In some embodiments, the therapeutic anti-CA19-9 antibody or functional fragment thereof includes one, two, three, four, or five CDRs selected from the group consisting of VH CDR1, VH CDR2, VH CDR3, VL CDR1, VL CDR2, and/or VL CDR3 of an antibody produced by a hybridoma deposited under ATCC. Accession No. HB-8059. In specific embodiments, the therapeutic anti-CA19-9 antibody or functional fragment thereof includes one, two, three, four, or five CDRs selected from the group consisting of VH CDR1, VH CDR2, VH CDR3, VL CDR1, VL CDR2, and/or VL CDR3 of clonal isolate No. SW-1116-19-9 (also known as 1116-NS-19-9, NS-19-9 or NS19-9), which was described in U.S. Pat. No. 4,471,057, which is incorporated in its entirety by reference.

In some embodiments, the disclosure provides an therapeutic anti-CA19-9 antibody or functional fragment thereof, wherein the antibody or functional fragment includes a variable heavy (VH) chain domain having the CDR1, CDR2 and CDR3 amino acid sequence of the VH chain domain CDR1, CDR2 and CDR3 sequence of an antibody produced by a hybridoma deposited under ATCC. Accession No. HB-8059. In another embodiment, the disclosure provides a therapeutic anti-CA19-9 antibody or functional fragment thereof, wherein the antibody includes a variable light (VL) chain domain having the CDR1, CDR2 and CDR3 amino acid sequence of the VL chain domain CDR1, CDR2 and CDR3 sequence of an antibody produced by a hybridoma deposited under ATCC. Accession No. HB-8059. In a further embodiment, the disclosure provides a therapeutic anti-CA19-9 antibody or functional fragment thereof, wherein the antibody includes a VL chain domain having the CDR1, CDR2 and CDR3 amino acid sequence of the VL chain domain CDR1, CDR2 and CDR3 sequence of an antibody produced by a hybridoma deposited under ATCC. Accession No. HB-8059 and a VH chain domain having the CDR1, CDR2 and CDR3 amino acid sequence of the VH chain domain CDR1, CDR2 and CDR3 sequence of an antibody produced by a hybridoma deposited under ATCC. Accession No. HB-8059

In some embodiments, the disclosure provides an isolated antibody or functional fragment thereof that binds to sLe$^a$, wherein the antibody or functional fragment thereof includes a VH domain having the amino acid sequence of the variable heavy chain of an antibody produced by a hybridoma deposited under ATCC. Accession No. HB-8059. In some embodiments, the disclosure provides a therapeutic anti-CA19-9 antibody or functional fragment thereof that binds to sLe$^a$, wherein the antibody or functional fragment thereof includes a VL domain having an amino acid sequence of the variable light chain of an antibody produced by a hybridoma deposited under ATCC. Accession No. HB-8059. In another embodiment, the disclosure provides a therapeutic anti-CA19-9 antibody or functional fragment thereof that binds to sLe$^a$, wherein the antibody or functional fragment thereof includes a VL domain having an amino acid sequence of the variable light chain of an antibody produced by a hybridoma deposited under ATCC. Accession No. HB-8059 and a VH domain having the amino acid sequence of the variable heavy chain of an antibody produced by a hybridoma deposited under ATCC. Accession No. HB-8059.

In some embodiments, the antibody that can be used in the methods provided herein can be an antibody or a functional fragment thereof that binds to a CA19-9 and/or Sialyl-Lewis$^a$, wherein the antibody includes a heavy chain consisting of the amino acid sequence of the heavy chain of the clonal isolate NS19-9. In another embodiment, the antibody that can be used in the methods provided herein can be an antibody or a functional fragment thereof that binds to a CA19-9 and/or Sialyl-Lewis$^a$, wherein the antibody includes a light chain consisting of the amino acid sequence of the light chain of the clonal isolate NS19-9. In a further embodiment, the antibody that can be used in the methods provided herein can be an antibody or a functional fragment thereof that binds to a CA19-9 and/or Sialyl-Lewis$^a$, wherein the antibody includes a light chain consisting of the amino acid sequence of the light chain of the clonal isolate NS19-9 and a heavy chain consisting of the amino acid sequence of the heavy chain of the clonal isolate NS19-9.

In some embodiments, the disclosure provides a therapeutic anti-CA19-9 antibody or functional fragment thereof in the methods, wherein the antibody includes a VH chain domain having the CDR1, CDR2 and CDR3 amino acid sequence of the clonal isolate NS19-9. In some embodiments, the disclosure provides a therapeutic anti-CA19-9 antibody or functional fragment thereof in the methods, wherein the antibody includes a VL chain domain having the CDR1, CDR2 and CDR3 amino acid sequence of the clonal isolate NS19-9. In another embodiment, the disclosure provides a therapeutic anti-CA19-9 antibody or functional fragment thereof in the methods, wherein the antibody includes a VH chain domain having the CDR1, CDR2 and CDR3 amino acid sequence of the clonal isolate NS19-9 and a VL chain domain having the CDR1, CDR2 and CDR3 amino acid sequence of the clonal isolate NS19-9.

In some additional aspects, the disclosure provides an isolated antibody or functional fragment thereof that binds to sLe$^a$, wherein the antibody or functional fragment thereof includes a VH domain having the amino acid sequence of the variable heavy chain of the clonal isolate NS19-9. In some embodiments, the disclosure provides a therapeutic anti-CA19-9 antibody or functional fragment thereof that binds to sLe$^a$, wherein the antibody or functional fragment thereof includes a VL domain having an amino acid sequence of the variable light chain of the clonal isolate NS19-9. In another embodiment, the disclosure provides a therapeutic anti-CA 19-9 antibody or functional fragment thereof that binds to sLe$^a$, wherein the antibody or functional fragment thereof includes a VL domain having an amino acid sequence of the variable light chain of the clonal isolate NS19-9 and a VH domain having the amino acid sequence of the variable heavy chain of the clonal isolate NS19-9.

In some embodiments, the therapeutic antibody or the functional fragment thereof in the methods can be produced by suitable means (for example recombinantly, biologically, or synthetically) and purified by suitable means (for example chromatography, centrifugation, tag-based affinity separation, or differential solubility) as described in U.S. Pat. No. 9,475,874, which is hereby incorporated in its entirety by reference.

The therapeutic antibody in the methods provided herein include a Fab fragment. A Fab fragment refers to a monovalent fragment consisting of the VL, VH, CL and CHI domains; a F(ab')$_2$ fragment is a bivalent fragment including two Fab fragments linked by a disulfide bridge at the hinge region; a Fd fragment consists of the VH and CHI domains; an Fv fragment consists of the VL and VH domains of a single arm of an antibody; and a dAb fragment (Ward et al., *Nature* 341:544-546, (1989)) consists of a VH domain.

The therapeutic antibody in the methods provided herein include can have one or more binding sites. If there is more than one binding site, the binding sites can be identical to one another or can be different. For example, a naturally occurring immunoglobulin has two identical binding sites, a single-chain antibody or Fab fragment has one binding site, while a "bispecific" or "bifunctional" antibody has two different binding sites.

The therapeutic antibody in the methods provided herein can also be a single-chain antibody. A single-chain antibody (scFv) refers to an antibody in which a VL and a VH region are joined via a linker (e.g., a synthetic sequence of amino acid residues) to form a continuous polypeptide chain wherein the linker is long enough to allow the protein chain to fold back on itself and form a monovalent antigen binding site (see, e.g., Bird et al., *Science* 242:423-26 (1988) and Huston et al., *Proc. Natl. Acad. Sci. USA* 85:5879-83 (1988)). Diabodies refer to bivalent antibodies including two polypeptide chains, wherein each polypeptide chain includes VH and VL domains joined by a linker that is too short to allow for pairing between two domains on the same chain, thus allowing each domain to pair with a complementary domain on another polypeptide chain (see, e.g., Holliger et al., *Proc. Natl. Acad. Sci. USA* 90:6444-48 (1993), and Poljak et al., *Structure* 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies including three and four polypeptide chains, respectively, and forming three and four antigen binding sites, respectively, which can be the same or different.

The present disclosure also provides a therapeutic antibody or functional fragment thereof that is derivative of 5B1, 9H3, 5H11 and/or 7E3 as described in U.S. Pat. No. 9,475,874 as well as NS19-9 as described in U.S. Pat. No. 4,471,057, wherein the antibody or functional fragment binds to CA19-9 and sLe$^a$. Standard techniques well known to those of skill in the art can be used to introduce mutations in the nucleotide sequence encoding an antibody or functional fragment thereof of the disclosure, including, for example, site-directed mutagenesis and PCR-mediated mutagenesis which results in amino acid substitutions. In some aspects, the derivative includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule.

In some embodiments, the disclosure provides a therapeutic antibody or functional fragment thereof having modified forms of naturally occurring amino acids, conservative substitutions, non-naturally occurring amino acids, amino acid analogues and mimetics so long as such the antibody or functional fragment retains functional activity as defined herein. In one embodiment, the derivative has conservative amino acid substitutions that are made at one or more predicted non-essential amino acid residues. A conservative amino acid substitution is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody or functional fragment thereof can be expressed and the activity of the antibody or functional fragment can be determined.

In some embodiments, the disclosure provides a therapeutic antibody or functional fragment thereof having modified fucosylation, galactosylation and/or sialylation of an Fc fragment contained within an antibody or functional fragment of the disclosure. Such modifications of an Fc fragment can effect Fc receptor-mediated activity as discussed in Peipp et al., *Blood*, 112(6):2390-2399 (2008). For example, glycoengineered therapeutic antibodies lacking core fucose residues from the Fc N-glycans exhibit strong ADCC at lower concentrations with much higher efficacy compared to fucosylated counterparts. Shields et al., *J. Biol. Chem.*, 277(30):26733-40 (2002); Okazaki et al., *J Mol Biol.*, 336: 1239-1249 (2004); Natsume et al., *J. Immunol. Methods.*, 306:93-103 (2005). Methods for modifying the fucosylation, galactosylation and/or sialylation of an antibody for functional fragment thereof are well known in the art. For example, defucosylation approaches can be grouped into three methodologies (1) conversion of the N-glycosylation pathway of nonmammalian cells to the 'humanized' non-fucosylation pathway; (2) inactivation of the N-glycan fucosylation pathway of mammalian cells and (3) in vitro chemical synthesis of non-fucosylated N-glycoprotein or enzymatic modification of N-glycans to non-fucosylated forms, as described in Yamane-Ohnuki et al., MAbs., 1(3): 230-236 (2009). It is understood that any one of these methods or any other method that is well known in the art can be used to produce an antibody or functional fragment thereof having modified fucosylation, galactosylation and/or sialylation.

6.2.1.2. Peptides and Peptidomimetics as Therapeutic Agents in the Methods

Peptides and peptidomimetics offer the structural diversity required for selective and high affinity interactions with a target protein. The disclosure provides peptides and peptidomimetics as a therapeutic agent in the methods. In some embodiments, the therapeutic agents that can be used in the methods provided herein are peptides or peptidomimetics that have the activities of inhibiting, blocking, reversing, reducing, or attenuating the elevated expression of CA19-9 in the pancreas, the elevated EGFR signaling pathway in the pancreas, elevated levels of Sialyl-Lewis$^a$ in the pancreas, or any combination thereof. Exemplary peptides or peptidomimetics suitable for the methods include those that specifically binds to a target selected from a group consisting of CA19-9 and Sialyl-Lewis$^a$. In one embodiment, the exemplary peptides suitable for the methods are blocking or neutralizing peptides. In another embodiment, the exemplary peptidomimetics suitable for the methods are blocking or neutralizing peptidomimetics.

The therapeutic peptides in the methods can be based on the sequence of the binding region between the two proteins. The linear sequences can originate from a loop within a structured domain, or from a disordered region in protein termini or between defined domains. In order to achieve desired efficacy, the therapeutic peptide can be targeted to the appropriate site in an organism, tissue or cell via fusion with a targeting sequence, and binds to the intended protein target in vivo. In one embodiment, a therapeutic peptide is a short peptide sequence, for example a peptide of no more than 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 amino acids, that will bind and block the function of a target protein to achieve the required activities as provided herein. These linear sequences can be determined according to the available structural information on the target protein—for example, structure-based design of the peptides or peptidomimetics. Furthermore, a therapeutic peptide and peptidomimetics can be screened and selected for preventing, treating, ameliorating, or managing pancreatitis related target as described herein using peptide libraries and array techniques as described in Section 6.2.1.2.

The activities of the therapeutic peptides or the variant thereof can be identified, tested, and verified in any of the assays as described in Section 6.3 and Examples from a library of peptides or peptidomimetics. The therapeutic peptides can be screened and identified according to the assays described in Section 6.3 and 6.2.1.2 from a library of peptides or peptidomimetics. The peptides can be produced, recombinantly or synthetically, according to methods well known to a person of ordinary skill in the art, for example as described in WO 2007/019545; WO 2015/009820A2; and WO 2009/094172 A2, which are hereby incorporated in their entirety by reference.

Peptide libraries and peptidomimetic libraries from which the therapeutic peptide can be identified and selected are well known to a person of ordinary skill in the art. For example, a suitable peptide library can be a biological peptide library, wherein the peptide libraries have a genotype, or DNA sequence encoding the peptide sequence, that is linked to the expression of the peptide, as part of the library's normal structure. Exemplary biological peptide libraries include those of phage, bacterial, ribosome, mRNA, yeast, cDNA, retrovirus, baculovirus, and mammalian cell display. A suitable peptide library can also be a chemical peptide library, wherein the peptide libraries are synthetically produced. Exemplary chemical peptide libraries include combinatorial peptide libraries such as one-bead one-compound (OBOC) libraries and positional scanning synthetic peptide combinatorial libraries (PS-SPCLs). For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks. Detailed protocols for producing the peptide libraries and for selecting target binding and/or target blocking peptides from various peptide libraries are described in Kehoe J W, et al., Chem. Rev. 2005; 105:4056; Hill H R, et al., Mol. Microbiol. 1996; 20:685; Smith G P, et al., Chem. Rev. 1997; 97:391; Cabilly S. Mol. Biotechnol. 1999; 12:143; Fukunaga K, et al., J. Nucleic Acids. 2012; 2012:9; Gray B P, et al., Chem Rev. 2014; 114(2): 1020-1081, all of which are hereby incorporated in their entirety by reference.

In certain embodiments, the peptides for use in the present methods can include certain structural or functional motif(s). Motif of a peptide refers either to a set of consecutive amino acids within the amino acid sequence of the peptide chain and/or to a set of linearly or spatially adjacent amino acids within the secondary and/or tertiary structure of said peptide. Because the motif can be formed all or in part as a result of protein folding, amino acids that are adjacent in the described motif can be separated by 0, 1 or more, 5 or more, 10 or more, 15 or more or 20 or more amino acids within the linear amino acid sequence of the peptide. For example, a therapeutic peptide can be a peptide or a variant thereof of any of the CDR sequences of any of the anti-CA19-9 as provided herein.

In certain embodiments, peptides for use in the present methods include peptides that have 30%, 35%, 40%, 45%, 50%, 55%, 60%, 65%, 70%, 75%, 80%, 85%, 90%, 95% sequence identity with any therapeutic peptide provided herein. To determine the percent identity of two amino acid sequences, the sequences are aligned for optimal comparison purposes. The amino acid residues at corresponding amino acid positions are then compared. When a position in the first sequence is occupied by the same amino acid residue as the corresponding position in the second sequence, then the molecules are identical at that position. The percent identity between the two sequences is a function of the number of identical positions shared by the sequences (i.e., % identity=number of identical overlapping positions× 100/total number of positions). In one embodiment, the two sequences are the same length. In an alternate embodiment, the sequences are of different length and, accordingly, the percent identity refers to a comparison of the shorter sequence to a portion of the longer sequence, wherein said portion is the same length as said shorter sequence.

Peptides with additional modifications can also be used in the methods provided herein for preventing, treating, ameliorating or managing pancreatitis. For example, the peptides of the above-noted structural motifs can be synthesized with one or more (D)-amino acids. The choice of including an (L)- or (D)-amino acid into a peptide useful in the methods provided herein depends, in part, upon the desired characteristics of the peptide. For example, the incorporation of one or more (D)-amino acids can confer increasing stability on the peptide in vitro or in vivo. The incorporation of one or more (D)-amino acids can also increase or decrease the binding activity of the peptide as determined, for example, using the bioassays described herein, or other methods well known in the art.

Replacement of all or part of a sequence of (L)-amino acids by the respective sequence of entatiomeric (D)-amino acids renders an optically isomeric structure in the respective part of the peptide chain. Inversion of the sequence of all or part of a sequence of (L)-amino acids renders retro-analogues of the peptide. Combination of the enantiomeric (L to D, or D to L) replacement and inversion of the sequence renders retro-inverso-analogues of the peptide. It is known to those skilled in the art that enantiomeric peptides, their retro-analogues, and their retro-inverso-analogues maintain significant topological relationship to the parent peptide, and especially high degree of resemblance is often obtained for the parent and its retro-inverso-analogues. This relationship and resemblance can be reflected in biochemical properties of the peptides, especially high degrees of binding of the respective peptides and analogs to a receptor protein. The synthesis of the properties of retro-inverso analogues of peptides have been discussed for example in Methods of Organic Chemistry (Houben-Weyl), Synthesis of Peptides and Peptidomimetics—Workbench Edition Volume E22c (Editor-in-chief Goodman M.) 2004 (George Thieme Verlag Stuttgart, New York), and in references cited therein, all of which are hereby incorporated by reference herein in their entireties.

The therapeutic peptides provided herein also include peptides with amino acid modifications. Amino acid "modification" refers to the alteration of a naturally occurring amino acid to produce a non-naturally occurring amino acid. Derivatives of the peptides that can be used with the methods provided herein having non-naturally occurring amino acids can be created by chemical synthesis or by site specific incorporation of unnatural amino acids into peptides during biosynthesis, as described in Christopher J. Noren, Spencer J. Anthony-Cahill, Michael C. Griffith, Peter G. Schultz, 1989 Science, 244:182-188, hereby incorporated by reference herein in its entirety.

Peptidomimetics (peptide mimetics) that are structurally similar to therapeutically useful peptides can be used to produce an equivalent therapeutic or prophylactic effect. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —$CH_2$—NH—, —$CH_2$S—, —$CH_2$—$CH_2$—, —CH=CH— (cis and trans), —$COCH_2$—, —CH(OH)$CH_2$—, and —$CH_2$SO—, by methods known in the art and further described in the following references: Spatola, A. F. in "Chemistry and Biochemistry of Amino Acids, Peptides, and Proteins," B. Weinstein, eds., Marcel Dekker, New York, p 267 (1983); Spatola, A. F., Vega Data (March 1983), Vol. 1. Issue 3, "Peptide Backbone Modifications" (general review); Morely, J. S., Trends Pharma Sci (1980) pp. 463-468 (general review); Hudson, D. et al., (1979) Int J Pept Prot Re 14: 177-185 (—$CH_2$—NH—, —$CH_2$—$CH_2$—); Spatola, A. F. et al., (1986) Life Sci 38:1243-1249 (—$CH_2$—S—); Hann, M. M., (1982) J Chem Soc Perkin Trans I 307-314 (—CH=CH—, cis and trans); Almquist, R. G. et al., (1980) J Med Chem 23: 1392 (—$COCH_2$—); Jennings-White, C et al., (1982) Tetrahedron Lett 23:2533 (—$COCH_2$—); Szelke, M et al., European Appln. EP 45665 (1982) CA: 97: 39405 (1982) (—CH(OH)$CH_2$—); Holladay, M. W. et al., (1983) Tetrahedron Lett 24:4401-4404 (—C(OH)$CH_2$—); and Hruby, V. J., (1982) Life Sci 31:189-199 (—$CH_2$—S—); each of which is incorporated herein by reference.

In another embodiment of peptidomimetics, the non-peptide linkage is —$CH_2$NH—. Such peptide mimetics can have significant advantages over peptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

A variety of designs for peptide mimetics are possible. For example, cyclic peptides, in which the necessary conformation is stabilized by non-peptides, are specifically contemplated, U.S. Pat. No. 5,192,746 to Lobl, et al., U.S. Pat. No. 5,576,423 to Aversa, et al., U.S. Pat. No. 5,051,448 to Shashoua, and U.S. Pat. No. 5,559,103 to Gaeta, et al., all hereby incorporated by reference, describe multiple methods for creating such compounds. Synthesis of nonpeptide compounds that mimic peptide sequences is also known in the art. Eldred et al., J. Med. Chem. 37:3882 (1994), hereby incorporated by reference herein in its entirety) describe non-peptide antagonists that mimic the peptide sequence. Likewise, Ku et al., J. Med. Chem 38:9 (1995) (hereby incorporated by reference herein in its entirety) further elucidates the synthesis of a series of such compounds.

Additionally, the therapeutic peptides can be peptides with mutations in the peptide sequences. The mutations provided herein can be substitutions including conservative or non-conservative substitutions of internal or terminal amino acid residues, deletions including internal deletions and deletions of terminal residues, additions including internal additions and additions to the two termini of the peptides, all of which can be made according to methods well known to a person of ordinary skill in the art, for example, as described in Molecular Cloning: A Laboratory Manual (Fourth Edition); ISBN 978-1-936113-42-2.

Either conservative or non-conservative amino acid substitutions can be made at one or more amino acid residues in the therapeutic peptides. Both conservative and non-conservative substitutions can also be made. Conservative replacements are those that take place within a family of amino acids that are related in their side chains. Non-conservative substitutions are substitution of amino acid of one family with an amino acid from a different family. Genetically encoded amino acids can be divided into four families: (1) acidic=Asp (D), Glu (G); (2) basic=Lys (K), Arg (R), His (H); (3) nonpolar (hydrophobic)=Cys (C), Ala (A), Val (V), Leu (L), Ile (I), Pro (P), Phe (F), Met (M), Trp (W), Gly (G), Tyr (Y); and (4) uncharged polar=Asn (N), Gln (Q), Ser (S), Thr (T). Non-polar can be subdivided into: strongly hydrophobic=Ala (A), Val (V), Leu (L), Ile (I), Met (M), Phe (F); and moderately hydrophobic=Gly (G), Pro (P), Cys (C), Tyr (Y), Trp (W). In alternative fashion, the amino acid repertoire can be grouped as (1) acidic=Asp (D), Glu (G); (2) basic=Lys (K), Arg (R), His (H), (3) aliphatic=Gly (G), Ala (A), Val (V), Leu (L), Ile (I), Ser (S), Thr (T), with Ser (S) and Thr (T) optionally be grouped separately as aliphatic-hydroxyl; (4) aromatic=Phe (F), Tyr (Y), Trp (W); (5) amide=Asn (N), Glu (Q); and (6) sulfur-containing=Cys (C) and Met (M). (See, for example, Biochemistry, 4th ed., Ed. by L. Stryer, WH Freeman and Co., 1995, which is incorporated by reference herein in its entirety).

In certain embodiments, the peptides for use with the present methods can be isolated or purified peptides. An isolated or purified peptide refers to a peptide that is substantially free of at least one component as the referenced peptide is found in the cell or microbial that produced the peptide, or is substantially free of at least one component as the referenced peptide is found in the mixture when it was first synthesized. As such, the peptide can be substantially free of cellular materials (such as lipids, DNA, and/or carbohydrates) or other contaminating proteins from the cell or tissue source from which the protein or peptide is derived, or substantially free of chemical precursors or other chemicals when chemically synthesized. The language "substantially free of" includes preparations of a peptide in which the peptide is separated from one or more components of the mixture from which the peptide is isolated. Thus, a peptide that is substantially free of cellular material includes preparations of peptides having less than about 30%, 20%, 10%, or 5% (by dry weight) of heterologous protein (also referred to herein as a "contaminating protein"). When the peptide is recombinantly produced, it can be substantially free of culture medium, e.g., culture medium represents less than about 20%, 10%, or 5% of the volume of the protein preparation. When the peptide is produced by chemical synthesis, it can be substantially free of chemical precursors or other chemicals, e.g., it is separated from chemical precursors or other chemicals which are involved in the synthesis of the protein. Accordingly such preparations of the peptide have less than about 30%, 20%, 10%, 5% (by dry weight) of chemical precursors or compounds other than the peptide of interest. For examples, peptides provided herein and/or the peptides useful in the methods as provided herein can be isolated or purified peptides, or peptides that have not been isolated or purified.

6.2.2 Patient Populations, Biomarkers, and Therapeutic Outcome

As discussed above, pancreatitis can be classified as chronic pancreatitis and acute pancreatitis. In some embodiments, the difference between acute and chronic pancreatitis lies in the duration and persistence of pancreatic inflammation and pancreatic damage. Acute pancreatitis refers to an isolated (sometimes sudden or short) episode of pancreatitis that is often accompanied by sharp abdominal pain. Chronic pancreatitis refers to a continuous irreversible inflammatory and fibrotic condition in the pancreas that leads to prolonged impairment of exocrine and/or endocrine function of pancreas. As such, chronic pancreatitis can encompass pancreatitis in which inflammation persists in the pancreas, or even if the inflammation has resolved, the resultant damage to pancreas such as that characterized by fibrosis, calcification and ductal injuries persists to affect pancreatic function. As is clear from the discussions above and below, the causes and mechanisms for developing acute and chronic pancreatitis overlap. Accordingly, a person skilled in the art will understand that acute pancreatitis can lead to chronic pancreatitis, chronic pancreatitis patients can develop an episode of acute pancreatitis. Furthermore, patients can develop chronic pancreatitis, having resolved one or more episodes of acute pancreatitis.

Acute pancreatitis can be further classified into different stages according to various markers described herein. For example, acute pancreatitis can be further classified as mild acute pancreatitis and severe acute pancreatitis according to the Atlanta Classification (Edward L. Bradley, Arch Surg. 1993; 128(5):586-590), which is herein incorporated in its entirety by reference. Mild acute pancreatitis refers to acute pancreatitis that has minimal organ dysfunction, has no pancreatic tissue necrosis, has no organ failure, and/or is associated with a self-limited course. Severe acute pancreatitis refers to pancreatitis accompanied by organ failure, local pancreatic complications such as pseudocyst, and/or tissue necrosis (necrotizing pancreatitis). Various scoring system has been adopted to further classify acute pancreatitis, including Ranson criteria, Glasgow-Imrie prognostic criteria, CT Severity Index, APACHE II classification system, and Balthazar CT-enhanced scoring system, as disclosed in Chapter 37 on Acute Pancreatitis, GI/Liver Secrets Plus, 4th edition, edited by McNally PR, 2010 and Carroll J K et al., Am Fam Physician 2007; 75:1513-20, which is herein incorporated in its entirety by reference. In some embodiments, the scores from the various acute pancreatitis scoring system can be used to classify acute pancreatitis. For example meeting less than 3 criteria of the 11 criteria Ranson system can indicate mild acute pancreatitis, whereas meeting 3 or more out of 11 criteria in Ranson system can indicate severe acute pancreatitis. In one embodiment, meeting 3 or more out of 8 criteria in Glasgow-Imrie scoring system can indicate severe acute pancreatitis, whereas meeting less than 3 criteria in the same system can indicate mild acute pancreatitis. In another embodiment, scoring 8 or more points in the 14 criteria APACHE II scoring system can indicate severe acute pancreatitis, whereas scoring less than 8 points in the same system can indicate mild acute pancreatitis. In a further embodiment, the criteria and the scoring system are well known to a person of ordinary skill in the art and have been described in detail in Chapter 37 on Acute Pancreatitis, GI/Liver Secrets Plus, 4th edition, edited by McNally PR, 2010, Carroll J K et al., Am Fam Physician 2007; 75:1513-20, and Matull W R et al., J Clin Pathol 2006; 59:340-344, all of which are herein incorporated in their entirety by reference. The methods provided herein can be used for patients of any stages of acute pancreatitis as classified by any classification system disclosed herein.

Alternatively, acute pancreatitis can be further classified as mild acute pancreatitis, moderate acute pancreatitis, and severe acute pancreatitis according to the Revised Atlanta Classification (Banks P A et al., Gut 2013; 62:102-111), which is herein incorporated in its entirety by reference. In the Revised Atlanta Classification, mild acute pancreatitis refers to acute pancreatitis in which the patients have no organ failure and no local or systemic complications; moderate acute pancreatitis refers to acute pancreatitis in which the patients have transient organ failure (organ failure that resolves within 48 hours) and/or local or systemic complications without persistent organ failure; and severe acute pancreatitis refers to acute pancreatitis in which the patients have persistent organ failure (single or multiple organ failure for over 48 hours). The methods provided herein can be used for patients of mild acute pancreatitis, moderate acute pancreatitis, and severe acute pancreatitis according to the Revised Atlanta Classification as disclosed and cited herein.

The classification of mild acute pancreatitis, moderate acute pancreatitis, and severe acute pancreatitis can also be determined in a scoring system. In one embodiment of such scoring system for acute pancreatitis classification, patients are evaluated in computed tomography severity index (CTSI). In CTSI, patients are first evaluated in Balthazar score, wherein normal pancreas gets a score of 0, enlargement of pancreas gets a score of 1, inflammatory changes in the pancreas and peripancreatic fat gets a score of 2, ill-defined single peripancreatic fluid collection gets a score of 3, and two or more poorly defined peripancreatic fluid collections gets a score of 4. The patients are further evaluated in pancreatic necrosis score, wherein no pancreatic necrosis gets a score of 0, no more than 30% of pancreatic necrosis gets a score of 2, over 30% but no more than 50% of pancreatic necrosis gets a score of 4, and over 50% of pancreatic necrosis gets a score of 6. In some embodiments, the summation of Balthazar score and pancreatic necrosis score can then be used for classifying acute pancreatitis, wherein a total score of 0 to 3 is classified as mild acute pancreatitis, a total score of 4 to 6 is classified as moderate acute pancreatitis, and a total score of 7 to 10 is classified as severe acute pancreatitis. The methods provided herein can be used for patients of mild acute pancreatitis, moderate acute pancreatitis, and severe acute pancreatitis as classified according to CTSI as disclosed herein.

Additionally, acute pancreatitis can be subdivided into two types: interstitial oedematous pancreatitis and necrotising pancreatitis, according to Banks P A et al., Gut 2013; 62:102-111. Interstitial oedematous pancreatitis refers to acute pancreatitis having diffuse (or occasionally localised) enlargement of the pancreas due to inflammatory oedema. Necrotising pancreatitis refers to acute pancreatitis having necrosis of the pancreatic parenchyma, the peripancreatic tissue, or both. The methods provided herein can be used for patients of interstitial oedematous pancreatitis or necrotising pancreatitis as disclosed herein.

Similarly, chronic pancreatitis can be further divided into mild chronic pancreatitis, moderate chronic pancreatitis, and severe chronic pancreatitis, (also known as Cambridge Class or Cambridge Stage I, II, and III respectively), according to Cambridge Classification system as described in Sai J K, et al., *World J Gastroenterol.* 2008 Feb. 28; 14(8):1218-21; Sarner M, et al., Gut. 1984 July; 25(7):756-9; Axon A T, et al., Gut. 1984 October; 25(10):1107-12, all of which are herein incorporated in their entirety by reference. Mild chronic pancreatitis refers to pancreatitis having 3 or more abnormal branches in endoscopic retrograde cholangiopancreatography (ERCP) findings and 2 or more from one of the following group in ultrasound or computed tomography (CT) findings: cavities <10 mm, duct irregularity, focal acute necrosis, panrenchymal heterogeneity, increased echogenicity of duct wall, and contour irregularity of head or body. Moderate chronic pancreatitis refers to pancreatitis having more than 3 abnormal side branches and abnormal main duct in ERCP findings and 2 or more from one of the following group in ultrasound or CT findings: cavities <10 mm, duct irregularity, focal acute necrosis, panrenchymal heterogeneity, increased echogenicity of duct wall, and contour irregularity of head or body. Severe chronic pancreatitis refers to pancreatitis having at least those abnormalities of mild and moderate chronic pancreatitis and additionally 1 or more of selected from large cavity >10 mm, intraductal filling defects, duct obstruction (stricture), and duct dilatation or irregularity in ERCP findings, as well as 1 or more of selected from large cavity >10 mm, intraductal filling defects, duct obstruction (stricture), duct dilatation or irregularity, calculi and/or pancreatic calcification, and contiguous organ invasion. The methods provided herein can be used for patients of mild chronic pancreatitis, moderate chronic pancreatitis, and severe chronic pancreatitis as disclosed herein.

As described above and below, the methods provided herein can improve any one or more pancreatitis marker as described herein in pancreatitis patients. The terms "improve," "improving," or "improvement," when referring to a pancreatitis marker include any change of the pancreatitis marker as long as the change is in the direction from what the marker would be in a subject having pancreatitis to that in a subject free of pancreatitis or to a normal reference range. Therefore, for pancreatitis markers that correlate with the severity of pancreatitis, such an "improvement" of the pancreatitis markers would mean a reduction of the pancreatitis markers. Examples of such correlative markers include immune cell invasion, collagen deposition, fibrotic tissue, fat necrosis, interstitial edema, acinar and blood vessel destruction, interstitial hemorrhage, ductal dilation, acinar cell homogenization, expression levels of $sLe^a$, expression levels of CA19-9, serum lipase level, serum amylase level, serum C reactive protein level, weight loss, malabsorption of food, pancreatic atrophy, pancreatic enlargement, pancreatic inflammation, bile reflux, and penetrance of pancreatitis. For pancreatitis markers that inversely correlate with the severity of pancreatitis, such an "improvement" of the pancreatitis markers would mean an increase of the pancreatitis markers. Examples of the inversely correlative pancreatitis markers include percentage of pancreatic function, the number of pancreatic acinus, and the number of acinar cells. Further disclosures regarding the markers and treatment outcome are provided herein.

In some specific embodiments, the disclosure further provides that the methods provided herein can improve the therapeutic outcome for the patients by resolving the pancreatitis for the patients or reversing the stages of pancreatitis, for example from severe acute/chronic pancreatitis to moderate acute/chronic pancreatitis, from severe acute/chronic pancreatitis to mild acute/chronic pancreatitis, or from moderate acute/chronic pancreatitis to mild acute/chronic pancreatitis as classified by any classification system described herein. Such improvement as a result of the methods provided herein can also be a retardation of the progression of the patient's pancreatitis stages, such as less rapid progression from one stage to another when compared with a similar patients not treated or treated with a placebo, or a stabilization of the patient's pancreatitis stage, such as the patients' pancreatitis staying at mild, moderate, or severe pancreatitis without worsening of the disease into the next stage.

Alternatively, chronic pancreatitis can be classified according to Marseilles-Rome classification modified by Sarlesas. This classification divides chronic pancreatitis into four groups based on epidemiology, molecular biology, and morphology. In such a classification system, chronic pancreatitis is classified as calcifying chronic pancreatitis, which is characterized by irregular fibrosis, intraductal protein plugs, intraductal stones, and/or ductal injury; obstructive chronic pancreatitis, which is characterized by glandular changes, uniform fibrosis, ductal dilation, acinar atrophy, and/or improvement with pancreatic duct obstruction removal; inflammatory chronic pancreatitis, which is characterized by mononuclear cell infiltration, exocrine parenchymal destruction, diffuse fibrosis, and/or atrophy; and asymptomatic pancreatic fibrosis, which is characterized by silent diffuse perilobular fibrosis. The methods provided herein can be used for patients of any stage of chronic pancreatitis classified according to the Marseilles-Rome classification scheme as discussed in Chapter 38 on Chronic Pancreatitis, GI/Liver Secrets Plus, 4th edition, edited by McNally PR, 2010.

Various physiological, biological, histological, serological, and/or signaling parameters can be used as biomarkers to monitor the course of treatment and to adjust the dosing of the therapeutic agents described herein (such as the therapeutic agents described in Section 6.2.1). Additionally or alternatively, biomarkers can be used to select patients for treatment with the methods disclosed herein. In this section, various such biomarkers that can be used with the methods provided herein are described.

As disclosed above, an underlying symptom of pancreatitis is pancreatic inflammation and pancreatic tissue damages. Exemplary pancreatic tissue damages in pancreatitis patients include damages to islets of Langerhans, acinar cells, pancreatic blood vessel, pancreatic ducts, pancreatic duct cells, exocrine components in the pancreatic organ system, endocrine components in the pancreatic organ system, and/or other pancreatic tissues. The pancreatic damage can have microscopic or even macroscopic structural manifestation.

As described above, pancreatitis includes, for example, acute pancreatitis and chronic pancreatitis, each can be caused by or associate with various factors and/or pathophysiology. For example, acute pancreatitis can be caused by obstructions in a tissue or an organ, including but not limited to gallstones, microlithiasis (biliary sludge), ampullary or pancreatic tumors, papillary stenosis, worms or foreign bodies obstructing the ampulla, sphincter of Oddi dysfunction, choledochocele, duodenal diverticula, and possibly pancreas divisum. Acute pancreatitis can also be induced by toxins such as alcohol (ethyl alcohol, methyl alcohol), scorpion venom, organophosphate insecticides, and other drugs. Additionally acute pancreatitis can be caused by trauma such as accidental blunt trauma to abdomen and iatrogenic trauma (for example, postoperative trauma). Other causes of acute pancreatitis can include metabolic abnormalities such as hypertriglyceridemia and hypercalcemia; inherited conditions such as cystic fibrosis and hereditary pancreatitis; infectious diseases such as parasitic, viral, bacterial infections; vascular diseases such as ischemia (for example after heart surgery), atherosclerotic emboli, vasculitis (for example systemic lupus erythematosus and polyarteritis nodosa); other miscellaneous or idiopathic causes such as peptic ulcer disease, Crohn's disease, Reye syndrome and hypothermia. Of the various causes, gallstones and alcohol are the most common causes of acute pancreatitis. The methods provided herein can be used for preventing, treating, ameliorating, or managing pancreatitis including acute pancreatitis caused by any or any combination of the causes disclosed herein.

Similarly, chronic pancreatitis can be caused by or associate with various factors and/or pathophysiology, for example alcohol use or alcohol abuse, autoimmune diseases, metabolic abnormalities (such as hyperparathyroidism (hypercalcemia), diabetes mellitus, or hypertriglyceridemia), nutritional or tropical factors, obstructions of tissues or organs due to strictures (such as trauma or previous episodes of pancreatitis) or malignancies, genetic diseases including hereditary pancreatitis and cystic fibrosis, and other idiopathic causes. The methods provided herein can be used for preventing, treating, ameliorating, or managing pancreatitis including chronic pancreatitis caused by any or any combination of the causes disclosed herein.

As pancreatitis can have various causes, the methods provided herein can be used for preventing, treating, ameliorating, or managing pancreatitis, including both acute and chronic pancreatitis, that is a result of a selective cause or a selective group of causes. Similarly, methods provided herein can be used for preventing, treating, ameliorating, or managing pancreatitis, including both acute and chronic pancreatitis, that is a result of causes excluding any particular factor or cause, or excluding a group of selective factors or causes. For example, methods provided herein can be used for preventing, treating, ameliorating, or managing pancreatitis, including both acute and chronic pancreatitis, that is not caused by or associated with any cancer or neoplastic disorder. In some embodiments, methods provided herein can be used for preventing, treating, ameliorating, or managing pancreatitis in patients having pancreatitis, wherein the patients do not have or have not progressed to a cancer, for example pancreatic cancer, or a neoplastic disorder, for example, a pancreatic neoplastic disorder.

Pancreatitis can be measured and observed by determining, measuring, or observing various markers for pancreatic inflammation and pancreatic damages. Such markers can include histological markers indicating histology changes in the pancreas, serological marker indicating abnormalities in the blood, signaling markers indicating changes in the signaling pathway that underlies the pathological mechanism of pancreatitis or changes in the signaling pathways that are phenotypic of the pathology of pancreatitis, or physiological markers indicating physiological signs or changes in pancreatitis patients (for example readily observable physiological signs without an invasive procedures or a blood draw).

6.2.2.1. Serological Markers, Urinary Markers, and Fecal Markers for Pancreatitis One or more specific substances in blood or urine of a pancreatitis patient, the ratio of the level of one substance against another in blood or urine, the aggregate level of one kind of substance (for example the aggregate level of a particular enzyme) in blood or urine, or the ratio involving such aggregate level can be used as biomarkers for pancreatitis. The substance that serves as the marker can be cells, tissue, protein (such as enzymes), DNA, RNA, microRNA, lipid, metabolite or any other matter that can reflect pancreatitis inflammation or damages. Examples of such serological pancreatitis markers include serum lipase level, serum CA19-9 level, serum amylase level (including levels for amylase, isoamylase, and total amylase), serum C reactive protein level, carbohydrate-deficient transferrin, trypsinogen activation products (including for example trypsigen activation peptide, trypsin-1, trypsin-2, complexes of trypsin-1 or trypsin-2 with α-antitrypsin (also known as trypsin-1-AAT and trypsin-2-AAT), elastase-1, phospholipase A2, procalcitonin (precursor of calcitonin), lipids, inflammatory cytokines and chemokines, microRNAs, peptides (RA1609 and RT2864, as disclosed in Walgren J L et al., *Toxicol Sci.* 2007 March; 96(1):184-93), herein incorporated in its entirety by reference), alcohol and alcohol metabolites (fatty acid ethyl esters), and toxins or metabolites of toxins. An elevated level of any of the serological markers or any combination of the serological markers disclosed herein can be used in methods provided herein.

Exemplary urinary abnormalities as markers of pancreatitis can include amylase, isoamylase, trypsingen activation peptide, carboxypeptidase activation peptide, and phospholipase A2. An elevated level of any of the urinary markers can be used alone in the methods provided herein or in any permutation or combination with any markers as disclosed herein.

Additionally, the markers for pancreatitis also encompass fecal markers, including fecal elastase 1, fecal chymotrypsin, and fecal fat content. An elevated level of any of the fecal markers can be used alone in the methods provided herein or in any permutation or combination with any markers as disclosed herein.

Other markers from other sources of bodily fluid can be used as markers for pancreatitis as well. In some embodiments, markers from pancreatic juice, including CA19-9, cathepsins B, cathepsins L, cathepsins S, lysosomal hydrolases, and carboxypeptidase B activation peptide (CACAP), can be used as markers for pancreatitis. An elevated level of any of the pancreatic juice markers can be used alone in the methods provided herein or in any permutation or combination with any markers as disclosed herein.

As discussed above, one of the serological markers is the level of serum amylase. Normal serum amylase of a healthy human being can vary according to the methods used for measuring the amylase and the laboratory that conducts the assay. A wide range of commercial kits are available for measuring serum amylase levels, for example, Amylase Assay Kit (Colorimetric) (ab102523) from Abcam and Amylase Activity Assay Kit (MAK009-1KT) from Sigma-Aldrich, Inc. An exemplary normal range of serum amylase in a healthy individual is 23-85 U/L, although the exemplary normal serum amylase can be 0-140 U/L in some laboratory. Various levels of serum amylase can be used as indicators of pancreatitis. In some embodiments, serum amylase at the level of ≥140 U/L, ≥150 U/L, 160 U/L, ≥170 U/L, ≥180 U/L, ≥190 U/L, ≥200 U/L, ≥210 U/L, ≥220 U/L, ≥230 U/L, ≥240 U/L, ≥250 U/L, ≥260 U/L, ≥270 U/L, ≥280 U/L, ≥290 U/L, ≥300 U/L, ≥350 U/L, ≥400 U/L, ≥450 U/L, ≥500 U/L, ≥600 U/L, ≥700 U/L, ≥800 U/L, ≥900 U/L, 1000 U/L, ≥1500 U/L, ≥2000 U/L, ≥3000 U/L, or higher can be used as a marker in the methods provided herein. In a specific embodiment, serum amylase at the level of ≥200 U/L is used as a pancreatitis marker. In another embodiment, serum amylase at the level of ≥140 U/L is used as a pancreatitis marker.

Because the serum amylase level can vary according to the assay methods and the laboratory operating the assay, the ratio between the serum amylase of a pancreatitis patient and that of a healthy control subject can be used as an alternative marker for pancreatitis. For example, the ratio between the serum amylase of a pancreatitis patient and the upper limit of that in a healthy control subject can be used as a marker in the methods provided herein. In some embodiments, the pancreatitis markers include exemplary amylase ratio (that in a pancreatitis patient over the upper limit of a healthy individual) of ≥1, 1.5, ≥2, ≥2.5, 3, ≥3.5, ≥4, ≥4.5, ≥5, ≥6, 37, ≥8, ≥9, ≥10, or higher. In a specific embodiment, a ratio of ≥3 is used as a pancreatitis marker. In another embodiment, a ratio of ≥5 is used as a pancreatitis marker.

As discussed above, another serological marker is the level of serum lipase. Normal serum lipase level of a healthy human being can vary according to the methods used for measuring the lipase and the laboratory that conducts the assay. A wide range of commercial kits are available for measuring serum lipase levels, for example, Lipase Activity Assay Kit (Colorimetric) (ab102524) from Abcam, Lipase Assay Kit (DZ132A-K) from Diazyme Laboratories, Inc., and Lipase Activity Assay Kit (MAK046-1KT) from Sigma-Aldrich, Inc. An exemplary range of normal serum lipase in a healthy individual is 12-70 U/L, although the exemplary normal serum lipase can be as high as 0-160 U/L in some laboratory. Various levels of serum lipase can be used as indicators of pancreatitis. In some embodiments, serum lipase at the level of ≥140 U/L, ≥150 U/L, ≥160 U/L, ≥170 U/L, 180 U/L, ≥190 U/L, ≥200 U/L, ≥210 U/L, ≥220 U/L, ≥230 U/L, ≥240 U/L, ≥250 U/L, 2260 U/L, ≥270 U/L, ≥280 U/L, ≥290 U/L, 3300 U/L, ≥350 U/L, ≥400 U/L, ≥450 U/L, ≥500 U/L, ≥600 U/L, ≥700 U/L, 3800 U/L, 3900 U/L, ≥1000 U/L, ≥1500 U/L, ≥2000 U/L, ≥3000 U/L, or higher can be used as a marker in the methods provided herein. In a specific embodiment, serum lipase at the level of ≥200 U/L is used as a pancreatitis marker. In another embodiment, serum lipase at the level of ≥140 U/L is used as a pancreatitis marker.

Because the serum lipase level can vary according to the assay methods and the laboratory operating the assay, the ratio between the serum lipase of a pancreatitis patient and that of a healthy control subject can be used as an alternative marker for pancreatitis. For example, the ratio of between the serum lipase of a pancreatitis patient and the upper limit of that in a healthy control subject can be used as a marker in the methods provided herein. In some embodiments, the pancreatitis markers include exemplary lipase ratio (that in a pancreatitis patient over the upper limit of a healthy individual) of ≥1, ≥1.5, ≥2, ≥2.5, ≥3, ≥3.5, ≥4, ≥4.5, ≥5, ≥6, ≥7, ≥8, ≥9, ≥10, or higher. In a specific embodiment, a ratio of ≥3 is used as a pancreatitis marker. In another embodiment, a ratio of ≥5 is used as a pancreatitis marker.

An additional serological marker is the level of serum CA19-9. A wide range of commercial kits are available for measuring serum CA19-9 levels, for example, CA19-9 Human ELISA Kit (cat #EHCA199) from Thermo Fisher Scientific, Human CA-19-9 ELISA Test kit (Item #6909-16) from Diagnostic Automation/Cortez Diagnostics Inc., and Human Cancer Antigen CA19-9 ELISA Kit (ab108642) from Abcam. Serum CA19-9 is also routinely determined in a CA 19-9 Radioimmunoassay as is known to a person of ordinary skill in the art.

An exemplary normal range of serum CA19-9 in a healthy individual is 0-37 U/ml. Various levels of serum CA19-9 can be used as indicators of pancreatitis. In some embodiments, serum CA19-9 at the level of ≥37 U/ml, ≥37 U/ml, ≥40 U/ml, ≥50 U/ml, ≥60 U/ml, ≥70 U/ml, ≥80 U/ml, ≥90 U/ml, ≥100 U/ml, 110 U/ml, ≥120 U/ml, ≥130 U/ml, ≥140 U/ml, ≥150 U/ml, ≥160 U/ml, ≥170 U/ml, ≥180 U/ml, ≥190 U/ml, ≥200 U/ml, ≥210 U/ml, 220 U/ml, ≥230 U/ml, ≥240 U/ml, 250 U/ml, ≥260 U/ml, 270 U/ml, ≥280 U/ml, ≥290 U/ml, ≥300 U/ml, ≥350 U/ml, ≥400 U/ml, ≥450 U/ml, ≥500 U/ml, ≥600 U/ml, ≥700 U/ml, ≥800 U/ml, ≥900 U/ml, ≥1000 U/ml, or higher can be used as a marker in the methods provided herein. In a specific embodiment, serum CA19-9 at the level of over 37 but no more than 40 U/ml is used as a pancreatitis marker. In another embodiment, serum CA19-9 at the level of more than 40 but no more than 100 U/ml is used as a pancreatitis marker. In another embodiment, serum CA19-9 at the level of more than 100 U/ml is used as a pancreatitis marker.

As is known to a person with ordinary skill in the art, C-reactive protein (CRP; also known as high-sensitivity C-reactive protein (hs-CRP) or ultra-sensitive C-reactive protein (us-CRP)) is a protein found in blood plasma and produced by the liver in response to inflammation. Therefore, CRP can be used as a marker for pancreatitis, which as discussed above is a disease of pancreatic inflammation and damages. The level of CRP can correlates with the level of inflammation in the body. Accordingly, the higher the CRP level, the more inflammation there is in the body. The normal range of blood serum CRP in a healthy human subject is under 1 mg/L. A level of blood serum CRP between 1 and 2.9 mg/L can indicate intermediate level of inflammation in the human subject, that between 3 and 10 mg/L can indicate high level of inflammation in the human subject, and that over 10 mg/L can indicate severe level of inflammation in the human subject. In some embodiments, the pancreatitis markers in the methods provided herein include an exemplary level of blood serum CRP of over 1, 2, 3, 4, 5, 6, 7, 8, 9, 10, 11, 12, 13, 14, 15, 16, 17, 18, 19, or 20 mg/L. A wide range of commercial kits are available for measuring serum CRP levels, for example, Human C-Reactive Protein/CRP Quantikine ELISA Kit (cat #DCRP00) from R&D Systems Inc., CRP (human) ELISA kit (ENZ-KIT102-0001) from Enzo Life Sciences, Inc., and Human C-Reactive Protein ELISA Kit (RAB0096-1KT) from Sigma-Aldrich, Inc.

A person of ordinary skill in the art would further understand that various other serological markers or other markers from bodily fluid can be used for identifying the therapeutic agents, characterizing pancreatitis, identifying pancreatitis patients, and determining the therapeutic outcomes of a treatment method for pancreatitis. Therefore, a person of ordinary skill in the art would understand that various other known pancreatitis markers can be used in the methods provided herein. Such pancreatitis markers are disclosed in publications such as Chapter 37 and 38 on Acute Pancreatitis and Chronic Pancreatitis respectively, GI/Liver Secrets Plus, 4th edition, edited by McNally PR, 2010; Matull W R et al., J Clin Pathol 2006; 59:340-344; Basnayake C. et al., Aust Prescr 2015; 38:128-30; Carroll J K et al., Am Fam Physician 2007; 75:1513-20; Kaphalia B S, Chapter 16 in Biomarkers in Toxicology, ISBN: 978-0-12-404630-6, (2014); Jasdanwala S et al., Integr Mol Med, 2015; 2(3): 189-195; BUchler M W et al., BMC Gastroenterology 2009, 9:93; Duggan S N et al., World J Gastroenterol 2016; 22(7): 2304-2313; Etemad B et al., Gastroenterology 2001; 120: 682-707, all of which are herein incorporated in their entirety by reference. A person of ordinary skill in the art will further understand that any and any permutation or combination of the markers disclosed above and below can be used in the methods provided herein.

Accordingly, the disclosure provides that patients suitable for the methods include patients having elevated one or more serological markers, urinary markers, and fecal markers, including the enumerated markers, as described in this section 6.2.2.1. More specifically, the methods provided herein can be used in patients having any one or more of the markers of the enumerated values as described in this section 6.2.2.1.

The disclosure further provides that the methods provided herein can improve the therapeutic outcomes for the patients by reversing or improving any one or more or any combination of these pancreatitis serological markers, urinary markers, and fecal markers as described in this section 6.2.2.1, for example lowering the serum amylase, lowering the serum lipase, or lowering serum CRP.

6.2.2.2. Histological Markers

As discussed above, the markers based on abnormalities in pancreatic histology (for example from histology staining or IHC staining of the pancreatic tissue samples) can also be used in the methods provided herein. Such histological markers include abnormalities in the expression of one or more proteins in the pancreas, presence or abnormal numbers of certain type of non-pancreatic cells (for example immune cells including leukocytes, macrophages, and neutrophils) in the pancreas, abnormal changes in the abundance or number of certain cells in the pancreas, and abnormalities in the structure of pancreatic cells or pancreatic tissues (for example abnormalities in pancreatic parenchyma, pancreatic ducts, islets of Langerhans, and the acinar cells/tissues). The pancreatic structural abnormalities can be localized in specific pancreatic areas or structures such as pancreatic parenchyma, pancreatic ducts, islets of Langerhans, the acinar cells/tissues, the exocrine component of the pancreas, the endocrine component of the pancreas, or cysts.

Examples of histological markers in the pancreas as shown in histology staining or IHC staining of pancreas or pancreatic tissues include, parenchymal fibrosis, acinar atrophy, ductal distortion, intraductal calcification, immune cell invasion or infiltration (for example invasion/infiltration of macrophages, neutrophils, and leukocytes), collagen deposition, fibrotic tissue, fat necrosis, interstitial edema, acinar cell destruction, enlarged gland (edema), irregular sclerosis, loss of pancreatic parenchyma, pancreatic blood vessel destruction, interstitial hemorrhage, ductal dilation, large confluent foci fat necrosis around the pancreas, focal hemorrhage, acinar cell necrosis, acinar cell homogenization, expression levels of $sLe^a$, and expression levels of CA19-9.

These histological markers can be used for various stages of acute or chronic pancreatitis. An elevated level of any of the histological markers can be used alone in the methods provided herein or in any permutation or combination with any markers as disclosed herein.

In some embodiments, the histological markers for chronic pancreatitis can include irregular sclerosis in the pancreas, loss of exocrine parenchyma in the pancreas. In other embodiments, fat necrosis, enlarged gland (edema), large confluent foci fat necrosis around the pancreas, focal hemorrhage, and acinar cell necrosis can be used as markers for acute pancreatitis.

As is well known to a person of ordinary skill in the art, various histology or IHC assays for the histological markers have been developed and can be used in the methods provided here, for example assays as disclosed in Matull W R et al., J Clin Pathol 2006; 59:340-344; Basnayake C. et al., Aust Prescr 2015; 38:128-30; Carroll J K et al., Am Fam Physician 2007; 75:1513-20; Kaphalia B S, Chapter 16 in Biomarkers in Toxicology, ISBN: 978-0-12-404630-6, (2014); Jasdanwala S et al., Integr Mol Med, 2015; 2(3): 189-195; Buchler M W et al., BMC Gastroenterology 2009, 9:93; Duggan S N et al., *World J Gastroenterol* 2016; 22(7): 2304-2313; Etemad B et al., Gastroenterology 2001; 120: 682-707, all of which are herein incorporated in their entirety by reference.

Because imaging techniques often measure the histological structures, a person skilled in the art will understand that histological markers often correlate with structural abnormalities detected by imaging that can be used as markers of pancreatic inflammation and pancreatic damage. Accordingly, markers, for example abnormalities detected in various imaging techniques, can be used as histological markers for pancreatitis in the methods provided herein. Pancreas structures can be imaged as described further below in Section 6.2.2.2 and 6.3.2.2. Exemplary histological markers of pancreatic inflammation and pancreatic damage detected by imaging include pancreatic atrophy, obstruction of bile ducts or pancreatic duct (such as gallstones), dilated pancreatic duct, pancreatic calcification, biliary strictures, parenchymal and ductal scarring in the pancreas, stricture of the pancreatic duct, or any combination thereof.

In some embodiments, histological markers in the methods provided herein include abnormal pancreatic morphology shown in computed tomography (CT) that reflects inflammation or damages caused by pancreatitis or reflects the complications associated with pancreatitis. For example, histological markers observable in CT imaging that reflect pancreatitis include pancreatic calcifications such as calcifications within the pancreatic ducts or parenchyma, dilated pancreatic ducts such as the main ducts, and pancreatic atrophy such as pancreatic parenchymal atrophy. Histological markers observable in CT imaging that reflect pancreatitis complications include pseudocysts, dilated common bile duct, splenic vein thrombosis, gastric varices, pseudoaneurysm, duodenal stenosis, malignancy, and any combination thereof.

Similarly, histological markers in the methods provided herein include abnormal pancreatic morphology shown in endoscopic retrograde cholangiopancreatography (ERCP) that reflects inflammation or damages caused by pancreatitis or reflects the complications associated with pancreatitis. For example, histological markers observable in ERCP imaging that reflect pancreatitis include dilation and irregularity of the smaller ducts and branches of the pancreas for mild pancreatitis, dilation and irregularity of the main ducts in the pancreas for moderate pancreatitis, and tortuosity, stricture, calcifications, and cysts in the pancreas for severe pancreatitis. In some embodiments, pancreatic histological markers found in ERCP including the number of ductal abnormalities, ecstatic side branches, intraductal filling defects, and ductular abnormalities (such as multiple areas of stenosis, dilation, irregular branching ducts, and intraductal calculi) can be used as markers for pancreatitis in the methods provided herein.

In other embodiments, histological markers in the methods provided herein include abnormalities in the pancreas shown in endoscopic ultrasonography (EUS) that reflect inflammation or damages caused by pancreatitis or reflect the complications associated with pancreatitis. In some specific embodiments, histological markers observable in EUS that reflect mild pancreatitis include mild irregularity and dilation of the main pancreatic duct, hyperechoic duct margins, and hyperechoic stranding in the pancreatic parenchyma. Histological markers observable in EUS that reflect severe pancreatitis include lobular outline of the pancreas and dilation of the main pancreatic duct. Other pancreatitis markers observable in EUS include those described in Rosemont criteria such as hyperechoic foci with stranding, lobularity with honeycombing, hyperechoic foci, lobularity, cysts, hyperechoic strands, calculi, irregular main pancreatic duct contour, hyperechoic main pancreatic duct margin, dilated side branches, or any combination thereof.

In further embodiments, histological markers in the methods provided herein include abnormalities in the pancreas shown in magnetic resonance imaging such as magnetic resonance cholangiopancreatography (MRCP) that reflect inflammation or damages caused by pancreatitis or reflect the complications associated with pancreatitis. Such histological markers observable in MRCP of pancreas include dilated ducts, communicating pseudocysts, short strictures, pancreatic or ductal stone, or any combination thereof.

Additional histological markers shown in an imaging test further include those described in Etemad B et al., Gastroenterology 2001; 120:682-707; Duggan, S N, et al., World J Gastroenterol 2016; 22(7): 2304-2313; and Chapter 37 and 38 on Acute Pancreatitis and Chronic Pancreatitis respectively, GI/Liver Secrets Plus, 4th edition, edited by McNally PR, 2010, all of which are hereby incorporated in their entirety by reference. One or more histological markers can be used alone or in any combination of any number of other markers as disclosed herein for a method as provided herein.

Accordingly, the disclosure provides that patients suitable for the methods include patients having any one or more histological markers, including the enumerated histological markers, as described in this section 6.2.2.2.

The disclosure further provides that the methods provided herein can improve the therapeutic outcome for the patients by reversing or improving any one or more or any combination of these pancreatitis histological markers as described in this section 6.2.2.2.

6.2.2.3. Functional Markers

As the severity of pancreatitis can be reflected in the functionality of the pancreas, markers for pancreatitis can also include functional markers. Functional markers refer to any markers that correlate, directly or inversely, with pancreatic function. As a person skilled in the art would understand, two of the major functions of pancreas are pancreatic exocrine function and pancreatic endocrine function. Accordingly, the disclosure provides that deficiencies in pancreatic exocrine function, deficiencies in pancreatic endocrine function, or both can be used as markers for pancreatitis in the methods provided herein. As is also known to a person of ordinary skill in the art, pancreatic exocrine secretions are high in bicarbonate. Therefore, a secretin stimulation test, with or without the administration of cholecystokinin (CCK), can be used to directly measure the pancreatic function by monitoring the volume of these pancreatic secretions and the concentration of bicarbonate after the injection of secretin. In some embodiments, a bicarbonate level of less than 50 mEq/L in a secretin stimulation test (with or without CCK administration) can be a marker for patients with pancreatitis and used in the methods provided herein. In other embodiments, a bicarbonate level of less than 5 mEq/L, 10 mEq/L, 15 mEq/L, 20 mEq/L, 25 mEq/L, 30 mEq/L, 35 mEq/L, 40 mEq/L, 45 mEq/L, 50 mEq/L, 55 mEq/L, 60 mEq/L, 65 mEq/L, 70 mEq/L, 75 mEq/L, or 80 mEq/L in a secretin stimulation test (with or without CCK administration) can be a marker for patients with pancreatitis and used in the methods provided herein.

Alternatively, pancreatic function can be determined by measuring pancreatic enzymes in the serum and stool or any metabolites of the enzymes in serum or urine after an orally administered compound. Because these markers reflect the level of pancreatic maldigestion, the more advanced the disease, the more sensitive the markers can be for detecting or diagnosing pancreatitis. Such functional markers that can be used in the methods provided herein include serum trypsinogen, wherein a very low value (for example 20 ng/mL or less) in patients marks advanced chronic pancreatitis and steatorrhea, fecal chymotrypsin, wherein a fecal chymotrypsin below 3 U/g of stool suggests advanced chronic pancreatitis, fecal elastase, wherein fecal elastase of less than 100 mcg/g of stool indicates severe pancreatic insufficiency, and fecal fat, wherein fecal fat of more than 7 g/d indicates pancreatitis and fecal fat of more than 20 g/d indicates severe pancreatitis. Other exemplary values as functional markers for pancreatitis include serum trypsinogen less than 5, 10, 15, 20, 25, 30, 35, or 40 ng/mL; fecal chymotrypsin below 1, 2, 3, 4, 5, 6, 7, 8, 9, or 10 U/g of stool; fecal elastase less than 10, 20, 30, 40, 50, 60, 70, 80, 90, 100, 110, 120, 130, 140, or 150 mcg/g of stool; fecal fat more than 5, 6, 7, 8, 9, 10, 11, 12, 13, 14, 15, 16, 17, 18, 19, 20, 21, 22, 23, 24, 25, 26, 27, 28, 29, or 30 g/d of fecal fat; or any combination thereof.

A person of ordinary skilled in the art would understand any functional markers that can correlate with pancreatitis, including those described herein, can be used in the methods provided herein. Other functional markers that can be used in the methods provided herein further include those described in John G Lieb II and Peter V Draganov, World J Gastroenterol. 2008 May 28; 14(20): 3149-3158; Clain J E, et al., Surg Clin North Am 1999; 79:829-845; Couper R. Can J Gastroenterol 1997; 11:153-156; Layer P, et al., J Clin Gastroenterol 1999; 28:3-10; Toskes P P. Curr Gastroenterol Rep 1999; 1:145-153; Chapter 38 on Chronic Pancreatitis, GI/Liver Secrets Plus, 4th edition, edited by McNally PR, 2010; all of which are hereby incorporated in their entirety by reference. One or more functional markers can be used alone or in any combination of any number of other markers as disclosed herein for a method as provided herein.

Accordingly, the disclosure provides that patients suitable for the methods include patients having any one or more functional markers, including the enumerated functional markers, as described in this section 6.2.2.3.

The disclosure further provides that the methods provided herein can improve the therapeutic outcome for the patients by reversing or improving any one or more of these pancreatitis functional markers as described in this section 6.2.2.3. In some specific embodiments, the disclosure provides that the methods provided herein can improve the therapeutic outcome for the patients by increasing the a bicarbonate level in a secretin stimulation test, increasing serum trypsinogen, increasing fecal chymotrypsin, increasing fecal elastase, decreasing fecal fat, or any combination of thereof.

6.2.2.4. Signaling Markers

The disclosure provides that pancreatitis correlates with levels of a CA19-9 and Sialyl-Lewis$^a$ in the pancreas, and elevated CA19-9 and Sialyl-Lewis$^a$ are factors in the underlying mechanism causing pancreatitis.

Additionally, the disclosure provides that elevated CA19-9 in the pancreas activate epidermal growth factor receptor (EGFR) signaling pathway in the pancreas. Activation of EGFR signaling is triggered by ligand-induced receptor dimerization following which the intrinsic kinase domain of one receptor cross phosphorylates specific residues in the C-terminal tail of the partnering receptor, thus providing a scaffold for the recruitment of other proteins in the EGFR signaling pathway (effector and adaptor proteins). This occurs via the Src homology 2 (SH2) and phosphotyrosine binding (PTB) domains on the effector proteins and the phosphotyrosine motif present on the intracellular tyrosine kinase domain of the EGFR. The activated adaptor and effector proteins will further stimulate their corresponding signaling cascades, which include the RAS, RAF, MEK, and ERK axis of signaling pathway, the phosphoinositide 3-kinase (PI3K), phospholipase C gamma protein axis of signaling pathway, and the PKB/Akt kinase pathway, and the STAT signaling pathway, which leads to a variety of biological responses including cell proliferation, angiogenesis, migration, survival, and adhesion.

Accordingly, the disclosure provides that markers for pancreatitis can include all indicators for an activated EGFR signaling pathway, including changes of expression level, locational changes, changes in binding partners, or any biochemical or biophysical changes (such as phosphorylation, ubiquitylation, and conformational changes) for a molecule in a EGFR signaling pathway. In some embodiments, markers for pancreatitis suitable for the methods provided herein can be Akt phosphorylation in the pancreas, EGFR phosphorylation in the pancreas, Erk1/2 phosphorylation in the pancreas, activation of RAS (for example GTP loading of RAS) in the pancreas, phosphorylation of RAF in the pancreas, and phosphorylation of MEK in the pancreas. Other markers of activated EGFR signaling pathway suitable for the methods provided herein are further described in Seshacharyulu, P et al., Expert Opin Ther Targets. 2012 January; 16(1): 15-31; Normanno N et al., Gene. 2006 Jan. 17; 366(1):2-16; Oda K et al., Mol Syst Biol. 2005; 1: 2005.0010; Lurje G et al., Oncology. 2009; 77(6):400-10; Yarden, Y et al., 2007; 131(5): 1018-1018, all of which are hereby incorporated in their entirety by reference.

In addition, because the disclosure provides that pancreatitis correlates with levels of CA19-9 in the pancreas and that elevated CA19-9 is a factor in the underlying mechanism causing pancreatitis, a person of ordinary skill in the art would understand that CA19-9 and any other signaling markers in pancreatitis that can be induced in response to elevated levels of CA19-9 can be used as markers in the methods provided herein. Furthermore, CA19-9 can be used either alone or in combination with any markers disclosed above and below in the methods provided herein.

Accordingly, the disclosure provides that patients suitable for the methods include patients having any one or more signaling markers, including the enumerated signaling markers, as described in this section 6.2.2.4. The disclosure further provides that the methods provided herein can improve the therapeutic outcome for the patients by reversing or improving any one or more of these pancreatitis signaling markers as described in this section 6.2.2.4.

6.2.2.5. Physiological Marker

As pancreatitis can affect the physiology and cause other observable symptoms in the subject, any markers that reflects the physiological symptoms of a pancreatitis patient can be used in the methods provided herein. Such physiological markers include weight loss, pain such as abdominal pain, malabsorption of food, pancreatic atrophy, pancreatic enlargement, pancreatic inflammation, and bile reflux. Such physiological markers can be directly observed or determined based on the descriptions of the patient's symptomatic feelings. Accordingly, the disclosure provides that patients suitable for the methods include patients having any one or more of these physiological markers and the methods provided herein can improve the therapeutic outcome for the patients by reversing or improving any one or more of these pancreatitis signaling markers.

In certain embodiments, any 1, 2, 3, 4, 5, 6, 7, 8, 9, 10, 15, 20, 25, 30, 35, 40, 45, 50 or more of the markers described herein can be used, in any permutation or combination, in the methods provided herein. In other embodiments, any number of the markers provided herein can be used in any permutation or combination with the assays, selection of the patient populations (for example using any one or more markers as patient selection criteria), dosing regimens (for example increasing or lowering the dose based on the improvement or worsening in one or more of the markers), therapeutic outcomes (for example evaluating the improvement in one or more of the markers), and/or therapeutic agents (for example using one or more markers to confirm the functional property of the therapeutic agents) in the methods as provided herein.

6.2.3 Dosing Regimens, Pharmaceutical Compositions, and Routes of Administration In one embodiment, the methods provided herein use a pharmaceutical composition comprising a therapeutic agent that can be administered systemically to prevent, treat, ameliorate, or manage pancreatitis. Such administration can be parenterally or transmucosally, e.g., orally, bucally, nasally, sublingually, submucosally or transdermally. In some embodiments, administration is parenteral, for example, via intravenous or intraperitoneal injection, intra-arterial, intramuscular administration, intradermal administration, and subcutaneous administration.

For other routes of administration, such as by use of a perfusate, injection into an organ, or other local administration, a pharmaceutical composition will be provided which results in similar levels of a therapeutic agent as described further below.

The pharmaceutical compositions of the therapeutic agent provided herein can comprise a therapeutically effective amount of a therapeutic agent, and a pharmaceutically acceptable carrier. In a specific embodiment, the term "pharmaceutically acceptable" means approved by a regulatory agency of the Federal or a state government or listed in the U.S. Pharmacopeia or other generally recognized foreign pharmacopeia for use in animals, and more particularly in humans. The term "carrier" refers to a diluent, adjuvant, excipient, or vehicle with which the therapeutic is administered. Such pharmaceutical carriers can be sterile liquids, such as saline solutions in water and oils, including those of petroleum, animal, vegetable or synthetic origin, such as peanut oil, soybean oil, mineral oil, sesame oil and the like. A saline solution can be a carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. The therapeutic agents provided herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Examples of suitable pharmaceutical carriers are described in "Remington's Pharmaceutical Sciences" by E. W. Martin, which is hereby incorporated by reference in its entirety. Such compositions will contain a therapeutically effective amount of the therapeutic agent, for example, in purified or unpurified form, together with a suitable amount of carrier so as to provide the form for proper administration to the patient. A person of ordinary skill in the art would know that the formulation can be selected to suit the mode of administration.

Formulations for increasing transmucosal adsorption of a therapeutic agent such as a peptide are also provided herein. Pharmaceutical compositions adapted for oral administration can be provided as capsules or tablets; as powders or granules; as solutions, syrups or suspensions (in aqueous or non-aqueous liquids); as edible foams or whips; or as emulsions. Tablets or hard gelatine capsules can comprise lactose, starch or derivatives thereof, magnesium stearate, sodium saccharine, cellulose, magnesium carbonate, stearic acid or salts thereof. Soft gelatine capsules can comprise vegetable oils, waxes, fats, semi-solid, or liquid polyols etc. Solutions and syrups can comprise water, polyols and sugars.

A therapeutic agent intended for oral administration can be coated with or admixed with a material that delays disintegration and/or absorption of the active agent in the gastrointestinal tract (e.g., glyceryl monostearate or glyceryl distearate can be used). Thus, the sustained release of an active agent can be achieved over many hours and, if necessary, the active agent can be protected from being degraded in the stomach. Pharmaceutical compositions for oral administration can be formulated to facilitate release of an active agent at a particular gastrointestinal location due to specific pH or enzymatic conditions.

Pharmaceutical compositions adapted for transdermal administration can be provided as discrete patches intended to remain in intimate contact with the epidermis of the recipient for a prolonged period of time. Pharmaceutical compositions adapted for topical administration can be provided as ointments, creams, suspensions, lotions, powders, solutions, pastes, gels, sprays, aerosols or oils. For topical administration to the skin, mouth, eye or other external tissues a topical ointment or cream can be used. When formulated in an ointment, the active ingredient can be employed with either a paraffinic or a water-miscible ointment base. Alternatively, the active ingredient can be formulated in a cream with an oil-in-water base or a water-in-oil base. Pharmaceutical compositions adapted for topical administration to the eye include eye drops. In these compositions, the active ingredient can be dissolved or suspended in a suitable carrier, e.g., in an aqueous solvent.

Pharmaceutical compositions adapted for parenteral administration include aqueous and non-aqueous sterile injectable solutions or suspensions, which can contain antioxidants, buffers, bacteriostats and/or solutes that render the compositions substantially isotonic with the blood of an intended recipient. Other components that can be present in such compositions include water, alcohols, polyols, glycerine and vegetable oils, for example. Compositions adapted for parenteral administration can be presented in unit-dose or multi-dose containers, for example sealed ampules and vials, and can be stored in a freeze-dried (lyophilized) condition requiring only the addition of a sterile liquid carrier, e.g., sterile saline solution for injections, immediately prior to use. Extemporaneous injection solutions and suspensions can be prepared from sterile powders, granules and tablets. In one embodiment, an autoinjector comprising an injectable solution of a therapeutic agent can be provided for emergency use by ambulances, emergency rooms, and even for self-administration in a domestic setting, such as a stay-at-home pancreatic patient.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically-sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampule of sterile saline can be provided so that the ingredients can be mixed prior to administration.

Suppositories generally contain active ingredient in the range of 0.5% to 10% by weight; oral formulations can contain 10% to 95% active ingredient.

The disclosure also provides a pharmaceutical pack or kit comprising one or more containers filled with one or more of the ingredients of the pharmaceutical compositions of one or more therapeutic agent provided herein. Optionally associated with such container(s) can be a notice in the form prescribed by a governmental agency regulating the manufacture, use or sale of pharmaceuticals or biological products, which notice reflects approval by the agency of manufacture, use or sale for human administration.

In another embodiment, for example, a therapeutic agent can be delivered in a controlled-release system. For example, the therapeutic agent can be administered using intravenous infusion, an implantable osmotic pump, a transdermal patch, liposomes, or other modes of administration. In one embodiment, a pump can be used (see Langer, *Science* 249:1527-1533 (1990); Sefton, 1987, CRC Crit. Ref. Biomed. Eng. 14:201; Buchwald et al., 1980, Surgery 88:507; Saudek et al., 1989, N. Engl. J. Med. 321:574, each of which is incorporated by reference herein in its entirety). In another embodiment, the therapeutic agent can be delivered in a vesicle, e.g. a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); WO 91/04014; U.S. Pat. No. 4,704,355; Lopez-Berestein, ibid., pp. 317-327). In another embodiment, polymeric materials can be used (see Medical Applications of Controlled Release, Langer and Wise (eds.), CRC Press: Boca Raton, Florida, 1974; Controlled Drug Bioavailability, Drug Product Design and Performance, Smolen and Ball (eds.), Wiley: New York (1984); Ranger and Peppas, J. Macromol. Sci. Rev. Macromol. Chem. 23:61, 1953; see also Levy et al., 1985, Science 228:190; During et al., 1989, Ann. Neurol. 25:351; Howard et al., 1989, J. Neurosurg. 71:105, all of which are incorporated by reference herein in their entirety).

In yet another embodiment, a controlled release system can be placed in proximity of the therapeutic target, i.e., the target cells, tissue or organ, thus requiring only a fraction of the systemic dose (see, e.g., Goodson, pp. 115-138 in Medical Applications of Controlled Release, vol. 2, 1984, which is incorporated by reference herein in its entirety). Other controlled release systems are discussed in the review by Langer (1990, Science 249:1527-1533, which is incorporated by reference herein in its entirety).

In another embodiment, a therapeutic agent, as properly formulated, can be administered by nasal, bucal, oral, rectal, ocular, transdermal, parenteral, inhalation or sublingual administration.

In a specific embodiment, it can be useful to administer a therapeutic agent provided herein locally to the area in need of treatment; this can be achieved by, for example, and not by way of limitation, local infusion during surgery, topical application, e.g., by injection, by means of a catheter, by means of a suppository, or by means of an implant, said implant being of a porous, non-porous, or gelatinous material, including membranes, such as silastic membranes, or fibers. A non-limiting example of such an embodiment include a stent or other scaffolding coated with a therapeutic agent provided herein that is implanted in a portion of the vasculature, duct, etc.

Selection of an effective dose will be readily determinable by a skilled artisan based upon considering several factors, which are known to one of ordinary skill in the art. Such factors include the particular form of the therapeutic agent, and its pharmacokinetic parameters such as bioavailability, metabolism, half-life, etc., which is established during the usual development procedures typically employed in obtaining regulatory approval for a therapeutic agent. Further factors in considering the dose include the condition or stage of disease to be treated or the benefit to be achieved in a normal individual, the body mass of the patient, the route of administration, whether administration is acute or chronic, concomitant medications, and other factors well known to affect the efficacy of administered pharmaceutical agents.

While the contemplated recipient of a therapeutic agent for the purposes herein throughout is a human, the methods herein apply equally to other mammals, particularly domesticated animals, livestock, companion, and zoo animals. However, the methods provided herein are not limiting and the benefits can be applied to any mammal. In further aspects of methods provided herein, any therapeutic agent as described in Section 6.2.1 can be employed in any combination or permutation with the formulation provided herein.

In certain embodiments, the disclosure provides a pharmaceutical composition in dosage unit form adapted for the methods provided herein, which comprises an amount of a therapeutic agent within the range from about 0.1 pg to 30 mg, 0.5 pg to 25 mg, 1 pg to 20 mg, 500 pg to 10 mg, 1 ng to 10 mg, 500 ng to 10 mg, 1 g to 10 mg, 500 g to 10 mg, 1 mg to 5 mg, or 1 mg to 10 mg of the therapeutic agent, and a pharmaceutically acceptable carrier. In one embodiment, the amount of the therapeutic agent is within the range from about 0.5 pg to 1 mg.

A range of doses can be administered to the patients, as contemplated in the methods provided herein, depending on the type and severity of the disease. In one embodiment, a dose of between about 1 mg and 12 mg of therapeutic agent is administered to the patient. In certain embodiments, the dose is in a range from about 2 mg to about 12 mg, about 2 mg to about 11 mg, about 3 mg to about 10 mg, about 4 mg to about 9 mg, about 5 mg to about 8 mg, or about 6 mg to about 7 mg. In certain embodiments, the dose is about 2 mg to about 8 mg. In certain embodiments, the dose is about 1 mg, about 2 mg, about 3 mg, about 4 mg, about 5 mg, about 6 mg, about 7 mg, about 8 mg, about 9 mg, about 10 mg, about 11 mg, or about 12 mg. In certain embodiments, the dose is 4 mg.

The dose at which a therapeutic agent is administered to the patients can be based on the body weight of the patient. In one such embodiment, a dose of between about 0.1 µg/kg to about 120 µg/kg body weight of a therapeutic agent is administered to the patient. In certain embodiments, the dose is in a range from about 0.4 µg/kg to about 110 µg/kg, about 0.5 µg/kg to about 100 µg/kg, about 1 µg/kg to about 95 µg/kg, about 5 µg/kg to about 90 µg/kg, about 10 µg/kg to about 85 µg/kg, about 15 µg/kg to about 80 µg/kg, about 20 µg/kg to about 75 µg/kg, about 25 µg/kg to about 70 µg/kg, about 30 µg/kg to about 65 µg/kg, about 35 µg/kg to about 60 µg/kg, or about 40 µg/kg to about 50 µg/kg body weight. In certain embodiments, the dose of the therapeutic agent is in a range from about 0.2 µg/kg to about 120 µg/kg body weight. In certain embodiments, the dose is in a range from about 1 µg/kg to about 60 µg/kg, about 10 µg/kg to about 30 µg/kg, about 20 µg/kg to about 50 µg/kg, or about 30 µg/kg to about 60 µg/kg. In certain embodiments, the dose is about 1 µg/kg, about 2 µg/kg, about 3 µg/kg, about 4 µg/kg, about 5 µg/kg, about 6 µg/kg, about 7 µg/kg, about 8 µg/kg, about 9 µg/kg, about 10 µg/kg, about 11 µg/kg, about 12 µg/kg, about 13 µg/kg, about 14 µg/kg, about 15 µg/kg, about 16 µg/kg, about 17 µg/kg, about 18 µg/kg, about 19 µg/kg, about 20 µg/kg, about 21 µg/kg, about 22 µg/kg, about 23 µg/kg, about 24 µg/kg, about 25 µg/kg, about 26 µg/kg, about 27 µg/kg, about 28 µg/kg, about 29 µg/kg, or about 30 µg/kg. In certain embodiments, the dose is less than about 80 µg/kg, less than about 50 µg/kg, less than about 30 µg/kg, less than about 20 µg/kg, less than about 15 µg/kg, or less than about 10 µg/kg. In certain embodiments, the dose is 10 µg/kg. In certain embodiments, the dose is 30 µg/kg. In other embodiments, a therapeutic agent provided herein can be administered systemically at a dosage between about 1 ng and about 300 µg/kg body weight, about 5-150 µg/kg-body weight, or about 10-100 µg/kg-body weight, per administration.

In other embodiments of the methods provided herein, the therapeutic agent is administered at a dose range from about 0.1 mg/kg/dose to about 10 mg/kg/dose. In some embodiments, the therapeutic agent is administered at a dose of about 0.1 mg/kg/dose, about 0.2 mg/kg/dose, about 0.3 mg/kg/dose, about 0.4 mg/kg/dose, about 0.5 mg/kg/dose, about 0.6 mg/kg/dose, about 0.7 mg/kg/dose, or about 0.8 mg/kg/dose, about 0.9 mg/kg/dose, about 1 mg/kg/dose, about 2 mg/kg/dose, about 3 mg/kg/dose, about 4 mg/kg/dose, about 5 mg/kg/dose, about 6 mg/kg/dose, about 7 mg/kg/dose, or about 8 mg/kg/dose, about 9 mg/kg/dose, about 10 mg/kg/dose, or higher.

In certain embodiments, the therapeutic agents for use in the present methods can be administered in a prophylactically effective amount. A prophylactically effective amount refers to the amount of a therapeutic agent sufficient to prevent pancreatitis, and/or the damage, effects or symptoms resulting from pancreatitis. Used in connection with an amount of a therapeutic agent, prophylactically effective amount can encompass an amount that improves overall prophylaxis or enhances the prophylactic efficacy in preventing pancreatitis or provides a synergistic affect with another prophylactic agent that can prevent pancreatitis.

Additionally, the therapeutic agents in the methods provided herein can be administered at regular intervals over time. In certain such embodiments, the therapeutic agents are administered daily, every other day, once every week, once every 10 days, once every two weeks, once every three weeks, once every four weeks, once every six weeks, or once every eight weeks. In other embodiments, administration of therapeutic agents can be repeated hourly, daily, as long as clinically necessary, or after an appropriate interval, e.g., every 1-12 hours, every 6 to 12 hours; every 2-6 days, every 2-4 days; every 1 to 12 weeks, every 1 to 3 weeks. In additional embodiments, the therapeutic agents are administered once every month (monthly), once every two months (bimonthly), once every three months, once every four months, once every five months, or once every six months.

In some embodiments, the therapeutic agents provided herein in the methods are administered for about 1 week to about 48 weeks. In certain embodiments, the therapeutic agents provided herein in the methods are administered for about 1 week to about 44 weeks; about 1 week to about 40 weeks, about 1 week to about 36 weeks; about 1 week to about 32 weeks; about 1 week to about 28 weeks; about 1 week to about 24 weeks; about 1 week to about 20 weeks; about 1 week to about 16 weeks; or about 1 week to about 12 weeks. In other embodiments, the therapeutic agents provided herein in the methods are administered for about 1 week to about 48 weeks; about 4 weeks to about 44 weeks; about 8 weeks to about 40 weeks; about 12 weeks to about 36 weeks; about 16 weeks to about 32 weeks; or about 20 weeks to about 28 weeks. In certain embodiments, the therapeutic agents provided herein in the methods are administered for about 1 week to about 24 weeks; about 2 weeks to about 24 weeks; about 4 weeks to about 24 weeks; about 6 weeks to about 24 weeks; about 8 weeks to about 24 weeks; about 10 weeks to about 24 weeks; about 12 weeks to about 24 weeks; about 14 weeks to about 24 weeks; about 16 weeks to about 24 weeks; about 18 weeks to about 24 weeks; about 20 weeks to about 24 weeks; or about 22 weeks to about 24 weeks.

In some specific embodiments, the therapeutic agents provided herein in the methods can be used for long term administration. In certain embodiments, the administration can last as long as the pancreatitis is present in the patient.

In other embodiments, the effective amount of a therapeutic agent and a pharmaceutically acceptable carrier can be packaged in a single dose vial or other container. In additional embodiments, the therapeutic agents, which are capable of exerting the activities described herein are used in a long term to counter a chronic pancreatitis.

As is well-known to a person of ordinary skill in the art, formulations, routes of administration and doses for therapeutic proteins including therapeutic antibodies and therapeutic polypeptide can be different. Various formulations, routes of administration and doses specific for therapeutic proteins including therapeutic antibodies and therapeutic polypeptide are well-known in the art. Exemplary formulations, routes of administration and doses for therapeutic antibodies are described in WO2015112886 and WO2017019957; exemplary formualtions, routes of administration and doses for therapeutic polypeptides are described in WO2007019545, WO2009094172, and WO2015009820, all of which are hereby incorporated in their entirety by reference.

6.3 Assays for Testing Therapeutic Agents

Various assays can be used to determine the activities and efficacy of the therapeutic agents described in Section 6.2.1 for use in the therapeutic methods provided herein. The assays for various markers are also provided herein. The disclosure further provides that the activities, utilities, and efficacy of various therapeutic agents as described in Section 6.2.1 can be assayed according to the biomarkers or the patient therapeutic outcome as described in Section 6.2.2. Additionally, one of ordinary skill in the art will recognize that the suitability of various therapeutic agents in the methods provided herein can be confirmed through various in vitro and in vivo pancreatitis assays known in the art or provided herein.

6.3.1 Binding Assays

Various routine assays can be used to readily determine the binding between a therapeutic agent and a CA19-9 or Sialyl-Lewis$^a$ or between any two molecules (such as between two proteins) in the methods provided herein. Exemplary routine binding assays include an immunohistochemistry assay, an Enzyme Immune Assay (EIA) or an ELISA, a FACS assay, an immunoblotting assay, a surface plasmon resonance (SPR) assay, a co-immunoprecipitation assay, chromatography or gel shifting assays, isothermal titration calorimetry, various fluorescence assays (such fluorescence correlation spectroscopy and fluorescence polarization/anisotropy), competitive binding assays, equilibrium dialysis, fluorescence resonance energy transfer (FRET), and any other assays for testing the binding between two molecules known to a person of ordinary skill in the art. Details of these routine assays were described below and in Wu, Ge. Chapter 5, General Protein Binding Assay Formats, in Assay Development: Fundamentals and Practices, Online ISBN: 9780470583128; Print ISBN: 9780470191156 (2010); Wan H et al., Journal of Liquid Chromatography & Related Technologies, (2007) 30: 681-700, both of which are hereby incorporated in their entirety by reference.

As is well known to a person of ordinary skill in the art, it is routine to use an immunohistochemistry assay to determine the interaction between a therapeutic agent (for example a protein such as an antibody) and a target in a cell or a tissue. In an example of an IHC assays, the IHC assay determines a protein (such as an antibody) binding to a target molecule in cells or tissues in situ, generally by using chromogenic or fluorescent signals well known in the art as the final measurements. In some embodiments, the tissue sample is contacted with a protein (such as a primary antibody) intended to bind a specific target for a period of time sufficient for the protein-target binding to occur. The bound protein (such as the bound primary antibody) can be detected by direct labels on the proteins themselves, for example, radioactive labels, fluorescent labels, hapten labels such as biotin, or an enzyme such as horse radish peroxidase or alkaline phosphatase. Alternatively, an unlabeled protein (such as an unlabeled primary antibody) is used in conjunction with a labeled secondary antibody, comprising antisera, polyclonal antisera or a monoclonal antibody specific for the protein (such as the primary antibody). As such, an enzyme-labeled secondary antibody can be applied, which specifically recognize the protein (for example, recognizing the antibody isotype of the primary antibody). The secondary antibody reacts with the protein bound to the sample (for example, primary antibody bound to the sample), followed by signal development and/or detection. The second-layer detection antibody can be labeled with an enzyme such as a peroxidase, which reacts with the chromogen 3, 3'-diaminobenzidine (DAB) to produce brown precipitate at the reaction site. The final signal from the labels on the secondary antibody, such as chromogenic signal, fluorescence and radioactivity, can be used to determine the level, strength, and specificity of the binding between the protein (such as the primary antibody) to the target in the cell or tissue. Automated systems for IHC processing are available commercially and enable routine performance of the assay in a moderate to high throughput format. The Leica BOND Autostainer and Leica Bond Refine Detection system is an example of such an automated system.

Alternatively, an Enzyme Immune Assay (EIA) or an ELISA can be routinely used to determine the binding between two proteins such as a therapeutic agent and a CA19-9. Both EIA and ELISA assays are known in the art. A wide range of ELISA assay formats are available, see, e.g., U.S. Pat. Nos. 4,016,043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target protein. Sandwich assays are also commonly used assays. A number of variations of the ELISA assay technique are available. For example, to test the binding between protein X and protein Y, protein X can be immobilized on a solid substrate, and protein Y or a sample containing protein Y can be brought into contact with the immobilized protein X. After a suitable period of incubation, for a period of time sufficient to allow formation of protein X and protein Y binding complex, a second antibody specific to protein Y, labeled with a reporter molecule capable of producing a detectable signal is then added and incubated, allowing time sufficient for the formation of another complex of protein X, protein Y, and labeled secondary antibody. Any unreacted material is washed away, and the binding between protein X and protein Y is determined by observation of a signal produced by the reporter molecule. The results can either be qualitative, by simple observation of the visible signal, or can be quantitated by determining levels of binding in a series of increasing concentrations of either protein X or protein Y and fitting binding curves as known to a person of ordinary skill in the art.

In some embodiments of the EIA or ELISA assays, an enzyme is conjugated to the second antibody. In other embodiments, fluorescently labeled secondary antibodies can be used in lieu of the enzyme-labeled secondary antibody to produce a detectable signal in an ELISA assay format. When activated by illumination with light of a particular wavelength, the fluorochrome-labeled antibody adsorbs the light energy, inducing an excited state in the molecule, followed by emission of the light at a characteristic color detectable by a detection equipment. As in the EIA and ELISA, the fluorescently labeled antibody is allowed to bind to the complex formed by the pair of binding proteins being tested. After washing off the unbound reagent, the remaining tertiary complex is then exposed to the light of the appropriate wavelength, and, with appropriate controls known to a person of ordinary skill in the art, the fluorescence observed indicates the level, strength, and specificity of binding. Immunofluorescence and EIA techniques are both very well established in the art and are disclosed herein. As is well known to a person skilled in the art, it is routine to perform EIA or ELISA assays to test the binding between two molecules and routine to adopted such assays for a highthroughput format.

Similarly, a immunoblotting assay can be used to determine the binding between two proteins such as a therapeutic agent and a CA19-9. Details of immunoblotting assays were further described in Section 6.3.2.5. In one embodiment, a CA19-9 can be on a membrane and the binding between a therapeutic antibody and the CA19-9 can be determined in any immunoblotting assays described in Section 6.3.2.5.

Additionally, a FACS assay can be used to determine the binding between two proteins such as a therapeutic agent and a CA19-9. Details of FACS assays were further described in Section 6.3.2.5. In one embodiment, a cell that normally express no CA19-9 can be engineered to express one or more CA19-9 and the binding between a therapeutic agent (such as a therapeutic antibody, a therapeutic protein, or a therapeutic peptide) and the CA19-9 can be determined in any FACS assays described in Section 6.3.2.5 by measuring the increase in the binding of the therapeutic agents to the cells expressing CA19-9 over to the control cells expressing no CA19-9.

Binding between a therapeutic agent and a CA19-9 can also be determined in a immunoprecipitation assay, a co-precipitation assay or a co-immunoprecipitation assay. In an immunoprecipitation assay, an antibody (such as a therapeutic antibody) against a specific target protein (such as CA19-9) forms an immune complex with that target in a sample, such as a cell lysate. The immune complex is then captured, or precipitated, on a beaded support to which an antibody-binding protein is immobilized (such as Protein A or G), and any proteins not precipitated on the beads are washed away. Finally, the target protein (and antibody, if it is not covalently attached to the beads and/or when using denaturing buffers) is eluted from the support and analyzed by a variety of means, such as by mass spectrometry (with or without enzyme digestion) or by sodium dodecyl sulfate-polyacrylamide gel electrophoresis (SDS-PAGE) (often combined with western blotting).

Co-immunoprecipitation is an extension of immunoprecipitation that is based on the potential of immunoprecipitation reactions to capture and purify the primary target (such as a CA19-9) as well as other macromolecules that are bound to the primary target by interactions in the sample solution. For example, if protein X can bind to protein Y, a immunoprecipitation of protein X as described above will cause some protein Y to be co-immunoprecipitated because protein Y is bound to protein X. Protein Y can be eluted from the immunoprecipitated complex and analyzed by a variety of means, such as by mass spectrometry (with or without enzyme digestion) or by sodium dodecyl sulfate-polyacrylamide gel electrophoresis (SDS-PAGE) (often combined with western blotting). As such, the binding between protein X and protein Y can be determined. A co-precipitation assay is performed according to essentially the same principle and format as an immunoprecipitation or co-immunoprecipitation assay, except that no antibody is used in a co-precipitation assay. For example, glutathione-agarose beads can be used to precipitate a GST-fused protein X. Protein Y bound to protein X can be identified together with protein X in the precipitant by a variety of means as in immunoprecipitation and such co-precipitation of protein X and protein Y would indicate that the two protein can interact.

In an immunoprecipitation assay, a co-immunoprecipitation assay, or a co-precipitation assay, the binding partner of the precipitated target protein can be also be detected or determined by mass spectrometry (including combination of liquid chromatography and mass spectrometry, LC-MS) to identified thousands of binding partners in one assay. For example, if a CA19-9 is the target protein being precipitated in any of the precipitation assay provided herein, any and all interacting partners bound to the CA19-9 can be eluted and subject to mass spectrometry (including LC-MS) for identification. As such, if a CA19-9 had been contacted with a library of molecules, all molecules from the library that can bind to the CA19-9 can be identified all at once in one assay. As is well known to a person skilled in the art, it is routine to perform an immunoprecipitation assay, a co-immunoprecipitation assay, or a co-precipitation assay to test the binding between two molecules and routine to adopted such assays for a highthroughput format.

Furthermore, binding between a therapeutic agent and a CA19-9 can also be determined in a surface plasmon resonance (SPR) assay. In SPR assays, target molecules, most frequently proteins are immobilized on a prepared gold sensor surface and a sample containing a potential interacting partner in solution is injected over the surface through a series of flow cells. During the course of the interaction, polarized light is directed toward the sensor surface and the angle of minimum intensity reflected light is detected. This angle changes as molecules bind and dissociate and the interaction profile is thus recorded in real time in a sensorgram. In an example of such SPR assay for binding between Sialyl-Lewis$^a$ and a therapeutic antibody, biotin-labeled univalent sLe$^a$ (Cat #02-044) or polyvalent sLe$^a$-PAA-biotin (Cat #01-044) can be coupled to separate flow cells of an SPA biosensor chip according to the manufacturer's instructions. A flow cell blocked with HSA and culture medium containing free biotin is used as a reference cell. The binding kinetic parameters can be determined from several known concentrations of antibody diluted in HBS-EP buffer (10 mmol/L HEPES, pH 7.4, 150 mmol/L NaCl, 3.4 mmol/L EDTA, 0.005% surfactant P20) using the sLe$^a$-PAA-biotin-coated flow cell. The curve-fitting software provided by the Biacore instrument is then used to generate estimates of the association and dissociation rates from which affinities are calculated. Commercial SPR assay system is available such as a Biacore 3000 (GE Healthcare). Examples of implemented SPR assays were described in U.S. Pat. No. 9,475,874. As is well known to a person skilled in the art, it is routine to perform an SPR assay to test the binding between two molecules.

Additionally, it is routine to use chromatography or gel shifting assays to measure interactions between a therapeutic agent and CA19-9 (or Sialyl Lewis$^a$), as described in Hellman L M et al., Nat Protoc. 2007; 2(8): 1849-1861; Mallik R et al., J Chromatogr A. 2010 Apr. 23; 1217(17): 2796-2803; Koeplinger K A et al., Analytical Biochemistry (1996) 243(1): 66-73; Chan J et al., Mol Cell Proteomics. 2012

July; 11(7): M111.016642. Bloustine J, et al., Biophys J. 2003 October; 85(4): 2619-2623, all of which are hereby incorporated in their entirety by reference. It is also routine to use isothermal titration calorimetry for measuring interactions between a therapeutic agent and CA19-9 (or Sialyl Lewis$^a$), as described in Freyer M W et al., Methods Cell Biol. 2008; 84:79-113, all of which are hereby incorporated in their entirety by reference.

Furthermore, it is routine to use fluorescence assays (such fluorescence correlation spectroscopy and fluorescence polarization/anisotropy) to measure interactions between a therapeutic agent and CA19-9 (or Sialyl Lewis$^a$), as described in Langowski J, Methods Cell Biol. 2008; 85:471-84; Lagerkvist A C et al., Protein Science (2001), 10:1522-1528; Melo A M, et al., Quantifying Lipid-Protein Interaction by Fluorescence Correlation Spectroscopy (FCS). In: Engelborghs Y., Visser A. (eds) Fluorescence Spectroscopy and Microscopy. Methods in Molecular Biology (Methods and Protocols), vol 1076. Humana Press, Totowa, NJ; Hall M D et al., Methods and Applications in Fluorescence, 2016; volume 4, number 2, 022001; Gijsbers A et al., J Vis Exp. 2016 Oct. 21; (116); James N G et al., Methods Mol Biol. 2014; 1076:29-42; Jameson D M et al., Methods Mol Biol. 2005; 305:301-22, all of which are hereby incorporated in their entirety by reference.

A person of ordinary skill in the art can also use routine competitive binding assays to measure interactions between a therapeutic agent and CA19-9 (or Sialyl Lewis$^a$), as described in Hu L et al., Anal Chem. 2013 May 21; 85(10): 5071-7; Crolla L J et al., Clinical Chemistry, Chapter 3, pp 57-68, ACS Symposium Series, Vol. 36, ISBN13: 9780841203457; Schmidt K J et al., Laboratory Medicine, October 1972 page 42-45, all of which are hereby incorporated in their entirety by reference.

Similarly, it is also routine to use fluorescence resonance energy transfer (FRET) to measure interactions between a therapeutic agent and CA19-9 (or Sialyl Lewis$^a$), as described in Margineanu A et al, Sci Rep. 2016 Jun. 24; 6:28186; Vercruysse T et al., RNA Biology, 8:2, 316-324; Du Y et al., Assay Drug Dev Technol. 2013 July; 11(6): 367-381, all of which are hereby incorporated in their entirety by reference. On the same vein, it is routine to use bioluminescence resonance energy transfer (BRET) to measure interactions between a therapeutic agent and CA19-9 (or Sialyl Lewis$^a$) in the methods provided herein, as described in Cui B, et al., MBio, 5(3), e01050-14; Dimri S et al., Methods Mol Biol. 2016; 1443:57-78; Mild J G, et al., Mol Biotechnol (2018). pp 1-11, all of which are hereby incorporated in their entirety by reference.

Other available well-known routine binding assays are described in Ligand-Binding Assays: Development, Validation, and Implementation in the Drug Development Arena, Edited by Khan M N and Findlay J W, ISBN: 9780470041383; Golemis E Protein-protein interactions: A molecular cloning manual. Cold Spring Harbor (NY): Cold Spring Harbor Laboratory Press. p ix, 682. (2002); Phizicky E M, et al., Protein-protein interactions: Methods for detection and analysis. Microbiol Rev (1995) 59:94-123, all of which are hereby incorporated in their entirety by reference.

6.3.2 Assays for Therapeutic Activities Against Pancreatitis

As disclosed above, an underlying cause of pancreatitis is pancreatic inflammation and pancreatic damage. Therefore, assays useful for assessing the effectiveness of the methods provided herein for preventing, treating, ameliorating, or managing pancreatitis can include employing one or more steps of the methods as provided herein, e.g. administering by various dosing regimen of a therapeutic agent provided herein to an assay system, determining one or more readouts from the assay system, and comparing the readouts between the therapeutic-agent-treated group and the control (placebo)-treated group (or a reference range). Changes in the readouts are used to determine the activities of the therapeutic agent for preventing, treating, ameliorating, or managing pancreatitis.

As disclosed in Section 6.2.2, pancreatitis can be determined and observed by determining, measuring or observing various indicators and/or markers. Therefore, the assay systems described in this Section can use one or more readouts based on one or more markers as discussed above in Section 6.2.2 Biomarkers.

6.3.2.1. Immunohistochemistry (IHC) or Histology Staining Assays for Pancreatitis As disclosed in Section 6.2.2, the markers for pancreatitis include abnormalities in pancreatic histology (for example from histology staining or IHC staining of the pancreatic tissue samples). Such histological markers include abnormalities in the expression of one or more proteins in the pancreas, presence or abnormal numbers of certain type of non-pancreatic cells (for example immune cells including leukocytes, macrophages, and neutrophils) in the pancreas, abnormal changes in the abundance or number of certain cells in the pancreas, and abnormalities in the structure of pancreatic cells or pancreatic tissues (for example abnormalities in pancreatic parenchyma, pancreatic ducts, islets of Langerhans, and the acinar cells/tissues). Therefore, assays useful for assessing the effectiveness of the methods provided herein for preventing, treating, ameliorating, or managing pancreatitis include assays for histopathological staining and/or IHC assays for detecting such abnormalities in pancreatic histology.

In some embodiments of the assay in the methods provided herein, a therapeutic agent is administered according to the methods provided herein to a model assay system as discussed further below in Section 6.3.3, and one or more histological markers are determined by the assays as described in this section. The therapeutic agents that reverse the abnormalities of the histological markers in pancreatitis or change the histological markers towards a normal reference level or that of a healthy control subject can be used in the methods provided herein.

As is well-known to a person of ordinary skill in the art, it is routine to perform an IHC assay to determine any of the histological pancreatitis markers. For IHC assays, IHC techniques utilizing an antibody to probe and visualize cellular antigens in situ, generally by chromogenic or fluorescent methods are well known in the art. Primary antibodies or antisera, such as polyclonal antisera and monoclonal antibodies that specifically bind a target protein, can be used to detect levels of a target in an IHC assay. In some embodiments, the tissue sample is contacted with a primary antibody for a specific target for a period of time sufficient for the antibody-target binding to occur. The antibodies can be detected by direct labels on the antibodies themselves, for example, radioactive labels, fluorescent labels, hapten labels such as biotin, or an enzyme such as horse radish peroxidase or alkaline phosphatase. Alternatively, an unlabeled primary antibody is used in conjunction with a labeled secondary antibody, such as antisera, polyclonal antisera or a monoclonal antibody specific for the primary antibody. An enzyme-labeled secondary antibody can then be applied, which specifically recognize the antibody isotype of the primary antibody (second layer). The secondary antibody reacts with the primary antibody and can be followed by development of a detection signal such as substrate-chromogen application. The second-layer antibody can be labeled with an enzyme such as a peroxidase, which reacts with the chromogen 3, 3'-diaminobenzidine (DAB) to produce brown precipitate at the reaction site. This method is sensitive and versatile due to the potential signal amplification through application of a signal amplification system. IHC protocols and kits are well known in the art and are commercially available. Automated systems for slide preparation and IHC processing are available commercially. The Leica BOND Autostainer and Leica Bond Refine Detection system is an example of such an automated system.

The assays provided herein can also use routine histolopathological staining utilizing molecules other than antibodies to visualize pancreatic histological structures and detect abnormalities in pancreatic histology. In histopathological staining, one or more staining dyes are used to mark cells, tissues, nucleic acids, proteins, lipids, and/or other cellular or tissue components to aid in the microscopic examination of the pancreatic histology. Typical procedure of the histopathological staining involves fixation, processing, embedding, sectioning, staining, washing/developing as disclosed in Alturkistani et al., Histological Stains: A Literature Review and Case Study, *Glob J Health Sci.*, (March 2016), 8(3): 72-79, or as available commercially from Leica Biosystems (e.g. Infinity Stain Kit System from Leica). An exemplary histolopathological staining is hematoxylin and eosin stain (H&E) that is used routinely with all tissue specimens to reveal the underlying tissue structures and conditions. As is clear for a person skilled in the art, the histopathological staining and IHC can be combined in various permutations and combinations for the assays contemplated by this disclosure.

Accordingly, in some embodiments of the assay for the therapeutic agents or the methods provided herein, a therapeutic agent is administered according to the methods provided herein to a model assay system as discussed further below in Section 6.3.3, and the abnormalities in the pancreas is determined by histopathological and/or IHC staining as described in this section. Therapeutic agents that reduce, change, or reverse the abnormalities in pancreatic histology towards normal reference pancreatic histology or that of a healthy control subject can be used in the methods provided herein.

6.3.2.2. Assays for Pancreatitis by Imaging

As discussed above, pancreatitis markers can also be detected by imaging assays. Abnormalities in pancreatic structures can be imaged, for example, with ultrasound (such as EUS), computed tomography, endoscopic retrograde cholangiopancreatography (ERCP), and magnetic resonance imaging (such as MRCP), with or without contrast enhancement, as is well known to a person skilled in the art. Exemplary pancreatitis markers detected by imaging were described above in Section 6.2.2.2. Therefore, in some embodiments of the assays for activities of the therapeutic agents provided herein, therapeutic agents are administered according to the methods provided herein to a model assay system as discussed further below in Section 6.3.3, and the abnormalities in the pancreas is determined by the imaging assays as described in this section. Therapeutic agents that reduce, improve, change or reverse the abnormalities in pancreatitis markers (described in Section 6.2.2 and 6.2.1) detected by the imaging assays towards normal reference range of the markers or that of a healthy control subject can be used in the methods provided herein.

As is well-known to a person of ordinary skill in the art, it is routine to perform an imaging assay to determine any of the pancreatitis markers provided herein. Detailed protocols for the imaging assays are well known to a person of ordinary skill in the art and have been described in Etemad B et al., Gastroenterology 2001; 120:682-707; Duggan, S N, et al., World J Gastroenterol 2016; 22(7): 2304-2313; and Chapter 37 and 38 on Acute Pancreatitis and Chronic Pancreatitis respectively, GI/Liver Secrets Plus, 4th edition, edited by McNally PR, 2010; Sai J K et al, World J Gastroenterol 2008 Feb. 28; 14(8): 1218-1221; Banks P A et al., Gut 2013; 62:102-111; Iglesias-Garia J et al., Gut 2006; 55:1661-1684, all of which are hereby incorporated in their entirety by reference.

6.3.2.3. Assays for Pancreatitis Based on Serological Markers

Serological, urinary and fecal markers provided in Section 6.2.2.1 can be detected by biochemical assays such as an immunological assay as is well known to a person skilled in the art. The format of such assays can include ELISA assay, a strip test, a bead-based FACS assay, a western blotting assay, a chromatography assay (e.g. FPLC and HPLC), a spectroscopy assay, a colorimetric assay, and mass spectrometry.

In some embodiments of the assay in the methods provided herein, a therapeutic agent is administered according to the methods provided herein to a model assay system as discussed further below in Section 6.3.3, and one or more serological markers are determined by the assays as described in this section. The therapeutic agents that reverse the abnormalities of the serological markers in pancreatitis or change the level serological markers towards a normal reference range or that of a healthy control subject can be used in the methods provided herein.

Serum amylase, lipase, CRP and other markers provided in Section 6.2.2.1 can be detected using immunoassays such as an Enzyme Immune Assay (EIA) or an ELISA. Both EIA and ELISA assays are known in the art, e.g. for assaying a wide variety of tissues and samples, including blood, urine, serum or pancreatic tissues. A wide range of ELISA assay formats are available, see, e.g., U.S. Pat. Nos. 4,016,043, 4,424,279, and 4,018,653, which are hereby incorporated by reference in their entireties. These include both single-site and two-site or "sandwich" assays of the non-competitive types, as well as in the traditional competitive binding assays. These assays also include direct binding of a labeled antibody to a target protein. Sandwich assays are commonly used assays. A number of variations of the sandwich assay technique exist. For example, in a typical forward assay, an unlabelled antibody is immobilized on a solid substrate, and the sample to be tested brought into contact with the immobilized antibody. After a suitable period of incubation, for a period of time sufficient to allow formation of an antibody-antigen complex, a second antibody specific to the antigen, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results can either be qualitative, by simple observation of the visible signal, or can be quantitated by comparing with a control sample containing known amounts of target protein.

In some embodiments of the EIA or ELISA assays, an enzyme is conjugated to the second antibody. In other embodiments, fluorescently labeled secondary antibodies can be used in lieu of the enzyme-labeled secondary antibody to produce a detectable signal in an ELISA assay format. When activated by illumination with light of a particular wavelength, the fluorochrome-labeled antibody adsorbs the light energy, inducing an excited state in the molecule, followed by emission of the light at a characteristic color detectable by a detection equipment. As in the EIA and ELISA, the fluorescently labeled antibody is allowed to bind to the first antibody-target protein complex. After washing off the unbound reagent, the remaining tertiary complex is then exposed to the light of the appropriate wavelength, and the fluorescence observed indicates the presence or quantity of the target protein of interest. Immunofluorescence and EIA techniques are both very well established in the art and are disclosed herein.

In one embodiment, the assay provided herein employs a quantitative sandwich enzyme immunoassay technique. A monoclonal antibody specific for a pancreatitis marker provided herein is pre-coated onto a microplate. Standards and samples (e.g. blood or serum samples) are pipetted into the wells and any marker present is bound by the immobilized antibody. After washing away any unbound substances, an enzyme-linked polyclonal antibody specific for the marker is added to the wells. Following a wash to remove any unbound antibody-enzyme reagent, a substrate solution is added to the wells and color develops in proportion to the amount of the marker bound in the initial step, which correlates with the marker level in the sample (e.g. blood or serum samples). The color development is stopped and the intensity of the color is measured. The measurements are used as a proxy for the marker level in the sample (e.g. blood or serum samples).

As is well-known to a person of ordinary skill in the art, it is routine to perform an EIA or ELISA assay to determine any of the pancreatitis markers provided herein. Exemplary commercial assays for measuring serum amylase, serum lipase, CRP, and other pancreatitis markers have been provided in Section 6.2.2.1. Accordingly, in some embodiments of the assay in the methods provided herein, a therapeutic agent is administered according to the methods provided herein to a model assay system as discussed further below in Section 6.3.3, and the levels of a serological marker such as amylase, lipase or CRP is determined by the assays as described in this section. The therapeutic agents that reduce the marker level or change the level of the marker towards a normal reference range or that of a healthy control subject can be used in the methods provided herein.

In some embodiments, the methods provided herein can be used with some specific amylase, lipase, and CRP assays, as are well known to a person of ordinary skill in the art. Examples of such specific assays for amylase, lipase, CRP, and other serological markers are described in Kaphalia B S, Chapter 16, Biomarkers of acute and chronic pancreatitis in Biomarkers in Toxicology, edited by Gupta R., ISBN: 978-0-12-404630-6 (2014); Sutton P A, et al., Ann R Coll Surg Engl 2009; 91: 381-384; Matull W R, et al., J Clin Pathol 2006; 59:340-344; Basnayake C et al., Aust Prescr 2015; 38:128-30; and Jasdanwala S et al., Integr Mol Med, 2015; 2(3): 189-195, all of which are hereby incorporated in their entirety by reference.

6.3.2.4. Assays for the Function of the Pancreas

In some embodiments of the assay in the methods provided herein, a therapeutic agent is administered according to the methods provided herein to a model assay system as discussed further below in Section 6.3.3, and the function of pancreas is determined by the assays as described in this section. The therapeutic agents that restore the function of pancreas or change the level pancreas function towards a normal reference range or that of a healthy control subject can be used in the methods provided herein. Various detailed protocols to assay pancreas function are well known to a person of ordinary skill in the art and routine to perform, as described, for example, in John G Lieb II and Peter V Draganov, World J Gastroenterol. 2008 May 28; 14(20): 3149-3158; Clain J E, et al., Surg Clin North Am 1999; 79:829-845; Couper R. Can J Gastroenterol 1997; 11:153-156; Layer P, et al., J Clin Gastroenterol 1999; 28:3-10; Toskes P P. Curr Gastroenterol Rep 1999; 1:145-153; Chapter 38 on Chronic Pancreatitis, GI/Liver Secrets Plus, 4th edition, edited by McNally PR, 2010; all of which are hereby incorporated in their entirety by reference.

6.3.2.5. Assays for Signaling Markers

In some embodiments of the assay in the methods provided herein, a therapeutic agent is administered according to the methods provided herein to a model assay system as discussed further below in Section 6.3.3, and one or more signaling markers are determined by the assays as described in this section. The therapeutic agents that reduce the level of the signaling markers or change the level of the signaling markers towards a normal reference range or that of a healthy control subject can be used in the methods provided herein. Signaling markers that can be used in the assays are described above in Section 6.2.2.4.

In some embodiments, the signaling markers can be detected with antibodies described herein using an immunoblotting assay. In some embodiments of an immunoblotting assay, proteins can be (but do not have to be) separated by electrophoresis and transferred onto membranes (usually nitrocellulose or PVDF membrane), for example in a Western blotting assay. Similar to the IHC assays, primary antibodies or antisera, such as polyclonal antisera and monoclonal antibodies that specifically target a signaling marker can be used to detect the level of the signaling marker. In some embodiments, the membrane is contacted with a primary antibody for a specific target for a period of time sufficient for the antibody-antigen binding to occur and the bound antibodies can be detected by direct labels on the primary antibodies themselves, e.g. with radioactive labels, fluorescent labels, hapten labels such as biotin, or enzymes such as horseradish peroxidase or alkaline phosphatase. In other embodiments, an unlabeled primary antibody is used in an indirect assay as described above for IHC assays in conjunction with a labeled secondary antibody specific for the primary antibody. As described herein, the secondary antibodies can be labeled, for example, with enzymes or other detectable labels such as fluorescent labels, luminescent labels, colorimetric labels, or radioisotopes. Immunoblotting protocols and kits are well known in the art and are commercially available. Automated systems for immunoblotting, e.g. iBind Western Systems for Western blotting (ThermoFisher, Waltham, MA USA 02451), are available commercially. Immunoblotting includes, but is not limited to, Western blot, in-cell Western blot, and dot blot. Dot blot is a simplified procedure in which protein samples are not separated by electrophoresis but are spotted directly onto a membrane. In cell Western blot involves seeding cells in microtiter plates, fixing/permeabilizing the cells, and subsequent detection with a labeled primary antibody or an unlabelled primary antibody followed by labeled secondary antibody as described herein.

In other embodiments, the levels of signaling markers can also be detected with the antibodies described herein in a flow cytometry assay, including a fluorescence-activated cell sorting (FACS) assay. Similar to the IHC or immunoblotting assays, primary antibodies or antisera, such as polyclonal antisera and monoclonal antibodies that specifically target a signaling marker, can be used to detect the levels of the signaling marker in a FACS assay. In some embodiments, cells are stained with primary antibodies against a specific signaling marker for a period of time sufficient for the antibody-antigen binding to occur and the bound antibodies can be detected by direct labels on the primary antibodies, for example, fluorescent labels or hapten labels such as biotin on the primary antibodies. In other embodiments, an unlabeled primary antibody is used in an indirect assay as described above for IHC assays in conjunction with a fluorescently labeled secondary antibody specific for the primary antibody. FACS provides a method for sorting or analyzing a mixture of fluorescently labeled biological cells, one cell at a time, based upon the specific light scattering and fluorescent characteristics of each cell. The flow cytometer thus detects and reports the intensity of the fluorichrome-tagged antibody, which indicates the levels of the signaling marker in each cell. Therefore, the levels of signaling markers can be detected using antibodies against the signaling marker. A cytoplasmic signaling marker can also be observed by staining permeablized cells. Methods for performing FACS staining and analyses are well know to a person skilled in the art and are described by Teresa S. Hawley and Robert G. Hawley in Flow Cytometry Protocols, Humana Press, 2011 (ISBN 1617379506, 9781617379505). It is routine for a person of ordinary skill in the art to perform a FACS assay and an immunoblotting assay to determine any of the signaling markers provided herein.

As is known to a person of ordinary skill in the art, the levels of signaling markers can also be routinely detected using immunoassays such as an Enzyme Immune Assay (EIA) or an ELISA as described above in Section 6.3.2.3.

6.3.3 Model Systems for the Assays

6.3.3.1. Animal Models

The disclosure provides animal models (e.g. transgenic mouse model), wherein the animal (e.g. mouse) is genetically engineered to express CA19-9 in the pancreas and develop pancreatitis. The following disclosures are provided using mouse as the exemplary animal model but a person skilled in the art would understand that the disclosure includes and is applicable to other animals, for example, monkey, pig, dog, rat, and/or rabbit. The disclosure further provides that CA19-9 is generated by the stepwise addition of different sugar moieties to Type 1 precursor chains, culminating in the $\alpha 1,4$ linkage of fucose to GlcNAc. As used herein, Fut3 refers to a fucosyltransferase with the ability to add fucose moieties through an $\alpha 1,4$ linkage. In one embodiment of a transgenic mouse pancreatitis model, mouse embryonic stem cells (mESCs) can be generated, wherein the mESCs express Fut3 and $\beta$GalT5 via an inducible promoter dependent upon tissue-specific expression of Cre, recombination of a LoxP flanked stop cassette (LSL) and administration of Doxycycline (Dox). Mice can be generated from mESCs with and without Cre transfection to generate lines that are either dependent or independent of Cre expression. In these transgenic mouse, expression of Fut3 and $\beta$GalT5 and thus expression of CA19-9 can be induced with administration of Dox. As such, the disclosure provides mice wherein the CA19-9 expression can be induced in the whole pancreas of the mice, mice wherein the CA19-9 expression can be induced in focal areas of the pancreas of the mice, and mice wherein the CA19-9 expression can be induced in the whole body of the mice. These mice are referred to as CA19-9 mouse models and each can be used in the methods provided herein.

In all CA19-9 mouse models wherein CA19-9 expression is induced in the pancreas, non-pancreatic tissues exhibit normal histology relative to genetically negative littermate controls following a time course of Dox treatment. Induction of CA19-9 expression in the pancreas of the mouse model results in pancreatitis, including multiple physiological, histological and serological signs of pancreatitis (for example, acinar atrophy, immune cell invasion, collagen deposition, elevated lipase and amylase), whereas no pancreatitis can be observed in Dox treated genetic negative controls or untreated mice. Additionally, CA19-9 mice having induced CA19-9 expression in the whole mice exhibit body weight loss and pancreatic atrophy following CA19-9 expression, in some cases resulting in loss of more than 20% of body mass and subsequent euthanasia. All tissues other than the pancreas remain healthy in the CA19-9 mice having induced CA19-9 expression in the whole mice, demonstrating that the pancreatitis in CA19-9 mice following CA19-9 expression is not autoimmune-mediated.

CA19-9 mice having induced CA19-9 expression in the whole pancreas develop highly penetrant pancreatitis and elevated amylase and lipase levels without loss in body or pancreatic weight. The immune cell types present in the spleen, lymph nodes and pancreata of CA19-9 mice having induced CA19-9 expression in the whole pancreas are comparable to the cerulein model (discussed below) of acute pancreatitis. Both CA19-9 mice having induced CA19-9 expression in the whole pancreas and cerulein models exhibit a treatment-dependent influx of inflammatory monocytes and macrophages in the pancreas without any change to the immune cell type representation in the spleen or lymph nodes. CA19-9 mice having induced CA19-9 expression in focal areas of pancreas develop smaller pancreatitis foci and elevated amylase and lipase levels relative to genetic and untreated controls without loss in body or pancreatic weight and exhibited the expected CA19-9 expression pattern. All CA19-9 mouse models exhibit chronic pancreatitis with multiple histological markers for chronic pancreatitis. CA19-9 is also detectable in the plasma of CA19-9 mouse model having CA19-9 expression in the whole body of the mice and CA19-9 mouse model having CA19-9 expression in the whole pancreas of the mice. In one embodiment, CA19-9 mice having CA19-9 expression in the whole pancreas provides the high penetrance of the pancreatitis phenotype without weight loss. As used herein, penetrance of pancreatitis refers to the percentage of area in the pancreas that is affected by pancreatitis: the higher the percentage of areas affected, the higher the penetrance.

Additionally, the pancreatitis models suitable for the methods provided herein include clinical human pancreatitis patients. Such patients for clinical testing can be identified according to the pancreatitis markers and classification scheme as described above in Section 6.2.2.

6.3.3.2. Cell Models

Alternatively, the cell models that recapture some or all of the signaling pathways or mechanisms in pancreatitis can be used in the methods provided herein for identifying the therapeutic agents, confirming the activities of the therapeutic agents in reducing or increasing signaling markers as described above, determining the therapeutic outcomes of the therapeutic agents in pancreatitis, and testing the efficacies of the therapeutic agents in pancreatitis. Furthermore, as discussed above, any of the cell models provided herein can be used in any permutation or combination with the assays disclosed herein. These cell models suitable for the methods provided herein include mouse pancreatic ductal adenocarcinoma (PDAC) cell lines that have been engineered to express CA19-9 (for example by introducing expression of Fut3 and/or β3GalT5 in the mouse PDAC cells) and human PDAC cell lines (such as Suit2). The disclosure provides that the PDAC cells expressing CA19-9, naturally or recombinantly, recapitulate some or all of the signaling pathways and mechanisms underlying human pancreatitis, and can be used in the methods and assays provided herein.

Additionally, primary acinar cells isolated from animals (such as pigs, monkeys or humans) or acinar cell lines (such as rat pancreatic acinar cell line AR42J) can be used as cells models in the methods provided herein for identifying the therapeutic agents, confirming the activities of the therapeutic agents in reducing or increasing signaling markers as described above, determining the therapeutic outcomes of the therapeutic agents in pancreatitis, and testing the efficacies of the therapeutic agents in pancreatitis. Single, double, and large cluster acinar cells are obtained using a collagenase digestion protocol as described in Burnham D B, et al., J Physiol 349: 475-482, 1984; Criddle D N, et al., J Gastroenterol Hepatol 21 Suppl 3: S14-17, 2006; Peikin S R, et al., Am J Physiol 235(6): E743-749, 1978; Schultz G S, et al., Exp Cell Res 130(1): 49-62, 1980; Williams J A, et al., Am J Physiol 235(5): 517-524, 1978, all of which are hereby incorporated in their entirety by reference. The disclosure provides that the acinar cells recapitulate some or all of the signaling pathways and mechanisms underlying human pancreatitis, and can be used in the methods and assays provided herein.

Three-dimensional (3D) cells cultures, either in vitro 3D culture or 3D structures isolated from pancreata of animals, can also be used as cells models in the methods provided herein as discussed above. Such 3D cultures recapitulate some or all of the signaling pathways and mechanisms underlying human pancreatitis, including both intra-cellular signaling and inter-cellular signaling, and can be used in the methods and assays provided herein. 3D structures isolated from pancreas of animals include pancreatic lobules, pancreatic organoids, and pancreas slice.

As is known to a person of ordinary skill in the art, pancreatic lobules can be prepared by spreading them apart via injecting Krebs-Ringer bicarbonate buffer into the loose connective tissue of the pancreas and then individually excising the lobules by micro-dissection under a stereomicroscope. This procedure minimizes damage to acinar cells since most of the surgical trauma is limited to ducts and vessels. The excised lobules preserve the overall acinar architecture of the tissue and their small size and allows for easy penetration of oxygen and solutes from the incubation medium. Following this method, lobules can be maintained for several hours in culture and used for subsequence assays including high-throughput assays. The procedure for isolating pancreatic lobules suitable for the assays and the methods are described in details in Barreto S G, et al., Am J Physiol Gastrointest Liver Physiol 299(1): G10-22, 2010; Barreto S G, et al., Am J Physiol Gastrointest Liver Physiol 297(2): G333-339, 2009; Flowe K M, et al., Pancreas 9(4): 513-517, 1994; Linari G, et al., Pharmacol Res Society 43(3): 219-223, 2001; Scheele G A et al., J Biol Chem 250(7): 2660-2670, 1975; Schloithe A C, et al., Neurogastroenterol Motil 20(9): 1060-1069, 2008, all of which are hereby incorporated in their entirety by reference.

As is known, organoids refers to three-dimensional cell, tissue, or organ cultures. Pancreatic organoids can be rapidly generated from resected pancreatic tumors, pancreatic tissues, and pancreatic biopsies following digestion with collagenase XI and seeding in growth factor-reduced Matrigel. Conditioning the medium with the growth factor R-spondin promotes a predominantly ductal cell population. These pancreatic organoids survive cryopreservation and exhibit ductal- and disease stage-specific characteristics. Further, pancreatic organoids from mice accurately recapitulated physiologically relevant aspects of disease progression in vitro. Following orthotopic transplantation, pancreatic organoids were capable of regenerating normal ductal architectures. In a particular embodiment for preparing pancreatic organoids, ducts from pancreata can be harvested after enzymatic digestion with 0.012% collagenase XI (Sigma) and 0.12% dispase (GIBCO) in DMEM containing 1% FBS (GIBCO), and embedded in 100% growth factor-reduced (GFR) Matrigel (BD) for the maintenance of the isolated pancreatic organoids. Detailed procedures for isolating and culturing pancreatic organoids are described in Boj S F, et al., Cell 160(1-2): 324-338, 2015; Huch M, et al., EMBO J 32(20): 2708-2721, 2013, both of which are incorporated hereby in their entirety by reference.

To obtain a pancreas slice, a low melting agarose gel can be infused into the pancreatic duct of an anesthetized mouse via a transduodenal puncture and cannulation of the common bile duct. The pancreas can then be excised and trimmed. The agarose renders the pancreas firm enough to then slice, using a vibratome, at a thickness of 80-140 µm. Moreover, agarose is porous and thus provides free exchange of tissue with buffer, ensuring optimal health in culture for up to two days. Detailed procedures for isolating and culturing pancreatic slices are described in Huang Y C, et al., J Physiol 589 (Pt 2): 395-408, 2011; Huch M, et al., EMBO J 32(20): 2708-2721, 2013, both of which are incorporated hereby in their entirety by reference.

These cells and 3D cell structures can be used in any assays as provided herein for measuring any or any combination of pancreatitis markers as provided herein, for example, signaling markers, histological markers, physiological markers, functional markers and serological markers. In some particular embodiments, the cells and 3D cell structures are used for testing the therapeutic agents using EGFR signaling, for example, phosphorylation of EGFR, phosphorylation of Erk1/2, phosphorylation of Akt, or any combination thereof, as the measurement of the assay. In other particular embodiments, the cells and 3D cell structures are used for testing the therapeutic agents using CA19-9, Sialyl-Lewis$^a$ or any combination thereof as the measurement of the assay.

6.3.4 High Throughput Screening Assays

The assays using the cells and 3D cell structures can be a high-throughput assay. As is known to a person of ordinary skill in the art, any of the assays described in Sections 6.3.1, 6.3.2 and in Examples can be adopted for a high throughput assay when using cells or 3D cell structures as the model system. The assay can be designed to use 36-well, 64-well, 96-well, 384-well, and 1536-well plate screening by measuring any one of the signaling markers, histological markers, and serological markers as described herein. For setting up such high throughput assays, liquid handling systems are known in the art for transferring therapeutic agents and other assay reagents, for example, PlateMate Plus systems from Matrix (Hudson, NH) and the MiniTrak and the Multiprobe II HTEX from PerkinElmer systems. Data based on the measurements of any one of the signaling markers, histological markers, and serological markers as described herein can be collected using commercially available imaging systems such as the ViewLux Imaging System (PerkinElmer). In a specific embodiment, wild type cells, wild type 3D cell structures, cells from healthy subjects, or 3D cell structures from heathy subjects can be used as controls in the high throughput assays to indicate the normal or reference range of the measurements of any one of the signaling markers, histological markers, and serological markers.

In some specific embodiments, any of the binding assays provided herein can be routinely adopted in high throughput assay format to readily test binding of thousands of pairs of binding partners, for example between a therapeutic agent and a CA19-9 (or Sialyl Lewis$^a$), to screen a library of molecules for a therapeutic agent that binds a CA19-9 (or Sialyl Lewis$^a$), or to identify or to screen a library of CA19-9.

Alternatively, any of the assays provided herein can be combined with mass spectrometry, such as LC-MS, to identify a CA19-9 or a therapeutic agent from a library of potential molecules. For example, immunoprecipitation, co-immunoprecipitation, or co-precipitation assays can be combined with mass spectrometry (MS) or liquid chromatography-mass spectrometry (LC-MS) to identify either CA19-9 by precipitating anti-Sialyl-Lewis$^a$ antibody or identify a molecule that binds to a CA19-9 by precipitating the CA19-9. In one embodiment of such adapted high throughput assay, co-immunoprecipitation with an anti-Sialyl-Lewis$^a$ antibody is combined with LC-MS to identify a list of CA19-9.

As is well-known to a person of ordinary skill in the art, it is routine to adopt one or more assays provided herein in a high throughput format to test the binding between a therapeutic agent and CA19-9 (or Sialyl-Lewis$^a$) and test the effects of a therapeutic agent on one or more markers in a model system provided herein. Detailed protocols and various formats for adapting assays for high throughput assays are described in Szymanski P et al., Int J Mol Sci. 2012; 13(1): 427-452; Klumpp, M., et al., Journal of biomolecular screening, 11(6), 617-633; Mayr, L. M., et al., Journal of Biomolecular Screening, 2008; 13(6), 443-448; Mayr, L. M., et al., 2009; 9(5). 580-588; D Cronk, D, Chapter 8, in Drug Discovery and Development (Second Edition), 2013, edited by Hill R G, ISBN: 978-0-7020-4299-7, all of which are hereby incorporated in their entirety by reference.

7. EXAMPLES

Example 1

The materials used in the embodiments in the EXAMPLES were prepared, manufactured, acquired, purchased, determined, evaluated, validated, and/or obtained as follows.

Human Specimens:

Human specimens were obtained following approval from the human ethics committee Ethikkommission an der Technischen Universitat Dresden (Institute of Pathology, University Hospital Dresden, Dresden, Germany) and the Institutional Review Board (IRB) of Cold Spring Harbor Laboratory. Normal pancreatic tissue was obtained from islet transplant programs at the University of Illinois at Chicago and University of Miami Miller School of Medicine. A tissue microarray was prepared from chronic pancreatitis patient samples obtained after appropriate informed consent in Dresden (Institute of Pathology, University Hospital Dresden). Informed consent was obtained for each patient, following review by the human ethics committee: Ethikkommission an der Technischen Universitat Dresden (EK59032007). The chronic pancreatitis samples were collected from 1993 to 2009 from patients undergoing surgery. The diagnosis of chronic pancreatitis was confirmed by a pathologist (D.A.). The final diagnosis was established by a pathologist based on histology examination and PDAC ruled out in the disease groups by a medium follow up time of 24 months. For pancreatitis patients, inclusion criteria for all cohorts included written informed consent given by patients and preexisting chronic pancreatitis. The diagnosis of chronic pancreatitis was made if one or more of the following criteria were met and no other diagnosis was more likely (Mayerle, J. et al., Dtsch Arztebl Int 110, 387-393, (2013), which is hereby incorporated in its entirety by reference): recurrent bouts of pancreatic pain with documented rise in amylase or lipase activity for a duration of more than one year and radiological evidence supporting the diagnosis, pancreatic calcifications, histological proof of chronic pancreatitis, unequivocal changes in pancreatic duct morphology, severely abnormal pancreatic function tests with maldigestion. Calcifications were identified on CT-scan, diabetes was diagnosed as suggested by the WHO definition and exocrine insufficiency was determined by either fecal elastase measurement or concurrent pancreatic enzyme supplementation. Exclusion criteria were other concomitant malignant diseases, curative treatment for malignant disease within the last 2 years before recruitment, concomitant cystic diseases of the pancreas, pregnancy or patients unable to give informed consent. CA19-9 determination was performed centralized at a certified clinical laboratory.

Antibodies:

CD4 (100428, clone GK1.5), CD8 (100714, clone 53.6.7), TcR beta clone (109222, clone H57-597), TcR gamma delta (118106, clone GL3), CD19 (152406, clone 1D3), CD45 (103138, clone 30-F11), NKp46 (137716, clone 29A1.4), CD11b (101224, clone M1/70), CD11c (117318, clone N418), Ly6C (128016, clone HK1.4), Ly6G (27606, clone 1A8), PDGFRa (APA5), anti-rat BV421 (4054) and streptavidin (405214) were purchased from Biolegend. CA19-9 (r5B-1, Mabvax (Sawada, R. et al. Clin Cancer Res 17, 1024-1032, (2011); Viola-Villegas, N. T. et al. Journal of nuclear medicine: official publication, Society of Nuclear Medicine 54, 1876-1882, (2013), both of which are herein incorporated in their entirety by reference)), CA19-9 (ATCC Hybridoma 1116-NS-19-9 HB8059), phospho-EGFR (8G6.2, EMD Millipore, IHC), phospho-ERK1/2 (4370, Cell Signaling), ERK1/2 (4695, Cell Signaling), phospho-Akt (4060,2965, Cell Signaling), Akt (4685, Cell Signaling), phosphor-ribosomal S6 (4858, Cell Signaling), and S6 Ribosomal Protein (2317, Cell Signaling), phospho-EGFR (3777, Cell Signaling), EGFR (71655, Cell Signaling), EGFR (4267, Cell Signaling), recombinant mouse EGFR-Fc (RnD), Ki67 (Spring Bioscience M3062), CK19 (TROMA III, DSHB), eGFP (A-11122, Thermofisher), FLAG (Sigma, F7425), human isotype control (Synagis), mouse isotype control (MOPC21).

Example 2

Cloning:

Human FUT3 cDNA was PCR amplified, subcloned into pBabe-Neo and confirmed using Sanger sequencing. Human FUT3 and β3GalT5 (Dharmacon, CCSB-broad lentiviral expression OHS6085-213580074) were PCR amplified and subcloned as a T2A fusion (Fut3-T2A-β3GalT5) into pBabe-Neo and into the ColA1 targeting cassette (Beard C, et al., Genesis. 2006; 44(1):23-8).

Embryonic Stem Cell Targeting:

D34 mES cells (129/C57Bl/6J F1 hybrid) containing the ColA1 pre-targeted FRT site for recombinase mediated cassette exchange (Beard, C., Genesis 44, 23-28, (2006), which is incorporated herein in its entirety by reference) and the CAGS-LSL-rtTA3-IRES-mKate2 (Dow L E, et al., PLoS One. 2014; 9(4):e95236, which is incorporated herein in its entirety by reference) alleles were used to introduce the TRE driven Fut3-T2A-β3GalT5-IRES-eGFP construct. In brief, the mES cell line D34 was thawed in mES cell media containing LIF at passage 3 onto irradiated DR4 mouse embryonic fibroblast feeders in gelatin coated tissue culture plates and were switched to 2i conditions (Ying, Q. L. et al., Nature 453, 519-523 (2008), which is incorporated herein in its entirety by reference) 48 hours later. mES cells were trypsinized and the irradiated DR4 feeders were allowed to re-attach for 45 minutes at 37° C. Electroporation was performed using 2.5 µg of FlpE and 5 µg of the targeting cassette containing the TRE-Fut3-T2A-β3GalT5-IRES-eGFP transgene. 600,000 mES cells were resuspended in electroporation buffer (P3, Amaxa from Lonza), mixed with DNA, transferred to electroporation strip wells and electroporated using the mES cell optimized Amaxa electroporation program. Following electroporation, mES cells were transferred to 6 cm plates containing irradiated DR4 feeders. Hygromycin B selection (140 µg/ml, Roche) was started 48 hours later and surviving colonies were picked 11 days later for expansion and evaluation. The mES cell clones were treated in a separate plate with Geneticin to confirm correct recombination 364 and restoration of Neomycin sensitivity. In addition, in an additional plate, mES cells were transfected with CRE and treated with Doxycycline to confirm Cre-dependent mKate fluorescence and Cre- and Dox-dependent eGFP fluorescence.

Mice were generated from mES cells with and without Cre transfection to generate lines that are either dependent or independent of Cre expression. Mice harboring Rosa26:CAGGS-rtTA-mKate, and ColA1:TRE-Fut3-β3GalT5-GFP (R;F—whole body), Pdx1- OR p48-Cre, Rosa26:CAGGS-LSL-rtTA371 mKate, and ColA1:TRE-LSL-Fut3-β3GalT5-GFP ($C^{PDX/p78}$;$R^{LSL}$;$F^{LSL}$—focal pancreas), and Pdx1-Cre, Rosa26:CAGGS-LSL-rtTA-mKate, and ColA1:TRE-Fut3-β3GalT5-GFP ($C^{PDX}$;$R^{LSL}$;F—whole pancreas) were generated.

gDNA Isolation for Southern Blotting:

mES cell gDNA was harvested from 15 clones (Gentra, Puregene). In brief, cells were washed twice with PBS and 300 µl of cell lysis solution was added per well and cells were scraped using a cell lifter. The lysate was transferred to a new tube and incubated at 37° C. for 45 minutes. 100 µl of protein precipitation solution was added and the tube was inverted ten times. Lysate was centrifuged for 2 minutes at maximum speed and the supernatant was transferred to a new tube. 300 µl of isopropanol was added and the tube inverted 50 times followed by centrifugation for 2 minutes at maximum speed. The supernatant was carefully decanted, blotted on absorbent paper, and allowed to air dry. The DNA pellet was resuspended in 50 µl of water and incubated at 65° C. for one hour and room temperature while shaking gently for 4 hours before being stored at −20° C.

Southern Blotting and PCR:

ES cell gDNA was digested with EcoRI (NEB) at 37° C. for 18 hours while gently shaking. Digested gDNA was run on a 0.8% TAE Agarose gel for 22 hours at 20-35V. The gel was stained with ethidium bromide while rotating for 10 minutes and imaged prior to washing in water. The gel was incubated in denaturing solution (0.5N NaOH, 1.5M NaCl) while rotating for 30 minutes followed by a wash in water. The gel was incubated for 30 minutes in neutralization solution (1M Tris, 3M NaCl, pH7.0) while rotating for 30 minutes followed by a wash in water. The gel was transferred by capillary flow in 20×SSC overnight at room temperature onto a nylon membrane (Schleicher & Schuell Nytran). The membrane was rinsed in 2×SSC and placed on Whatman paper to air dry followed by UV crosslinking for 60 seconds. The membrane was placed in 10 ml of Pre-Hyb solution in a Robbins tube and incubated at 68° C. for 30 minutes while rotating. The Pre-hyb wash was repeated at 42° C. while rotating. The membrane was then incubated overnight in Hybridization solution containing the appropriate probe at 42° C. while rotating. Probes were generated against eGFP (482958 CPM, Rediprime) and Puromycin (186409 CPM, Rediprime). The membrane was then washed twice in 3×SSC/0.5% SDS at 68° C. for 30 minutes while rotating before being exposed to film overnight at −80° C. gDNA was also sent to Transnetyx for genotyping for eGFP to exclude clones with signal higher than validated single copy insertions. Clones FB8 and FB12 were selected for tetraploid complementation (NYU), both of which generated germline transmitted founders. Both clones exhibited the same CA19-9 expression pattern and clone FB12 founders were selected for further evaluation.

Mice:

KPC mice (Kras$^{+/LSL-G12D}$; Trp53$^{+/R172H}$; Pdx1-Cre) have been described previously (Hingorani S R, et al., Cancer Cell. 2003; 4(6):437-50; Hingorani S R, et al., Cancer Cell. 2005; 7(5):469-83) and were backcrossed onto the C57Bl/6J background (The Jackson Laboratory, strain 000664). All animal experiments were conducted in accordance with procedures approved by the IACUC at Cold Spring Harbor Laboratory. Mice were enrolled onto experimental studies between 6 and 8 weeks of age. Mice were administered Doxycycline through drinking water (0.5-2 mg/ml) supplemented with 10 mg/ml Sucrose for study durations up to one week. Doxycycline was administered through chow for experimental studies longer than one week, which is designed to deliver 2-3 mg of doxycycline per day based on the consumption of 4-5 g/day per mouse (Harlan Teklad, dietTD.01306, Doxycycline 625 mg). EdU (300 µg, Santa Cruz) was intraperitoneally administered bi-daily for three consecutive days. Cerulein was administered in 8 hourly doses of 200 µl (10 µg/ml) intraperitoneally for 48 hours and C57Bl/6J mice were allowed to recover for 24 or 72 hours. Blood glucose levels were measured using the ACCU-CHECK Nano (Roche) on the 414 lateral saphenous vein.

Retroviral Production and Infection:

Ecotropic Phoenix cells (ATCC) were seeded at 4×10$^6$ cells per 10 cm tissue culture plate. 24 hours later, the cells were 70-80% confluent. One hour before transfection, the media was replaced with 10% FBS, 25 µm Chloroquin in DMEM. 10 µg of plasmid DNA in a total volume of 438 µl of water was added to 62 µl of CaCl$_2$). While adding the DNA/CaCl$_2$) mixture dropwise to 500 µl 2×HBS, air was bubbled simultaneously through the solution. The mixture was incubated at room temperature for 30 minutes. The solution was vortexed and then added dropwise to the tissue culture plates. 16 hours later, the media was replaced with 10% FBS supplemented DMEM. Viral supernatant was harvested at 24 and 48 hours and filtered (0.45 m). One volume of Retro-X concentrator (Clontech) was added to three volumes of viral supernatant and incubated at 4° C. overnight. After centrifugation at 1500×g for 45 minutes at 4° C., the virus pellet was resuspended with appropriate media for infection. For infection of monolayer cells, the virus was resuspended in 10% FBS supplemented DMEM containing 10 µg/ml polybrene. Selection was initiated 48 hours post-infection. For infection of organoids, the viral pellet was resuspended in organoid media containing 10 µg/ml polybrene and 10.5 µM Rho kinase inhibitor Y-27632 (Sigma). Organoid infections were performed following single cell dissociation using spinoculation at 600 RCF for 1 hour at room temperature (100,000-250,000 cells) followed by resuspension in Matrigel and propagation as organoids in the presence of 10.5 µM Rho kinase inhibitor Y-27632 (Sigma) for the first 72 hours. Two days after infection, organoids were treated with 1 mg/ml Geneticin (Life technologies) or blasticidin (10 µg/mL, final concentration) for selection.

Immunohistochemistry:

Formalin-fixed, paraffin-embedded blocks were sectioned and de-paraffinized. Antigen retrieval was performed in Citrate buffer for 6 minutes in a pressure cooker unless otherwise specified. Phospho-EGFR IHC was performed as described previously (Ardito C M, et al., Cancer Cell. 2012; 22(3):304-17) following 30 minutes of citrate buffer antigen retrieval Endogenous peroxidase was quenched in 3% Hydrogen Peroxide in TBS for 20 minutes at room temperature. The slides were then rinsed in tap water and transferred to the Cadenza system. Slides were blocked in 3% BSA in TBST for one hour at room temperature and incubated in primary antibody overnight. Slides were washed three times in TBST, then incubated in horse radish peroxidase-conjugated secondary antibody for one hour at room temperature. The slides were washed three times in TBST and disassembled from the Cadenza system. ImmPACT DAB (Vector) was incubated for 1-10 minutes followed by a water wash and incubation in Hematoxylin counterstain. The slides were then dehydrated and coverslipped in cytoseal 60.

Automated immunohistochemistry was performed on formalin-fixed, paraffin-embedded, 5-µm sections collected on Plus Slides (Fischer Scientific) and stored at room temperature. Prior to staining, slides were incubated for 1 hour at 60° C. convection oven. Chromogenic immunohistochemistry was performed on a Ventana Medical Systems Discovery XT platform with online deparaffinization using Ventana's reagents and detection kits unless otherwise noted and as previously described (Perez-Aso M, et al., FASEB J. 2016; 30(1):457-65). In brief, sections were deparaffinized in xylene (3 changes), rehydrated through graded alcohols (3 changes 100% ethanol, 3 changes 95% ethanol) and rinsed in distilled water. Heat induced epitope retrieval was performed in a 1200-Watt microwave oven at 100% power in 10 mM sodium citrate buffer, pH 6.0 for 20 minutes. Sections were allowed to cool for 30 minutes and then rinsed in distilled water. Endogenous peroxidase activity was blocked. Primary antibodies were diluted 1:1000-1:10000 in Tris buffered saline (25 mM Tris, 0.15 M NaCl) and incubated for 10 hours at room temperature. Secondary antibodies conjugated to horseradish peroxidase (Jackson ImmunoResearch Laboratories) were diluted 1:200 in Tris buffer and incubated for 1 hour at 37° C. The complex was visualized with 3.3 diaminobenzidene and enhanced with copper sulfate. Slides were washed in distilled water, counterstained with hematoxylin, dehydrated and mounted with permanent media. Negative controls substituted antibody diluent alone for primary antibody.

Histologic Quantification:

Slides were scanned using an Aperio CS2 scanner (Leica) and the total occupied pixel area was calculated in Imagescope (Leica). Affected pancreatitis areas on H&E stained slides were manually annotated and the uninvolved and affected areas were measured. Pancreatitis areas were defined by the presence of infiltrating lymphocytes, acinar intralobular swelling, acinar to ductal metaplasia, fibrosis and fat cell replacement. The number of Ki67-positive nuclei were counted manually in five representative highpowered fields from least four animals per group.

Serologic Measurements:

Amylase and Lipase levels in plasma (lithium heparin, BD biosciences) was measured by IDEXX Pathology services. CA19-9 levels were measured using the human cancer biomarker assay (EMD Millipore) on the MagPIX multiplex ELISA platform (Luminex). Blood glucose levels were measured using an Accu-Chek Nano monitor (Roche) on the lateral saphenous vein. Levels of CA19-9-directed antibodies were measured by coating high binding polystyrene flat bottom plates with 275 units of CA19-9 (MyBioSource, MBS318287) overnight at room temperature. The CA19-9 coated plates were washed in 0.05% Tween 20 in PBS and blocked in 1% BSA in wash buffer before incubation 10 µl of mouse plasma in a final volume of 100 µl of blocking buffer Fecal Measurements:

Fresh fecal samples were collected and processed using manual disruption (Biomasher II) in each respective assay buffer. The Chymotrypsin (BioVision) and Elastase (EnzChek, ThermoFisher) measurements were performed according to manufacturer's instructions.

Organoids, Acinar Explant, Monolayer Cell Lines, and Culture Conditions:

Detailed procedures for the isolation and propagation of pancreatic ductal organoids cultures have been previously described (Boj Sylvia F, et al., Cell. 2015; 160(1-2):324-38). Briefly, ducts from pancreata were harvested after enzymatic digestion with 0.012% collagenase XI (Sigma) and 0.12% dispase (GIBCO) in DMEM containing 1% FBS (GIBCO), and embedded in 100% growth factor-reduced (GFR) Matrigel (BD). Organoids were treated with a final concentration of 100 ng-1 µg/ml Doxycycline. When necessary (e.g. growth curves), organoids were dissociated into a single cell suspension using 2 mg/ml dispase followed by 10 min TrypLE incubation at 37° C. Cells were filtered with a 40 µm cell strainer. Cell concentration was determined using Acridine Orange and Propidium Iodide on a Nexcelom Cellometer. Organoid single cells were plated in 384-well plates at 500 cells per well in 10% Matrigel for growth curve analyses using CellTiter-Glo. Antibody blocking experiments were performed using 2-4 µg of antibody.

Acinar explants were performed on minced pancreatic tissue following a brief digestion of 5-10 minutes in Advanced DMEM/F12 (GIBCO) containing 5 mg/ml Collagenase II (GIBCO), 1 mg/ml dispase (GIBCO), 2.50%

FBS (GIBCO), and 1 mg/ml Soybean Trypsin Inhibitor (GIBCO). Acinar clusters were monitored every 3-5 minutes while digesting at 37° C. until the acinar clumps reached cluster sizes of approximately 20-200 cells. Acinar clusters were washed once and then plated in Advanced DMEM/F12 (GIBCO) containing 1× Glutamax (GIBCO), 1× Penicilllin/Streptomycin (P/S, GIBCO), 1× HEPES (GIBCO), 3× NEAA (GIBCO) and 0.1% BSA (Sigma-Aldrich).

Monolayer cell lines from mouse pancreatic tumors were created by dissecting the primary tumor away from adjacent normal pancreata and manually minced into ~1 mm$^3$ fragments. Minced tissue was enzymatically digested in 100 mg/ml Collagenase V for 45 minutes at 37° C. while rotating. The digestion was quenched with 10% FBS, P/S in DMEM and the digested material was centrifuged at 300 RCF for 5 minutes. The supernatant was discarded and the digested material resuspended in 10% FBS, P/S, DMEM and plated on a 10 cm tissue culture plate for cryopreservation and propagation. Human pancreatic cancer cell lines, Capan2, Suit2, Miapaca2 (ATCC), and hM1-2D were propagated in 10% FBS, P/S in RPMI (GIBCO).

Single Cell Suspension of Primary Mouse Tissues for Flow Cytometry:

Spleens and lymph nodes were mechanically dissociated, homogenized, and passed through a nylon cell strainer (BD Falcon) in FACS buffer (eBioscience). Pancreas were mechanically dissociated and digested with 0.4 mg/mL liberase, 0.05 mg/mL collagenase D, and 0.1 mg/mL DNase I (Roche) in DMEM (Gibco) supplemented with 10% FCS at 37° C. for 30 min and suspensions were passed through a nylon cell strainer.

Flow Cytometric Analyses:

Staining was performed by incubating cells on a plate shaker, for 15 min at 4° C., with antibodies in in FACS buffer (eBioscience). Multicolor flow cytometric analyses were performed using a LSR Fortessa cytometer (BD Biosciences). Gating strategies for all flow cytometric experiments are further described below.

Western Blotting:

Standard techniques were employed for immunoblotting. In brief, protein lysates were separated on 4-12% Bis-Tris NuPAGE gels (Life technologies), transferred to PVDF membrane (Millipore), and blocked in 3% BSA (Sigma) in 0.1% Tween20 in TBS for one hour. The membranes were then incubated in primary antibody overnight with rocking at 4° C. followed by incubation in appropriate secondary antibodies conjugated to horse radish peroxidase for one hour and detection by ECL (GE Healthcare). The normalized changes to the indicated protein targets were quantified relative to the loading control Cofilin and the untreated time point.

Protein Isolation from Cell Lines:

Tissue culture plates were washed three times with ice cold PBS and lysed on the plate in 1% Triton X-100, 50 mM Tris-HCl pH 7.5, 150 mM NaCl, 5 mM EDTA with 1× protease and phosphatase inhibitor cocktails on ice for 30 minutes. The lysate was transferred to a micro-centrifuge tube and clarified at 16100 RCF for 10 minutes at 4° C., and aliquoted into new tubes for storage at −20° C.

Protein Isolation from Organoids:

Liquid overlay media was aspirated from organoids and ice-cold Cell Recovery Solution (Corning) containing 0.5× complete mini protease inhibitor cocktail (Roche, EDTA-free) and 0.5× PhosSTOP (Roche). The organoids were incubated in CRS with 0.5× protease and phosphatase inhibitors on ice for 10 minutes followed by centrifugation at 1500 RCF for 5 minutes at 4° C. The supernatant was discarded and the organoids were washed once in CRS with 0.5× protease and phosphatase inhibitors. Organoid pellets were snap frozen in liquid nitrogen and stored at −80° C. Organoids were lysed in 1% Triton X-100, 50 mM Tris-HCl pH 7.5, 150 mM NaCl, 5 mM EDTA with 1× protease and phosphatase inhibitor cocktails on ice for 30 minutes, clarified at 16100 RCF for 10 minutes at 4° C., and aliquoted into new tubes for storage at −20° C.

Immunoprecipitation:

CA19-9 immunoprecipitation was performed in IP buffer containing 20 mM HEPES, 150 mM NaCl in the presence of 0.5× complete mini protease inhibitor cocktail (Roche, EDTA-free). Monoclonal antibodies were conjugated to M-270 Epoxy Dynabeads (Thermo Fisher) according to manufacturer's instructions. 100 μl of mAb-conjugated Dynabeads were washed 3 times in IP buffer and incubated with 500 μg whole cell lysates from monolayer cell lines in 1 ml of IP buffer in a 1.5 ml LoBind micro-centrifuge tube (Eppendorf) or with 4 ml of organoid conditioned media in a 5.0 ml LoBind tube (Eppendorf) while rotating at 4° C. for one hour. The samples were allowed to bind to the magnet for one minute before the supernatant was removed and the beads were washed three times in IP buffer.

Flag immunoprecipitation was performed in TBS (50 mM Tris, pH7.6; 150 mM NaCl) using 5 ml of conditioned media, 10 μg of Rabbit anti-Flag antibody (Sigma) and Protein G conjugated Dynabeads (ThermoFisher) according to manufacturer's instructions. Immunoprecipitated proteins were eluted on ice using DYK peptide (100 μg/ml) with gentle shaking for 1 hour or ice-cold, amine-based, low pH IgG Elution buffer (ThermoFisher) and quenched with 10×TBS.

EGFR immunoprecipitation was performed in 1% Triton X-100, 150 mM NaCl, and 50 mM Tris, pH7.5.

RNA Isolation, cDNA Synthesis and Quantitative RT-PCR from Organoids:

RNA was extracted from cell and organoid cultures using Trizol and the PureLink RNA isolation kit according to the manufacturer's instructions (Thermo Fisher). cDNA was synthesized using 1 μg of total RNA and TaqMan Reverse Transcription Reagents (Applied Biosystems). All targets were amplified (40 cycles) using gene-specific Taqman primers and probe sets (Applied Biosystems) on a QuantStudio 6-flex Real time-PCR instrument (Applied Biosystems). Relative gene expression quantification was performed using the DDCt method with the QuantStudio Real-Time PCR software v1.1 (Applied Biosystems). Expression levels were normalized to Hprt. Exemplary gene analyzed includ: Mm01187858_m1 (EGFR); Mm00658541_m1 (Her2); Mm01159999_m1 (Erbb3); MmO1256793_m1 (Erbb4); Mm00438696_m1 (EGF); Mm00446232_m1 (TGFa); Mm01354339_m1 (Areg); Mm00514794_m1 (Ereg); Mm00446968_m1 (Hprt).

RNA Sequencing and Analysis

RNA sequencing was performed at the Judith Sulzberger Columbia Genome Center with 60× coverage and 100 bp paired end reads on an Illumina HiSeq 2500 instrument. Kallisto 0.44 (Bray, N. L., et al., Nat Biotechnol 34, 525-527 (2016), which is hereby incorporated in its entirety by reference) quantified transcript abundances using the Ensembl GRCh38 mouse transcriptome, combined with cDNA for p3GALT5 (ENST00000380620.8, ENST00000475838.1, ENST00000380618.5, ENST00000398714.3, ENST00000615480.4, ENST00000615480.4), FUT3 (ENST00000458379.6, ENST00000458379.6, ENST00000303225.10, ENST00000589620.5, ENST00000589620.5, ENST00000587048.1, ENST00000587048.1, ENST00000585715.1, ENST00000587183.1, ENST00000588539.1), eGFP (pBS31'-RBGpA\TRE), rtTA3 (pRosa-pA-CAGGs-L), and mKate2 (Akama-Garren, E. H. et al. Sci Rep 6, 16836, (2016), which is hereby incorporated in its entirety by reference).

Transcript-level abundances were summarized at the gene level using tximport 1.8 (R/Bioconductor (Soneson, C., et al., F1000Research 4, 1036 (2015), which is hereby incorporated in its entirety by reference)). DESeq2 1.2 (R/Bioconductor (Love, M. I., et al., Genome Biol 15, 550, (2014), which is hereby incorporated in its entirety by reference)) performed differential expression on gene-level counts with the following timepoint and condition contrasts: 4 h genetic negative organoids vs 0 h genetic negative organoids, 24 h genetic negative organoids vs 0 h genetic negative organoids, 24 h genetic negative organoids vs 4 h genetic negative organoids, 4 h $C^{PDX};R^{LSL};F$ organoids vs 0 h $C^{PDX};R^{LSL};F$ organoids, 24 h $C^{PDX};R^{LSL};F$ organoids vs 0 h $C^{PDX};R^{LSL};F$ organoids, and 24 h $C^{PDX};R^{LSL};F$ organoids vs 4 h $C^{PDX};R^{LSL};F$ organoids. The reporter gene eGFP and human transgenes β3GALT5 and FUT3 were excluded to avoid biasing differential expression analyses (which pool information across genes). The genes Oprd1 and Gstm5 were identified as outliers due to their extreme differential expression and were also excluded.

Genes were ranked using −log 10(q-value)*sign(log 2FoldChange), where q-value is a p-value corrected for multiple testing (Benjamini & Hochberg method). Gene set enrichment was performed on the 24 h treated vs 0 h treated ranked gene list using GSEA 3.0 (Subramanian, A. et al. Proc Natl Acad Sci USA 102, 15545-15550, (2005), which is hereby incorporated in its entirety by reference) with the following MSigDB 6.1 databases: C2 KEGG, C5, C6, and H. GSEA used the following non-default parameters: -nperm 2000, -set_min 10, -set_max 1000. Genes differentially expressed in the 24 h genetic negative organoids vs 0 h genetic negative organoids contrast were removed from the ranked list of genes before running GSEA.

For visualizations, raw counts were normalized to control for library size and dispersion-mean relationships using the variance Stabilizing Transformation function of DESeq2

Tryptic Digestion and iTRAQ Labeling:

The beads were reconstituted with 20 µL of 50 mM triethylammonium bicarbonate buffer (TEAB). RapiGest was added to a final concentration of 0.1% and tris(2-carboxyethyl)phosphine (TCEP) was added to final concentration of 5 mM. Samples were then heated to 55° C. for 20 min, allowed to cool to room temperature and methyl methanethiosulfonate (MMTS) added to a final concentration of 10 mM. Samples were incubated at room temperature for 20 min to complete blocking of free sulfhydryl groups. 2 µg of sequencing grade trypsin (Promega) was then added to the samples and they were digested overnight at 37° C. After digestion, the supernatant was removed from the beads and was dried in vacuo. Peptides were reconstituted in 50 µL of 0.5M TEAB/70% ethanol and labeled with 8-plex iTRAQ reagent for 1 hour at room temperature (Ross P L, et al., Mol Cell Proteomics. 2004; 3(12):1154-69). Labeled samples were then acidified to pH 4 using formic acid, combined and concentrated in vacuo until ~10 µL remained.

2-Dimensional Fractionation Using Spin Columns:

Peptides were fractionated using a Pierce High pH Reversed-Phase Peptide Fractionation Kit (Thermo Scientific) according to the manufacturer's instructions with slight modifications. Briefly, peptides were reconstituted in 150 µL of 0.1% TFA, loaded onto the spin column and centrifuged at 3000 g for 2 minutes. Column was washed with water and then peptides were eluted with the following percentages of acetonitrile (ACN) in 0.1% triethylalmine (TEA): 5%, 7.5%, 10%, 12.5%, 15%, 20%, 30% and 50%. Each of the 8 fractions was then separately injected into the mass spectrometer using capillary reverse phase LC at low pH.

2-Dimensional Fractionation by LC:

Peptides were fractionated using a high-low pH reverse phase separation strategy (adapted from Gilar, M., et al., Journal of separation science 28, 1694-1703 (2005), which is hereby incorporated in its entirety by reference). For the first (high pH) dimension, peptides were fractionated on a 10 cm×1.0 mm column packed with Gemini 3u C18 resin (Phenomenex, Ventura, CA) at a flow rate of 100 µl/min. Mobile phase A consisted of 20 mM ammonium formate pH 10 and mobile phase B consisted of 90% acetonitrile/20 mM ammonium formate pH 10. Samples were reconstituted with 50 µL of mobile phase A and the entire sample injected onto the column. Peptides were separated using a 35-minute linear gradient from 5% B to 70% B and then increasing mobile phase to 95% B for 10 minutes. Fractions were collected every minute for 40 minutes and were then combined into 8 fractions using the concatenation strategy described by Wang, Y. et al. Proteomics 11, 2019-2026 (2011) (which is hereby incorporated in its entirety by reference). Each of the 8 fractions was then separately injected into the mass spectrometer using capillary reverse phase LC at low pH.

Mass Spectrometry (Velos):

An Orbitrap Velos Pro mass spectrometer (Thermo Scientific), equipped with a nano-ion spray source was coupled to an EASY-nLC system (Thermo Scientific). The nano-flow LC system was configured with a 180-µm id fused silica capillary trap column containing 3 cm of Aqua 5-µm C18 material (Phenomenex), and a self-pack PicoFrit™ 100-µm analytical column with an 8-µm emitter (New Objective, Woburn, MA) packed to 15 cm with Aqua 3-µm C18 material (Phenomenex). Mobile phase A consisted of 2% acetonitrile; 0.1% formic acid and mobile phase B consisted of 90% acetonitrile; 0.1% formic Acid. 3 µL of each sample dissolved in mobile phase A, were injected through the autosampler onto the trap column. Peptides were then separated using the following linear gradient steps at a flow rate of 400 nL/min: 5% B for 1 min, 5% B to 35% B over 70 min, 35% B to 75% B over 15 min, held at 75% B for 8 min, 75% B to 8% B over 1 min and the final 5 min held at 8% B.

Eluted peptides were directly electrosprayed into the Orbitrap Velos Pro mass spectrometer with the application of a distal 2.3 kV spray voltage and a capillary temperature of 275° C. Each full-scan mass spectrum (Res=60,000; 380-1700 m/z) was followed by MS/MS spectra for the top 12 masses. High-energy collisional dissociation (HCD) was used with the normalized collision energy set to 35 for fragmentation, the isolation width set to 1.2 and activation time of 0.1. A duration of 70 seconds was set for the dynamic exclusion with an exclusion list size of 500, repeat count of 1 and exclusion mass width of 10 ppm. We used monoisotopic precursor selection for charge states 2+ and greater, and all data were acquired in profile mode.

Mass Spectrometry (Fusion):

An Orbitrap Fusion Lumos mass spectrometer (Thermo Scientific), equipped with a nano-ion spray source was coupled to an EASY-nLC 1200 system (Thermo Scientific). The LC system was configured with a self-pack PicoFrit™ 75-µm analytical column with an 8-µm emitter (New Objective, Woburn, MA) packed to 25 cm with ReproSil-Pur C18-AQ, 1.9 uM material (Dr. Maish GmbH). Mobile phase A consisted of 2% acetonitrile; 0.1% formic acid and mobile phase B consisted of 90% acetonitrile; 0.1% formic Acid. Peptides were then separated using the following steps: at a flow rate of 200 nL/min: 2% B to 6% B over 1 min, 6% B to 30% B over 84 min, 30% B to 60% B over 9 min, 60% B to 90% B over 1 min, held at 90% B for 5 min, 90% B to 50% B over 1 min and then flow rate was increased to 500 nL/min as 50% B was held for 9 min.

Eluted peptides were directly electrosprayed into the Fusion Lumos mass spectrometer with the application of a distal 2.3 kV spray voltage and a capillary temperature of 300° C. Full-scan mass spectrum (Res=60,000; 400-1600 m/z) were followed by MS/MS using the "Top Speed" method for selection. High-energy collisional dissociation (HCD) was used with the normalized collision energy set to 35 for fragmentation, the isolation width set to 1.2 and a duration of 10 seconds was set for the dynamic exclusion with an exclusion mass width of 10 ppm. We used monoisotopic precursor selection for charge states 2+ and greater, and all data were acquired in profile mode.

Database Searching:

Peaklist (.MGF) files were generated by Mascot Distiller 2.6 (Matrix Science). Protein identification and quantification was carried using Mascot 2.6 (Perkins, D. N. et al., Electrophoresis 20, 3551-3567 (1999), which is hereby incorporated in its entirety by reference) searching against the UniProt mouse or human reference proteomes (60,725 and 93,799 sequences respectively). Methylthiolation of cysteine and N-terminal and lysine iTRAQ modifications were set as fixed modifications, methionine oxidation and deamidation (NQ) as variable. Trypsin was used as cleavage enzyme with one missed cleavage allowed. Mass tolerance was set at 30 ppm for intact peptide mass and 0.3 Da for fragment ions. Search results were rescored to give a final 1% or 5% FDR using a randomized version of the same Uniprot human or mouse databases. Protein-level iTRAQ ratios were calculated as intensity weighted, using only peptides with expectation values <1% or 5% FDR. As these were protein IP experiments, no global ratio normalization was applied. Protein enrichment was then calculated by dividing the true sample protein ratios by the corresponding control sample ratios with a value of 1.8 used as a cutoff for enrichment (>2 SD).

Figure 1A:
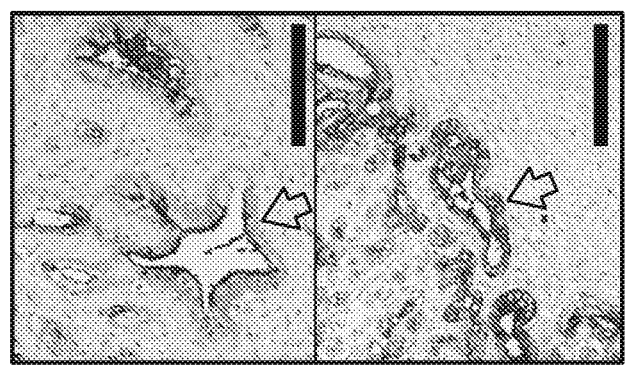
Figure 1A:
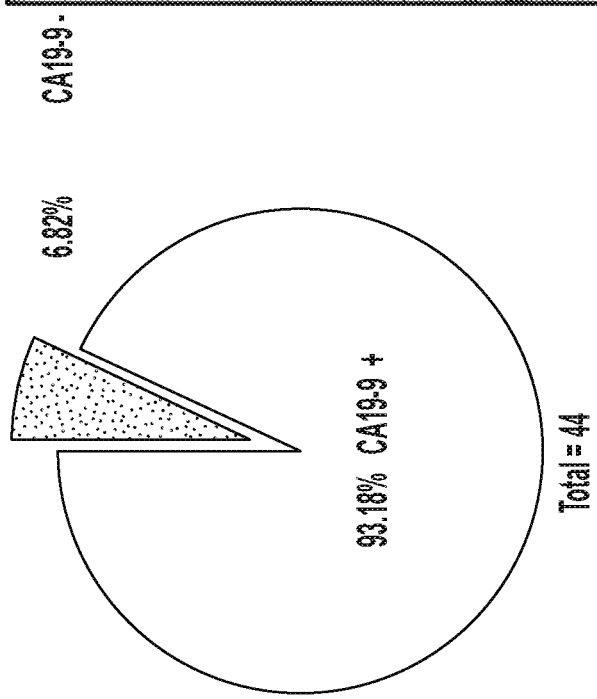
Figure 1B:
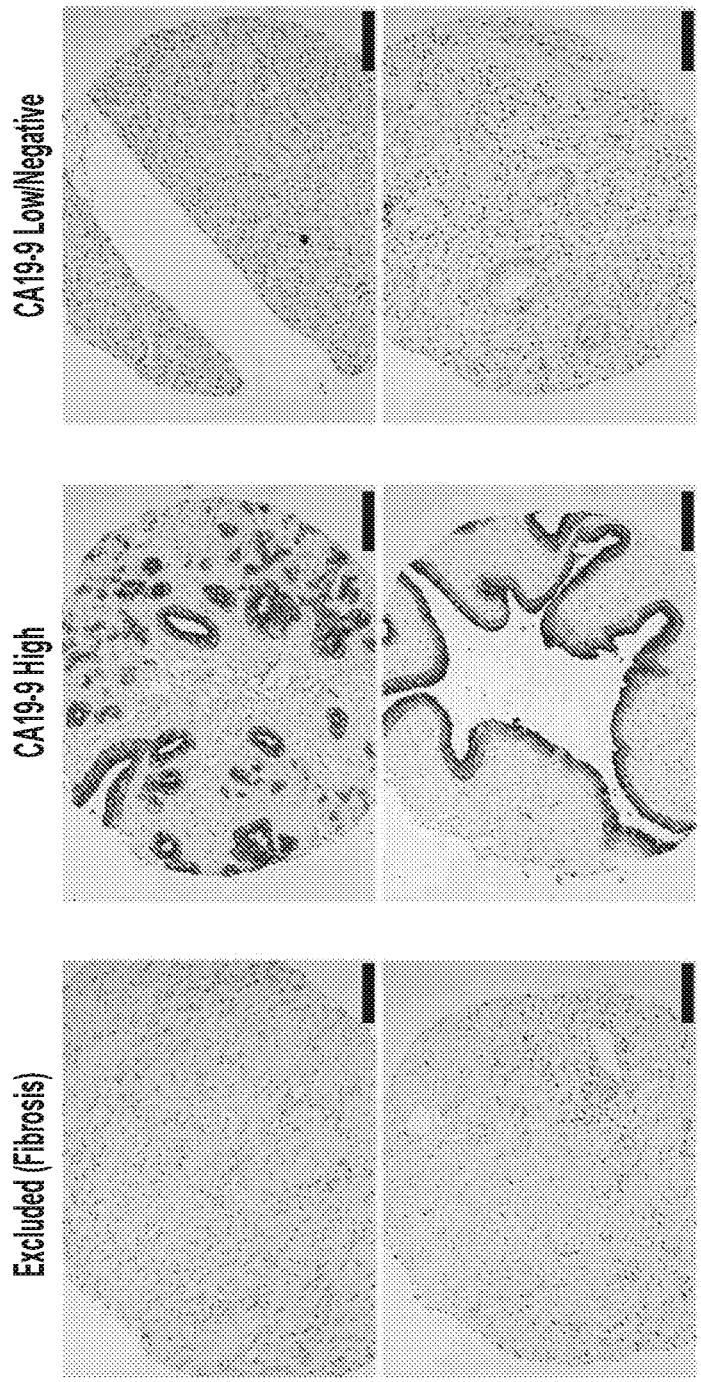
Figure 1C:
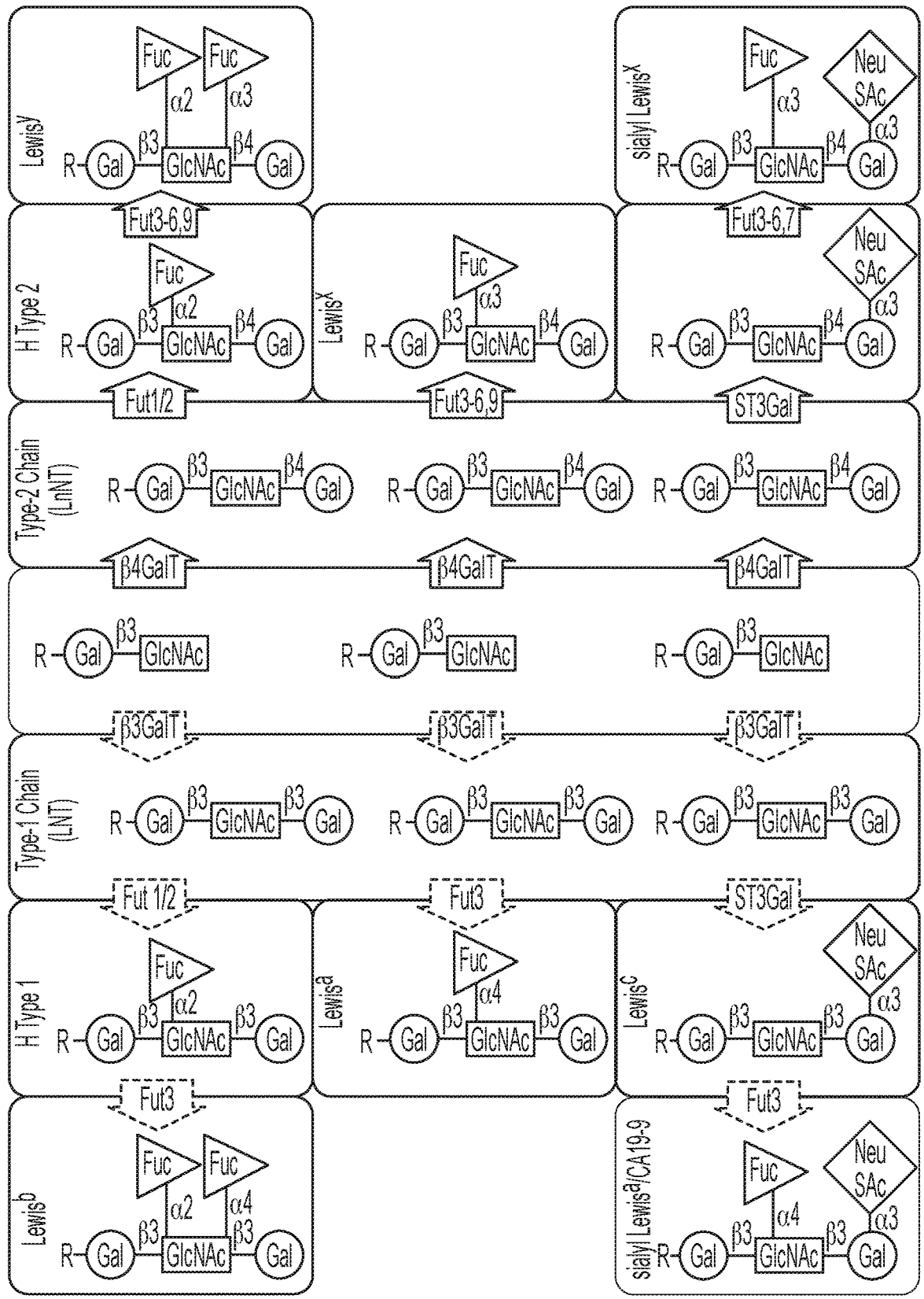
Figure 1:
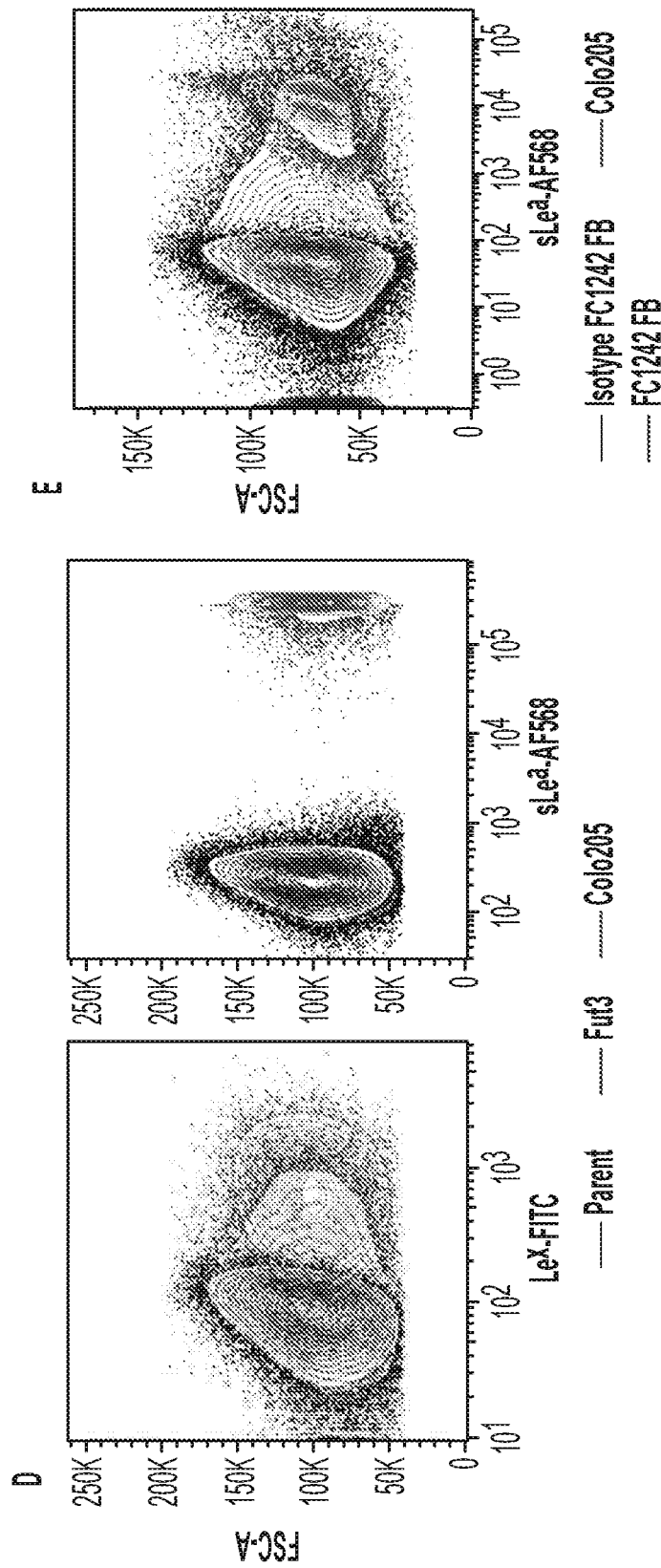
Figure 1:
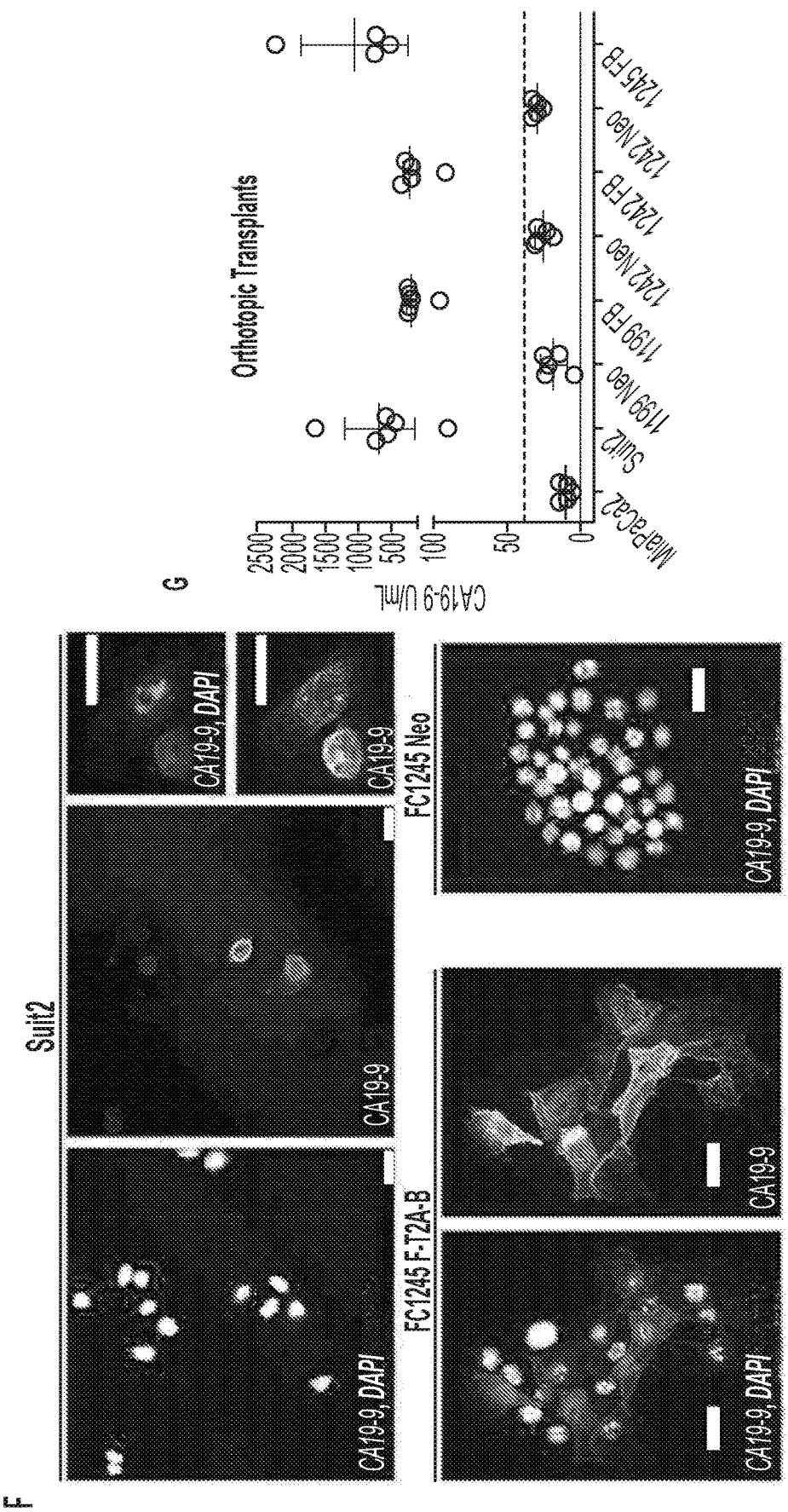

CA19-9 Expression is Elevated in Pancreatitis Patients:

Pancreatitis is a severe and common medical condition that can lead to death or a chronic condition with significant morbidity, systemic inflammatory response and multiple organ dysfunction syndromes. Pancreatitis is also associated with a 16.5-fold elevated risk for developing pancreatic cancer (Lowenfels, A. B. et al. N Engl J Med 328, 1433-1437 (1993), which is hereby incorporated in its entirety by reference), clearly indicating that further study into the etiology and treatment of pancreatitis is needed. Glycosylation changes, including the elevation of CA19-9, have been noted in the serum of some pancreatitis patients (10-30%), but no role has been ascribed to this glycan epitope in disease progression (Haglund, C. et al., Br J Cancer 53, 189-195 (1986); Makovitzky, J. Virchows Archiv. B, Cell pathology including molecular pathology 51, 535-544 (1986); both of which are hereby incorporated in their entirety by reference). We assessed a tissue microarray (TMA) of resected pancreatitis specimens and found that CA19-9 was predominantly expressed in the ductal, but not acinar epithelial cells in over 90% of patients (FIG. 1A, 1B), demonstrating its prominent presence in this disease. CA19-9 is generated by the stepwise addition of different sugar moieties to Type 1 precursor chains, culminating in the α1,4 linkage of fucose to N-Acetylglucosamine (GlcNAc) (FIG. 1C) and can be multivalently added to secreted and cell surface proteins. Evaluation of the functional significance of CA19-9 in mice has been hampered by their lack of Fut3, which is a pseudogene in rodents (Xia, B. et al., Anal Biochem 387, 162-170 (2009); Narimatsu, H. in Handbook of Glycosyltransferases and Related Genes (eds Naoyuki Taniguchi et al.) 218-225 (Springer Japan, 2002); both of which are hereby incorporated in their entirety by reference). Fut3 is the only fucosyltransferase with the ability to add fucose moieties through an α1,4 linkage. We found that the expression of both FUT3 and β3GALT5, which is required for the production of Type I chain precursors (Ishijima, N. et al. J Biol Chem 286, 25256-25264 (2011), which is hereby incorporated in its entirety by reference), was necessary for the production of CA19-9 (Sialyl-Lewis$^a$, SLe$^a$) in cultures of mouse pancreatic ductal adenocarcinoma (PDAC) cells (FIG. 1C-E). The expression of both FUT3 and β3GALT5 led to the cell surface expression of CA19-9 at levels equivalent to those observed in a human cancer cell line (Colo205) (FIG. 1E). To confirm that the CA19-9 epitope was expressed in an appropriate manner in the engineered mouse PDAC cells, they were compared to human PDAC cell lines and found to also exhibit the expected membrane localization in culture (FIG. 1F). Furthermore, CA19-9 conjugated proteins were secreted in vivo following orthotopic transplantation, demonstrating CA19-9 production at levels comparable to human PDAC cell line transplant recipients (FIG. 1G).

Figure 2:
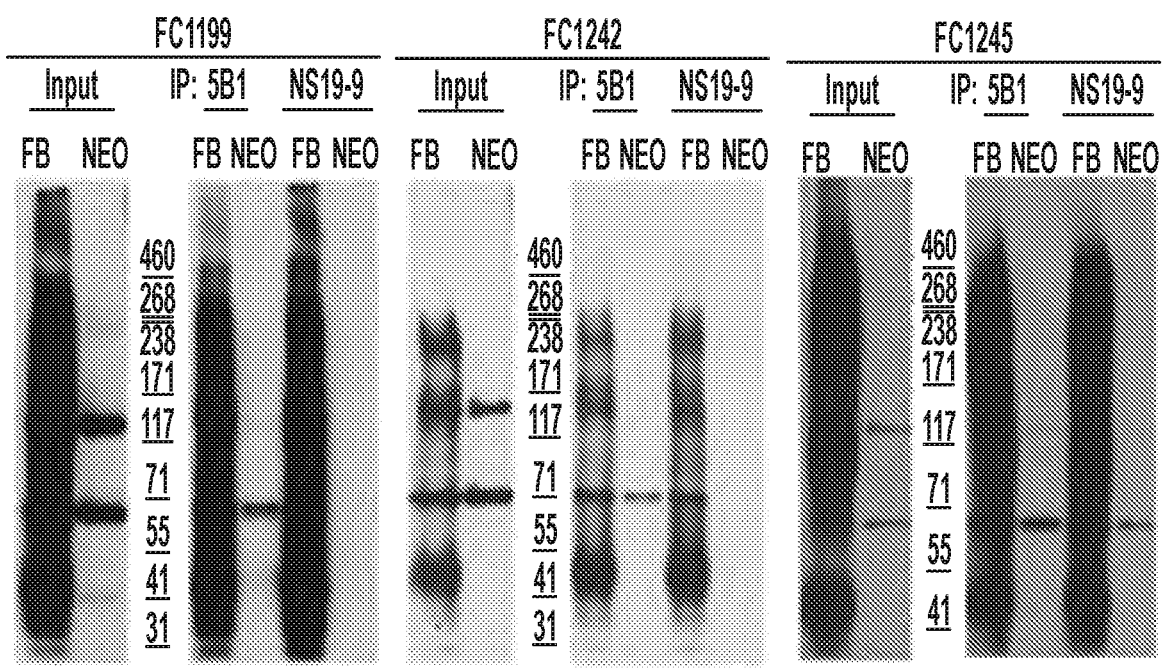
Figure 2:
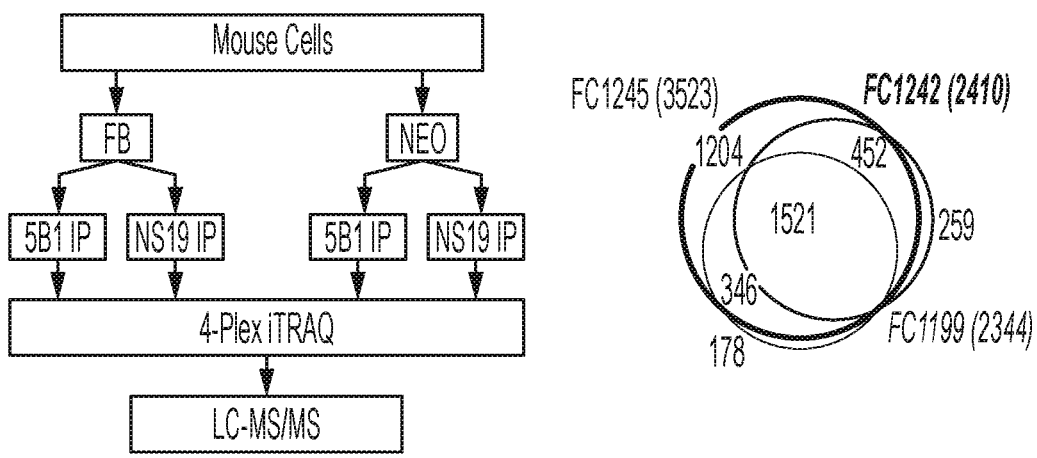
Figure 2:
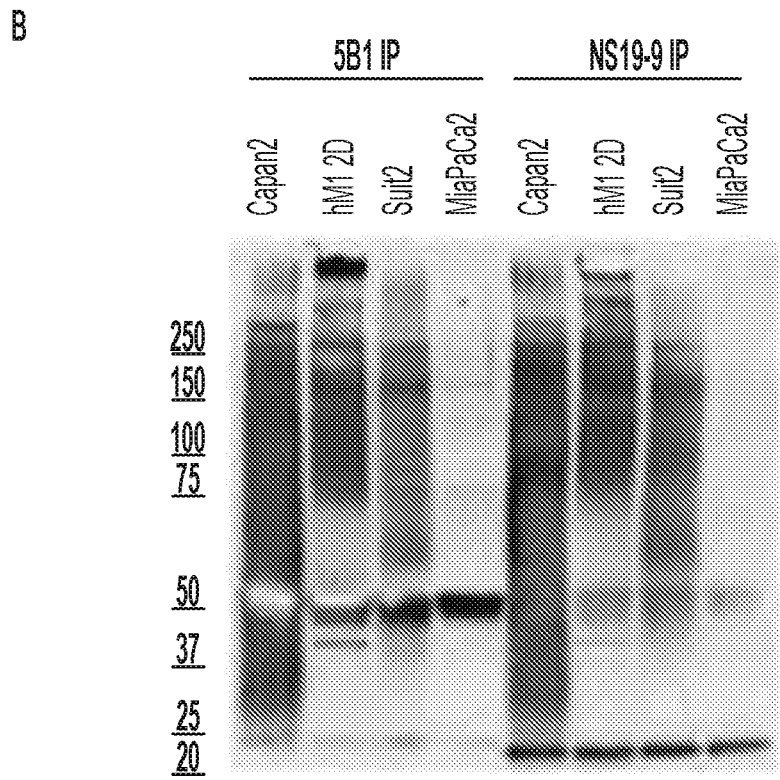
Figure 2:
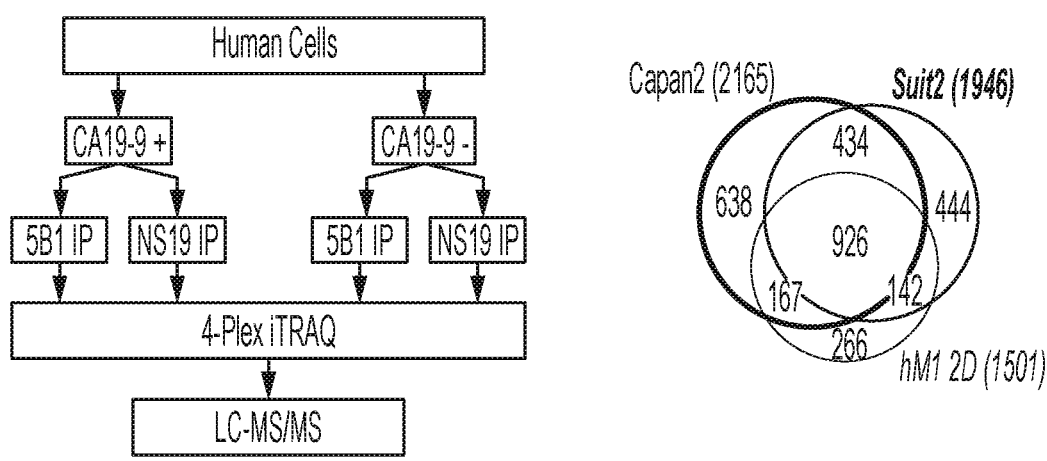
Figure 2C:
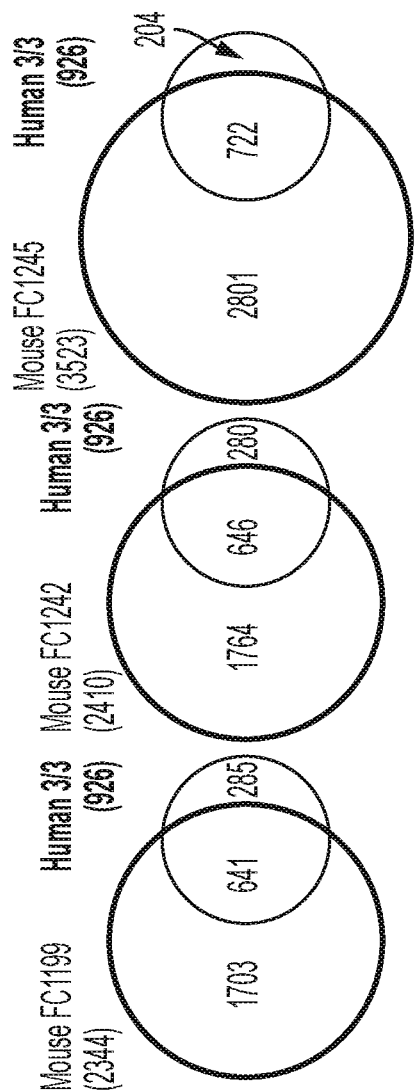
Figure 3:
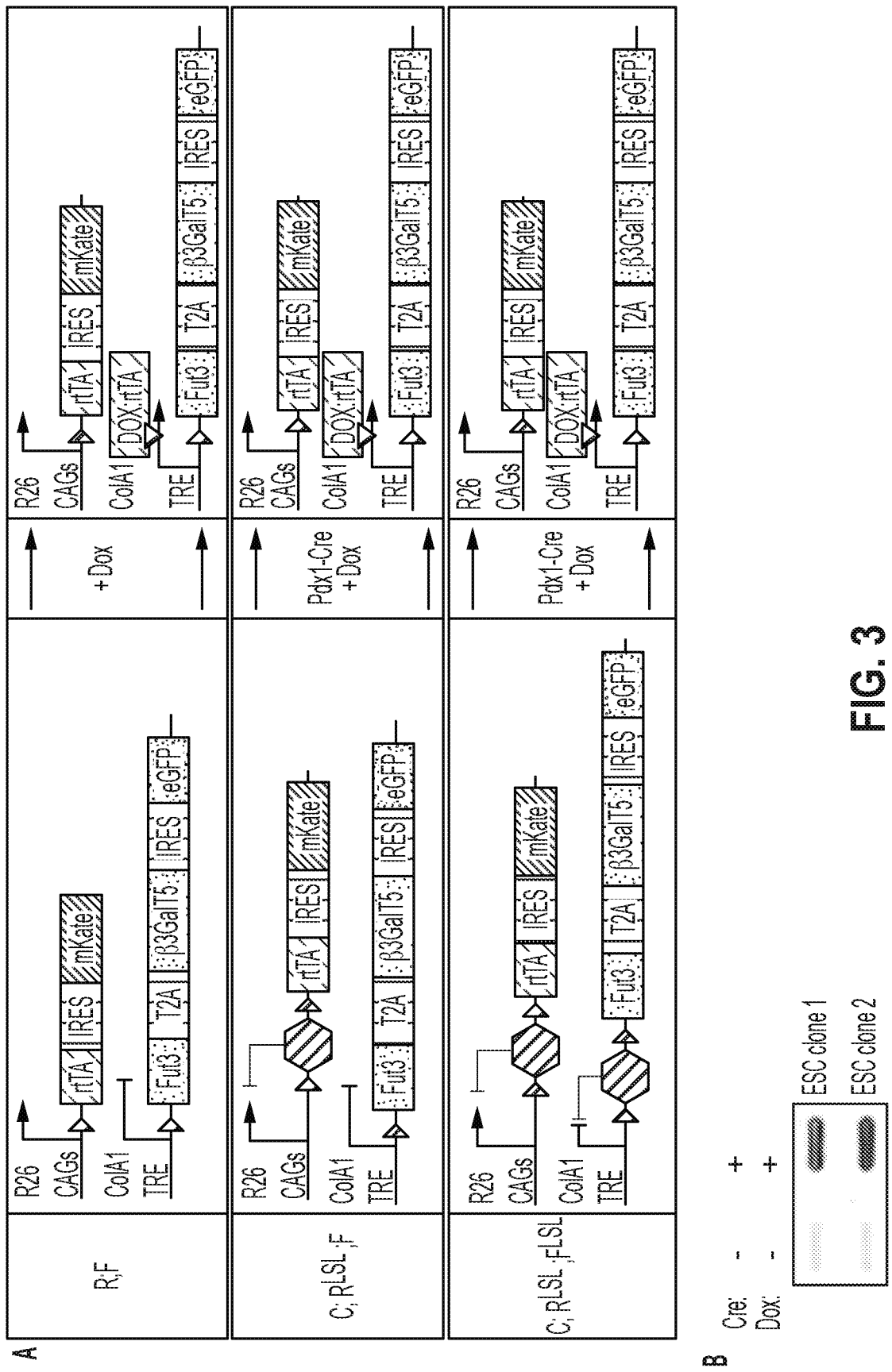
Figure 3:
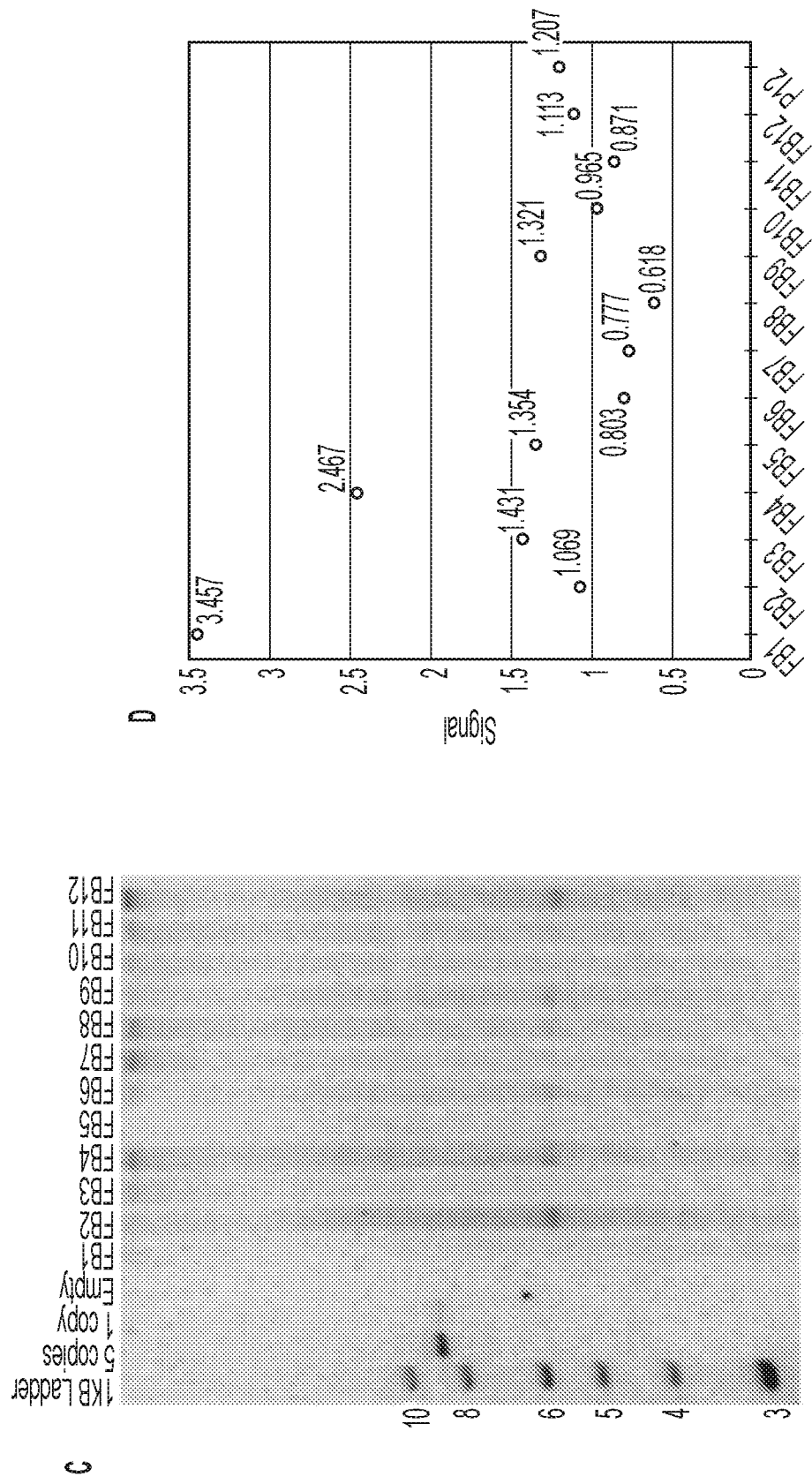
Figure 4:
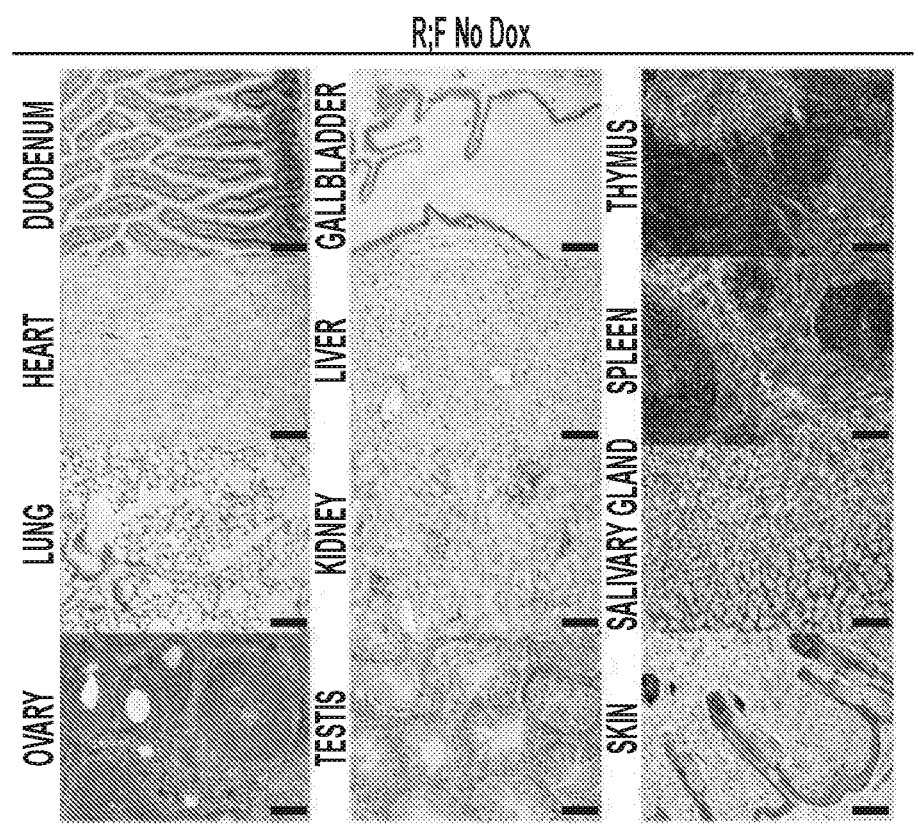
FIG. 4 shows whole body CA19-9 mouse model, whole body histology in haematoxylin and eosin (H&E) histological evaluation of mouse tissues from untreated R;F mice. Scale bars=100 µm.
Figure 5:
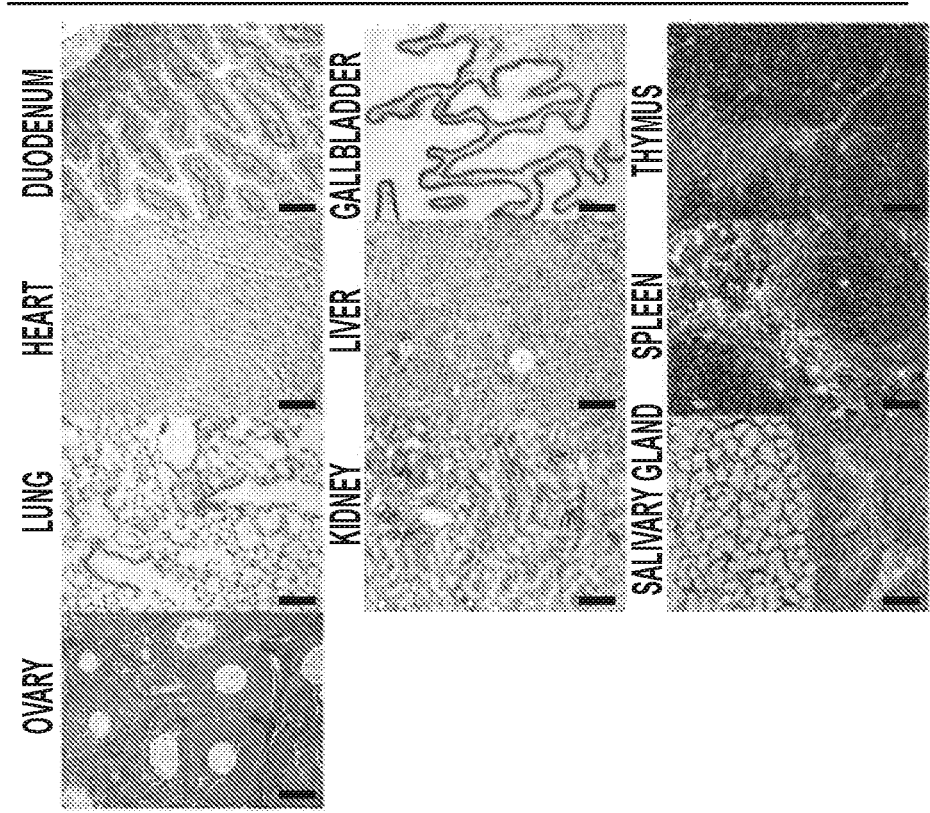
FIG. 5 shows whole body CA19-9 mouse model, whole body histology in H&E histological evaluation of mouse tissues from R;F mice treated with Dox for 7 days. Scale bars=100 µm.
Figure 6:
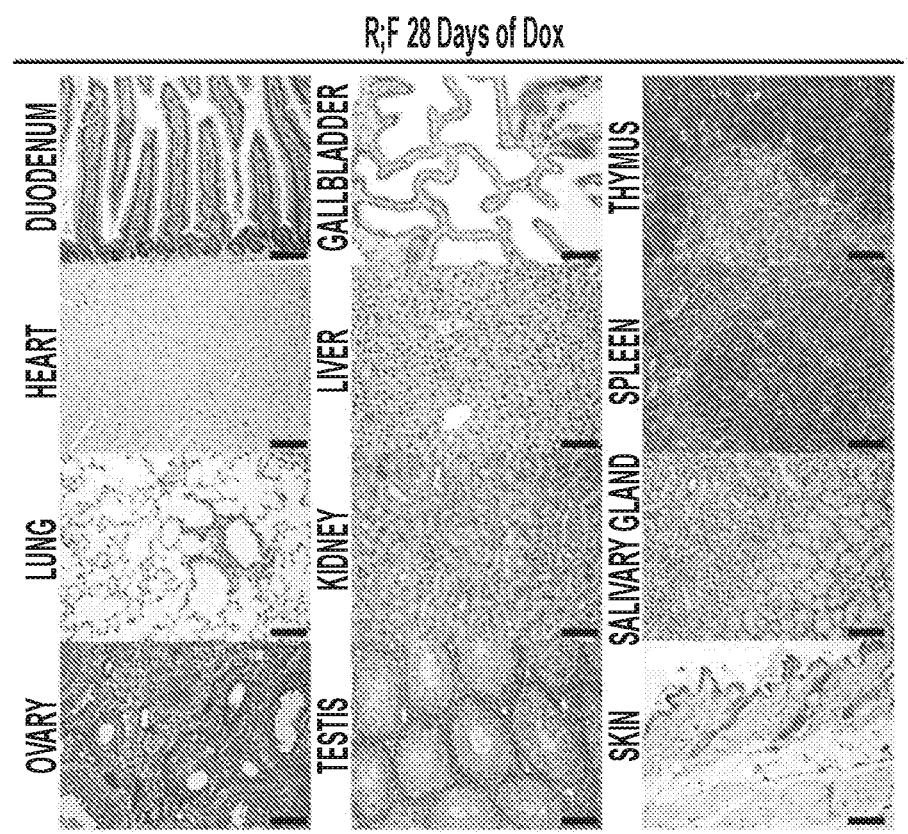
FIG. 6 shows whole body CA19-9 mouse model, whole body histology in H&E histological evaluation of mouse tissues from R;F mice treated with Dox for 28 days. Scale bars=100 µm.
Figure 7:
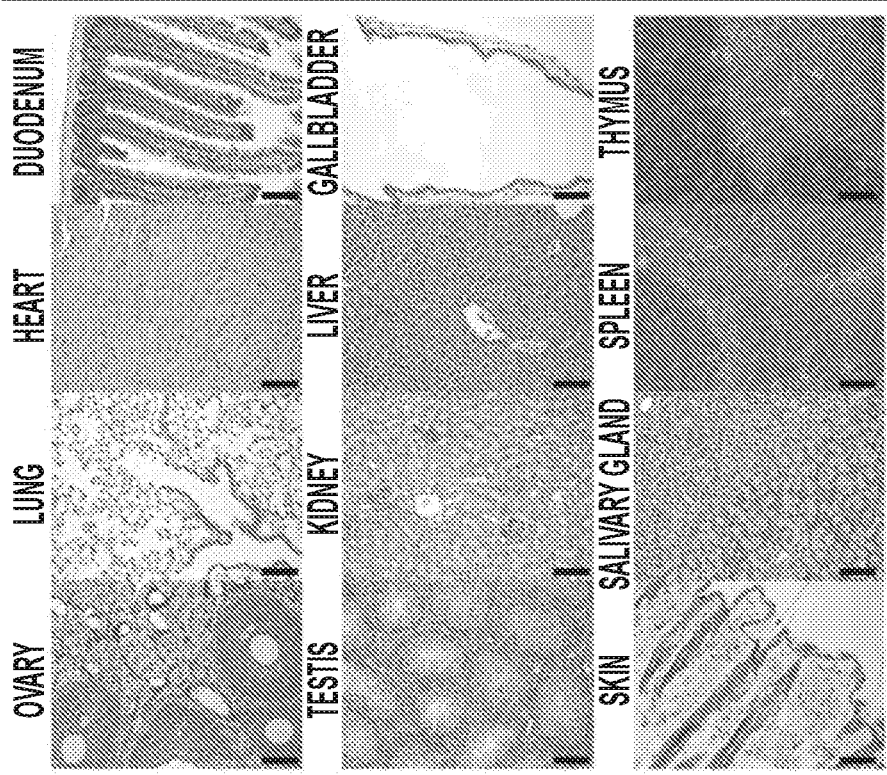
FIG. 7 shows whole body CA19-9 mouse model genetic negative control littermates, whole body histology in H&E histological evaluation of mouse tissues from untreated R;F genetically negative control littermates. Scale bars=100 µm.
Figure 8:
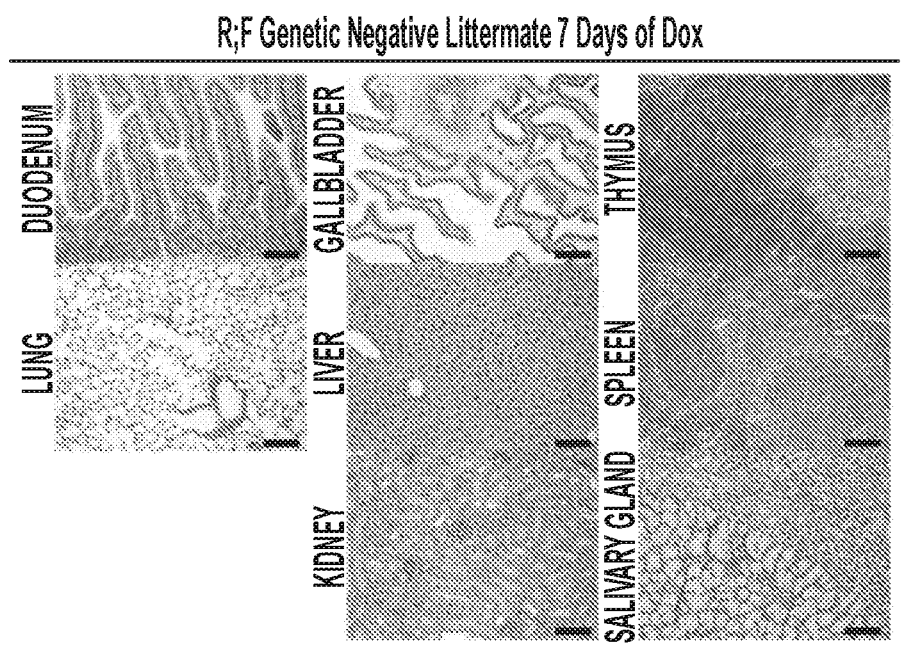
FIG. 8 shows whole body CA19-9 mouse model genetic negative control littermates, whole body histology in H&E histological evaluation of mouse tissues from R;F genetically negative control littermates treated with Dox for 7 days. Scale bars=100 µm.
Figure 9:
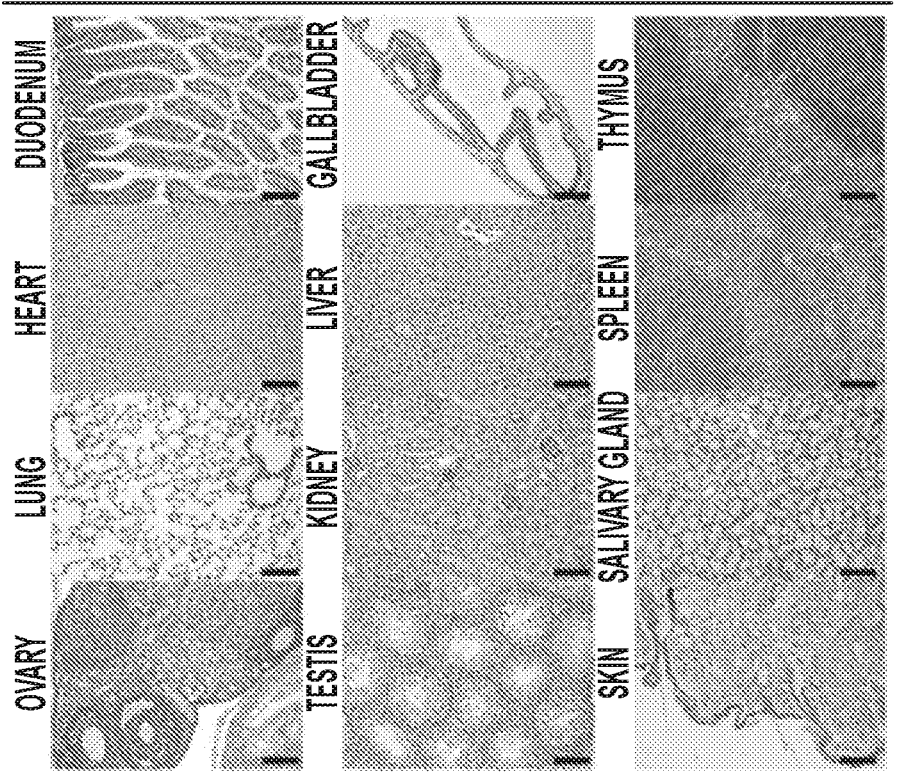
FIG. 9 shows whole body CA19-9 mouse model genetic negative control littermates, whole body histology in H&E histological evaluation of mouse tissues from R;F genetically negative control littermates treated with Dox for 28 days. Scale bars=100 µm.
Figure 10:
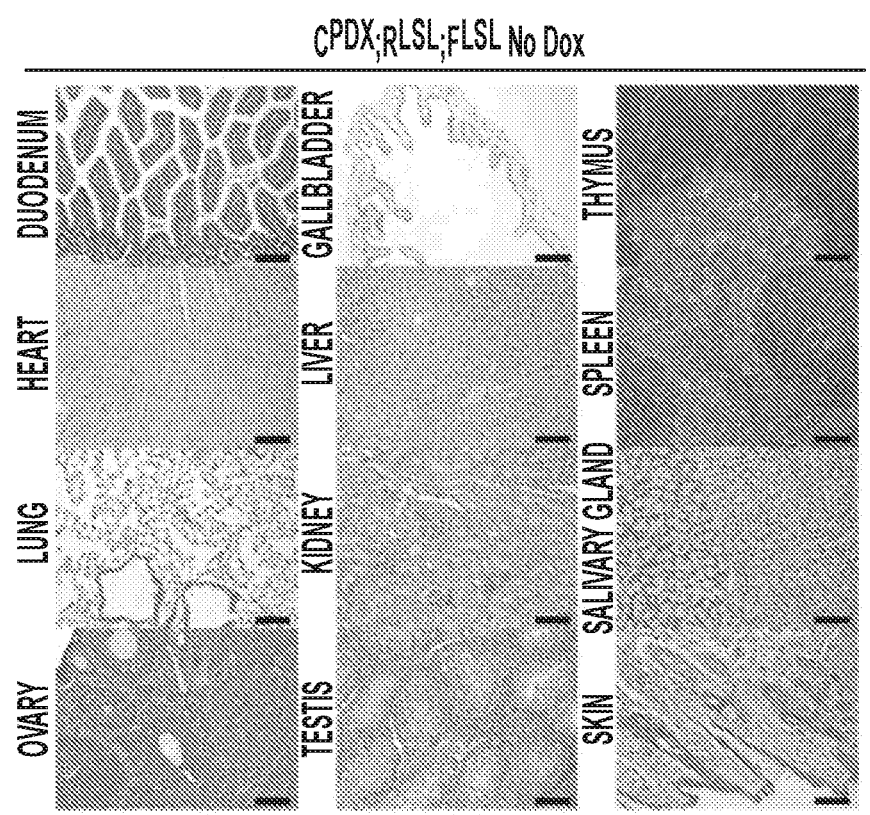
FIG. 10 shows focal pancreas, PDX1-Cre-driven CA19-9 mouse model, whole body histology in H&E histological evaluation of mouse tissues from untreated $C^{PDX};R^{LSL};F^{LSL}$ mice. Scale bars=100 µm.
Figure 11:
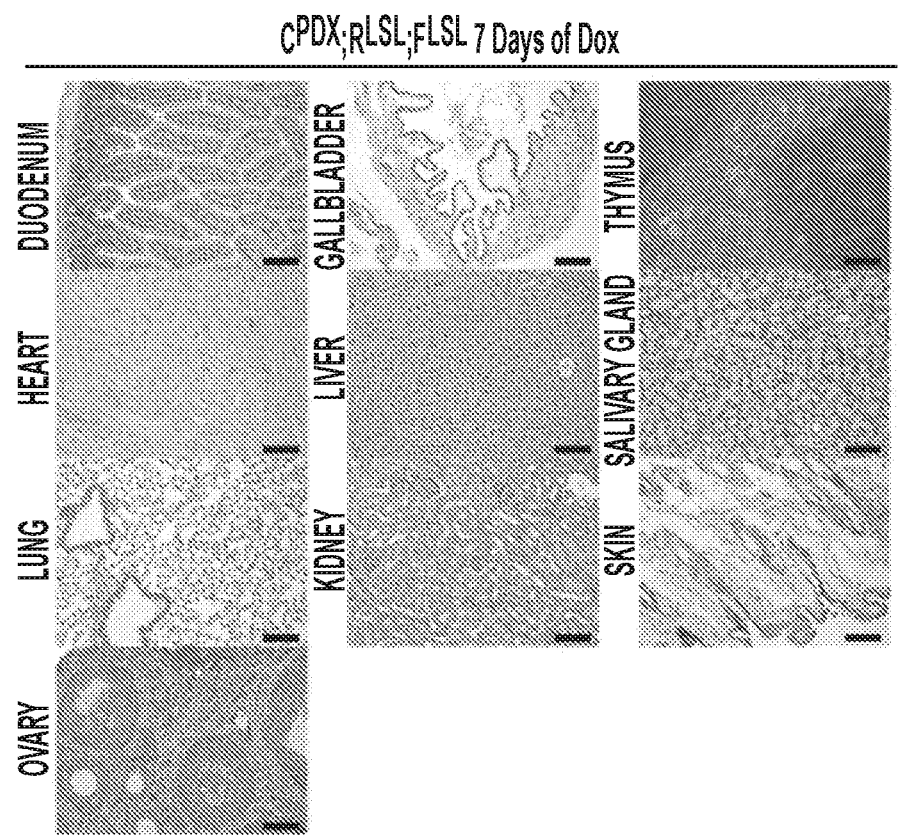
FIG. 11 shows focal pancreas, PDX1-Cre-driven CA19-9 mouse model, whole body histology in H&E histological evaluation of mouse tissues from $C^{PDX};R^{LSL};F^{LSL}$ mice treated with Dox for 7 days. Scale bars=100 µm.
Figure 12:
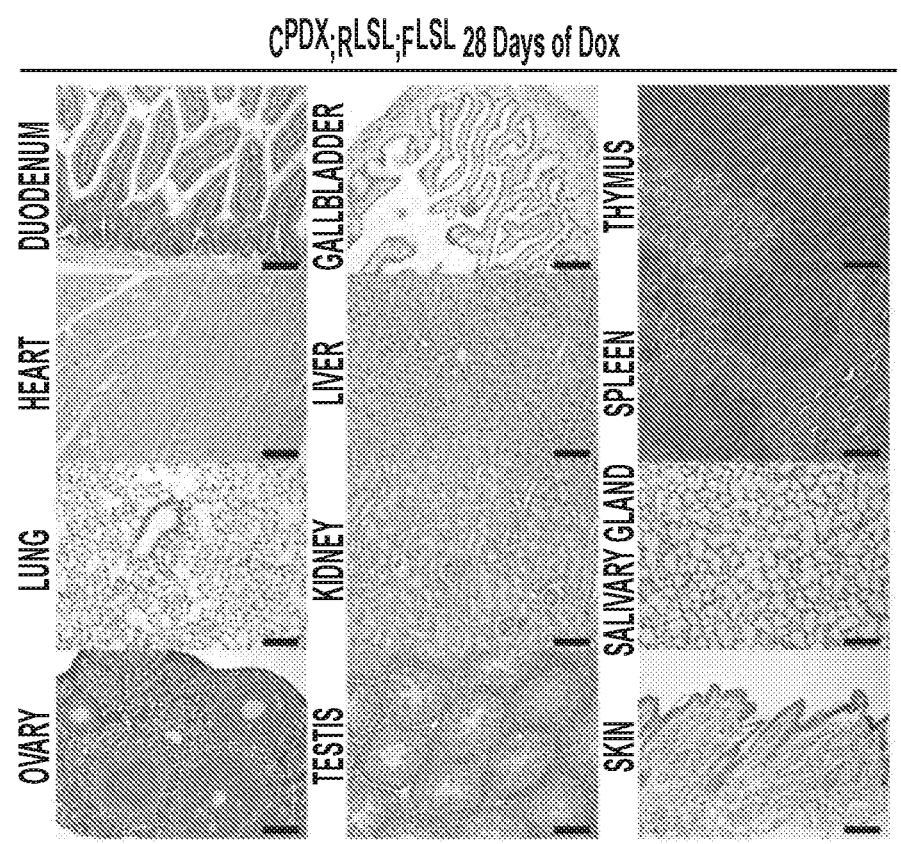
FIG. 12 shows focal pancreas, PDX1-Cre-driven CA19-9 mouse model, whole body histology in H&E histological evaluation of mouse tissues from $C^{PDX};R^{LSL};F^{LSL}$ mice treated with Dox for 28 days. Scale bars=100 µm.
Figure 13:
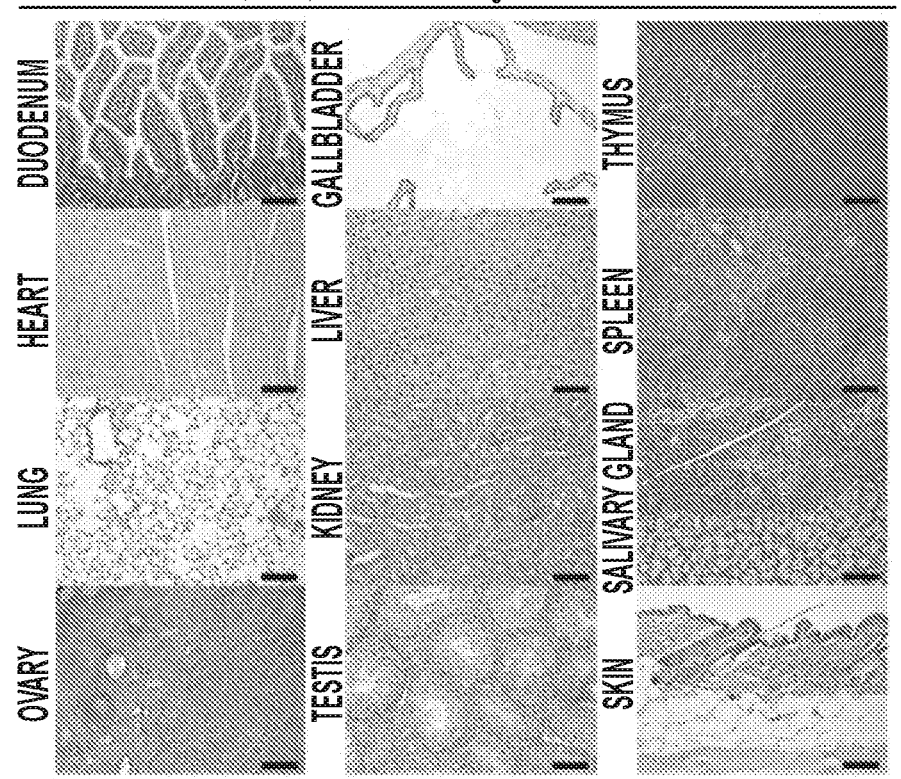
FIG. 13 shows focal pancreas, CA19-9 mouse model genetic negative control littermates, whole body histology in H&E histological evaluation of mouse tissues from untreated $C^{PDX/P48};R^{LSL};F^{LSL}$ genetically negative control littermates. Scale bars=100 µm.
Figure 14:
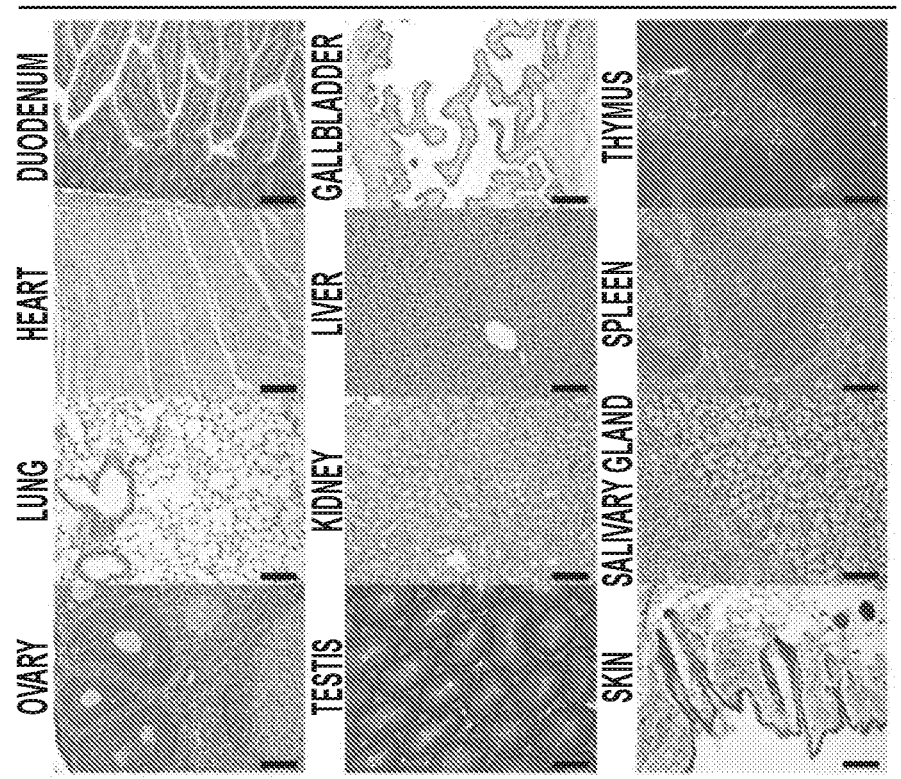
FIG. 14 shows focal pancreas, CA19-9 mouse model genetic negative control littermates, whole body histology in H&E histological evaluation of mouse tissues from $C^{PDX/p48};R^{LSL};F^{LSL}$ untreated genetically negative control littermates treated with Dox for 7 days. Scale bars=100 µm.
Figure 15:
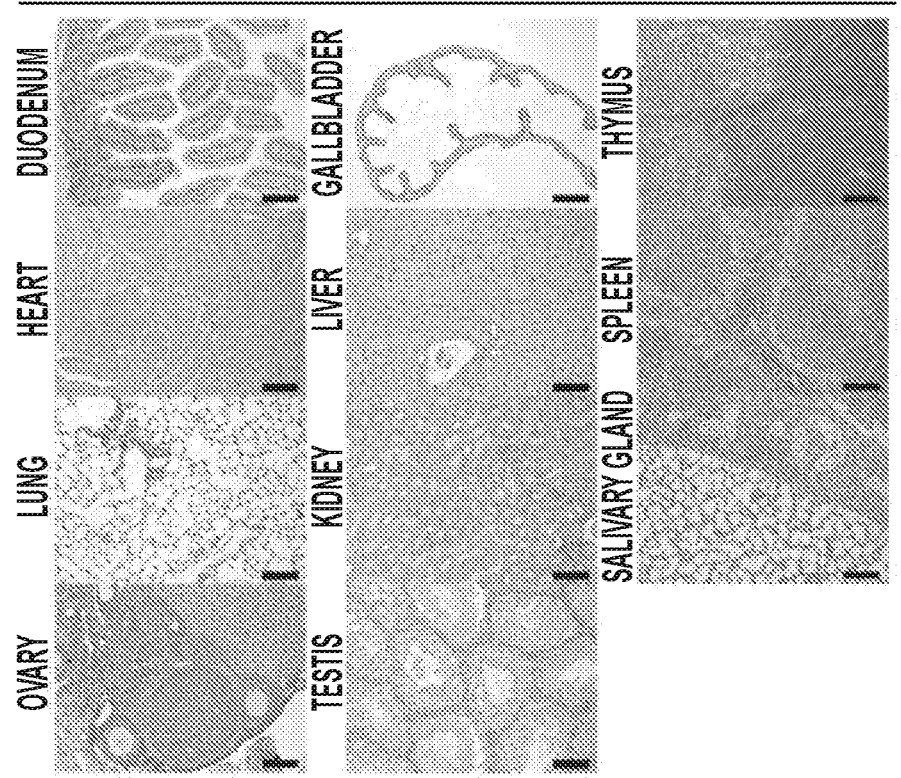
FIG. 15 shows focal pancreas, CA19-9 mouse model genetic negative control littermates, whole body histology in H&E histological evaluation of mouse tissues from $C^{PDX/p48};R^{LSL};F^{LSL}$ genetically negative control littermates treated with Dox for 28 days. Scale bars=100 µm.
Figure 16:
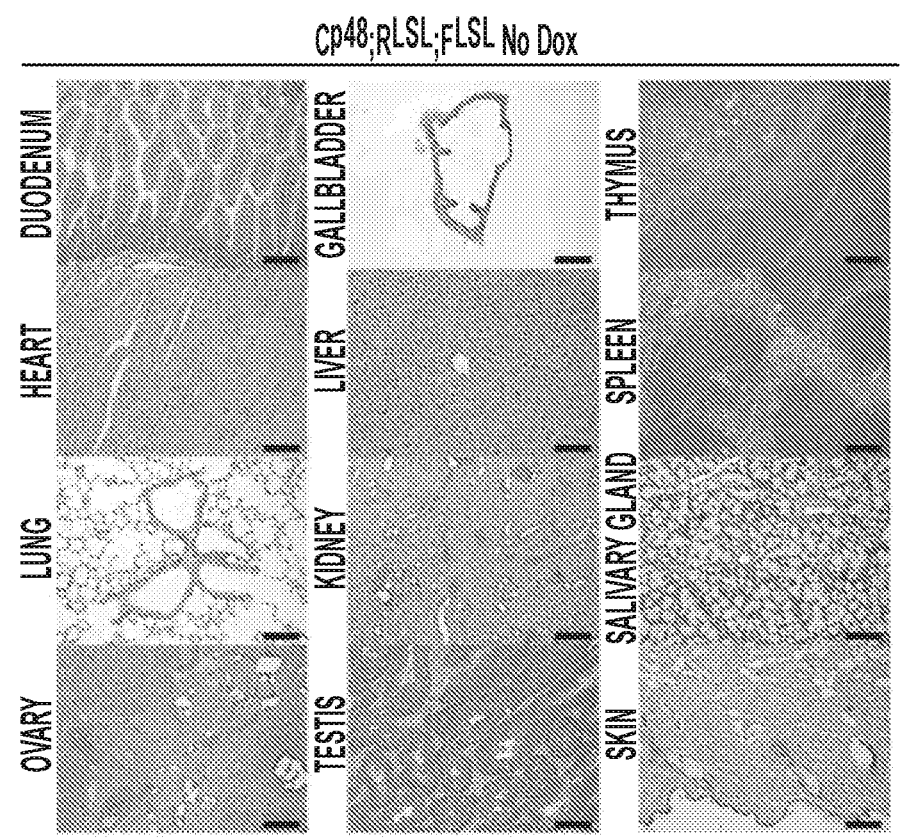
FIG. 16 shows focal pancreas, p48-Cre-driven CA19-9 mouse model, whole body histology in H&E histological evaluation of mouse tissues from untreated $C^{p48};R^{LSL};F^{LSL}$ mice. Scale bars=100 µm.
Figure 17:
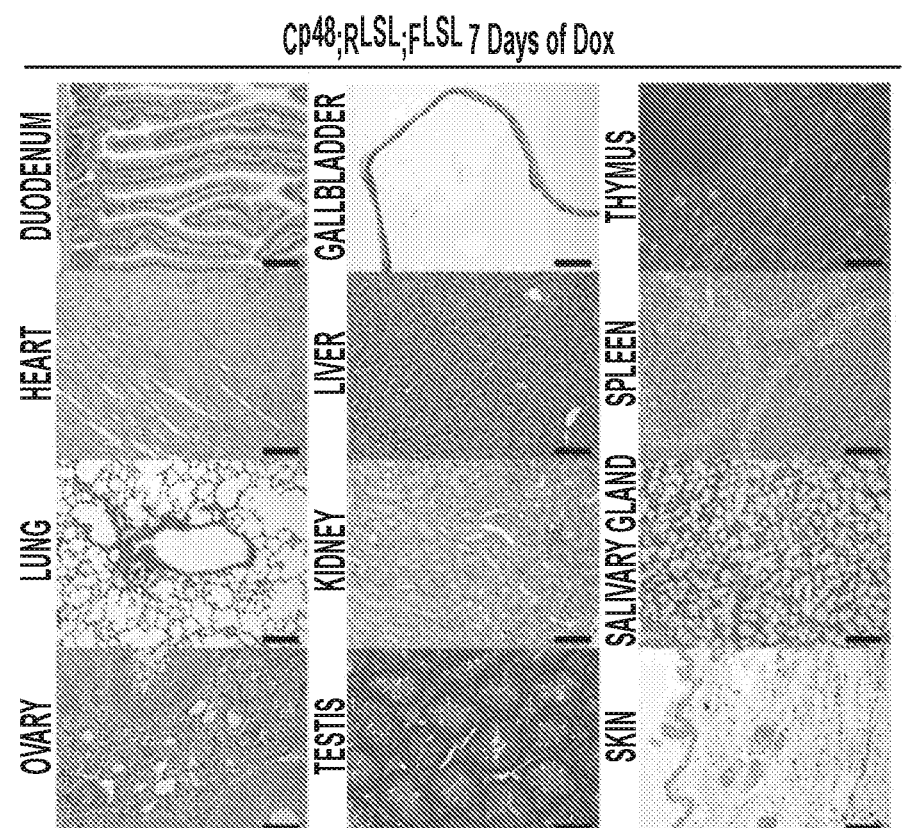
FIG. 17 shows focal pancreas, p48-Cre-driven CA19-9 mouse model, whole body histology in H&E histological evaluation of mouse tissues from $C^{p48};R^{LSL};F^{LSL}$ mice treated with Dox for 7 days. Scale bars=100 µm.
Figure 18:
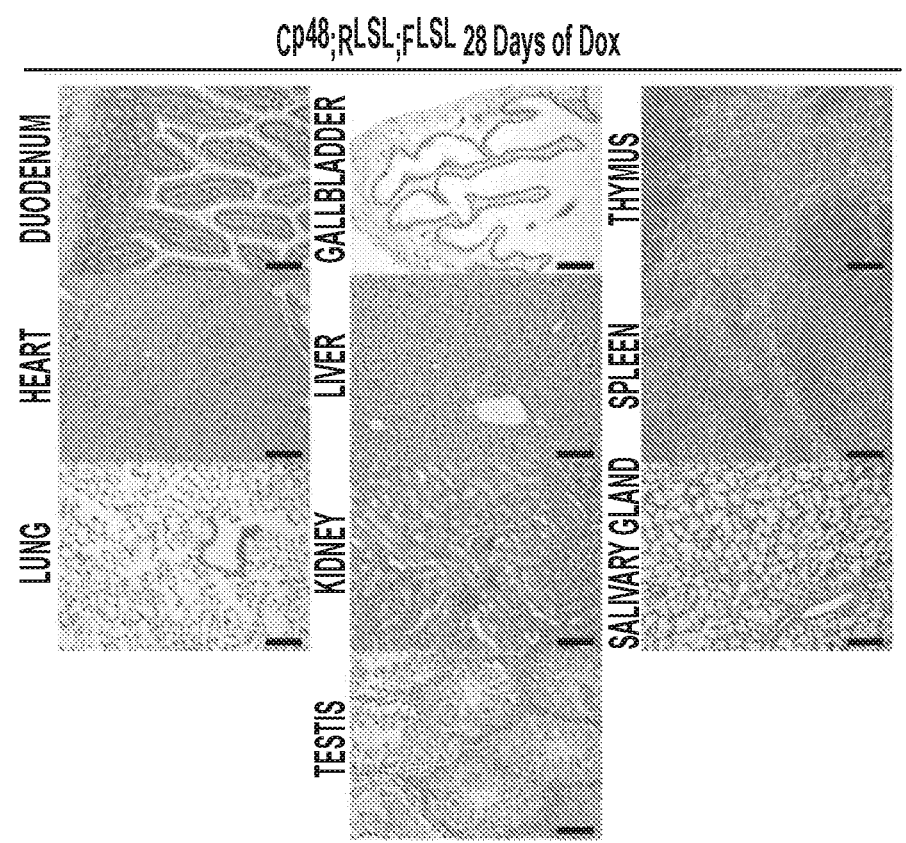
FIG. 18 shows focal pancreas, p48-Cre-driven CA19-9 mouse model, whole body histology in H&E histological evaluation of mouse tissues from $C^{p48};R^{LSL};F^{LSL}$ mice treated with Dox for 28 days. Scale bars=100 µm.
Figure 19:
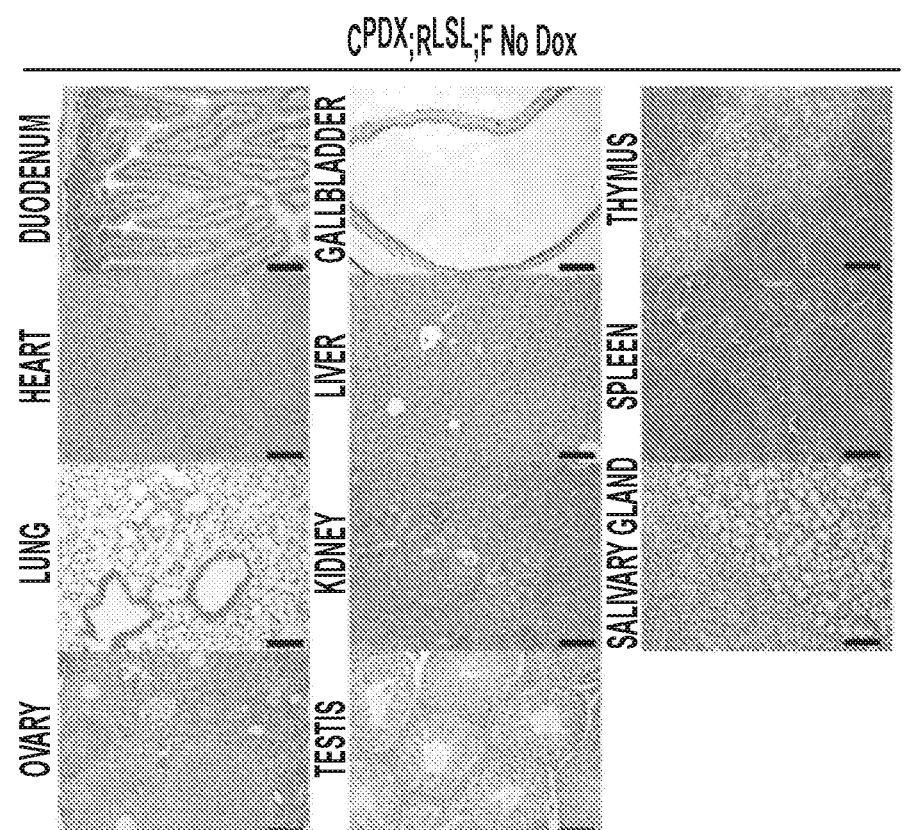
FIG. 19 shows whole pancreas CA19-9 mouse model, whole body histology in H&E histological evaluation of mouse tissues from untreated $C^{PDX};R^{LSL};F$ mice. Scale bars=100 µm.
Figure 20:
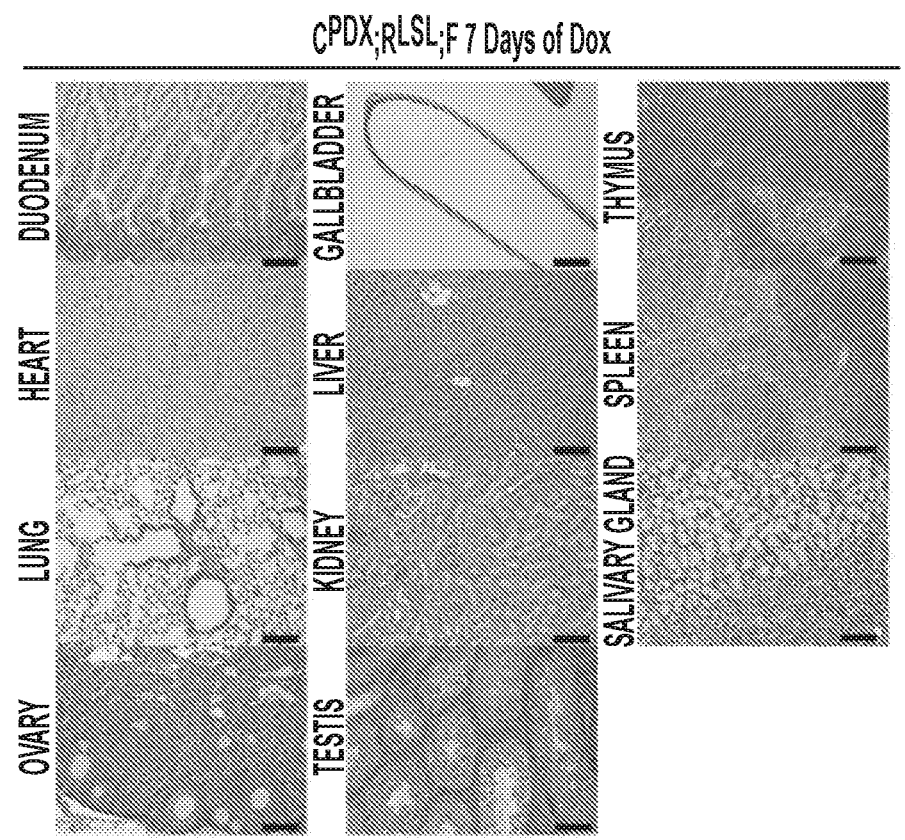
FIG. 20 shows whole pancreas CA19-9 mouse model, whole body histology in H&E histological evaluation of mouse tissues from $C^{PDX};R^{LSL};F$ mice treated with Dox for 7 days. Scale bars=100 µm.
Figure 21:
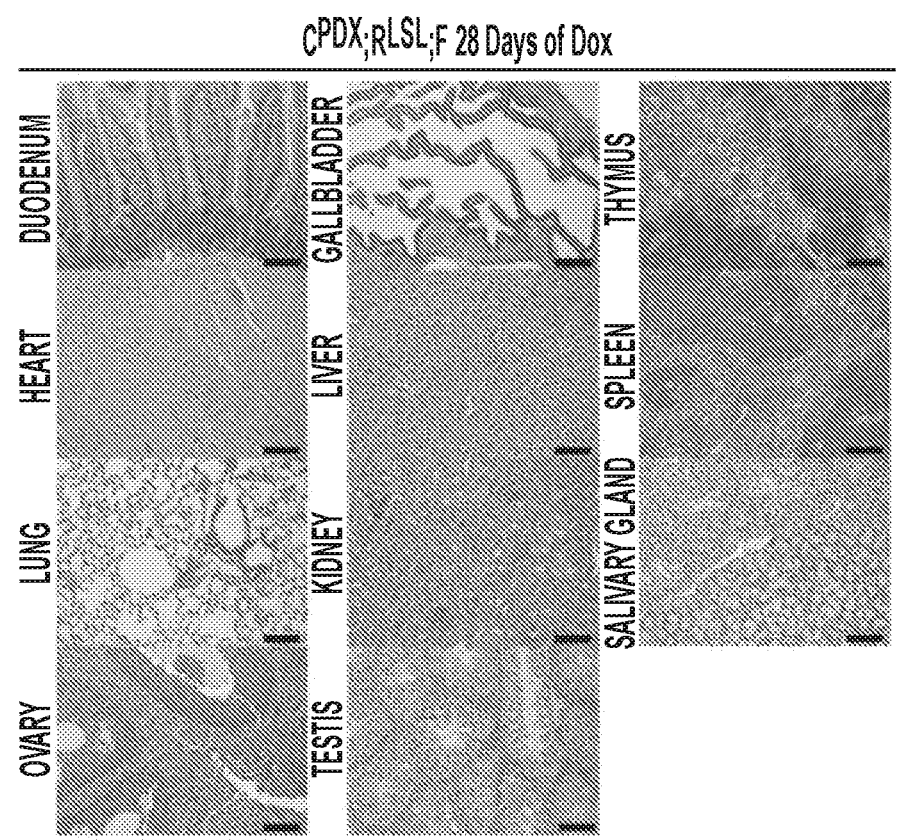
FIG. 21 shows whole pancreas CA19-9 mouse model, whole body histology in H&E histological evaluation of mouse tissues from $C^{PDX};R^{LSL};F$ mice treated with Dox for 28 days. Scale bars=100 µm.
Figure 22:
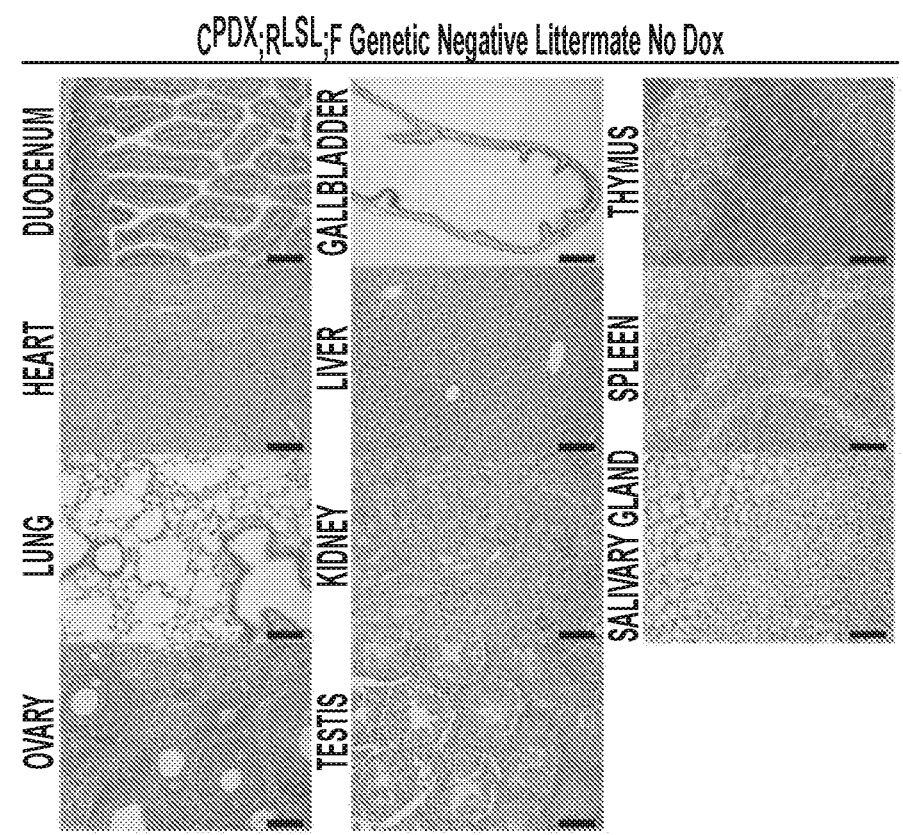
FIG. 22 shows whole pancreas CA19-9 mouse model genetic negative control littermates, whole body histology in H&E histological evaluation of mouse tissues from untreated $C^{PDX};R^{LSL};F$ genetically negative control littermates. Scale bars=100 µm.
Figure 23:
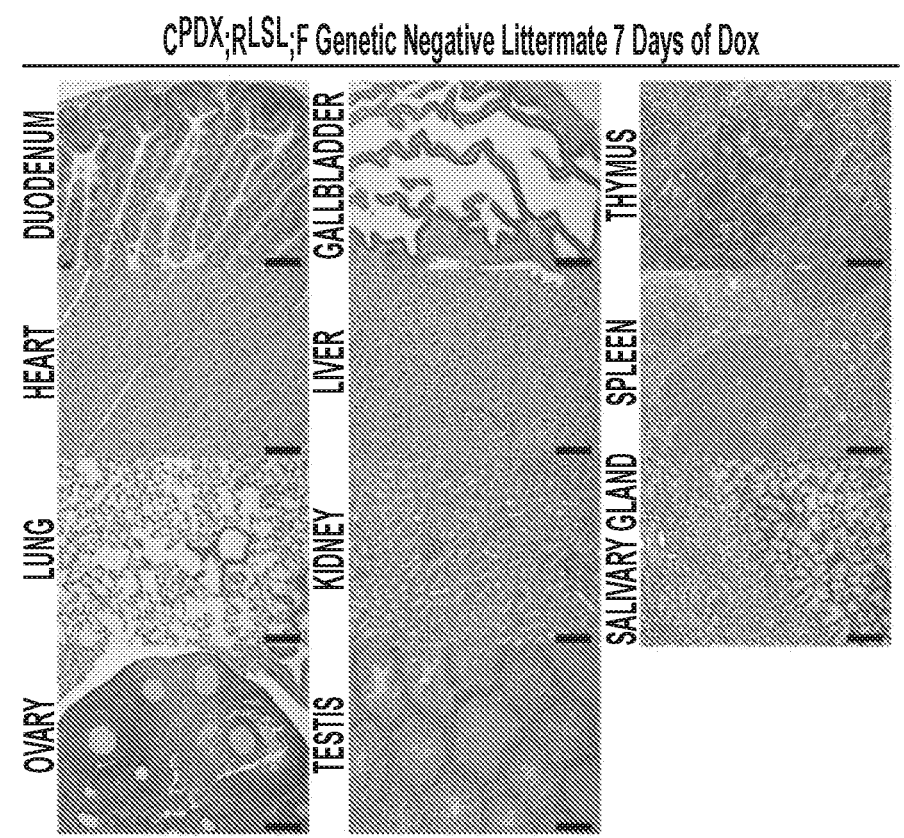
FIG. 23 shows whole pancreas CA19-9 mouse model genetic negative control littermates, whole body histology in H&E histological evaluation of mouse tissues from untreated $C^{PDX};R^{LSL};F$ genetically negative control littermates treated with Dox for 7 days. Scale bars=100 µm.
Figure 24:
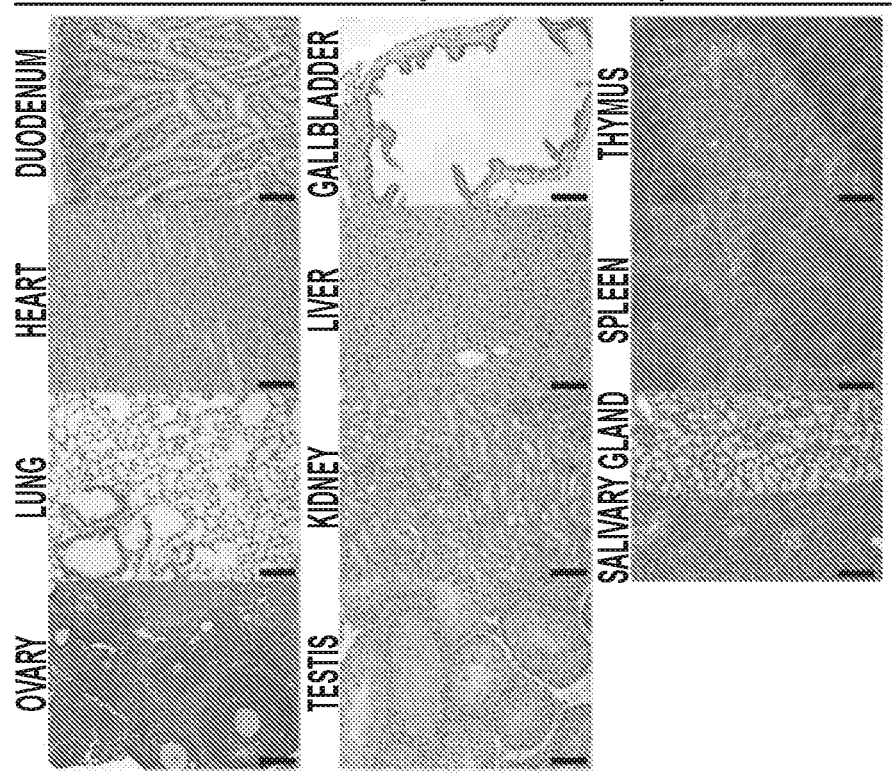
FIG. 24 shows whole pancreas CA19-9 mouse model genetic negative control littermates, whole body histology in H&E histological evaluation of mouse tissues from untreated $C^{PDX};R^{LSL};F$ genetically negative control littermates treated with Dox for 28 days. Scale bars=100 µm.

In order to determine whether CA19-9 is spuriously appended to proteins in the rodent expression system, CA19-9 modified proteins present in the engineered mouse PDAC cell lines were compared to the endogenous CA19-9 modified proteins present in human PDAC cells. The CA19-9 protein carriers were immunoprecipitated (IP) and identified by mass spectrometric (MS) comparison of the CA19-9 expressing cells (FB) to empty-vector transduced controls (Neo) (FIG. 2A). Differences in relative protein abundance between CA19-9 positive and negative cells were determined using isobaric Tags for Relative and Absolute Quantification (iTRAQ) (Ross, P. L. et al. Mol Cell Proteomics 3, 1154-1169 (2004), which is hereby incorporated in its entirety by reference). Two CA19-9 antibody clones were selected based on their use in the literature (5B1, NS19-9) (Koprowski, H. et al. Somatic Cell Genet 5, 957-971 (1979); Sawada, R. et al. Clin Cancer Res 17, 1024-1032 (2011); both of which are hereby incorporated in their entirety by reference). CA19-9 protein carriers were defined as up-regulated at least 1.5-fold in the CA19-9 positive relative to negative samples using either CA19-9 antibody. These analyses identified known CA19-9 protein carriers in the FB mouse cells, including Muc1, Lga1s3 bp, CD44 and Muc5ac (Sperandio, M. et al., Immunological reviews 230, 97-113 (2009); Yue, T. et al. PLoS One 6, e29180 (2011); Yue, T. et al. Proteomics 11, 3665-3674 (2011); Hirao, Y. et al., Journal of Molecular Biomarkers & Diagnosis 03, (2012); all of which are hereby incorporated in their entirety by reference). The human PDAC cell line, MiaPaCa-2, is CA19-9 negative and used as a control to identify human CA19-9 core proteins in the CA19-9 positive cell lines, Capan2, Suit2, and hM1-2D (FIG. 2B). We compared mouse and human CA19-9 protein carriers and found an average of 72.3% (95% CI 60.3-84.3%) of the CA19-9 modified proteins identified in three out of three human PDAC cell lines were also found in three mouse FB PDAC cell lines, demonstrating that FUT3 and β3GALT5 expression in mouse cells largely recapitulates the human CA19-9 carrier profile (FIG. 2C). A total of 4260 non-redundant proteins that are Sialyl Lewis$^a$ carriers in three model mouse pancreatic ductal adenocarcinoma (PDAC) cells, a total of 1521 common proteins that are Sialyl Lewis$^a$ carriers in three model mouse PDAC cells, a total of 3017 non-redundant proteins that are Sialyl Lewis$^a$ carriers in three model human PDAC cells, and a total of 926 common proteins that are Sialyl Lewis$^a$ carriers in three model human PDAC cells were identified.

CA19-9 Expression Causes Pancreatitis:

We generated mouse embryonic stem (mES) cells that multi-genically express FUT3, β3GALT5 and eGFP via an inducible and conditional promoter regulated by a LoxP flanked STOP cassette (LSL) and a tetracycline responsive promoter element (TRE) (FIG. 3A-3D) (Beard, C. et al., Genesis 44, 23-28 (2006), which is hereby incorporated in its entirety by reference). Several types of mouse models were generated that either harbored whole body (R;F), whole pancreatic ($C^{PDX}$;$R^{LSL}$;F), or focal pancreatic ($C^{PDX\ or\ p48}$;$R^{LSL}$;$F^{LSL}$) expression of CA19-9. In all CA19-9 mouse models, non-pancreatic tissues exhibited normal histology relative to genetically negative littermate controls following a time course of Dox treatment (FIGS. 4-24). Surprisingly, all models selectively demonstrated physiological, histological and serological signs of pancreatitis (acinar atrophy, immune cell invasion, collagen deposition, elevated lipase and amylase), whereas no pancreatitis was observed in Dox treated genetic negative controls or untreated mice (FIGS. 25A-25C, FIGS. 26-27, FIGS. 28A-28C).

eGFP and CA19-9 expression following Dox administration indicated expression in the expected tissues of each CA19-9 mouse model (FIG. 25A, FIGS. 29A-29B, FIGS. 30A-30B, FIGS. 31-47). In the R;F and $C^{PDX}$;$R^{LSL}$;F models, eGFP expression was detected by immunohistochemistry (IHC) in the majority of pancreatic ductal and acinar cells, in a mosaic fashion in islets, and never in the pancreatic stroma or endothelial compartments (FIG. 29A, FIGS. 30A-30B, FIG. 31). eGFP was also detected in a Dox-dependent manner in all other organs of R;F mice (FIGS. 32-33). By contrast, the $C^{PDX\ or\ p48}$;$R^{LSL}$;$F^{LSL}$ models exhibited eGFP positivity sporadically in the acinar compartment, rarely in the ductal compartment, and never in the islet, stromal, or endothelial pancreatic compartments (FIG. 29A). As expected, recombination driven by the PDX promoter also resulted in Dox-dependent, mosaic eGFP expression in the duodenum and gall bladder whereas p48-CRE mediated recombination did not result in eGFP expression in non-pancreatic organs (FIGS. 34-39). In the R;F and C;$R^{LSL}$;F models, CA19-9 was predominantly detected in intralobular and intercalated ductal cells and islet cells of the pancreas, with rare positive acinar cells (FIG. 25A, FIG. 29B). CA19-9 was primarily detected in the acinar compartment and rarely in ductal cells of the C;$R^{LSL}$;$F^{LSL}$ model using either PDX1- or p48-driven CRE with sporadic islet positivity limited to the PDX-Cre driven model (FIG. 29B). In R;F mice, CA19-9 was detected in all tissues examined following Dox treatment (FIGS. 40-43). CA19-9 expression was limited to the pancreas, duodenum, and gall bladder in PDX1-CRE driven models but no non-pancreatic expression of CA19-9 was observed in p48-CRE driven mice (FIGS. 44-47). Detailed immunofluorescent evaluation of R;F pancreata revealed co-expression of CA19-9, eGFP and the ductal marker, CK19. Interestingly, while acinar cells often also expressed eGFP, they remained CA19-9-negative. In addition, islets were often double positive for eGFP and CA19-9, although some eGFP-negative islet cells were also CA19-9 positive. CA19-9 expression was also detected in eGFP-negative vasculature and stromal cells. Additional immunofluorescent analyses indicated that eGFP-negative, Podoplanin-positive cells (fibroblasts) exist in both CA19-9 positive and negative states. These data demonstrate accumulation of secreted CA19-9 on the eGFP negative vasculature and stroma (FIGS. 29B, 30A-30B, and 31).

R;F mice exhibited highly penetrant pancreatitis, body weight loss, and pancreatic atrophy following CA19-9 expression, in some cases resulting in loss of more than 20% of body mass and subsequent euthanasia (FIGS. 48A-48B). R;F mice did not generate a discernable CA 19-9-directed antibody response (FIG. 49A) and all non-pancreatic tissues appeared histologically healthy (FIGS. 4-6), indicating that the observed pancreatitis is not autoimmune-mediated. Instead, it is likely that the weight loss in the R;F following Dox administration is due to the high penetrance of pancreatitis given that this model does not rely on Cre-mediated recombination. Indeed, pancreatic exocrine insufficiency is often observed in cases of chronic pancreatitis and is accompanied by severe weight loss in patients (Struyvenberg M R et al., BMC Med.; 15(1):29-, (Feb. 10, 2017)). The significant degree of pancreatic atrophy observed in the R;F model (FIG. 48B) and insufficient production of digestive enzymes (FIG. 49B) suggests that these mice suffer from pancreatic exocrine insufficiency. It is also unlikely that the weight loss is due to loss of glycemic regulation as random-fed status R;F and $C^{PDx}$;$R^{LSL}$;F mice expressing CA19-9 exhibited normal blood glucose levels relative to vehicle treated and untreated counterparts (FIG. 49C).

Dox treatment of $C^{PDX}$;$R^{LSL}$;F mice also revealed highly penetrant pancreatitis and elevated amylase and lipase levels without loss in body or pancreatic weight (FIGS. 25A-25C and 48A-48B). Dox treatment of $C^{PDX\ or\ p48}$;$R^{LSL}$;$F^{LSL}$ mice revealed smaller pancreatitis foci and elevated amylase and lipase levels relative to genetic and untreated controls without loss in body or pancreatic weight (FIGS. 26-27, 28A-28C, and 48A-48B). All models exhibited normalization of amylase and lipase levels after 4 weeks of Dox treatment, but exhibited histologic signs of chronic pancreatitis (FIGS. 25A-25C, 26-27, and 28A-28C). Elevated CA19-9 levels were detectable in the plasma of R;F and C;$R^{LSL}$;F mice after Dox treatment, but not in the $C^{PDX}$;$R^{LSL}$;$F^{LSL}$ model (FIGS. 49D and 50A). Further studies focused on the $C^{PDX}$;$R^{LSL}$;F mice given the high penetrance of the pancreatitis phenotype without pancreatic insufficiency and weight loss with the correct pancreatic localization and secretion of CA19-9.

The immune cell types present in the spleen, lymph nodes and pancreata of $C^{PDX}$;$R^{LSL}$;F mice relative to the Cerulein model of acute pancreatitis were characterized by flow cytometry, and revealed an influx of inflammatory monocytes and macrophages in the pancreas of both models without change to the immune cell type representation in the spleen or lymph nodes following induction of pancreatitis (FIGS. 50B and 51A). Neither model exhibited recruitment of T- or B-cells at the time points examined (1-3 days) (FIG. 51B).

Example 3

Methods and assays described in Example 2 are hereby incorporated in this Example.

CA19-9 Expression Causes Ductal Proliferation and Signaling Changes:

CA19-9 expression in the genetic mouse model led to an increase in pancreatic proliferation, particularly in ductal cells and immune cells as evaluated by Ki67 immunohistochemistry (IHC) and Edu incorporation in vivo (FIGS. 52A and 53A-53B). There was no evidence of Dox-dependent induction of Atf4 and Bip in acinar explant cultures despite stimulation of enzyme release, reducing the likelihood that proteotoxic stress played a role in the observed pancreatitis (FIGS. 52B-52C).

To dissect the signaling pathway changes that occur in direct response to CA19-9 expression we isolated pancreatic ductal organoids from $C^{PDX}; R^{LSL}; F$ mice (Boj, Sylvia F. et al. Cell 160, 324-338 (2015), which is incorporated in its entirety by reference). RNA-seq analyses of the $C^{PDX}; R^{LSL}; F$ organoids following induction of CA19-9 expression revealed the expected changes in transgene expression (FIGS. 54A-54F) and enabled expression of FUT3 and β3GALT5 in mouse ductal organoids at levels within the range endogenously observed in human ductal organoids (FIG. 54D) (Tiriac, H. et al. Cancer Discov, doi: 10.1158/2159-8290.CD-18-0349. [Epub ahead of print](2018), which is incorporated in its entirety by reference). Gene Set Enrichment Analysis (GSEA) revealed a reduction of an Unfolded Protein Response gene set and the enrichment of pathways associated with Chemokine, and TGF Beta signaling following CA19-9 expression (FIGS. 55A-55C and 56A-56B). We further explored enrichment of Erbb and PI3K and Akt signaling following CA19-9 expression (FIGS. 55A-55C and 56A-56B). Dox-induced CA19-9 expression in $C^{PDX}; R^{LSL}; F$ organoids selectively and prominently elevated EGFR phosphorylation while decreasing levels of total EGFR, indicating greater flux through this pathway (FIG. 57A). The increase in phospho-EGFR was accompanied by increased levels of phospho-Akt and phospho-Erk1/2 (FIG. 57A). No consistent changes to total- or phospho-S6, Her2 and p65 were observed (FIG. 57B). These findings were independent of the inclusion of murine Egf in the media of the cultures (FIG. 57C). Additionally, phospho-EGFR was present in vivo in the pancreatic ducts of $C; R^{LSL}; F$ mice following Dox treatment (FIG. 57D). CA19-9 expression did not alter $C; R^{LSL}; F$, $R; F$ or $C; R^{LSL}; F^{LSL}$ organoid proliferation following Dox induction of CA19-9 expression as well as in mouse normal pancreatic ductal organoids with constitutive CA19-9 expression (FIGS. 58A-58D), suggesting additional extrinsic cues are required for increased ductal proliferation in vivo.

It has been reported that the glycosylation state of EGFR can affect its ability to activate and to respond to targeted kinase inhibitors (Liu, Y. C. et al. Proc Natl Acad Sci USA 108, 11332-11337 (2011); Matsumoto, K. et al. Cancer science 99, 1611-1617 (2008); both of which are hereby incorporated in their entirety by reference), but we did not find CA19-9 modification of EGFR (FIG. 59A). Also, CA19-9 expression also did not impact the EC50 or growth inhibitory phenotype of ERBB kinase inhibitors Erlotinib and Neratinib on $C^{PDX}; R^{LSL}; F$ organoids (FIGS. 59B-59C). On the other hand, addition of a monoclonal antibody to CA19-9 was sufficient to block EGFR phosphorylation in normal organoids induced to express CA19-9 with Dox (FIG. 60).

Example 4

Methods and assays described in Examples 2 and 3 are hereby incorporated in this Example.
CA19-9-Induced Pancreatitis is Reversible and can be Treated with CA19-9-Specific Antibodies:

We further found in the genetic mouse model that CA19-9 mediated pancreatitis was completely reversible following a 3-day Dox pulse and 4-day recovery period (FIGS. 61A-61B). These data suggest that targeting CA19-9 may be therapeutically useful for attenuating the severity and recurrence of pancreatitis episodes. Importantly, antibodies directed against CA19-9 also ameliorated the histological and serological signs of pancreatitis and reduced the hyperactivation of EGFR in vivo in cases of acute (24 hours of 2 g/L Dox, NS19-9 clone) and severe acute (7 days of 0.5 g/L Dox, 5B1 clone) pancreatitis, suggesting a role of the glycan and the core polypeptides it is affixed to in disease pathogenesis (FIGS. 62A-62D, 63A-63C, and 64A-64C). However, the EGFR inhibitor, Erlotinib, paradoxically was unable to substitute for anti-CA19-9 therapy since treatment with Erlotinib 24 hours prior to the induction of pancreatitis resulted in severe weight loss of more than 20%, resulting in humane end point prior to study completion. Pancreatic atrophy was evident at necropsy and vacuolization of the acinar compartment was apparent by histology (FIGS. 65A-65B). These effects were unrelated to toxicity associated with Erlotinib in normal mice (C57Bl/6J) (FIGS. 65C-65D). These data suggest that EGFR activation serves as a protective mechanism for the acinar compartment following instigation of the inflammatory cascade by CA19-9.

To discern whether the CA19-9 dependent activation of EGFR was due to a soluble ligand, conditioned media from CA19-9 positive organoids was evaluated and found to stimulate EGFR phosphorylation in control murine ductal organoids (FIG. 66A). This activity was attenuated by the addition of EGFR-Fc (EGFR Trap), further supporting the presence of one or more EGFR ligands (FIG. 66B). Since these findings suggested the presence of a CA19-9 modified, secreted EGFR ligand, exemplary CA19-9 modified proteins were identified by IP/MS (Table 3 and Table 4 below).

TABLE 3

CA19-9 IP/MS data from C; $R^{LSL}$; F or genetic megative organoid (A220 and A217, respectively) conditioned media after 8 hours of Dox treatment.

| Family | Member | UniProt_ mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 1 | 1 | P01868 | 1 | 1.113 | 0.158 | 0.094 | 1.102 | 1.139 | 0.098 | 0.181 | Ig gamma-1 chain C region secreted form OS = Mus musculus GN = Ighg1 PE = 1 SV = 1 |
| 1 | 2 | A0A075B5P4 | 1 | 1.116 | 0.152 | 0.09 | 1.099 | 1.136 | 0.092 | 0.171 | Ig gamma-1 chain C region secreted form (Fragment) OS = Mus musculus GN = Ighg1 PE = 1 SV = 1 |
| 2 | 1 | P07724 | 1 | 1.1 | 0.409 | 0.388 | 1.072 | 1.113 | 0.288 | 0.405 | Serum albumin OS = Mus musculus GN = Alb PE = 1 SV = 3 |
| 3 | 1 | P01637 | 1 | 0.661 | 0.17 | 0.158 | 0.991 | 1.149 | 0.133 | 0.202 | Ig kappa chain V-V region T1 OS = Mus musculus PE = 4 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 3 | 2 | A0A140T8P9 | 1 | 0.548 | 0.235 | 0.197 | 0.987 | 1.184 | 0.173 | 0.313 | Immunoglobulin kappa variable 14-111 (Fragment) OS = Mus musculus GN = Igkv14-111 PE-4 SV = 2 |
| 4 | 1 | P01837 | 1 | 0.885 | 0.072 | 0.091 | 0.931 | 1.189 | 0.057 | 0.103 | Ig kappa chain C region OS = Mus musculus PE = 1 SV = 1 |
| 4 | 2 | A0A075B5P2 | 1 | 0.882 | 0.072 | 0.09 | 0.932 | 1.192 | 0.057 | 0.103 | Immunoglobulin kappa constant (Fragment) OS = Mus musculus GN = Igkc PE = 1 SV = 1 |
| 5 | 1 | P20152 | 1 | 0.527 | 10.657 | 10.327 | 0.566 | 0.661 | 10.501 | 10.411 | Vimentin OS = Mus musculus GN = Vim PE = 1 SV = 3 |
| 5 | 2 | P50446 | 1 | 1.21 | 1.494 | 0.796 | 0.708 | 0.462 | 1.064 | 1.845 | Keratin, type II cytoskeletal 6A OS = Mus musculus GN = Krt6a PE = 1 SV = 3 |
| 5 | 3 | Q922U2 | 1 | 1.206 | 1.435 | 0.816 | 0.707 | 0.482 | 1.016 | 1.859 | Keratin, type II cytoskeletal 5 OS = Mus musculus GN = Krt5 PE = 1 SV = 1 |
| 5 | 4 | E9Q1Z0 | 1 | 1.128 | 1.417 | 0.778 | 0.71 | 0.468 | 0.988 | 1.828 | Keratin 90 OS = Mus musculus GN = Krt90 PE = 1 SV = 1 |
| 5 | 5 | P04104 | 1 | 1.547 | 1.458 | 0.711 | 0.521 | 0.596 | 1.083 | 2.299 | Keratin, type II cytoskeletal 1 OS = Mus musculus GN = Krt1 PE = 1 SV = 4 |
| 5 | 6 | P11679 | 1 | 1.075 | 3.427 | 3.472 | 0.475 | 0.566 | 2.793 | 3.151 | Keratin, type II cytoskeletal 8 OS = Mus musculus GN = Krt8 PE = 1 SV = 4 |
| 5 | 7 | P31001 | 1 | 0.743 | 22.1 | 21.134 | 0.914 | 1.1 | 20.623 | 20.94 | Desmin OS = Mus musculus GN = Des PE = 1 SV = 3 |
| 5 | 8 | Q6IFZ6 | 1 | 2.003 | 1.722 | 0.85 | 0.434 | 0.57 | 1.282 | 2.155 | Keratin, type II cytoskeletal 1b OS = Mus musculus GN = Krt77 PE = 1 SV = 1 |
| 5 | 9 | Q3TTY5 | 1 | 2.077 | 1.234 | 0.65 | 0.466 | 0.496 | 1.285 | 1.328 | Keratin, type II cytoskeletal 2 epidermal OS = Mus musculus GN = Krt2 PE = 1 SV = 1 |
| 5 | 10 | Q3UV17 |  | 1.383 | 1.233 | 0.725 | 0.829 | 0.433 | 1.003 | 1.926 | Keratin, type II cytoskeletal 2 oral OS = Mus musculus GN = Krt76 PE = 1 SV = 1 |
| 5 | 11 | Q8VED5 | 1 | 1.679 | 2.503 | 0.726 | 0.478 | 0.383 | 1.138 | 1.565 | Keratin, type II cytoskeletal 79 OS = Mus musculus GN = Krt79 PE = 1 SV = 2 |
| 5 | 12 | Q9DCV7 | 1 | 1.01 | 4.42 | 3.691 | 0.557 | 0.578 | 3.596 | 3.895 | Keratin, type II cytoskeletal 7 OS = Mus musculus GN = Krt7 PE = 1 SV = 1 |
| 6 | 1 | Q68FD5 | 1 | 0.654 | 3.27 | 3.203 | 0.549 | 0.569 | 2.822 | 3.475 | Clathrin heavy chain 1 OS = Mus musculus GN = Cltc PE = 1 SV = 3 |
| 7 | 1 | P52480 | 1 | 0.517 | 5.698 | 6.066 | 0.592 | 0.633 | 5.275 | 6.739 | Pyruvate kinase PKM OS = Mus musculus GN = Pkm PE = 1 SV = 4 |
| 8 | 1 | Q9WVF5 | 1 | 1.022 | 0.277 | 0.206 | 1.044 | 0.325 | 0.288 | 0.925 | Epidermal growth factor receptor OS = Mus musculus GN = Egfr PE = 1 SV = 1 |
| 9 | 1 | P05213 | 1 | 0.679 | 6.255 | 6.52 | 0.623 | 0.665 | 4.707 | 6.258 | Tubulin alpha-1B chain OS = Mus musculus GN = Tuba1b PE = 1 SV = 2 |
| 9 | 2 | P68373 | 1 | 0.65 | 6.066 | 6.264 | 0.588 | 0.627 | 4.46 | 5.891 | Tubulin alpha-1C chain OS = Mus musculus GN = Tuba1c PE = 1 SV = 1 |
| 10 | 1 | P11499 | 1 | 0.678 | 5.162 | 5.452 | 0.681 | 0.748 | 4.681 | 5.627 | Heat shock protein HSP 90-beta OS = Mus musculus GN = Hsp90ab1 PE = 1 SV = 3 |
| 10 | 2 | P07901 | 1 | 0.689 | 4.213 | 4.407 | 0.616 | 0.728 | 3.683 | 4.413 | Heat shock protein HSP 90-alpha OS = Mus musculus GN = Hsp90aa1 PE = 1 SV = 4 |
| 10 | 3 | P08113 | 1 | 0.927 | 3.5 | 3.435 | 0.525 | 0.585 | 2.739 | 3.536 | Endoplasmin OS = Mus musculus GN = Hsp90b1 PE = 1 SV = 2 |
| 11 | 1 | P99024 | 1 | 0.649 | 4.289 | 4.365 | 0.567 | 0.615 | 3.894 | 4.685 | Tubulin beta-5 chain OS = Mus musculus GN = Tubb5 PE = 1 SV = 1 |
| 11 | 2 | P68372 | 1 | 0.585 | 4.286 | 4.135 | 0.593 | 0.671 | 3.906 | 4.686 | Tubulin beta-4B chain OS = Mus musculus GN = Tubb4b PE = 1 SV = 1 |
| 11 | 3 | Q9CWF2 | 1 | 0.687 | 4.532 | 4.413 | 0.612 | 0.674 | 4.113 | 4.992 | Tubulin beta-2B chain OS = Mus musculus GN = Tubb2b PE = 1 SV = 1 |
| 12 | 1 | A0A075B5T3 | 1 | 1.062 | 0.242 | 0.177 | 0.944 | 0.958 | 0.178 | 0.34 | Immunoglobulin heavy variable 6-6 (Fragment) OS = Mus musculus GN = Ighv6-6 PE = 4 SV = 1 |
| 12 | 2 | P01796 | 1 | 0.872 | 0.201 | 0.164 | 0.867 | 0.951 | 0.159 | 0.267 | Ig heavy chain V-III region A4 OS = Mus musculus PE = 1 SV = 1 |
| 13 | 1 | P26443 | 1 | 0.564 | 6.728 | 7.206 | 0.637 | 0.609 | 6.1 | 7.041 | Glutamate dehydrogenase 1, mitochondrial OS = Mus musculus GN = Glud1 PE = 1 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 14 | 1 | P58252 | 1 | 0.555 | 4.768 | 5.051 | 0.55 | 0.638 | 4.22 | 5.289 | Elongation factor 2 OS = Mus musculus GN = Eef2 PE = 1 SV-2 |
| 15 | 1 | A0A075B5P3 | 1 | 1.005 | 0.466 | 0.454 | 1.157 | 1.16 | 0.397 | 0.454 | Immunoglobulin heavy constant gamma 2B (Fragment) OS = Mus musculus GN = Ighg2b PE = 1 SV = 1 |
| 15 | 2 | P01867 | 1 | 1.002 | 0.442 | 0.439 | 1.135 | 1.193 | 0.388 | 0.419 | Ig gamma-2B chain C region OS = Mus musculus GN = Igh-3 PE = 1 SV = 3 |
| 15 | 3 | P01863 | 1 | 0.984 | 0.471 | 0.46 | 1.392 | 1.411 | 0.417 | 0.488 | Ig gamma-2A chain C region, A allele OS = Mus musculus GN = Ighg PE = 1 SV = 1 |
| 16 | 1 | P50247 | 1 | 0.536 | 6.74 | 7.244 | 0.646 | 0.64 | 5.616 | 7.209 | Adenosylhomocysteinase OS = Mus musculus GN = Ahcy PE = 1 SV = 3 |
| 17 | 1 | A2A513 | 1 | 1.771 | 1.267 | 0.488 | 0.484 | 0.464 | 1.177 | 1.743 | Keratin, type I cytoskeletal 10 OS = Mus musculus GN = Krt10 PE = 1 SV = 1 |
| 17 | 2 | Q9QWL7 | 1 | 0.727 | 3.614 | 0.892 | 0.406 | 0.368 | 0.848 | 1.769 | Keratin, type I cytoskeletal 17 OS = Mus musculus GN = Krt17 PE = 1 SV = 3 |
| 17 | 3 | B1AQ77 | 1 | 1.273 | 1.809 | 0.654 | 0.433 | 0.447 | 1.023 | 1.772 | Keratin 15, isoform CRA_a OS = Mus musculus GN = Krt15 PE = 1 SV = 1 |
| 17 | 4 | Q9Z2K1 | 1 | 1.553 | 1.366 | 0.566 | 0.469 | 0.498 | 1.182 | 1.796 | Keratin, type I cytoskeletal 16 OS = Mus musculus GN = Krt16 PE = 1 SV = 3 |
| 17 | 5 | P19001 | 1 | 0.774 | 2.718 | 1.015 | 0.367 | 0.379 | 0.775 | 1.614 | Keratin, type I cytoskeletal 19 OS = Mus musculus GN = Krt19 PE = 1 SV = 1 |
| 18 | 1 | O35565 | 1 | 0.678 | 6.079 | 6.439 | 0.77 | 0.847 | 6.246 | 7.582 | Fibroblast growth factor 10 OS = Mus musculus GN = Fgf10 PE = 2 SV = 1 |
| 19 | 1 | P63017 | 1 | 0.77 | 6.36 | 6.817 | 0.778 | 0.746 | 5.57 | 6.947 | Heat shock cognate 71 kDa protein OS = Mus musculus GN = Hspa8 PE = 1 SV = 1 |
| 19 | 2 | P17879 | 1 | 0.65 | 3.157 | 3.557 | 0.511 | 1.538 | 3.1 | 3.903 | Heat shock 70 kDa protein 1B OS = Mus musculus GN = Hspa1b PE = 1 SV = 3 |
| 19 | 3 | P16627 | 1 | 0.657 | 3.45 | 3.954 | 0.55 | 1.549 | 3.284 | 4.238 | Heat shock 70 kDa protein 1-like OS = Mus musculus GN = Hspa1l PE = 1 SV = 4 |
| 19 | 4 | P20029 | 1 | 0.748 | 5.836 | 6.854 | 0.833 | 0.721 | 5.533 | 7.259 | 78 kDa glucose-regulated protein OS = Mus musculus GN = Hspa5 PE = 1 SV = 3 |
| 20 | 1 | Q9Z1R9 | 1 | 1.142 | 0.931 | 0.878 | 0.182 | 0.169 | 0.282 | 0.231 | MCG124046 OS = Mus musculus GN = Prss1 PE = 1 SV = 1 |
| 20 | 2 | Q792Y8 | 1 | 1.165 | 0.901 | 0.816 | 0.151 | 0.137 | 0.24 | 0.17 | MCG15081 OS = Mus musculus GN = Gm10334 PE = 3 SV = 1 |
| 21 | 1 | P14206 | 1 | 0.674 | 5.639 | 5.687 | 0.707 | 0.791 | 5.321 | 6.366 | 40S ribosomal protein SA OS = Mus musculus GN = Rpsa PE = 1 SV = 4 |
| 22 | 1 | Q61838 | 1 | 1.026 | 0.396 | 0.354 | 1.187 | 1.182 | 0.309 | 0.339 | Pregnancy zone protein OS = Mus musculus GN = Pzp PE = 1 SV = 3 |
| 23 | 1 | A0A075B5P6 | 1 | 1.032 | 0.45 | 0.468 | 1.045 | 0.973 | 0.41 | 0.531 | Ig mu chain C region (Fragment) OS = Mus musculus GN = Ighm PE = 1 SV = 1 |
| 24 | 1 | A0A0A0MQF6 | 1 | 0.717 | 7.518 | 7.779 | 0.795 | 0.656 | 6.46 | 8.331 | Glyceraldehyde-3-phosphate dehydrogenase OS = Mus musculus GN = Gapdh PE = 1 SV = 1 |
| 25 | 1 | P10126 | 1 | 0.652 | 5.036 | 4.381 | 0.694 | 0.804 | 3.724 | 4.767 | Elongation factor 1-alpha 1 OS = Mus musculus GN = Eef1a1 PE = 1 SV = 3 |
| 25 | 2 | P62631 | 1 | 0.615 | 5.35 | 4.606 | 0.687 | 0.783 | 4.076 | 5.042 | Elongation factor 1-alpha 2 OS = Mus musculus GN = Eef1a2 PE = 1 SV = 1 |
| 26 | 1 | P97466 | 1 | 0.71 | 10.036 | 10.991 | 0.805 | 0.762 | 9.104 | 10.895 | Noggin OS = Mus musculus GN = Nog PE = 2 SV = 1 |
| 27 | 1 | P68040 | 1 | 0.639 | 4.614 | 4.672 | 0.69 | 0.617 | 3.944 | 5.059 | Receptor of activated protein C kinase 1 OS = Mus musculus GN = Rack1 PE = 1 SV = 3 |
| 28 | 1 | P80314 | 1 | 0.712 | 2.306 | 2.255 | 0.731 | 0.642 | 1.964 | 2.584 | T-complex protein 1 subunit beta OS = Mus musculus GN = Cct2 PE = 1 SV = 4 |
| 29 | 1 | Q07797 | 1 | 0.777 | 4.31 | 4.679 | 0.613 | 0.795 | 4.024 | 6.366 | Galectin-3-binding protein OS = Mus musculus GN = Lgals3bp PE = 1 SV = 1 |
| 30 | 1 | P80315 | 1 | 0.596 | 2.439 | 2.546 | 0.462 | 0.599 | 2.235 | 2.701 | T-complex protein 1 subunit delta OS = Mus musculus GN = Cct4 PE = 1 SV = 3 |
| 30 | 2 | P80316 | 1 | 0.44 | 3.653 | 2.923 | 0.648 | 0.526 | 2.631 | 3.033 | T-complex protein 1 subunit epsilon OS = Mus musculus GN = Cct5 PE = 1 SV = 1 |
| 31 | 1 | P99027 | 1 | 0.448 | 4.432 | 4.951 | 0.523 | 0.625 | 4.357 | 4.495 | 60S acidic ribosomal protein P2 OS = Mus musculus GN = Rplp2 PE = 1 SV = 3 |
| 32 | 1 | Q02053 | 1 | 0.563 | 3.51 | 3.389 | 0.499 | 0.55 | 2.73 | 3.229 | Ubiquitin-like modifier-activating enzyme 1 OS = Mus musculus GN = Uba1 PE = 1 SV = 1 |
| 33 | 1 | Q9ET01 | 1 | 0.651 | 2.278 | 2.313 | 0.5 | 0.366 | 1.898 | 2.282 | Glycogen phosphorylase, liver form OS = Mus musculus GN = Pygl PE = 1 SV = 4 |
| 33 | 2 | E9PUM3 | 1 | 0.522 | 2.479 | 2.508 | 0.457 | 0.424 | 2.245 | 2.793 | Alpha-1,4 glucan phosphorylase OS = Mus musculus GN = Pygm PE = 1 SV = 1 |
| 34 | 1 | Q9D8N0 | 1 | 0.711 | 3.914 | 3.944 | 0.68 | 0.54 | 3.488 | 4.008 | Elongation factor 1-gamma OS = Mus musculus GN = Eef1g PE = 1 SV = 3 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 35 | 1 | A0A0A0MQA3 | 1 | 0.966 | 0.444 | 0.372 | 0.882 | 0.942 | 0.291 | 0.285 | Alpha-1-antitrypsin 1-1 OS = Mus musculus GN = Serpina1a PE = 1 SV = 1 |
| 35 | 2 | P22599 | 1 | 1.003 | 0.416 | 0.39 | 0.9 | 0.944 | 0.277 | 0.297 | Alpha-1-antitrypsin 1-2 OS = Mus musculus GN = Serpina1b PE = 1 SV = 2 |
| 35 | 3 | Q00897 | 1 | 1.015 | 0.385 | 0.397 | 0.869 | 0.935 | 0.282 | 0.284 | Alpha-1-antitrypsin 1-4 OS = Mus musculus GN = Serpina1d PE = 1 SV = 1 |
| 36 | 1 | P60710 | 1 | 0.835 | 2.534 | 1.997 | 0.762 | 0.661 | 1.67 | 1.935 | Actin, cytoplasmic 1 OS = Mus musculus GN = Actb PE = 1 SV = 1 |
| 37 | 1 | P01670 | 1 | 1.113 | 0.134 | 0.095 | 0.775 | 0.921 | 0.066 | 0.142 | Ig kappa chain V-III region PC 6684 OS = Mus musculus PE = 1 SV = 1 |
| 37 | 2 | P01654 | 1 | 0.717 | 0.676 | 0.844 | 0.849 | 0.875 | 0.743 | 0.894 | Ig kappa chain V-III region PC 2880/PC 1229 OS = Mus musculus PE = 1 SV = 1 |
| 37 | 3 | P01659 | 1 | 0.711 | 0.557 | 0.746 | 0.844 | 0.915 | 0.652 | 0.816 | Ig kappa chain V-III region TEPC 124 OS = Mus musculus PE = 1 SV = 1 |
| 37 | 4 | P01644 | 1 | 1.128 | 0.107 | 0.072 | 0.774 | 0.92 | 0.045 | 0.077 | Ig kappa chain V-V region HP R16.7 OS = Mus musculus PE = 1 SV = 1 |
| 38 | 1 | O35490 | 1 | 0.438 | 4.545 | 4.685 | 0.493 | 0.407 | 4.172 | 5.147 | Betaine-homocysteine S-methyltransferase 1 OS = Mus musculus GN = Bhmt PE = 1 SV = 1 |
| 39 | 1 | P24270 | 1 | 0.606 | 3.37 | 3.427 | 0.565 | 0.629 | 3.106 | 3.732 | Catalase OS = Mus musculus GN = Cat PE = 1 SV = 4 |
| 40 | 1 | F8VQJ3 | 1 | 0.589 | 3.141 | 3.222 | 0.559 | 0.591 | 2.723 | 3.368 | Laminin subunit gamma-1 OS = Mus musculus GN = Lamc1 PE = 1 SV = 1 |
| 41 | 1 | P35979 | 1 | 0.817 | 3.185 | 2.918 | 0.545 | 0.622 | 2.718 | 3.167 | 60S ribosomal protein L12 OS = Mus musculus GN = Rpl12 PE = 1 SV = 2 |
| 42 | 1 | E9Q0F0 | 1 | 1.094 | 1.235 | 0.783 | 0.652 | 0.524 | 0.83 | 2.297 | Keratin 78 OS = Mus musculus GN = Krt78 PE = 1 SV = 1 |
| 43 | 1 | A0A1B0GSR9 | 1 | 0.599 | 3.14 | 3.281 | 0.451 | 0.587 | 2.911 | 3.571 | L-lactate dehydrogenase OS = Mus musculus GN = Ldha PE = 1 SV = 1 |
| 43 | 2 | P16125 | 1 | 0.614 | 3.417 | 3.424 | 0.491 | 0.548 | 2.825 | 3.633 | L-lactate dehydrogenase B chain OS = Mus musculus GN = Ldhb PE = 1 SV = 2 |
| 44 | 1 | Q3V117 | 1 | 0.706 | 3.971 | 4.041 | 0.551 | 0.65 | 3.59 | 4.242 | ATP-citrate synthase OS = Mus musculus GN = Acly PE = 1 SV = 1 |
| 45 | 1 | Q06890 | 1 | 1.306 | 2.559 | 3.943 | 0.65 | 0.929 | 1.709 | 3.742 | Clusterin OS = Mus musculus GN = Clu PE = 1 SV = 1 |
| 46 | 1 | P62827 | 1 | 0.535 | 3.969 | 3.832 | 0.588 | 0.624 | 3.991 | 4.723 | GTP-binding nuclear protein Ran OS = Mus musculus GN = Ran PE = 1 SV = 3 |
| 47 | 1 | P11983 | 1 | 0.605 | 3.461 | 3.706 | 0.603 | 0.562 | 3.052 | 3.845 | T-complex protein 1 subunit alpha OS = Mus musculus GN = Tcp1 PE = 1 SV = 3 |
| 48 | 1 | P17182 | 1 | 0.499 | 2.205 | 2.195 | 0.396 | 0.419 | 1.789 | 2.184 | Alpha-enolase OS = Mus musculus GN = Eno1 PE = 1 SV = 3 |
| 49 | 1 | Q8BSL7 | 1 | 0.495 | 1.545 | 1.57 | 0.321 | 0.349 | 1.376 | 1.671 | ADP-ribosylation factor 2 OS = Mus musculus GN = Arf2 PE = 1 SV = 2 |
| 50 | 1 | P05784 | 1 | 0.888 | 1.55 | 2.148 | 0.563 | 0.485 | 1.589 | 1.915 | Keratin, type I cytoskeletal 18 OS = Mus musculus GN = Krt18 PE = 1 SV = 5 |
| 51 | 1 | P55937 | 1 | 0.697 | 2.495 | 2.198 | 0.538 | 0.51 | 1.942 | 2.181 | Golgin subfamily A member 3 OS = Mus musculus GN = Golga3 PE = 1 SV = 3 |
| 52 | 1 | P80318 | 1 | 0.584 | 5.751 | 5.943 | 0.645 | 0.613 | 4.809 | 6.133 | T-complex protein 1 subunit gamma OS = Mus musculus GN = Cct3 PE = 1 SV = 1 |
| 53 | 1 | P47738 | 1 | 0.665 | 2.599 | 2.783 | 0.433 | 0.411 | 2.399 | 2.839 | Aldehyde dehydrogenase, mitochondrial OS = Mus musculus GN = Aldh2 PE = 1 SV = 1 |
| 54 | 1 | Q8C483 | 1 | 0.615 | 5.397 | 5.208 | 0.527 | 0.6 | 4.274 | 5.248 | Serine-tRNA ligase, cytoplasmic OS = Mus musculus GN = Sars PE = 1 SV = 1 |
| 55 | 1 | Q61753 | 1 | 0.617 | 4.268 | 3.794 | 0.665 | 0.543 | 3.294 | 3.744 | D-3-phosphoglycerate dehydrogenase OS = Mus musculus GN = Phgdh PE = 1 SV = 3 |
| 56 | 1 | A0A075B5P5 | 1 | 0.9 | 0.713 | 0.622 | 0.896 | 0.913 | 0.526 | 0.562 | Immunoglobulin heavy constant gamma 3 (Fragment) OS = Mus musculus GN = Ighg3 PE = 4 SV = 1 |
| 57 | 1 | P80317 | 1 | 0.66 | 2.494 | 2.42 | 0.466 | 0.696 | 2.041 | 2.439 | T-complex protein 1 subunit zeta OS = Mus musculus GN = Cct6a PE = 1 SV = 3 |
| 58 | 1 | F8VQ40 | 1 | 0.673 | 4.307 | 3.634 | 0.625 | 0.532 | 3.366 | 3.523 | Laminin subunit alpha-1 OS = Mus musculus GN = Lama1 PE = 1 SV = 1 |
| 59 | 1 | P61164 | 1 | 0.722 | 3.698 | 3.748 | 0.827 | 0.979 | 3.399 | 4.202 | Alpha-centractin OS = Mus musculus GN = Actr1a PE = 1 SV = 1 |
| 60 | 1 | P14869 | 1 | 0.534 | 5.899 | 6.377 | 0.489 | 0.497 | 5.955 | 6.89 | 60S acidic ribosomal protein P0 OS = Mus musculus GN = Rplp0 PE = 1 SV = 3 |
| 61 | 1 | G3UY38 | 1 | 0.705 | 4.154 | 4.438 | 0.492 | 0.667 | 3.312 | 4.421 | Heterogeneous nuclear ribonucleoprotein L OS = Mus musculus GN = Hnrnpl PE = 1 SV = 1 |
| 62 | 1 | Q9DBJ1 | 1 | 0.714 | 2.958 | 2.747 | 0.584 | 0.514 | 2.313 | 2.967 | Phosphoglycerate mutase 1 OS = Mus musculus GN = Pgam1 PE = 1 SV = 3 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 63 | 1 | Q00623 | 1 | 0.86 | 10.507 | 11.86 | 0.911 | 0.735 | 8.414 | 11.419 | Apolipoprotein A-I OS = Mus musculus GN = Apoa1 PE = 1 SV = 2 |
| 64 | 1 | H3BL49 | 1 | 0.677 | 5.168 | 4.93 | 0.505 | 0.574 | 4.114 | 5.44 | T-complex protein 1 subunit theta OS = Mus musculus GN = Cct8 PE = 1 SV = 1 |
| 65 | 1 | A0A087WPL5 | 1 | 0.791 | 5.944 | 7.331 | 0.502 | 0.93 | 6.152 | 6.652 | ATP-dependent RNA helicase A OS = Mus musculus GN = Dhx9 PE = 1 SV = 1 |
| 66 | 1 | Q5XJF6 | 1 1 | 0.67 | 5.135 | 5.499 | 0.621 | 0.587 | 5.037 | 5.953 | Ribosomal protein OS = Mus musculus GN = Rpl10a PE = 1 SV = 1 |
| 67 | 1 | B2M1R6 | 1 | 0.339 | 3.136 | 2.928 | 0.346 | 0.64 | 2.275 | 2.869 | Heterogeneous nuclear ribonucleoprotein K OS = Mus musculus GN = Hnrnpk PE = 1 SV = 1 |
| 68 | 1 | P01027 | 1 | 0.758 | 1.291 | 1.298 | 0.716 | 0.786 | 1.026 | 1.333 | Complement C3 OS = Mus musculus GN = C3 PE = 1 SV = 3 |
| 69 | 1 | D3YX34 | 1 | 0.708 | 12.653 | 9.271 | 1.254 | 1.49 | 7.798 | 9.476 | Dynactin subunit 1 OS = Mus musculus GN = Dctn1 PE = 1 SV = 1 |
| 70 | 1 | P09411 | 1 | 0.798 | 3.736 | 3.461 | 0.631 | 0.542 | 2.25 | 2.901 | Phosphoglycerate kinase 1 OS = Mus musculus GN = Pgk1 PE = 1 SV = 4 |
| 71 | 1 | A0A087WR50 | 1 | 1.051 | 1.541 | 2.37 | 0.785 | 0.885 | 1.116 | 1.747 | Fibronectin OS = Mus musculus GN = Fn1 PE = 1 SV = 1 |
| 72 | 1 | Q3U367 | 1 | 0.47 | 2.658 | 2.622 | 0.526 | 0.684 | 2.35 | 2.634 | 4-trimethylaminobutyraldehyde dehydrogenase OS = Mus musculus GN = Aldh9a1 PE = 1 SV = 1 |
| 73 | 1 | Q9CPN9 | 1 | 0.707 | 1.371 | 1.106 | 0.339 | 0.347 | 0.752 | 0.708 | RIKEN cDNA 2210010C04 gene OS = Mus musculus GN = 2210010C04Rik PE = 1 SV = 1 |
| 74 | 1 | P10493 | 1 | 0.472 | 2.974 | 2.984 | 0.412 | 0.485 | 2.449 | 3.146 | Nidogen-1 OS = Mus musculus GN = Nid1 PE = 1 SV = 2 |
| 75 | 1 | A0A140T8P6 | 1 | 0.657 | 1.018 | 0.803 | 0.764 | 0.97 | 0.823 | 1.101 | Immunoglobulin kappa variable 12-46 (Fragment) OS = Mus musculus GN = Igkv12-46 PE = 1 SV = 2 |
| 75 | 2 | A0A140T8Q1 | 1 | 0.849 | 0.604 | 0.577 | 1.073 | 1.247 | 0.449 | 0.425 | Protein Igkv12-41 (Fragment) OS = Mus musculus GN = Igkv12-41 PE = 1 SV = 2 |
| 76 | 1 | A0A075B5K2 | 1 | 0.719 | 0.488 | 0.496 | 0.856 | 0.858 | 0.341 | 0.379 | Immunoglobulin kappa chain variable 9-124 OS = Mus musculus GN = Igkv9-124 PE = 1 SV = 7 |
| 77 | 1 | Q8C196 | 1 | 0.633 | 2.958 | 3.227 | 0.469 | 0.478 | 2.679 | 3.558 | Carbamoyl-phosphate synthase [ammonia], mitochondrial OS = Mus musculus GN = Cps1 PE = 1 SV = 2 |
| 78 | 1 | P80313 | 1 | 0.704 | 2.255 | 2.089 | 0.558 | 0.556 | 1.829 | 2.158 | T-complex protein 1 subunit eta OS = Mus musculus GN = Cct7 PE = 1 SV = 1 |
| 79 | 1 | P12023 | 1 | 1.207 | 1.775 | 3.393 | 0.44 | 1.229 | 1.115 | 4.568 | Amyloid-beta A4 protein OS = Mus musculus GN = App PE = 1 SV = 3 |
| 80 | 1 | D6RGQ0 | 1 | 0.893 | 0.923 | 0.899 | 0.761 | 0.869 | 0.842 | 0.816 | Complement factor H OS = Mus musculus GN = Cfh PE = 1 SV = 1 |
| 81 | 1 | P20918 | 1 | 0.973 | 0.987 | 0.903 | 0.983 | 1.044 | 0.756 | 0.879 | Plasminogen OS = Mus musculus GN = Plg PE = 1 SV = 3 |
| 82 | 1 | P60122 | 1 | 0.608 | 2.081 | 1.961 | 0.469 | 0.544 | 1.597 | 2.044 | RuvB-like 1 OS = Mus musculus GN = Ruvbl1 PE = 1 SV = 1 |
| 83 | 1 | P01786 | 1 | 0.976 | 0.93 | 0.786 | 1.034 | 1.028 | 0.724 | 0.703 | Ig heavy chain V region MOPC 47A OS = Mus musculus PE = 1 SV = 1 |
| 84 | 1 | A0A171KXD3 | 1 | 0.789 | 3.859 | 3.809 | 0.616 | 0.553 | 3.271 | 4.228 | Protein arginine N-methyltransferase 1 OS = Mus musculus GN = Prmt1 PE = 1 SV = 1 |
| 85 | 1 | O70475 | 1 | 0.596 | 2.177 | 1.917 | 0.367 | 0.574 | 1.929 | 2.18 | UDP-glucose 6-dehydrogenase OS = Mus musculus GN = Ugdh PE = 1 SV = 1 |
| 86 | 1 | O70310 | 1 | 0.643 | 2.454 | 2.24 | 0.699 | 0.691 | 2.047 | 2.201 | Glycylpeptide N-tetradecanoyltransferase 1 OS = Mus musculus GN = Nmt1 PE = 1 SV = 1 |
| 87 | 1 | A0A140T8V5 | 1 | 0.73 | 3.129 | 3.124 | 0.687 | 0.803 | 2.62 | 3.306 | Proliferating cell nuclear antigen OS = Mus musculus GN = Pcna-ps2 PE = 3 SV = 1 |
| 88 | 1 | A0A0U1RNJ1 | 1 | 0.789 | 3.48 | 3.49 | 0.568 | 0.494 | 3.075 | 3.575 | Fatty acid synthase OS = Mus musculus GN = Fasn PE = 1 SV = 1 |
| 89 | 1 | P19324 | 1 | 0.505 | 2.255 | 2.356 | 0.447 | 0.413 | 2.045 | 2.588 | Serpin H1 OS = Mus musculus GN = Serpinh1 PE = 1 SV = 3 |
| 90 | 1 | Q9CQ62 | 1 | 0.557 | 2.269 | 2.301 | 0.284 | 0.366 | 1.91 | 2.611 | 2,4-dienoyl-CoA reductase, mitochondrial OS = Mus musculus GN = Decr1 PE = 1 SV = 1 |
| 91 | 1 | G3X8Q5 | 1 | 0.837 | 0.468 | 0.388 | 0.696 | 0.931 | 0.347 | 0.436 | Ceruloplasmin OS = Mus musculus GN = Cp PE = 1 SV = 1 |
| 92 | 1 | G3UXL2 | 1 | 0.23 | 0.995 | 0.713 | 0.168 | 0.213 | 0.818 | 0.931 | Phosphoribosyl pyrophosphate synthetase 1-like 3 OS = Mus musculus GN = Prps1l3 PE = 3 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 93 | 1 | A0A140LI59 | 1 | 0.679 | 1.403 | 0.984 | 0.391 | 0.608 | 0.956 | 1.137 | Deleted in malignant brain tumors 1 protein OS = Mus musculus GN = Dmbt1 PE = 1 SV = 1 |
| 94 | 1 | A0A0G2JE99 | 1 | 1.075 | 0.737 | 0.674 | 1.146 | 1.166 | 0.662 | 0.884 | Immunoglobulin lambda constant 1 (Fragment) OS = Mus musculus GN = Iglc1 PE = 4 SV = 1 |
| 95 | 1 | P70168 | 1 | 0.404 | 1.805 | 1.796 | 0.316 | 0.235 | 1.571 | 1.906 | Importin subunit beta-1 OS = Mus musculus GN = Kpnb1 PE = 1 SV = 2 |
| 96 | 1 | P52196 | 1 | 0.484 | 4.304 | 4.508 | 0.806 | 0.39 | 3.105 | 4.241 | Thiosulfate sulfurtransferase OS = Mus musculus GN = Tst PE = 1 SV = 3 |
| 97 | 1 | A0A140T8N9 | 1 | 0.988 | 0.246 | 0.208 | 0.999 | 1.139 | 0.203 | 0.196 | Immunoglobulin kappa variable 6-32 (Fragment) OS = Mus musculus GN = Igkv6-32 PE-4 SV = 2 |
| 98 | 1 | D3YYM6 | 1 | 0.765 | 3.263 | 3.719 | 0.878 | 1.101 | 3.14 | 3.89 | 40S ribosomal protein S5 (Fragment) OS = Mus musculus GN = Rps5 PE = 1 SV = 1 |
| 99 | 1 | P62908 | 1 | 0.529 | 3.92 | 4.071 | 0.491 | 0.533 | 3.44 | 4.57 | 40S ribosomal protein S3 OS = Mus musculus GN = Rps3 PE = 1 SV = 1 |
| 100 | 1 | Q9ERK4 | 1 | 0.669 | 7.384 | 8.429 | 0.701 | 0.659 | 5.471 | 8.396 | Exportin-2 OS = Mus musculus GN = Cse1l PE = 1 SV = 1 |
| 101 | 1 | P28665 | 1 | 0.906 | 0.755 | 0.583 | 0.864 | 0.837 | 0.447 | 0.473 | Murinoglobulin-1 OS = Mus musculus GN = Mug1 PE = 1 SV = 3 |
| 102 | 1 | P62264 | 1 | 0.704 | 3.021 | 2.647 | 0.5 | 0.58 | 2.435 | 3.4 | 40S ribosomal protein S14 OS = Mus musculus GN = Rps14 PE = 1 SV = 3 |
| 103 | 1 | P31254 | 1 | 0.694 | 2.673 | 3.007 | 0.445 | 0.364 | 2.462 | 3.477 | Ubiquitin-like modifier-activating enzyme 1 Y OS = Mus musculus GN = Uba1y PE = 1 SV = 2 |
| 104 | 1 | G5E866 | 1 | 0.72 | 1.673 | 1.776 | 0.349 | 0.484 | 1.517 | 1.707 | Splicing factor 3B subunit 1 OS = Mus musculus GN = Sf3b1 PE = 1 SV = 1 |
| 105 | 1 | E9Q035 | 1 | 0.776 | 0.456 | 0.52 | 0.739 | 0.757 | 0.436 | 0.371 | Predicted gene 20425 OS = Mus musculus GN = Gm20425 PE = 4 SV = 1 |
| 106 | 1 | P24549 | 1 | 0.713 | 5.531 | 5.654 | 0.547 | 0.572 | 4.672 | 5.436 | Retinal dehydrogenase 1 OS = Mus musculus GN = Aldh1a1 PE = 1 SV = 5 |
| 107 | 1 | A0A140T8N0 | 1 | 0.712 | 0.639 | 0.79 | 1.113 | 0.761 | 0.457 | 0.467 | Immunoglobulin kappa chain variable 9-120 (Fragment) OS = Mus musculus GN = Igkv9-120 PE = 1 SV = 2 |
| 108 | 1 | A0A075B5K8 | 1 | 0.891 | 0.183 | 0.175 | 0.782 | 0.913 | 0.235 | 0.151 | Immunoglobulin kappa variable 1-99 OS = Mus musculus GN = Igkv1-99 PE = 4 SV = 7 |
| 109 | 1 | P07759 | 1 | 0.955 | 0.782 | 0.945 | 0.858 | 0.934 | 0.95 | 1.165 | Serine protease inhibitor A3K OS = Mus musculus GN = Serpina3k PE = 1 SV = 2 |
| 110 | 1 | F6VW30 | 1 | 0.683 | 2.926 | 2.422 | 0.438 | 0.62 | 1.985 | 2.674 | 14-3-3 protein theta (Fragment) OS = Mus musculus GN = Ywhaq PE = 1 SV = 1 |
| 111 | 1 | E9Q0U1 | 1 | 0.955 | 0.997 | 0.996 | 0.254 | 0.189 | 0.632 | 0.97 | 26S proteasome non-ATPase regulatory subunit 13 OS = Mus musculus GN = Psmd13 PE = 1 SV = 1 |
| 112 | 1 | Q8R1B4 | 1 | 0.281 | 1.054 | 0.914 | 0.236 | 0.315 | 0.96 | 1.002 | Eukaryotic translation initiation factor 3 subunit C OS = Mus musculus GN = Eif3c PE = 1 SV = 1 |
| 113 | 1 | P60843 | 1 | 0.617 | 3.747 | 3.945 | 0.571 | 0.554 | 2.78 | 3.653 | Eukaryotic initiation factor 4A-I OS = Mus musculus GN = Eif4a1 PE = 1 SV = 1 |
| 114 | 1 | Q9DCH4 | 1 | 0.378 | 3.567 | 3.033 | 0.607 | 0.519 | 2.683 | 3.151 | Eukaryotic translation initiation factor 3 subunit F OS = Mus musculus GN = Eif3f PE = 1 SV = 2 |
| 115 | 1 | Q8VDM4 | 1 | 0.322 | 0.882 | 1.196 | 0.279 | 0.354 | 0.932 | 1.387 | 26S proteasome non-ATPase regulatory subunit 2 OS = Mus musculus GN = Psmd2 PE = 1 SV = 1 |
| 116 | 1 | A0A075B666 | 1 | 0.857 | 0.479 | 0.496 | 0.876 | 0.966 | 0.539 | 0.582 | Immunoglobulin kappa chain variable 13-85 (Fragment) OS = Mus musculus GN = Igkv13-85 PE-4 SV = 5 |
| 117 | 1 | Q99LF4 | 1 | 0.711 | 1.252 | 1.032 | 0.705 | 0.754 | 0.765 | 0.844 | tRNA-splicing ligase RtcB homolog OS = Mus musculus GN = Rtcb PE = 1 SV = 1 |
| 118 | 1 | E9QN70 | 1 | 0.691 | 5.329 | 5.611 | 0.373 | 0.241 | 4.703 | 5.203 | Laminin subunit beta-1 OS = Mus musculus GN = Lamb1 PE = 1 SV = 1 |
| 119 | 1 | P01675 | 1 | 0.863 | 1.7 | 1.759 | 1.09 | 0.799 | 1.768 | 1.771 | Ig kappa chain V-VI region XRPC 44 OS = Mus musculus PE = 1 SV = 1 |
| 120 | 1 | P56480 | 1 | 0.622 | 2.126 | 2.174 | 0.312 | 0.293 | 1.758 | 1.902 | ATP synthase subunit beta, mitochondrial OS = Mus musculus GN = Atp5b PE = 1 SV = 2 |
| 121 | 1 | A0A075B5Q4 | 1 | 0.907 | 1.108 | 0.961 | 0.849 | 0.878 | 0.776 | 1.366 | Immunoglobulin heavy variable 5-12 (Fragment) OS = Mus musculus GN = Ighv5-12 PE = 4 SV = 1 |
| 122 | 1 | P01806 | 1 | 0.897 | 0.85 | 0.663 | 1.175 | 1.18 | 0.639 | 0.615 | Ig heavy chain V region 441 OS = Mus musculus PE = 4 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 122 | 2 | P18524 | 1 | 1.131 | 1.305 | 1.188 | 2.4 | 2.359 | 1.014 | 1.061 | Ig heavy chain V region RF OS = Mus musculus PE = 1 SV = 1 |
| 123 | 1 | D3YYB1 | 1 | 0.472 | 6.722 | 7.098 | 0.94 | 1.072 | 5.336 | 6.996 | Septin-2 (Fragment) OS = Mus musculus GN = Sept2 PE = 1 SV = 1 |
| 124 | 1 | A0A075B5K1 | 1 | 1.467 | 0.646 | 0.456 | 1.598 | 1.499 | 0.467 | 0.483 | Immunoglobulin kappa variable 11-125 OS = Mus musculus GN = Igkv11-125 PE-4 SV = 7 |
| 125 | 1 | A0A075B663 | 1 | 0.962 | 0.392 | 0.334 | 1.195 | 1.289 | 0.303 | 0.335 | Immunoglobulin lambda variable 1 (Fragment) OS = Mus musculus GN = Iglv1 PE = 4 SV = 1 |
| 126 | 1 | Q8R2K3 | 1 | 0.387 | 2.152 | 2.022 | 0.453 | 0.309 | 1.458 | 1.69 | Single-stranded DNA binding protein 1 OS = Mus musculus GN = Ssbp1 PE = 1 SV = 1 |
| 127 | 1 | Q6ZWY9 | 1 | 0.825 | 1.189 | 1.261 | 0.755 | 0.77 | 0.965 | 1.144 | Histone H2B type 1-C/E/G OS = Mus musculus GN = Hist1h2bc PE = 1 SV = 3 |
| 128 | 1 | A0A0R4J039 | 1 | 0.531 | 0.504 | 0.44 | 0.415 | 0.459 | 0.324 | 0.453 | Histidine-rich glycoprotein OS = Mus musculus GN = Hrg PE = 1 SV = 1 |
| 129 | 1 | Q3U741 | 1 | 0.367 | 2.749 | 2.768 | 0.314 | 0.319 | 2.176 | 2.404 | DEAD (Asp-Glu-Ala-Asp) box polypeptide 17, isoform CRA_a OS-Mus musculus GN = Ddx17 PE = 1 SV = 1 |
| 130 | 1 | A0A0G2JGC1 | 1 | 0.642 | 2.827 | 2.814 | 0.679 | 0.43 | 2.401 | 2.729 | Serine/threonine-protein phosphatase OS = Mus musculus GN = Ppp1cc PE = 1 SV = 1 |
| 131 | 1 | A0A0A0MQ68 | 1 | 0.266 | 7.236 | 6.761 | 0.403 | 0.189 | 3.793 | 7.116 | Glutaryl-CoA dehydrogenase, mitochondrial OS = Mus musculus GN = Gcdh PE = 1 SV = 1 |
| 132 | 1 | Q9CXY6 | 1 | 0.299 | 0.953 | 1.028 | 0.171 | 0.201 | 0.822 | 1.052 | Interleukin enhancer-binding factor 2 OS = Mus musculus GN = Ilf2 PE = 1 SV = 1 |
| 133 | 1 | Q91VC3 | 1 | 0.595 | 2.581 | 1.984 | 0.6 | 0.621 | 2.076 | 2.196 | Eukaryotic initiation factor 4A-III OS = Mus musculus GN = Eif4a3 PE = 1 SV = 3 |
| 134 | 1 | D3YVB4 | 1 | 1.095 | 2.686 | 3.063 | 0.881 | 0.525 | 2.888 | 3.237 | 40S ribosomal protein S15a (Fragment) OS = Mus musculus GN = Rps15a PE = 1 SV = 1 |
| 135 | 1 | Q3TYH2 | 1 | 0.382 | 1.547 | 1.566 | 0.432 | 0.517 | 1.304 | 1.603 | Ras-related protein Rab-15 OS = Mus musculus GN = Rab15 PE = 1 SV = 1 |
| 136 | 1 | A0A0B4J1I1 | 1 | 0.922 | 0.624 | 0.773 | 0.652 | 0.356 | 0.297 | 0.634 | Immunoglobulin kappa variable 16-104 (Fragment) OS = Mus musculus GN = Igkv16-104 PE = 4 SV = 1 |
| 137 | 1 | P60229 | 1 | 0.576 | 1.577 | 1.379 | 0.594 | 0.613 | 1.597 | 1.421 | Eukaryotic translation initiation factor 3 subunit E OS = Mus musculus GN = Eif3e PE = 1 SV = 1 |
| 138 | 1 | A2AL12 | 1 | 0.827 | 3.032 | 3.011 | 0.54 | 0.53 | 2.714 | 3.239 | Heterogeneous nuclear ribonucleoprotein A3 OS = Mus musculus GN = Hnrnpa3 PE = 1 SV = 1 |
| 139 | 1 | A0A0B4J1H7 | 1 | 0.887 | 0.515 | 0.447 | 0.789 | 0.824 | 0.424 | 0.487 | Immunoglobulin kappa variable 1-135 (Fragment) OS = Mus musculus GN = Igkv1-135 PE = 4 SV = 1 |
| 140 | 1 | A0A0G2JFB4 | 1 | 0.629 | 2.67 | 2.762 | 0.503 | 0.501 | 3.114 | 3.355 | Eukaryotic translation initiation factor 4E OS = Mus musculus GN = Eif4e PE = 1 SV = 1 |
| 141 | 1 | A2AWQ2 | 1 | 0.206 | 0.921 | 0.599 | 0.155 | 0.349 | 0.649 | 0.649 | Protein RCC2 (Fragment) OS = Mus musculus GN = Rcc2 PE = 1 SV = 1 |
| 142 | 1 | Q8BGQ7 | I | 0.555 | 2.945 | 2.891 | 0.412 | 0.567 | 2.559 | 2.638 | Alanine-tRNA ligase, cytoplasmic OS = Mus musculus GN = Aars PE = 1 SV = 1 |
| 143 | 1 | Q9CWJ9 | 1 | 0.716 | 1.491 | 1.223 | 0.546 | 0.696 | 1.099 | 1.417 | Bifunctional purine biosynthesis protein PURH OS = Mus musculus GN = Atic PE = 1 SV = 2 |
| 144 | 1 | A0A075B5V1 | 1 | 0.808 | 0.458 | 0.317 | 1.218 | 1.466 | 0.283 | 0.265 | Immunoglobulin heavy variable 1-31 OS = Mus musculus GN = Ighv1-31 PE-4 SV = 1 |
| 145 | 1 | Q8BWT1 | 1 | 0.344 | 2.253 | 2.21 | 0.218 | 0.285 | 1.806 | 2.223 | 3-ketoacyl-CoA thiolase, mitochondrial OS = Mus musculus GN = Acaa2 PE = 1 SV = 3 |
| 146 | 1 | Q8BH00 | 1 | 0.558 | 3.014 | 2.803 | 0.585 | 0.525 | 2.783 | 3.523 | Aldehyde dehydrogenase family 8 member A1 OS = Mus musculus GN = Aldh8a1 PE = 1 SV = 1 |
| 147 | 1 | A0A0R4J1E2 | 1 | 0.674 | 2.127 | 2.067 | 0.493 | 0.615 | 1.481 | 1.7 | Elongation factor 1-delta OS = Mus musculus GN = Eef1d PE = 1 SV = 1 |
| 148 | 1 | Q3THK7 | 1 | 0.747 | 2.58 | 2.592 | 0.699 | 0.653 | 2.124 | 2.54 | GMP synthase [glutamine-hydrolyzing] OS = Mus musculus GN = Gmps PE = 1 SV = 2 |
| 149 | 1 | Q3UH59 | 1 | 0.545 | 2.477 | 1.898 | 0.313 | 0.308 | 1.684 | 2.31 | Myosin-10 OS = Mus musculus GN = Myh10 PE = 1 SV = 1 |
| 149 | 2 | Q8VDD5 | 1 | 0.936 | 2.228 | 1.89 | 0.624 | 0.47 | 1.638 | 1.937 | Myosin-9 OS = Mus musculus GN = Myh9 PE = 1 SV = 4 |
| 150 | 1 | D3YVC1 | 1 | 0.693 | 3.287 | 3.337 | 0.493 | 0.586 | 3.002 | 3.478 | 40S ribosomal protein S2 (Fragment) OS = Mus musculus GN = Rps2 PE = 1 SV = 1 |

TABLE 3-continued

CA19-9 IP/MS data from C; $R^{LSL}$; F or genetic megative organoid (A220 and A217, respectively) conditioned media after 8 hours of Dox treatment.

| Family | Member | UniProt_ mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 151 | 1 | Q9EPL8 | 1 | 0.552 | 1.741 | 2.393 | 0.382 | 0.335 | 1.635 | 2.319 | Importin-7 OS = Mus musculus GN = Ipo7 PE = 1 SV = 2 |
| 152 | 1 | Q04447 | 1 | 0.673 | 3.09 | 2.713 | 0.421 | 0.685 | 1.888 | 2.804 | Creatine kinase B-type OS = Mus musculus GN = Ckb PE = 1 SV = 1 |
| 153 | 1 | P62855 | 1 | 0.977 | 2.823 | 2.867 | 0.462 | 0.523 | 2.057 | 3.891 | 40S ribosomal protein S26 OS = Mus musculus GN = Rps26 PE = 1 SV = 3 |
| 154 | 1 | A0A087WS46 | 1 | 0.558 | 3.435 | 2.962 | 0.703 | 0.676 | 2.743 | 3.453 | Eukaryotic translation elongation factor 1 beta 2 OS = Mus musculus GN = Eef1b2 PE = 1 SV = 1 |
| 155 | 1 | P60766 | 1 | 0.616 | 2.402 | 2.179 | 0.408 | 0.421 | 1.597 | 1.894 | Cell division control protein 42 homolog OS = Mus musculus GN = Cdc42 PE = 1 SV = 2 |
| 156 | 1 | A0A140LIM5 | 1 | 0.545 | 2.759 | 2.667 | 0.612 | 0.472 | 2.019 | 2.837 | Mitotic checkpoint protein BUB3 OS = Mus musculus GN = Bub3 PE = 1 SV = 1 |
| 157 | 1 | A0A140T8N7 | 1 | 1.052 | 0.316 | 0.258 | 1.19 | 1.444 | 0.253 | 0.242 | Immunoglobulin kappa chain variable 6-25 (Fragment) OS-Mus musculus GN = Igkv6-25 PE = 4 SV = 2 |
| 157 | 2 | A0A075B5N7 | 1 | 0.954 | 0.267 | 0.215 | 0.888 | 1.086 | 0.212 | 0.215 | Immunoglobulin kappa variable 6-13 OS = Mus musculus GN = Igkv6-13 PE = 1 SV = 7 |
| 158 | 1 | Q91X72 | 1 | 0.661 | 1.347 | 0.697 | 0.662 | 0.941 | 0.649 | 0.738 | Hemopexin OS = Mus musculus GN = Hpx PE = 1 SV = 2 |
| 159 | 1 | A0A075B5R4 | 1 | 0.829 | 0.575 | 0.568 | 0.922 | 0.843 | 0.55 | 0.593 | Immunoglobulin heavy variable 14-1 (Fragment) OS = Mus musculus GN = Ighv14-1 PE = 4 SV = 1 |
| 160 | 1 | A0A1L1SST0 | 1 | 0.683 | 4.099 | 4.39 | 0.552 | 0.821 | 4.053 | 5.038 | Peptidyl-prolyl cis-trans isomerase OS = Mus musculus GN = Ppia PE = 1 SV = 1 |
| 161 | 1 | A0A075B5M7 | 1 | 1.107 | 0.336 | 0.388 | 0.968 | 1.205 | 0.432 | 0.271 | Immunoglobulin kappa variable 5-39 OS = Mus musculus GN = Igkv5-39 PE = 1 SV = 7 |
| 162 | 1 | P62305 | 1 | 0.459 | 1.19 | 0.955 | 0.438 | 0.41 | 0.906 | 0.912 | Small nuclear ribonucleoprotein E OS = Mus musculus GN = Snrpe PE = 1 SV = 1 |
| 163 | 1 | P97351 | 1 | 0.664 | 2.005 | 1.73 | 0.438 | 0.376 | 1.336 | 1.611 | 40S ribosomal protein S3a OS = Mus musculus GN = Rps3a PE = 1 SV = 3 |
| 164 | 1 | A0A087WP24 | 1 | 0.215 | 1.002 | 0.804 | 0.112 | 0.059 | 0.712 | 0.874 | Protein ABHD14B (Fragment) OS = Mus musculus GN = Abhd14b PE = 1 SV = 1 |
| 165 | 1 | I7HIQ2 | 1 | 0.734 | 1.17 | 1.547 | 0.587 | 0.983 | 1.072 | 1.996 | C-X-C motif chemokine 16 (Fragment) OS = Mus musculus GN = Cxcl16 PE = 1 SV = 1 |
| 166 | 1 | A0A0A6YW67 | 1 | 0.699 | 2.344 | 1.81 | 0.54 | 0.718 | 1.418 | 1.512 | MCG23377, isoform CRA_b OS = Mus musculus GN = Gm8797 PE = 4 SV = 1 |
| 167 | 1 | Q3U2G2 | 1 | 0.934 | 3.186 | 2.905 | 0.746 | 0.588 | 2.703 | 3.188 | Heat shock 70 kDa protein 4 OS = Mus musculus GN = Hspa4 PE = 1 SV = 1 |
| 168 | 1 | A0A0G2JGQ8 | 1 | 0.871 | 0.426 | 0.359 | 0.703 | 0.649 | 0.434 | 0.483 | Ig lambda-3 chain C region (Fragment) OS = Mus musculus GN = Iglc3 PE = 1 SV = 1 |
| 169 | 1 | A0A075B5W4 | 1 | 1.101 | 0.186 | 0.152 | 1.099 | 1.097 | 0.112 | 0.183 | Immunoglobulin heavy variable V8-6 OS = Mus musculus GN = Ighv8-6 PE = 4 SV = 1 |
| 170 | 1 | A0A0R4J038 | 1 | 0.761 | 1.46 | 0.879 | 0.92 | 0.956 | 0.865 | 1.951 | Kininogen-1 OS = Mus musculus GN = Kng1 PE = 1 SV = 1 |
| 171 | 1 | A0A1W2P733 | 1 | 0.613 | 1.997 | 1.523 | 0.458 | 0.53 | 1.294 | 1.772 | C-1-tetrahydrofolate synthase, cytoplasmic OS = Mus musculus GN = Mthfd1 PE = 1 SV = 1 |
| 172 | 1 | G3UY93 | 1 | 0.387 | 3.882 | 3.251 | 0.396 | 0.362 | 3.07 | 3.604 | Valine-tRNA ligase (Fragment) OS = Mus musculus GN = Vars PE = 1 SV = 1 |
| 173 | 1 | P63325 | 1 | 0.825 | 2.226 | 2.15 | 0.775 | 0.663 | 1.537 | 1.784 | 40S ribosomal protein S10 OS = Mus musculus GN = Rps10 PE = 1 SV = 1 |
| 174 | 1 | Q01853 | 1 | 0.773 | 1.352 | 1.814 | 0.443 | 0.536 | 1.283 | 1.618 | Transitional endoplasmic reticulum ATPase OS = Mus musculus GN = Vcp PE = 1 SV = 4 |
| 175 | 1 | P23116 | 1 | 0.436 | 3.536 | 3.66 | 0.572 | 0.598 | 3.444 | 4.49 | Eukaryotic translation initiation factor 3 subunit A OS = Mus musculus GN = Eif3a PE = 1 SV = 5 |
| 176 | 1 | O88844 | 1 | 0.735 | 3.39 | 2.947 | 0.536 | 0.585 | 2.088 | 2.763 | Isocitrate dehydrogenase [NADP] cytoplasmic OS = Mus musculus GN = Idh1 PE = 1 SV = 2 |
| 177 | 1 | A0A0A6YX19 | 1 | 0.595 | 0.61 | 0.511 | 0.523 | 0.566 | 0.408 | 0.468 | Immunoglobulin heavy variable V6-4 (Fragment) OS = Mus musculus GN = Ighv6-4 PE-4 SV = 1 |
| 178 | 1 | P14131 | 1 | 0.356 | 1.975 | 1.839 | 0.275 | 0.342 | 1.656 | 1.966 | 40S ribosomal protein S16 OS = Mus musculus GN = Rps16 PE = 1 SV = 4 |
| 179 | 1 | Q6P5F9 | 1 | 0.494 | 2.119 | 1.927 | 0.494 | 0.591 | 1.524 | 1.994 | Exportin-1 OS = Mus musculus GN = Xpo1 PE = 1 SV = 1 |
| 180 | 1 | A0A1B0GRW3 | 1 | 0.583 | 8.795 | 9.344 | 0.737 | 1.042 | 8.734 | 8.967 | RuvB-like helicase (Fragment) OS = Mus musculus GN = Ruvbl2 PE = 1 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 181 | 1 | P62715 | 1 | 0.814 | 3.192 | 3.071 | 0.723 | 0.703 | 2.716 | 3.299 | Serine/threonine-protein phosphatase 2A catalytic subunit beta isoform OS = Mus musculus GN = Ppp2cb PE = 1 SV = 1 |
| 182 | 1 | A2A5F5 | 1 | 0.717 | 3.079 | 3.471 | 0.539 | 0.572 | 2.769 | 3.56 | Ras-related protein Rab-5C (Fragment) OS = Mus musculus GN = Rab5c PE = 1 SV = 1 |
| 183 | 1 | P18528 | 1 | 0.679 | 1.187 | 0.387 | 0.957 | 0.939 | 0.369 | 0.366 | Ig heavy chain V region 6.96 OS = Mus musculus PE = 4 SV = 1 |
| 184 | 1 | P40142 | 1 | 0.524 | 2.337 | 1.672 | 0.311 | 0.193 | 1.923 | 1.611 | Transketolase OS = Mus musculus GN = Tkt PE = 1 SV = 1 |
| 185 | 1 | P98086 | 1 | 0.082 | 0.236 | 0.151 | 0.085 | 0.112 | 0.068 | 0.135 | Complement C1q subcomponent subunit A OS = Mus musculus GN = C1qa PE = 1 SV = 2 |
| 186 | 1 | A0A1Y7VKY1 | 1 | 1.04 | 19.293 | 19.615 | 0.837 | 0.935 | 16.389 | 20.137 | MCG116671 OS = Mus musculus GN = mCG_116671 PE = 3 SV = 1 |
| 187 | 1 | H3BKL5 | 1 | 1.564 | 10.925 | 12.367 | 4.29 | 1.025 | 9.639 | 12.804 | 3-ketoacyl-CoA thiolase A, peroxisomal OS = Mus musculus GN = Acaa1a PE = 1 SV = 1 |
| 188 | 1 | A0A075B5S9 | 1 | 0.83 | 0.711 | 0.786 | 3.619 | 3.835 | 0.49 | 0.822 | Immunoglobulin heavy variable 9-4 OS = Mus musculus GN = Ighv9-4 PE-4 SV = 1 |
| 189 | 1 | Q9Z1Z2 | 1 | 0.914 | 3.069 | 2.843 | 0.738 | 0.658 | 2.352 | 2.934 | Serine-threonine kinase receptor-associated protein OS = Mus musculus GN = Strap PE = 1 SV = 2 |
| 190 | 1 | Q9JHU4 | 1 | 0.538 | 1.357 | 1.14 | 0.291 | 0.325 | 1.088 | 1.125 | Cytoplasmic dynein 1 heavy chain 1 OS = Mus musculus GN = Dync1h1 PE = 1 SV = 2 |
| 191 | 1 | Q8BH95 | — | — | — | — | — | — | — | — | Enoyl-CoA hydratase, mitochondrial OS = Mus musculus GN = Echs1 PE = 1 SV = 1 |
| 192 | 1 | Q61171 | 1 | 0.513 | 1.942 | 2.046 | 0.51 | 0.507 | 1.655 | 2.44 | Peroxiredoxin-2 OS = Mus musculus GN = Prdx2 PE = 1 SV = 3 |
| 193 | 1 | P62806 | 1 | 0.796 | 2.562 | 1.797 | 0.521 | 0.859 | 1.499 | 1.654 | Histone H4 OS = Mus musculus GN = Hist1h4a PE = 1 SV = 2 |
| 194 | 1 | I7HFT9 | 1 | 0.714 | 1.104 | 0.895 | 0.69 | 0.525 | 0.933 | 1.072 | Histone H1t OS = Mus musculus GN = Hist1h1t PE = 1 SV = 1 |
| 195 | 1 | Q8JZQ9 | 1 | 0.455 | 1.607 | 1.39 | 0.397 | 0.434 | 1.286 | 1.475 | Eukaryotic translation initiation factor 3 subunit B OS = Mus musculus GN = Eif3b PE = 1 SV = 1 |
| 196 | 1 | P02104 | 1 | 0.977 | 3.916 | 3.568 | 0.602 | 0.812 | 2.878 | 3.735 | Hemoglobin subunit epsilon-Y2 OS = Mus musculus GN = Hbb-y PE = 1 SV = 2 |
| 197 | 1 | O55135 | 1 | 0.402 | 2.848 | 2.479 | — | 0.687 | 1.496 | 2.106 | Eukaryotic translation initiation factor 6 OS = Mus musculus GN = Eif6 PE = 1 SV = 2 |
| 198 | 1 | Q8BHN3 | 1 | 0.476 | 5.616 | 6.225 | 0.867 | 0.631 | 4.305 | 5.769 | Neutral alpha-glucosidase AB OS = Mus musculus GN = Ganab PE = 1 SV = 1 |
| 199 | 1 | Q6PE01 | 1 | 0.17 | 2.914 | 3.131 | 0.62 | 0.396 | 2.697 | 2.906 | U5 small nuclear ribonucleoprotein 40 kDa protein OS = Mus musculus GN = Snrnp40 PE = 1 SV = 1 |
| 200 | 1 | A0A075B6A3 | 1 | 0.975 | 1.966 | 1.423 | 0.844 | 0.928 | 1.037 | 1.596 | Immunoglobulin heavy constant alpha (Fragment) OS = Mus musculus GN = Igha PE = 1 SV = 1 |
| 201 | 1 | P60867 | 1 | 0.708 | 2.743 | 2.328 | 0.777 | 0.754 | 1.677 | 2.143 | 40S ribosomal protein S20 OS = Mus musculus GN = Rps20 PE = 1 SV = 1 |
| 202 | 1 | A0A140T8N2 | 1 | 0.857 | 2.045 | 1.563 | 0.726 | 0.806 | 1.284 | 1.539 | Protein Igkv5-48 (Fragment) OS = Mus musculus GN = Igkv5-48 PE = 1 SV = 2 |
| 203 | 1 | Q8BP47 | 1 | 0.588 | 2.357 | 2.31 | 0.613 | 0.549 | 1.962 | 2.34 | Asparagine-tRNA ligase, cytoplasmic OS = Mus musculus GN = Nars PE = 1 SV = 2 |
| 204 | 1 | A2A7S7 | 1 | 0.659 | 3.017 | 3.098 | 0.412 | 0.505 | 2.508 | 3.12 | Tyrosine-tRNA ligase OS = Mus musculus GN = Yars PE = 1 SV = 1 |
| 205 | 1 | P21614 | 1 | 0.901 | 0.609 | 0.365 | 0.767 | 0.928 | 0.412 | 0.659 | Vitamin D-binding protein OS = Mus musculus GN = Gc PE = 1 SV = 2 |
| 206 | 1 | E9Q718 | 1 | 0.989 | 3.378 | 3.203 | 1.158 | 0.793 | 2.934 | 3.103 | Procollagen-lysine, 2-oxoglutarate 5-dioxygenase 2 OS = Mus musculus GN = Plod2 PE = 1 SV = 1 |
| 207 | 1 | O70514 | 1 | 0.606 | 2.317 | 3.106 | 0.656 | 0.694 | 1.595 | 3.708 | Fibroblast growth factor-binding protein 1 OS = Mus musculus GN = Fgfbp1 PE = 1 SV = 1 |
| 208 | 1 | A0A075B5L8 | 1 | 0.281 | 0.432 | 0.357 | 0.223 | 0.296 | 0.409 | 0.29 | Immunoglobulin kappa variable 4-79 (Fragment) OS = Mus musculus GN = Igkv4-79 PE = 4 SV = 2 |
| 209 | 1 | D3Z5M7 | 1 | 0.588 | 2.844 | 2.785 | 0.425 | 0.758 | 2.348 | 2.342 | Peroxidasin homolog OS = Mus musculus GN = Pxdn PE = 1 SV = 2 |
| 210 | 1 | P63038 | 1 | 0.534 | 1.687 | 1.65 | 0.45 | 0.547 | 1.241 | 1.434 | 60 kDa heat shock protein, mitochondrial OS = Mus musculus GN = Hspd1 PE = 1 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_ mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 211 | 1 | P51150 | 1 | 0.671 | 1.645 | 1.178 | 0.493 | 0.53 | 1.253 | 1.16 | Ras-related protein Rab-7a OS = Mus musculus GN = Rab7a PE = 1 SV = 2 |
| 212 | 1 | P10639 | 1 | 0.442 | 1.254 | 1.833 | 0.368 | 0.353 | 1.19 | 1.885 | Thioredoxin OS = Mus musculus GN = Txn PE = 1 SV = 3 |
| 213 | 1 | D6RDC7 | 1 | 0.487 | 3.274 | 2.775 | — | 0.384 | 2.327 | 3.359 | WD repeat-containing protein 61 OS = Mus musculus GN = Wdr61 PE = 1 SV = 2 |
| 214 | 1 | E9Q7D8 | 1 | 0.527 | 1.612 | 1.444 | 0.596 | 0.547 | 1.503 | 1.84 | Poly(rC)-binding protein 3 OS = Mus musculus GN = Pcbp3 PE = 1 SV = 1 |
| 215 | 1 | P32261 | 1 | 0.345 | 3.046 | 3.193 | 0.421 | 0.408 | 2.519 | 3.052 | Antithrombin-III OS = Mus musculus GN = Serpinc1 PE = 1 SV = 1 |
| 216 | 1 | Q3THE2 | 1 | 1.372 | 6.315 | 5.784 | 0.484 | 0.697 | 4.18 | 5.643 | Myosin regulatory light chain 12B OS = Mus musculus GN = Myl12b PE = 1 SV = 2 |
| 217 | 1 | Q921I9 | 1 | 0.62 | 1.712 | 1.445 | 0.471 | 0.54 | 0.996 | 1.83 | Exosome complex component RRP41 OS = Mus musculus GN = Exosc4 PE = 1 SV = 3 |
| 218 | 1 | A0A0J9YKD4 | 1 | — | 42.422 | 39.008 | 0.894 | 1.008 | 29.919 | 38.247 | Creatine kinase M-type OS = Mus musculus GN = Ckm PE = 1 SV = 1 |
| 219 | 1 | Q9JHU9 | 1 | 0.219 | 1.548 | 1.629 | 0.08 | 0.159 | 1.283 | 1.42 | Inositol-3-phosphate synthase 1 OS = Mus musculus GN = Isyna1 PE = 1 SV = 1 |
| 220 | 1 | A0A075B6D5 | 1 | 0.875 | 0.582 | 0.541 | 1.199 | 1.34 | 0.687 | 0.616 | Immunoglobulin kappa chain variable 19-93 OS = Mus musculus GN = Igkv19-93 PE = 1 SV = 7 |
| 221 | 1 | Q9QWK4 | 1 | 0.536 | 0.774 | 0.455 | 0.655 | 0.456 | 0.67 | 0.55 | CD5 antigen-like OS = Mus musculus GN = Cd5l PE = 1 SV = 3 |
| 222 | 1 | G3X8P9 | 1 | 0.419 | 5.103 | 5.022 | 0.738 | 0.706 | 6.295 | 8.275 | Aldehyde oxidase 1 OS = Mus musculus GN = Aox1 PE = 1 SV = 1 |
| 223 | 1 | Q6PDM2 | 1 | 0.234 | 0.997 | 0.883 | 0.214 | 0.269 | 0.809 | 0.879 | Serine/arginine-rich splicing factor 1 OS = Mus musculus GN = Srsf1 PE = 1 SV = 3 |
| 224 | 1 | Q91VB8 | 1 | 0.45 | 2.337 | 2.3 | 0.669 | 0.478 | 1.884 | 2.099 | Alpha globin 1 OS = Mus musculus GN = Hba-a2 PE = 1 SV = 1 |
| 225 | 1 | P61161 | 1 | 0.405 | 2.223 | 1.903 | 0.48 | 0.544 | 1.744 | 2.012 | Actin-related protein 2 OS = Mus musculus GN = Actr2 PE = 1 SV = 1 |
| 226 | 1 | A0A075B5L7 | 1 | 0.482 | 0.979 | 0.767 | 0.378 | 0.357 | 0.933 | 1.005 | Immunoglobulin kappa variable 4-80 (Fragment) OS = Mus musculus GN = Igkv4-80 PE = 4 SV = 2 |
| 227 | 1 | E9Q1G8 | 1 | 0.56 | 1.883 | 2.321 | 0.478 | 0.501 | 1.933 | 2.256 | Septin-7 OS = Mus musculus GN = Sept7 PE = 1 SV = 2 |
| 228 | 1 | D3YUG4 | 1 | 0.582 | 3.576 | 2.537 | 0.67 | 0.469 | 2.335 | 2.531 | Acyl-protein thioesterase 1 (Fragment) OS = Mus musculus GN = Lypla1 PE = 1 SV = 1 |
| 229 | 1 | Q8R317 | 1 | 0.684 | 1.305 | 0.595 | 0.631 | 0.572 | 0.798 | 1.503 | Ubiquilin-1 OS = Mus musculus GN = Ubqln1 PE = 1 SV = 1 |
| 230 | 1 | P27641 | 1 | — | 3.472 | 3.891 | — | — | 3.988 | 5.176 | X-ray repair cross-complementing protein 5 OS = Mus musculus GN = Xrcc5 PE = 1 SV = 4 |
| 231 | 1 | Q6ZQ38 | 1 | 0.164 | 2.632 | 2.648 | 0.324 | 0.369 | 1.833 | 2.094 | Cullin-associated NEDD8-dissociated protein 1 OS = Mus musculus GN = Cand1 PE = 1 SV = 2 |
| 232 | 1 | A0A140T8M4 | 1 | 0.771 | 1.063 | 1.01 | 0.779 | 0.926 | 1.073 | 0.667 | Immunoglobulin kappa variable 8-19 OS = Mus musculus GN = Igkv8-19 PE = 1 SV = 2 |
| 233 | 1 | Q8CIH9 | 1 | 0.848 | 2.005 | 1.656 | 0.543 | 0.891 | 1.507 | 1.925 | Amidophosphoribosyltransferase OS = Mus musculus GN = Ppat PE = 1 SV = 1 |
| 234 | 1 | A0A075B5L2 | 1 | 1.618 | 0.869 | 0.58 | 1.297 | 1.512 | 0.707 | 0.596 | Immunoglobulin kappa chain variable 4-91 (Fragment) OS = Mus musculus GN = Igkv4-91 PE = 4 SV = 2 |
| 235 | 1 | A0A075B5R6 | 1 | 1.07 | 0.084 | 0.118 | 1.421 | 1.81 | — | 0.15 | Immunoglobulin heavy variable 11-1 (Fragment) OS = Mus musculus GN = Ighv11-1 PE = 4 SV = 1 |
| 236 | 1 | A2AFQ2 | 1 | 0.528 | 1.617 | 1.628 | 0.393 | 0.267 | 0.776 | 1.206 | 3-hydroxyacyl-CoA dehydrogenase type-2 OS = Mus musculus GN = Hsd17b10 PE = 1 SV = 1 |
| 237 | 1 | Q8VIJ6 | 1 | 0.874 | 4.604 | 4.737 | 0.799 | 0.654 | 3.735 | 4.567 | Splicing factor, proline- and glutamine-rich OS = Mus musculus GN = Sfpq PE = 1 SV = 1 |
| 238 | 1 | A0A1W2P6P4 | 1 | 0.369 | 0.706 | 0.725 | 0.154 | 0.127 | 0.49 | 0.611 | RNA-binding protein Nova-1 (Fragment) OS = Mus musculus GN = Nova1 PE = 1 SV = 1 |
| 239 | 1 | Q9WU78 | 1 | 1.143 | 1.766 | 1.966 | 3.037 | 0.475 | 1.201 | 1.952 | Programmed cell death 6-interacting protein OS = Mus musculus GN = Pdcd6ip PE = 1 SV = 3 |
| 240 | 1 | A0A1C7ZMZ5 | 1 | 0.65 | 0.989 | 0.86 | 0.52 | 0.8 | 0.668 | 0.655 | Glutathione peroxidase (Fragment) OS = Mus musculus GN = Gpx3 PE = 1 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 241 | 1 | P59016 | 1 | 0.297 | 2.626 | 1.678 | 0.113 | 0.258 | 1.306 | 1.554 | Vacuolar protein sorting-associated protein 33B OS=Mus musculus GN=Vps33b PE=1 SV=1 |
| 242 | 1 | A0A140LJ59 | 1 | 0.838 | 4.938 | 4.606 | 0.474 | 0.435 | 3.987 | 4.082 | Eukaryotic translation initiation factor 3 subunit K OS=Mus musculus GN=Eif3k PE=1 SV=1 |
| 243 | 1 | F6RV17 | 1 | 0.511 | 1.423 | 1.147 | 0.239 | 0.165 | 1.297 | 1.313 | Serine/threonine-protein phosphatase 2A 55 kDa regulatory subunit B OS=Mus musculus GN=Ppp2r2d PE=1 SV=2 |
| 244 | 1 | Q3TGU7 | 1 | 0.397 | 1.061 | 1.051 | 0.652 | 0.812 | 1.125 | 1.148 | Proliferation-associated 2G4 OS=Mus musculus GN=Pa2g4 PE=1 SV=1 |
| 245 | 1 | A2CEK3 | 1 | 0.555 | 1.813 | 1.523 | 0.433 | 0.504 | 1.154 | 1.418 | Phosphoglucomutase-2 OS=Mus musculus GN=Pgm2 PE=1 SV=1 |
| 246 | 1 | Q8BGJ5 | 1 | 0.466 | 2.224 | 1.5 | 0.319 | 0.486 | 1.944 | 2.36 | MCG13402, isoform CRA_a OS=Mus musculus GN=Ptbp1 PE=1 SV=1 |
| 247 | 1 | Q9CZD3 | 1 | 0.441 | 5.688 | 5.299 | 1.021 | 1.066 | 4.688 | 4.333 | Glycine-tRNA ligase OS=Mus musculus GN=Gars PE=1 SV=1 |
| 248 | 1 | P97310 | 1 | 0.409 | 1.542 | 1.411 | 0.512 | 0.44 | 1.777 | 2.25 | DNA replication licensing factor MCM2 OS=Mus musculus GN=Mcm2 PE=1 SV=3 |
| 249 | 1 | Q64674 | 1 | 0.569 | 2.696 | 3.056 | 0.412 | 0.466 | 2.561 | 3.135 | Spermidine synthase OS=Mus musculus GN=Srm PE=1 SV=1 |
| 250 | 1 | Q6PFB2 | 1 | 0.247 | 9.766 | 9.927 | 0.467 | 0.574 | 8.042 | 9.76 | Rcc1 protein OS=Mus musculus GN=Rcc1 PE=1 SV=1 |
| 251 | 1 | Q3UE92 | 1 | 0.842 | 1.966 | 1.961 | 0.633 | 0.56 | 1.66 | 1.535 | X-prolyl aminopeptidase (Aminopeptidase P) 1, soluble, isoform CRA_b OS=Mus musculus GN=Xpnpep1 PE=1 SV=1 |
| 252 | 1 | A0A1B0GR44 | 1 | 0.616 | 1.44 | 1.073 | 0.53 | 0.469 | 1.068 | 1.077 | U1 small nuclear ribonucleoprotein 70 kDa (Fragment) OS=Mus musculus GN=Snrnp70 PE=1 SV=1 |
| 253 | 1 | A0A1L1SSH9 | 1 | 0.545 | 2.279 | 1.444 | 0.401 | 0.483 | 1.601 | 2.096 | SPARC OS=Mus musculus GN=Sparc PE=1 SV=1 |
| 254 | 1 | Q99KP6 | 1 | 0.411 | 4.136 | 3.436 | 0.514 | 0.591 | 3.364 | 4.537 | Pre-mRNA-processing factor 19 OS=Mus musculus GN=Prpf19 PE=1 SV=1 |
| 255 | 1 | Q9QZD9 |  | 0.455 | 3.088 | 3.321 | 0.427 | 0.338 | 2.689 | 2.871 | Eukaryotic translation initiation factor 3 subunit I OS=Mus musculus GN=Eif3i PE=1 SV=1 |
| 256 | 1 | Q6P5H2 | 1 | 1.712 | 1.513 | 0.707 | 0.553 | 0.582 | 1.036 | 2.072 | Nestin OS=Mus musculus GN=Nes PE=1 SV=1 |
| 257 | 1 | F6RPJ9 | 1 | 0.385 | 1.047 | 0.65 | 0.157 | 0.215 | 0.737 | 0.975 | Insulin-degrading enzyme (Fragment) OS=Mus musculus GN=Ide PE=1 SV=1 |
| 258 | 1 | P52955 | 1 | 0.826 | 0.11 | 0.108 | 0.643 | 0.732 | 0.092 | 0.084 | Transcription factor LBX1 OS=Mus musculus GN=Lbx1 PE=1 SV=2 |
| 259 | 1 | O35988 | — | — | — | — | — | — | — | — | Syndecan-4 OS=Mus musculus GN=Sdc4 PE=1 SV=1 |
| 260 | 1 | P61407 | 1 | 0.823 | 0.571 | 0.525 | 0.185 | 0.224 | 0.299 | — | Tudor domain-containing protein 6 OS=Mus musculus GN=Tdrd6 PE=1 SV=1 |
| 261 | 1 | A0A075B5N4 | 1 | 0.92 | 1.061 | 1.095 | 1.518 | 1.742 | 0.846 | 1.239 | Immunoglobulin kappa chain variable 8-27 OS=Mus musculus GN=Igkv8-27 PE=4 SV=1 |
| 262 | 1 | A0A0B4J1I5 | 1 | 0.818 | 0.286 | 0.254 | 0.798 | 0.786 | 0.217 | 0.256 | Immunoglobulin kappa chain variable 4-70 (Fragment) OS=Mus musculus GN=Igkv4-70 PE=4 SV=1 |
| 263 | 1 | A0A075B5T9 | 1 | 1.1 | 0.778 | 0.907 | 0.606 | 0.542 | 0.474 | 0.52 | Immunoglobulin heavy variable V1-9 OS=Mus musculus GN=Ighv1-9 PE=4 SV=1 |
| 264 | 1 | A0A075B5V8 | 1 | 0.889 | 0.661 | 0.553 | 1.051 | 1.289 | 0.855 | 0.576 | Immunoglobulin heavy variable 1-47 OS=Mus musculus GN=Ighv1-47 PE=4 SV=1 |
| 265 | 1 | A0A0A6YXN4 | 1 | 0.594 | 0.727 | 0.677 | 1.999 | 1.876 | 0.521 | 0.789 | Immunoglobulin heavy variable V1-18 (Fragment) OS=Mus musculus GN=Ighv1-18 PE=1 SV=1 |
| 266 | 1 | Q8VGI4 | 1 | 0.255 | 3.468 | 3.627 | 0.322 | 0.366 | 3.109 | 3.6 | Olfactory receptor 476 OS=Mus musculus GN=Olfr476 PE=3 SV=1 |
| 267 | 1 | Q8VEK3 | 1 | 0.595 | 2.14 | 2.123 | 0.665 | 0.658 | 1.932 | 1.931 | Heterogeneous nuclear ribonucleoprotein U OS=Mus musculus GN=Hnrnpu PE=1 SV=1 |
| 268 | 1 | F8WHL2 | 1 | 0.632 | 2.507 | 1.658 | 0.567 | 0.548 | 1.993 | 2.252 | Coatomer subunit alpha OS=Mus musculus GN=Copa PE=1 SV=1 |
| 269 | 1 | P53994 | 1 | 0.459 | 0.562 | 0.541 | 1.278 | 0.775 | 0.584 | 0.527 | Ras-related protein Rab-2A OS=Mus musculus GN=Rab2a PE=1 SV=1 |
| 270 | 1 | L7MTU6 | 1 | 0.522 | 2.822 | 2.248 | 0.64 | 0.374 | 1.801 | 1.848 | Interferon alpha B OS=Mus musculus GN=Ifnab PE=3 SV=1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 271 | 1 | Q61646 | 1 | 1.119 | 0.356 | 0.181 | 1.098 | 0.849 | 0.214 | 0.467 | Haptoglobin OS = Mus musculus GN = Hp PE = 1 SV = 1 |
| 272 | 1 | B8JK32 | 1 | 0.602 | 1.644 | 1.661 | 0.272 | 0.432 | 1.681 | 2.273 | Heterogeneous nuclear ribonucleoprotein M OS = Mus musculus GN = Hnrnpm PE = 1 SV = 1 |
| 273 | 1 | A2A4J1 | 1 | 0.398 | 3.341 | 3.345 | 0.386 | 0.305 | 1.98 | 2.971 | Proteasome activator complex subunit 3 (Fragment) OS = Mus musculus GN = Psme3 PE = 1 SV = 1 |
| 274 | 1 | Q9D892 | 1 | 0.855 | 1.766 | 2.106 | 0.278 | 0.635 | 1.611 | 2.111 | Inosine triphosphate pyrophosphatase OS = Mus musculus GN = Itpa PE = 1 SV = 2 |
| 275 | 1 | Q8QZY1 | 1 | 0.853 | 3.805 | 3.518 | 0.79 | 1.255 | 2.789 | 3.222 | Eukaryotic translation initiation factor 3 subunit L OS = Mus musculus GN = Eif3l PE = 1 SV = 1 |
| 276 | 1 | Q9JKR6 | 1 | 0.486 | 2.282 | 2.379 | 0.728 | 0.521 | 3.009 | 2.585 | Hypoxia up-regulated protein 1 OS = Mus musculus GN = Hyou1 PE = 1 SV = 1 |
| 277 | 1 | D3Z6N3 | 1 | 0.601 | 1.4 | 1.368 | 0.583 | 0.617 | 1.317 | 1.481 | DNA replication licensing factor MCM7 OS = Mus musculus GN = Mcm7 PE = 1 SV = 1 |
| 278 | 1 | G3UXG7 | 1 | 0.548 | 2.638 | 1.143 | 0.348 | 0.662 | 1.637 | 1.452 | Casein kinase II subunit beta OS = Mus musculus GN = Csnk2b PE = 1 SV = 1 |
| 279 | 1 | Q9D8E6 | 1 | 0.665 | 1.529 | 1.612 | 0.437 | 0.615 | 1.246 | 1.554 | 60S ribosomal protein L4 OS = Mus musculus GN = Rpl4 PE = 1 SV = 3 |
| 280 | 1 | A0A0R4J1N1 | 1 | 0.708 | 0.956 | 0.865 | 0.496 | 0.309 | 0.869 | 0.937 | Inter alpha-trypsin inhibitor, heavy chain 4 OS = Mus musculus GN = Itih4 PE = 1 SV = 1 |
| 281 | 1 | P17751 | 1 | 0.734 | 1.87 | 1.45 | 0.73 | 0.882 | 1.528 | 1.534 | Triosephosphate isomerase OS = Mus musculus GN = Tpi1 PE = 1 SV = 4 |
| 282 | 1 | P62334 | 1 | 0.561 | 1.651 | 1.432 | 0.524 | 0.454 | 1.279 | 1.73 | 26S proteasome regulatory subunit 10B OS = Mus musculus GN = Psmc6 PE = 1 SV = 1 |
| 283 | 1 | Q8C2Q7 | 1 | 0.404 | 3.867 | 2.918 | 0.454 | 0.286 | 2.215 | 2.192 | Heterogeneous nuclear ribonucleoprotein H OS = Mus musculus GN = Hnrnph1 PE = 1 SV = 1 |
| 284 | 1 | S4R1I6 | 1 | 0.563 | 2.671 | 2.6 | 0.786 | 0.709 | 2.209 | 2.164 | MCG2872, isoform CRA_b OS = Mus musculus GN = Ddx5 PE = 1 SV = 1 |
| 286 | 1 | Q6ZWN5 | 1 | 0.849 | 3.088 | 3.404 | 0.637 | 0.586 | 2.497 | 3.102 | 40S ribosomal protein S9 OS = Mus musculus GN = Rps9 PE = 1 SV = 3 |
| 287 | 1 | F6YZU5 | 1 | 0.779 | 1.055 | 1.159 | 0.453 | 0.558 | 0.728 | 0.8 | Disks large homolog 5 (Fragment) OS = Mus musculus GN = Dlg5 PE = 1 SV = 1 |
| 288 | 1 | A2AW05 | 1 | 0.675 | 2.062 | 1.466 | 0.544 | 0.49 | 0.983 | 1.427 | FACT complex subunit SSRP1 (Fragment) OS = Mus musculus GN = Ssrp1 PE = 1 SV = 1 |
| 289 | 1 | A0A0R4J187 | 1 | 0.68 | 1.446 | 1.537 | 0.714 | 0.948 | 0.913 | 1.425 | X-ray repair cross-complementing protein 6 OS = Mus musculus GN = Xrcc6 PE = 1 SV = 1 |
| 290 | 1 | Q9QZE5 | 1 | 0.139 | 1.108 | 1.278 | 0.14 | 0.121 | 1.15 | 1.413 | Coatomer subunit gamma-1 OS = Mus musculus GN-Copg1 PE = 1 SV = 1 |
| 291 | 1 | Q9DB16 | 1 | 1.149 | 1.254 | 1.843 | 0.826 | 4.987 | 1.682 | 1.847 | Calcium-binding protein 39-like OS = Mus musculus GN = Cab39l PE = 1 SV = 3 |
| 292 | 1 | P62962 | 1 | 0.347 | 1.223 | 1.112 | 0.603 | 0.804 | 1.099 | 1.127 | Profilin-1 OS = Mus musculus GN = Pfn1 PE = 1 SV = 2 |
| 293 | 1 | F6XI62 | 1 | 0.74 | 1.544 | 0.92 | 0.223 | 0.435 | 1.142 | 1.34 | 60S ribosomal protein L7 (Fragment) OS = Mus musculus GN = Rpl7 PE = 1 SV = 1 |
| 294 | 1 | F8WIV5 | 1 | 0.248 | 0.84 | 0.965 | 0.206 | 0.165 | 0.74 | 0.913 | Dynamin-2 OS = Mus musculus GN = Dnm2 PE = 1 SV = 2 |
| 295 | 1 | A0A075B5P8 | 1 | 0.916 | 0.462 | 0.425 | 0.92 | 0.975 | 0.391 | 0.424 | Immunoglobulin heavy variable 2-2 (Fragment) OS = Mus musculus GN = Ighv2-2 PE = 4 SV = 1 |
| 296 | 1 | P62702 | 1 | 0.891 | 3.453 | 2.239 | 0.603 | 0.663 | 2.145 | 2.252 | 40S ribosomal protein S4, X isoform OS = Mus musculus GN = Rps4x PE = 1 SV = 2 |
| 297 | 1 | O55142 | 1 | 0.555 | 2.709 | 1.631 | 0.568 | 0.815 | 1.045 | 1.647 | 60S ribosomal protein L35a OS = Mus musculus GN = Rpl35a PE = 1 SV = 2 |
| 298 | 1 | A0A1Y7VJM8 | 1 | 0.388 | 1.598 | 1.726 | 0.381 | 0.35 | 1.092 | 1.161 | Zinc finger protein 934 OS = Mus musculus GN = Zfp934 PE = 4 SV = 1 |
| 299 | 1 | Q9JJN6 | 1 | 1.192 | 2.975 | 3.304 | 1.111 | 0.337 | 1.111 | 0.93 | Beta-catenin-interacting protein 1 OS = Mus musculus GN = Ctnnbip1 PE = 1 SV = 1 |
| 300 | 1 | Q9DCC4 | 1 | 0.614 | 2.17 | 1.789 | 0.831 | 0.195 | 2.244 | 3.024 | Pyrroline-5-carboxylate reductase 3 OS = Mus musculus GN = Pycr3 PE = 1 SV = 2 |
| 301 | 1 | P32233 | 1 | 1 | 0.465 | 1.123 | 0.577 | 0.122 | 0.269 | 0.459 | 0.738 | Developmentally-regulated GTP-binding protein 1 OS = Mus musculus GN = Drg1 PE = 1 SV = 1 |

TABLE 3-continued

CA19-9 IP/MS data from C; R$^{LSL}$; F or genetic megative organoid (A220 and A217, respectively) conditioned media after 8 hours of Dox treatment.

| Family | Member | UniProt_ mouse Accession | 17 0H NS19 | 17 8H NS19 | 17 0H 5B1 | 17 8H 5B1 | 20 0H NS19 | 20 8H NS19 | 20 0H 5B1 | 20 8H 5B1 | Description |
|---|---|---|---|---|---|---|---|---|---|---|---|
| 302 | 1 | D3Z4Q4 | 1 | 0.874 | 1.145 | 1.259 | 0.601 | 0.509 | 0.672 | 0.923 | Quinone oxidoreductase (Fragment) OS = Mus musculus GN = Cryz PE = 1 SV = 1 |
| 303 | 1 | A2AC16 | 1 | 0.626 | 3.389 | 3.384 | 0.57 | 0.268 | 3.272 | 3.683 | Dicarbonyl L-xylulose reductase, isoform CRA_a OS = Mus musculus GN = Dcxr PE = 1 SV = 1 |
| 304 | 1 | Q8BVN8 | 1 | 0.656 | 4.731 | 4.234 | 1.352 | 1.133 | 4.175 | 4.589 | Axonemal dynein light intermediate polypeptide 1 OS-Mus musculus GN-Dnali1 PE = 1 SV = 1 |
| 305 | 1 | Q9D964 | 1 | 0.442 | 1.699 | 1.883 | 0.456 | 0.518 | 1.674 | 1.752 | Glycine amidinotransferase, mitochondrial OS = Mus musculus GN = Gatm PE = 1 SV = 1 |
| 306 | 1 | Q6GQT1 | 1 | 0.494 | 1.798 | 1.95 | 0.154 | 0.214 | 1.105 | 1.629 | Alpha-2-macroglobulin-P OS = Mus musculus GN = A2m PE = 2 SV = 2 |

"17 0H NS19" indicates A217 organoids before treatment with NS19-9;
"17 8H NS19" indicates A217 organoids after 8 hours of treatment with NS19-9;
"17 0H 5B1" indicates A217 organoids before treatment with 51B;
"17 8H 5B1" indicates A217 organoids after 8 hours treatment with 51B;
"20 0H NS19" indicates A220 organoids before treatment with NS19-9;
"20 8H NS19" indicates A220 organoids after 8 hours treatment with NS19-9;
"20 0H 5B1" indicates A220 organoids before treatment with 5B1;
"20 8H 5B1" indicates A220 organoids after 8 hours treatment with 5B1.

TABLE 4

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of Dox treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 1 | 1 | P01868 | 1 | 1.069 | 0.117 | 0.069 | 1.086 | 0.956 | 0.091 | 0.177 | Ig gamma-1 chain C region secreted form OS = Mus musculus GN = Ighg1 PE = 1 SV = 1 |
| 1 | 2 | A0A075B5P4 | 1 | 1.072 | 0.112 | 0.066 | 1.088 | 0.957 | 0.088 | 0.164 | Ig gamma-1 chain C region secreted form (Fragment) OS = Mus musculus GN = Ighg1 PE = 1 SV = 1 |
| 2 | 1 | P01637 | 1 | 1.139 | 0.285 | 0.202 | 2.018 | 1.655 | 0.243 | 0.336 | Ig kappa chain V-V region T1 OS = Mus musculus PE = 4 SV = 1 |
| 2 | 2 | A0A140T8P9 | 1 | 1.105 | 0.31 | 0.166 | 1.879 | 1.578 | 0.207 | 0.29 | Immunoglobulin kappa variable 14-111 (Fragment) OS = Mus musculus GN = Igkv14-111 PE = 4 SV = 2 |
| 3 | 1 | P01837 | 1 | 1.164 | 0.109 | 0.081 | 1.443 | 1.363 | 0.058 | 0.142 | Ig kappa chain C region OS = Mus musculus PE = 1 SV = 1 |
| 3 | 2 | A0A075B5P2 | 1 | 1.153 | 0.107 | 0.081 | 1.433 | 1.347 | 0.058 | 0.141 | Immunoglobulin kappa constant (Fragment) OS = Mus musculus GN = Igkc PE = 1 SV = 1 |
| 4 | 1 | P07724 | 1 | 0.929 | 0.204 | 0.187 | 1.061 | 0.903 | 0.146 | 0.27 | Serum albumin OS = Mus musculus GN = Alb PE = 1 SV = 3 |
| 5 | 1 | P20152 | 1 | 0.542 | 11.23 | 9.977 | 0.724 | 0.767 | 10.68 | 14.82 | Vimentin OS = Mus musculus GN = Vim PE = 1 SV = 3 |
| 5 | 2 | P50446 | 1 | 0.685 | 1.22 | 1.07 | 0.934 | 0.691 | 1.425 | 1.126 | Keratin, type II cytoskeletal 6A OS = Mus musculus GN = Krt6a PE = 1 SV = 3 |
| 5 | 3 | P11679 | 1 | 0.895 | 1.633 | 1.507 | 0.791 | 0.683 | 2.206 | 2.604 | Keratin, type II cytoskeletal 8 OS = Mus musculus GN = Krt8 PE = 1 SV = 4 |
| 5 | 4 | P04104 | 1 | 0.646 | 1.089 | 0.866 | 0.804 | 0.547 | 1.751 | 0.905 | Keratin, type II cytoskeletal 1 OS = Mus musculus GN = Krt1 PE = 1 SV = 4 |
| 5 | 5 | P31001 | 1 | 0.295 | 11.52 | 9.866 | 0.409 | 0.458 | 13.22 | 15.16 | Desmin OS = Mus musculus GN = Des PE = 1 SV = 3 |
| 5 | 6 | Q8VED5 | 1 | 0.851 | 1.532 | 1.103 | 1.045 | 0.696 | 1.186 | 1.292 | Keratin, type II cytoskeletal 79 OS = Mus musculus GN = Krt79 PE = 1 SV = 2 |
| 5 | 7 | Q6NXH9 | 1 | 0.653 | 1.123 | 0.848 | 0.989 | 0.665 | 1.323 | 1.156 | Keratin, type II cytoskeletal 73 OS = Mus musculus GN = Krt73 PE = 1 SV = 1 |
| 5 | 8 | Q9DCV7 | 1 | 0.872 | 1.337 | 1.401 | 0.846 | 0.656 | 1.772 | 2.35 | Keratin, type II cytoskeletal 7 OS = Mus musculus GN = Krt7 PE = 1 SV = 1 |
| 5 | 9 | Q3TTY5 | 1 | 0.754 | 1.446 | 0.913 | 0.921 | 0.753 | 1.105 | 1.215 | Keratin, type II cytoskeletal 1 epidermal OS = Mus musculus GN = Krt2 PE = 1 SV = 1 |
| 5 | 10 | Q3UV17 | 1 | 0.658 | 1.197 | 0.991 | 1.028 | 0.651 | 1.621 | 1.025 | Keratin, type II cytoskeletal 2 oral OS = Mus musculus GN = Krt76 PE = 1 SV = 1 |
| 5 | 11 | P07744 | 1 | 0.82 | 1.422 | 1.192 | 1.102 | 0.83 | 1.561 | 1.751 | Keratin, type II cytoskeletal 4 OS = Mus musculus GN = Krt4 PE = 1 SV = 2 |
| 6 | 1 | A0A075B5T3 | 1 | 1.127 | 0.303 | 0.276 | 1.156 | 1.077 | 0.323 | 0.514 | Immunoglobulin heavy variable 6-6 (Fragment) OS = Mus musculus GN = Ighv6-6 PE = 4 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 6 | 2 | P01796 | 1 | 1.112 | 0.337 | 0.301 | 1.535 | 1.245 | 0.343 | 0.512 | Ig heavy chain V-III region A4 OS = Mus musculus PE = 1 SV = 1 |
| 7 | 1 | P05213 | 1 | 0.75 | 4.685 | 4.035 | 0.727 | 0.665 | 3.521 | 5.493 | Tubulin alpha-1B chain OS = Mus musculus GN = Tuba1b PE = 1 SV = 2 |
| 8 | 1 | P52480 | 1 | 0.571 | 5.34 | 4.177 | 0.653 | 0.569 | 4.463 | 6.417 | Pyruvate kinase PKM OS = Mus musculus GN = Pkm PE = 1 SV = 4 |
| 9 | 1 | P11499 | 1 | 0.818 | 4.865 | 3.988 | 0.922 | 0.76 | 3.98 | 5.618 | Heat shock protein HSP 90-beta OS = Mus musculus GN = Hsp90ab1 PE = 1 SV = 3 |
| 9 | 2 | P07901 | 1 | 0.848 | 3.685 | 3.04 | 0.913 | 0.784 | 2.998 | 4.086 | Heat shock protein HSP 90-alpha OS = Mus musculus GN = Hsp90aa1 PE = 1 SV = 4 |
| 9 | 3 | P08113 | 1 | 0.832 | 3.586 | 2.899 | 0.715 | 0.779 | 3.001 | 3.873 | Endoplasmin OS = Mus musculus GN = Hsp90b1 PE = 1 SV = 2 |
| 10 | 1 | Q68FD5 | 1 | 0.765 | 3.631 | 3.184 | 0.854 | 0.723 | 2.825 | 4.176 | Clathrin heavy chain 1 OS = Mus musculus GN = Cltc PE = 1 SV = 3 |
| 11 | 1 | P26443 | 1 | 0.681 | 8.259 | 6.636 | 0.947 | 0.77 | 6.399 | 8.311 | Glutamate dehydrogenase 1, mitochondrial OS = Mus musculus GN = Glud1 PE = 1 SV = 1 |
| 12 | 1 | A0A075B5P3 | 1 | 0.897 | 0.331 | 0.27 | 0.975 | 0.846 | 0.257 | 0.29 | Immunoglobulin heavy constant gamma 2B (Fragment) OS = Mus musculus GN = Ighg2b PE = 1 SV = 1 |
| 12 | 2 | P01867 | 1 | 0.9 | 0.318 | 0.262 | 0.973 | 0.859 | 0.259 | 0.292 | Ig gamma-2B chain C region OS = Mus musculus GN = Igh-3 PE = 1 SV = 3 |
| 12 | 3 | P01863 | 1 | 0.798 | 0.245 | 0.227 | 0.997 | 0.879 | 0.19 | 0.244 | Ig gamma-2A chain C region, A allele OS = Mus musculus GN = Ighg PE = 1 SV = 1 |
| 13 | 1 | Q61838 | 1 | 0.855 | 0.243 | 0.208 | 0.959 | 0.856 | 0.202 | 0.212 | Pregnancy zone protein OS = Mus musculus GN = Pzp PE = 1 SV = 3 |
| 14 | 1 | P58252 | 1 | 0.737 | 4.985 | 4.221 | 0.824 | 0.806 | 4.117 | 5.373 | Elongation factor 2 OS = Mus musculus GN = Eef2 PE = 1 SV = 2 |
| 14 | 2 | A2AH85 | 1 | 0.776 | 3.331 | 2.779 | 0.634 | 0.659 | 2.615 | 3.589 | 116 kDa U5 small nuclear ribonucleoprotein component OS = Mus musculus GN = Eftud2 PE = 1 SV = 1 |
| 15 | 1 | Q9Z1R9 | 1 | 3.838 | 2.933 | 3.243 | 3.829 | 3.089 | 1.806 | 1.209 | MCG124046 OS = Mus musculus GN = Prss1 PE = 1 SV = 1 |
| 15 | 2 | Q792Y8 | 1 | 3.987 | 2.916 | 3.244 | 3.904 | 3.133 | 1.63 | 1.07 | MCG15081 OS = Mus musculus GN = Gm10334 PE = 3 SV = 1 |
| 15 | 3 | Q792Z1 | 1 | 4.18 | 3.033 | 3.368 | 4.081 | 3.265 | 1.651 | 1.092 | MCG140784 OS = Mus musculus GN = Try 10 PE = 1 SV = 1 |
| 16 | 1 | P63017 | 1 | 0.81 | 5.69 | 4.331 | 0.939 | 0.841 | 4.318 | 6.09 | Heat shock cognate 71 kDa protein OS = Mus musculus GN = Hspa8 PE = 1 SV = 1 |
| 16 | 2 | P17879 | 1 | 0.753 | 4.922 | 3.812 | 0.758 | 1.484 | 3.99 | 5.519 | Heat shock 70 kDa protein 1B OS = Mus musculus GN = Hspa1b PE = 1 SV = 1 |
| 16 | 3 | P16627 | 1 | 0.782 | 5.422 | 4.224 | 0.779 | 1.774 | 4.494 | 6.214 | Heat shock 70 kDa protein 1-like OS = Mus musculus GN = Hspa1l PE = 1 SV = 4 |
| 16 | 4 | P20029 | 1 | 0.697 | 5.037 | 4.064 | 0.821 | 0.688 | 4.271 | 5.732 | 78 kDa glucose-regulated protein OS = Mus musculus GN = Hspa5 PE = 1 SV = 3 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 17 | 1 | P99024 | 1 | 0.963 | 4.791 | 3.931 | 1.143 | 0.766 | 3.722 | 5.468 | Tubulin beta-5 chain OS = Mus musculus GN = Tubb5 PE = 1 SV = 1 |
| 17 | 2 | P68372 | 1 | 0.932 | 4.251 | 3.488 | 1.103 | 0.855 | 3.267 | 4.92 | Tubulin beta-4B chain OS = Mus musculus GN = Tubb4b PE = 1 SV = 1 |
| 18 | 1 | A2A513 | 1 | 0.751 | 1.352 | 0.812 | 0.914 | 0.699 | 1.102 | 1.021 | Keratin, type I cytoskeletal 10 OS = Mus musculus GN = Krt10 PE = 1 SV = 1 |
| 18 | 2 | P19001 | 1 | 0.883 | 1.432 | 1.473 | 0.776 | 0.588 | 1.738 | 1.856 | Keratin, type I cytoskeletal 19 OS = Mus musculus GN = Krt19 PE = 1 SV = 1 |
| 18 | 3 | Q61781 | 1 | 0.845 | 1.295 | 1.106 | 0.917 | 0.816 | 1.16 | 1.543 | Keratin, type I cytoskeletal 14 OS = Mus musculus GN = Krt14 PE = 1 SV = 2 |
| 19 | 1 | P50247 | 1 | 0.586 | 7.664 | 6.361 | 0.736 | 0.693 | 6.445 | 8.288 | Adenosylhomocysteinase OS = Mus musculus GN = Ahcy PE = 1 SV = 3 |
| 20 | 1 | A0A0A0MQF6 | 1 | 0.919 | 7.123 | 6.146 | 1.076 | 0.88 | 5.781 | 8.724 | Glyceraldehyde-3-phosphate dehydrogenase OS = Mus musculus GN = Gapdh PE = 1 SV = 1 |
| 21 | 1 | P14206 | 1 | 0.679 | 3.016 | 2.309 | 0.65 | 0.605 | 2.401 | 3.355 | 40S ribosomal protein SA OS = Mus musculus GN = Rpsa PE = 1 SV = 4 |
| 22 | 1 | O35565 | 1 | 0.798 | 6.656 | 5.286 | 0.898 | 0.87 | 4.8 | 7.394 | Fibroblast growth factor 10 OS = Mus musculus GN = Fgf10 PE = 2 SV = 1 |
| 23 | 1 | A0A140L159 | 1 | 1.507 | 1.729 | 1.959 | 0.882 | 0.721 | 1.57 | 2.088 | Deleted in malignant brain tumors 1 protein OS = Mus musculus GN = Dmbt1 PE = 1 SV = 1 |
| 24 | 1 | Q06890 | 1 | 2.011 | 2.26 | 4.091 | 0.94 | 0.775 | 1.915 | 2.594 | Clusterin OS = Mus musculus GN = Clu PE = 1 SV = 1 |
| 25 | 1 | P97466 | 1 | 0.93 | 24.74 | 21.19 | 1.461 | 1.273 | 19.15 | 25.6 | Noggin OS = Mus musculus GN = Nog PE = 2 SV = 1 |
| 26 | 1 | A0A075B5P6 | 1 | 0.905 | 0.292 | 0.253 | 1.017 | 0.869 | 0.202 | 0.235 | Ig mu chain C region (Fragment) OS = Mus musculus GN = Ighm PE = 1 SV = 1 |
| 27 | 1 | Q07797 | 1 | 0.959 | 3.086 | 2.687 | 0.701 | 0.663 | 7.637 | 10.25 | Galectin-3-binding protein OS = Mus musculus GN = Lgals3bp PE = 1 SV = 1 |
| 28 | 1 | P99027 | 1 | 0.831 | 4.398 | 2.989 | 0.98 | 0.658 | 2.758 | 4.68 | 60S acidic ribosomal protein P2 OS = Mus musculus GN-Rplp2 PE = 1 SV = 3 |
| 29 | 1 | A0A0A0MQA3 | 1 | 0.969 | 0.269 | 0.193 | 0.964 | 0.924 | 0.196 | 0.187 | Alpha-1-antitrypsin 1-1 OS = Mus musculus GN = Serpina1a PE = 1 SV = 1 |
| 29 | 2 | Q00897 | 1 | 0.972 | 0.394 | 0.321 | 0.983 | 0.908 | 0.309 | 0.33 | Alpha-1-antitrypsin 1-4 OS = Mus musculus GN = Serpina1d PE = 1 SV = 1 |
| 29 | 3 | P22599 | 1 | 0.937 | 0.321 | 0.218 | 0.935 | 0.901 | 0.227 | 0.203 | Alpha-1-antitrypsin 1-2 OS = Mus musculus GN = Serpina1b PE = 1 SV = 2 |
| 30 | 1 | P01654 | 1 | 0.889 | 0.884 | 0.741 | 1.005 | 0.828 | 0.759 | 0.816 | Ig kappa chain V-III region PC 2880/PC 1229 OS = Mus musculus PE = 1 SV = 1 |
| 30 | 2 | P01670 | 1 | 1.493 | 0.117 | 0.076 | 1.446 | 1.375 | 0.067 | 0.055 | Ig kappa chain V-III region PC 6684 OS = Mus musculus PE = 1 SV = 1 |
| 30 | 3 | P01644 | 1 | 1.493 | 0.11 | 0.073 | 1.447 | 1.376 | 0.063 | 0.053 | Ig kappa chain V-V region HP R16.7 OS = Mus musculus PE = 1 SV = 1 |
| 31 | 1 | E9Q1F2 | 1 | 1 | 2.055 | 1.8 | 0.728 | 0.681 | 1.843 | 2.192 | Actin, cytoplasmic 1 OS = Mus musculus GN = Actb PE = 1 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 32 | 1 | O35490 | 1 | 0.678 | 6.665 | 5.406 | 0.973 | 0.775 | 5.071 | 6.826 | Betaine-homocysteine S-methyltransferase 1 OS = Mus musculus GN = Bhmt PE = 1 SV = 1 |
| 33 | 1 | P05784 | 1 | 0.78 | 2.038 | 1.825 | 0.685 | 0.489 | 2.324 | 2.98 | Keratin, type I cytoskeletal 18 OS = Mus musculus GN = Krt18 PE = 1 SV = 5 |
| 34 | 1 | Q9WVF5 | 1 | 1.078 | 0.287 | 0.241 | 0.979 | 0.499 | 1.161 | 0.887 | Epidermal growth factor receptor OS = Mus musculus GN = Egfr PE = 1 SV = 1 |
| 35 | 1 | Q9D8N0 | 1 | 0.816 | 5.581 | 4.469 | 1.407 | 0.84 | 4.612 | 6.075 | Elongation factor 1-gamma OS = Mus musculus GN = Eef1g PE = 1 SV = 3 |
| 36 | 1 | Q02053 | 1 | 0.681 | 4.983 | 3.921 | 0.662 | 0.701 | 3.541 | 5.333 | Ubiquitin-like modifier-activating enzyme 1 OS = Mus musculus GN = Uba1 PE = 1 SV = 1 |
| 36 | 2 | P31254 | 1 | 0.669 | 3.674 | 3.008 | 0.687 | 0.699 | 2.289 | 3.93 | Ubiquitin-like modifier-activating enzyme 1 Y OS = Mus musculus GN = Uba1y PE = 1 SV = 2 |
| 37 | 1 | E9Q0F0 | 1 | 0.696 | 1.095 | 1.01 | 1.003 | 0.687 | 1.598 | 0.949 | Keratin 78 OS = Mus musculus GN = Krt78 PE = 1 SV = 1 |
| 38 | 1 | P68040 | 1 | 0.791 | 5.071 | 4.13 | 0.87 | 0.748 | 3.508 | 6.026 | Receptor of activated protein C kinase 1 OS = Mus musculus GN = Rack1 PE = 1 SV = 3 |
| 39 | 1 | A0A0R4J1H6 | 1 | 0.616 | 3.521 | 2.512 | 0.697 | 0.651 | 3.101 | 3.308 | Golgin subfamily A member 3 OS = Mus musculus GN = Golga3 PE = 1 SV = 1 |
| 40 | 1 | A0A087WR50 | 1 | 0.617 | 0.763 | 1.423 | 0.559 | 0.5 | 0.582 | 0.766 | Fibronectin OS = Mus musculus GN = Fn1 PE = 1 SV = 1 |
| 41 | 1 | Q3V117 | 1 | 0.442 | 1.513 | 1.21 | 0.44 | 0.418 | 1.312 | 1.657 | ATP-citrate synthase OS = Mus musculus GN = Acly PE = 1 SV = 1 |
| 42 | 1 | A0A075B5P5 | 1 | 0.899 | 0.434 | 0.399 | 0.951 | 0.845 | 0.368 | 0.443 | Immunoglobulin heavy constant gamma 3 (Fragment) OS = Mus musculus GN = Ighg3 PE = 4 SV = 1 |
| 43 | 1 | Q9ET01 | 1 | 0.683 | 3.434 | 2.589 | 0.744 | 0.693 | 2.841 | 3.593 | Glycogen phosphorylase, liver form OS = Mus musculus GN = Pygl PE = 1 SV = 4 |
| 44 | 1 | P07759 | 1 | 0.906 | 0.366 | 0.325 | 0.999 | 0.863 | 0.36 | 0.315 | Serine protease inhibitor A3K OS = Mus musculus GN = Serpina3k PE = 1 SV = 2 |
| 45 | 1 | Q6PHC1 | 1 | 0.695 | 2.278 | 1.775 | 1.08 | 0.761 | 2.074 | 2.582 | Alpha-enolase OS = Mus musculus GN = Eno1 PE = 1 SV = 1 |
| 46 | 1 | P80313 | 1 | 0.772 | 2.707 | 2.055 | 0.762 | 0.655 | 2.115 | 2.694 | T-complex protein 1 subunit eta OS = Mus musculus GN = Cct7 PE = 1 SV = 1 |
| 47 | 1 | P10126 | 1 | 0.903 | 7.373 | 5.512 | 1.136 | 0.954 | 5.789 | 7.761 | Elongation factor 1-alpha 1 OS = Mus musculus GN = Eef1a1 PE = 1 SV = 3 |
| 47 | 2 | P62631 | 1 | 0.848 | 7.304 | 5.43 | 1.075 | 0.891 | 5.657 | 7.616 | Elongation factor 1-alpha 2 OS = Mus musculus GN = Eef1a2 PE = 1 SV = 1 |
| 48 | 1 | F8VQJ3 | 1 | 0.828 | 4.689 | 4.676 | 0.991 | 0.819 | 4.401 | 4.925 | Laminin subunit gamma-1 OS = Mus musculus GN = Lamc1 PE = 1 SV = 1 |
| 49 | 1 | P62827 | 1 | 0.656 | 4.222 | 3.003 | 0.709 | 0.669 | 2.961 | 4.721 | GTP-binding nuclear protein Ran OS = Mus musculus GN = Ran PE = 1 SV = 3 |
| 50 | 1 | P80318 | 1 | 0.761 | 5.679 | 4.817 | 0.928 | 0.87 | 5.117 | 6.078 | T-complex protein 1 subunit gamma OS = Mus musculus GN = Cct3 PE = 1 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 51 | 1 | P47738 | 1 | 0.756 | 3.736 | 3.021 | 0.847 | 0.771 | 3.327 | 4.109 | Aldehyde dehydrogenase, mitochondrial OS = Mus musculus GN = Aldh2 PE = 1 SV = 1 |
| 52 | 1 | P80317 | 1 | 0.597 | 2.931 | 2.39 | 0.67 | 0.594 | 2.25 | 2.964 | T-complex protein 1 subunit zeta OS = Mus musculus GN = Cct6a PE = 1 SV = 3 |
| 53 | 1 | A0A1B0GSR9 | 1 | 0.612 | 3.981 | 4.162 | 0.868 | 0.646 | 2.106 | 5.322 | L-lactate dehydrogenase OS = Mus musculus GN = Ldha PE = 1 SV = 1 |
| 54 | 1 | A0A075B5K2 | 1 | 0.902 | 0.466 | 0.505 | 1.049 | 0.919 | 0.446 | 0.851 | Immunoglobulin kappa chain variable 9-124 OS = Mus musculus GN = Igkv9-124 PE = 1 SV = 7 |
| 55 | 1 | Q00623 | 1 | 0.891 | 12.55 | 11.79 | 1.144 | 0.789 | 11.71 | 13.38 | Apolipoprotein A-I OS = Mus musculus GN = Apoa1 PE = 1 SV = 2 |
| 56 | 1 | P11983 | 1 | 0.672 | 2.953 | 2.222 | 0.727 | 0.616 | 2.329 | 2.897 | T-complex protein 1 subunit alpha OS = Mus musculus GN = Tcp1 PE = 1 SV = 3 |
| 57 | 1 | P80315 | 1 | 0.791 | 2.472 | 1.835 | 0.804 | 0.734 | 1.783 | 2.212 | T-complex protein 1 subunit delta OS = Mus musculus GN = Cct4 PE = 1 SV = 3 |
| 57 | 2 | P80316 | 1 | 0.468 | 2.224 | 1.598 | 0.448 | 0.637 | 1.177 | 1.906 | T-complex protein 1 subunit epsilon OS = Mus musculus GN = Cct5 PE = 1 SV = 1 |
| 58 | 1 | P24270 | 1 | 0.653 | 3.375 | 2.819 | 0.648 | 0.636 | 2.665 | 3.665 | Catalase OS = Mus musculus GN = Cat PE = 1 SV = 4 |
| 59 | 1 | Q9CPN9 | 1 | 1.328 | 2.28 | 1.42 | 1.086 | 1.029 | 1.495 | 1.245 | RIKEN cDNA 2210010C04 gene OS = Mus musculus GN = 2210010C04Rik PE = 1 SV = 1 |
| 60 | 1 | P35979 | 1 | 0.919 | 2.929 | 2.082 | 0.768 | 0.902 | 1.99 | 2.755 | 60S ribosomal protein L12 OS = Mus musculus GN = Rpl12 PE = 1 SV = 2 |
| 61 | 1 | Q61753 | 1 | 0.647 | 5.947 | 4.971 | 0.937 | 0.699 | 5.211 | 6.535 | D-3-phosphoglycerate dehydrogenase OS = Mus musculus GN = Phgdh PE = 1 SV = 3 |
| 62 | 1 | P16125 | 1 | 0.749 | 5.136 | 4.409 | 0.743 | 0.923 | 4.467 | 5.374 | L-lactate dehydrogenase B chain OS = Mus musculus GN = Ldhb PE = 1 SV = 2 |
| 63 | 1 | F8VQ40 | 1 | 0.577 | 2.046 | 1.465 | 0.594 | 0.538 | 1.559 | 1.939 | Laminin subunit alpha-1 OS = Mus musculus GN = Lama1 PE = 1 SV = 1 |
| 64 | 1 | P14869 | 1 | 0.515 | 4.374 | 3.251 | 0.58 | 0.49 | 3.427 | 4.934 | 60S acidic ribosomal protein P0 OS = Mus musculus GN = Rplp0 PE = 1 SV = 3 |
| 65 | 1 | A0A0G2JE99 | 1 | 0.86 | 0.559 | 0.454 | 0.935 | 0.775 | 0.46 | 0.681 | Immunoglobulin lambda constant 1 (Fragment) OS = Mus musculus GN = Iglc1 PE = 4 SV = 1 |
| 66 | 1 | A2AFS0 | 1 | 0.714 | 6.183 | 4.995 | 0.775 | 0.72 | 3.808 | 6.214 | Serine-tRNA ligase, cytoplasmic (Fragment) OS = Mus musculus GN = Sars PE = 1 SV = 1 |
| 67 | 1 | P61164 | 1 | 0.635 | 2.686 | 1.837 | 0.906 | 0.786 | 2.038 | 2.084 | Alpha-centractin OS = Mus musculus GN = Actr1a PE = 1 SV = 1 |
| 68 | 1 | A0A140T8P6 | 1 | 0.772 | 0.9 | 0.611 | 1.086 | 0.837 | 0.794 | 0.885 | Immunoglobulin kappa variable 12-46 (Fragment) OS = Mus musculus GN = Igkv12-46 PE = 1 SV = 2 |
| 68 | 2 | A0A140T8Q1 | 1 | 0.718 | 0.485 | 0.313 | 1.063 | 0.897 | 0.399 | 0.324 | Protein Igkv12-41 (Fragment) OS = Mus musculus GN = Igkv12-41 PE = 1 SV = 2 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 69 | 1 | P10493 | 1 | 0.534 | 1.72 | 1.254 | 0.466 | 0.451 | 1.561 | 2.03 | Nidogen-1 OS = Mus musculus GN = Nid1 PE = 1 SV = 2 |
| 70 | 1 | P80314 | 1 | 0.837 | 2.152 | 1.558 | 0.637 | 0.851 | 1.543 | 1.551 | T-complex protein 1 subunit beta OS = Mus musculus GN = Cct2 PE = 1 SV = 4 |
| 71 | 1 | A0A075B5L8 | 1 | 0.986 | 0.464 | 0.483 | 1.332 | 1.19 | 0.447 | 0.557 | Immunoglobulin kappa variable 4-79 (Fragment) OS = Mus musculus GN = Igkv4-79 PE = 4 SV = 2 |
| 72 | 1 | A0A075B666 | 1 | 0.85 | 0.59 | 0.559 | 0.989 | 0.759 | 0.551 | 0.487 | Immunoglobulin kappa chain variable 13-85 (Fragment) OS = Mus musculus GN = Igkv13-85 PE-4 SV = 5 |
| 73 | 1 | P01027 | 1 | 0.634 | 0.647 | 0.555 | 0.755 | 0.659 | 0.499 | 0.474 | Complement C3 OS = Mus musculus GN = C3 PE = 1 SV = 3 |
| 74 | 1 | Q5XJF6 | 1 | 0.918 | 5.197 | 4.599 | 1.07 | 0.713 | 3.512 | 6.136 | Ribosomal protein OS = Mus musculus GN = Rpl10a PE = 1 SV = 1 |
| 75 | 1 | A0A0B4JIH7 | 1 | 1.057 | 0.283 | 0.227 | 1.095 | 1.076 | 0.239 | 0.254 | Immunoglobulin kappa variable 1-135 (Fragment) OS = Mus musculus GN = Igkv1-135 PE = 4 SV = 1 |
| 76 | 1 | Q8BH00 | 1 | 0.971 | 8.707 | 5.73 | 1.256 | 0.712 | 7.142 | 8.854 | Aldehyde dehydrogenase family 8 member A1 OS = Mus musculus GN = Aldh8a1 PE = 1 SV = 1 |
| 77 | 1 | A0A075B5V1 | 1 | 0.894 | 0.146 | 0.117 | 0.969 | 0.871 | 0.076 | 0.139 | Immunoglobulin heavy variable 1-31 OS = Mus musculus GN = Ighv1-31 PE-4 SV = 1 |
| 78 | 1 | P09411 | 1 | 0.913 | 4.417 | 3.703 | 1.07 | 0.72 | 3.796 | 3.6 | Phosphoglycerate kinase 1 OS = Mus musculus GN = Pgk1 PE = 1 SV = 4 |
| 79 | 1 | A0A0B4J119 | 1 | 1.115 | 0.544 | 0.482 | 1.345 | 1.118 | 0.539 | 0.537 | Immunoglobulin kappa variable 4-55 (Fragment) OS = Mus musculus GN = Igkv4-55 PE = 1 SV = 1 |
| 80 | 1 | P61205 | 1 | 0.621 | 2.889 | 1.862 | 0.618 | 0.567 | 1.905 | 2.099 | ADP-ribosylation factor 3 OS = Mus musculus GN = Arf3 PE = 2 SV = 2 |
| 81 | 1 | Q8C196 | 1 | 0.592 | 4.622 | 3.601 | 0.544 | 0.598 | 3.901 | 4.472 | Carbamoyl-phosphate synthase [ammonia], mitochondrial OS = Mus musculus GN = Cps1 PE = 1 SV = 2 |
| 82 | 1 | A0AQUIRNJ1 | 1 | 0.646 | 3.434 | 3.151 | 0.816 | 0.544 | 2.52 | 4.353 | Fatty acid synthase OS = Mus musculus GN = Fasn PE = 1 SV = 1 |
| 83 | 1 | Q91X72 | 1 | 0.771 | 1.287 | 0.407 | 0.882 | 0.924 | 0.64 | 0.52 | Hemopexin OS = Mus musculus GN = Hpx PE = 1 SV = 2 |
| 84 | 1 | A0A087WPL5 | 1 | 0.496 | 2.36 | 1.85 | 0.487 | 0.606 | 2.273 | 3.053 | ATP-dependent RNA helicase A OS = Mus musculus GN = Dhx9 PE = 1 SV = 1 |
| 85 | 1 | O70475 | 1 | 0.596 | 1.243 | 0.962 | 0.623 | 0.57 | 1.03 | 1.347 | UDP-glucose 6-dehydrogenase OS = Mus musculus GN = Ugdh PE = 1 SV = 1 |
| 86 | 1 | E9Q035 | 1 | 0.874 | 0.473 | 0.474 | 0.945 | 0.788 | 0.402 | 0.356 | Predicted gene 20425 OS = Mus musculus GN = Gm20425 PE = 4 SV = 1 |
| 87 | 1 | A0A075B5K8 | 1 | 1.063 | 0.379 | 0.106 | 1.094 | 1.122 | 0.17 | 0.129 | Immunoglobulin kappa variable 1-99 OS = Mus musculus GN = Igkv1-99 PE = 4 SV = 7 |

TABLE 4-continued

CA19-9 IP/MS data from C: RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 88 | 1 | G3X8Q5 | 1 | 1.046 | 0.683 | 0.639 | 1.057 | 0.948 | 0.632 | 0.7 | Ceruloplasmin OS = Mus musculus GN = Cp PE = 1 SV = 1 |
| 89 | 1 | P60843 | 1 | 0.803 | 1.821 | 1.395 | 0.875 | 0.818 | 1.333 | 1.596 | Eukaryotic initiation factor 4A-I OS = Mus musculus GN = Eif4a1 PE = 1 SV = 1 |
| 90 | 1 | A0A171KXD3 | 1 | 0.669 | 4.437 | 3.854 | 0.757 | 0.772 | 3.222 | 4.845 | Protein arginine N-methyltransferase 1 OS = Mus musculus GN = Prmt1 PE = 1 SV = 1 |
| 91 | 1 | Q9CQ62 | 1 | 1.242 | 2.245 | 2.229 | 1.1 | 1.078 | 2.376 | 2.962 | 2,4-dienoyl-CoA reductase, mitochondrial OS = Mus musculus GN = Decr1 PE = 1 SV = 1 |
| 92 | 1 | H3BL49 | 1 | 0.96 | 2.355 | 1.784 | 1.091 | 0.855 | 1.923 | 2.541 | T-complex protein 1 subunit theta OS = Mus musculus GN = Cct8 PE = 1 SV = 1 |
| 93 | 1 | Q9DBJ1 | 1 | 0.669 | 2.125 | 1.66 | 0.655 | 0.65 | 1.363 | 2.045 | Phosphoglycerate mutase 1 OS = Mus musculus GN = Pgam1 PE = 1 SV = 3 |
| 94 | 1 | A0A075B6A3 | 1 | 0.959 | 0.886 | 0.652 | 1.179 | 0.991 | 0.815 | 0.777 | Immunoglobulin heavy constant alpha (Fragment) OS = Mus musculus GN = Igha PE = 1 SV = 1 |
| 95 | 1 | D6RGQ0 | 1 | 0.798 | 1.123 | 0.787 | 0.832 | 0.644 | 0.733 | 0.828 | Complement factor H OS = Mus musculus GN = Cfh PE = 1 SV = 1 |
| 96 | 1 | A0A075B5Q4 | 1 | 0.74 | 0.468 | 0.33 | 0.969 | 0.715 | 0.528 | 0.54 | Immunoglobulin heavy variable 5-12 (Fragment) OS = Mus musculus GN = Ighv5-12 PE = 4 SV = 1 |
| 97 | 1 | Q8VDD5 | 1 | 0.669 | 1.14 | 1.011 | 0.638 | 0.545 | 0.992 | 1.244 | Myosin-9 OS = Mus musculus GN = Myh9 PE = 1 SV = 4 |
| 98 | 1 | P20918 | 1 | 0.592 | 0.746 | 0.487 | 0.759 | 0.707 | 0.464 | 0.682 | Plasminogen OS = Mus musculus GN = Plg PE = 1 SV = 3 |
| 99 | 1 | B2M1R6 | 1 | 0.823 | 2.359 | 1.977 | 0.664 | 0.789 | 2.092 | 2.45 | Heterogeneous nuclear ribonucleoprotein K OS = Mus musculus GN = Hnrnpk PE = 1 SV = 1 |
| 100 | 1 | A2AKJ6 | 1 | 0.802 | 2.573 | 2.422 | 0.621 | 0.408 | 2.226 | 2.769 | Syntenin-1 (Fragment) OS = Mus musculus GN = Sdcbp PE = 1 SV = 1 |
| 101 | 1 | D3YYM6 | 1 | 1.054 | 5.753 | 4.191 | 1.059 | 0.849 | 3.93 | 5.708 | 40S ribosomal protein S5 (Fragment) OS = Mus musculus GN = Rps5 PE = 1 SV = 1 |
| 102 | 1 | G5E866 | 1 | 0.698 | 3.211 | 2.738 | 0.619 | 0.537 | 2.469 | 3.562 | Splicing factor 3B subunit 1 OS = Mus musculus GN = Sf3b1 PE = 1 SV = 1 |
| 103 | 1 | Q8BWT1 | 1 | 0.557 | 2.794 | 2.312 | 0.465 | 0.792 | 2.157 | 3.201 | 3-ketoacyl-CoA thiolase, mitochondrial OS = Mus musculus GN = Acaa2 PE = 1 SV = 3 |
| 104 | 1 | A0A075B5K1 | 1 | 0.772 | 0.639 | 0.495 | 0.856 | 0.759 | 0.516 | 0.514 | Immunoglobulin kappa variable 11-125 OS = Mus musculus GN = Igkv11-125 PE = 4 SV = 7 |
| 105 | 1 | P01806 | 1 | 0.858 | 0.792 | 0.599 | 0.958 | 0.802 | 0.594 | 0.751 | Ig heavy chain V region 441 OS = Mus musculus PE = 4 SV = 1 |
| 106 | 1 | Q8R2K3 | 1 | 0.528 | 2.234 | 1.797 | 0.591 | 0.658 | 1.677 | 1.733 | Single-stranded DNA binding protein 1 OS = Mus musculus GN = Ssbp1 PE = 1 SV = 1 |
| 107 | 1 | A0A0G2JGQ8 | 1 | 0.884 | 0.544 | 0.401 | 0.999 | 0.79 | 0.617 | 0.417 | Ig lambda-3 chain C region (Fragment) OS = Mus musculus GN = Iglc3 PE = 1 SV = 1 |
| 108 | 1 | P28665 | 1 | 0.936 | 0.405 | 0.38 | 1.184 | 1.04 | 0.373 | 0.492 | Murinoglobulin-1 OS = Mus musculus GN = Mug1 PE = 1 SV = 3 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 109 | 1 | A0A0B4J1I1 | 1 | 0.986 | — | 0.161 | 1.099 | 0.589 | 0.181 | 0.224 | Immunoglobulin kappa variable 16-104 (Fragment) OS = *Mus musculus* GN = Igkv16-104 PE = 4 SV = 1 |
| 110 | 1 | A0A140T8M3 | 1 | 0.913 | 0.369 | 0.364 | 1.235 | 1.038 | 0.375 | 0.445 | Immunoglobulin kappa chain variable 8-30 (Fragment) OS = *Mus musculus* GN = Igkv8-30 PE = 4 SV = 2 |
| 111 | 1 | Q6ZWY9 | 1 | 1.434 | 1.176 | 1.527 | 0.811 | 0.735 | 0.941 | 1.167 | Histone H2B type 1-C/E/G OS = *Mus musculus* GN = Hist1h2bc PE = 1 SV = 3 |
| 112 | 1 | A0A0A6YW67 | 1 | 1.138 | 2.633 | 2.465 | 0.715 | 0.551 | 2.181 | 2.53 | MCG23377, isoform CRA_b OS = *Mus musculus* GN = Gm8797 PE = 4 SV = 1 |
| 113 | 1 | P14131 | 1 | 0.574 | 4.228 | 4.052 | 0.57 | 0.541 | 4.522 | 6.059 | 40S ribosomal protein S16 OS = *Mus musculus* GN = Rps16 PE = 1 SV = 4 |
| 114 | 1 | P01675 | 1 | 1.304 | 1.889 | 1.658 | 1.721 | 1.52 | 2.056 | 1.925 | Ig kappa chain V-VI region XRPC 44 OS = *Mus musculus* PE = 1 SV = 1 |
| 115 | 1 | Q91VC3 | 1 | 0.817 | 2.843 | 1.736 | 0.793 | 0.875 | 1.653 | 2.195 | Eukaryotic initiation factor 4A-III OS = *Mus musculus* GN = Eif4a3 PE = 1 SV = 3 |
| 116 | 1 | D3YV76 | — | — | — | — | — | — | — | — | Septin-2 (Fragment) OS = *Mus musculus* GN = Sept2 PE = 1 SV = 1 |
| 117 | 1 | Q8BKC5 | 1 | 0.805 | 3.081 | 2.221 | 0.763 | 0.963 | 2.833 | 3.389 | Importin-5 OS = *Mus musculus* GN = Ipo5 PE = 1 SV = 3 |
| 118 | 1 | P12023 | 1 | 1.458 | 1.244 | 3.728 | 0.673 | 0.588 | 1.016 | 1.259 | Amyloid-beta A4 protein OS = *Mus musculus* GN = App PE = 1 SV = 3 |
| 119 | 1 | P62264 | 1 | 0.61 | 2.494 | 1.853 | 0.507 | 0.666 | 1.532 | 2.602 | 40S ribosomal protein S14 OS = *Mus musculus* GN = Rps14 PE = 1 SV = 3 |
| 120 | 1 | Q99LF4 | 1 | 0.862 | 1.955 | 1.269 | 0.875 | 0.774 | 1.39 | 2.119 | tRNA-splicing ligase RtcB homolog OS = *Mus musculus* GN = Rtcb PE = 1 SV = 1 |
| 121 | 1 | B1ASC1 | 1 | 0.586 | 2.543 | 2.2 | 0.612 | 0.551 | 2.265 | 3.046 | R-spondin homolog (*Xenopus laevis*) OS = *Mus musculus* GN = Rspo1 PE = 2 SV = 1 |
| 122 | 1 | P24549 | 1 | 0.652 | 3.779 | 2.987 | 0.831 | 0.581 | 2.88 | 3.877 | Retinal dehydrogenase 1 OS = *Mus musculus* GN = Aldh1a1 PE = 1 SV = 5 |
| 123 | 1 | Q04447 | 1 | 0.413 | 1.231 | 1.006 | 0.533 | 0.485 | 1.068 | 1.529 | Creatine kinase B-type OS = *Mus musculus* GN = Ckb PE = 1 SV = 1 |
| 124 | 1 | Q3U367 | 1 | 0.695 | 4.579 | 3.932 | 1.149 | 0.803 | 3.815 | 5.041 | 4-trimethylaminobutyraldehyde dehydrogenase OS = *Mus musculus* GN = Aldh9a1 PE = 1 SV = 1 |
| 125 | 1 | A0A075B663 | 1 | 0.908 | 0.527 | 0.479 | 1.343 | 1.118 | 0.557 | 0.454 | Immunoglobulin lambda variable 1 (Fragment) OS = *Mus musculus* GN = Iglv1 PE = 4 SV = 1 |
| 126 | 1 | A0A087WP24 | 1 | 0.061 | 0.474 | 0.454 | 0.074 | 0.262 | 0.432 | 0.649 | Protein ABHD14B (Fragment) OS = *Mus musculus* GN = Abhd14b PE = 1 SV = 1 |
| 127 | 1 | E9QN70 | 1 | 0.662 | 4.071 | 3.185 | 0.631 | 0.617 | 3.203 | 4.593 | Laminin subunit beta-1 OS = *Mus musculus* GN = Lamb1 PE = 1 SV = 1 |
| 128 | 1 | A0A140T8M4 | 1 | 0.819 | 0.618 | 0.482 | 0.909 | 0.82 | 0.596 | 0.604 | Immunoglobulin kappa variable 8-19 OS = *Mus musculus* GN = Igkv8-19 PE = 1 SV = 2 |
| 128 | 2 | A0A075B5N3 | 1 | 0.793 | 0.71 | 0.508 | 0.881 | 0.825 | 0.692 | 0.617 | Immunoglobulin kappa variable 8-28 OS = *Mus musculus* GN = Igkv8-28 PE = 1 SV = 7 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 129 | 1 | P25444 | 1 | 0.785 | 3.186 | 1.785 | 0.82 | 0.682 | 2.471 | 3.23 | 40S ribosomal protein S2 OS = Mus musculus GN = Rps2 PE = 1 SV = 3 |
| 130 | 1 | P70168 | 1 | 0.539 | 4.492 | 3.545 | 0.521 | 0.575 | 4.218 | 6.126 | Importin subunit beta-1 OS = Mus musculus GN = Kpnb1 PE = 1 SV = 2 |
| 131 | 1 | F6ZEW4 | 1 | 0.83 | 3.768 | 1.979 | 0.596 | 0.677 | 2.003 | 4.373 | Exportin-2 (Fragment) OS = Mus musculus GN = Csel1 PE = 1 SV = 1 |
| 132 | 1 | A0A0A6YX19 | 1 | 1.155 | 0.559 | 0.389 | 1.537 | 1.25 | 0.525 | 0.445 | Immunoglobulin heavy variable V6-4 (Fragment) OS = Mus musculus GN = Ighv6-4 PE-4 SV = 1 |
| 133 | 1 | Q9CXY6 | 1 | 0.51 | 1.72 | 1.464 | 0.304 | 0.447 | 1.414 | 1.656 | Interleukin enhancer-binding factor 2 OS = Mus musculus GN = Ilf2 PE = 1 SV = 1 |
| 134 | 1 | A0A075B5R4 | 1 | 0.664 | 0.609 | 0.617 | 0.671 | 0.533 | 0.553 | 0.74 | Immunoglobulin heavy variable 14-1 (Fragment) OS = Mus musculus GN = Ighv14-1 PE = 4 SV = 1 |
| 135 | 1 | P63038 | 1 | 0.798 | 2.367 | 2.301 | 0.694 | 0.633 | 2.059 | 2.225 | 60 kDa heat shock protein, mitochondrial OS = Mus musculus GN = Hspd1 PE = 1 SV = 1 |
| 136 | 1 | P18528 | 1 | 0.73 | 1.01 | 0.283 | 1.083 | 0.742 | 0.206 | 0.242 | Ig heavy chain V region 6.96 OS = Mus musculus PE = 4 SV = 1 |
| 137 | 1 | O70310 | 1 | 0.708 | 2.875 | 2.291 | 0.873 | 0.748 | 2.11 | 2.722 | Glycylpeptide N-tetradecanoyltransferase 1 OS = Mus musculus GN = Nmt1 PE = 1 SV = 1 |
| 138 | 1 | P52196 | 1 | 0.742 | 9.942 | 8.506 | 1.497 | 0.901 | 9.523 | 12.71 | Thiosulfate sulfurtransferase OS = Mus musculus GN = Tst PE = 1 SV = 3 |
| 139 | 1 | A0A140T8N0 | 1 | 0.71 | 0.47 | 0.44 | 1.022 | 0.906 | 0.255 | 0.451 | Immunoglobulin kappa chain variable 9-120 (Fragment) OS = Mus musculus GN = Igkv9-120 PE = 1 SV = 2 |
| 140 | 1 | A0A075B5U4 | 1 | 0.822 | 0.465 | 0.317 | 1.16 | 0.758 | 0.568 | 0.535 | Immunoglobulin heavy variable V1-18 OS = Mus musculus GN = Ighv1-18 PE = 1 SV = 1 |
| 141 | 1 | A0A140T8N2 | 1 | 0.85 | 2.578 | 0.967 | 1.003 | 0.979 | 0.724 | 0.965 | Protein Igkv5-48 (Fragment) OS = Mus musculus GN = Igkv5-48 PE = 1 SV = 2 |
| 142 | 1 | A0A0A6YXF6 | 1 | 0.566 | 2.457 | 1.54 | 0.519 | 0.674 | 1.654 | 1.901 | Transforming protein RhoA (Fragment) OS = Mus musculus GN = Rhoa PE = 1 SV = 1 |
| 143 | 1 | P62908 | 1 | 0.786 | 2.418 | 1.699 | 0.811 | 0.84 | 1.86 | 2.706 | 40S ribosomal protein S3 OS = Mus musculus GN = Rps3 PE = 1 SV = 1 |
| 144 | 1 | P19324 | 1 | 0.539 | 3.575 | 2.845 | 0.604 | 0.55 | 2.902 | 4.009 | Serpin H1 OS = Mus musculus GN = Serpinh1 PE = 1 SV = 3 |
| 145 | 1 | Q9Z1Z2 | 1 | 0.812 | 2.715 | 1.945 | 0.745 | 0.575 | 1.599 | 2.388 | Serine-threonine kinase receptor-associated protein OS = Mus musculus GN = Strap PE = 1 SV = 2 |
| 146 | 1 | P23116 | 1 | 0.64 | 3.48 | 2.798 | 0.603 | 0.556 | 3.719 | 3.382 | Eukaryotic translation initiation factor 3 subunit A OS = Mus musculus GN = Eif3a PE = 1 SV = 5 |
| 147 | 1 | A0A140T8N7 | 1 | 0.627 | 0.306 | 0.276 | 1.256 | 0.797 | 0.238 | 0.237 | Immunoglobulin kappa chain variable 6-25 (Fragment) OS = Mus musculus GN = Igkv6-25 PE = 4 SV = 2 |
| 148 | 1 | Q922D8 | 1 | 1.045 | 3.527 | 2.432 | 1.031 | 0.708 | 2.798 | 3.674 | C-1-tetrahydrofolate synthase, cytoplasmic OS = Mus musculus GN = Mthfd1 PE = 1 SV = 4 |
| 149 | 1 | P56480 | 1 | 0.773 | 1.813 | 1.371 | 0.723 | 0.567 | 1.378 | 1.609 | ATP synthase subunit beta, mitochondrial OS = Mus musculus GN = Atp5b PE = 1 SV = 2 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of Dox treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 150 | 1 | P62806 | 1 | 1.939 | 1.724 | 2.005 | 0.716 | 0.733 | 1.387 | 1.866 | Histone H4 OS = *Mus musculus* GN = Hist1h4a PE = 1 SV = 2 |
| 151 | 1 | P60229 | 1 | 0.502 | 2.269 | 1.69 | 0.438 | 0.565 | 3.016 | 2.497 | Eukaryotic translation initiation factor 3 subunit E OS = *Mus musculus* GN = Eif3e PE = 1 SV = 1 |
| 152 | 1 | Q9Z204 | 1 | 0.897 | 2.679 | 1.695 | 0.788 | 0.831 | 1.806 | 2.301 | Heterogeneous nuclear ribonucleoproteins C1/C2 OS = *Mus musculus* GN = Hnrnpc PE = 1 SV = 1 |
| 153 | 1 | Q9CWJ9 | 1 | 0.663 | 1.121 | 0.831 | 0.969 | 0.739 | 1.186 | 1.274 | Bifunctional purine biosynthesis protein PURH OS = *Mus musculus* GN = Atic PE = 1 SV = 2 |
| 154 | 1 | F6RV17 | 1 | 0.629 | 2.732 | 1.901 | 0.339 | 0.617 | 2.154 | 3.066 | Serine/threonine-protein phosphatase 2A 55 kDa regulatory subunit B OS = *Mus musculus* GN = Ppp2r2d PE = 1 SV = 2 |
| 155 | 1 | Q8R1B4 | 1 | 0.543 | 2.75 | 2.33 | 0.528 | 0.454 | 2.333 | 3.091 | Eukaryotic translation initiation factor 3 subunit C OS = *Mus musculus* GN = Eif3c PE = 1 SV = 1 |
| 156 | 1 | A0A0G2JFF1 | 1 | 0.641 | 3.91 | 2.733 | 0.786 | 0.924 | 2.983 | 3.887 | Serine/threonine-protein phosphatase (Fragment) OS = *Mus musculus* GN = Ppp1cc PE = 1 SV = 1 |
| 157 | 1 | Q8BGJ5 | 1 | 0.979 | 4.003 | 3.142 | 0.527 | 0.335 | 3.705 | 4.143 | MCG13402, isoform CRA_a OS = *Mus musculus* GN = Ptbp1 PE = 1 SV = 1 |
| 158 | 1 | A0A140T8N9 | 1 | 0.99 | 0.109 | 0.107 | 1.032 | 0.94 | 0.107 | 0.114 | Immunoglobulin kappa variable 6-32 (Fragment) OS = *Mus musculus* GN = Igkv6-32 PE = 4 SV = 2 |
| 159 | 1 | F7D439 | 1 | 1.602 | 3.631 | 2.671 | 1.331 | 1.011 | 3.021 | 3.901 | Argininosuccinate lyase (Fragment) OS = *Mus musculus* GN = Asl PE = 1 SV = 2 |
| 160 | 1 | A0A0R4J1E2 | 1 | 0.559 | 2.128 | 2.002 | 0.855 | 0.703 | 2.074 | 2.565 | Elongation factor 1-delta OS = *Mus musculus* GN = Eef1d PE = 1 SV = 1 |
| 161 | 1 | P21614 | 1 | 0.791 | 0.598 | 0.515 | 0.731 | 0.662 | 0.485 | 0.491 | Vitamin D-binding protein OS = *Mus musculus* GN = Gc PE = 1 SV = 2 |
| 162 | 1 | Q922B2 | 1 | 0.11 | 0.253 | 0.287 | 0.084 | 0.175 | 0.168 | 0.401 | Aspartate-tRNA ligase, cytoplasmic OS = *Mus musculus* GN-Dars PE = 1 SV = 2 |
| 163 | 1 | Q3U741 | 1 | 0.335 | 3.982 | 2.718 | 0.415 | 0.278 | 3.047 | 3.797 | DEAD (Asp-Glu-Ala-Asp) box polypeptide 17, isoform CRA_a OS = *Mus musculus* GN = Ddx17 PE = 1 SV = 1 |
| 164 | 1 | Q8BH95 | 1 | 1.051 | 21.16 | 22.42 | 1.342 | 1.957 | 16.57 | 28.68 | Enoyl-CoA hydratase, mitochondrial OS = *Mus musculus* GN = Echs1 PE = 1 SV = 1 |
| 165 | 1 | Q61171 | 1 | 0.73 | 2.132 | 1.704 | 0.523 | 0.5 | 1.814 | 2.604 | Peroxiredoxin-2 OS = *Mus musculus* GN = Prdx2 PE = 1 SV = 3 |
| 166 | 1 | F6ZDS4 | 1 | 1.181 | 2.139 | 1.56 | 0.834 | 0.454 | 1.627 | 1.347 | Nucleoprotein TPR OS = *Mus musculus* GN = Tpr PE = 1 SV = 1 |
| 167 | 1 | P01741 | 1 | 1.17 | 1.141 | 0.923 | 1.256 | 1.199 | 0.912 | 1.116 | Ig heavy chain V region OS = *Mus musculus* PE = 1 SV = 1 |
| 168 | 1 | A0A0R4I038 | 1 | 0.84 | 0.556 | 0.238 | 0.928 | 0.75 | 0.182 | 0.392 | Kininogen-1 OS = *Mus musculus* GN = Kng1 PE = 1 SV = 1 |
| 169 | 1 | Q60972 | 1 | 0.606 | 2.145 | 1.544 | 0.641 | 0.668 | 1.741 | 1.73 | Histone-binding protein RBBP4 OS = *Mus musculus* GN = Rbbp4 PE = 1 SV = 5 |
| 170 | 1 | A0A140LIM5 | 1 | 0.691 | 1.942 | 1.625 | 1.344 | 1.218 | 1.653 | 1.917 | Mitotic checkpoint protein BUB3 OS = *Mus musculus* GN = Bub3 PE = 1 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 171 | 1 | P40124 | 1 | 0.541 | 1.505 | 1.145 | 0.432 | 0.342 | 1.139 | 1.146 | Adenylyl cyclase-associated protein 1 OS = Mus musculus GN = Cap1 PE = 1 SV = 4 |
| 172 | 1 | P01592 | 1 | 0.672 | 0.384 | 0.273 | 0.711 | 0.679 | 0.401 | 0.434 | Immunoglobulin J chain OS = Mus musculus GN = Jchain PE = 1 SV = 4 |
| 173 | 1 | P01786 | 1 | 0.648 | 0.976 | 0.736 | 0.787 | 0.764 | 0.881 | 0.703 | Ig heavy chain V region MOPC 47A OS = Mus musculus PE = 1 SV = 1 |
| 174 | 1 | A0A075B5Q0 | 1 | 0.752 | 0.94 | 0.556 | 0.669 | 0.675 | 0.827 | 0.655 | Immunoglobulin heavy variable 5-6 (Fragment) OS = Mus musculus GN = Ighv5-6 PE = 4 SV = 1 |
| 175 | 1 | A0A1L1SV25 | 1 | 0.99 | 1.259 | 0.912 | 0.811 | 0.537 | 1.245 | 1.262 | Alpha-actinin-4 OS = Mus musculus GN = Actn4 PE = 1 SV = 1 |
| 176 | 1 | Q6PDM2 | 1 | 0.339 | 1.964 | 1.135 | 0.342 | 0.216 | 1.55 | 2.017 | Serine/arginine-rich splicing factor 1 OS = Mus musculus GN = Srsf1 PE = 1 SV = 3 |
| 177 | 1 | Q9QWK4 | 1 | 0.717 | 0.696 | 0.497 | 0.721 | 0.695 | 0.469 | 0.566 | CD5 antigen-like OS = Mus musculus GN = Cd51 PE = 1 SV = 3 |
| 178 | 1 | P62305 | 1 | 0.354 | 1.164 | 0.863 | 0.528 | 0.304 | 0.895 | 1.062 | Small nuclear ribonucleoprotein E OS = Mus musculus GN = Snrpe PE = 1 SV = 1 |
| 179 | 1 | Q8JZQ9 | 1 | 0.817 | 2.585 | 1.903 | 0.89 | 0.709 | 2.229 | 2.667 | Eukaryotic translation initiation factor 3 subunit B OS = Mus musculus GN = Eif3b PE = 1 SV = 1 |
| 180 | 1 | P10639 | 1 | 0.771 | 1.301 | 0.916 | 0.602 | 0.664 | 1.283 | 1.6 | Thioredoxin OS = Mus musculus GN = Txn PE = 1 SV = 3 |
| 181 | 1 | P62267 | 1 | 0.597 | 1.519 | 1.175 | 0.543 | 0.582 | 1.179 | 1.855 | 40S ribosomal protein S23 OS = Mus musculus GN = Rps23 PE = 1 SV = 3 |
| 182 | 1 | P97351 | 1 | 0.789 | 1.784 | 1.398 | 0.872 | 0.633 | 1.351 | 1.844 | 40S ribosomal protein S3a OS = Mus musculus GN = Rps3a PE = 1 SV = 3 |
| 183 | 1 | Q3U2G2 | 1 | 0.686 | 2.57 | 2.18 | 0.662 | 0.366 | 2.075 | 3.023 | Heat shock 70 kDa protein 4 OS = Mus musculus GN = Hspa4 PE = 1 SV = 1 |
| 184 | 1 | F8WHL2 | 1 | 0.601 | 1.941 | 1.322 | 0.711 | 0.829 | 1.331 | 1.651 | Coatomer subunit alpha OS = Mus musculus GN = Copa PE = 1 SV = 1 |
| 185 | 1 | Q8BGQ7 | 1 | 1.395 | 4.22 | 2.427 | 0.811 | 0.564 | 2.555 | 2.632 | Alanine-tRNA ligase, cytoplasmic OS = Mus musculus GN = Aars PE = 1 SV = 1 |
| 186 | 1 | H7BXC3 | 1 | 0.651 | 1.294 | 1.139 | 0.682 | 0.775 | 1.177 | 1.362 | Triosephosphate isomerase OS = Mus musculus GN = Tpi1 PE = 1 SV = 1 |
| 188 | 1 | A0A019YKD4 | 1 | 0.471 | 7.699 | 5.593 | 0.472 | 0.744 | 6.653 | 8.402 | Creatine kinase M-type OS = Mus musculus GN = Ckm PE = 1 SV = 1 |
| 189 | 1 | Q9JKK7 | 1 | 0.972 | 5.912 | 4.983 | 0.829 | 0.982 | 4.575 | 7.092 | Tropomodulin-2 OS = Mus musculus GN = Tmod2 PE = 1 SV = 2 |
| 190 | 1 | G3UYR8 | 1 | 0.571 | 2.114 | 1.386 | 0.637 | 0.653 | 1.364 | 1.74 | Alpha-aminoadipic semialdehyde dehydrogenase OS = Mus musculus GN = Aldh7a1 PE = 1 SV = 1 |
| 191 | 1 | A0A075B5W4 | 1 | 0.988 | 0.08 | 0.083 | 1.101 | 1.037 | 0.093 | 0.079 | Immunoglobulin heavy variable V8-6 OS = Mus musculus GN = Ighv8-6 PE-4 SV = 1 |
| 192 | 1 | E9Q1G8 | 1 | 0.386 | 1.968 | 1.927 | 0.581 | 0.474 | 1.439 | 1.984 | Septin-7 OS = Mus musculus GN = Sept7 PE = 1 SV = 2 |
| 193 | 1 | Q61646 | 1 | 1.065 | 0.521 | 0.449 | 1.072 | 0.864 | 0.461 | 0.446 | Haptoglobin OS = Mus musculus GN = Hp PE = 1 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 194 | 1 | Q3UH59 | 1 | 0.65 | 2.34 | 1.833 | 0.547 | 0.384 | 1.817 | 1.717 | Myosin-10 OS = Mus musculus GN = Myh10 PE = 1 SV = 1 |
| 195 | 1 | A2AFQ2 | 1 | 0.313 | 0.888 | 0.378 | 0.245 | 0.399 | 0.253 | 0.421 | 3-hydroxyacyl-CoA dehydrogenase type-2 OS = Mus musculus GN = Hsd17b10 PE = 1 SV = 1 |
| 196 | 1 | A0A075B5R6 | 1 | 0.73 | 0.091 | 0.064 | 0.83 | 0.625 | 0.084 | 0.279 | Immunoglobulin heavy variable 11-1 (Fragment) OS = Mus musculus GN = Ighv11-1 PE = 4 SV = 1 |
| 197 | 1 | A0A0U1RQ71 | 1 | 0.705 | 1.893 | 1.404 | 0.988 | 0.848 | 1.465 | 1.84 | 40S ribosomal protein S13 OS = Mus musculus GN = Rps13 PE = 1 SV = 1 |
| 198 | 1 | P29699 | 1 | 0.78 | 0.638 | 0.56 | 0.947 | 0.467 | 0.514 | 0.547 | Alpha-2-HS-glycoprotein OS = Mus musculus GN = Ahsg PE = 1 SV = 1 |
| 199 | 1 | A0A0G2JFB4 | 1 | 0.78 | 3.393 | 3.102 | 0.947 | 0.731 | 2.011 | 5.569 | Eukaryotic translation initiation factor 4E OS = Mus musculus GN = Eif4e PE = 1 SV = 1 |
| 200 | 1 | A0A1L1SST0 | 1 | 1.42 | 3.701 | 5.268 | 0.583 | 0.472 | 1.758 | 8.143 | Peptidyl-prolyl cis-trans isomerase OS = Mus musculus GN = Ppia PE = 1 SV = 1 |
| 201 | 1 | A0A1B0GR44 | 1 | 0.669 | 1.342 | 1.061 | 0.66 | 0.689 | 0.965 | 1.089 | U1 small nuclear ribonucleoprotein 70 kDa (Fragment) OS = Mus musculus GN = Snrnp70 PE = 1 SV = 1 |
| 202 | 1 | Q01853 | 1 | 0.676 | 1.251 | 1.048 | 0.612 | 0.862 | 1.085 | 1.421 | Transitional endoplasmic reticulum ATPase OS = Mus musculus GN = Vcp PE = 1 SV = 4 |
| 203 | 1 | Q60749 | 1 | 0.624 | 3.408 | 2.905 | 0.798 | 0.587 | 2.493 | 3.944 | KH domain-containing, RNA-binding, signal transduction-associated protein 1 OS = Mus musculus GN = Khdrbs1 PE = 1 SV = 2 |
| 204 | 1 | A0A1Y7VKY1 | 1 | 0.442 | 7.321 | 7.263 | 0.495 | 0.692 | 6.824 | 11.35 | MCG116671 OS = Mus musculus GN = mCG_116671 PE = 3 SV = 1 |
| 205 | 1 | Q9JMA2 | 1 | 0.564 | 1.636 | 1.208 | 0.431 | 0.603 | 1.284 | 1.426 | Queuine tRNA-ribosyltransferase catalytic subunit 1 OS = Mus musculus GN = Qtrt1 PE = 1 SV = 2 |
| 206 | 1 | P62715 | 1 | 0.899 | 2.474 | 2.39 | 1.319 | 0.993 | 1.872 | 2.717 | Serine/threonine-protein phosphatase 2A catalytic subunit beta isoform OS = Mus musculus GN = Ppp2cb PE = 1 SV = 1 |
| 207 | 1 | A0A0R4J039 | 1 | 0.756 | 0.75 | 0.523 | 0.664 | 0.631 | 0.703 | 0.54 | Histidine-rich glycoprotein OS = Mus musculus GN = Hrg PE = 1 SV = 1 |
| 208 | 1 | A0A0R4J187 | 1 | 0.501 | 1.78 | 1.823 | 0.636 | 0.542 | 1.376 | 2.66 | X-ray repair cross-complementing protein 6 OS = Mus musculus GN = Xrcc6 PE = 1 SV = 1 |
| 209 | 1 | P98086 | 1 | 0.159 | 0.323 | 0.449 | 0.139 | 0.245 | 0.206 | 0.172 | Complement C1q subcomponent subunit A OS = Mus musculus GN = C1qa PE = 1 SV = 1 |
| 210 | 1 | I7HIQ2 | 1 | 0.933 | 1.068 | 0.993 | 0.577 | 0.648 | 0.843 | 1.107 | C-X-C motif chemokine 16 (Fragment) OS = Mus musculus GN = Cxcl16 PE = 1 SV = 1 |
| 211 | 1 | P60867 | 1 | 0.647 | 3.082 | 2.083 | 1.342 | 0.794 | 1.787 | 2.503 | 40S ribosomal protein S20 OS = Mus musculus GN = Rps20 PE = 1 SV = 1 |
| 212 | 1 | Q3UW83 | 1 | 0.647 | 2.877 | 2.172 | 0.479 | 0.584 | 2.52 | 3.016 | 40S ribosomal protein S10 OS = Mus musculus GN = Rps10 PE = 1 SV = 1 |
| 213 | 1 | Q91Z50 | 1 | 0.942 | 4.109 | 3.591 | 1.232 | 1.161 | 3.891 | 5.233 | Flap endonuclease 1 OS = Mus musculus GN = Fen1 PE = 1 SV = 1 |

TABLE 4-continued

CA19-9 IP/MS data from C: RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 214 | 1 | P62334 | 1 | 0.576 | 1.367 | 1.037 | 0.815 | 0.623 | 1.176 | 1.751 | 26S proteasome regulatory subunit 10B OS = *Mus musculus* GN = Psmc6 PE = 1 SV = 1 |
| 215 | 1 | P62259 | 1 | 1.086 | 2.463 | 2.3 | 1.552 | 0.884 | 2.109 | 2.692 | 14-3-3 protein epsilon OS = *Mus musculus* GN = Ywhae PE = 1 SV = 1 |
| 216 | 1 | P40142 | 1 | 0.51 | 1.608 | 1.303 | 0.563 | 0.472 | 1.76 | 1.48 | Transketolase OS = *Mus musculus* GN = Tkt PE = 1 SV = 1 |
| 217 | 1 | D3Z5M7 | 1 | 0.816 | 2.945 | 2.318 | 0.725 | 0.634 | 1.654 | 3.259 | Peroxidasin homolog OS = *Mus musculus* GN = Pxdn PE = 1 SV = 2 |
| 218 | 1 | A2AC16 | 1 | 0.958 | 3.258 | 2.421 | 0.655 | 0.766 | 2.743 | 3.667 | Dicarbonyl L-xylulose reductase, isoform CRA_a OS = *Mus musculus* GN = Dcxr PE = 1 SV = 1 |
| 219 | 1 | G3UY38 | 1 | 0.416 | 2.856 | 2.158 | 0.935 | 0.943 | 2.207 | 3.335 | Heterogeneous nuclear ribonucleoprotein L OS = *Mus musculus* GN = Hnrnpl PE = 1 SV = 1 |
| 220 | 1 | P57784 | 1 | 0.6 | 2.382 | 1.774 | 0.952 | 0.524 | 1.629 | 2.484 | U2 small nuclear ribonucleoprotein A' OS = *Mus musculus* GN = Snrpa1 PE = 1 SV = 2 |
| 221 | 1 | A0A0RAJ1N1 | 1 | 0.817 | 0.725 | 0.415 | 0.984 | 0.716 | 0.419 | 0.451 | Inter alpha-trypsin inhibitor, heavy chain 4 OS = *Mus musculus* GN = Itih4 PE = 1 SV = 1 |
| 222 | 1 | A0A1B0GRW3 | 1 | 0.551 | 5.757 | 5.295 | 0.896 | 0.823 | 4.836 | 6.175 | RuvB-like helicase (Fragment) OS = *Mus musculus* GN = Ruvbl2 PE = 1 SV = 1 |
| 223 | 1 | G3UWL2 | 1 | 0.768 | 1.683 | 1.493 | 0.388 | 0.595 | 1.853 | 2.25 | Serine/threonine-protein phosphatase 2A 65 kDa regulatory subunit A alpha isoform (Fragment) OS = *Mus musculus* GN = Ppp2r1a PE = 1 SV = 1 |
| 224 | 1 | Q8C2Q7 | 1 | 0.595 | 3.223 | 2.042 | 0.569 | 0.469 | 2.529 | 3.748 | Heterogeneous nuclear ribonucleoprotein H OS = *Mus musculus* GN = Hnrnph1 PE = 1 SV = 1 |
| 225 | 1 | B1AWD8 | 1 | 1.082 | 5.08 | 4.94 | 0.926 | 0.939 | 4.153 | 6.096 | Clathrin light chain OS = *Mus musculus* GN = Clta PE = 1 SV = 1 |
| 226 | 1 | A0A075B5L2 | 1 | 1.059 | 0.519 | 0.38 | 1.033 | 1.01 | 0.38 | 0.397 | Immunoglobulin kappa chain variable 4-91 (Fragment) OS = *Mus musculus* GN = Igkv4-91 PE = 4 SV = 2 |
| 227 | 1 | V9GWY0 | 1 | 0.835 | 2.199 | 1.811 | 0.26 | 0.415 | 1.626 | 2.482 | 40S ribosomal protein S4 OS = *Mus musculus* GN = Gm15013 PE = 3 SV = 1 |
| 228 | 1 | Q3THK7 | 1 | 0.64 | 1.606 | 1.179 | 0.753 | 0.486 | 1.36 | 1.278 | GMP synthase [glutamine-hydrolyzing] OS = *Mus musculus* GN = Gmps PE = 1 SV = 2 |
| 229 | 1 | A2AWQ2 | 1 | 0.344 | 1.932 | 1 | 0.562 | 1.199 | 1.1 | 0.966 | Protein RCC2 (Fragment) OS = *Mus musculus* GN = Rcc2 PE = 1 SV = 1 |
| 230 | 1 | P60766 | 1 | 0.582 | 2.072 | 1.481 | 0.687 | 0.672 | 1.104 | 1.633 | Cell division control protein 42 homolog OS = *Mus musculus* GN = Cdc42 PE = 1 SV = 2 |
| 231 | 1 | A0A087WNS9 | 1 | 1.117 | 4.913 | 3.616 | 0.86 | 0.561 | 2.397 | 5.72 | Lymphocyte antigen 6E (Fragment) OS = *Mus musculus* GN = Ly6e PE = 1 SV = 6 |
| 232 | 1 | A0A1C7ZMZ5 | 1 | 0.501 | 1.013 | 0.719 | 0.53 | 0.708 | 0.885 | 0.764 | Glutathione peroxidase (Fragment) OS = *Mus musculus* GN = Gpx3 PE = 1 SV = 1 |
| 233 | 1 | P32233 | 1 | 0.352 | 1.29 | 0.902 | 0.186 | 0.328 | 1.039 | 1.249 | Developmentally-regulated GTP-binding protein 1 OS = *Mus musculus* GN = Drg1 PE = 1 SV = 1 |
| 234 | 1 | A0A0B4J1I5 | 1 | 1.001 | 0.511 | 0.404 | 1.199 | 1.217 | 0.361 | 0.369 | Immunoglobulin kappa chain variable 4-70 (Fragment) OS = *Mus musculus* GN = Igkv4-70 PE = 4 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 235 | 1 | A0A1W2P6P4 | 1 | 0.898 | 4.327 | 3.723 | 0.847 | 1.075 | 4.47 | 5.501 | RNA-binding protein Nova-1 (Fragment) OS = Mus musculus GN = Nova1 PE = 1 SV = 1 |
| 236 | 1 | B1AXW5 | 1 | 0.844 | 2.601 | 2.066 | 1.097 | 0.646 | 3.007 | 3.446 | Peroxiredoxin-1 (Fragment) OS = Mus musculus GN = Prdx1 PE = 1 SV = 8 |
| 237 | 1 | A0A140T8V5 | 1 | 0.703 | 2.519 | 1.723 | 0.817 | 0.705 | 1.221 | 1.876 | Proliferating cell nuclear antigen OS = Mus musculus GN = Pcna-ps2 PE = 3 SV = 1 |
| 238 | 1 | P46664 | 1 | 0.639 | 3.463 | 2.71 | 0.717 | 0.599 | 3.222 | 3.957 | Adenylosuccinate synthetase isozyme 2 OS = Mus musculus GN = Adss PE = 1 SV = 2 |
| 239 | 1 | A0A075B5J9 | 1 | 0.722 | 0.238 | 0.317 | 0.893 | 0.713 | 0.152 | 0.291 | Immunoglobulin kappa variable 17-127 OS = Mus musculus GN = Igkv17-127 PE = 4 SV = 7 |
| 240 | 1 | A0A1B0GRR3 | 1 | 0.603 | 1.916 | 1.799 | 1.021 | 0.306 | 1.717 | 1.482 | 40S ribosomal protein S11 OS = Mus musculus GN = Rps11 PE = 1 SV = 1 |
| 241 | 1 | P01029 | 1 | 1.517 | 2.155 | 1.795 | 1.651 | 1.178 | 2.882 | 2.078 | Complement C4-B OS = Mus musculus GN = C4b PE = 1 SV = 3 |
| 242 | 1 | A0A087WS46 | 1 | 0.95 | 10.1 | 6.903 | 0.715 | 1.096 | 6.002 | 9.535 | Eukaryotic translation elongation factor 1 beta 2 OS = Mus musculus GN = Eef1b2 PE = 1 SV = 1 |
| 243 | 1 | A2A7S7 | 1 | 0.715 | 3.249 | 2.641 | 1.017 | 0.526 | 2.289 | 3.412 | Tyrosine-tRNA ligase OS = Mus musculus GN = Yars PE = 1 SV = 1 |
| 244 | 1 | Q8BHN3 | 1 | 0.948 | 4.175 | 3.14 | 0.737 | 0.752 | 3.069 | 4.272 | Neutral alpha-glucosidase AB OS = Mus musculus GN = Ganab PE = 1 SV = 1 |
| 245 | 1 | P51881 | 1 | 0.798 | 1.039 | 1.116 | 0.628 | 0.475 | 0.908 | 1.481 | ADP/ATP translocase 2 OS = Mus musculus GN = Slc25a5 PE = 1 SV = 3 |
| 246 | 1 | Q6P5H2 | 1 | 0.694 | 1.281 | 0.855 | 1.057 | 0.684 | 1.845 | 0.812 | Nestin OS = Mus musculus GN = Nes PE = 1 SV = 1 |
| 247 | 1 | Q8IZK9 | 1 | 0.643 | 1.079 | 0.805 | 0.519 | 0.506 | 0.999 | 1.157 | Hydroxymethylglutaryl-CoA synthase, cytoplasmic OS = Mus musculus GN = Hmgcs1 PE = 1 SV = 1 |
| 248 | 1 | P97310 | 1 | 0.553 | 2.77 | 1.723 | 0.608 | 0.568 | 2.23 | 2.508 | DNA replication licensing factor MCM2 OS = Mus musculus GN = Mcm2 PE = 1 SV = 3 |
| 249 | 1 | Q91VB8 | 1 | 0.67 | 2.657 | 1.646 | 0.622 | 0.569 | 2.44 | 3.115 | Alpha globin 1 OS = Mus musculus GN = Hba-a2 PE = 1 SV = 1 |
| 250 | 1 | Q9JHU4 | 1 | 0.288 | 1.94 | 1.655 | 0.308 | 0.284 | 1.785 | 2.339 | Cytoplasmic dynein 1 heavy chain 1 OS = Mus musculus GN = Dync1h1 PE = 1 SV = 2 |
| 251 | 1 | Q8BP47 | 1 | 0.256 | 1.381 | 0.972 | 0.208 | 0.29 | 1.067 | 1.751 | Asparagine-tRNA ligase, cytoplasmic OS = Mus musculus GN = Nars PE = 1 SV = 2 |
| 252 | 1 | Q9Z1F9 | 1 | 0.795 | 1.577 | 1.046 | 0.5 | 0.754 | 1.08 | 1.258 | SUMO-activating enzyme subunit 2 OS = Mus musculus GN = Uba2 PE = 1 SV = 1 |
| 253 | 1 | A2AAW9 | 1 | 0.748 | 2.627 | 1.897 | 1.018 | 1.212 | 1.731 | 2.578 | Eukaryotic translation initiation factor 2 subunit 3, X-linked OS = Mus musculus GN = Eif2s3x PE = 1 SV = 1 |
| 254 | 1 | P11103 | 1 | 0.423 | 3.322 | 2.828 | 0.731 | 0.485 | 2.75 | 2.51 | Poly [ADP-ribose] polymerase 1 OS = Mus musculus GN = Parp1 PE = 1 SV = 3 |
| 255 | 1 | A0A075B5Y1 | 1 | 0.78 | 0.601 | 0.484 | 0.775 | 0.682 | 0.267 | 0.528 | Immunoglobulin heavy variable V1-74 OS = Mus musculus GN = Ighv1-74 PE = 4 SV = 1 |
| 256 | 1 | G3UXL2 | 1 | 1.318 | 6.131 | 5.212 | 1.095 | 1.168 | 3.681 | 7.362 | Phosphoribosyl pyrophosphate synthetase 1-like 3 OS = Mus musculus GN = Prps1l3 PE = 3 SV = 1 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 257 | 1 | Q9CR49 | 1 | 0.622 | 1.032 | 5.211 | 0.773 | 0.779 | 0.758 | 5.878 | Globin b1 OS = Mus musculus GN = Hbb-y PE = 1 SV = 1 |
| 258 | 1 | A0A140T8M5 | 1 | 0.759 | 0.557 | 0.499 | 1.163 | 1.017 | 0.441 | 0.596 | Immunoglobulin kappa variable 6-15 (Fragment) OS = Mus musculus GN = Igkv6-15 PE = 1 SV = 2 |
| 259 | 1 | A0A0A0MQ68 | 1 | 0.497 | 1.552 | 1.494 | 0.202 | 0.33 | 1.788 | 2.288 | Glutaryl-CoA dehydrogenase, mitochondrial OS = Mus musculus GN = Gcdh PE = 1 SV = 1 |
| 260 | 1 | A0A087WP86 | 1 | 0.137 | 1.201 | 0.946 | 0.234 | — | 1.135 | 1.151 | Actin-related protein 3 (Fragment) OS = Mus musculus GN = Actr3 PE = 1 SV = 1 |
| 261 | 1 | A0A075B5K9 | 1 | 0.708 | 1.305 | 0.869 | 1.045 | 0.949 | 2.026 | 0.941 | Immunoglobulin kappa variable 12-98 OS = Mus musculus GN = Igkv12-98 PE = 4 SV = 7 |
| 262 | 1 | Q63870 | 1 | 0.762 | 8.637 | 8.601 | 2.41 | 0.796 | 11.59 | 10.74 | Collagen alpha-1(VII) chain OS = Mus musculus GN = Col7a1 PE = 1 SV = 3 |
| 263 | 1 | S4R116 | 1 | 0.583 | 1.989 | 1.672 | 0.757 | 0.557 | 1.714 | 2.148 | MCG2872, isoform CRA_b OS = Mus musculus GN = Ddx5 PE = 1 SV = 1 |
| 264 | 1 | Q9QXK3 | 1 | 0.239 | 1.444 | 1.214 | 0.308 | 0.374 | 1.218 | 1.822 | Coatomer subunit gamma-2 OS = Mus musculus GN = Copg2 PE = 1 SV = 1 |
| 265 | 1 | Q9DBM2 | 1 | 0.647 | 2.24 | 1.909 | 0.715 | 0.636 | 1.734 | 2.203 | Peroxisomal bifunctional enzyme OS = Mus musculus GN = Ehhadh PE = 1 SV = 4 |
| 266 | 1 | A0A075B6D5 | 1 | 0.439 | 0.689 | 0.46 | 0.664 | 0.645 | 0.462 | 0.51 | Immunoglobulin kappa chain variable 19-93 OS = Mus musculus GN = Igkv19-93 PE = 1 SV = 7 |
| 267 | 1 | Q921M3 | 1 | 0.66 | 1.836 | 1.273 | 0.455 | 0.587 | 1.506 | 2.593 | Splicing factor 3B subunit 3 OS = Mus musculus GN = Sf3b3 PE = 1 SV = 1 |
| 268 | 1 | A0A075B5LA | 1 | 1.021 | 2.049 | 1.249 | 1.053 | 0.897 | 2.002 | 2.169 | Immunoglobulin kappa chain variable 12-89 OS = Mus musculus GN = Igkv12-89 PE-4 SV = 7 |
| 269 | 1 | G3UY93 | 1 | 0.304 | 4.516 | 3.545 | 0.504 | 0.606 | 4.105 | 4.936 | Valine-tRNA ligase (Fragment) OS = Mus musculus GN = Vars PE = 1 SV = 1 |
| 270 | 1 | D3YW60 | 1 | 0.571 | 1.2 | 1.144 | 0.445 | 0.538 | 1.162 | 1.567 | RuvB-like helicase (Fragment) OS = Mus musculus GN = Ruvbl1 PE = 1 SV = 1 |
| 271 | 1 | Q9CZD3 | 1 | 0.609 | 2.335 | 1.447 | 0.583 | 0.699 | 1.325 | 1.647 | Glycine-tRNA ligase OS = Mus musculus GN = Gars PE = 1 SV = 1 |
| 272 | 1 | Q9D892 | 1 | 1.197 | 1.796 | 1.328 | 1.036 | 1.643 | 1.366 | 1.483 | Inosine triphosphate pyrophosphatase OS = Mus musculus GN = Itpa PE = 1 SV = 2 |
| 273 | 1 | E9Q0U7 | 1 | 0.687 | 2.999 | 2.083 | 0.529 | 0.738 | 2.032 | 2.387 | Heat shock protein 105 kDa OS = Mus musculus GN = Hsph1 PE = 1 SV = 1 |
| 274 | 1 | Q9D8E6 | 1 | 0.982 | 1.863 | 0.85 | 1.229 | 0.873 | 1.51 | 2.251 | 60S ribosomal protein L4 OS = Mus musculus GN = Rpl4 PE = 1 SV = 3 |

TABLE 4-continued

CA19-9 IP/MS data from C; RLSL; F or genetic negative organoid (A225 and A223, respectively) conditioned media after 8 hours of Dox treatment. "25 0H NS19" indicates A225 organoids before treatment with NS19-9; "25 8H NS19" indicates A225 organoids after 8 hours of Dox treatment with NS19-9; "25 0H 5B1" indicates A225 organoids before treatment with 5B1; "25 8H 5B1" indicates A225 organoids after 8 hours of treatment with 5B1; "23 0H NS19" indicates A223 organoids before treatment with NS19-9; "23 8H NS19" indicates A223 organoids after 8 hours of treatment with NS19-9; "23 0H 5B1" indicates A223 organoids before treatment with 5B1; "23 8H 5B1" indicates A223 organoids after 8 hours of treatment with 5B1.

| Family | Member | UniProt_mouse Accession | 25 0H NS19 | 25 8H NS19 | 25 0H 5B1 | 25 8H 5B1 | 23 0H NS19 | 23 8H NS19 | 23 0H 5B1 | 23 8H 5B1 | Description |
|---|---|---|---|---|---|---|---|---|---|---|---|
| 275 | 1 | A0A075B5V8 | 1 | 0.826 | 0.303 | 0.151 | 1.223 | 0.752 | 0.083 | 0.095 | Immunoglobulin heavy variable 1-47 OS = Mus musculus GN = Ighv1-47 PE-4 SV = 1 |
| 276 | 1 | Q9EQH3 | 1 | 0.506 | 1.431 | 1.263 | 0.444 | 0.434 | 1.231 | 1.506 | Vacuolar protein sorting-associated protein 35 OS = Mus musculus GN = Vps35 PE = 1 SV = 1 |
| 277 | 1 | Q8K2G4 | 1 | 0.318 | 1.008 | 0.544 | 0.324 | 0.345 | 0.755 | 0.899 | Bardet-Biedl syndrome 7 protein homolog OS = Mus musculus GN = Bbs7 PE = 1 SV = 1 |
| 278 | 1 | P32261 | 1 | 0.572 | 1.315 | 1.028 | 0.633 | 0.309 | 1.164 | 1.288 | Antithrombin-III OS = Mus musculus GN = Serpinc1 PE = 1 SV = 1 |
| 279 | 1 | Q9D964 | 1 | 0.56 | 2.718 | 2.328 | 1.064 | 0.883 | 2.362 | 2.36 | Glycine amidinotransferase, mitochondrial OS = Mus musculus GN = Gatm PE = 1 SV = 1 |
| 280 | 1 | A0A075B5Q5 | 1 | 1.001 | 4.747 | 3.097 | 2.198 | 1.585 | 7.816 | 4.239 | Immunoglobulin heavy variable 2-9 (Fragment) OS = Mus musculus GN = Ighv2-9 PE = 4 SV = 1 |
| 281 | 1 | A0A1W2P6F6 | 1 | 0.732 | 2.193 | 1.027 | 0.764 | 0.857 | 1.399 | 1.959 | Myosin light polypeptide 6 OS = Mus musculus GN = My16 PE = 1 SV = 1 |

An imbalance in glycosylation has been commonly described in human disease, but the biological role of glycan changes in mediating disease has been largely unexplored. While elevation of CA19-9 has been correlated with pancreatitis, it has not been previously considered to directly contribute to disease pathogenesis. The ability of CA19-9 expression to instigate and perpetuate pancreatitis in mice suggests that this glycan epitope and its downstream effector pathways may represent new treatment strategies for the resolution of pancreatitis and prevention of pancreatic tumorigenesis. Currently, the treatment options for pancreatitis patients remain limited despite the risk of morbidity and pancreatic cancer. The anti-CA19-9 antibodies provided herein (Sawada, R. et al. Clin Cancer Res 17, 1024-1032 (2011), which is hereby incorporated in its entirety by reference) can facilitate rapid translation of CA19-9 targeted therapy to the clinic for the treatment of pancreatitis patients.

What is claimed is:

1. A method for treating, ameliorating, or managing pancreatitis in a subject in need thereof comprising administering to the subject a therapeutically effective amount of an antibody or functional fragment thereof that binds to Sialyl-Lewis$^a$ (anti-sLe$^a$), wherein said anti-sLe$^a$ antibody or functional fragment comprises:

(i) a variable heavy chain (VH) domain comprising three VH complementarity defining regions (CDRs) present in the amino acid sequence of SEQ ID NO: 2; and a variable light chain (VL) domain comprising three VL CDRs present in the amino acid sequence of SEQ ID NO: 4;

(ii) a VH domain comprising three VH CDRs present in the amino acid sequence of SEQ ID NO: 6; and a VL domain comprising three VL CDRs present in the amino acid sequence of SEQ ID NO: 8;

(iii) a V5 domain comprising three V2 CDRs present in the amino acid sequence of SEQ ID NO: 10; and a VL domain comprising three VL CDRs present in the amino acid sequence of SEQ ID NO: 12;

(iv) a VH domain comprising three VH CDRs present in the amino acid sequence of SEQ ID NO: 14; and a VL domain comprising three VL CDRs present in the amino acid sequence of SEQ ID NO: 16: or (v) a VH domain comprising three VH CDRs present in the amino acid sequence of an antibody produced by a hybridoma deposited under American Type Culture Collection (ATCC) Accession No. HB-8059; and a VL domain comprising three VL CDRs present in the amino acid sequence of an antibody produced by a hybridoma deposited under American Type Culture Collection (ATCC) Accession No. HB-8059.

2. The method of claim 1, wherein the method further comprises:

determining a first severity of pancreatitis in said subject prior to administering said antibody or functional fragment thereof, determining a second severity of pancreatitis in said subject after administering said antibody or functional fragment thereof, and administering a second dose of the antibody or functional fragment thereof at the same or lower amount than the first dose if the second severity of pancreatitis in the subject is reduced in comparison to the first severity of pancreatitis in the subject, or administering a second dose of the antibody or functional fragment thereof at a higher amount than the first dose if the second severity of pancreatitis in the subject is not reduced compared to the first severity of pancreatitis.

3. The method of claim 1, wherein said VH domain and said VL domain respectively comprise an amino acid sequence selected from the group consisting of residues 20-142 of SEQ ID NO: 2 and residues 20-130 of SEQ ID NO: 4; residues 20-142 of SEQ ID NO: 6 and residues 20-129 of SEQ ID NO: 8; residues 20-142 of SEQ ID NO: 10 and residues 20-130 of SEQ ID NO: 12; and residues 20-145 of SEQ ID NO: 14 and residues 23-130 of SEQ ID NO: 16.

4. The method of claim 2, wherein said anti-sLe$^a$ antibody or functional fragment thereof comprises a heavy chain variable region consisting of the amino acid sequence of the heavy chain variable region of an antibody produced by a hybridoma deposited under American Type Culture Collection (ATCC) Accession No. HB-8059, and a light chain variable region consisting of the amino acid sequence of the light chain variable region of an antibody produced by a hybridoma deposited under ATCC Accession No. HB-8059.

5. The method of claim 2, wherein said anti-sLe$^a$ antibody or functional fragment thereof comprises a heavy chain consisting of the amino acid sequence of the heavy chain of an antibody produced by a hybridoma deposited under ATCC. Accession No. HB-8059, and a light chain consisting of the amino acid sequence of the light chain of an antibody produced by a hybridoma deposited under ATCC. Accession No. HB-8059.

6. The method of claim 1, wherein said anti-sLe$^a$ antibody functional fragment is selected from the group consisting of a Fab, a Fab', a F(ab')2, a scFV, a diabody, a triabody, and a minibody.

7. The method of claim 6, wherein said anti-sLe$^a$ antibody functional fragment is a diabody.

8. The method of claim 7, wherein said diabody comprises the amino acid sequence of SEQ ID NO: 18 or 20.

9. The method of claim 1, wherein said anti-sLe$^a$ antibody or functional fragment thereof is a monoclonal antibody.

10. The method of claim 1, wherein said anti-sLe$^a$ antibody or functional fragment thereof is an IgG or IgM isotype.

11. The method of claim 10, wherein said IgG antibody is an IgG1, IgG2, IgG3, or IgG4 subclass.

12. The method of claim 1, wherein the anti-sLe$^a$ antibody or functional fragment thereof is formulated as a pharmaceutical composition comprising a pharmaceutically acceptable carrier.

13. The method of claim 1, wherein the antibody or functional fragment thereof is administered by a parenteral route of administration.

14. The method of claim 13, wherein the parenteral administration is selected from a group consisting of subcutaneous injection, intramuscular injection, and intravenous injection.

15. The method of claim 1, wherein the antibody or functional fragment thereof is administered at a dose range from about 0.1 mg/kg/dose to about 10 mg/kg/dose.

16. The method of claim 1, wherein the antibody or functional fragment thereof is administered weekly, bi-weekly, monthly, or bi-monthly.

17. The method of claim 16, wherein the antibody or functional fragment thereof is administered for about one, two, three, four, five, or six months.

18. The method of claim 9, wherein the anti-sLe$^a$ antibody or functional fragment thereof is a mouse, a chimeric, a humanized, or a fully human monoclonal antibody.

19. The method of claim 1, wherein the pancreatitis is characterized by one or more markers.

20. The method of claim 2, wherein the severity of the pancreatitis is determined by one or more markers.

21. The method of claim 2, wherein the subject has elevated levels of one or more markers for pancreatitis.

22. The method of claim 2, wherein the administering of the therapeutic agent results in reduced levels of one or more markers for pancreatitis in the subject.

23. The method of claim 19, wherein the one or more markers are selected from a group consisting of a physiological marker, a histological marker, a serological marker, and a signaling marker.

24. The method of claim 23, wherein the histological marker is selected from a group consisting of immune cell invasion, collagen deposition, fibrotic tissue, fat necrosis, interstitial edema, acinar and blood vessel destruction, interstitial hemorrhage, ductal dilation, acinar cell homogenization, and expression level of CA19-9.

25. The method of claim 19, wherein the one or more markers comprise expression level of CA19-9.

26. The method of claim 25, wherein the one or more markers are determined by immunohistochemistry.

27. The method of claim 23, wherein the serological marker is selected from a group consisting of serum lipase level, serum amylase level, and serum C reactive protein level.

28. The method of claim 27, wherein the serum lipase level is over 200 U/L.

29. The method of claim 27, wherein the serum amylase level is over 200 U/L.

30. The method of claim 27, wherein the serum amylase level is three times over the upper limit of normal serum amylase level of a control subject.

31. The method of claim 27, wherein the serum lipase level is three times over the upper limit of normal serum lipase level of a control subject.

32. The method of claim 23, wherein the physiological marker is selected from a group consisting of weight loss, malabsorption of food, pancreatic atrophy, pancreatic enlargement, pancreatic inflammation, and bile reflux.

33. A method for treating, ameliorating, or managing pancreatitis in a subject having elevated pancreatic sLe$^a$, said method comprising administering to the subject a therapeutically effective amount of an antibody or functional fragment thereof that specifically binds to sLe$^a$, wherein said anti-sLe$^a$ antibody or functional fragment comprises:
  (i) a variable heavy chain (VH) domain comprising three VH complementarity defining regions (CDRs) present in the amino acid sequence of SEQ ID NO: 2; and a variable light chain (VL) domain comprising three VL CDRs present in the amino acid sequence of SEQ ID NO: 4;
  (ii) a VH domain comprising three VH CDRs present in the amino acid sequence of SEQ ID NO: 6; and a VL domain comprising three VL CDRs present in the amino acid sequence of SEQ ID NO: 8;
  (iii) a VH domain comprising three VH CDRs present in the amino acid sequence of SEQ ID NO: 10; and a VL domain comprising three VL CDRs present in the amino acid sequence of SEQ ID NO: 12;
  (iv) a VH domain comprising three VH CDRs present in the amino acid sequence of SEQ ID NO: 14; and a VL domain comprising three VL CDRs present in the amino acid sequence of SEQ ID NO: 16: or
  (v) a VH domain comprising three VH CDRs present in the amino acid sequence of an antibody produced by a hybridoma deposited under American Type Culture Collection (ATCC) Accession No. HB-8059; and a VL domain comprising three VL CDRs present in the amino acid sequence of an antibody produced by a hybridoma deposited under American Type Culture Collection (ATCC) Accession No. HB-8059.

34. The method of claim 33, wherein the pancreatitis is a pancreatitis selected from a group consisting of chronic pancreatitis and acute pancreatitis.

35. The method of claim 34, wherein the chronic pancreatitis is selected from a group consisting of mild chronic pancreatitis, moderate chronic pancreatitis, and severe chronic pancreatitis.

36. The method of claim 34, wherein the acute pancreatitis is selected from a group consisting of mild acute pancreatitis, moderate acute pancreatitis, and severe acute pancreatitis.

37. The method of claim 34, wherein the subject is a mammal.

38. The method of claim 37, wherein the mammal is a human.

* * * * *

UNITED STATES PATENT AND TRADEMARK OFFICE
CERTIFICATE OF CORRECTION

PATENT NO. : 12,378,320 B2  
APPLICATION NO. : 17/274783  
DATED : August 5, 2025  
INVENTOR(S) : Dannielle D. Engle et al.

Page 1 of 1

It is certified that error appears in the above-identified patent and that said Letters Patent is hereby corrected as shown below:

In the Claims

Column 161, Line 1 (Claim 1) delete "a V5 domain comprising three V2 CDRs" and insert -- a VH domain comprising three VH CDRs -- therefore.

Signed and Sealed this  
Eleventh Day of November, 2025

John A. Squires  
*Director of the United States Patent and Trademark Office*

SEQUENCE LISTING

<160> NUMBER OF SEQ ID NOS: 20

<210> SEQ ID NO 1
<211> LENGTH: 426
<212> TYPE: DNA
<213> ORGANISM: Artificial Sequence
<220> FEATURE:
<223> OTHER INFORMATION: VH chain domain of clone 5B1

<400> SEQUENCE: 1

```
atggagtttg ggctgagctg gcttttctt gtggctattt taaaaggcgt acagtgccag        60
gtgcagctgg tggagtctgg gggaggctcg gtgcagcctg gcaggtccct gagactctcc       120
tgtgaagcct ctggattcac ctttgaggcc tatgccatgc actgggtccg gcaacctcca       180
gggaagggcc tggagtgggt ctcaagtatt aattggaata gtggtcgcat agcctatgcg       240
gactctgtga agggccgatt caccatctcc agagacaacg ccaggaattc cctgtatctg       300
caaatgaaca gtctgagact tgaggacacg gccttctatt actgtgcaaa agatatacgg       360
aggtttagta ccggggggggc ggagtttgag tactggggcc agggaaccct ggtcaccgtc       420
tcctca                                                                  426
```

<210> SEQ ID NO 2
<211> LENGTH: 142
<212> TYPE: PRT
<213> ORGANISM: Artificial Sequence
<220> FEATURE:
<223> OTHER INFORMATION: VH chain domain of clone 5B1

<400> SEQUENCE: 2

```
Met Glu Phe Gly Leu Ser Trp Leu Phe Leu Val Ala Ile Leu Lys Gly
1               5                   10                  15

Val Gln Cys Gln Val Gln Leu Val Glu Ser Gly Gly Gly Ser Val Gln
            20                  25                  30

Pro Gly Arg Ser Leu Arg Leu Ser Cys Glu Ala Ser Gly Phe Thr Phe
        35                  40                  45

Glu Ala Tyr Ala Met His Trp Val Arg Gln Pro Pro Gly Lys Gly Leu
    50                  55                  60

Glu Trp Val Ser Ser Ile Asn Trp Asn Ser Gly Arg Ile Ala Tyr Ala
65                  70                  75                  80

Asp Ser Val Lys Gly Arg Phe Thr Ile Ser Arg Asp Asn Ala Arg Asn
                85                  90                  95

Ser Leu Tyr Leu Gln Met Asn Ser Leu Arg Leu Glu Asp Thr Ala Phe
            100                 105                 110

Tyr Tyr Cys Ala Lys Asp Ile Arg Arg Phe Ser Thr Gly Gly Ala Glu
        115                 120                 125

Phe Glu Tyr Trp Gly Gln Gly Thr Leu Val Thr Val Ser Ser
    130                 135                 140
```

<210> SEQ ID NO 3

```
<211> LENGTH: 390
<212> TYPE: DNA
<213> ORGANISM: Artificial Sequence
<220> FEATURE:
<223> OTHER INFORMATION: VL chain domain of clone 5B1

<400> SEQUENCE: 3
atggccggct ccctctcct cctcaccctc ctcactcact gtgcagggtc ttgggcccag    60
tctgtgctga ctcagccgcc ctcagcgtct gggaccccg ggcagagggt caccatctct   120
tgttctggaa gcagctccaa catcggaagt aattttgtat actggtacca gcagctccca   180
ggaacggccc ccaaactcct catatatagg aataatcagc ggccctcagg ggtccctgac   240
cgattctctg gctccaggtc tggcacctca gcctccctgg ccatcagtgg actccggtcc   300
gaggatgagg ctgattatta ctgtgcagca tgggatgaca gcctgggagg ccattatgtc   360
ttcggaactg ggaccaaggt caccgtcctt                                    390

<210> SEQ ID NO 4
<211> LENGTH: 130
<212> TYPE: PRT
<213> ORGANISM: Artificial Sequence
<220> FEATURE:
<223> OTHER INFORMATION: VL chain domain of clone 5B1

<400> SEQUENCE: 4

Met Ala Gly Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Phe Val Tyr Trp Tyr Gln Gln Leu Pro Gly Thr Ala Pro
    50                  55                  60

Lys Leu Leu Ile Tyr Arg Asn Asn Gln Arg Pro Ser Gly Val Pro Asp
65                  70                  75                  80

Arg Phe Ser Gly Ser Arg Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Gly Gly His Tyr Val Phe Gly Thr Gly Thr Lys Val Thr
        115                 120                 125

Val Leu
    130

<210> SEQ ID NO 5
<211> LENGTH: 426
<212> TYPE: DNA
<213> ORGANISM: Artificial Sequence
<220> FEATURE:
<223> OTHER INFORMATION: VH chain domain of clone 9H3

<400> SEQUENCE: 5
atggagtttg ggctgagctg gcttttttctt gtggctattt taaaaggcgt acagtgcgaa    60
gtgcagctgt tggagtctgg gggaggcttg gtacagcctg gcaggtccct gagactctcc   120
tgtgcggcct ctggatttac ctttgatgat tatgtcatgc actgggtccg gcaagctcca   180
gggaagggcc tggagtgggt ctcaagtatt agttggaata gtggtagcat aggctatgcg   240
gactctgtga agggccgatt catcatctcc agagacaacg ccaagaactc cctgtatctg   300
```

```
caaatgaaca gtctgagagc tgaggacacg gccttgtatt actgtgcaaa agatcgtcgt    360
attaggggtg actcgggggtt cgagggtgac tactggggcc agggaaccct ggtcaccgtc    420
tcctca                                                                426
```

<210> SEQ ID NO 6
<211> LENGTH: 142
<212> TYPE: PRT
<213> ORGANISM: Artificial Sequence
<220> FEATURE:
<223> OTHER INFORMATION: VH chain domain of clone 9H3

<400> SEQUENCE: 6

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Val Met His Trp Val Arg Gln Ala Pro Gly Lys Gly Leu
    50                  55                  60

Glu Trp Val Ser Ser Ile Ser Trp Asn Ser Gly Ser Ile Gly Tyr Ala
65                  70                  75                  80

Asp Ser Val Lys Gly Arg Phe Ile Ile Ser Arg Asp Asn Ala Lys Asn
                85                  90                  95

Ser Leu Tyr Leu Gln Met Asn Ser Leu Arg Ala Glu Asp Thr Ala Leu
            100                 105                 110

Tyr Tyr Cys Ala Lys Asp Arg Arg Ile Arg Gly Asp Ser Gly Phe Glu
        115                 120                 125

Gly Asp Tyr Trp Gly Gln Gly Thr Leu Val Thr Val Ser Ser
    130                 135                 140
```

<210> SEQ ID NO 7
<211> LENGTH: 387
<212> TYPE: DNA
<213> ORGANISM: Artificial Sequence
<220> FEATURE:
<223> OTHER INFORMATION: VL chain domain of clone 9H3

<400> SEQUENCE: 7

```
atggccggct ccctctcct cctcaccctc ctcactcact gtgcagggtc ttgggcccag    60
tctgtgttga cgcagccgcc ctcagcgtct gggaccccg gcagagggt caccatctct    120 tgttctggaa gcagctccaa catcggaagt aattatgtat actggtacca gcagctccca    180
ggaacggccc ccaaactcct catctatagg aataatcagc ggcccctcagg ggtccctgac    240 cgattctctg gctccaagtc tggcacctca gcctccctgg ccatcagtgg gctccggtcc    300
gaggatgagg ctgattatta ctgtgcagca tgggatgcca gcctgagtgg tgtggtattc    360
ggcggaggga ccaagctgac cgtccta                                         387
```

<210> SEQ ID NO 8
<211> LENGTH: 129
<212> TYPE: PRT
<213> ORGANISM: Artificial Sequence
<220> FEATURE:
<223> OTHER INFORMATION: VL chain domain of clone 9H3

<400> SEQUENCE: 8

```
Met Ala Gly Phe Pro Leu Leu Leu Thr Leu Leu Thr His Cys Ala Gly
1               5                   10                  15
```

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
            35                  40                  45

Gly Ser Asn Tyr Val Tyr Trp Tyr Gln Gln Leu Pro Gly Thr Ala Pro
    50                  55                  60

Lys Leu Leu Ile Tyr Arg Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Ala Ser Leu Ser Gly Val Val Phe Gly Gly Gly Thr Lys Leu Thr Val
            115                 120                 125

Leu

<210> SEQ ID NO 9
<211> LENGTH: 426
<212> TYPE: DNA
<213> ORGANISM: Artificial Sequence
<220> FEATURE:
<223> OTHER INFORMATION: VH chain domain of clone 5H11

<400> SEQUENCE: 9
atggagtttg ggctgagctg cttttttctt gtggctattt taaaaggcgt acagtgccag    60
gtgcagctgt tggagtctgg gggaggcttg gtacagcctg gcaggtccct gagactctcc   120
tgtgcagcct ctggattcac ctttgatgaa tatgccatgc actgggtccg gcaagctcca   180
gggaagggcc tggagtgggt ctcaagtgtt agttggaata gtggtagcat aggctatgcg   240
gactctgtga agggccgatt caccatctcc agagacaacg ccaagaactc cctgtatcta   300
caaatgaaca gtctgagagc tgaggacacg gccttgtatt actgtgcaaa agatatacgg   360
acctatagca ccggggggc ggagtttgcc tcctggggcc agggaaccct ggtcaccgcc   420
tcctca                                                              426

<210> SEQ ID NO 10
<211> LENGTH: 142
<212> TYPE: PRT
<213> ORGANISM: Artificial Sequence
<220> FEATURE:
<223> OTHER INFORMATION: VH chain domain of clone 5H11

<400> SEQUENCE: 10

Met Glu Phe Gly Leu Ser Trp Leu Phe Leu Val Ala Ile Leu Lys Gly
1               5                   10                  15

Val Gln Cys Gln Val Gln Leu Leu Glu Ser Gly Gly Gly Leu Val Gln
            20                  25                  30

Pro Gly Arg Ser Leu Arg Leu Ser Cys Ala Ala Ser Gly Phe Thr Phe
            35                  40                  45

Asp Glu Tyr Ala Met His Trp Val Arg Gln Ala Pro Gly Lys Gly Leu
    50                  55                  60

Glu Trp Val Ser Ser Val Ser Trp Asn Ser Gly Ser Ile Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Leu

```
              100                 105                 110
Tyr Tyr Cys Ala Lys Asp Ile Arg Thr Tyr Ser Thr Gly Gly Ala Glu
        115                 120                 125

Phe Ala Ser Trp Gly Gln Gly Thr Leu Val Thr Ala Ser Ser
    130                 135                 140
```

<210> SEQ ID NO 11
<211> LENGTH: 390
<212> TYPE: DNA
<213> ORGANISM: Artificial Sequence
<220> FEATURE:
<223> OTHER INFORMATION: VL chain domain of clone 5H11

<400> SEQUENCE: 11

```
atggccggct tccctctcct cctcaccctc ctcactcact gtgcagggtc ttgggcccag      60
tctgtgttga cgcagccgcc ctcagcgtct gggaccccccg gcagagggt caccatctct     120 tgttctggaa gcagctccaa catcggaagt aattatgtat actggtacca gcaggtccca     180
ggaacggccc ccaaactcct catctatagg aataatcagc ggccctcagg ggtccctgac     240
cgattctctg gctccaagtc tggcacctca gcctccctgg ccatcagtgg gctccggtcc     300
gaggatgagg ctgattatta ctgtgcagca tgggatgaca gcctgagtgg ccattatgtc     360
ttcggaactg ggaccaaggt caccgtccta                                      390
```

<210> SEQ ID NO 12
<211> LENGTH: 130
<212> TYPE: PRT
<213> ORGANISM: Artificial Sequence
<220> FEATURE:
<223> OTHER INFORMATION: VL chain domain of clone 5H11

<400> SEQUENCE: 12

```
Met Ala Gly Phe Pro Leu Leu Leu Thr Leu Leu Thr His Cys Ala Gly
1               5                   10                  15

Ser Trp Ala Gln Ser Val Leu Thr Gln Pro Pro Ser Ala Ser Gly Thr
            20                  25                  30

Pro Gly Gln Arg Val Thr Ile Ser Cys Ser Gly Ser Ser Ser Asn Ile
        35                  40                  45

Gly Ser Asn Tyr Val Tyr Trp Tyr Gln Gln Val Pro Gly Thr Ala Pro
    50                  55                  60

Lys Leu Leu Ile Tyr Arg Asn Asn Gln Arg Pro Ser Gly Val Pro Asp
65                  70                  75                  80

Arg Phe Ser Gly Ser Lys Ser Gly Thr Ser Ala Ser Leu Ala Ile Ser
                85                  90                  95

Gly Leu Arg Ser Glu Asp Glu Ala Asp Tyr Tyr Cys Ala Ala Trp Asp
            100                 105                 110

Asp Ser Leu Ser Gly His Tyr Val Phe Gly Thr Gly Thr Lys Val Thr
        115                 120                 125

Val Leu
    130
```

<210> SEQ ID NO 13
<211> LENGTH: 435
<212> TYPE: DNA
<213> ORGANISM: Artificial Sequence
<220> FEATURE:
<223> OTHER INFORMATION: VH chain domain of clone 7E3

<400> SEQUENCE: 13

```
atggagtttg gctgagctg cttttttctt gtggctattt taaaaggcgt acagtgccaa      60
gtgcagctgt tggagtctgg gggaggcgtg gtccagcctg gaggtccct gagactctcc    120 tgtgcagcct ctggattcac cttcagtttc tatggcatgc actgggtccg ccaggctcca   180
ggcaaggggc tggagtgggt ggcagctata tcatatgatg gaagtaataa atactatgca   240
gactccgtga agggccgatt caccatctcc agagacaatt ccaagaacac gctgtatctg   300
caaatgaaca gcctgagagc tgaggacacg gctgtgtatt actgtgcgaa aaggcccaac   360
caattttatt gtagtgatgg tagatgctac tccattgact actggggcca gggaaccctg   420
gtcaccgtct cctca                                                    435
```

<210> SEQ ID NO 14
<211> LENGTH: 145
<212> TYPE: PRT
<213> ORGANISM: Artificial Sequence
<220> FEATURE:
<223> OTHER INFORMATION: VH chain domain of clone 7E3

<400> SEQUENCE: 14

```
Met Glu Phe Gly Leu Ser Trp Leu Phe Leu Val Ala Ile Leu Lys Gly
1               5                   10                  15

Val Gln Cys Gln Val Gln Leu Leu Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ser Phe Tyr Gly Met His Trp Val Arg Gln Ala Pro Gly Lys Gly Leu
        50                  55                  60

Glu Trp Val Ala Ala Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Lys Arg Pro Asn Gln Phe Tyr Cys Ser Asp Gly Arg
        115                 120                 125

Cys Tyr Ser Ile Asp Tyr Trp Gly Gln Gly Thr Leu Val Thr Val Ser
    130                 135                 140

Ser
145
```

<210> SEQ ID NO 15
<211> LENGTH: 390
<212> TYPE: DNA
<213> ORGANISM: Artificial Sequence
<220> FEATURE:
<223> OTHER INFORMATION: VL chain domain of clone 7E3

<400> SEQUENCE: 15

```
atggacatga gggtccccgc tcagctcctg gggctcctgc tactctggct ccgaggtgcc      60
cggtgtgaaa ttgtaatgac gcagtctcca gccaccctgt ctgtgtctcc aggggagaga    120
gccaccctct cctgcagggc cagtcagagt gttagcagca acttagcctg gtaccagcag    180
aaacctggcc aggctcccag gctcctcatc tatggtgcat ccaccagggc cactggtatc    240
ccagccaggt tcagtggcag tgggtctggg acagacttca ctctcaccat cagcagcctg    300
cagtctgtag attctgcagt ttattactgt cagcagtata taaactggcc tccgtacact    360
tttggccagg ggaccaagct ggagatcaaa                                     390
```

<210> SEQ ID NO 16
<211> LENGTH: 130
<212> TYPE: PRT
<213> ORGANISM: Artificial Sequence
<220> FEATURE:
<223> OTHER INFORMATION: VL chain domain of clone 7E3

<400> SEQUENCE: 16

Met Asp Met Arg Val Pro Ala Gln Leu Leu Gly Leu Leu Leu Leu Trp
1               5                   10                  15

Leu Arg Gly Ala Arg Cys Glu Ile Val Met Thr Gln Ser Pro Ala Thr
            20                  25                  30

Leu Ser Val Ser Pro Gly Glu Arg Ala Thr Leu Ser Cys Arg Ala Ser
        35                  40                  45

Gln Ser Val Ser Ser Asn Leu Ala Trp Tyr Gln Lys Pro Gly Gln
    50                  55                  60

Ala Pro Arg Leu Leu Ile Tyr Gly Ala Ser Thr Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Gln Ser Val Asp Ser Ala Val Tyr Tyr Cys Gln Gln
            100                 105                 110

Tyr Asn Asn Trp Pro Pro Tyr Thr Phe Gly Gln Gly Thr Lys Leu Glu
        115                 120                 125

Ile Lys
    130

<210> SEQ ID NO 17
<211> LENGTH: 750
<212> TYPE: DNA
<213> ORGANISM: Artificial Sequence
<220> FEATURE:
<223> OTHER INFORMATION: Diabody 5B1CysDb sequence

<400> SEQUENCE: 17
cagtctgtgc tgacgcagcc gccctcagcg tctgggaccc ccgggcagag ggtcaccatc      60
tcttgttctg gaagcagctc caacatcgga agtaattttg tatactggta ccagcagctc     120
ccaggaacgg cccccaaact cctcatatat aggaataatc agcggccctc aggggtccct     180
gaccgattct ctggctccag gtctggcacc tcagcctccc tggccatcag tggactccgg     240
tccgaggatg aggctgatta ttactgtgca gcatgggatg acagcctggg aggccattat     300
gtcttcggaa ctgggaccaa ggtcaccgtc ctttctggtg gtggtggtca ggtgcagctg     360
gtggagtctg ggggaggctc ggtgcagcct ggcaggtccc tgagactctc ctgtgaagcc     420
tctggattca cctttgaggc ctatgccatg cactgggtcc ggcaacctcc agggaagggc     480
ctggagtggg tctcaagtat taattggaat agtggtcgca tagcctatgc ggactctgtg     540
aagggccgat tcaccatctc cagagacaac gccaggaatt ccctgtatct gcaaatgaac     600
agtctgagac ttgaggacac ggccttctat tactgtgcaa aagatatacg gaggtttagt     660 accgggggg cggagtttga gtactgggc cagggaaccc tggtcaccgt ctcctcaggt      720
tctcaccatc accatcacca tggcggttgc                                      750

<210> SEQ ID NO 18
<211> LENGTH: 250
<212> TYPE: PRT
<213> ORGANISM: Artificial Sequence
<220> FEATURE:
<223> OTHER INFORMATION: Diabody 5B1CysDb sequence

<400> SEQUENCE: 18

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Phe Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Arg Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Ser Leu
                85                  90                  95

Gly Gly His Tyr Val Phe Gly Thr Gly Thr Lys Val Thr Val Leu Ser
            100                 105                 110

Gly Gly Gly Gly Gln Val Gln Leu Val Glu Ser Gly Gly Gly Ser Val
            115                 120                 125

Gln Pro Gly Arg Ser Leu Arg Leu Ser Cys Glu Ala Ser Gly Phe Thr
130                 135                 140

Phe Glu Ala Tyr Ala Met His Trp Val Arg Gln Pro Pro Gly Lys Gly
145                 150                 155                 160

Leu Glu Trp Val Ser Ser Ile Asn Trp Asn Ser Gly Arg Ile Ala Tyr
                165                 170                 175

Ala Asp Ser Val Lys Gly Arg Phe Thr Ile Ser Arg Asp Asn Ala Arg
            180                 185                 190

Asn Ser Leu Tyr Leu Gln Met Asn Ser Leu Arg Leu Glu Asp Thr Ala
            195                 200                 205

Phe Tyr Tyr Cys Ala Lys Asp Ile Arg Arg Phe Ser Thr Gly Gly Ala
        210                 215                 220

Glu Phe Glu Tyr Trp Gly Gln Gly Thr Leu Val Thr Val Ser Ser Gly
225                 230                 235                 240

Ser His His His His His Gly Gly Cys
                245                 250

<210> SEQ ID NO 19
<211> LENGTH: 750
<212> TYPE: DNA
<213> ORGANISM: Artificial Sequence
<220> FEATURE:
<223> OTHER INFORMATION: Diabody 7E3CysDb sequence

<400> SEQUENCE: 19
gatgttgtgc tgacgcagtc tccagccacc ctgtctgtgt ctccagggga gagagccacc    60
ctctcctgca gggccagtca gagtgttagc agcaacttag cctggtacca gcagaaacct   120
ggccaggctc ccaggctcct catctatggt gcatccacca gggccactgg tatcccagcc   180
aggttcagtg gcagtgggtc tgggacagac ttcactctca ccatcagcag cctgcagtct   240
gaagattctg cagtttatta ctgtcagcag tataataact ggcctccgta cacttttggc   300
caggggacca aggtggatat caaatctggt ggtggtggtg aagtgcagct ggtggagtct   360
gggggaggcg tggtccagcc tgggaggtcc ctgagactct cctgtgcagc ctctggattc   420
accttcagtt ctatggcat gcactgggtc cgccaggctc aggcaaggg gctggagtgg   480

```
gtggcagcta tatcatatga tggaagtaat aaatactatg cagactccgt gaagggccga    540
ttcaccatct ccagagacaa ttccaagaac acgctgtatc tgcaaatgaa cagcctgaga    600
gctgaggaca cggctgtgta ttactgtgcg aaaaggccca accaatttta ttgtagtgat    660
ggtagatgct actccattga ctactggggc cagggaaccc tggtcaccgt ctcctcaggt    720
tctcaccatc accatcacca tggcggttgc                                     750

<210> SEQ ID NO 20
<211> LENGTH: 249
<212> TYPE: PRT
<213> ORGANISM: Artificial Sequence
<220> FEATURE:
<223> OTHER INFORMATION: Diabody 7E3CysDb sequence

<400> SEQUENCE: 20

Asp Val Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gln Ala Pro Arg Leu Leu Ile Tyr
            35                  40                  45

Gly Ala Ser Thr Arg Ala Thr Gly Ile Pro Ala Arg Phe Ser Gly Ser
        50                  55                  60

Gly Ser Gly Thr Asp Phe Thr Leu Thr Ile Ser Ser Leu Gln Ser Glu
65                  70                  75                  80

Asp Ser Ala Val Tyr Tyr Cys Gln Gln Tyr Asn Asn Trp Pro Pro Tyr
                85                  90                  95

Thr Phe Gly Gln Gly Thr Lys Val Asp Ile Lys Ser Gly Gly Gly Gly
            100                 105                 110

Glu Val Gln Leu Val Glu Ser Gly Gly Val Val Gln Pro Gly Arg
            115                 120                 125

Ser Leu Arg Leu Ser Cys Ala Ala Ser Gly Phe Thr Phe Ser Phe Tyr
        130                 135                 140

Gly Met His Trp Val Arg Gln Ala Pro Gly Lys Gly Leu Glu Trp Val
145                 150                 155                 160

Ala Ala Ile Ser Tyr Asp Gly Ser Asn Lys Tyr Tyr Ala Asp Ser Val
                165                 170                 175

Lys Gly Arg Phe Thr Ile Ser Arg Asp Asn Ser Lys Asn Thr Leu Tyr
            180                 185                 190

Leu Gln Met Asn Ser Leu Arg Ala Glu Asp Thr Ala Val Tyr Tyr Cys
        195                 200                 205

Ala Lys Arg Pro Asn Gln Phe Tyr Cys Ser Asp Gly Arg Cys Tyr Ser
    210                 215                 220

Ile Asp Tyr Trp Gly Gln Gly Thr Leu Val Thr Val Ser Ser Gly Ser
225                 230                 235                 240

His His His His His His Gly Gly Cys
                245
```